US012454529B2

(12) United States Patent
Su et al.

(10) Patent No.: US 12,454,529 B2
(45) Date of Patent: Oct. 28, 2025

(54) PIPERAZINE CYCLIC UREAS

(71) Applicant: SIRONAX LTD., Grand Cayman (KY)

(72) Inventors: Yaning Su, Beijing (CN); Zhaolan Zhang, Beijing (CN); Zhiyuan Zhang, San Diego, CA (US); Yanping Xu, Beijing (CN)

(73) Assignee: SIRONAX LTD., Grand Cayman (KY)

( * ) Notice: Subject to any disclaimer, the term of this patent is extended or adjusted under 35 U.S.C. 154(b) by 516 days.

(21) Appl. No.: 17/998,546

(22) PCT Filed: May 20, 2021

(86) PCT No.: PCT/CN2021/094993
§ 371 (c)(1),
(2) Date: Nov. 11, 2022

(87) PCT Pub. No.: WO2021/233397
PCT Pub. Date: Nov. 25, 2021

(65) Prior Publication Data

US 2023/0203019 A1 Jun. 29, 2023

(30) Foreign Application Priority Data

May 20, 2020 (WO) ................ PCT/CN2020/091436

(51) Int. Cl.

| | |
|---|---|
| ***C07D 403/14*** | (2006.01) |
| ***C07D 401/14*** | (2006.01) |
| ***C07D 405/14*** | (2006.01) |
| ***C07D 413/14*** | (2006.01) |
| ***C07D 417/14*** | (2006.01) |
| ***C07D 487/04*** | (2006.01) |

(52) U.S. Cl.
CPC ......... *C07D 403/14* (2013.01); *C07D 401/14* (2013.01); *C07D 405/14* (2013.01); *C07D 413/14* (2013.01); *C07D 417/14* (2013.01); *C07D 487/04* (2013.01)

(58) Field of Classification Search
CPC .. C07D 403/14; C07D 401/14; C07D 405/14; C07D 413/14; C07D 417/14; C07D 487/04; A61P 31/00; A61P 43/00
See application file for complete search history.

(56) References Cited

U.S. PATENT DOCUMENTS

| | | | |
|---|---|---|---|
| 6,756,394 | B1 | 6/2004 | Yuan et al. |
| 8,278,344 | B2 | 10/2012 | Cuny et al. |
| 9,974,762 | B2 | 5/2018 | Zhang et al. |
| 10,092,529 | B2 | 10/2018 | Zhang et al. |
| 2003/0083386 | A1 | 5/2003 | Yuan et al. |
| 2009/0099242 | A1 | 4/2009 | Cuny et al. |
| 2010/0317701 | A1 | 12/2010 | Cuny et al. |
| 2011/0144169 | A1 | 6/2011 | Cuny et al. |
| 2012/0122889 | A1 | 5/2012 | Yuan et al. |
| 2012/0309795 | A1 | 12/2012 | Cuny et al. |

FOREIGN PATENT DOCUMENTS

| | | | | |
|---|---|---|---|---|
| CN | 102316735 A | | 1/2012 | |
| CN | 107624111 A | | 1/2018 | |
| JP | 2005526091 A | | 9/2005 | |
| JP | 2018515555 A | | 6/2018 | |
| JP | 2019535728 A | | 12/2019 | |
| JP | 7577655 B | | 11/2024 | |
| WO | WO 03079973 A2 | | 10/2003 | |
| WO | WO 2009023272 A1 | | 2/2009 | |
| WO | WO 2010075290 A1 | | 7/2010 | |
| WO | WO 2010075561 A1 | | 7/2010 | |
| WO | WO 2012125544 A2 | | 9/2012 | |
| WO | 2016185423 A1 | | 11/2016 | |
| WO | WO-2018092089 A1 | * | 5/2018 | ............. A61P 43/00 |
| WO | WO 2019224773 A1 | | 11/2019 | |
| WO | WO 2020103884 A1 | | 5/2020 | |

OTHER PUBLICATIONS

Holler, N. et al., Fas triggers an alternative, caspase-8-independent cell death pathway using the kinase RIP as effector molecule, *Nature Immunology*, 2000, 1(6), pp. 489-495.
Degterev, A. et al., Identification of RIP1 kinase as a specific cellular target of necrostatins, *Nature Chemical Biology*, 2008, 4(5), pp. 313-321.
Dunai, Z., et al., Necroptosis: Biochemical, Physiological and Pathological Aspects, *Pathology & Oncology Research*, 2011, 17(4), pp. 791-800.
Degterev, A. et al., Chemical inhibitor of nonapoptotic cell death with therapeutic potential for ischemic brain injury, *Nature Chemical Biology*, 2005, 1(2), pp. 112-119.

(Continued)

*Primary Examiner* — Joseph K McKane
*Assistant Examiner* — Anna Grace Kuckla
(74) *Attorney, Agent, or Firm* — FINNEGAN, HENDERSON, FARABOW, GARRETT & DUNNER LLP

(57) ABSTRACT

Provided are piperazine cyclic urea compounds that inhibit cellular necrosis and/or human receptor interacting protein 1 kinase (RIP1), pharmaceutically acceptable salts, hydrates and stereoisomers thereof. Provided are also pharmaceutical compositions, methods of making, and methods of use which include treating a person in need thereof with an effective amount of the compound or composition, and detecting a resultant improvement in the person's health or condition.

28 Claims, No Drawings

(56) References Cited

OTHER PUBLICATIONS

Manguso, R. T. et al., In vivo CRISPR screening identifies Ptpn2 as a cancer immunotherapy target, *Nature*, 2017, 547(7664), pp. 413-418.
Wang, W. et al., RIP1 Kinase Drives Macrophage-Mediated Adaptive Immune Tolerance in Pancreatic Cancer, *Cancer Cell*, 2018, 34(5), pp. 757-774.
Berge, S. M., et al., Pharmaceutical Salts, Journal of Pharmaceutical Sciences, 1977, 66(1), pp. 1-19.
International Search Report and Written Opinion in counterpart PCT application No. PCT/CN2021/094993, mailed Aug. 26, 2021.
F. Meng et al., Medicinal Chemistry, China Medicine Science and Technology Press, Beijing, China, pp. 385-387 (2016).

* cited by examiner

PIPERAZINE CYCLIC UREAS

CROSS-REFERENCE TO RELATED APPLICATIONS

This is a national stage application of International Application No. PCT/CN2021/094993, filed May 20, 2021, which claims priority to PCT/CN2020/091436, filed May 20, 2020, all of which are incorporated herein by reference.

INTRODUCTION

Tumor necrosis factor alpha (TNF-α)-induced NF-κB activation plays a central role in the immune system and inflammatory responses. Receptor-interacting protein 1 (RIP1) is a multi-functional signal transducer involved in mediating nuclear factor κB (NF-κB) activation, apoptosis, and necroptosis. The kinase activity of RIP1 is critically involved in mediating necroptosis, a caspase-independent pathway of necrotic cell death. Holler et al. Nat Immunol 2000; 1: 489-495; Degterev et al. Nat Chem Biol 2008; 4: 313-321.

Necroptosis plays a role in various pathological forms of cell death, including ischemic brain injury, neurodegenerative diseases and viral infections. Dunai, et al., December 2011, Pathol. Oncol. Res.: POR 17 (4): 791-800. Necrostatin-1 (Nec-1), a small molecule inhibitor of RIP1 kinase activity, can block necroptosis. Degterev et al. Nat Chem Biol 2005; 1: 112-119.

RIP1 can contribute to D-1 immunotherapy resistance (e.g. Manguso et al., 2017 Nature 547, 413-418) and can act as a checkpoint kinase governing tumor immunity (e.g. Wang et al, Cancer Cell 34, 757-774, Nov. 12, 2018).

Related patent publications include: U.S. Pat. Nos. 9,974,762, 10/092,529, 6,756,394, 8,278,344, US2012022889, US2009099242, US20100317701, US20110144169, US20030083386, US201200309795, WO2009023272, WO2010075290, WO2010075561, WO2012125544, and WO 2020/103884.

SUMMARY OF THE INVENTION

The invention provides compounds that are inhibitors of necrosis, necroptosis, ferroptosis, human receptor interacting protein 1 kinase (RIP1) or related indications, and prodrugs thereof, which are hydrolyzed, typically in the gut or blood, to yield the corresponding inhibitors. In embodiments the inhibitors provide unexpectedly exceptional metabolic stability, evidenced by liver microsome data and PK data.

In an aspect the invention provides a compound of formula Ia:

Ia

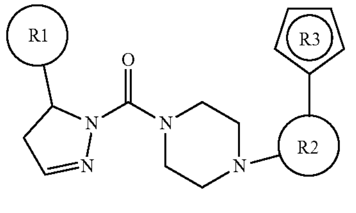

R1 is C6 aryl comprising 0 or 1 N heteroatoms or C5 aryl comprising 1 or 2 N heteroatoms and an O or S heteroatom, wherein the C5 aryl and C6 aryl are optionally substituted with halogen, CN, or C1 to C3 alkyl;

R2 is C6 aryl comprising 0, 1 or 2 N or 3N heteroatoms or C5 aryl comprising 1 or 2 N heteroatoms and an O or S heteroatom, wherein the C5 aryl and C6 aryl are optionally substituted with halogen, CN, C1 to C3 alkoxy, or C1 to C3 alkyl optionally substituted with OH;

R3 is C5 to C8 aryl comprising 1, 2, 3 or 4 N heteroatoms, or 1 or 2 N heteroatoms and an O or S heteroatom, substituted with 0-3 substituents selected from halide, optionally-substituted N, S or O, and optionally-substituted hydrocarbyl;

or a salt, hydrate or stereoisomer thereof.

In an aspect the invention provides a compound of formula I:

I

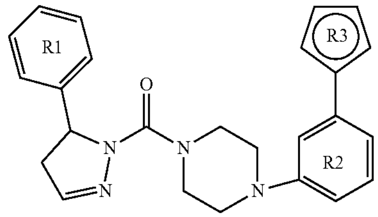

R1 is C6 aryl comprising 0 or 1 N heteroatoms, optionally substituted at C3 and/or C5 with F or CN;

R2 is C6 aryl comprising 0, 1 or 2 N heteroatoms, optionally substituted at C4 with F;

R3 is C5 aryl comprising 1, 2, 3 or 4 N heteroatoms, or 1 or 2 N heteroatoms and an O or S heteroatom, substituted with 0-3 substituents selected from halide, optionally-substituted N, S or O, and optionally-substituted hydrocarbyl;

or a salt, hydrate or stereoisomer thereof.

In embodiments:

the R3 substituents are independently C0-C6: aldehyde, aldimine, alkanoyloxy, alkoxy, alkoxycarbonyl, alkyloxy, alkyl, alkenyl, alkynyl, amine, azo, halogens, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3);

R2 comprises N2, N4 or N2/N4;

R3 comprises N1, N1/N2, N2/N3, N3/N4, N2/N5; N2/N4, S2/N4, N2/S4, S3/N4, N2/S3, N3/O4, N2/N3/S5, N2/N3/O5, N2/N3/N5, N2/N3/N4 or N2/N3/N4/N5; or any combination of the foregoing substituents.

In an aspect the invention provides a compound having a structure disclosed herein.

In an aspect the invention provides a pharmaceutical composition comprising a therapeutically effective amount of a compound, a salt, hydrate or stereoisomer thereof, disclosed herein and one or more pharmaceutically acceptable excipients, in predetermined, unit dosage form.

In an aspect the invention provides use of a compound, a salt, hydrate or stereoisomer thereof, or composition disclosed herein in the manufacture of a medicament for inhibiting necrosis, necroptosis, ferroptosis, human RIP1, or related indications, in a person in need thereof.

In an aspect the invention provides a compound, a salt, hydrate or stereoisomer thereof, or composition disclosed herein for use in inhibiting necrosis, necroptosis, ferroptosis, human RIP1, or related indications in a person in need thereof, or in the manufacture of a medicament thereof in a person in need thereof.

In an aspect the invention provides a method of using a compound, a salt, hydrate or stereoisomer thereof, or composition disclosed herein for to inhibit necrosis, necroptosis, ferroptosis, human RIP1, or related indications in a person in need thereof, or in the manufacture of a medicament thereof in a person in need thereof.

The invention encompasses all combination of the particular embodiments recited herein, as if each combination had been laboriously recited.

DESCRIPTION OF PARTICULAR EMBODIMENTS OF THE INVENTION

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The term "alkyl" refers to a hydrocarbon group selected from linear and branched saturated hydrocarbon groups of 1-18, or 1-12, or 1-6, or 1-3 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms, e.g., 1-3 carbon atoms; and lower alkenyl or alkynyl means 2-8, 2-6 or 2-4 carbon atoms.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6, or 3-4, or 5-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, e.g., 5- to 6-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered, e.g., 3- to 6-membered, or 3 to 5-membered, or 4 to 5-membered, or 5 to 6-membered, or 4- to 6-membered, monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In embodiments substituents are selected from optionally substituted heteroatom and optionally substituted, optionally hetero-, optionally cyclic C1-C18 hydrocarbyl, particularly wherein the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments, substituents are selected from: halogen, —R', —OR', =O, =NR', =N—OR', —NR'R", —SR', —SiR'R"R'", —OC(O)R', —C(O)R', —CO2R', —CONR'R", —OC(O)NR'R", —NR"C(O)R', —NR'—C(O)NR"R'", —NR'—SO2NR'", —NR"CO2R', —NH—C(NH2)=NH, —NR'C(NH2)=NH, —NH—C(NH2)=NR', —S(O)R', —SO2R', —SO2NR'R", —NR"SO2R, —CN and —NO2, —N3, —CH(Ph)2, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, (C1-C8)alkyl and heteroalkyl substituted with one to three halogens, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF3 and —CH2CF3), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R'", —OC(O)R', —C(O)R', —CO2R', —CONR'R", —OC(O)NR'R", —NR"C(O)R', —NR"CO2R', —NR'—SO2NR"R'", —S(O)R', —SO2R', —SO2NR'R", —NR"SO2R, —CN and —NO2, perfluoro(C1-C4)alkoxy and perfluoro(C1-C4)alkyl, where R' and R" are as defined above.

Preferred substituents are disclosed herein and exemplified in the tables, structures, examples, and claims, and may be applied across different compounds of the invention, i.e. substituents of any given compound may be combinatorically used with other compounds.

In particular embodiments applicable substituents are independently substituted or unsubstituted heteroatom, substituted or unsubstituted, 0-3 heteroatom C1-C6 alkyl, C1-C3 alkyl, or C1-C2 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, or C5-C6 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, alkenyl, alkynyl, amine, azo, halogen, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

Combinations of substituents as disclosed herein are those that result in the formation of stable or chemically feasible compounds. For abbreviation or according to common practice, certain hydrogen atoms attached to a certain atom (e.g., a carbon atom C or a nitrogen atom N) are not specifically spelled out in a chemical structure, formula, or notation; hydrogen atoms are deemed to be present to the extent the valences of the certain atom (e.g., C or N) are completed.

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl $—CH_2C(O)—$ groups (keto forms) may undergo tautomerism to form hydroxyl $—CH{=}C(OH)—$ groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with $HOOC—(CH_2)n-COOH$, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one hydrate thereof, and/or at least one pharmaceutically acceptable salt thereof to a subject in recognized need thereof.

An "effective amount" refers to an amount of at least one compound and/or at least one stereoisomer thereof, and/or at least one hydrate thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The subject compounds and stereoisomers thereof, hydrates thereof, and pharmaceutically acceptable salts thereof may be employed alone or in combination with at least one other therapeutic agent for treatment. In some embodiments, the compounds, stereoisomers thereof, hydrates thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, hydrates thereof, and/or pharmaceutically acceptable salts thereof, and at least one pharmaceutically acceptable carrier.

The composition comprising a subject compound and stereoisomers thereof, hydrates thereof, and/or pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, hydrates thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, hydrates thereof, and/or pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, hydrates thereof, and/or pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

For administration by inhalation, the subject compounds and stereoisomers thereof, hydrates thereof, and/or pharmaceutically acceptable salts thereof may be conveniently delivered in the form of an aerosol spray presentation from pressurized packs or nebulisers. The subject compounds and stereoisomers thereof, hydrates thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, hydrates thereof, and/or pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, hydrates thereof, and/or pharmaceutically acceptable salts thereof in an appropriate ophthalmic vehicle, such that the subject compound and stereoisomers thereof, hydrates thereof, and/or at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, hydrates thereof, and/or pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, hydrates thereof, and/or pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, hydrates thereof, and/or pharmaceutically acceptable salts thereof and a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, hydrates thereof, and/or pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, hydrates thereof, and/or pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, hydrates thereof, and/or pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, hydrates thereof, and/or pharmaceutically acceptable salt thereof disclosed herein can be administered as the sole active ingredient or in combination with at least one second active ingredient.

The subject compounds, stereoisomers thereof, hydrates thereof, and/or pharmaceutically acceptable salts are incorporated into pharmaceutical compositions or formulations. The compositions will contain pharmaceutically acceptable diluents and/or carriers, i.e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds, stereoisomers thereof, hydrates thereof, and/or pharmaceutically acceptable salts are administered for morning/daytime dosing, with off period at night.

The subject compounds, stereoisomers thereof, hydrates thereof, and/or pharmaceutically acceptable salts may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds, stereoisomers thereof, hydrates thereof, and/or pharmaceutically acceptable salts possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds, such as deuterium, e.g. —$CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound to treat applicable indications, or to treat programmed cell death. In embodiments applicable indications include brain injury, neurodegenerative diseases, viral infections, immune tolerance, and cancer e.g. promote tumor immunity in pancreatic cancer and melanoma.

In an aspect the invention provides a compound of formula Ia:

Ia

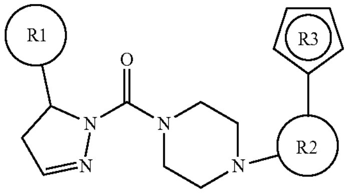

- R1 is C6 aryl comprising 0 or 1 N heteroatom or C5 aryl comprising 1 or 2 N heteroatoms and an O or S heteroatom, wherein the C5 aryl and C6 aryl are optionally substituted with halogen, CN, or C1 to C3 alkyl;
- R2 is C6 aryl comprising 0, 1 or 2 N or 3N heteroatoms or C5 aryl comprising 1 or 2 N heteroatoms and an O or S heteroatom, wherein the C5 aryl and C6 aryl are optionally substituted with halogen, CN, C1 to C3 alkoxy, or C1 to C3 alkyl optionally substituted with OH;
- R3 is C5 to C8 aryl comprising 1, 2, 3 or 4 N heteroatoms, or 1 or 2 N heteroatoms and an O or S heteroatom, substituted with 0-3 substituents selected from halide, optionally-substituted N, S or O, and optionally-substituted hydrocarbyl;

or a salt, hydrate or stereoisomer thereof.

In an aspect the invention provides a compound of formula I:

I

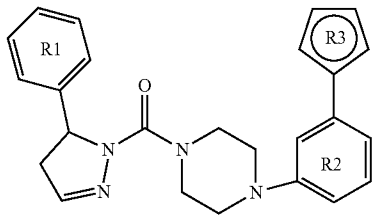

R1 is C6 aryl comprising 0 or 1 N heteroatoms, optionally substituted at C3 and/or C5 with F or CN;

R2 is C6 aryl comprising 0, 1 or 2 N heteroatoms, optionally substituted at C4 with F;

R3 is C5 aryl comprising 1, 2, 3 or 4 N heteroatoms, or 1 or 2 N heteroatoms and an O or S heteroatom, substituted with 0-3 substituents selected from halide, optionally-substituted N, S or O, and optionally-substituted hydrocarbyl;

or a salt, hydrate or stereoisomer thereof.

In embodiments: the R3 substituents are independently C0-C6: aldehyde, aldimine, alkanoyloxy, alkoxy, alkoxycarbonyl, alkyloxy, alkyl, alkenyl, alkynyl, amine, azo, halogens, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or triflurom-ethyl ether (OCF3);

R2 comprises N2, N4 or N2/N4;

R3 comprises N1, N1/N2, N2/N3, N3/N4, N2/N5; N2/N4, S2/N4, N2/S4, S3/N4,

N2/S3, N3/O4, N2/N3/S5, N2/N3/O5, N2/N3/N5, N2/N3/N4 or N2/N3/N4/N5; or any combination of the foregoing substituents.

In one embodiment, the present disclosure provides a compound, salt, hydrate or stereoisomer thereof, wherein the compound has the following structural formula II(1):

II(1)

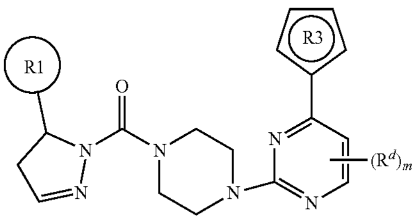

wherein $R^d$ is selected from halogen, CN, C1 to C3 alkoxy, and C1 to C3 alkyl optionally substituted with OH, and wherein m is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula II(2):

II(2)

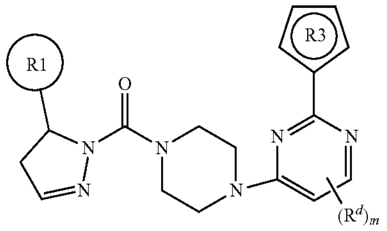

wherein $R^d$ is selected from halogen, CN, C1 to C3 alkoxy, and C1 to C3 alkyl optionally substituted with OH, and wherein m is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula II(3):

II(3)

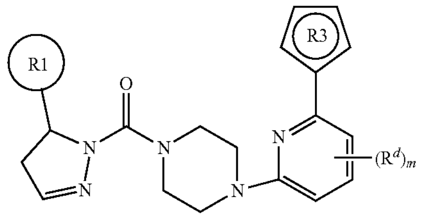

wherein $R^d$ is selected from halogen, CN, C1 to C3 alkoxy, and C1 to C3 alkyl optionally substituted with OH, and wherein m is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula II(4):

II(4)

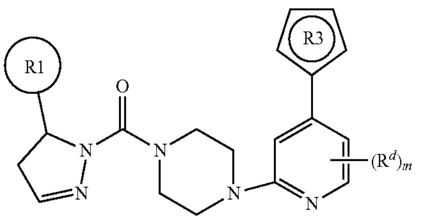

wherein $R^d$ is selected from halogen, CN, C1 to C3 alkoxy, and C1 to C3 alkyl optionally substituted with OH, and wherein m is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula II(5):

II(5)

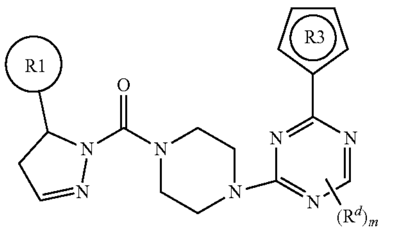

wherein $R^d$ is selected from halogen, CN, C1 to C3 alkoxy, and C1 to C3 alkyl optionally substituted with OH, and wherein m is 0 or 1; and all other variables not specifically defined herein are as defined in any one of the appropriate preceding embodiments.

In one embodiment, the present disclosure provides a compound, salt, hydrate or stereoisomer thereof, wherein the compound has the following structural formula II(6):

II(6)

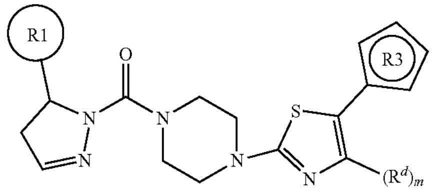

wherein $R^d$ is selected from halogen, CN, C1 to C3 alkoxy, and C1 to C3 alkyl optionally substituted with OH; and all other variables not specifically defined herein are as defined in any one of the appropriate preceding embodiments.

In one embodiment, the present disclosure provides a compound, salt, hydrate or stereoisomer thereof, wherein the compound has the following structural formula II(1):

II(7)

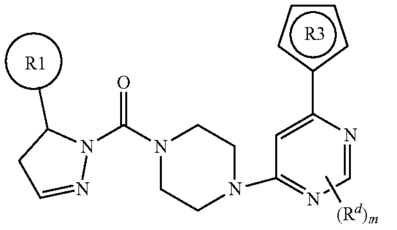

wherein $R^d$ is selected from halogen, CN, C1 to C3 alkoxy, and C1 to C3 alkyl optionally substituted with OH, and wherein m is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula II(1):

II(8)

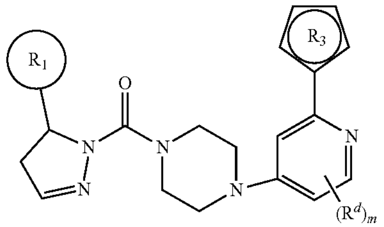

wherein $R^d$ is selected from halogen, CN, C1 to C3 alkoxy, and C1 to C3 alkyl optionally substituted with OH, and wherein m is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula III(1):

III(1)

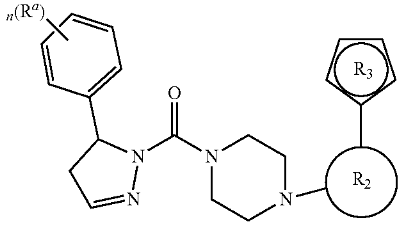

wherein $R^a$ is selected from halogen, CN, and C1 to C3 alkyl, and wherein n is 0, 1, 2, or 3; and all other variables not specifically defined herein are as defined in any one of the appropriate preceding embodiments.

In one embodiment, the present disclosure provides a compound, salt, hydrate or stereoisomer thereof, wherein the compound has the following structural formula III(2):

III(2)

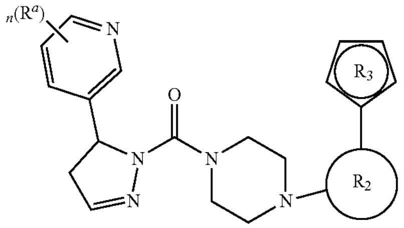

wherein $R^a$ is selected from halogen, CN, and C1 to C3 alkyl, and wherein n is 0, 1, 2, or 3; and all other variables not specifically defined herein are as defined in any one of the appropriate preceding embodiments.

In one embodiment, the present disclosure provides a compound, salt, hydrate or stereoisomer thereof, wherein the compound has the following structural formula III(3):

III(3)

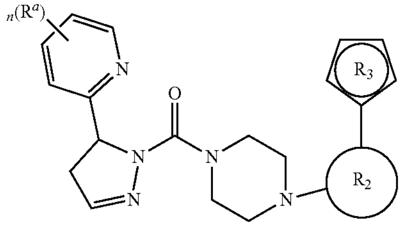

wherein $R^a$ is selected from halogen, CN, and C1 to C3 alkyl, and wherein n is 0, 1, 2, or 3; and all other variables not specifically defined herein are as defined in any one of the appropriate preceding embodiments.

In one embodiment, the present disclosure provides a compound, salt, hydrate or stereoisomer thereof, wherein the compound has the following structural formula III(4):

III(4)

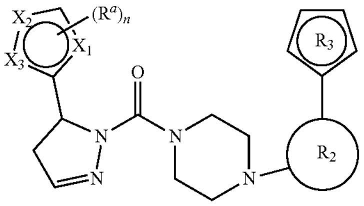

wherein $X_1$ is S, $X_2$ is C, and $X_3$ is N, or $X_1$ is S, $X_2$ is N, and $X_3$ is C, or $X_1$ is N, $X_2$ is O, and $X_3$ is C, or $X_1$ is N, $X_2$ is S, and $X_3$ is C; wherein $R^a$ is selected from halogen, CN, and C1 to C3 alkyl; and wherein n is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula IV(1):

IV(1)

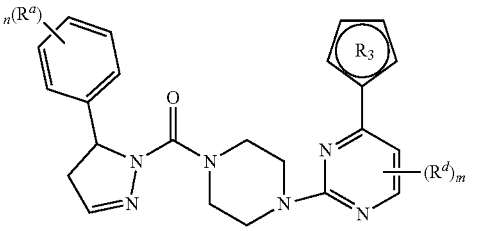

wherein $R^a$ is selected from halogen, CN, and C1 to C3 alkyl, n is 0, 1, 2, or 3; and wherein $R^d$ is selected from halogen, CN, C1 to C3 alkoxy, and C1 to C3 alkyl optionally substituted with OH, m is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula IV(2):

IV(2)

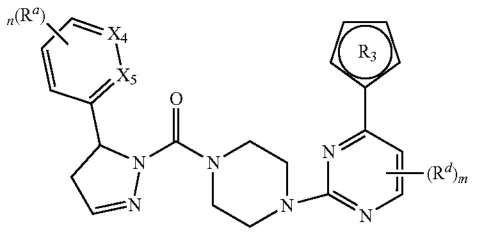

wherein $X_4$ is N and $X_5$ is C, or $X_4$ is C and $X_5$ is N; wherein $R^a$ is selected from halogen, CN, and C1 to C3 alkyl, n is 0, 1, 2, or 3; and wherein $R^d$ is selected from halogen, CN, C1 to C3 alkoxy, and C1 to C3 alkyl optionally substituted with OH, m is 0, 1, or 2; and all other variables not specifically defined herein are as defined in any one of the appropriate preceding embodiments.

In one embodiment, the present disclosure provides a compound, salt, hydrate or stereoisomer thereof, wherein the compound has the following structural formula IV(3):

IV(3)

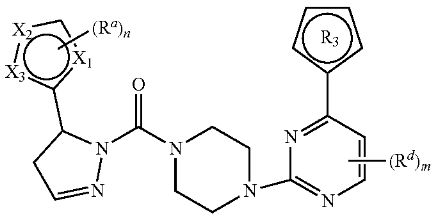

wherein $X_1$ is S, $X_2$ is C, and $X_3$ is N, or $X_1$ is S, $X_2$ is N, and $X_3$ is C, or $X_1$ is N, $X_2$ is O, and $X_3$ is C, or $X_1$ is N, $X_2$ is S, and $X_3$ is C; wherein $R^a$ is selected from halogen, CN, and C1 to C3 alkyl, n is 0, 1, 2, or 3; and wherein $R^d$ is selected from halogen, CN, C1 to C3 alkoxy, and C1 to C3 alkyl optionally substituted with OH, m is 0, 1, or 2; and all other variables not specifically defined herein are as defined in any one of the appropriate preceding embodiments.

In one embodiment, the present disclosure provides a compound, salt, hydrate or stereoisomer thereof, wherein R3 is

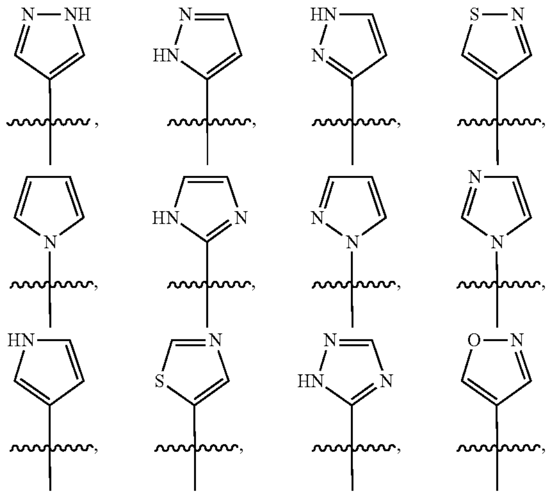

-continued

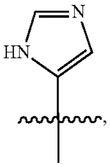, 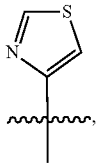, 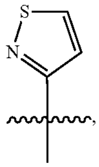, 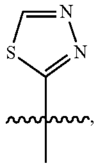,

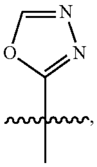, 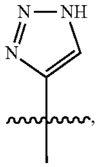, 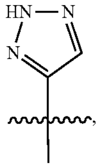, 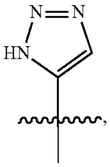,

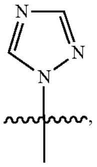, 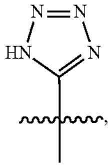, 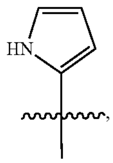, 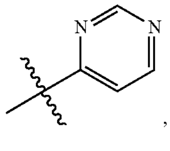,

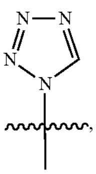, 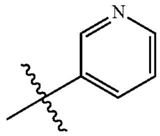, 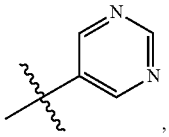,

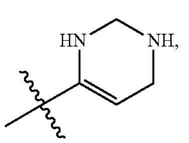 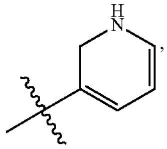

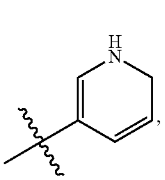, 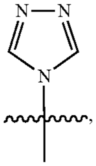, 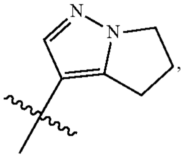,

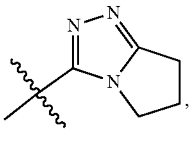, or 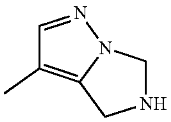

substituted with 0-3 substituents selected from halide, optionally-substituted N, S or O, and optionally-substituted hydrocarbyl; and all other variables not specifically defined herein are as defined in any one of the appropriate preceding embodiments.

In one embodiment, the present disclosure provides a compound, a salt, hydrate or stereoisomer thereof, wherein R3 is

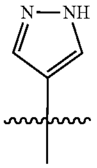, 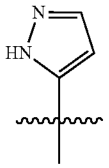, 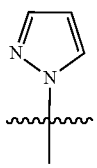,

-continued

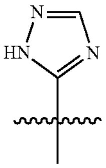, 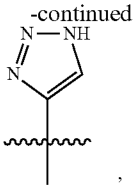, or 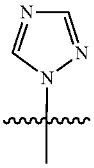;

and all other variables not specifically defined herein are as defined in any one of the appropriate preceding embodiments.

In one embodiment, the present disclosure provides a compound, salt, hydrate or stereoisomer thereof, wherein R3 is substituted with 0-3 $R^e$, wherein $R^e$, for each occurrence, is independently selected from:

halogen, cyano, $C_1$-$C_6$ alkyl, $C_3$-$C_6$ cycloalkyl, 3- to 6-membered heterocyclyl, $C_2$-$C_6$ alkenyl, $C_1$-$C_6$ alkoxy, —C(═O)($C_1$-$C_6$ alkyl), —C(═O)($C_3$-$C_6$ cycloalkyl), —C(═O)(3- to 6-membered heterocyclyl), ═O, —$NO_2$, —C(═O)$OR^s$, —C(═O)$NR^pR^q$, —$NR^pR^q$, —$NR^p$C(═O)$R^s$, —$NR^p$C(═O)$OR^s$, —$NR^p$C(═O)$NR^qR^r$, —$NR^p$S(═O)$_w$$R^s$, —$OR^s$, —OC(═O)$R^s$, —OC(═O)$OR^s$, —OC(═O)$NR^pR^q$, —S(═O)$_w$$R^s$, and —S(═O)$_w$$NR^pR^q$; wherein the $C_1$-$C_6$ alkyl, $C_3$-$C_6$ cycloalkyl, 3- to 6-membered heterocyclyl, the $C_2$-$C_6$ alkenyl, and the $C_1$-$C_6$ alkoxy of $R^e$, the $C_1$-$C_6$ alkyl of —C(═O)($C_1$-$C_6$ alkyl), the $C_3$-$C_6$ cycloalkyl of —C(═O)($C_3$-$C_6$ cycloalkyl), and the 3- to 6-membered heterocyclyl of —C(═O)(3- to 6-membered heterocyclyl) are each optionally substituted with 1 to 3 groups selected from halogen, cyano, ═O, —C(═O)$R^s$, —C(═O)$OR^s$, —C(═O)$NR^pR^q$, —$NR^pR^q$, —$NR^p$C(═O)$R^s$, —$NR^p$C(═O)$OR^s$, —$NR^p$C(═O)$NR^qR^r$, —$NR^p$S(═O)$_w$$R^s$, —$OR^s$, —OC(═O)$R^s$, —OC(═O)$OR^s$, —OC(═O)$NR^pR^q$, —S(═O)$_w$$R^s$, —S(═O)$_w$$NR^pR^q$, $C_3$-$C_6$ cycloalkyl, and 3- to 6-membered heterocyclyl; wherein $R^p$, $R^q$, $R^r$, and $R^s$, for each occurrence, are each independently selected from hydrogen, OH, $NH_2$, $C_1$-$C_4$ alkyl, $C_3$-$C_6$ cycloalkyl, and 3- to 6-membered heterocyclyl; wherein the $C_1$-$C_4$ alkyl, $C_3$-$C_6$ cycloalkyl, and 3- to 6-membered heterocyclyl of any one of $R^p$, $R^q$, $R^r$, and $R^s$ is optionally substituted with 1 to 3 groups selected from halogen, cyano, —OH, $C_1$-$C_6$ alkyl, —O($C_1$-$C_6$ alkyl), —C(═O)N($C_1$-$C_6$alkyl)($C_1$-$C_6$ alkyl), —C(═O)NH($C_1$-$C_6$ alkyl), —C(═O)(3- to 6-membered heterocyclyl), —C(═O)($C_3$-$C_6$ cycloalkyl), $C_3$-$C_6$ cycloalkyl, phenyl, and 3- to 6-membered heterocyclyl; and wherein w is an integer selected from 0, 1, and 2; and all other variables not specifically defined herein are as defined in any one of the appropriate preceding embodiments.

In one embodiment, the present disclosure provides a compound, salt, hydrate or stereoisomer thereof, wherein R3 is substituted with 0-3 $R^e$, wherein $R^e$, for each occurrence, is independently selected from: halogen; cyano; ═O, —$NO_2$, 4- to 6-membered heterocyclyl optionally substituted with oxo; —C(═O)($C_1$-$C_3$ alkyl); —C(═O)(4- to 6-membered heterocyclyl);

—C(═O)OR$^s$, wherein R$^s$ is H or $C_1$-$C_3$ alkyl;

—OR$^s$, wherein R$^s$ is H or $C_1$-$C_3$ alkyl; $C_1$-$C_3$ alkyl, optionally substituted with OH, $NH_2$, cyano, halogen, $C_1$-$C_3$ alkoxyl, 3- to 4-membered cycloalkyl, 4- to 6-membered heterocyclyl, —C(═O)OH, —C(═O)(4- to 6-membered heterocyclyl), —C(═O)NH$(CH_2)_2$OH, or —C(═O)$NH_2$;

—C(═O)NR$^p$R$^q$, wherein R$^p$ and R$^q$ each are independently selected from H and $C_1$-$C_3$ alkyl;

—NR$^p$R$^q$, wherein R$^p$ and R$^q$ each are independently selected from H and $C_1$-$C_3$ alkyl;

—NR$^p$C(═O)R$^s$, wherein R$^p$ is selected from H and $C_1$-$C_3$ alkyl, and R$^s$ is selected from 3- to 4-membered cycloalkyl and $C_1$-$C_3$ alkyl optionally substituted with 3- to 4-membered cycloalkyl;

—NR$^p$S(═O)$_w$R$^s$, wherein R$^p$ is selected from H and $C_1$-$C_3$ alkyl, and R$^s$ is selected from $C_1$-$C_3$ alkyl, and wherein w is 2;

—S(═O)$_w$R$^s$, wherein R$^s$ is selected from $C_1$-$C_3$ alkyl and wherein w is 0 or 2;

and all other variables not specifically defined herein are as defined in any one of the appropriate preceding embodiments.

In one embodiment, the present disclosure provides a compound, a salt, hydrate or stereoisomer thereof, wherein R3 is substituted with 1-3 R$^e$, wherein R$^e$, for each occurrence, is independently selected from:

Cl, Br, I, CN, methyl, ethyl, —$CF_3$, —$CH_2F$, —$CHF_2$, —$CH_2CF_3$, —$CH_2OH$, —$CH_2CN$, —$CH_2CH_2OH$, —$CH_2CH_2OCH_3$, —$CH_2$C(═O)$NH_2$,

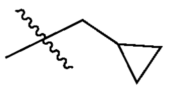,

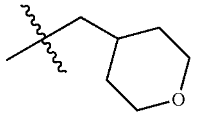,

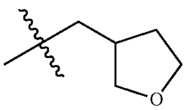,

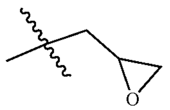,

-continued

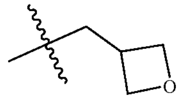,

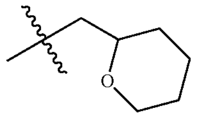,

—OH, —$OCH_3$, ═O, —C(═O)$CH_3$,

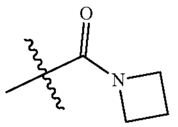,

—C(═O)$OCH_3$, —C(═O)$OCH_2CH_3$, —C(═O)$NH_2$, —C(═O)OH, $NH_2$, —NHC(═O)$CH_3$,

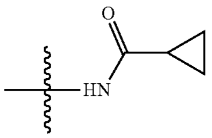,

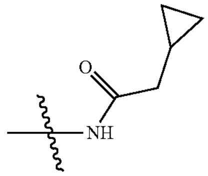,

—$NO_2$, —NHS(═O)$_2CH_2CH_3$, —S(═O)$_2CH_2CH_3$, and —S(═O)$_2CH_3$;

and all other variables not specifically defined herein are as defined in any one of the appropriate preceding embodiments.

In one embodiment, the present disclosure provides a compound, a salt, hydrate or stereoisomer thereof, wherein R3 is substituted with 1-3 R$^e$, wherein R$^e$, for each occurrence, is independently selected from: Cl, CN, methyl, —$CF_3$, —$CH_2OH$, —$CH_2$C(═O)$NH_2$, —C(═O)$OCH_3$, —C(═O)$NH_2$, and —C(═O)OH; and all other variables not specifically defined herein are as defined in any one of the appropriate preceding embodiments.

In one embodiment, the present disclosure provides a compound, a salt, hydrate or stereoisomer thereof, wherein R3 is substituted with 1-3 R$^e$, wherein R$^e$, for each occurrence, is independently selected from: CN, methyl, Cl, and —C(═O)$NH_2$; and all other variables not specifically defined herein are as defined in any one of the appropriate preceding embodiments.

In one embodiment, the present disclosure provides a compound, a salt, hydrate or stereoisomer thereof, wherein the C5 aryl and C6 aryl of R1 are optionally substituted with F, Cl, Br, CN, or methyl; wherein the C5 aryl and C6 aryl of R2 are optionally substituted with F, Cl, CN, —OCH3, or —CH2OH; and all other variables not specifically defined herein are as defined in any one of the appropriate preceding embodiments.

In one embodiment, the present disclosure provides a compound, a salt, hydrate or stereoisomer thereof, wherein the compound has one of structural formulae in Tables 1 and 2.

TABLE 1
| Active Compounds: Structures (Compounds 1-142) | |
|---|---|
| 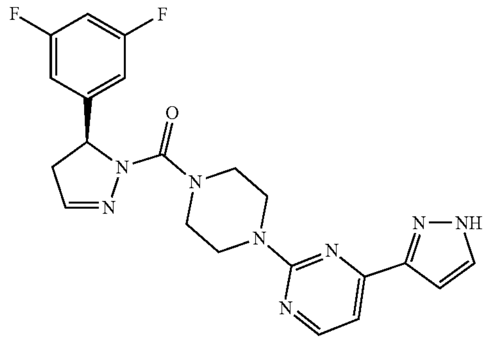 [SMILES: O=C(N1CCN(c2nccc(-c3cc[nH]n3)n2)CC1)N1N=CC[C@H]1c1cc(F)cc(F)c1] | 1 |
| 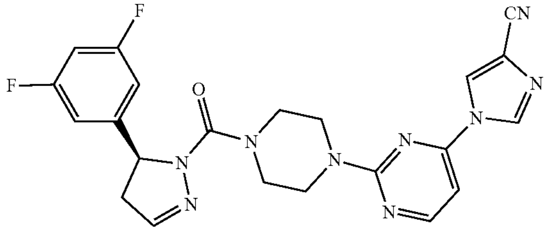 [SMILES: N#Cc1cn(-c2ccnc(N3CCN(C(=O)N4N=CC[C@H]4c4cc(F)cc(F)c4)CC3)n2)cn1] | 2 |
| 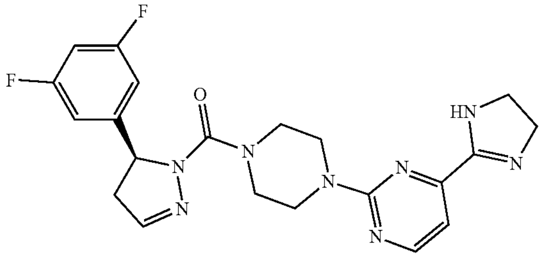 [SMILES: O=C(N1CCN(c2nccc(C3=NCCN3)n2)CC1)N1N=CC[C@H]1c1cc(F)cc(F)c1] | 3 |
| 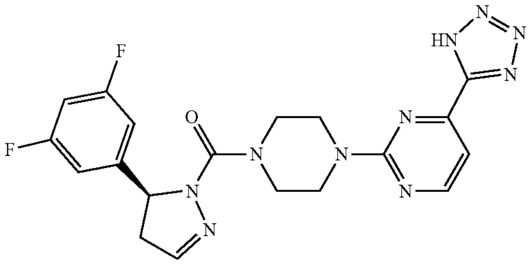 [SMILES: O=C(N1CCN(c2nccc(-c3nnn[nH]3)n2)CC1)N1N=CC[C@H]1c1cc(F)cc(F)c1] | 4 |
| 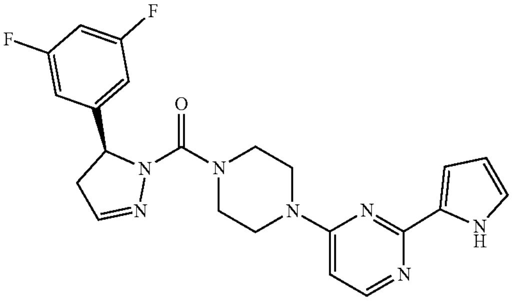 [SMILES: O=C(N1CCN(c2nccc(-c3ccc[nH]3)n2)CC1)N1N=CC[C@H]1c1cc(F)cc(F)c1] | 5 |

TABLE 1-continued
| Active Compounds: Structures (Compounds 1-142) |
| --- |
| 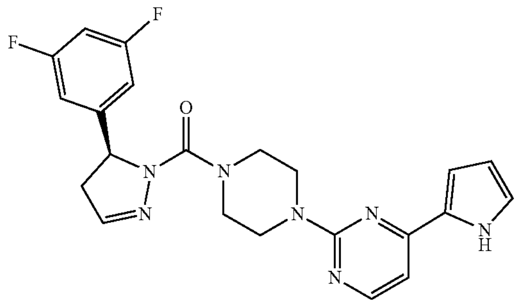 6 |
| 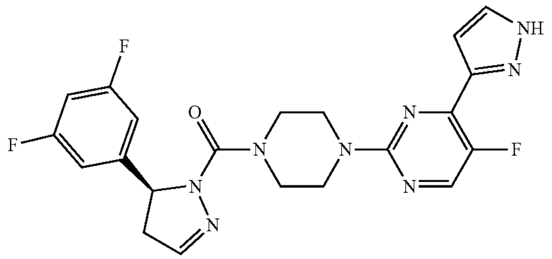 [SMILES: O=C(N1CCN(c2ncc(F)c(-c3cc[nH]n3)n2)CC1)N1N=CC[C@H]1c1cc(F)cc(F)c1] 7 |
| 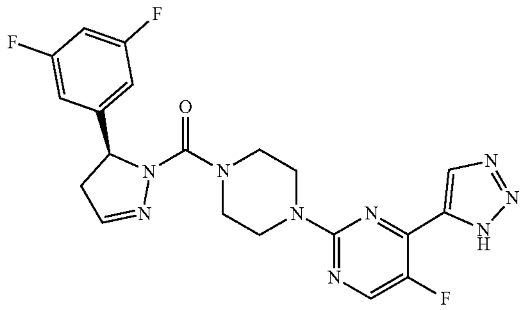 [SMILES: O=C(N1CCN(c2ncc(F)c(-c3cnn[nH]3)n2)CC1)N1N=CC[C@H]1c1cc(F)cc(F)c1] 8 |
| 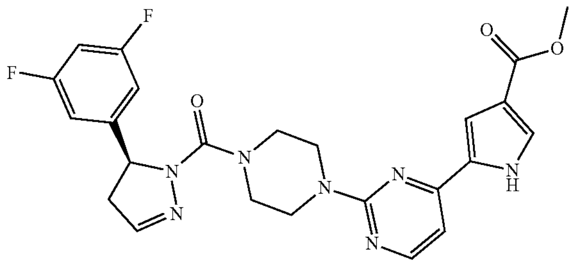 [SMILES: COC(=O)c1c[nH]c(-c2ccnc(N3CCN(C(=O)N4N=CC[C@H]4c4cc(F)cc(F)c4)CC3)n2)c1] 9 |
| 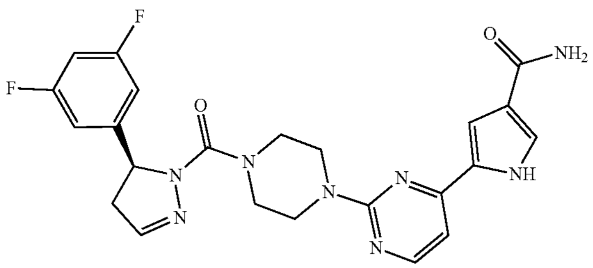 [SMILES: NC(=O)c1c[nH]c(-c2ccnc(N3CCN(C(=O)N4N=CC[C@H]4c4cc(F)cc(F)c4)CC3)n2)c1] 10 |

TABLE 1-continued
| Active Compounds: Structures (Compounds 1-142) | |
| --- | --- |
| 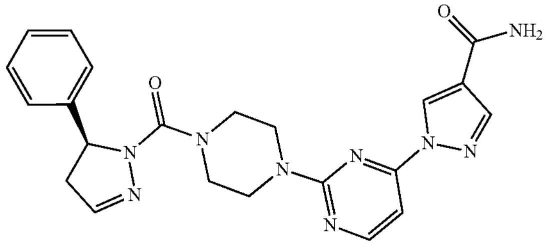 [SMILES: NC(=O)c1cnn(-c2ccnc(N3CCN(C(=O)N4N=CC[C@H]4c4ccccc4)CC3)n2)c1] | 11 |
| 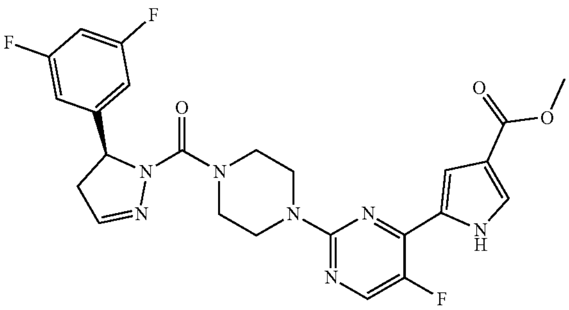 [SMILES: COC(=O)c1c[nH]c(-c2nc(N3CCN(C(=O)N4N=CC[C@H]4c4cc(F)cc(F)c4)CC3)ncc2F)c1] | 12 |
| 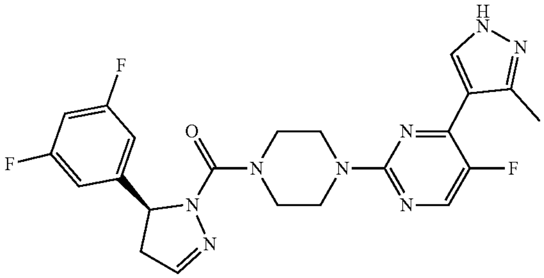 [SMILES: Cc1n[nH]cc1-c1nc(N2CCN(C(=O)N3N=CC[C@H]3c3cc(F)cc(F)c3)CC2)ncc1F] | 13 |
| 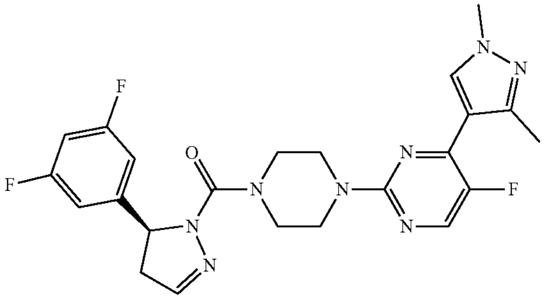 [SMILES: Cc1nn(C)cc1-c1nc(N2CCN(C(=O)N3N=CC[C@H]3c3cc(F)cc(F)c3)CC2)ncc1F] | 14 |
| 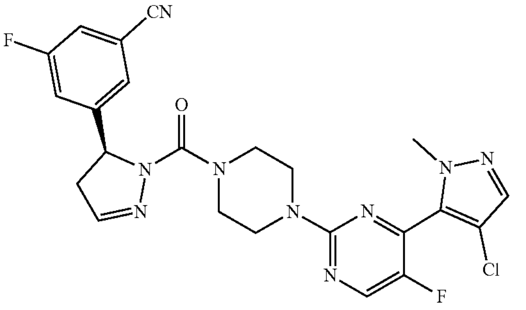 [SMILES: Cn1ncc(Cl)c1-c1nc(N2CCN(C(=O)N3N=CC[C@H]3c3cc(F)cc(C#N)c3)CC2)ncc1F] | 15 |

TABLE 1-continued
Active Compounds: Structures (Compounds 1-142)
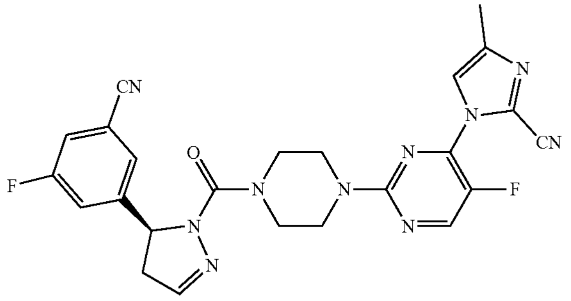 [SMILES: Cc1cn(-c2nc(N3CCN(C(=O)N4N=CC[C@H]4c4cc(F)cc(C#N)c4)CC3)ncc2F)c(C#N)n1]
16
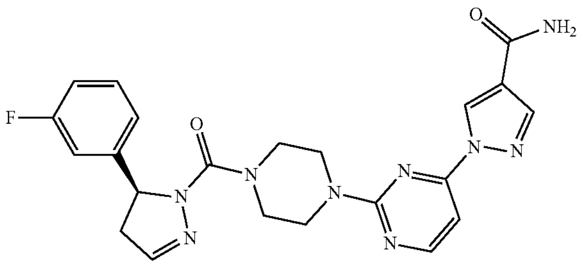 [SMILES: NC(=O)c1cnn(-c2ccnc(N3CCN(C(=O)N4N=CC[C@H]4c4cccc(F)c4)CC3)n2)c1]
17
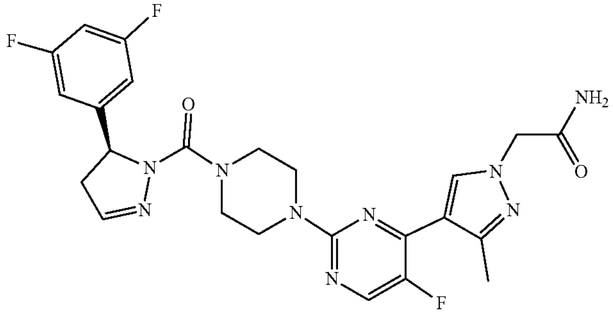 [SMILES: Cc1nn(CC(N)=O)cc1-c1nc(N2CCN(C(=O)N3N=CC[C@H]3c3cc(F)cc(F)c3)CC2)ncc1F]
18
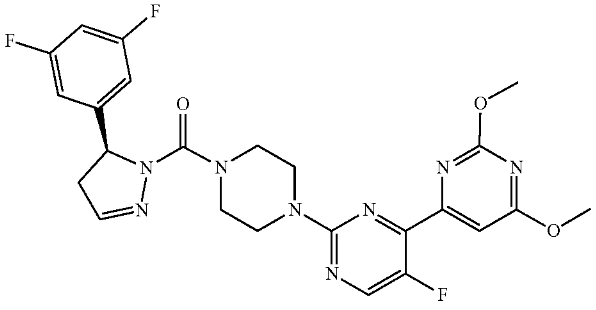 [SMILES: COc1cc(-c2nc(N3CCN(C(=O)N4N=CC[C@H]4c4cc(F)cc(F)c4)CC3)ncc2F)nc(OC)n1]
19
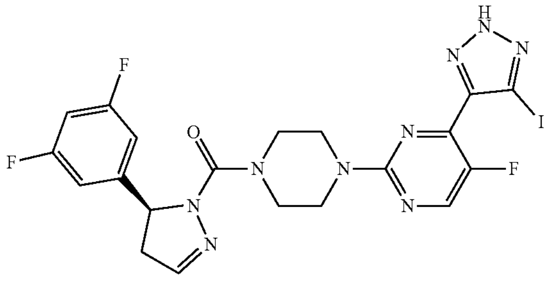 [SMILES: O=C(N1CCN(c2ncc(F)c(-c3n[nH]nc3I)n2)CC1)N1N=CC[C@H]1c1cc(F)cc(F)c1]
20

TABLE 1-continued
| Active Compounds: Structures (Compounds 1-142) |
| --- |
| 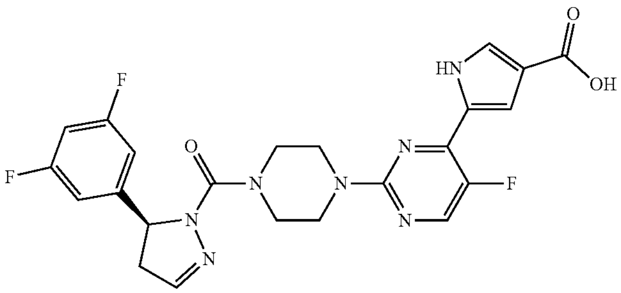 [SMILES: O=C(O)c1c[nH]c(-c2nc(N3CCN(C(=O)N4N=CC[C@H]4c4cc(F)cc(F)c4)CC3)ncc2F)c1] 21 |
| 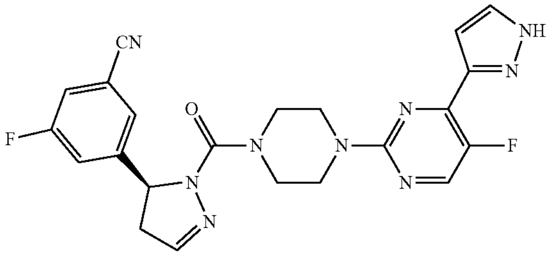 [SMILES: N#Cc1cc(F)cc([C@@H]2CC=NN2C(=O)N2CCN(c3ncc(F)c(-c4cc[nH]n4)n3)CC2)c1] 22 |
| 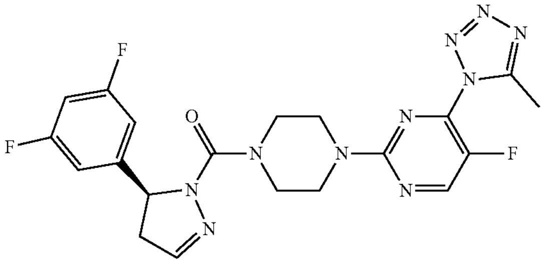 [SMILES: Cc1nnnn1-c1nc(N2CCN(C(=O)N3N=CC[C@H]3c3cc(F)cc(F)c3)CC2)ncc1F] 23 |
| 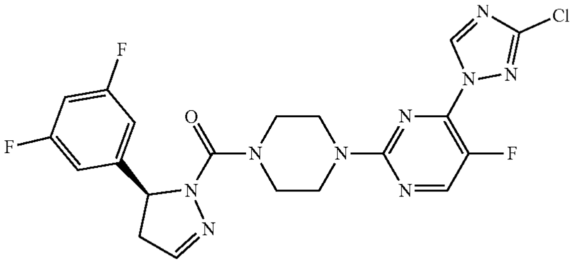 [SMILES: O=C(N1CCN(c2ncc(F)c(-n3cnc(Cl)n3)n2)CC1)N1N=CC[C@H]1c1cc(F)cc(F)c1] 24 |
| 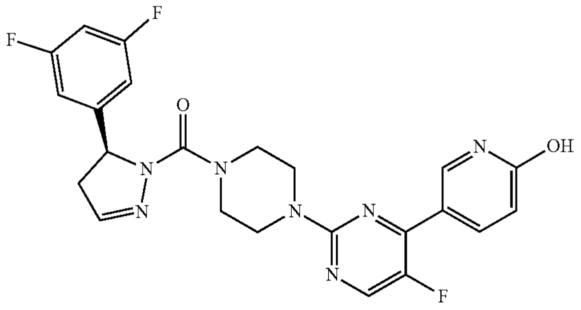 [SMILES: O=C(N1CCN(c2ncc(F)c(-c3ccc(O)nc3)n2)CC1)N1N=CC[C@H]1c1cc(F)cc(F)c1] 25 |
| 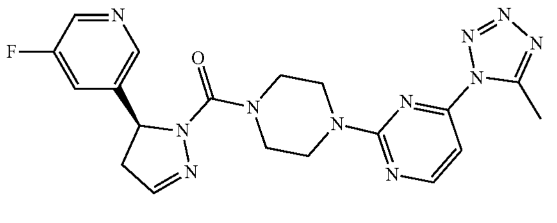 [SMILES: Cc1nnnn1-c1ccnc(N2CCN(C(=O)N3N=CC[C@H]3c3cncc(F)c3)CC2)n1] 26 |

TABLE 1-continued
| Active Compounds: Structures (Compounds 1-142) |
|---|
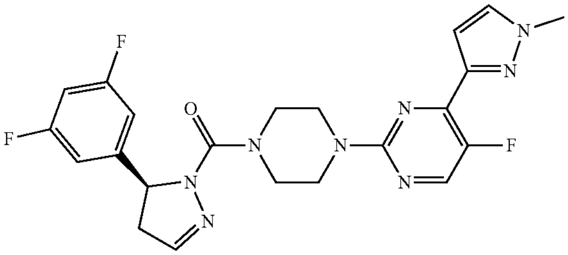 [SMILES: Cn1ccc(-c2nc(N3CCN(C(=O)N4N=CC[C@H]4c4cc(F)cc(F)c4)CC3)ncc2F)n1]
27
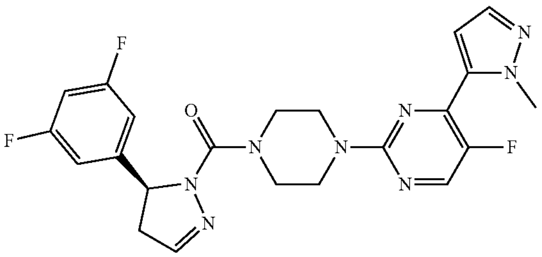 [SMILES: Cn1nccc1-c1nc(N2CCN(C(=O)N3N=CC[C@H]3c3cc(F)cc(F)c3)CC2)ncc1F]
28
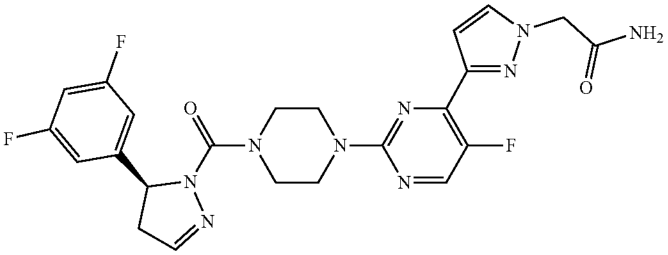 [SMILES: NC(=O)Cn1ccc(-c2nc(N3CCN(C(=O)N4N=CC[C@H]4c4cc(F)cc(F)c4)CC3)ncc2F)n1]
29
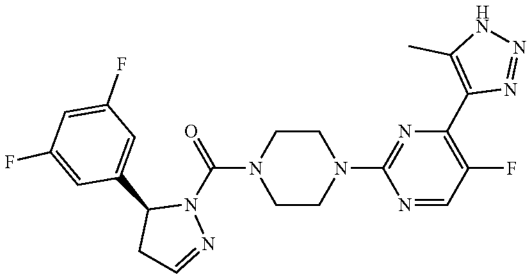 [SMILES: Cc1[nH]nnc1-c1nc(N2CCN(C(=O)N3N=CC[C@H]3c3cc(F)cc(F)c3)CC2)ncc1F]
30
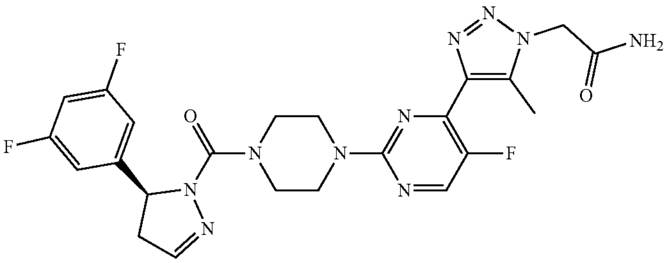 [SMILES: Cc1c(-c2nc(N3CCN(C(=O)N4N=CC[C@H]4c4cc(F)cc(F)c4)CC3)ncc2F)nnn1CC(N)=O]
31

TABLE 1-continued
| Active Compounds: Structures (Compounds 1-142) |
| --- |
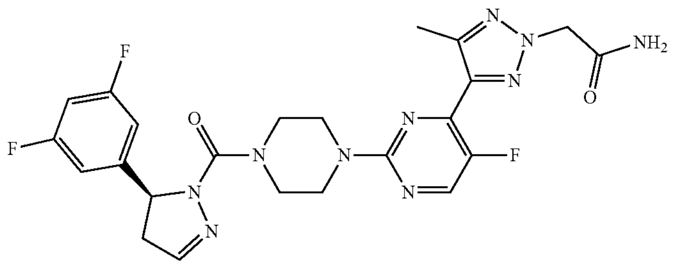 [SMILES: Cc1nn(CC(N)=O)nc1-c1nc(N2CCN(C(=O)N3N=CC[C@H]3c3cc(F)cc(F)c3)CC2)ncc1F]
32
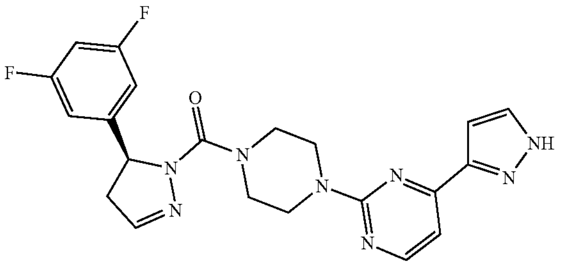 [SMILES: O=C(N1CCN(c2nccc(-c3cc[nH]n3)n2)CC1)N1N=CC[C@H]1c1cc(F)cc(F)c1]
33
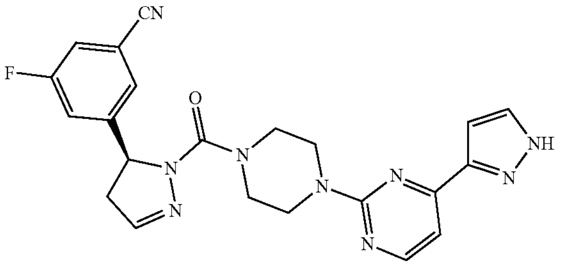 [SMILES: N#Cc1cc(F)cc([C@@H]2CC=NN2C(=O)N2CCN(c3nccc(-c4cc[nH]n4)n3)CC2)c1]
34
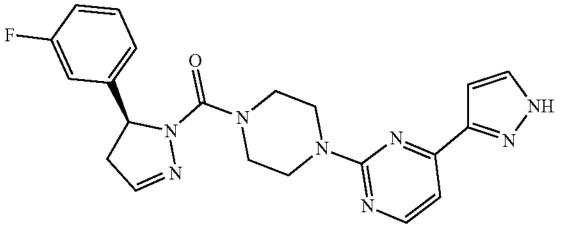 [SMILES: O=C(N1CCN(c2nccc(-c3cc[nH]n3)n2)CC1)N1N=CC[C@H]1c1cccc(F)c1]
35
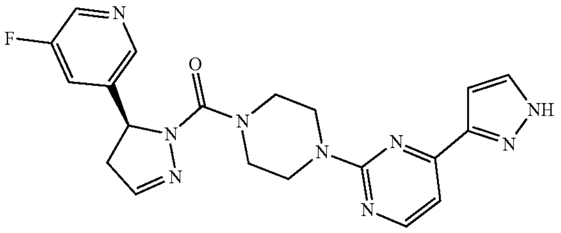 [SMILES: O=C(N1CCN(c2nccc(-c3cc[nH]n3)n2)CC1)N1N=CC[C@H]1c1cncc(F)c1]
36
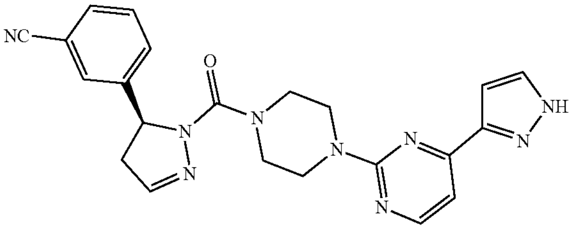 [SMILES: N#Cc1cccc([C@@H]2CC=NN2C(=O)N2CCN(c3nccc(-c4cc[nH]n4)n3)CC2)c1]
37

TABLE 1-continued
| Active Compounds: Structures (Compounds 1-142) | |
|---|---|
| 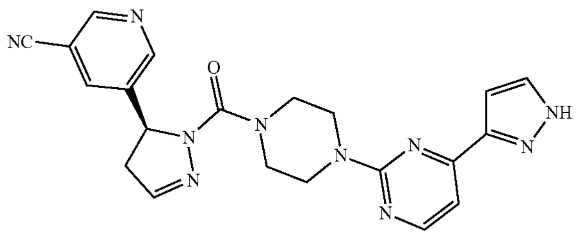 [SMILES: N#Cc1cncc([C@@H]2CC=NN2C(=O)N2CCN(c3nccc(-c4cc[nH]n4)n3)CC2)c1] | 38 |
| 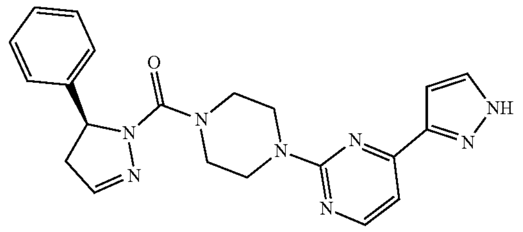 [SMILES: O=C(N1CCN(c2nccc(-c3cc[nH]n3)n2)CC1)N1N=CC[C@H]1c1ccccc1] | 39 |
| 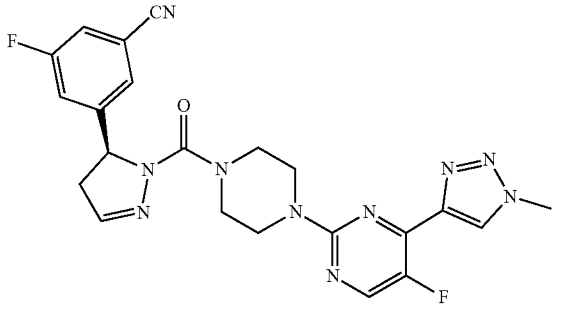 [SMILES: Cn1cc(-c2nc(N3CCN(C(=O)N4N=CC[C@H]4c4cc(F)cc(C#N)c4)CC3)ncc2F)nn1] | 40 |
| 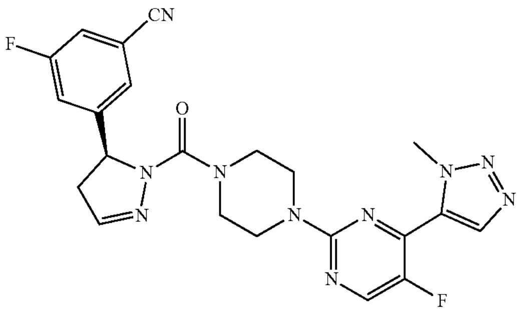 [SMILES: Cn1nncc1-c1nc(N2CCN(C(=O)N3N=CC[C@H]3c3cc(F)cc(C#N)c3)CC2)ncc1F] | 41 |
| 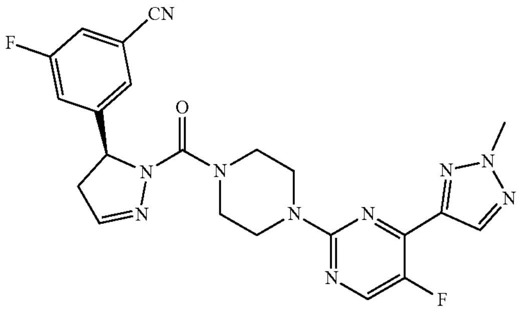 [SMILES: Cn1ncc(-c2nc(N3CCN(C(=O)N4N=CC[C@H]4c4cc(F)cc(C#N)c4)CC3)ncc2F)n1] | 42 |

TABLE 1-continued
| Active Compounds: Structures (Compounds 1-142) |
|---|
| 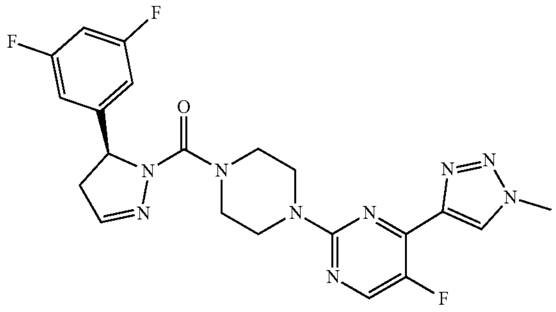 [SMILES: Cn1cc(-c2nc(N3CCN(C(=O)N4N=CC[C@H]4c4cc(F)cc(F)c4)CC3)ncc2F)nn1] 43 |
| 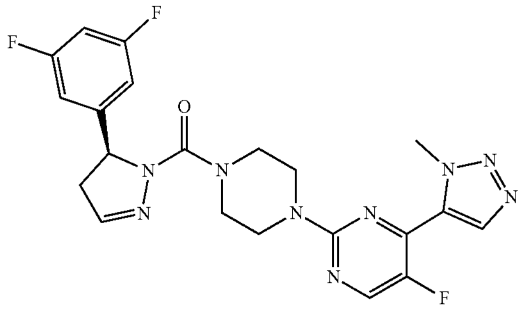 [SMILES: Cn1nncc1-c1nc(N2CCN(C(=O)N3N=CC[C@H]3c3cc(F)cc(F)c3)CC2)ncc1F] 44 |
| 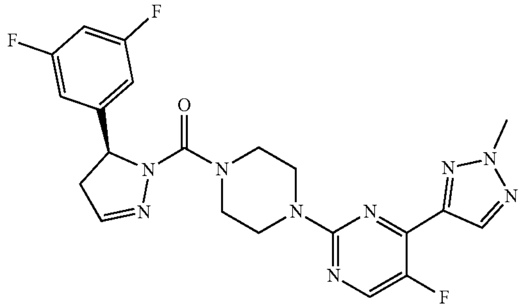 [SMILES: Cn1ncc(-c2nc(N3CCN(C(=O)N4N=CC[C@H]4c4cc(F)cc(F)c4)CC3)ncc2F)n1] 45 |
| 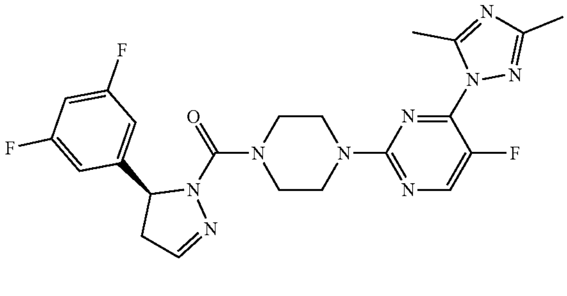 46 |
| 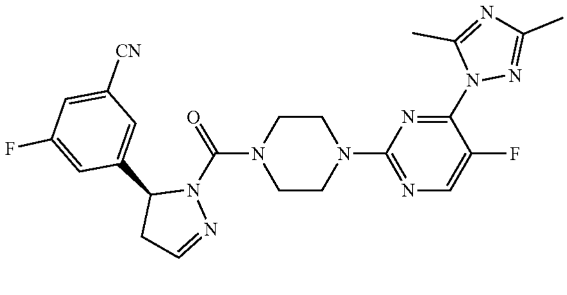 [SMILES: Cc1nc(C)n(-c2nc(N3CCN(C(=O)N4N=CC[C@H]4c4cc(F)cc(F)c4)CC3)ncc2F)n1] 47 |

TABLE 1-continued
Active Compounds: Structures (Compounds 1-142)
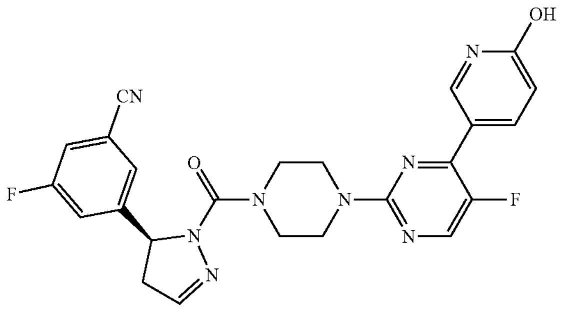 [SMILES: N#Cc1cc(F)cc([C@@H]2CC=NN2C(=O)N2CCN(c3ncc(F)c(-c4ccc(O)nc4)n3)CC2)c1]
48
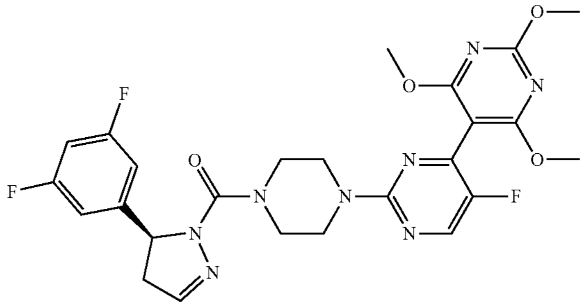 [SMILES: COc1nc(OC)c(-c2nc(N3CCN(C(=O)N4N=CC[C@H]4c4cc(F)cc(F)c4)CC3)ncc2F)c(OC)n1]
49
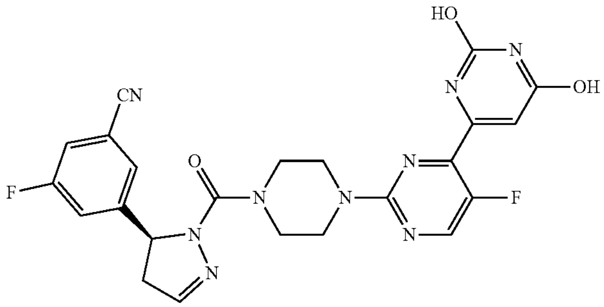 [SMILES: N#Cc1cc(F)cc([C@@H]2CC=NN2C(=O)N2CCN(c3ncc(F)c(-c4cc(O)nc(O)n4)n3)CC2)c1]
50
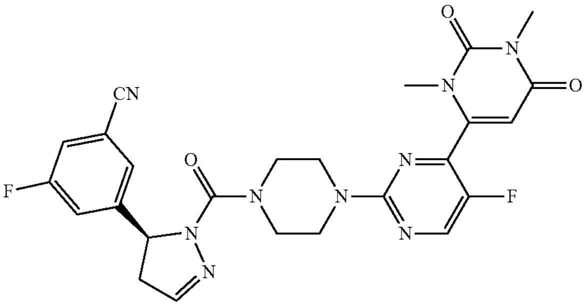 [SMILES: Cn1c(-c2nc(N3CCN(C(=O)N4N=CC[C@H]4c4cc(F)cc(C#N)c4)CC3)ncc2F)cc(=O)n(C)c1=O]
51
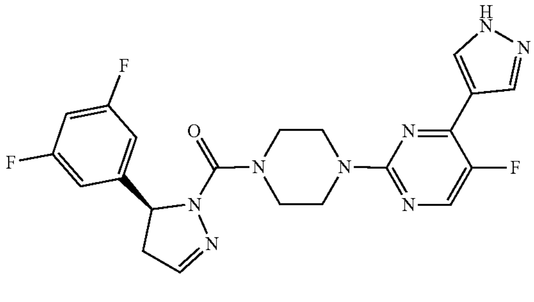 [SMILES: O=C(N1CCN(c2ncc(F)c(-c3cn[nH]c3)n2)CC1)N1N=CC[C@H]1c1cc(F)cc(F)c1]
52

TABLE 1-continued
| Active Compounds: Structures (Compounds 1-142) |
| --- |
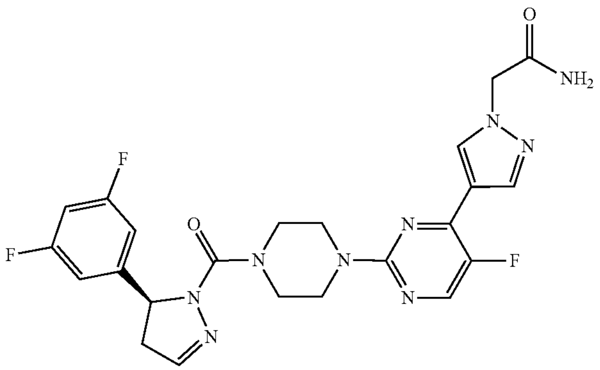 [SMILES: NC(=O)Cn1cc(-c2nc(N3CCN(C(=O)N4N=CC[C@H]4c4cc(F)cc(F)c4)CC3)ncc2F)cn1]
53
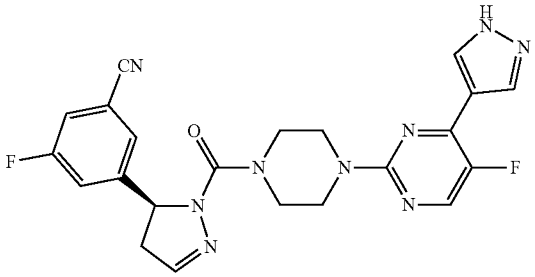 [SMILES: N#Cc1cc(F)cc([C@@H]2CC=NN2C(=O)N2CCN(c3ncc(F)c(-c4cn[nH]c4)n3)CC2)c1]
54
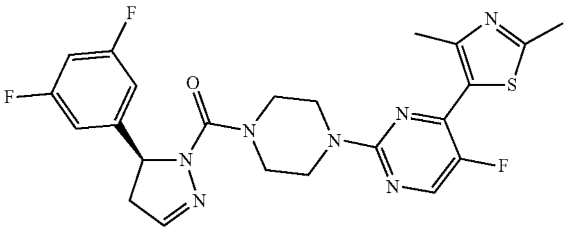 [SMILES: Cc1nc(C)c(-c2nc(N3CCN(C(=O)N4N=CC[C@H]4c4cc(F)cc(F)c4)CC3)ncc2F)s1]
55
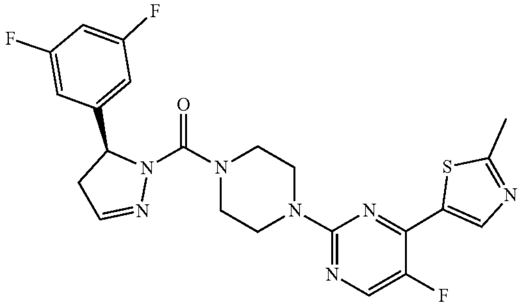 [SMILES: Cc1ncc(-c2nc(N3CCN(C(=O)N4N=CC[C@H]4c4cc(F)cc(F)c4)CC3)ncc2F)s1]
56
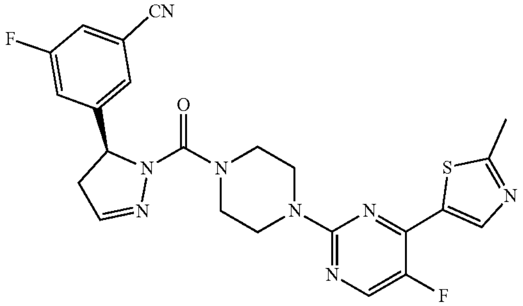 [SMILES: Cc1ncc(-c2nc(N3CCN(C(=O)N4N=CC[C@H]4c4cc(F)cc(C#N)c4)CC3)ncc2F)s1]
57

TABLE 1-continued
| Active Compounds: Structures (Compounds 1-142) | |
|---|---|
| 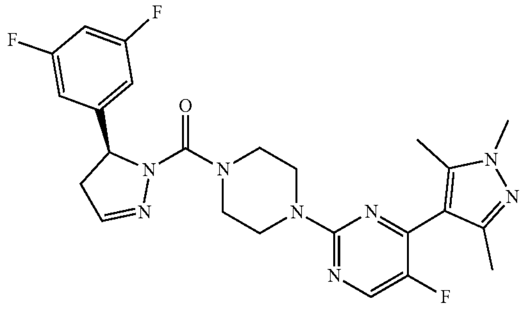 [SMILES: Cc1nn(C)c(C)c1-c1nc(N2CCN(C(=O)N3N=CC[C@H]3c3cc(F)cc(F)c3)CC2)ncc1F] | 58 |
| 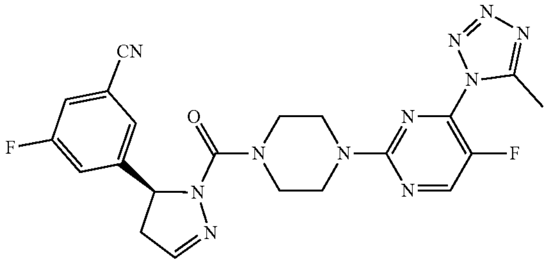 [SMILES: Cc1nnnn1-c1nc(N2CCN(C(=O)N3N=CC[C@H]3c3cc(F)cc(C#N)c3)CC2)ncc1F] | 59 |
| 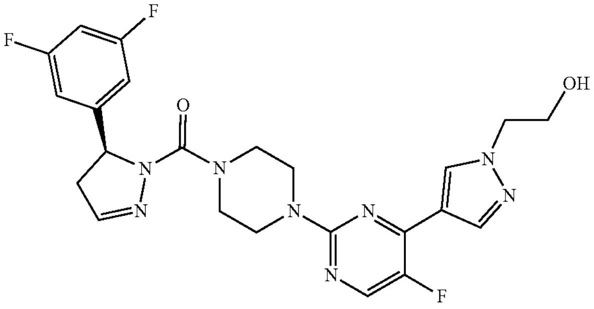 [SMILES: O=C(N1CCN(c2ncc(F)c(-c3cnn(CCO)c3)n2)CC1)N1N=CC[C@H]1c1cc(F)cc(F)c1] | 60 |
| 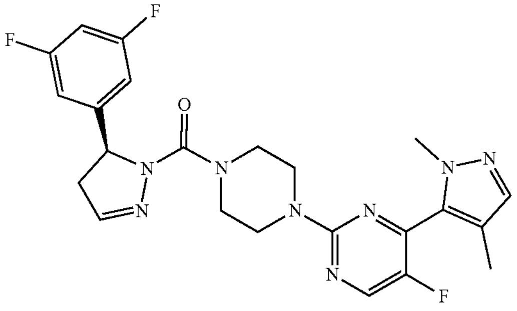 | 61 |
| 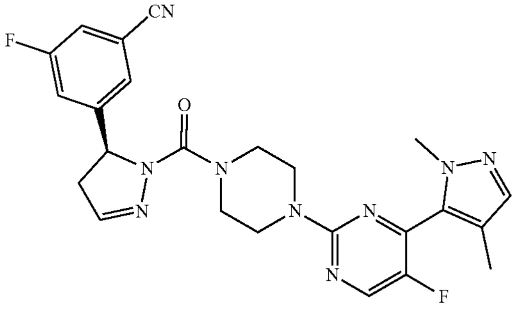 [SMILES: Cc1cnn(C)c1-c1nc(N2CCN(C(=O)N3N=CC[C@H]3c3cc(F)cc(C#N)c3)CC2)ncc1F] | 62 |

TABLE 1-continued
| Active Compounds: Structures (Compounds 1-142) |
| --- |
| 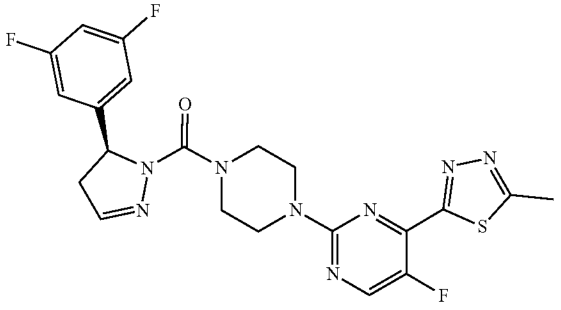 [SMILES: Cc1nnc(-c2nc(N3CCN(C(=O)N4N=CC[C@H]4c4cc(F)cc(F)c4)CC3)ncc2F)s1] 63 |
| 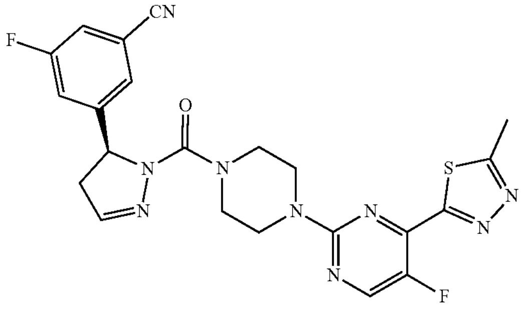 [SMILES: Cc1nnc(-c2nc(N3CCN(C(=O)N4N=CC[C@H]4c4cc(F)cc(C#N)c4)CC3)ncc2F)s1] 64 |
| 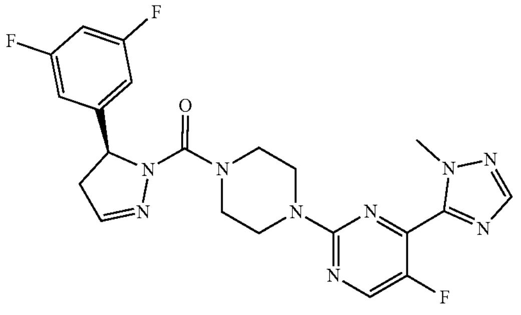 [SMILES: Cn1ncnc1-c1nc(N2CCN(C(=O)N3N=CC[C@H]3c3cc(F)cc(F)c3)CC2)ncc1F] 65 |
| 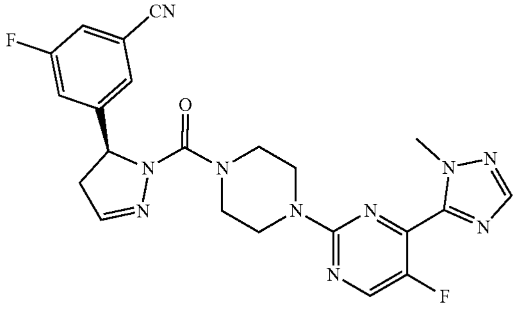 66 |
| 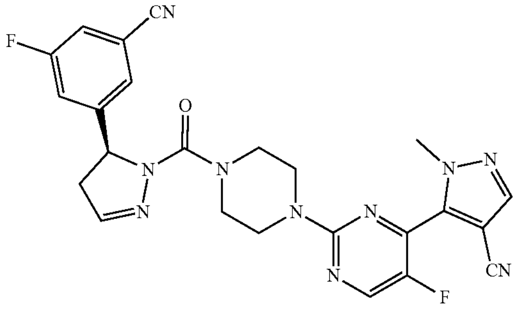 [SMILES: Cn1ncc(C#N)c1-c1nc(N2CCN(C(=O)N3N=CC[C@H]3c3cc(F)cc(C#N)c3)CC2)ncc1F] 67 |

TABLE 1-continued
| Active Compounds: Structures (Compounds 1-142) |
| --- |
| 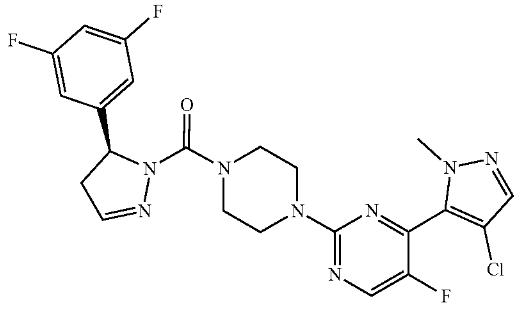 [SMILES: Cn1ncc(Cl)c1-c1nc(N2CCN(C(=O)N3N=CC[C@H]3c3cc(F)cc(F)c3)CC2)ncc1F] 68 |
| 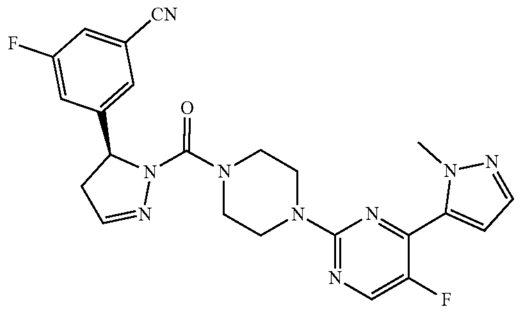 [SMILES: Cn1nccc1-c1nc(N2CCN(C(=O)N3N=CC[C@H]3c3cc(F)cc(C#N)c3)CC2)ncc1F] 69 |
| 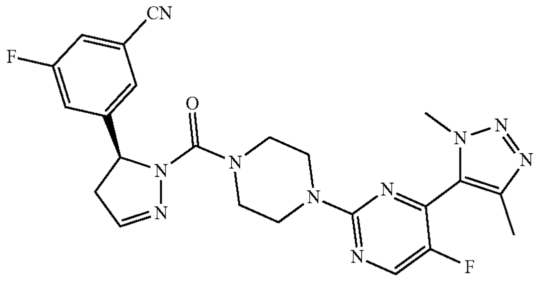 [SMILES: Cc1nnn(C)c1-c1nc(N2CCN(C(=O)N3N=CC[C@H]3c3cc(F)cc(C#N)c3)CC2)ncc1F] 70 |
| 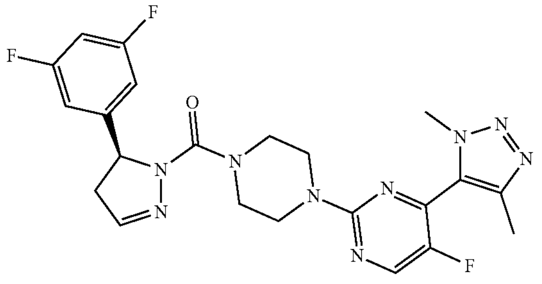 [SMILES: Cc1nnn(C)c1-c1nc(N2CCN(C(=O)N3N=CC[C@H]3c3cc(F)cc(F)c3)CC2)ncc1F] 71 |
| 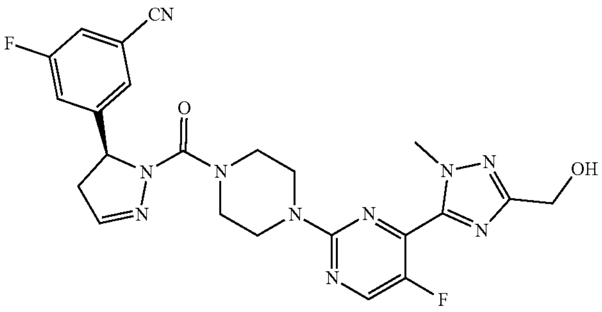 [SMILES: Cn1nc(CO)nc1-c1nc(N2CCN(C(=O)N3N=CC[C@H]3c3cc(F)cc(C#N)c3)CC2)ncc1F] 72 |

TABLE 1-continued
| Active Compounds: Structures (Compounds 1-142) | |
|---|---|
| 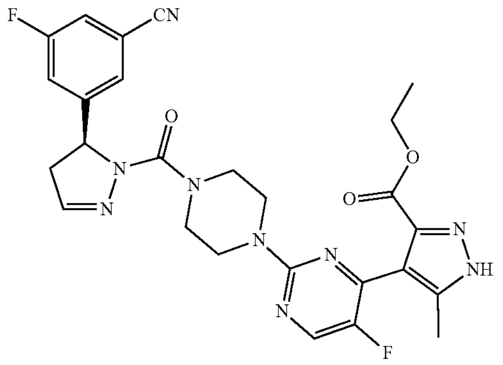 [SMILES: CCOC(=O)c1n[nH]c(C)c1-c1nc(N2CCN(C(=O)N3N=CC[C@H]3c3cc(F)cc(C#N)c3)CC2)ncc1F] | 73 |
| 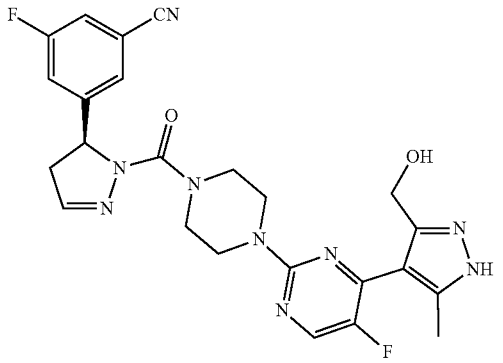 [SMILES: Cc1[nH]nc(CO)c1-c1nc(N2CCN(C(=O)N3N=CC[C@H]3c3cc(F)cc(C#N)c3)CC2)ncc1F] | 74 |
| 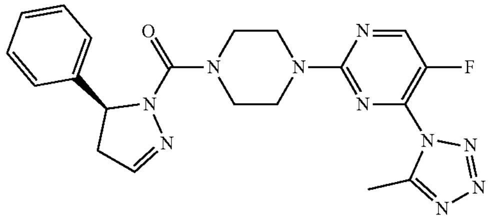 [SMILES: Cc1nnnn1-c1nc(N2CCN(C(=O)N3N=CC[C@H]3c3ccccc3)CC2)ncc1F] | 75 |
| 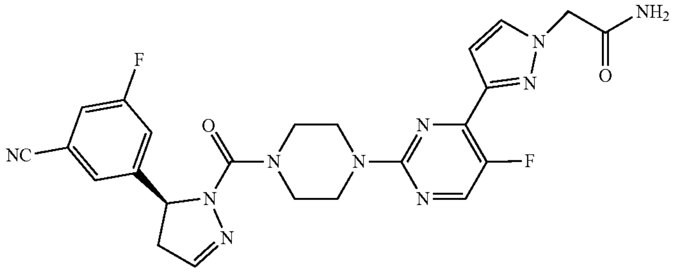 [SMILES: N#Cc1cc(F)cc([C@@H]2CC=NN2C(=O)N2CCN(c3ncc(F)c(-c4ccn(CC(N)=O)n4)n3)CC2)c1] | 76 |
| 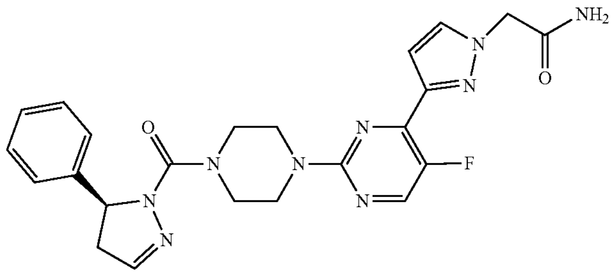 [SMILES: NC(=O)Cn1ccc(-c2nc(N3CCN(C(=O)N4N=CC[C@H]4c4ccccc4)CC3)ncc2F)n1] | 77 |

TABLE 1-continued
| Active Compounds: Structures (Compounds 1-142) | |
|---|---|
| 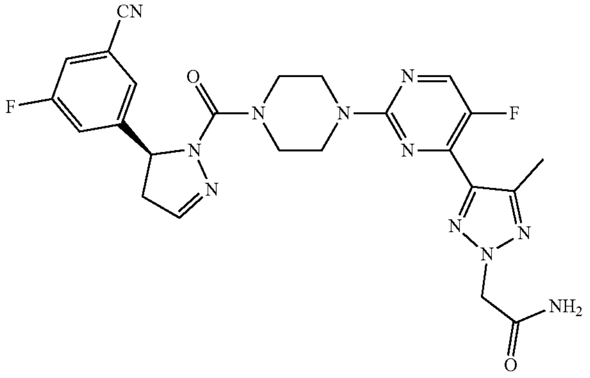 [SMILES: Cc1nn(CC(N)=O)nc1-c1nc(N2CCN(C(=O)N3N=CC[C@H]3c3cc(F)cc(C#N)c3)CC2)ncc1F] | 78 |
| 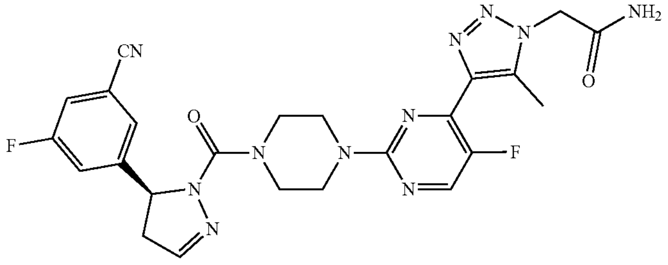 [SMILES: Cc1c(-c2nc(N3CCN(C(=O)N4N=CC[C@H]4c4cc(F)cc(C#N)c4)CC3)ncc2F)nnn1CC(N)=O] | 79 |
| 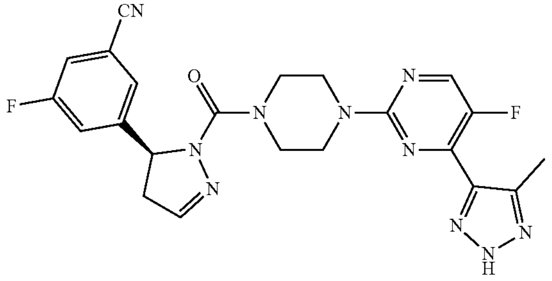 [SMILES: Cc1n[nH]nc1-c1nc(N2CCN(C(=O)N3N=CC[C@H]3c3cc(F)cc(C#N)c3)CC2)ncc1F] | 80 |
| 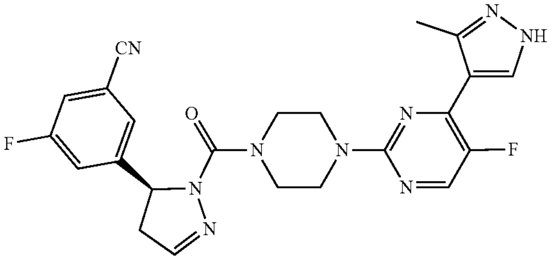 [SMILES: Cc1n[nH]cc1-c1nc(N2CCN(C(=O)N3N=CC[C@H]3c3cc(F)cc(C#N)c3)CC2)ncc1F] | 81 |
| 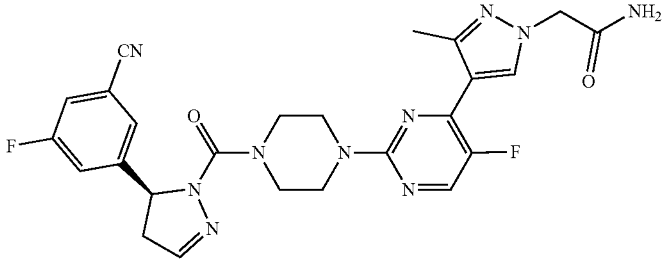 [SMILES: Cc1nn(CC(N)=O)cc1-c1nc(N2CCN(C(=O)N3N=CC[C@H]3c3cc(F)cc(C#N)c3)CC2)ncc1F] | 82 |

TABLE 1-continued
Active Compounds: Structures (Compounds 1-142)
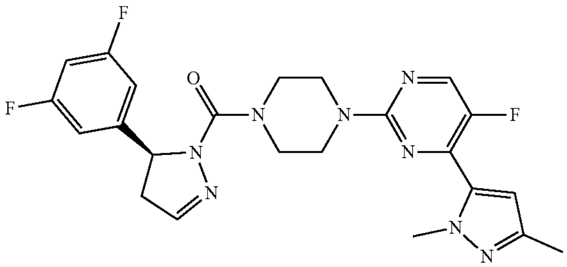 [SMILES: Cc1cc(-c2nc(N3CCN(C(=O)N4N=CC[C@H]4c4cc(F)cc(F)c4)CC3)ncc2F)n(C)n1]
83
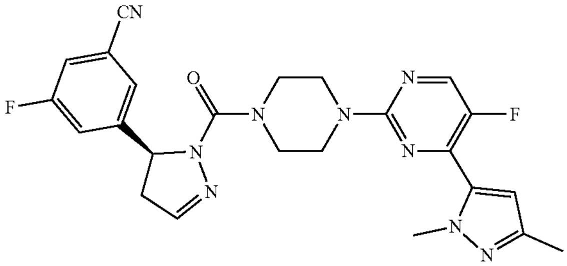 [SMILES: Cc1cc(-c2nc(N3CCN(C(=O)N4N=CC[C@H]4c4cc(F)cc(C#N)c4)CC3)ncc2F)n(C)n1]
84
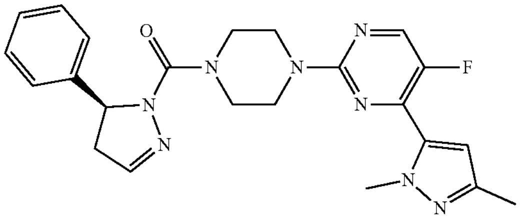 [SMILES: Cc1cc(-c2nc(N3CCN(C(=O)N4N=CC[C@H]4c4ccccc4)CC3)ncc2F)n(C)n1]
85
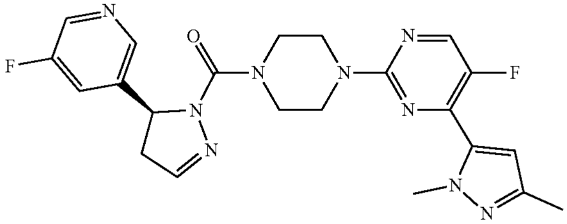 [SMILES: Cc1cc(-c2nc(N3CCN(C(=O)N4N=CC[C@H]4c4cncc(F)c4)CC3)ncc2F)n(C)n1]
86
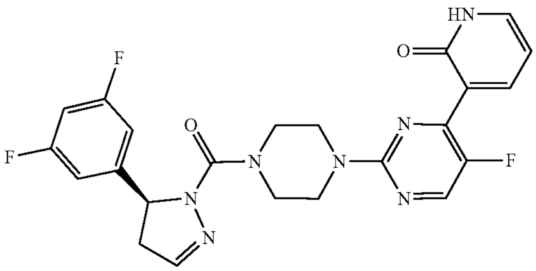 [SMILES: O=C(N1CCN(c2ncc(F)c(-c3ccc[nH]c3=O)n2)CC1)N1N=CC[C@H]1c1cc(F)cc(F)c1]
87
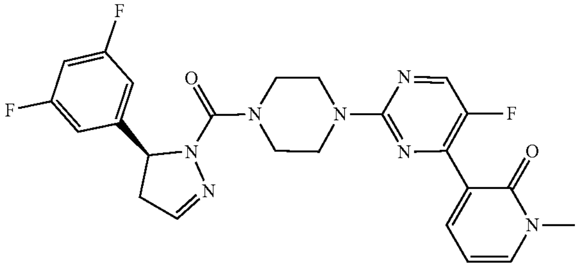 [SMILES: Cn1cccc(-c2nc(N3CCN(C(=O)N4N=CC[C@H]4c4cc(F)cc(F)c4)CC3)ncc2F)c1=O]
88

TABLE 1-continued
Active Compounds: Structures (Compounds 1-142)
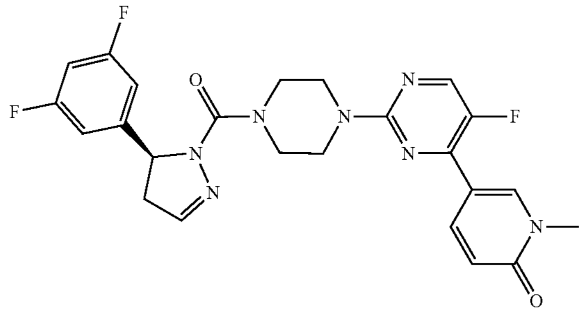 [SMILES: Cn1cc(-c2nc(N3CCN(C(=O)N4N=CC[C@H]4c4cc(F)cc(F)c4)CC3)ncc2F)ccc1=O]
89
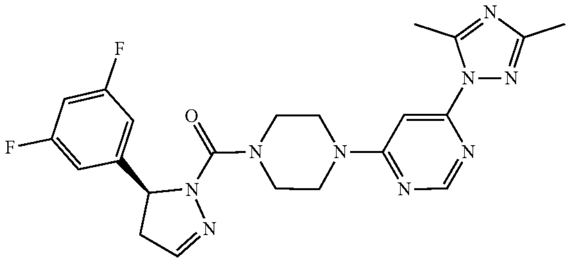 [SMILES: Cc1nc(C)n(-c2cc(N3CCN(C(=O)N4N=CC[C@H]4c4cc(F)cc(F)c4)CC3)ncn2)n1]
90
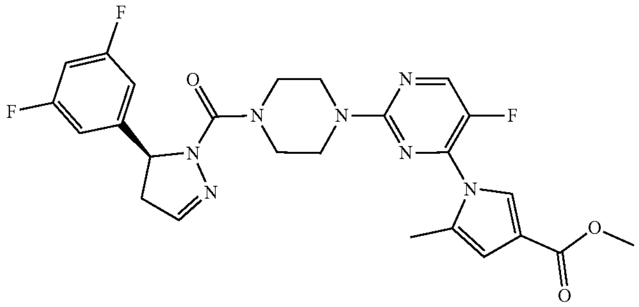 [SMILES: COC(=O)c1cc(C)n(-c2nc(N3CCN(C(=O)N4N=CC[C@H]4c4cc(F)cc(F)c4)CC3)ncc2F)c1]
91
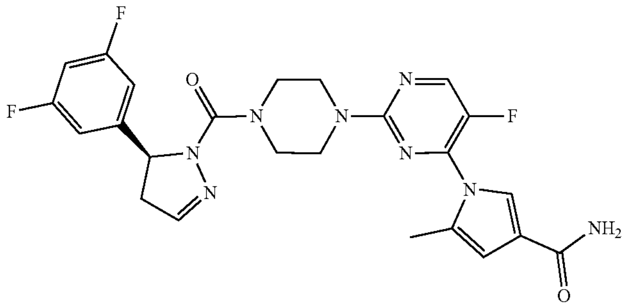 [SMILES: Cc1cc(C(N)=O)cn1-c1nc(N2CCN(C(=O)N3N=CC[C@H]3c3cc(F)cc(F)c3)CC2)ncc1F]
92
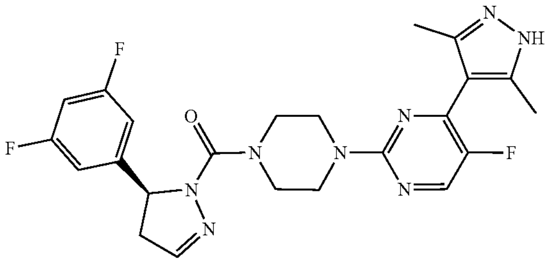 [SMILES: Cc1n[nH]c(C)c1-c1nc(N2CCN(C(=O)N3N=CC[C@H]3c3cc(F)cc(F)c3)CC2)ncc1F]
93

TABLE 1-continued
| Active Compounds: Structures (Compounds 1-142) |
| --- |
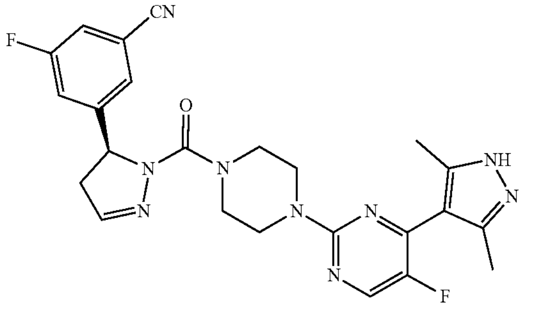 [SMILES: Cc1n[nH]c(C)c1-c1nc(N2CCN(C(=O)N3N=CC[C@H]3c3cc(F)cc(C#N)c3)CC2)ncc1F]
94
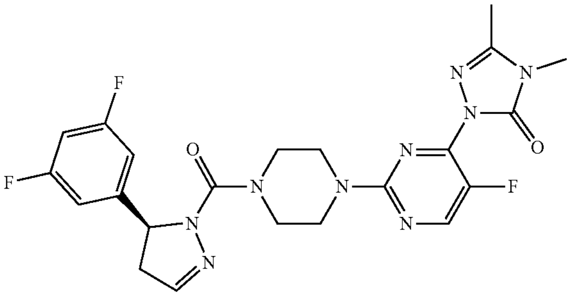 [SMILES: Cc1nn(-c2nc(N3CCN(C(=O)N4N=CC[C@H]4c4cc(F)cc(F)c4)CC3)ncc2F)c(=O)n1C]
95
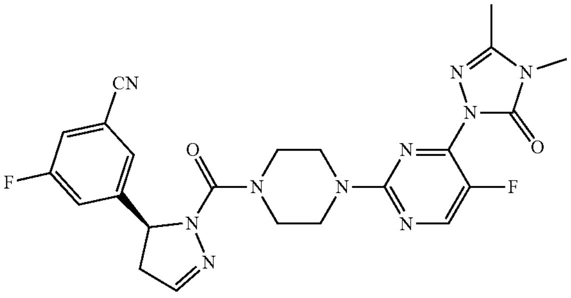 [SMILES: Cc1nn(-c2nc(N3CCN(C(=O)N4N=CC[C@H]4c4cc(F)cc(C#N)c4)CC3)ncc2F)c(=O)n1C]
96
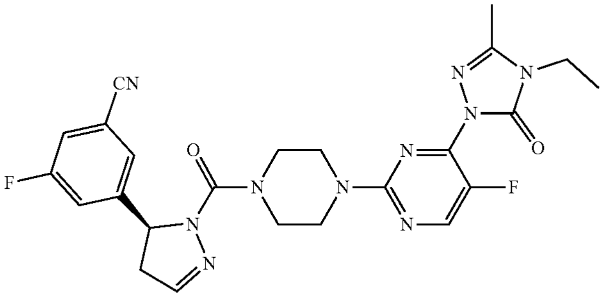 [SMILES: CCn1c(C)nn(-c2nc(N3CCN(C(=O)N4N=CC[C@H]4c4cc(F)cc(C#N)c4)CC3)ncc2F)c1=O]
97
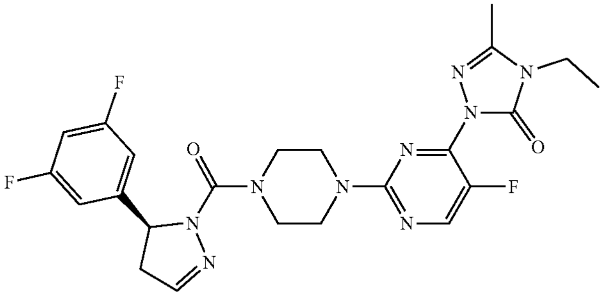 [SMILES: CCn1c(C)nn(-c2nc(N3CCN(C(=O)N4N=CC[C@H]4c4cc(F)cc(F)c4)CC3)ncc2F)c1=O]
98

TABLE 1-continued
Active Compounds: Structures (Compounds 1-142)
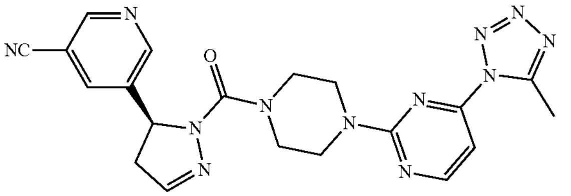 [SMILES: Cc1nnnn1-c1ccnc(N2CCN(C(=O)N3N=CC[C@H]3c3cncc(C#N)c3)CC2)n1]
99
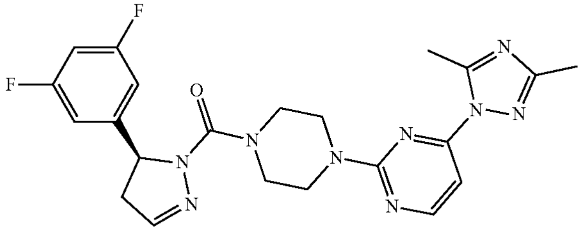 [SMILES: Cc1nc(C)n(-c2ccnc(N3CCN(C(=O)N4N=CC[C@H]4c4cc(F)cc(F)c4)CC3)n2)n1]
100
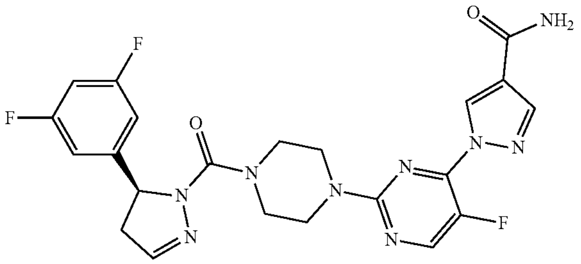 [SMILES: NC(=O)c1cnn(-c2nc(N3CCN(C(=O)N4N=CC[C@H]4c4cc(F)cc(F)c4)CC3)ncc2F)c1]
101
102
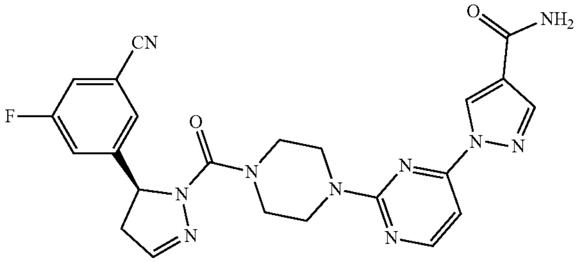 [SMILES: N#Cc1cc(F)cc([C@@H]2CC=NN2C(=O)N2CCN(c3nccc(-n4cc(C(N)=O)cn4)n3)CC2)c1]
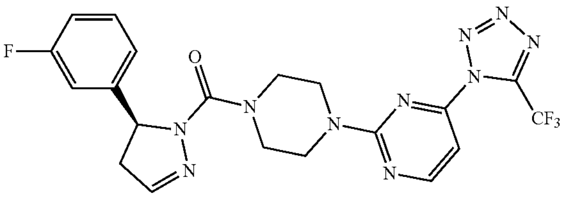 [SMILES: O=C(N1CCN(c2nccc(-n3nnnc3C(F)(F)F)n2)CC1)N1N=CC[C@H]1c1cccc(F)c1]
103
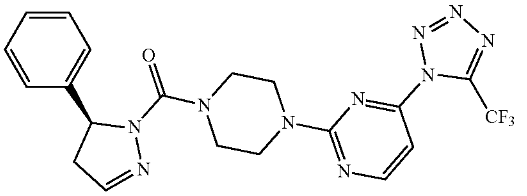 [SMILES: O=C(N1CCN(c2nccc(-n3nnnc3C(F)(F)F)n2)CC1)N1N=CC[C@H]1c1ccccc1]
104

TABLE 1-continued
Active Compounds: Structures (Compounds 1-142)
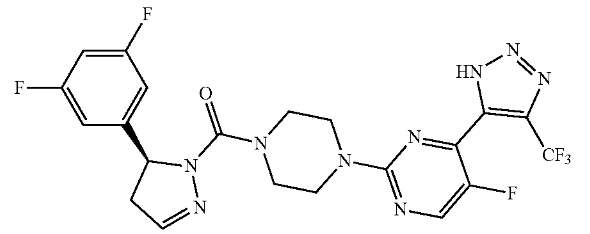 [SMILES: O=C(N1CCN(c2ncc(F)c(-c3[nH]nnc3C(F)(F)F)n2)CC1)N1N=CC[C@H]1c1cc(F)cc(F)c1]
105
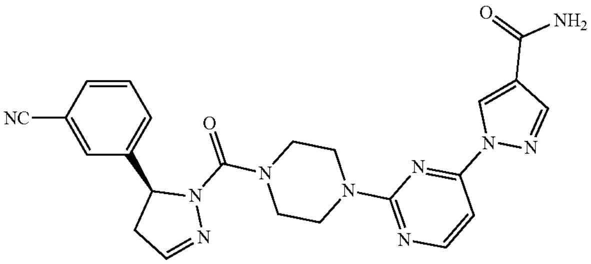 [SMILES: N#Cc1cccc([C@@H]2CC=NN2C(=O)N2CCN(c3nccc(-n4cc(C(N)=O)cn4)n3)CC2)c1]
106
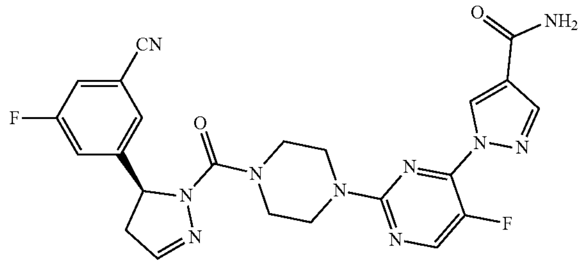 [SMILES: N#Cc1cc(F)cc([C@@H]2CC=NN2C(=O)N2CCN(c3ncc(F)c(-n4cc(C(N)=O)cn4)n3)CC2)c1]
107
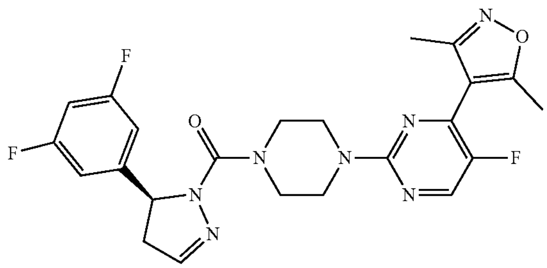 [SMILES: Cc1noc(C)c1-c1nc(N2CCN(C(=O)N3N=CC[C@H]3c3cc(F)cc(F)c3)CC2)ncc1F]
108
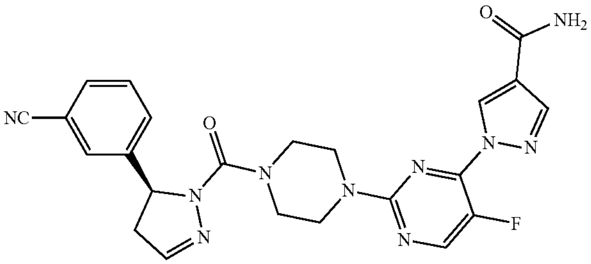 [SMILES: N#Cc1cccc([C@@H]2CC=NN2C(=O)N2CCN(c3ncc(F)c(-n4cc(C(N)=O)cn4)n3)CC2)c1]
109
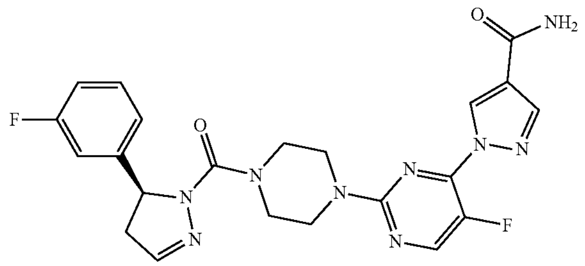 [SMILES: NC(=O)c1cnn(-c2nc(N3CCN(C(=O)N4N=CC[C@H]4c4cccc(F)c4)CC3)ncc2F)c1]
110

TABLE 1-continued
Active Compounds: Structures (Compounds 1-142)
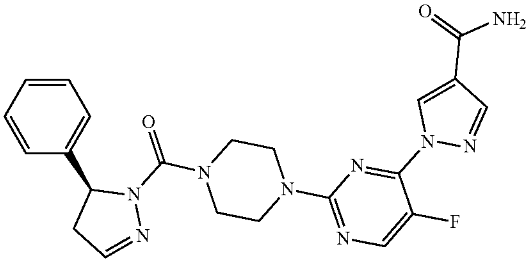 [SMILES: NC(=O)c1cnn(-c2nc(N3CCN(C(=O)N4N=CC[C@H]4c4ccccc4)CC3)ncc2F)c1]
111
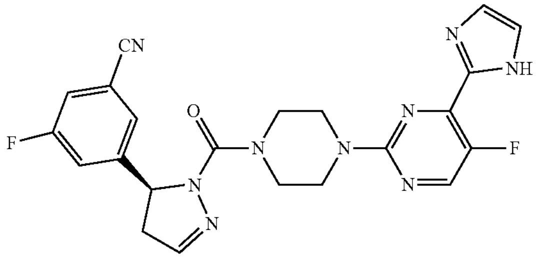 [SMILES: N#Cc1cc(F)cc([C@@H]2CC=NN2C(=O)N2CCN(c3ncc(F)c(-c4ncc[nH]4)n3)CC2)c1]
112
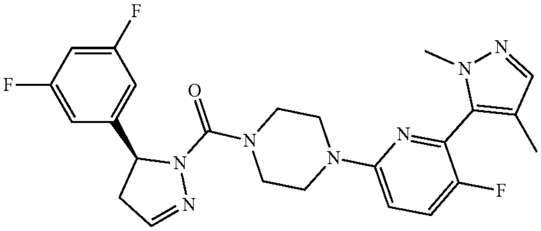 [SMILES: Cc1cnn(C)c1-c1nc(N2CCN(C(=O)N3N=CC[C@H]3c3cc(F)cc(F)c3)CC2)ccc1F]
113
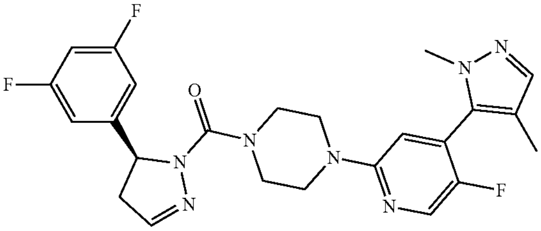 [SMILES: Cc1cnn(C)c1-c1cc(N2CCN(C(=O)N3N=CC[C@H]3c3cc(F)cc(F)c3)CC2)ncc1F]
114
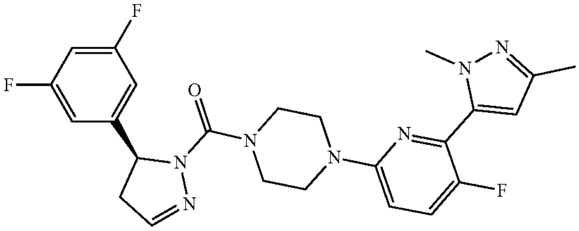 [SMILES: Cc1cc(-c2nc(N3CCN(C(=O)N4N=CC[C@H]4c4cc(F)cc(F)c4)CC3)ccc2F)n(C)n1]
115
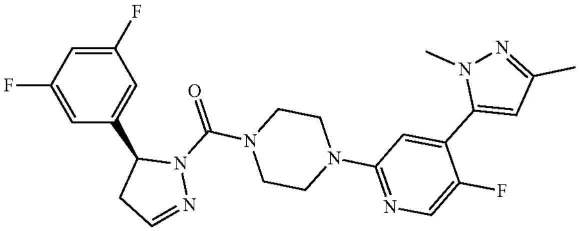 [SMILES: Cc1cc(-c2cc(N3CCN(C(=O)N4N=CC[C@H]4c4cc(F)cc(F)c4)CC3)ncc2F)n(C)n1]
116

TABLE 1-continued
| Active Compounds: Structures (Compounds 1-142) |
| --- |
| 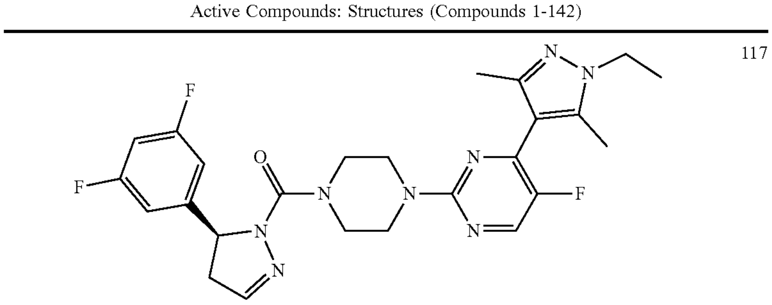 117 |
| 118 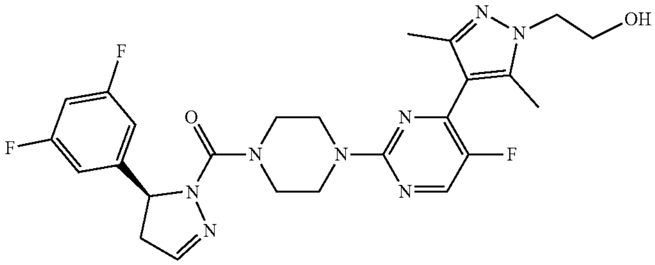 [SMILES: Cc1nn(CCO)c(C)c1-c1nc(N2CCN(C(=O)N3N=CC[C@H]3c3cc(F)cc(F)c3)CC2)ncc1F] |
| 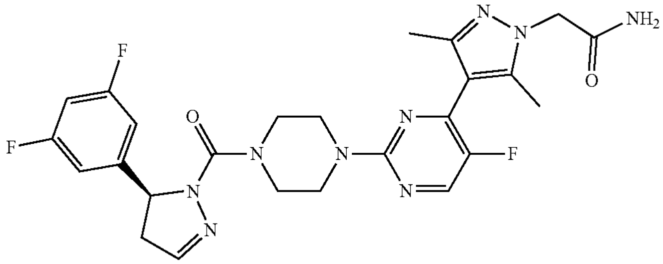 [SMILES: Cc1nn(CC(N)=O)c(C)c1-c1nc(N2CCN(C(=O)N3N=CC[C@H]3c3cc(F)cc(F)c3)CC2)ncc1F] 119 |
| 120 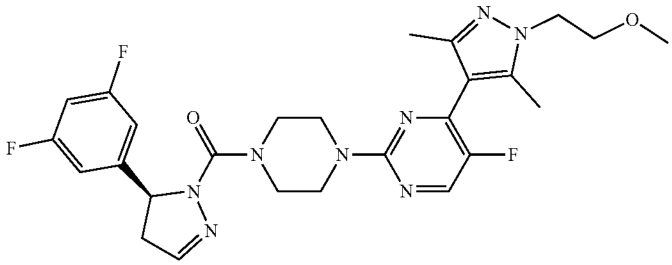 [SMILES: COCCn1nc(C)c(-c2nc(N3CCN(C(=O)N4N=CC[C@H]4c4cc(F)cc(F)c4)CC3)ncc2F)c1C] |
| 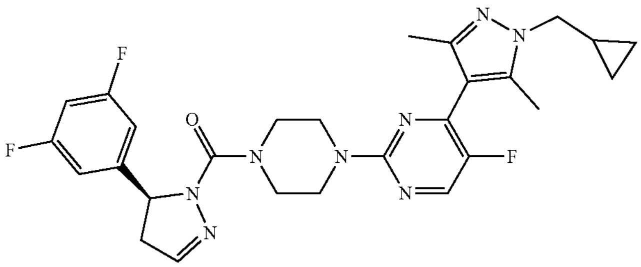 [SMILES: Cc1nn(CC2CC2)c(C)c1-c1nc(N2CCN(C(=O)N3N=CC[C@H]3c3cc(F)cc(F)c3)CC2)ncc1F] 121 |

TABLE 1-continued
Active Compounds: Structures (Compounds 1-142)
122
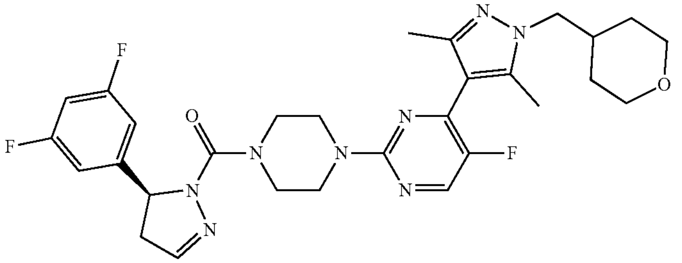 [SMILES: Cc1nn(CC2CCOCC2)c(C)c1-c1nc(N2CCN(C(=O)N3N=CC[C@H]3c3cc(F)cc(F)c3)CC2)ncc1F]
123
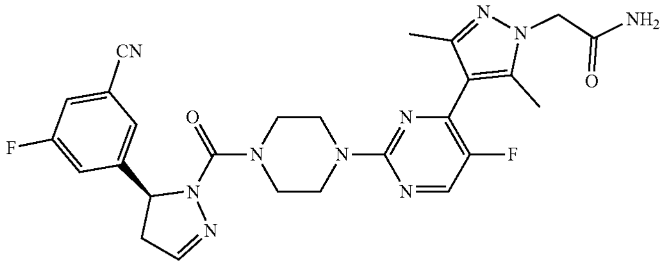 [SMILES: Cc1nn(CC(N)=O)c(C)c1-c1nc(N2CCN(C(=O)N3N=CC[C@H]3c3cc(F)cc(C#N)c3)CC2)ncc1F]
124
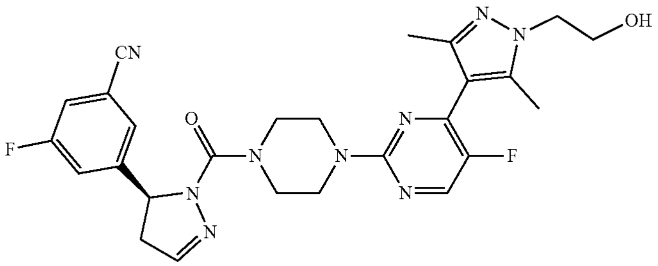 [SMILES: Cc1nn(CCO)c(C)c1-c1nc(N2CCN(C(=O)N3N=CC[C@H]3c3cc(F)cc(C#N)c3)CC2)ncc1F]
125
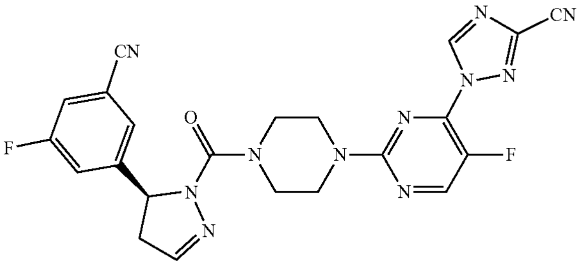 [SMILES: N#Cc1cc(F)cc([C@@H]2CC=NN2C(=O)N2CCN(c3ncc(F)c(-n4cnc(C#N)n4)n3)CC2)c1]
126
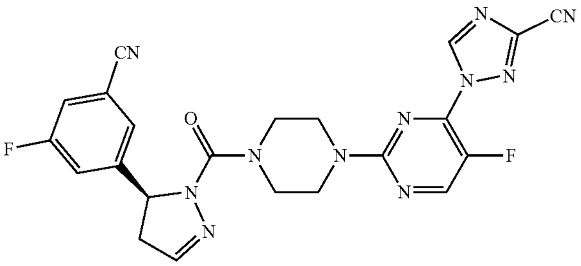 [SMILES: N#Cc1cc(F)cc([C@@H]2CC=NN2C(=O)N2CCN(c3ncc(F)c(-n4cnc(C#N)n4)n3)CC2)c1]

TABLE 1-continued
| Active Compounds: Structures (Compounds 1-142) | |
|---|---|
| 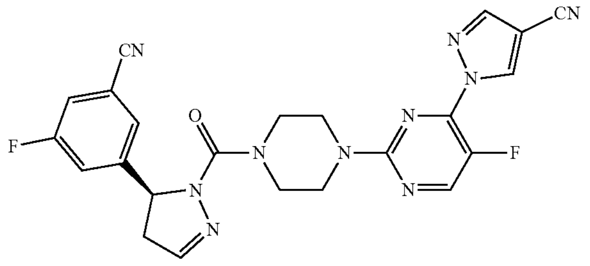 [SMILES: N#Cc1cc(F)cc([C@@H]2CC=NN2C(=O)N2CCN(c3ncc(F)c(-n4cc(C#N)cn4)n3)CC2)c1] | 127 |
| 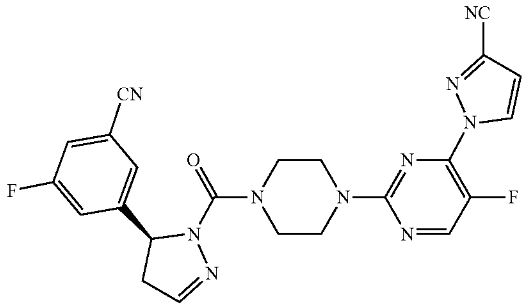 [SMILES: N#Cc1cc(F)cc([C@@H]2CC=NN2C(=O)N2CCN(c3ncc(F)c(-n4ccc(C#N)n4)n3)CC2)c1] | 128 |
| 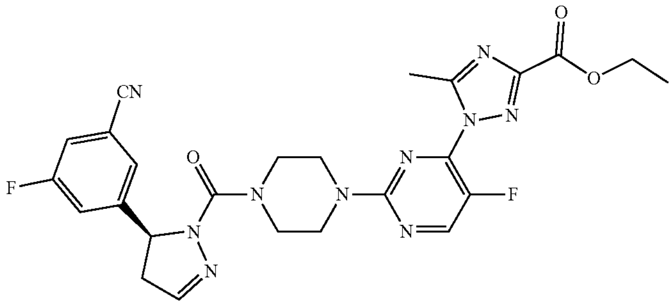 [SMILES: CCOC(=O)c1nc(C)n(-c2nc(N3CCN(C(=O)N4N=CC[C@H]4c4cc(F)cc(C#N)c4)CC3)ncc2F)n1] | 129 |
| 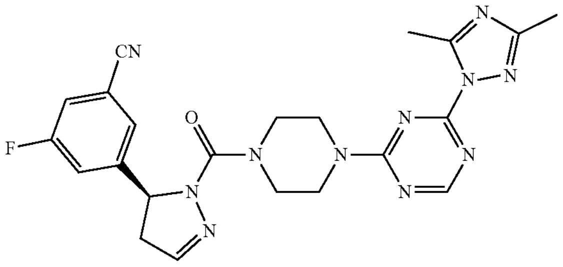 [SMILES: Cc1nc(C)n(-c2ncnc(N3CCN(C(=O)N4N=CC[C@H]4c4cc(F)cc(C#N)c4)CC3)n2)n1] | 130 |
| 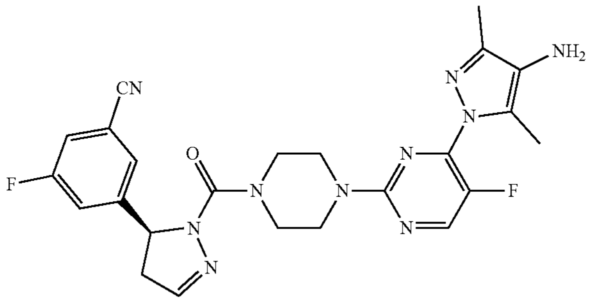 [SMILES: Cc1nn(-c2nc(N3CCN(C(=O)N4N=CC[C@H]4c4cc(F)cc(C#N)c4)CC3)ncc2F)c(C)c1N] | 131 |

TABLE 1-continued
Active Compounds: Structures (Compounds 1-142)
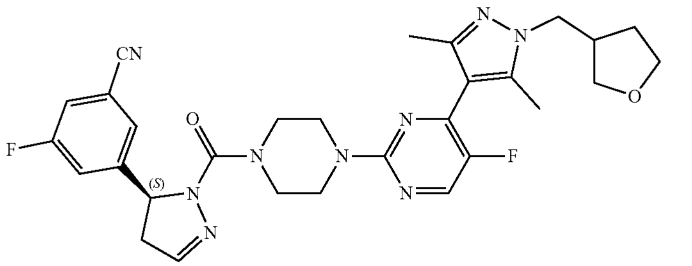
132
133
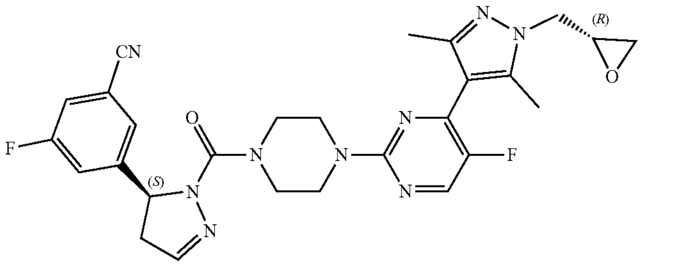
134
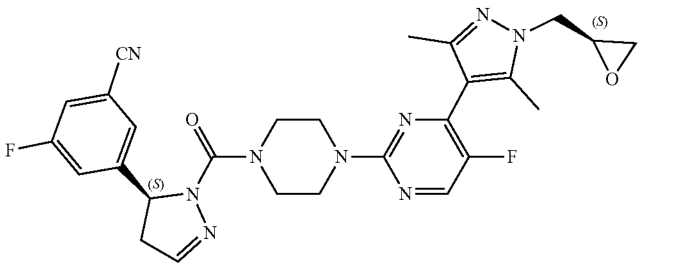
135
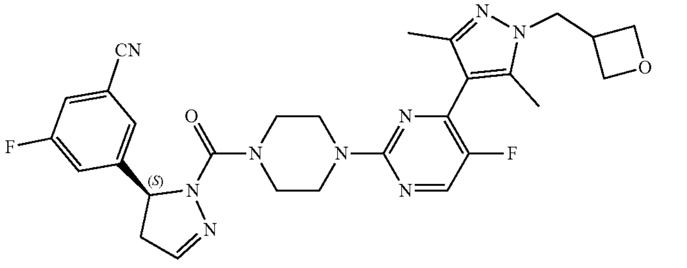
136
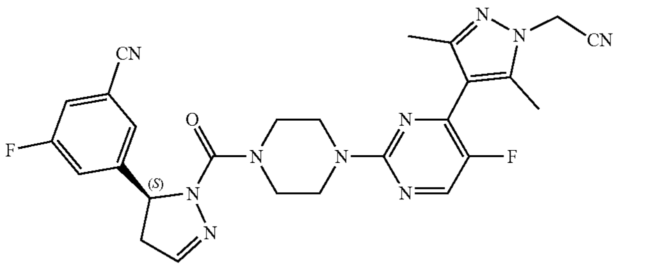

TABLE 1-continued
Active Compounds: Structures (Compounds 1-142)
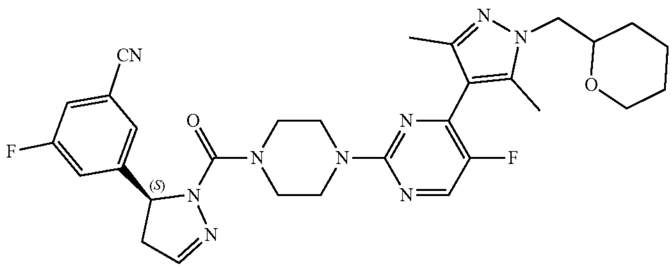
137
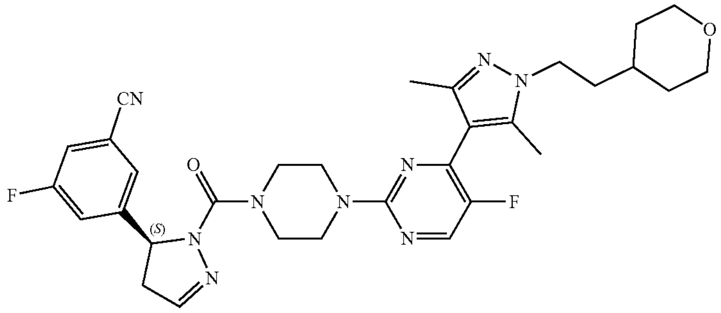
138
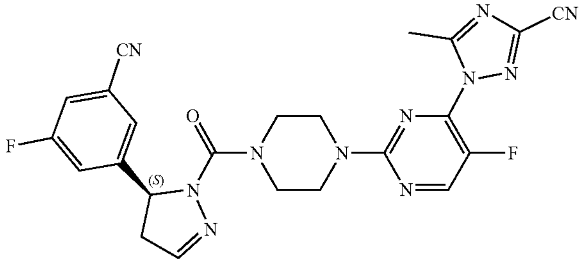
139
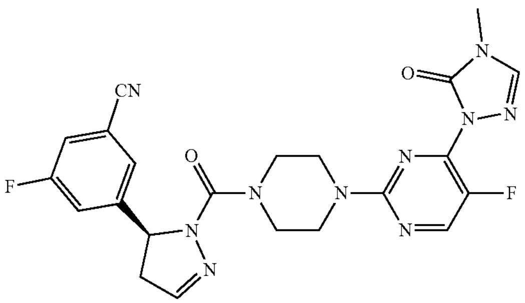 [SMILES: Cn1cnn(-c2nc(N3CCN(C(=O)N4N=CC[C@H]4c4cc(F)cc(C#N)c4)CC3)ncc2F)c1=O]
140
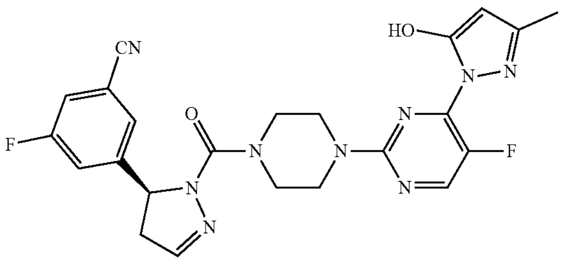 [SMILES: Cc1cc(O)n(-c2nc(N3CCN(C(=O)N4N=CC[C@H]4c4cc(F)cc(C#N)c4)CC3)ncc2F)n1]
141

TABLE 1-continued
| Active Compounds: Structures (Compounds 1-142) |
| --- |
| 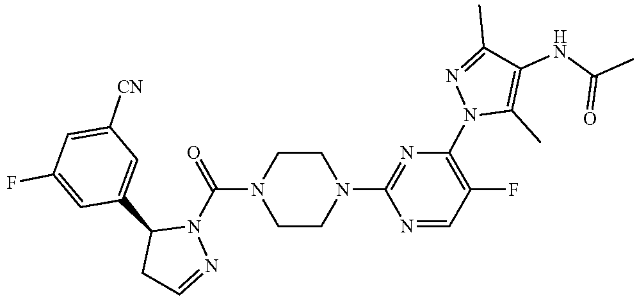 [SMILES: CC(=O)Nc1c(C)nn(-c2nc(N3CCN(C(=O)N4N=CC[C@H]4c4cc(F)cc(C#N)c4)CC3)ncc2F)c1C] 142 |
TABLE 2
| Active Compounds: Structures (Compounds 143-323) |
| --- |
| 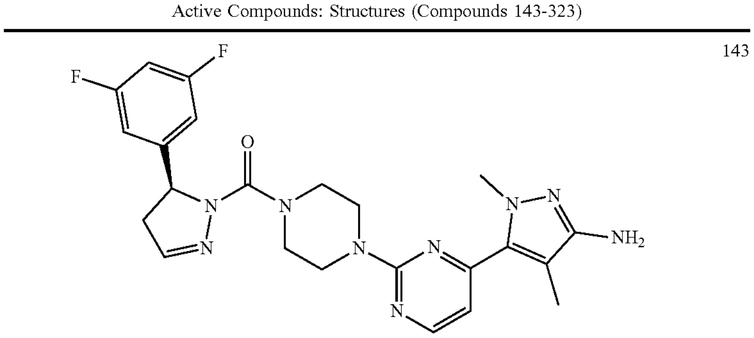 143 |
| 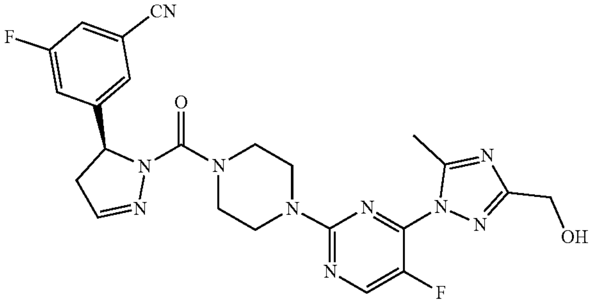 [SMILES: Cc1nc(CO)nn1-c1nc(N2CCN(C(=O)N3N=CC[C@H]3c3cc(F)cc(C#N)c3)CC2)ncc1F] 144 |
| 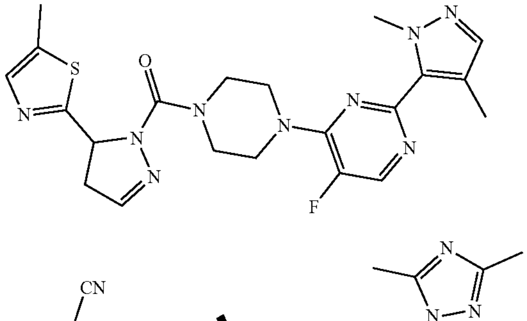 145 |
| 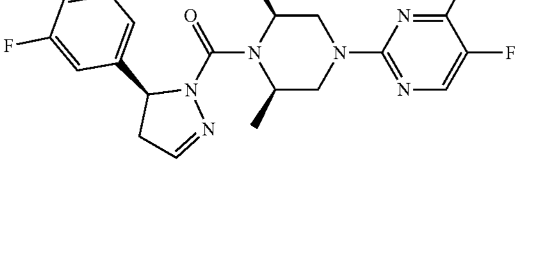 146 |

TABLE 2-continued
| Active Compounds: Structures (Compounds 143-323) | |
|---|---|
| 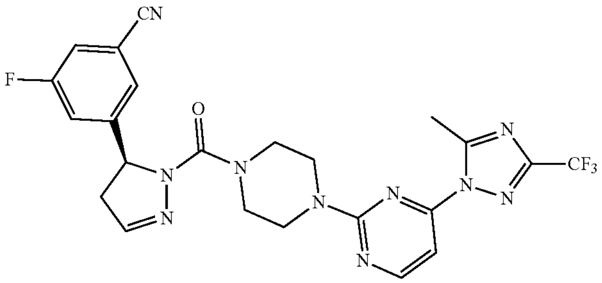 [SMILES: Cc1nc(C(F)(F)F)nn1-c1ccnc(N2CCN(C(=O)N3N=CC[C@H]3c3cc(F)cc(C#N)c3)CC2)n1] | 147 |
| 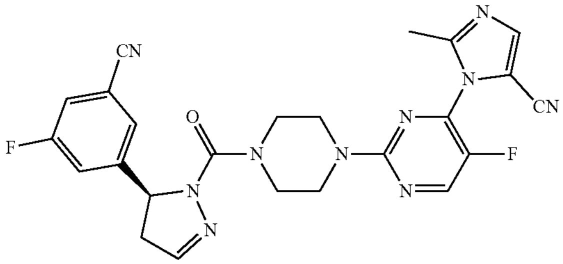 [SMILES: Cc1ncc(C#N)n1-c1nc(N2CCN(C(=O)N3N=CC[C@H]3c3cc(F)cc(C#N)c3)CC2)ncc1F] | 148 |
| 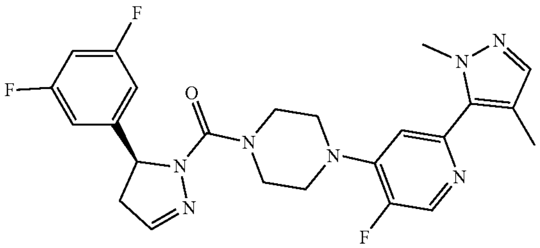 [SMILES: Cc1cnn(C)c1-c1cc(N2CCN(C(=O)N3N=CC[C@H]3c3cc(F)cc(F)c3)CC2)c(F)cn1] | 149 |
| 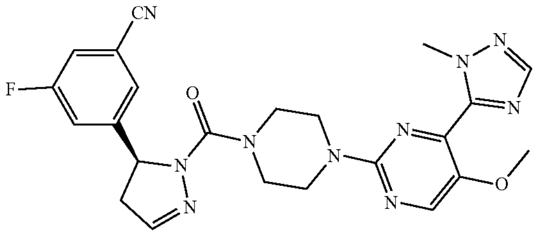 [SMILES: COc1cnc(N2CCN(C(=O)N3N=CC[C@H]3c3cc(F)cc(C#N)c3)CC2)nc1-c1ncnn1C] | 150 |
| 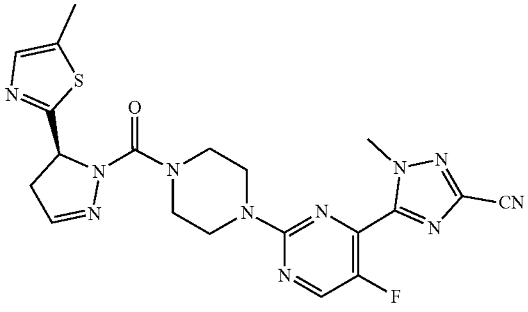 [SMILES: Cc1cnc([C@@H]2CC=NN2C(=O)N2CCN(c3ncc(F)c(-c4nc(C#N)nn4C)n3)CC2)s1] | 151 |

TABLE 2-continued
Active Compounds: Structures (Compounds 143-323)
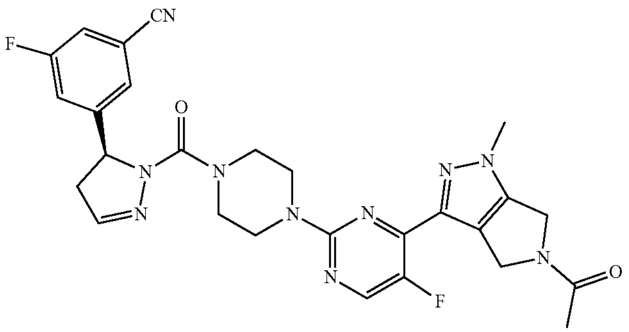 [SMILES: CC(=O)N1Cc2c(-c3nc(N4CCN(C(=O)N5N=CC[C@H]5c5cc(F)cc(C#N)c5)CC4)ncc3F)nn(C)c2C1]
152
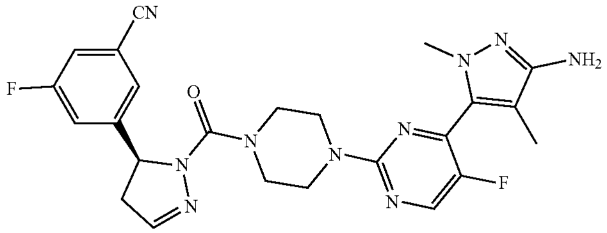 [SMILES: Cc1c(N)nn(C)c1-c1nc(N2CCN(C(=O)N3N=CC[C@H]3c3cc(F)cc(C#N)c3)CC2)ncc1F]
153
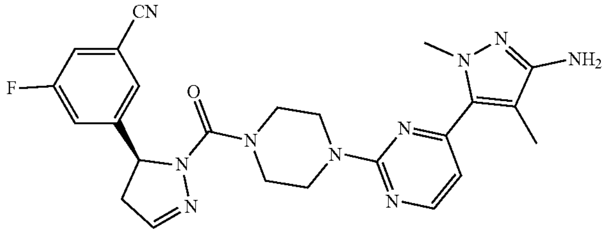 [SMILES: Cc1c(N)nn(C)c1-c1ccnc(N2CCN(C(=O)N3N=CC[C@H]3c3cc(F)cc(C#N)c3)CC2)n1]
154
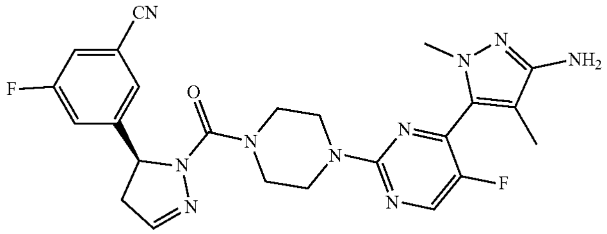 [SMILES: Cc1c(N)nn(C)c1-c1nc(N2CCN(C(=O)N3N=CC[C@H]3c3cc(F)cc(C#N)c3)CC2)ncc1F]
155
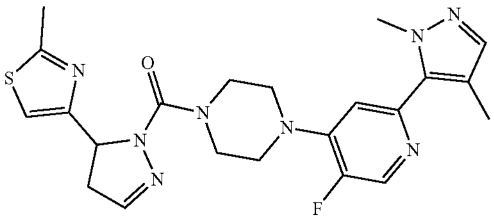 [SMILES: Cc1nc(C2CC=NN2C(=O)N2CCN(c3cc(-c4c(C)cnn4C)ncc3F)CC2)cs1]
156
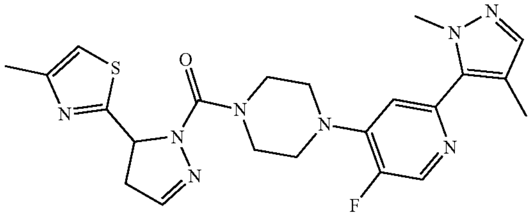
157

TABLE 2-continued
| Active Compounds: Structures (Compounds 143-323) | |
|---|---|
| 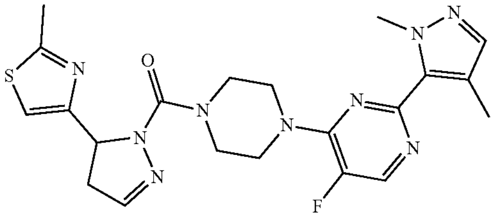 [SMILES: Cc1nc(C2CC=NN2C(=O)N2CCN(c3nc(-c4c(C)cnn4C)ncc3F)CC2)cs1] | 158 |
| 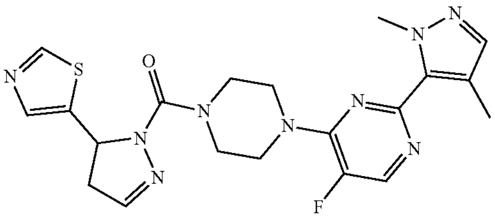 [SMILES: Cc1cnn(C)c1-c1ncc(F)c(N2CCN(C(=O)N3N=CCC3c3cncs3)CC2)n1] | 159 |
| 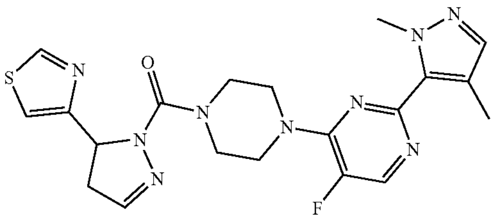 [SMILES: Cc1cnn(C)c1-c1ncc(F)c(N2CCN(C(=O)N3N=CCC3c3cscn3)CC2)n1] | 160 |
| 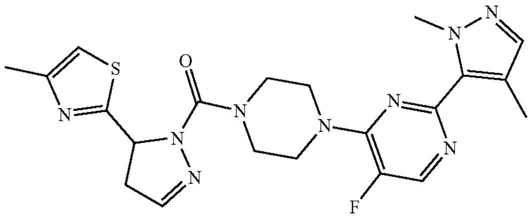 | 161 |
| 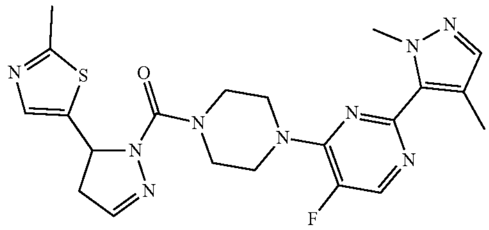 [SMILES: Cc1ncc(C2CC=NN2C(=O)N2CCN(c3nc(-c4c(C)cnn4C)ncc3F)CC2)s1] | 162 |
| 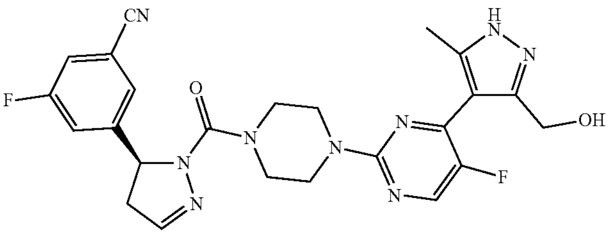 [SMILES: Cc1[nH]nc(CO)c1-c1nc(N2CCN(C(=O)N3N=CC[C@H]3c3cc(F)cc(C#N)c3)CC2)ncc1F] | 163 |

TABLE 2-continued
| Active Compounds: Structures (Compounds 143-323) | |
| --- | --- |
| 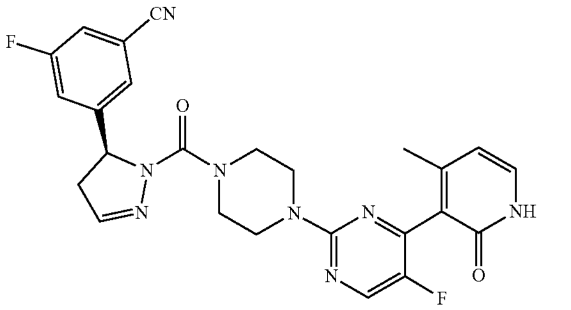 [SMILES: Cc1cc[nH]c(=O)c1-c1nc(N2CCN(C(=O)N3N=CC[C@H]3c3cc(F)cc(C#N)c3)CC2)ncc1F] | 164 |
| 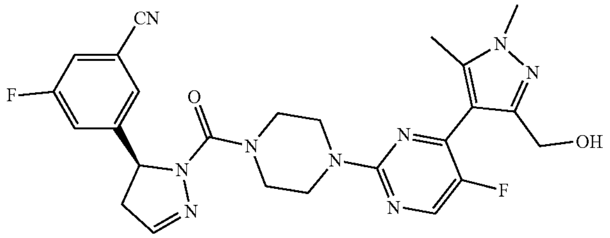 [SMILES: Cc1c(-c2nc(N3CCN(C(=O)N4N=CC[C@H]4c4cc(F)cc(C#N)c4)CC3)ncc2F)c(CO)nn1C] | 165 |
| 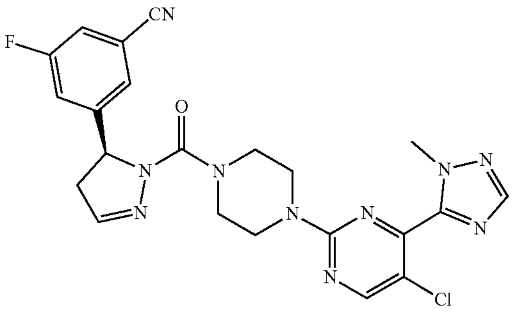 [SMILES: Cn1ncnc1-c1nc(N2CCN(C(=O)N3N=CC[C@H]3c3cc(F)cc(C#N)c3)CC2)ncc1Cl] | 166 |
| 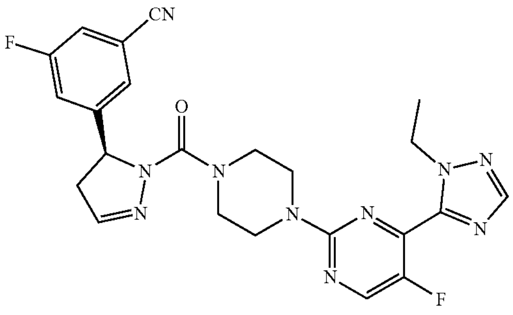 [SMILES: CCn1ncnc1-c1nc(N2CCN(C(=O)N3N=CC[C@H]3c3cc(F)cc(C#N)c3)CC2)ncc1Cl] | 167 |
| 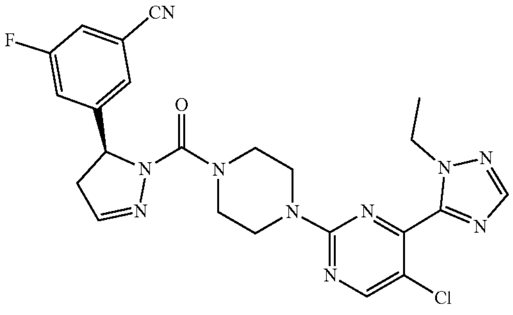 | 168 |

TABLE 2-continued
| Active Compounds: Structures (Compounds 143-323) |
|---|
| 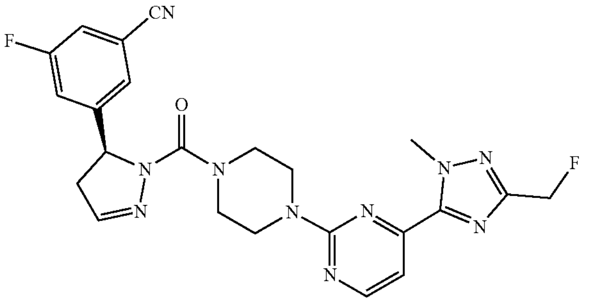 [SMILES: Cn1nc(CF)nc1-c1ccnc(N2CCN(C(=O)N3N=CC[C@H]3c3cc(F)cc(C#N)c3)CC2)n1] 169 |
| 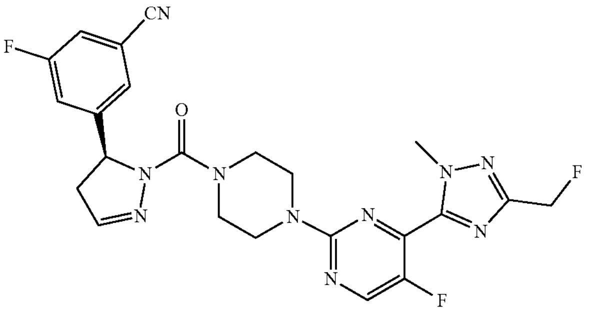 [SMILES: Cn1nc(CF)nc1-c1nc(N2CCN(C(=O)N3N=CC[C@H]3c3cc(F)cc(C#N)c3)CC2)ncc1F] 170 |
| 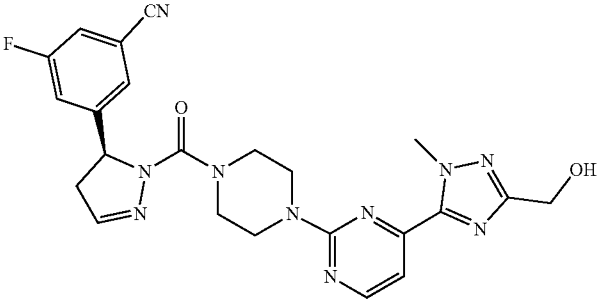 [SMILES: Cn1nc(CO)nc1-c1ccnc(N2CCN(C(=O)N3N=CC[C@H]3c3cc(F)cc(C#N)c3)CC2)n1] 171 |
| 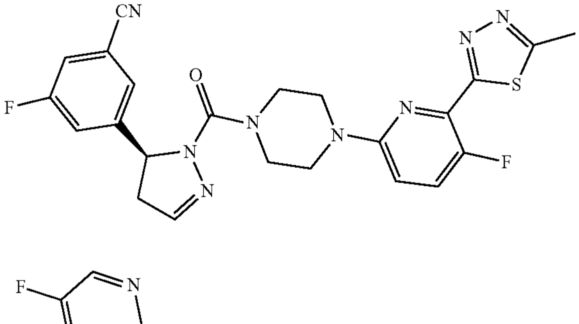 172 |
| 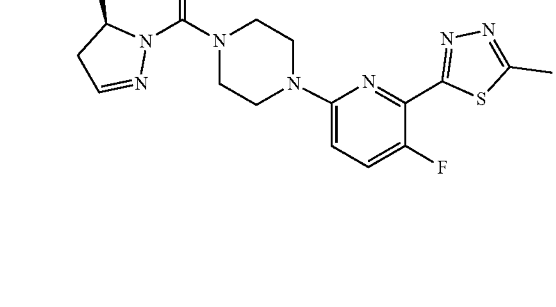 173 |

TABLE 2-continued
| Active Compounds: Structures (Compounds 143-323) | |
| --- | --- |
| 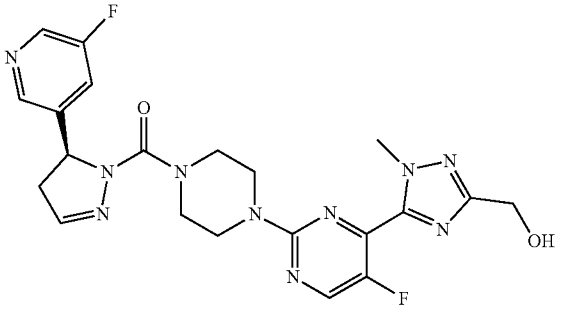 [SMILES: Cn1nc(CO)nc1-c1nc(N2CCN(C(=O)N3N=CC[C@H]3c3cncc(F)c3)CC2)ncc1F] | 174 |
| 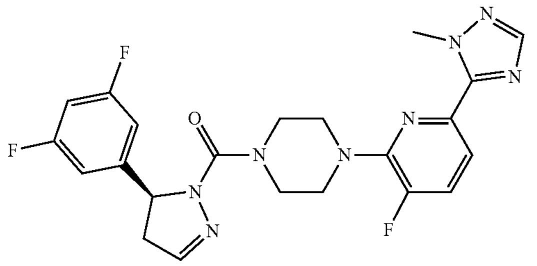 [SMILES: Cn1ncnc1-c1ccc(F)c(N2CCN(C(=O)N3N=CC[C@H]3c3cc(F)cc(F)c3)CC2)n1] | 175 |
| 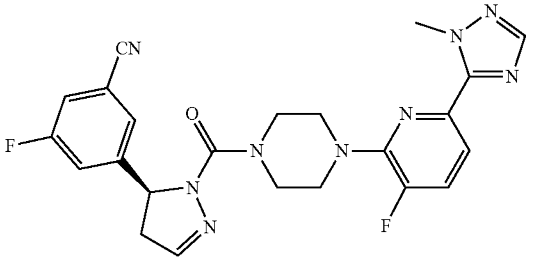 [SMILES: Cn1ncnc1-c1ccc(F)c(N2CCN(C(=O)N3N=CC[C@H]3c3cc(F)cc(C#N)c3)CC2)n1] | 176 |
| 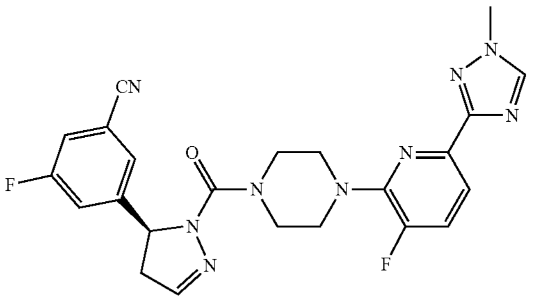 [SMILES: Cn1cnc(-c2ccc(F)c(N3CCN(C(=O)N4N=CC[C@H]4c4cc(F)cc(C#N)c4)CC3)n2)n1] | 177 |
| 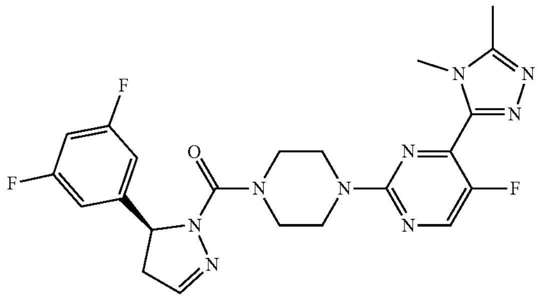 [SMILES: Cc1nnc(-c2nc(N3CCN(C(=O)N4N=CC[C@H]4c4cc(F)cc(F)c4)CC3)ncc2F)n1C] | 178 |

TABLE 2-continued
| Active Compounds: Structures (Compounds 143-323) |
| --- |
| 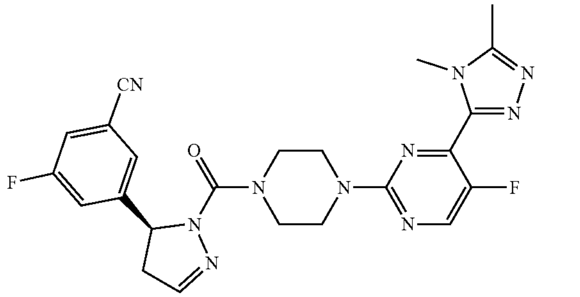 [SMILES: Cc1nnc(-c2nc(N3CCN(C(=O)N4N=CC[C@H]4c4cc(F)cc(C#N)c4)CC3)ncc2F)n1C] 179 |
| 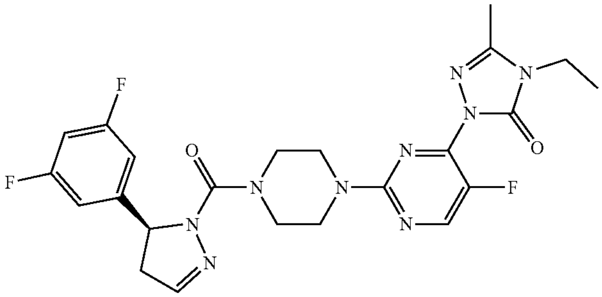 [SMILES: CCn1c(C)nn(-c2nc(N3CCN(C(=O)N4N=CC[C@H]4c4cc(F)cc(F)c4)CC3)ncc2F)c1=O] 180 |
| 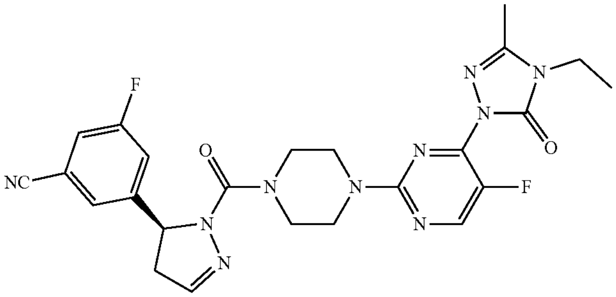 [SMILES: CCn1c(C)nn(-c2nc(N3CCN(C(=O)N4N=CC[C@H]4c4cc(F)cc(C#N)c4)CC3)ncc2F)c1=O] 181 |
| 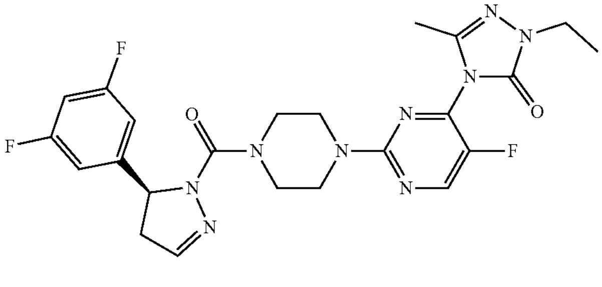 [SMILES: CCn1nc(C)n(-c2nc(N3CCN(C(=O)N4N=CC[C@H]4c4cc(F)cc(F)c4)CC3)ncc2F)c1=O] 182 |
| 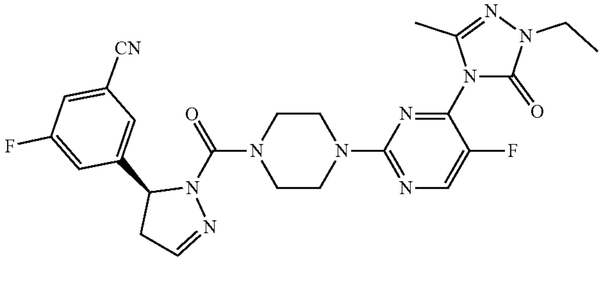 [SMILES: CCn1nc(C)n(-c2nc(N3CCN(C(=O)N4N=CC[C@H]4c4cc(F)cc(C#N)c4)CC3)ncc2F)c1=O] 183 |

TABLE 2-continued
Active Compounds: Structures (Compounds 143-323)
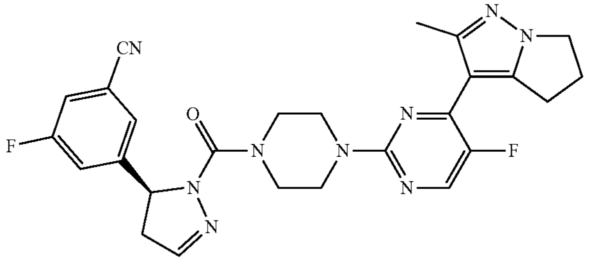 [SMILES: Cc1nn2c(c1-c1nc(N3CCN(C(=O)N4N=CC[C@H]4c4cc(F)cc(C#N)c4)CC3)ncc1F)CCC2]
184
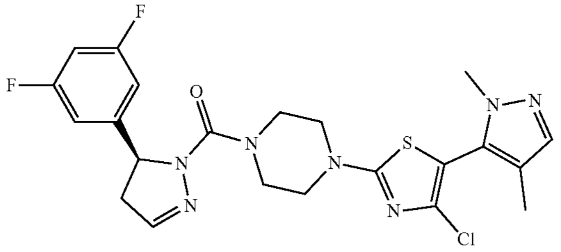 [SMILES: Cc1cnn(C)c1-c1sc(N2CCN(C(=O)N3N=CC[C@H]3c3cc(F)cc(F)c3)CC2)nc1Cl]
185
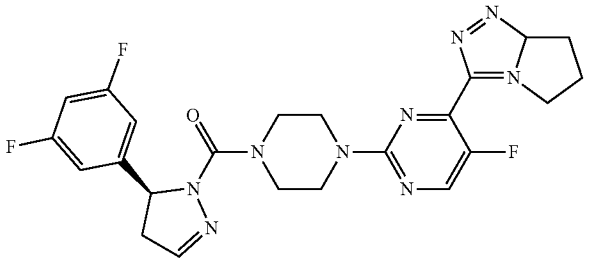
186
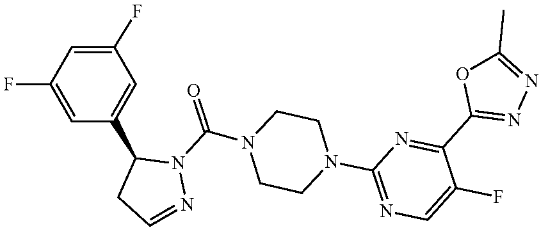 [SMILES: Cc1nnc(-c2nc(N3CCN(C(=O)N4N=CC[C@H]4c4cc(F)cc(F)c4)CC3)ncc2F)o1]
187
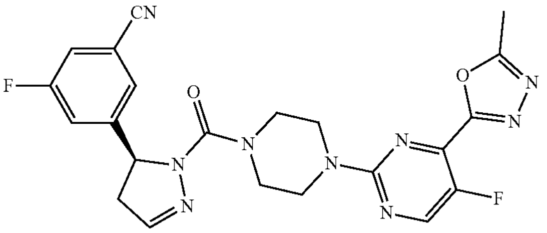 [SMILES: Cc1nnc(-c2nc(N3CCN(C(=O)N4N=CC[C@H]4c4cc(F)cc(C#N)c4)CC3)ncc2F)o1]
188
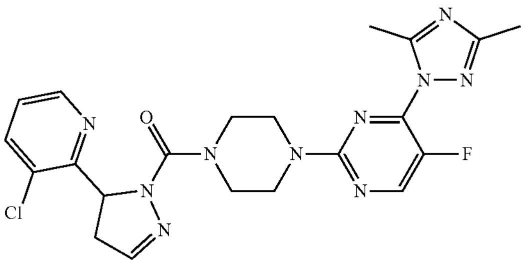 [SMILES: Cc1nc(C)n(-c2nc(N3CCN(C(=O)N4N=CCC4c4ncccc4Cl)CC3)ncc2F)n1]
189

TABLE 2-continued
Active Compounds: Structures (Compounds 143-323)
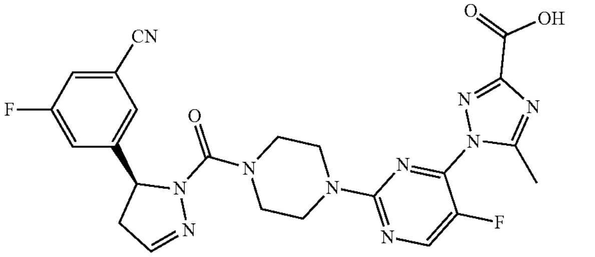 [SMILES: Cc1nc(C(=O)O)nn1-c1nc(N2CCN(C(=O)N3N=CC[C@H]3c3cc(F)cc(C#N)c3)CC2)ncc1F]
190
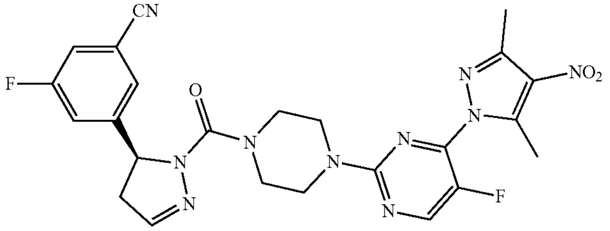 [SMILES: Cc1nn(-c2nc(N3CCN(C(=O)N4N=CC[C@H]4c4cc(F)cc(C#N)c4)CC3)ncc2F)c(C)c1[N+](=O)[O-]]
191
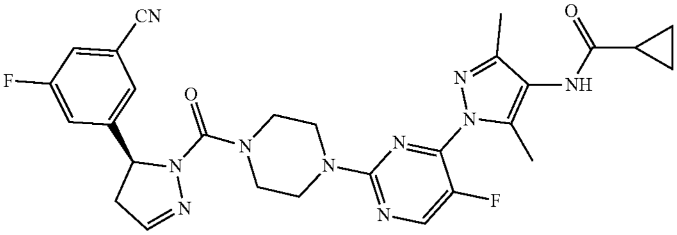 [SMILES: Cc1nn(-c2nc(N3CCN(C(=O)N4N=CC[C@H]4c4cc(F)cc(C#N)c4)CC3)ncc2F)c(C)c1NC(=O)C1CC1]
192
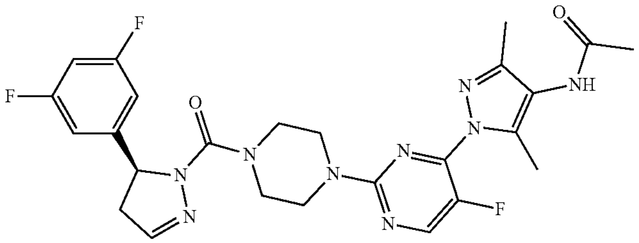 [SMILES: CC(=O)Nc1c(C)nn(-c2nc(N3CCN(C(=O)N4N=CC[C@H]4c4cc(F)cc(F)c4)CC3)ncc2F)c1C]
193
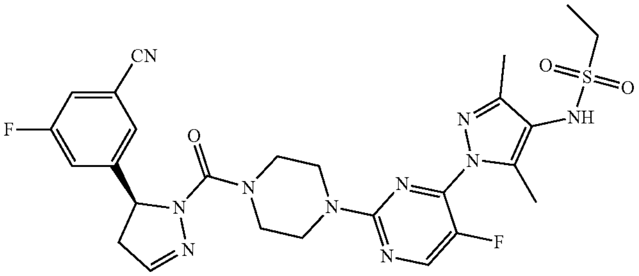 [SMILES: CCS(=O)(=O)Nc1c(C)nn(-c2nc(N3CCN(C(=O)N4N=CC[C@H]4c4cc(F)cc(C#N)c4)CC3)ncc2F)c1C]
194
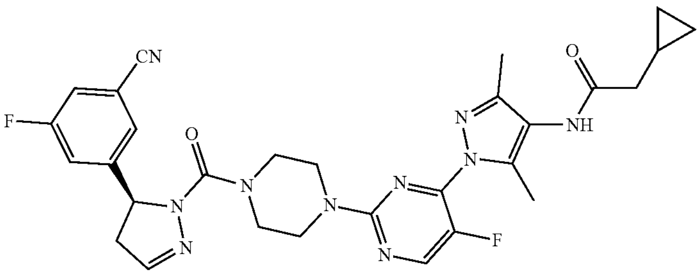 [SMILES: Cc1nn(-c2nc(N3CCN(C(=O)N4N=CC[C@H]4c4cc(F)cc(C#N)c4)CC3)ncc2F)c(C)c1NC(=O)CC1CC1]
195

TABLE 2-continued
Active Compounds: Structures (Compounds 143-323)
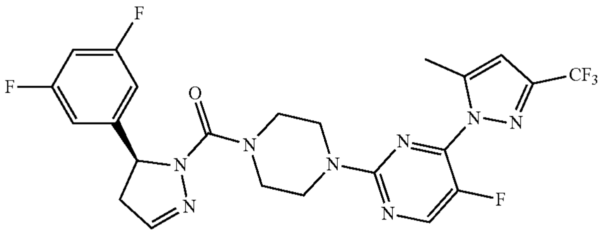 [SMILES: Cc1cc(C(F)(F)F)nn1-c1nc(N2CCN(C(=O)N3N=CC[C@H]3c3cc(F)cc(F)c3)CC2)ncc1F]
196
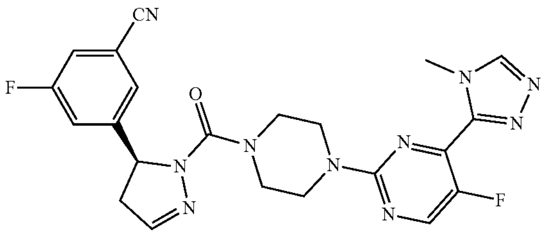 [SMILES: Cn1cnnc1-c1nc(N2CCN(C(=O)N3N=CC[C@H]3c3cc(F)cc(C#N)c3)CC2)ncc1F]
197
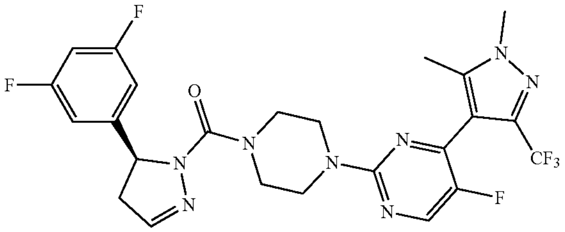 [SMILES: Cc1c(-c2nc(N3CCN(C(=O)N4N=CC[C@H]4c4cc(F)cc(F)c4)CC3)ncc2F)c(C(F)(F)F)nn1C]
198
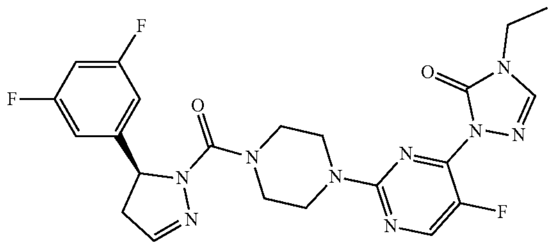 [SMILES: CCn1cnn(-c2nc(N3CCN(C(=O)N4N=CC[C@H]4c4cc(F)cc(F)c4)CC3)ncc2F)c1=O]
199
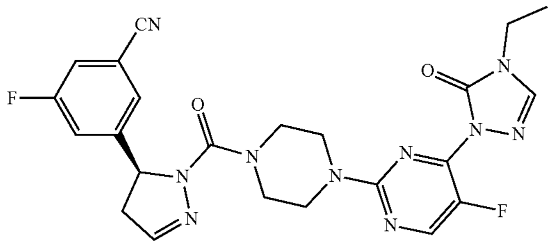 [SMILES: CCn1cnn(-c2nc(N3CCN(C(=O)N4N=CC[C@H]4c4cc(F)cc(C#N)c4)CC3)ncc2F)c1=O]
200
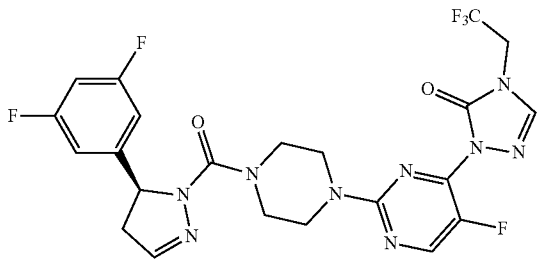 [SMILES: O=C(N1CCN(c2ncc(F)c(-n3ncn(CC(F)(F)F)c3=O)n2)CC1)N1N=CC[C@H]1c1cc(F)cc(F)c1]
201

TABLE 2-continued
Active Compounds: Structures (Compounds 143-323)
202
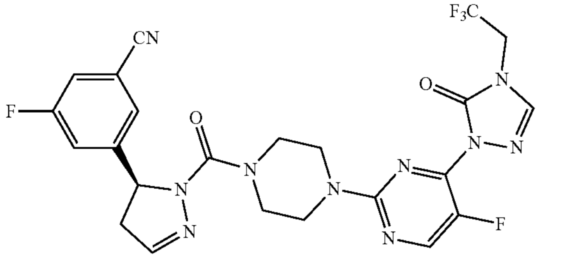 [SMILES: N#Cc1cc(F)cc([C@@H]2CC=NN2C(=O)N2CCN(c3ncc(F)c(-n4ncn(CC(F)(F)F)c4=O)n3)CC2)c1]
203
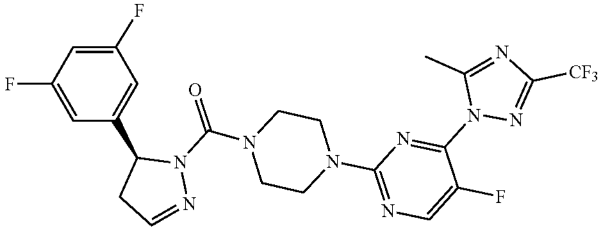 [SMILES: Cc1nc(C(F)(F)F)nn1-c1nc(N2CCN(C(=O)N3N=CC[C@H]3c3cc(F)cc(F)c3)CC2)ncc1F]
204
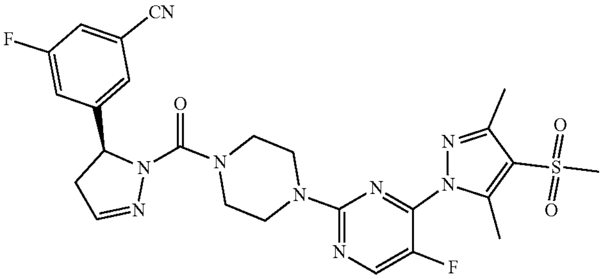 [SMILES: Cc1nn(-c2nc(N3CCN(C(=O)N4N=CC[C@H]4c4cc(F)cc(C#N)c4)CC3)ncc2F)c(C)c1S(C)(=O)=O]
205
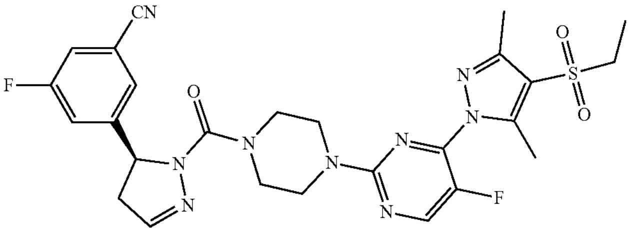 [SMILES: CCS(=O)(=O)c1c(C)nn(-c2nc(N3CCN(C(=O)N4N=CC[C@H]4c4cc(F)cc(C#N)c4)CC3)ncc2F)c1C]
206
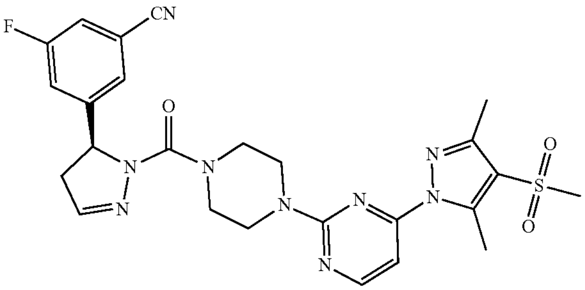 [SMILES: Cc1nn(-c2ccnc(N3CCN(C(=O)N4N=CC[C@H]4c4cc(F)cc(C#N)c4)CC3)n2)c(C)c1S(C)(=O)=O]
207
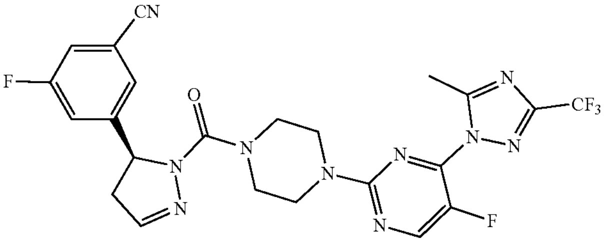 [SMILES: Cc1nc(C(F)(F)F)nn1-c1nc(N2CCN(C(=O)N3N=CC[C@H]3c3cc(F)cc(C#N)c3)CC2)ncc1F]

TABLE 2-continued
Active Compounds: Structures (Compounds 143-323)
208
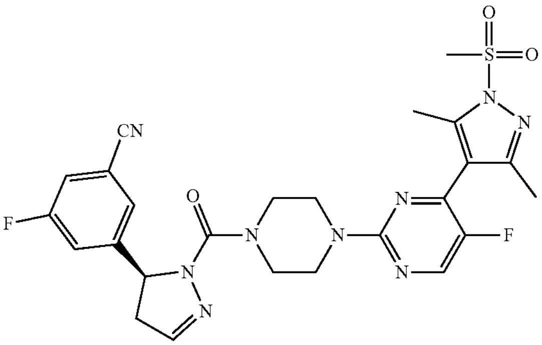 [SMILES: Cc1nn(S(C)(=O)=O)c(C)c1-c1nc(N2CCN(C(=O)N3N=CC[C@H]3c3cc(F)cc(C#N)c3)CC2)ncc1F]
209
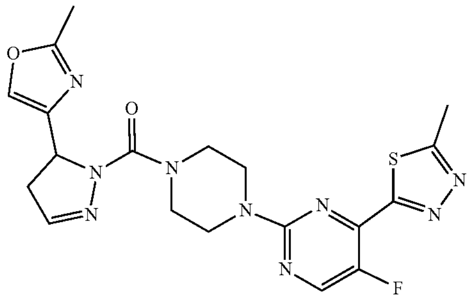 [SMILES: Cc1nc(C2CC=NN2C(=O)N2CCN(c3ncc(F)c(-c4nnc(C)s4)n3)CC2)co1]
210
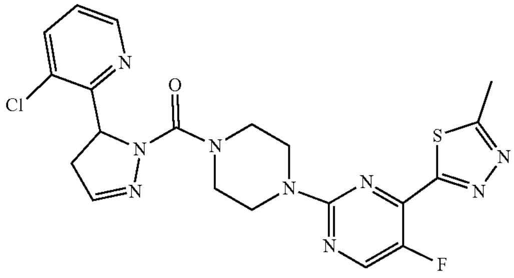 [SMILES: Cc1nnc(-c2nc(N3CCN(C(=O)N4N=CCC4c4ncccc4Cl)CC3)ncc2F)s1]
211
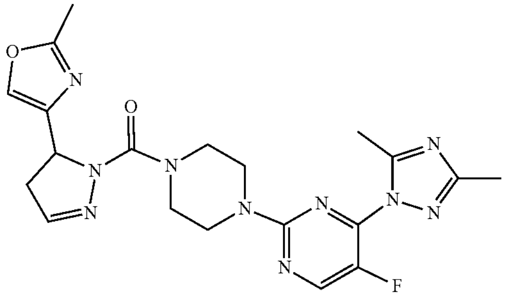
212
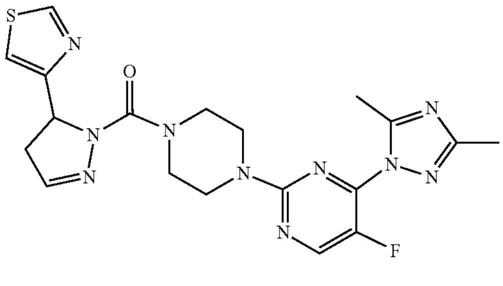 [SMILES: Cc1nc(C)n(-c2nc(N3CCN(C(=O)N4N=CCC4c4cscn4)CC3)ncc2F)n1]

TABLE 2-continued
| Active Compounds: Structures (Compounds 143-323) |
| --- |
| 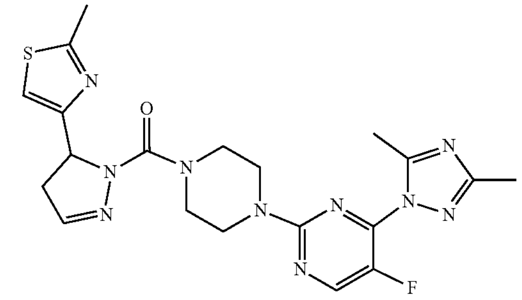 [SMILES: Cc1nc(C)n(-c2nc(N3CCN(C(=O)N4N=CCC4c4csc(C)n4)CC3)ncc2F)n1] 213 |
| 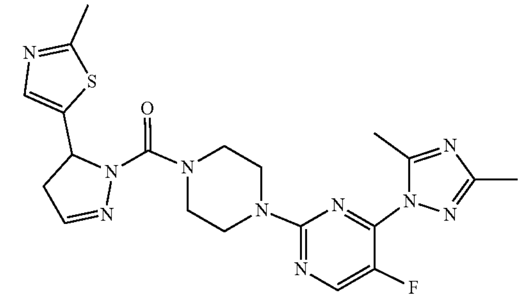 [SMILES: Cc1nc(C)n(-c2nc(N3CCN(C(=O)N4N=CCC4c4cnc(C)s4)CC3)ncc2F)n1] 214 |
| 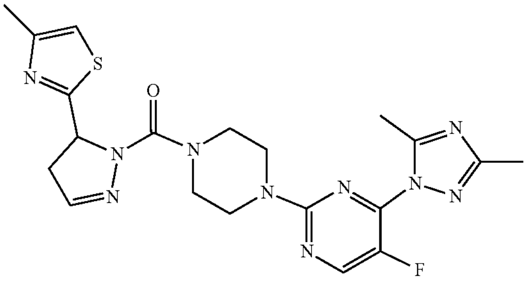 215 |
| 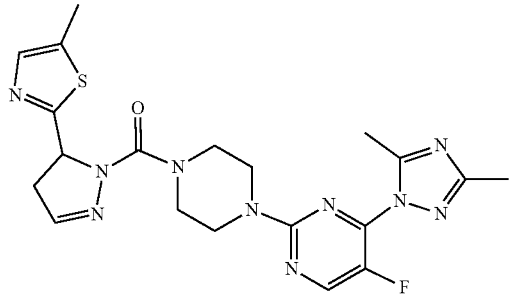 [SMILES: Cc1nc(C)n(-c2nc(N3CCN(C(=O)N4N=CCC4c4ncc(C)s4)CC3)ncc2F)n1] 216 |
| 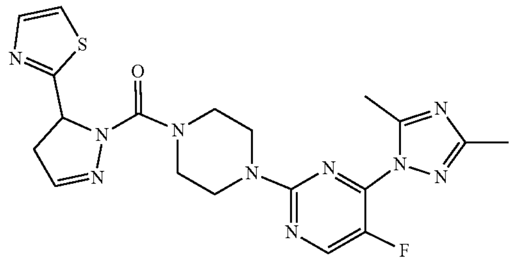 [SMILES: Cc1nc(C)n(-c2nc(N3CCN(C(=O)N4N=CCC4c4nccs4)CC3)ncc2F)n1] 217 |

TABLE 2-continued
| Active Compounds: Structures (Compounds 143-323) |
| --- |
| 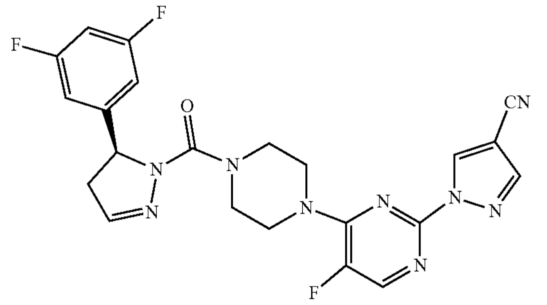 [SMILES: N#Cc1cnn(-c2ncc(F)c(N3CCN(C(=O)N4N=CC[C@H]4c4cc(F)cc(F)c4)CC3)n2)c1] 218 |
| 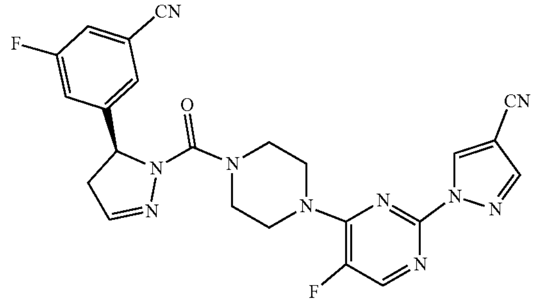 [SMILES: N#Cc1cc(F)cc([C@@H]2CC=NN2C(=O)N2CCN(c3nc(-n4cc(C#N)cn4)ncc3F)CC2)c1] 219 |
| 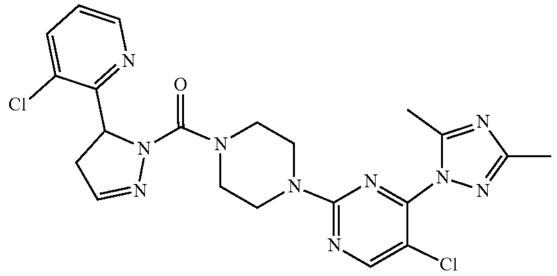 [SMILES: Cc1nc(C)n(-c2nc(N3CCN(C(=O)N4N=CCC4c4ncccc4Cl)CC3)ncc2Cl)n1] 220 |
| 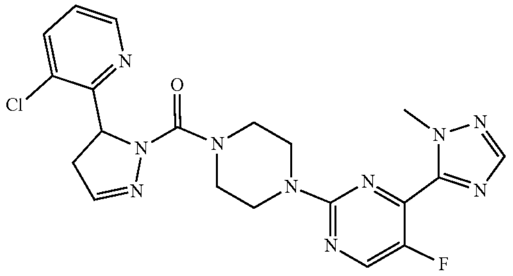 [SMILES: Cn1ncnc1-c1nc(N2CCN(C(=O)N3N=CCC3c3ncccc3Cl)CC2)ncc1F] 221 |
| 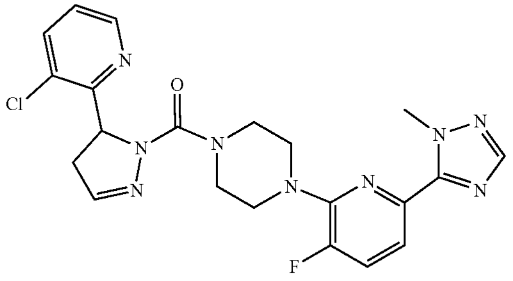 [SMILES: Cn1ncnc1-c1ccc(F)c(N2CCN(C(=O)N3N=CCC3c3ncccc3Cl)CC2)n1] 222 |

TABLE 2-continued
| Active Compounds: Structures (Compounds 143-323) |
| --- |
| 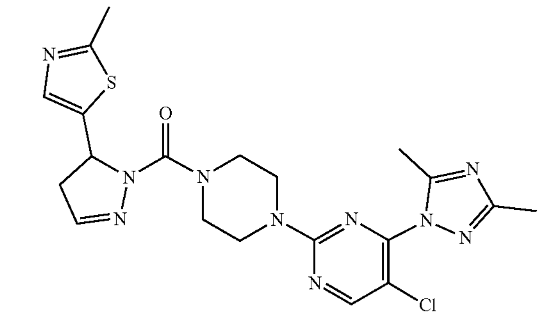 223 |
| 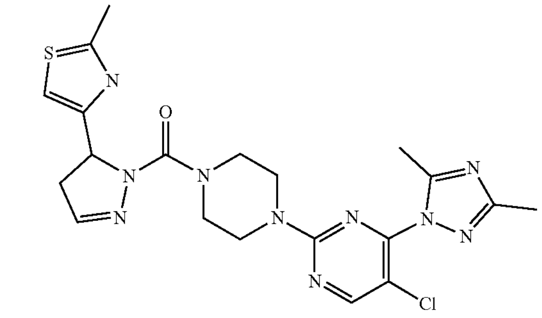 224 |
| 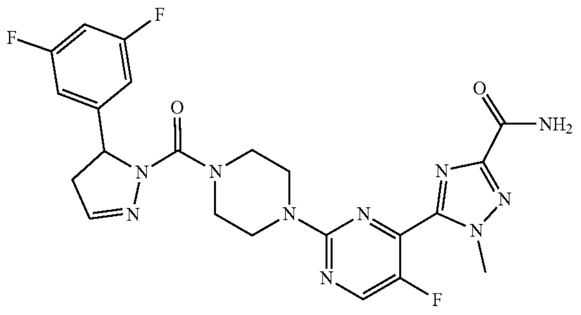 [SMILES: Cn1nc(C(N)=O)nc1-c1nc(N2CCN(C(=O)N3N=CCC3c3cc(F)cc(F)c3)CC2)ncc1F] 225 |
| 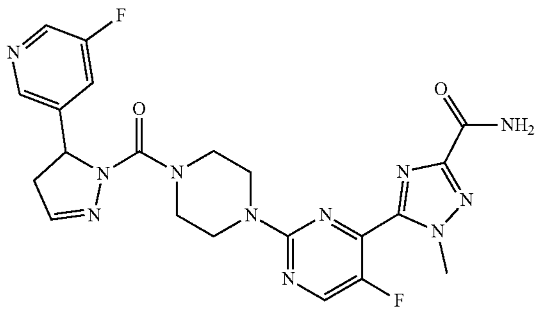 [SMILES: Cn1nc(C(N)=O)nc1-c1nc(N2CCN(C(=O)N3N=CCC3c3cncc(F)c3)CC2)ncc1F] 226 |
| 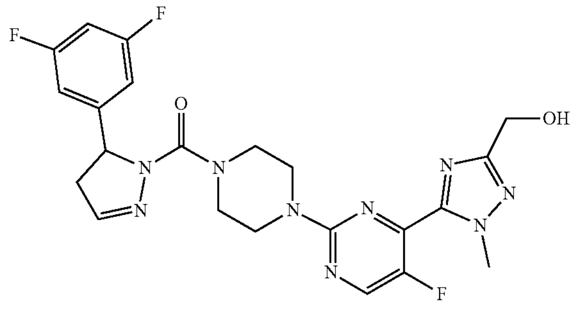 [SMILES: Cn1nc(CO)nc1-c1nc(N2CCN(C(=O)N3N=CCC3c3cc(F)cc(F)c3)CC2)ncc1F] 227 |

TABLE 2-continued
| Active Compounds: Structures (Compounds 143-323) |
| --- |
| 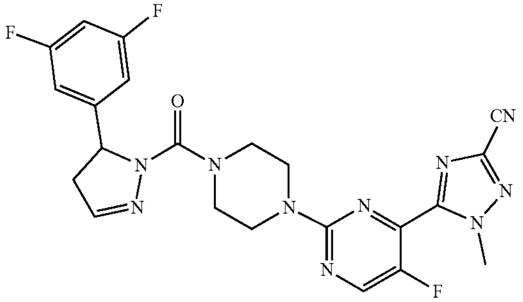 228 |
| 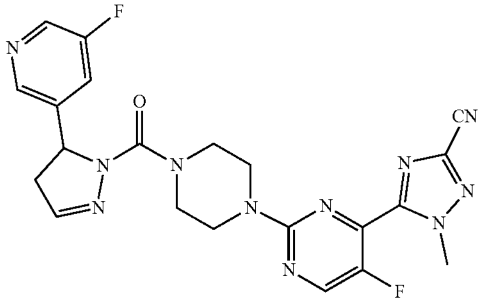 229 |
| 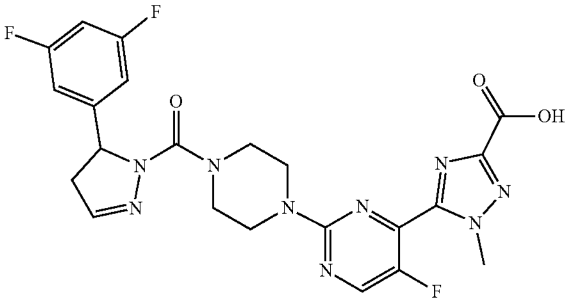 [SMILES: Cn1nc(C(=O)O)nc1-c1nc(N2CCN(C(=O)N3N=CCC3c3cc(F)cc(F)c3)CC2)ncc1F] 230 |
| 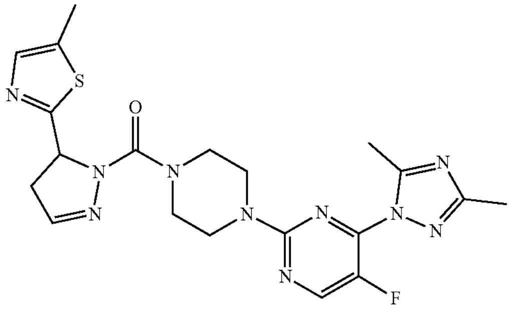 [SMILES: Cc1nc(C)n(-c2nc(N3CCN(C(=O)N4N=CCC4c4ncc(C)s4)CC3)ncc2F)n1] 231 |
| 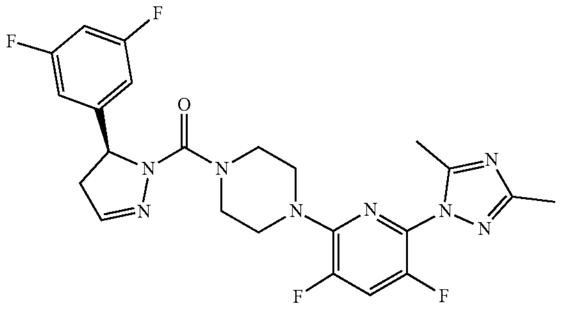 [SMILES: Cc1nc(C)n(-c2nc(N3CCN(C(=O)N4N=CC[C@H]4c4cc(F)cc(F)c4)CC3)c(F)cc2F)n1] 232 |

TABLE 2-continued
| Active Compounds: Structures (Compounds 143-323) |
| --- |
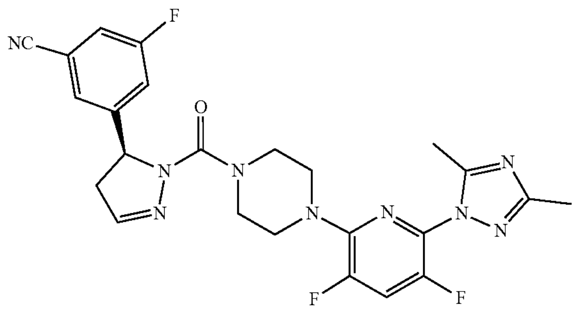 [SMILES: Cc1nc(C)n(-c2nc(N3CCN(C(=O)N4N=CC[C@H]4c4cc(F)cc(C#N)c4)CC3)c(F)cc2F)n1]
233
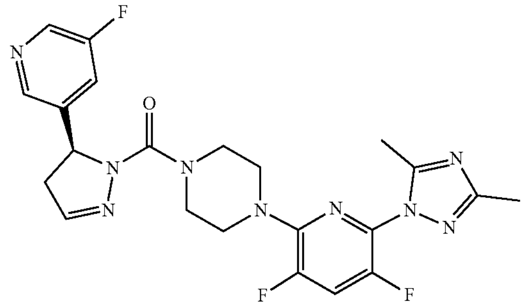 [SMILES: Cc1nc(C)n(-c2nc(N3CCN(C(=O)N4N=CC[C@H]4c4cncc(F)c4)CC3)c(F)cc2F)n1]
234
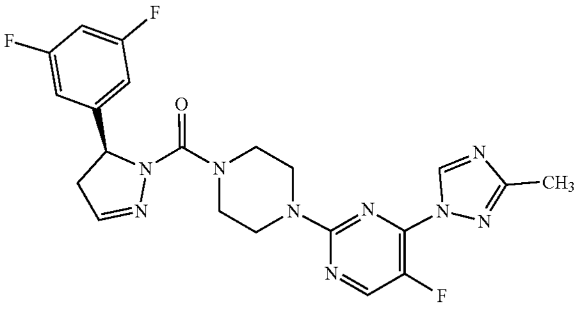 [SMILES: Cc1ncn(-c2nc(N3CCN(C(=O)N4N=CC[C@H]4c4cc(F)cc(F)c4)CC3)ncc2F)n1]
235
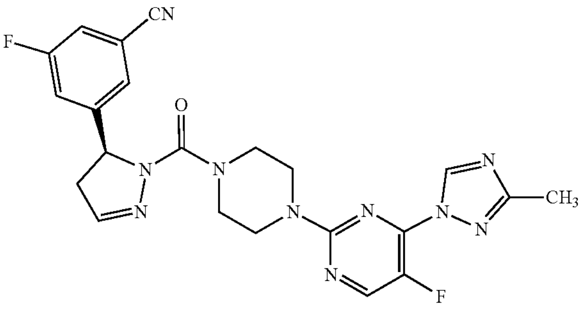 [SMILES: Cc1ncn(-c2nc(N3CCN(C(=O)N4N=CC[C@H]4c4cc(F)cc(C#N)c4)CC3)ncc2F)n1]
236
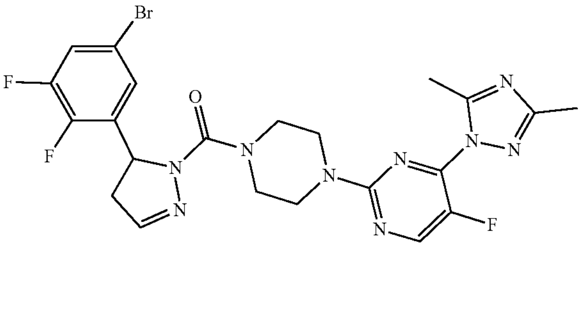 [SMILES: Cc1nc(C)n(-c2nc(N3CCN(C(=O)N4N=CCC4c4cc(Br)cc(F)c4F)CC3)ncc2F)n1]
237

TABLE 2-continued
Active Compounds: Structures (Compounds 143-323)
238
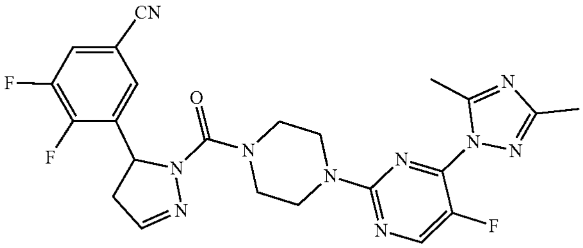
239
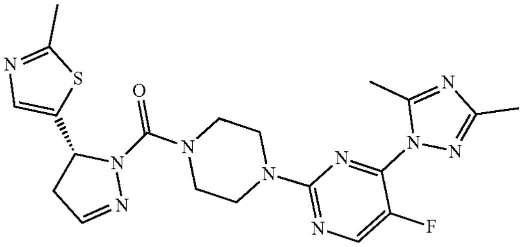 [SMILES: Cc1nc(C)n(-c2nc(N3CCN(C(=O)N4N=CC[C@@H]4c4cnc(C)s4)CC3)ncc2F)n1]
240
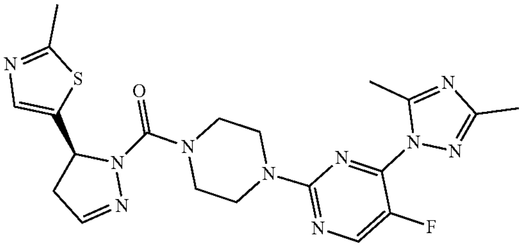 [SMILES: Cc1nc(C)n(-c2nc(N3CCN(C(=O)N4N=CC[C@H]4c4cnc(C)s4)CC3)ncc2F)n1]
241
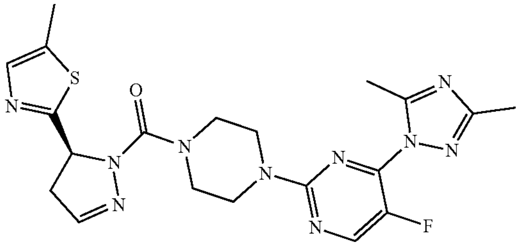 [SMILES: Cc1nc(C)n(-c2nc(N3CCN(C(=O)N4N=CC[C@H]4c4ncc(C)s4)CC3)ncc2F)n1]
242
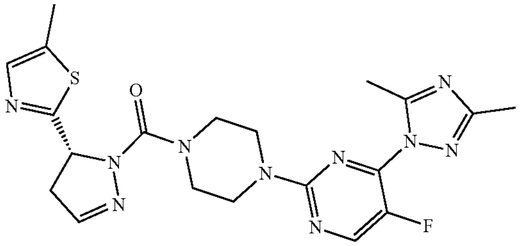 [SMILES: Cc1nc(C)n(-c2nc(N3CCN(C(=O)N4N=CC[C@@H]4c4ncc(C)s4)CC3)ncc2F)n1]
243
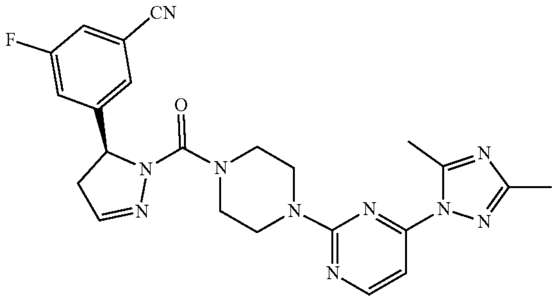

TABLE 2-continued
| Active Compounds: Structures (Compounds 143-323) | |
|---|---|
| 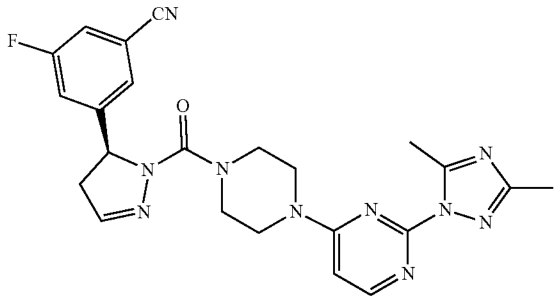 [SMILES: Cc1nc(C)n(-c2nccc(N3CCN(C(=O)N4N=CC[C@H]4c4cc(F)cc(C#N)c4)CC3)n2)n1] | 244 |
| 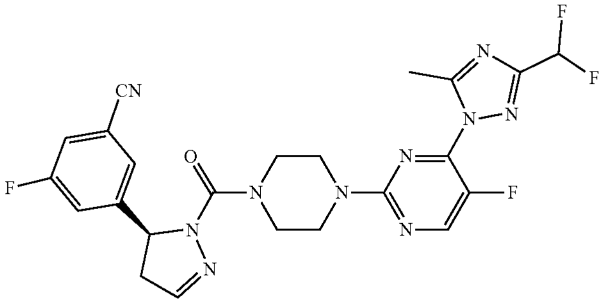 [SMILES: Cc1nc(C(F)F)nn1-c1nc(N2CCN(C(=O)N3N=CC[C@H]3c3cc(F)cc(C#N)c3)CC2)ncc1F] | 245 |
| 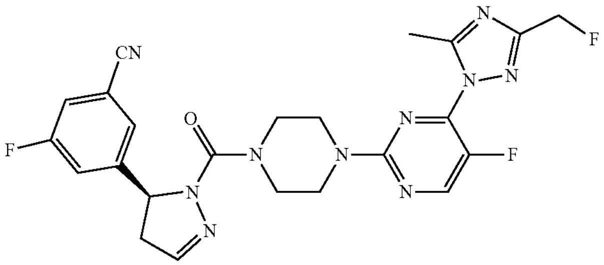 [SMILES: Cc1nc(CF)nn1-c1nc(N2CCN(C(=O)N3N=CC[C@H]3c3cc(F)cc(C#N)c3)CC2)ncc1F] | 246 |
| 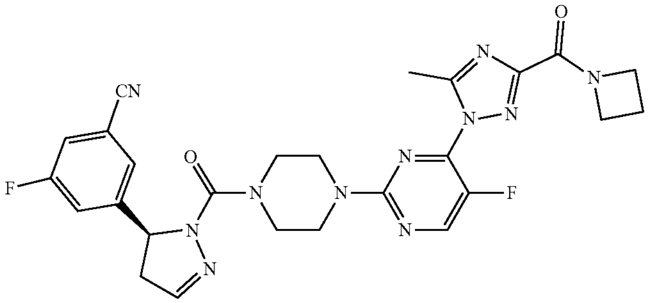 [SMILES: Cc1nc(C(=O)N2CCC2)nn1-c1nc(N2CCN(C(=O)N3N=CC[C@H]3c3cc(F)cc(C#N)c3)CC2)ncc1F] | 247 |
| 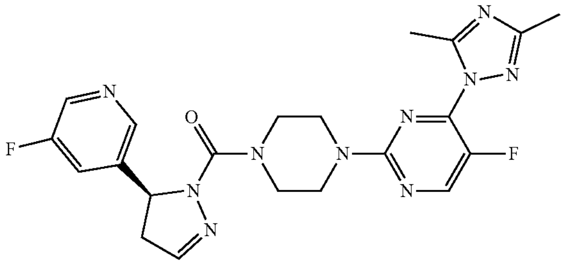 [SMILES: Cc1nc(C)n(-c2nc(N3CCN(C(=O)N4N=CC[C@H]4c4cncc(F)c4)CC3)ncc2F)n1] | 248 |

TABLE 2-continued
| Active Compounds: Structures (Compounds 143-323) | |
|---|---|
| 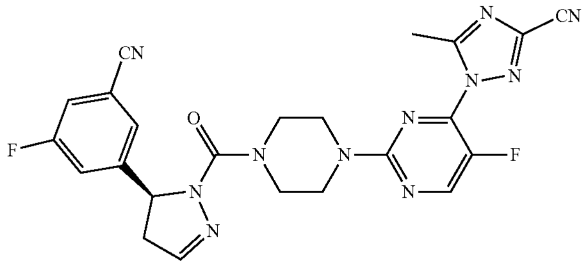 [SMILES: Cc1nc(C#N)nn1-c1nc(N2CCN(C(=O)N3N=CC[C@H]3c3cc(F)cc(C#N)c3)CC2)ncc1F] | 249 |
| 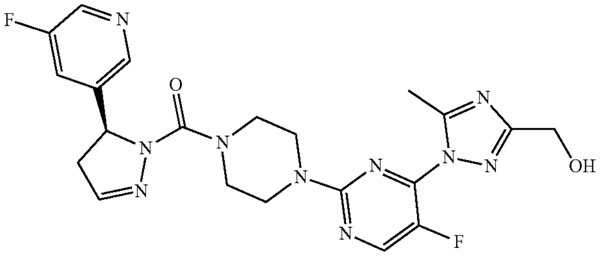 [SMILES: Cc1nc(CO)nn1-c1nc(N2CCN(C(=O)N3N=CC[C@H]3c3cncc(F)c3)CC2)ncc1F] | 250 |
| 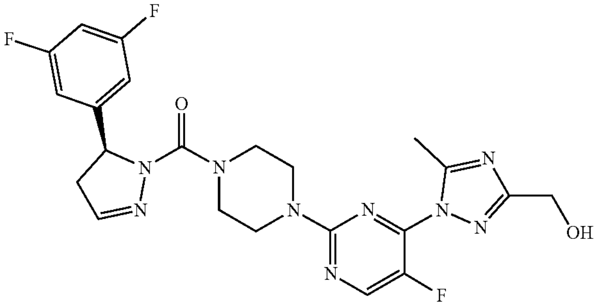 [SMILES: Cc1nc(CO)nn1-c1nc(N2CCN(C(=O)N3N=CC[C@H]3c3cc(F)cc(F)c3)CC2)ncc1F] | 251 |
| 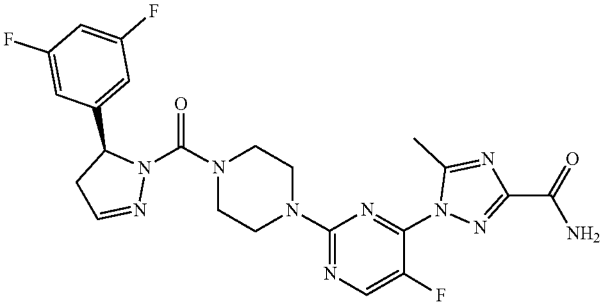 [SMILES: Cc1nc(C(N)=O)nn1-c1nc(N2CCN(C(=O)N3N=CC[C@H]3c3cc(F)cc(F)c3)CC2)ncc1F] | 252 |
| 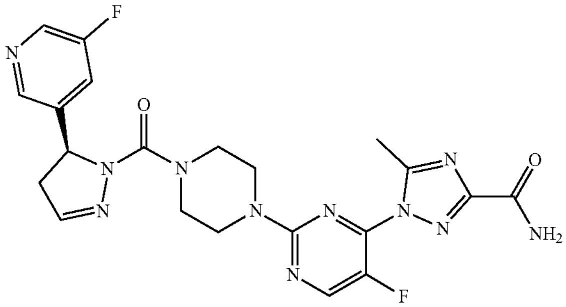 [SMILES: Cc1nc(C(N)=O)nn1-c1nc(N2CCN(C(=O)N3N=CC[C@H]3c3cncc(F)c3)CC2)ncc1F] | 253 |

TABLE 2-continued
| Active Compounds: Structures (Compounds 143-323) |
| --- |
| 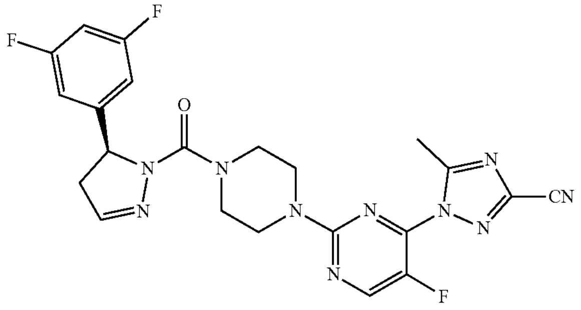 [SMILES: Cc1nc(C#N)nn1-c1nc(N2CCN(C(=O)N3N=CC[C@H]3c3cc(F)cc(F)c3)CC2)ncc1F] 254 |
| 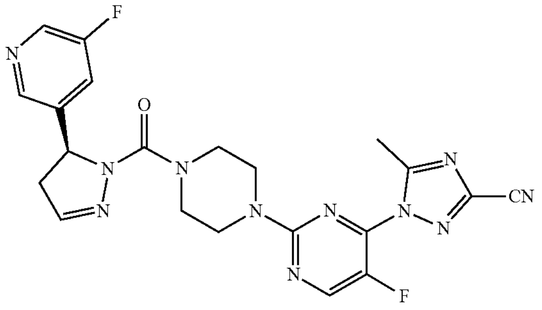 [SMILES: Cc1nc(C#N)nn1-c1nc(N2CCN(C(=O)N3N=CC[C@H]3c3cncc(F)c3)CC2)ncc1F] 255 |
| 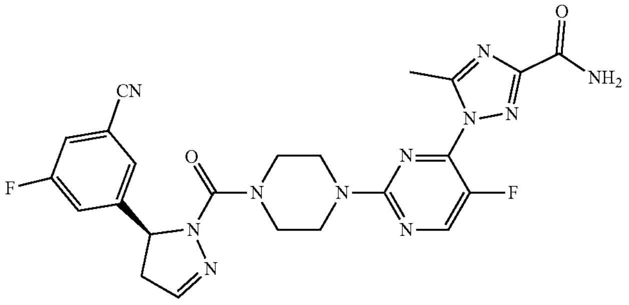 [SMILES: Cc1nc(C(N)=O)nn1-c1nc(N2CCN(C(=O)N3N=CC[C@H]3c3cc(F)cc(C#N)c3)CC2)ncc1F] 256 |
| 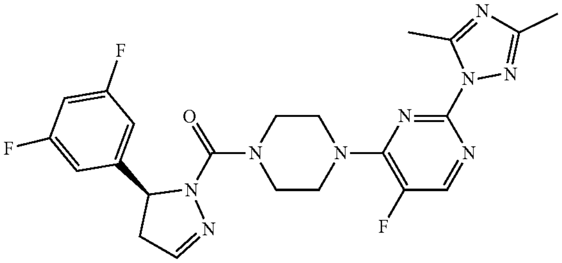 [SMILES: Cc1nc(C)n(-c2ncc(F)c(N3CCN(C(=O)N4N=CC[C@H]4c4cc(F)cc(F)c4)CC3)n2)n1] 257 |
| 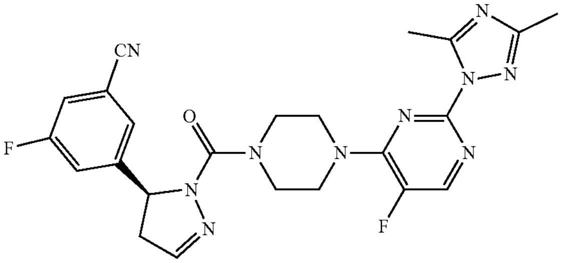 [SMILES: Cc1nc(C)n(-c2ncc(F)c(N3CCN(C(=O)N4N=CC[C@H]4c4cc(F)cc(C#N)c4)CC3)n2)n1] 258 |

TABLE 2-continued
Active Compounds: Structures (Compounds 143-323)
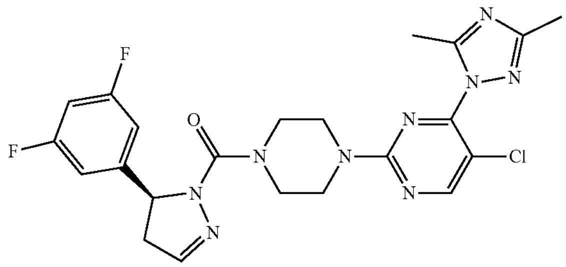 [SMILES: Cc1nc(C)n(-c2nc(N3CCN(C(=O)N4N=CC[C@H]4c4cc(F)cc(F)c4)CC3)ncc2Cl)n1]
259
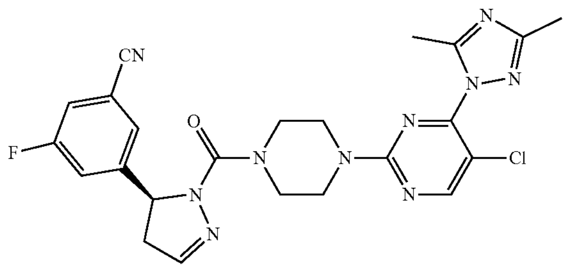 [SMILES: Cc1nc(C)n(-c2nc(N3CCN(C(=O)N4N=CC[C@H]4c4cc(F)cc(C#N)c4)CC3)ncc2Cl)n1]
260
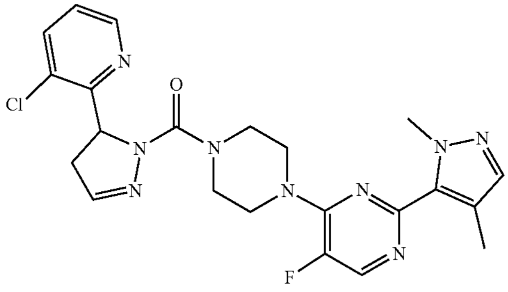 [SMILES: Cc1cnn(C)c1-c1ncc(F)c(N2CCN(C(=O)N3N=CCC3c3ncccc3Cl)CC2)n1]
261
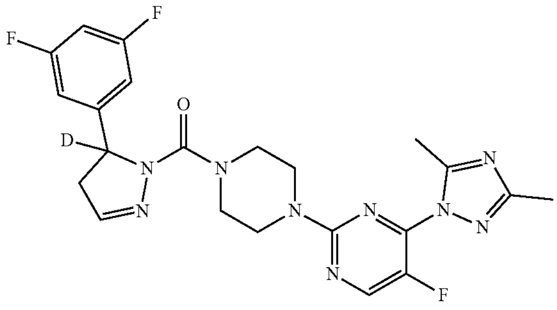 [SMILES: [2H]C1(c2cc(F)cc(F)c2)CC=NN1C(=O)N1CCN(c2ncc(F)c(-n3nc(C)nc3C)n2)CC1]
262
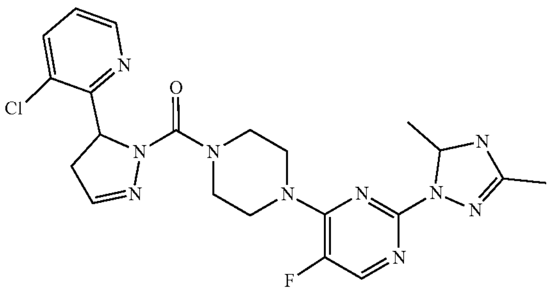 [SMILES: CC1=NN(c2ncc(F)c(N3CCN(C(=O)N4N=CCC4c4ncccc4Cl)CC3)n2)C(C)N1]
263

TABLE 2-continued
| Active Compounds: Structures (Compounds 143-323) |
| --- |
| 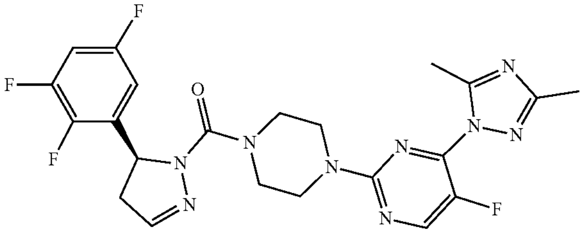 [SMILES: Cc1nc(C)n(-c2nc(N3CCN(C(=O)N4N=CC[C@H]4c4cc(F)cc(F)c4F)CC3)ncc2F)n1] 264 |
| 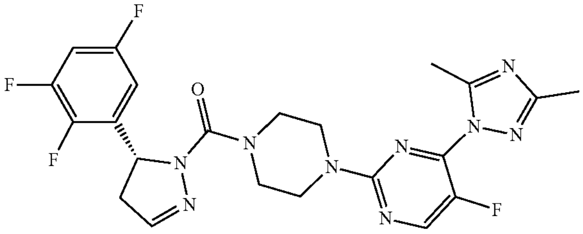 [SMILES: Cc1nc(C)n(-c2nc(N3CCN(C(=O)N4N=CC[C@@H]4c4cc(F)cc(F)c4F)CC3)ncc2F)n1] 265 |
| 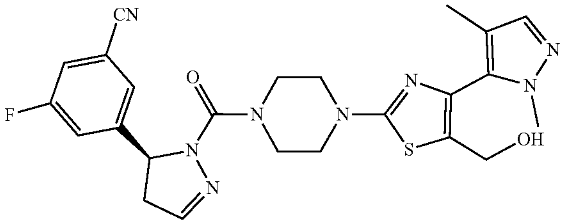 [SMILES: Cc1cnn(C)c1-c1nc(N2CCN(C(=O)N3N=CC[C@H]3c3cc(F)cc(C#N)c3)CC2)sc1CO] 266 |
| 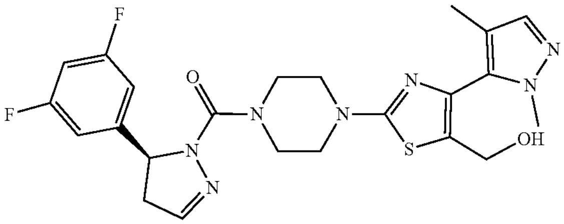 [SMILES: Cc1cnn(C)c1-c1nc(N2CCN(C(=O)N3N=CC[C@H]3c3cc(F)cc(F)c3)CC2)sc1CO] 267 |
| 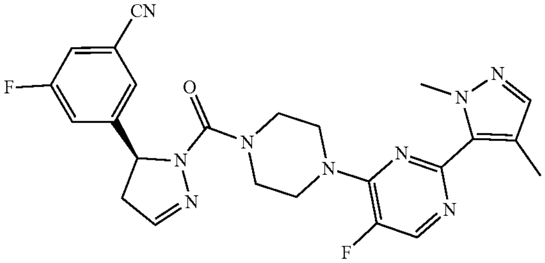 [SMILES: Cc1cnn(C)c1-c1ncc(F)c(N2CCN(C(=O)N3N=CC[C@H]3c3cc(F)cc(C#N)c3)CC2)n1] 268 |
| 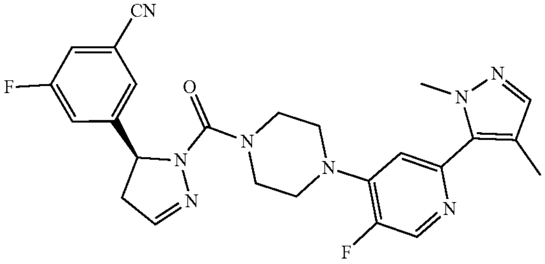 [SMILES: Cc1cnn(C)c1-c1cc(N2CCN(C(=O)N3N=CC[C@H]3c3cc(F)cc(C#N)c3)CC2)c(F)cn1] 269 |

TABLE 2-continued
| Active Compounds: Structures (Compounds 143-323) | |
|---|---|
| 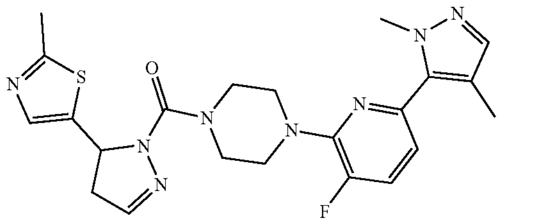 [SMILES: Cc1ncc(C2CC=NN2C(=O)N2CCN(c3nc(-c4c(C)cnn4C)ccc3F)CC2)s1] | 270 |
| 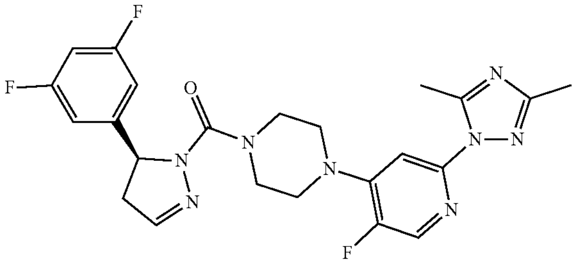 [SMILES: Cc1nc(C)n(-c2cc(N3CCN(C(=O)N4N=CC[C@H]4c4cc(F)cc(F)c4)CC3)c(F)cn2)n1] | 271 |
| 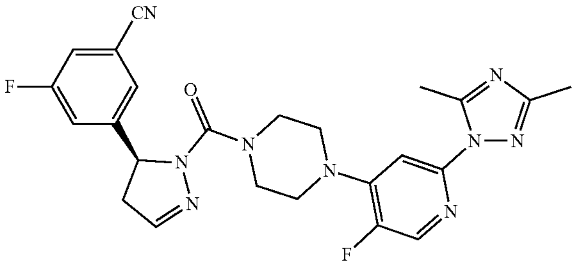 [SMILES: Cc1nc(C)n(-c2cc(N3CCN(C(=O)N4N=CC[C@H]4c4cc(F)cc(C#N)c4)CC3)c(F)cn2)n1] | 272 |
| 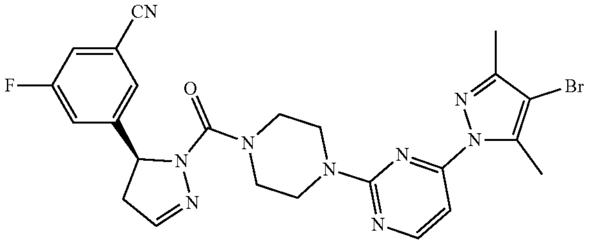 [SMILES: Cc1nn(-c2ccnc(N3CCN(C(=O)N4N=CC[C@H]4c4cc(F)cc(C#N)c4)CC3)n2)c(C)c1Br] | 273 |
| 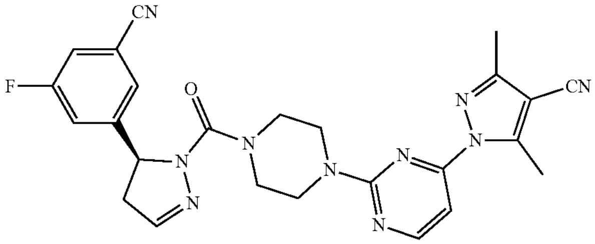 [SMILES: Cc1nn(-c2ccnc(N3CCN(C(=O)N4N=CC[C@H]4c4cc(F)cc(C#N)c4)CC3)n2)c(C)c1C#N] | 274 |
| 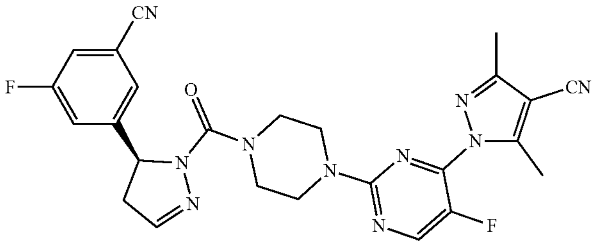 [SMILES: Cc1nn(-c2nc(N3CCN(C(=O)N4N=CC[C@H]4c4cc(F)cc(C#N)c4)CC3)ncc2F)c(C)c1C#N] | 275 |

TABLE 2-continued
Active Compounds: Structures (Compounds 143-323)
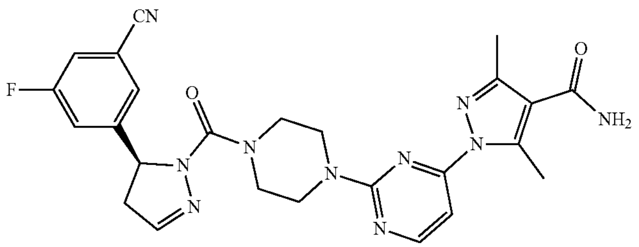 [SMILES: Cc1nn(-c2ccnc(N3CCN(C(=O)N4N=CC[C@H]4c4cc(F)cc(C#N)c4)CC3)n2)c(C)c1C(N)=O]
276
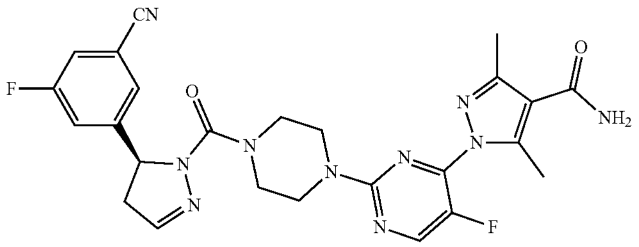 [SMILES: Cc1nn(-c2nc(N3CCN(C(=O)N4N=CC[C@H]4c4cc(F)cc(C#N)c4)CC3)ncc2F)c(C)c1C(N)=O]
277
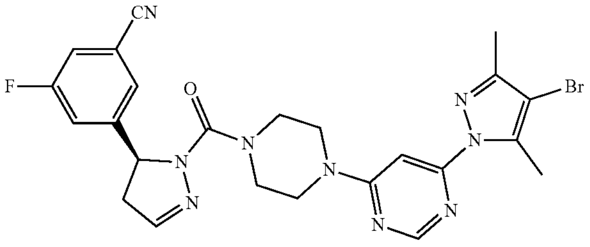 [SMILES: Cc1nn(-c2cc(N3CCN(C(=O)N4N=CC[C@H]4c4cc(F)cc(C#N)c4)CC3)ncn2)c(C)c1Br]
278
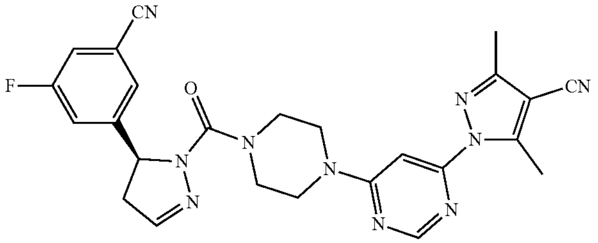 [SMILES: Cc1nn(-c2cc(N3CCN(C(=O)N4N=CC[C@H]4c4cc(F)cc(C#N)c4)CC3)ncn2)c(C)c1C#N]
279
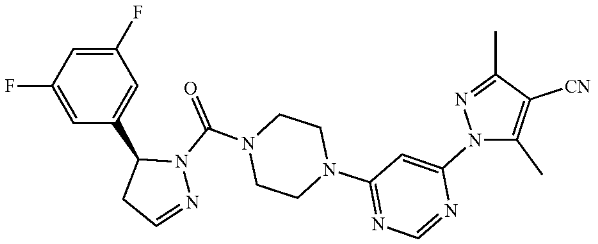 [SMILES: Cc1nn(-c2cc(N3CCN(C(=O)N4N=CC[C@H]4c4cc(F)cc(F)c4)CC3)ncn2)c(C)c1C#N]
280
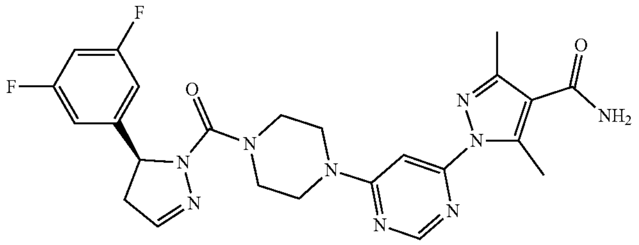 [SMILES: Cc1nn(-c2cc(N3CCN(C(=O)N4N=CC[C@H]4c4cc(F)cc(F)c4)CC3)ncn2)c(C)c1C(N)=O]
281

TABLE 2-continued
| Active Compounds: Structures (Compounds 143-323) | |
|---|---|
| 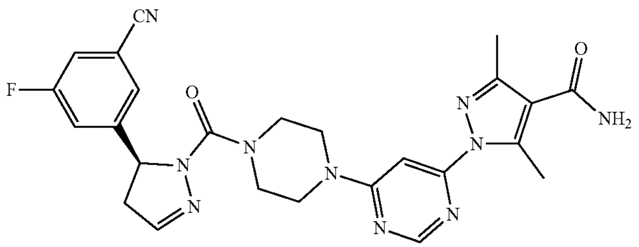 [SMILES: Cc1nn(-c2cc(N3CCN(C(=O)N4N=CC[C@H]4c4cc(F)cc(C#N)c4)CC3)ncn2)c(C)c1C(N)=O] | 282 |
| 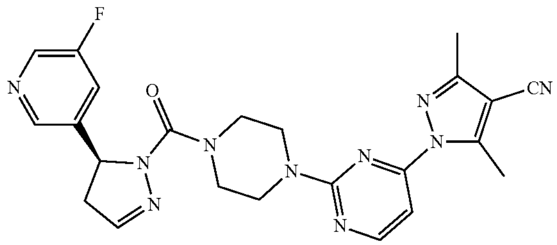 [SMILES: Cc1nn(-c2ccnc(N3CCN(C(=O)N4N=CC[C@H]4c4cncc(F)c4)CC3)n2)c(C)c1C#N] | 283 |
| 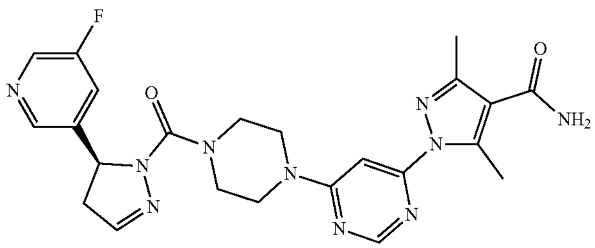 [SMILES: Cc1nn(-c2cc(N3CCN(C(=O)N4N=CC[C@H]4c4cncc(F)c4)CC3)ncn2)c(C)c1C(N)=O] | 284 |
| 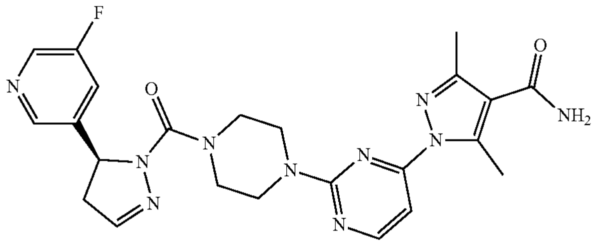 [SMILES: Cc1nn(-c2ccnc(N3CCN(C(=O)N4N=CC[C@H]4c4cncc(F)c4)CC3)n2)c(C)c1C(N)=O] | 285 |
| 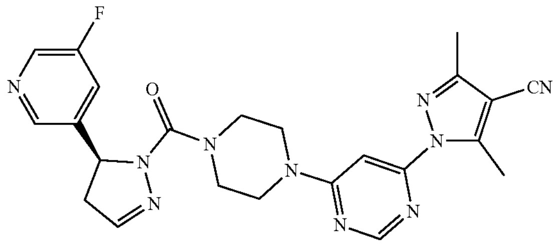 [SMILES: Cc1nn(-c2cc(N3CCN(C(=O)N4N=CC[C@H]4c4cncc(F)c4)CC3)ncn2)c(C)c1C#N] | 286 |
| 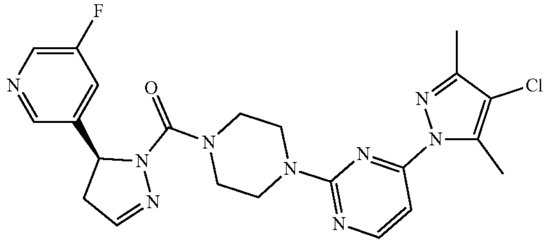 [SMILES: Cc1nn(-c2ccnc(N3CCN(C(=O)N4N=CC[C@H]4c4cncc(F)c4)CC3)n2)c(C)c1Cl] | 287 |

TABLE 2-continued
Active Compounds: Structures (Compounds 143-323)
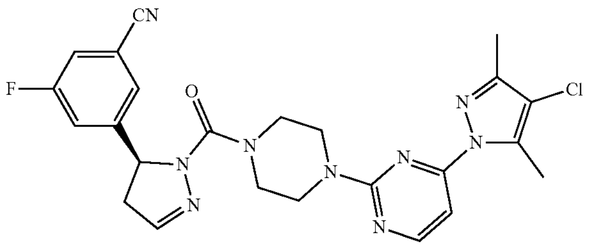
288
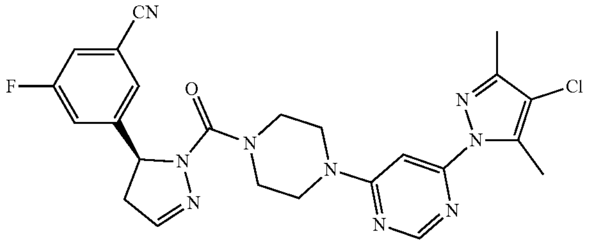
289
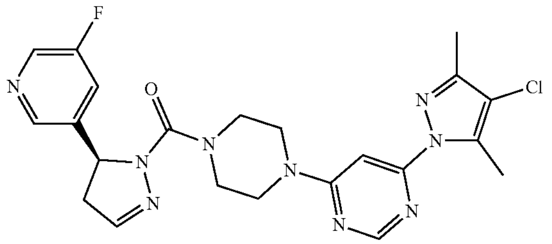 [SMILES: Cc1nn(-c2cc(N3CCN(C(=O)N4N=CC[C@H]4c4cncc(F)c4)CC3)ncn2)c(C)c1Cl]
290
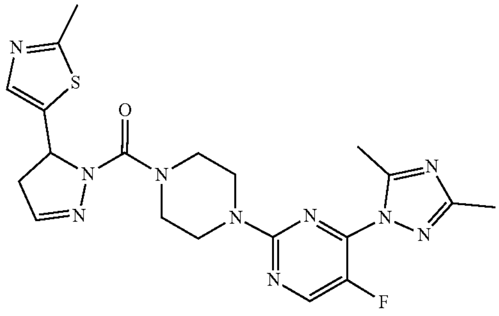 [SMILES: Cc1nc(C)n(-c2nc(N3CCN(C(=O)N4N=CCC4c4cnc(C)s4)CC3)ncc2F)n1]
291
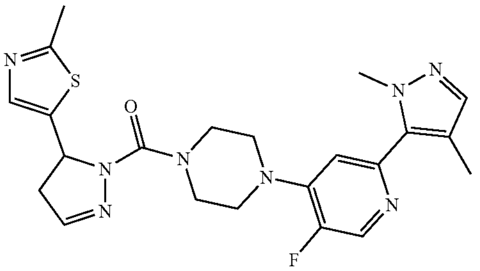 [SMILES: Cc1ncc(C2CC=NN2C(=O)N2CCN(c3cc(-c4c(C)cnn4C)ncc3F)CC2)s1]
292
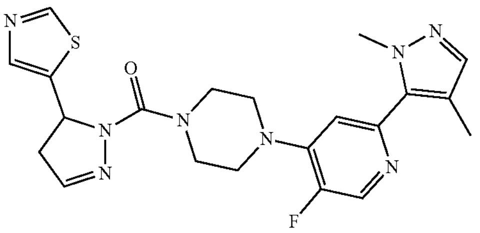 [SMILES: Cc1cnn(C)c1-c1cc(N2CCN(C(=O)N3N=CCC3c3cncs3)CC2)c(F)cn1]
293

TABLE 2-continued
| Active Compounds: Structures (Compounds 143-323) | |
|---|---|
| 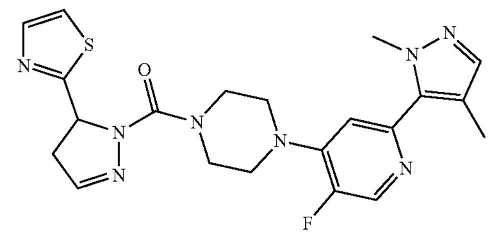 [SMILES: Cc1cnn(C)c1-c1cc(N2CCN(C(=O)N3N=CCC3c3nccs3)CC2)c(F)cn1] | 294 |
| 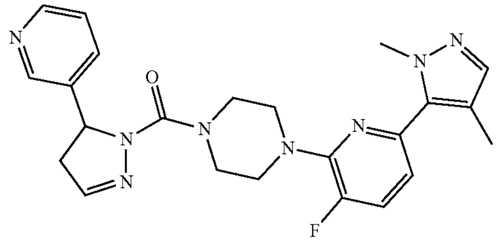 [SMILES: Cc1cnn(C)c1-c1ccc(F)c(N2CCN(C(=O)N3N=CCC3c3cccnc3)CC2)n1] | 295 |
| 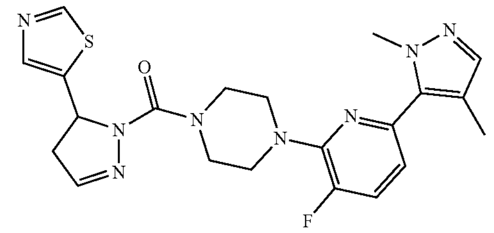 [SMILES: Cc1cnn(C)c1-c1ccc(F)c(N2CCN(C(=O)N3N=CCC3c3cncs3)CC2)n1] | 296 |
| 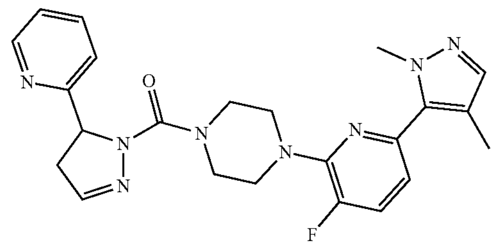 [SMILES: Cc1cnn(C)c1-c1ccc(F)c(N2CCN(C(=O)N3N=CCC3c3ccccn3)CC2)n1] | 297 |
| 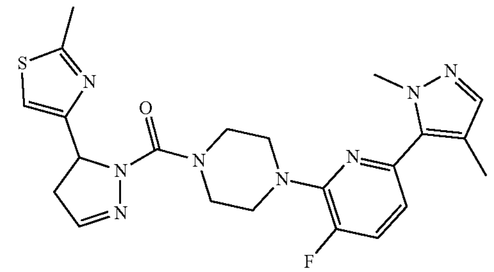 [SMILES: Cc1nc(C2CC=NN2C(=O)N2CCN(c3nc(-c4c(C)cnn4C)ccc3F)CC2)cs1] | 298 |
| 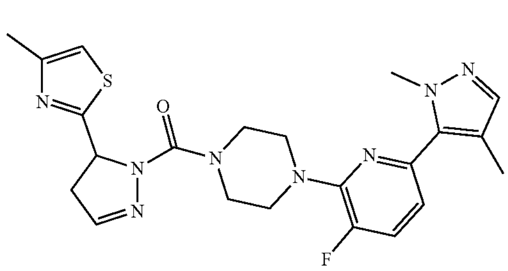 | 299 |

TABLE 2-continued
| Active Compounds: Structures (Compounds 143-323) |
| --- |
300
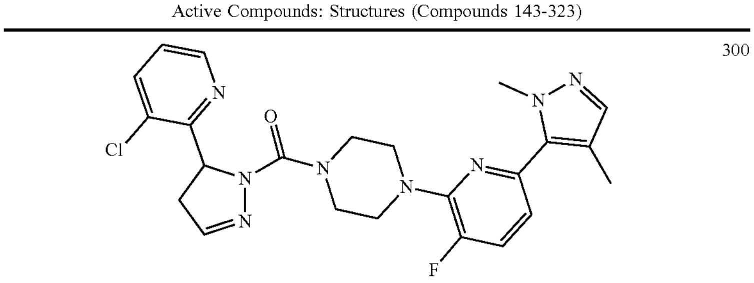
301
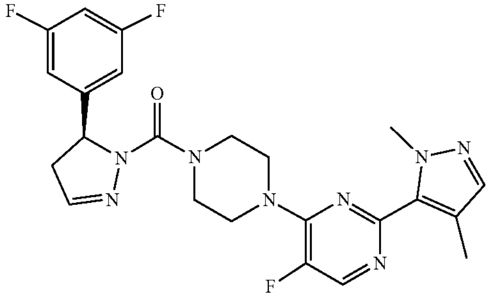 [SMILES: Cc1cnn(C)c1-c1ncc(F)c(N2CCN(C(=O)N3N=CC[C@H]3c3cc(F)cc(F)c3)CC2)n1]
302
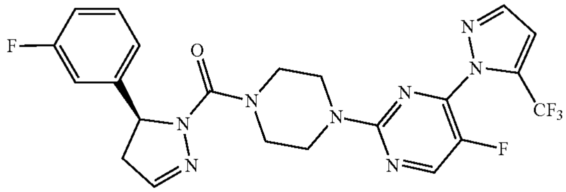 [SMILES: O=C(N1CCN(c2ncc(F)c(-n3nccc3C(F)(F)F)n2)CC1)N1N=CC[C@H]1c1cccc(F)c1]
303
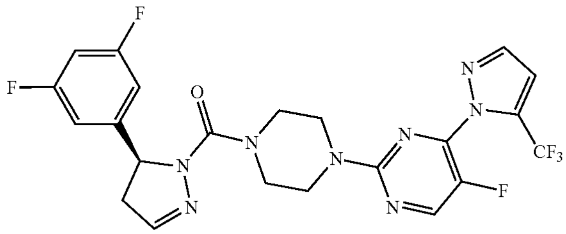 [SMILES: O=C(N1CCN(c2ncc(F)c(-n3nccc3C(F)(F)F)n2)CC1)N1N=CC[C@H]1c1cc(F)cc(F)c1]
304
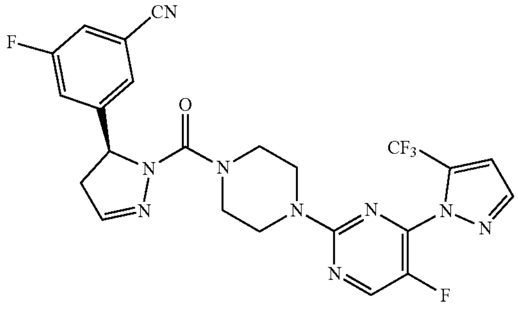 [SMILES: N#Cc1cc(F)cc([C@@H]2CC=NN2C(=O)N2CCN(c3ncc(F)c(-n4nccc4C(F)(F)F)n3)CC2)c1]

TABLE 2-continued
Active Compounds: Structures (Compounds 143-323)
305
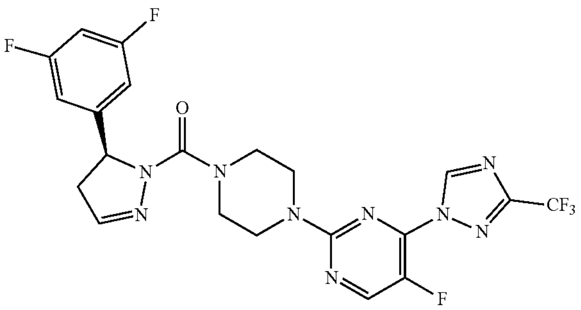 [SMILES: O=C(N1CCN(c2ncc(F)c(-n3cnc(C(F)(F)F)n3)n2)CC1)N1N=CC[C@H]1c1cc(F)cc(F)c1]
306
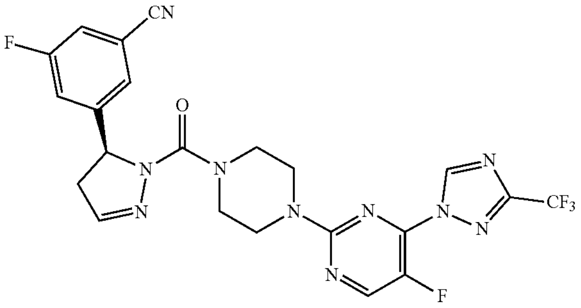 [SMILES: N#Cc1cc(F)cc([C@@H]2CC=NN2C(=O)N2CCN(c3ncc(F)c(-n4cnc(C(F)(F)F)n4)n3)CC2)c1]
307
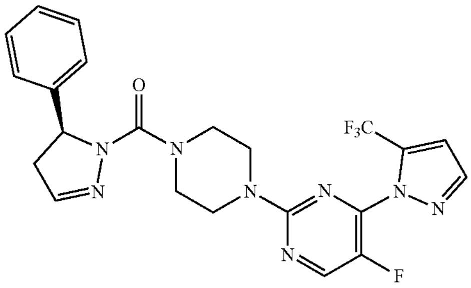 [SMILES: O=C(N1CCN(c2ncc(F)c(-n3nccc3C(F)(F)F)n2)CC1)N1N=CC[C@H]1c1ccccc1]
308
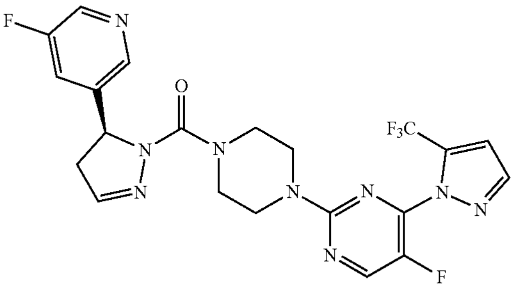 [SMILES: O=C(N1CCN(c2ncc(F)c(-n3nccc3C(F)(F)F)n2)CC1)N1N=CC[C@H]1c1cncc(F)c1]
309
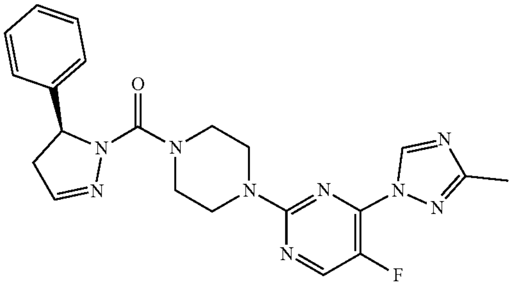 [SMILES: Cc1ncn(-c2nc(N3CCN(C(=O)N4N=CC[C@H]4c4ccccc4)CC3)ncc2F)n1]

TABLE 2-continued
| Active Compounds: Structures (Compounds 143-323) |
| --- |
| 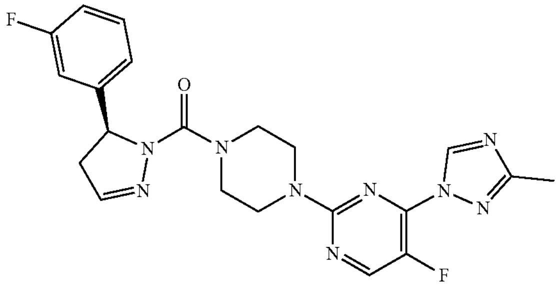 [SMILES: Cc1ncn(-c2nc(N3CCN(C(=O)N4N=CC[C@H]4c4cccc(F)c4)CC3)ncc2F)n1] 310 |
| 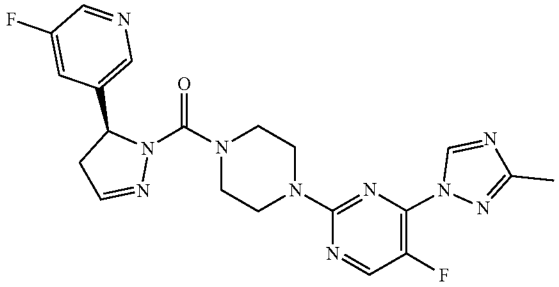 [SMILES: Cc1ncn(-c2nc(N3CCN(C(=O)N4N=CC[C@H]4c4cncc(F)c4)CC3)ncc2F)n1] 311 |
| 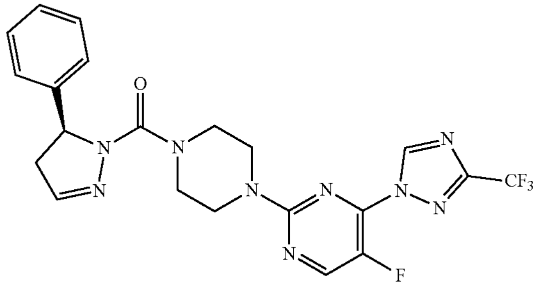 [SMILES: O=C(N1CCN(c2ncc(F)c(-n3cnc(C(F)(F)F)n3)n2)CC1)N1N=CC[C@H]1c1ccccc1] 312 |
| 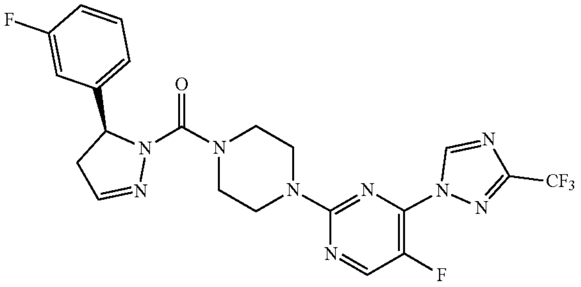 [SMILES: O=C(N1CCN(c2ncc(F)c(-n3cnc(C(F)(F)F)n3)n2)CC1)N1N=CC[C@H]1c1cccc(F)c1] 313 |
| 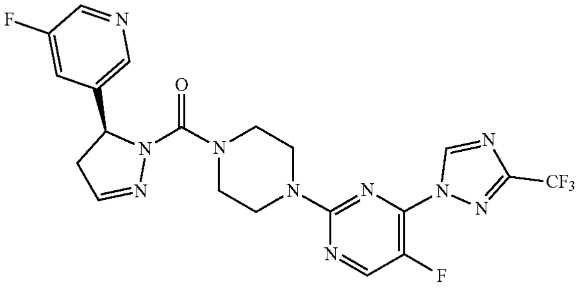 [SMILES: O=C(N1CCN(c2ncc(F)c(-n3cnc(C(F)(F)F)n3)n2)CC1)N1N=CC[C@H]1c1cncc(F)c1] 314 |

TABLE 2-continued
Active Compounds: Structures (Compounds 143-323)
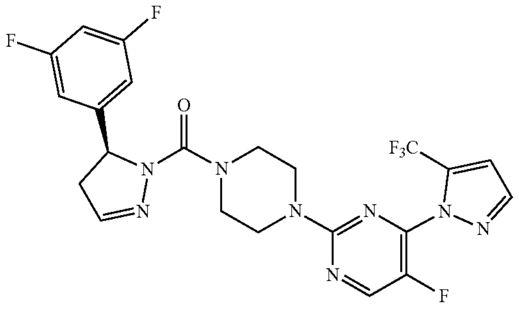 [SMILES: O=C(N1CCN(c2ncc(F)c(-n3nccc3C(F)(F)F)n2)CC1)N1N=CC[C@H]1c1cc(F)cc(F)c1]
315
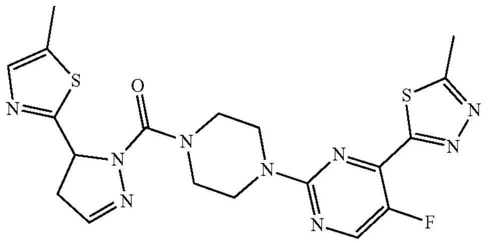 [SMILES: Cc1cnc(C2CC=NN2C(=O)N2CCN(c3ncc(F)c(-c4nnc(C)s4)n3)CC2)s1]
316
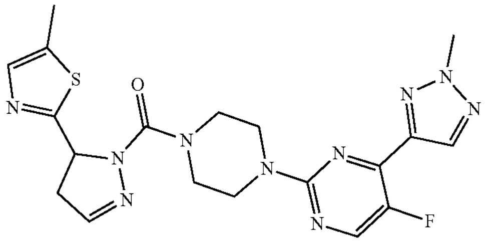 [SMILES: Cc1cnc(C2CC=NN2C(=O)N2CCN(c3ncc(F)c(-c4cnn(C)n4)n3)CC2)s1]
317
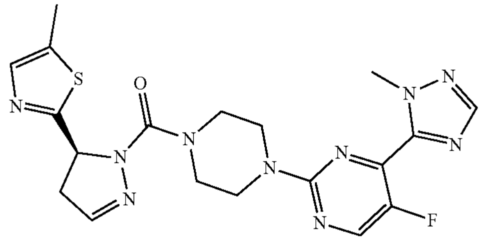 [SMILES: Cc1cnc([C@@H]2CC=NN2C(=O)N2CCN(c3ncc(F)c(-c4ncnn4C)n3)CC2)s1]
318
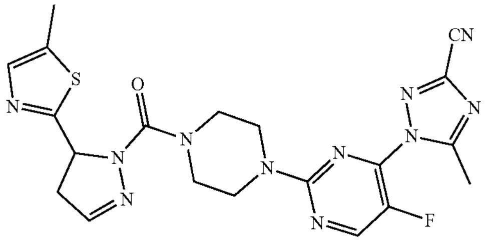 [SMILES: Cc1cnc(C2CC=NN2C(=O)N2CCN(c3ncc(F)c(-n4nc(C#N)nc4C)n3)CC2)s1]
319
TABLE 3
| Cell activity; Necrosis/Necroptosis Inhibitory Activity (Compounds 1-142) | |
|---|---|
| # | $EC_{50}$ |
| 1 | +++ |
| 2 | +++ |
| 3 | +++ |
| 4 | +++ |
TABLE 3-continued
| Cell activity; Necrosis/Necroptosis Inhibitory Activity (Compounds 1-142) | |
|---|---|
| # | $EC_{50}$ |
| 5 | +++ |
| 6 | +++ |
| 7 | +++ |
| 8 | +++ |

TABLE 3-continued

| Cell activity; Necrosis/Necroptosis Inhibitory Activity (Compounds 1-142) | |
|---|---|
| # | $EC_{50}$ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | +++ |
| 48 | +++ |
| 49 | +++ |
| 50 | +++ |
| 51 | +++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |
| 72 | +++ |
| 73 | +++ |
| 74 | +++ |
| 75 | +++ |
| 76 | +++ |
| 77 | +++ |
| 78 | +++ |
| 79 | +++ |
| 80 | +++ |
| 81 | +++ |
| 82 | +++ |
| 83 | +++ |

TABLE 3-continued

| Cell activity; Necrosis/Necroptosis Inhibitory Activity (Compounds 1-142) | |
|---|---|
| # | $EC_{50}$ |
| 84 | +++ |
| 85 | +++ |
| 86 | +++ |
| 87 | +++ |
| 88 | +++ |
| 89 | +++ |
| 90 | +++ |
| 91 | +++ |
| 92 | +++ |
| 93 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | +++ |
| 112 | +++ |
| 113 | +++ |
| 114 | +++ |
| 115 | +++ |
| 116 | +++ |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | +++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |

TABLE 4

| Cell activity; Necrosis/Necroptosis Inhibitory Activity (Compounds 143-323) | |
|---|---|
| Compd No. | $EC_{50}$ |
| 143 | +++ |
| 144 | +++ |
| 145 | +++ |
| 146 | + |
| 147 | +++ |

TABLE 4-continued

Cell activity; Necrosis/Necroptosis Inhibitory Activity (Compounds 143-323)

| Compd No. | $EC_{50}$ |
|---|---|
| 148 | +++ |
| 149 | +++ |
| 150 | +++ |
| 151 | +++ |
| 152 | + |
| 153 | +++ |
| 154 | +++ |
| 155 | +++ |
| 156 | ++ |
| 157 | ++ |
| 158 | +++ |
| 159 | +++ |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | +++ |
| 173 | +++ |
| 174 | +++ |
| 175 | +++ |
| 176 | +++ |
| 177 | ++ |
| 178 | +++ |
| 179 | +++ |
| 180 | +++ |
| 181 | +++ |
| 182 | +++ |
| 183 | +++ |
| 184 | +++ |
| 185 | +++ |
| 186 | +++ |
| 187 | +++ |
| 188 | +++ |
| 189 | +++ |
| 190 | + |
| 191 | +++ |
| 192 | +++ |
| 193 | +++ |
| 194 | +++ |
| 195 | +++ |
| 196 | +++ |
| 197 | + |
| 198 | +++ |
| 199 | +++ |
| 200 | +++ |
| 201 | +++ |
| 202 | +++ |
| 203 | +++ |
| 204 | +++ |
| 205 | +++ |
| 206 | +++ |
| 207 | +++ |
| 208 | +++ |
| 209 | ++ |
| 210 | +++ |
| 211 | +++ |
| 212 | ++ |
| 213 | ++ |
| 214 | +++ |
| 215 | +++ |
| 216 | +++ |
| 217 | +++ |
| 218 | +++ |
| 219 | +++ |
| 220 | +++ |
| 221 | +++ |
| 222 | +++ |

TABLE 4-continued

Cell activity; Necrosis/Necroptosis Inhibitory Activity (Compounds 143-323)

| Compd No. | $EC_{50}$ |
|---|---|
| 223 | +++ |
| 224 | ++ |
| 225 | +++ |
| 226 | +++ |
| 227 | +++ |
| 228 | +++ |
| 229 | +++ |
| 230 | ++ |
| 231 | +++ |
| 232 | +++ |
| 233 | +++ |
| 234 | +++ |
| 235 | +++ |
| 236 | +++ |
| 237 | +++ |
| 238 | +++ |
| 239 | + |
| 240 | +++ |
| 241 | +++ |
| 242 | +++ |
| 243 | +++ |
| 244 | +++ |
| 245 | +++ |
| 246 | +++ |
| 247 | +++ |
| 248 | +++ |
| 249 | +++ |
| 250 | +++ |
| 251 | +++ |
| 252 | +++ |
| 253 | +++ |
| 254 | +++ |
| 255 | +++ |
| 256 | +++ |
| 257 | +++ |
| 258 | +++ |
| 259 | +++ |
| 260 | +++ |
| 261 | +++ |
| 262 | +++ |
| 263 | ++ |
| 264 | +++ |
| 265 | ++ |
| 266 | + |
| 267 | + |
| 268 | +++ |
| 269 | +++ |
| 270 | +++ |
| 271 | +++ |
| 272 | +++ |
| 273 | +++ |
| 274 | +++ |
| 275 | +++ |
| 276 | +++ |
| 277 | +++ |
| 278 | +++ |
| 279 | +++ |
| 280 | +++ |
| 281 | +++ |
| 282 | +++ |
| 283 | +++ |
| 284 | ++ |
| 285 | +++ |
| 286 | +++ |
| 287 | +++ |
| 288 | +++ |
| 289 | +++ |
| 290 | +++ |
| 291 | +++ |
| 292 | ++ |
| 293 | +++ |
| 294 | ++ |
| 295 | +++ |
| 296 | +++ |
| 297 | +++ |

TABLE 4-continued

| Cell activity; Necrosis/Necroptosis Inhibitory Activity (Compounds 143-323) | |
|---|---|
| Compd No. | $EC_{50}$ |
| 298 | +++ |
| 299 | +++ |
| 300 | +++ |
| 301 | +++ |
| 302 | +++ |
| 303 | +++ |
| 304 | +++ |
| 305 | +++ |
| 306 | +++ |
| 307 | +++ |
| 308 | +++ |
| 309 | +++ |
| 310 | +++ |
| 311 | +++ |
| 312 | +++ |
| 313 | +++ |
| 314 | +++ |
| 315 | +++ |
| 316 | +++ |
| 317 | ++ |
| 318 | +++ |
| 319 | +++ |

Active Compounds: Representative Synthesis

Compound 1: (S)-(4-(4-(1H-pyrazol-5-yl)pyrimidin-2-yl)piperazin-1-yl)(5-(3,5-difluorophenyl)-4,5-dihydro-1H-pyrazol-1-yl)methanone

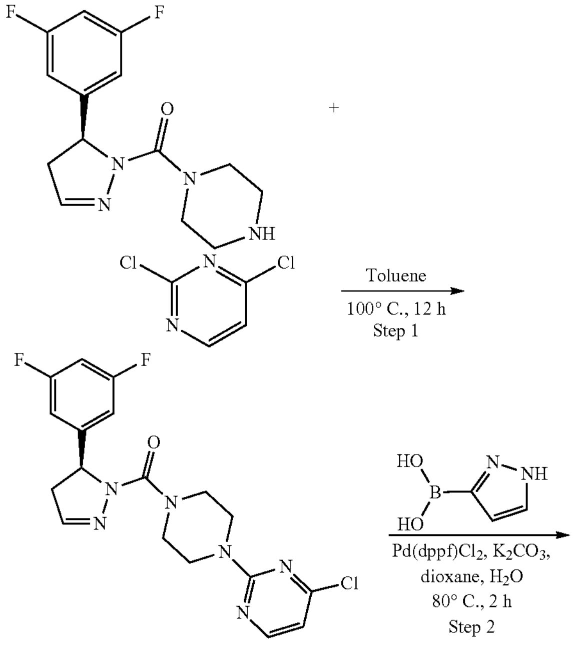

-continued

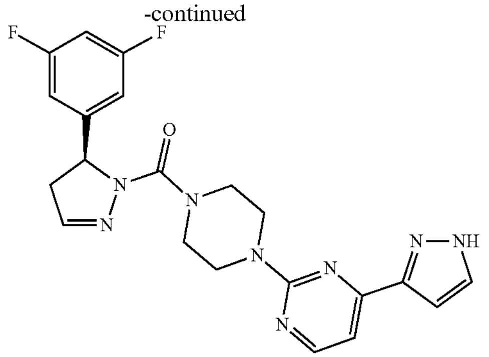

Step 1: To a solution of (S)-(5-(3,5-difluorophenyl)-4,5-dihydro-1H-pyrazol-1-yl) (piperazin-1-yl)methanone (800 mg, 2.72 mmol) in toluene (50 mL) was added 2,4-dichloropyrimidine (446 mg, 3.0 mmol). The reaction mixture was stirred at 100° C. for 12 h. The solvent was removed under vacuum and the crude purified by reversed-phase chromatography. 210 mg target was obtained as a white solid. Yield: 19.0%. LC-MS (m/z) 407.1 ($M+H^+$).

Step 2: To a solution of (S)-(4-(4-chloropyrimidin-2-yl) piperazin-1-yl)(5-(3,5-difluorophenyl)-4,5-dihydro-1H-pyrazol-1-yl)methanone (50 mg, 122.9 umol) in dioxane (3 mL) and $H_2O$ (1 mL) was added (1H-pyrazol-3-yl)boronic acid (28 mg, 184.4 umol), $Pd(dppf)Cl_2$ (20 mg, 24.6 umol) and $K_2CO_3$ (35 mg, 245.8 umol) under Ar. The reaction mixture was stirred at 80° C. for 2 h. The crude was purified by Pre-HPLC. 18 mg of the titled compound 1 was obtained as a white solid. Yield: 33.4%. LC-MS (m/z) 407.1 ($M+H^+$). $^1H$ NMR (400 MHz, $CDCl_3$) δ (ppm): 8.37 (dd, J=5.1, 0.9 Hz, 1H), 7.64 (d, J=2.1, 1H), 6.93 (d, J=5.1, 1H), 6.88-6.77 (m, 4H), 6.71-6.65 (m, 1H), 5.34 (dd, J=11.7, 9.8 Hz, 1H), 4.02-3.96 (m, 2H), 3.90-3.76 (m, 4H), 3.69-3.62 (m, 2H), 3.36-3.27 (m, 1H), 2.72-2.64 (m, 1H).

Compound 2: (S)-1-(2-(4-(5-(3,5-difluorophenyl)-4,5-dihydro-1H-pyrazole-1-carbonyl)piperazin-1-yl)pyrimidin-4-yl)-1H-imidazole-4-carbonitrile

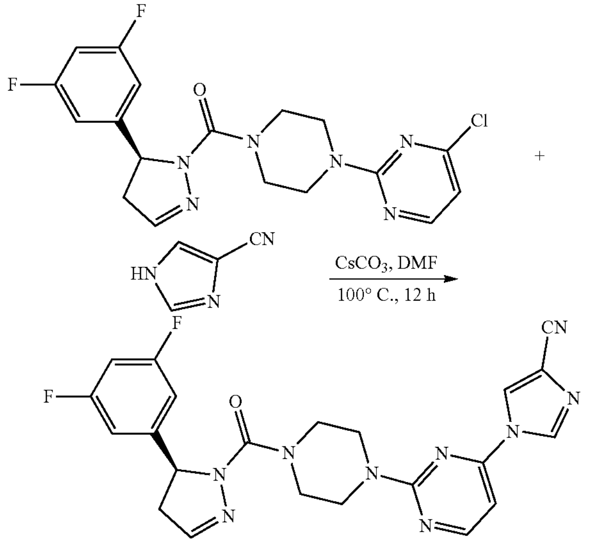

To a solution of (S)-(4-(4-chloropyrimidin-2-yl)piperazin-1-yl)(5-(3,5-difluorophenyl)-4,5-dihydro-1H-pyrazol-1-yl)methanone (100 mg, 0.246 mmol) in DMF (5 mL) was added 1H-imidazole-4-carbonitrile (26 mg, 0.271 mmol) and $CsCO_3$ (95 mg, 0.492 mmol). The reaction was stirred at 100° C. for 12 h. The crude product was purified by Pre-HPLC to give the titled compound 2 (15 mg) was obtained as a white solid. Yield: 13.2%. LC-MS (m/z) 464.1 ($M+H^+$). $^1H$ NMR (400 MHz, $CDCl_3$) δ (ppm): 8.37 (d, J=5.2 Hz, 1H), 8.25 (d, J=1.3 Hz, 1H), 8.10 (d, J=1.3 Hz, 1H), 6.83-6.69 (m, 3H), 6.62 (tt, J=8.9, 2.3 Hz, 1H), 6.47 (d, J=5.3 Hz, 1H), 5.26 (dd, J=11.7, 9.8 Hz, 1H), 3.95-3.53 (m, 8H), 3.25 (ddd, J=18.3, 11.8, 1.8 Hz, 1H), 2.62 (ddd, J=18.3, 9.8, 1.6 Hz, 1H).

Compound 3: (S)-(5-(3,5-difluorophenyl)-4,5-dihydro-1H-pyrazol-1-yl)(4-(4-(4,5-dihydro-1H-imidazol-2-yl)pyrimidin-2-yl)piperazin-1-yl)methanone

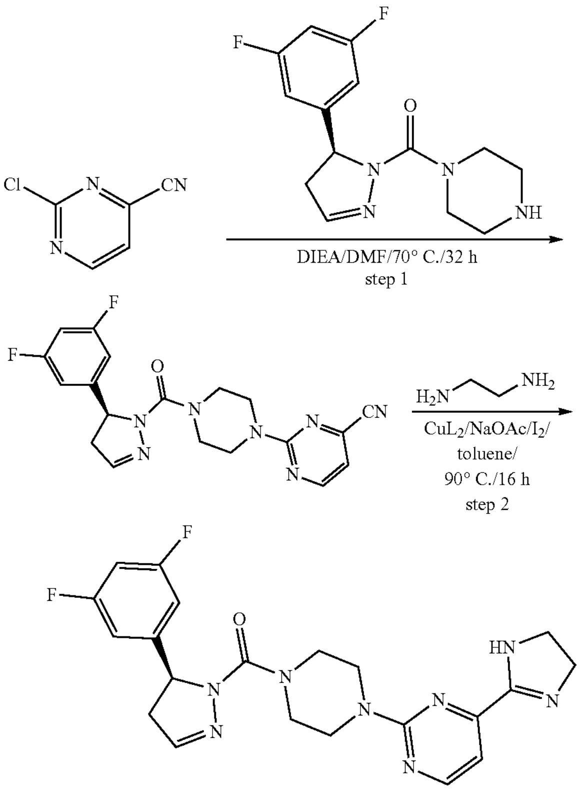

Step1: (R)-2-hydroxy-2-phenylacetic acid (1.52 g, 0.01 mol) was added in portions to the solution of NaOH (0.32 g, 0.008 mol) in 14 ml $H_2O$. Copper(II) chloride (0.538 g, 0.004 mol) in 14 ml $H_2O$ was added dropwise to the solution. Let it stir at r.t for 5 min. The blue solid was filtered and washed with $H_2O$. It was dried in vacuo to give 1.328 g bis((R)-2-hydroxy phenylacetoxy)copper ligand as blue solid. Yield: 90.2%. 2-chloropyrimidine-4-carbonitrile (52.2 mg, 0.37 mmol) and (S)-(5-(3,5-difluorophenyl)-4,5-dihydro-1H-pyrazol-1-yl)(piperazin-1-yl)methanone (100 mg, 0.34 mmol) were dissolved in 3 mL DMF. 0.3 mL DIEA was added. Let it stir at 70° C. for 32 hrs. Water was added to the reaction and extracted with EtOAc (15 mL×3). The organic layers were combined and evaporated to dryness and purified by column chromatography (PE/EA=1/1) to give 140 mg (S)-2-(4-(5-(3,5-difluorophenyl)-4,5-dihydro-1H-pyrazole-1-carbonyl)piperazin-1-yl)pyrimidine-4-carbonitrile as brown oil. Yield: quantitative. LC-MS (m/z): 398.2 $[M+H]^+$.

Step 2: (S)-2-(4-(5-(3,5-difluorophenyl)-4,5-dihydro-1H-pyrazole-1-carbonyl)piperazin-1-yl)pyrimidine-4-carbonitrile (140 mg, 0.35 mmol) and bis((R)-2-hydroxy-2-phenylacetoxy)copper ligand (12.9 mg, 0.035 mmol) and AcONa (9.8 mg, 0.12 mmol) and $I_2$ (9 mg, 0.035 mmol) were mixed in 5 ml toluene. Then ethane-1,2-diamine (26.6 mg, 0.443 mmol) was added. Let it stir at 90° C. for 16 hrs. The mixture was filtered and the filtrate was evaporated to dryness and recrystallized with MeOH/EA/PE to give 70 mg of (S)-(5-(3,5-difluorophenyl)-4,5-dihydro-1H-pyrazol-1-yl)(4-(4-(4,5-dihydro-1H-imidazol-2-yl)pyrimidin-2-yl)piperazin-1-yl)methanone as white solid. Yield: 45.5%. $^1H$ NMR (400 MHz, $CDCl_3$) δ (ppm): 8.54 (d, J=4.8 Hz, 1H), 6.99-6.93 (m, 3H), 6.82 (tt, J=8.8, 2.4 Hz, 1H), 5.46 (dd, J=11.6, 10.0 Hz, 1H), 4.10-4.04 (m, 2H), 4.01-3.85 (m, 8H), 3.79-3.74 (m, 2H), 3.45 (ddd, J=18.4, 11.6, 1.6 Hz, 1H), 2.82 (ddd, J=18.4, 10.0, 1.6 Hz, 1H). LC-MS (m/z): 441.3$[M+H]^+$.

Compound 4: (S)-(4-(4-(1H-tetrazol-5-yl)pyrimidin-2-yl)piperazin-1-yl)(5-(3,5-difluorophenyl)-4,5-dihydro-1H-pyrazol-1-yl)methanone

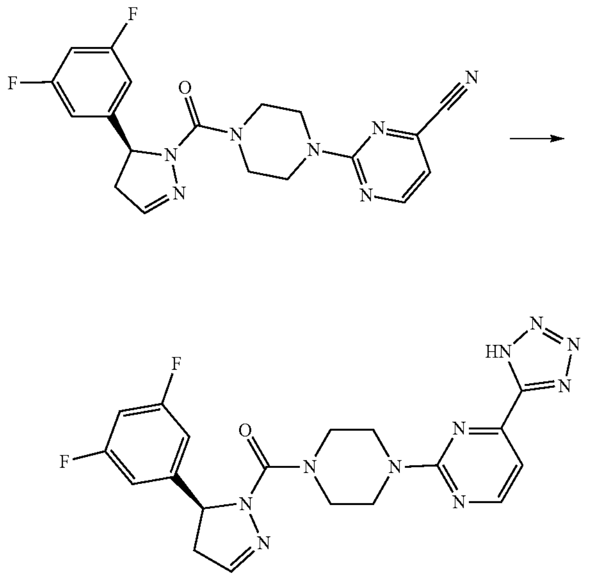

To a solution of (S)-2-(4-(5-(3,5-difluorophenyl)-4,5-dihydro-1H-pyrazole-1-carbonyl)piperazin-1-yl)pyrimidine-4-carbonitrile (40 mg, 100.7 umol) in DMF (4 mL) was added $NaN_3$ (18 mg, 261.7 umol) under Ar. The reaction mixture was stirred at 120° C. for 4 h. The crude was purified by Pre-HPLC (5)-(4-(4-(1H-tetrazol-5-yl)pyrimidin-2-yl)piperazin-1-yl)(5-(3,5-difluorophenyl)-4,5-dihydro-1H-pyrazol-1-yl)methanone (13 mg, 29%) was obtained as a off-white solid. LC-MS (m/z) 441.1 ($M+H^+$).

$^1H$ NMR (400 MHz, DMSO) δ 8.23 (d, J=6.1 Hz, 1H), 7.15-7.05 (m, 2H), 7.05-6.94 (m, 2H), 6.72 (d, J=6.2 Hz, 1H), 5.25 (dd, J=11.6, 9.9 Hz, 1H), 3.87-3.52 (m, 8H), 3.35 (ddd, J=18.3, 11.7, 1.8 Hz, 1H), 2.64 (ddd, J=18.3, 9.9, 1.7 Hz, 1H).

Compound 5: (S)-(4-(2-(1H-pyrrol-2-yl)pyrimidin-4-yl)piperazin-1-yl)(5-(3,5-difluorophenyl)-4,5-dihydro-1H-pyrazol-1-yl)methanone

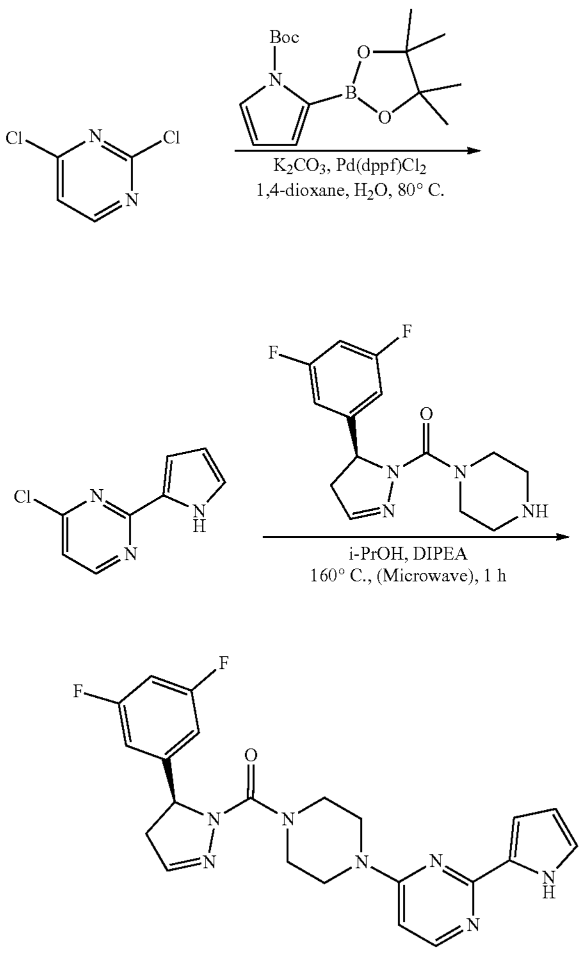

Step 1. 2,4-dichloropyrimidine (360 mg, 2.416 mmoL) and tert-butyl 2-(4,4,5,5-tetramethyl-1,3,2-dioxaborolan-2-yl)-1H-pyrrole-1-carboxylate (608 mg, 2.073 mmoL) and $K_2CO_3$ (666 mg, 4.826 mmoL) were mixed in 15 mL 1,4-dioxane/$H_2O$ (9/1). Pd(dppf)$Cl_2$ (180 mg, 0.246 mmoL) was added. Let it stir at 80° C. under nitrogen for 16 hrs. The solvent was evaporated to dryness and purified by column chromatography (PE/EA=4/1) to give 85 mg mixture as brown oil. Yield: 22.9%. LC-MS (m/z) 180.2 $[M+H]^+$.

Step 2. The above mixture (73 mg, 0.408 mmoL) and (S)-(5-(3,5-difluorophenyl)-4,5-dihydro-1H-pyrazol-1-yl) (piperazin-1-yl)methanone (120 mg, 0.408 mmoL) were mixed in 8 mL i-PrOH. 0.5 mL DIEA was added. Let it stir at 160° C. under microwave for 1 h. The solvent was evaporated to dryness and purified by Prep-TLC (PE/EA=2/1) to give 10 mg of 5 as a light-yellow solid. Yield: 5.6%. LC-MS (m/z) 438.4 $(M+H^+)$. $^1$H NMR (400 MHz, $CDCl_3$) δ (ppm): δ 8.28 (d, J=5.6 Hz, 1H), 7.50 (t, J=2.4 Hz, 2H), 6.82-6.86 (m, 3H), 6.67-6.72 (m, 1H), 6.51 (d, J=5.6 Hz, 1H), 6.34 (t, J=2.4 Hz, 2H), 5.34 (dd, J=10.0, 11.6 Hz, 1H), 3.94-4.00 (m, 2H), 3.75-3.89 (m, 4H), 3.62-3.67 (m, 2H), 3.32 (ddd, J=2.0, 11.6, 13.6 Hz, 1H), 2.69 (ddd, J=1.6, 10.0, 11.6 Hz, 1H).

Compound 6: (S)-(4-(4-(1H-pyrrol-2-yl)pyrimidin-2-yl)piperazin-1-yl)(5-(3,5-difluorophenyl)-4,5-dihydro-1H-pyrazol-1-yl)methanone

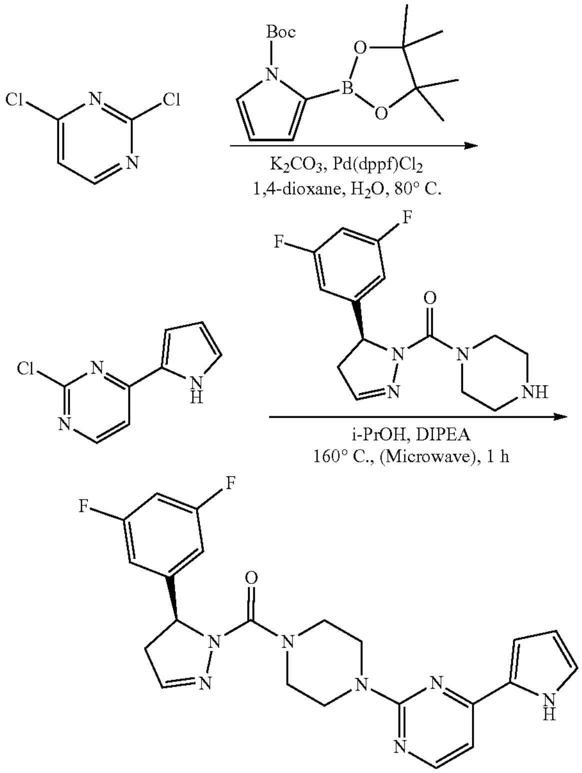

The titled compound 6 was prepared in two steps 7% yield from 2,4-dichloropyrimidine, tert-butyl 2-(4,4,5,5-tetramethyl-1,3,2-dioxaborolan-2-yl)-1H-pyrrole-1-carboxylate and (S)-(5-(3,5-difluorophenyl)-4,5-dihydro-1H-pyrazol-1-yl)(piperazin-1-yl)methanone according to the procedure outlined for compound 5. LC-MS (m/z) 438.4 $(M+H^+)$. $^1$H NMR (400 MHz, $CDCl_3$) δ (ppm): δ 9.60 (s, 1H), 8.22 (d, J=5.2 Hz, 1H), 6.92-6.94 (m, 1H), 6.79-6.85 (m, 4H), 6.73 (d, J=5.2 Hz, 1H), 6.66-6.74 (m, 1H), 6.29-6.31 (m, 1H), 5.33 (dd, J=10.0, 11.6 Hz, 1H), 3.92-3.98 (m, 2H), 3.75-3.82 (m, 4H), 3.61-3.66 (m, 2H), 3.29 (ddd, J=1.6, 11.6, 13.6 Hz, 1H), 2.66 (ddd, J=1.6, 10.0, 11.6 Hz, 1H).

found 463.3 $[M+H]^+$. $^1$H NMR (400 MHz, $CDCl_3$) δ (ppm): δ 8.34 (d, J=2.0 Hz, 1H), 6.78-6.85 (m, 3H), 6.66-6.71 (m, 1H), 5.32 (dd, J=10.0, 11.2 Hz, 1H), 4.43 (q, J=7.2 Hz, 2H), 3.86-3.91 (m, 2H), 3.72-3.81 (m, 4H), 3.59-3.65 (m, 2H), 3.30 (ddd, J=1.6, 11.6, 13.6 Hz, 1H), 2.68 (ddd, J=1.6, 10.0, 11.6 Hz, 1H), 1.40 (t, J=7.2 Hz, 3H).

Compound 7: (S)-(5-(3,5-difluorophenyl)-4,5-dihydro-1H-pyrazol-1-yl)(4-(5-fluoro-4-(1H-pyrazol-3-yl)pyrimidin-2-yl)piperazin-1-yl)methanone

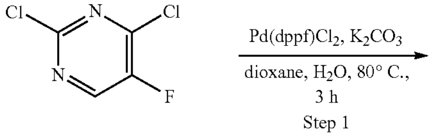

-continued

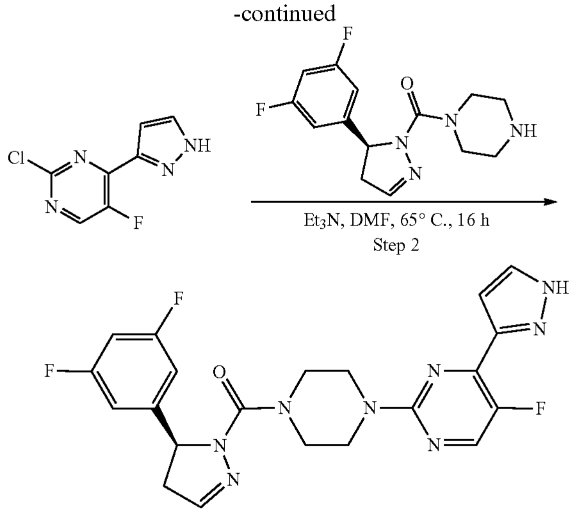

Step1: To a solution 2,4-dichloro-5-fluoropyrimidine (1.0 g, 6.0 mmol) was dissolved in 10 mL of 1.4-dioxane/H2O (5:1) was $K_2CO_3$ (1.65 g, 11.98 mmol) and $Pd(dppf)_2Cl_2$ (240 mg, 2.37 mmol) and were added to the above solution under nitrogen at room temperature. The mixture was stirred for 1.0 h at 80° C. The mixture was extracted with EA, washed with brine, dried (Na2SO4), and concentrated in vacuo. Purification by silica gel chromatography to give the titled compound (700 mg, 58%) as a white solid. (ES, m/s): 199.1 [M+H]+

Step2: To a solution of (S)-(5-(3,5-difluorophenyl)-4,5-dihydro-1H-pyrazol-1-yl)(piperazin-1-yl)methanone (91 mg, 0.3 mmol) and 2-chloro-5-fluoro-4-(1H-pyrazol-3-yl) pyrimidine (68 mg, 0.3 mmol) in DMF (5 mL) was added Et3N (63 mg, 0.6 mmol). The mixture was stirred at 65° C. for overnight. The mixture was extracted with EA, washed with brine, dried (Na2SO4), and concentrated in vacuo. The crude product was purified by pre-TLC (petrol ether/EtOAc=1/1) to give the titled compound 7 (28.6 mg, 45% yield) as a white solid. LCMS (ES, m/z): 457.2$[M+H]^+$. $^1H$ NMR (400 MHz, $CDCl_3$) δ 8.31 (d, J=2.8 Hz, 1H), 7.73-7.63 (m, 1H), 7.04-6.94 (m, 1H), 6.86-6.80 (m, 3H), 6.72-6.66 (m, 1H), 5.34 (dd, J=7.6, 11.2 Hz, 1H), 4.02-3.58 (m, 8H), 3.36 (dd, J=17.3, 12.3 Hz, 1H), 2.71 (ddd, J=18.6, 6.5, 1.7 Hz, 1H).

Compound 8: (S)-(5-(3,5-difluorophenyl)-4,5-dihydro-1H-pyrazol-1-yl)(4-(5-fluoro-4-(1H-1,2,3-triazol-5-yl)pyrimidin-2-yl)piperazin-1-yl)methanone

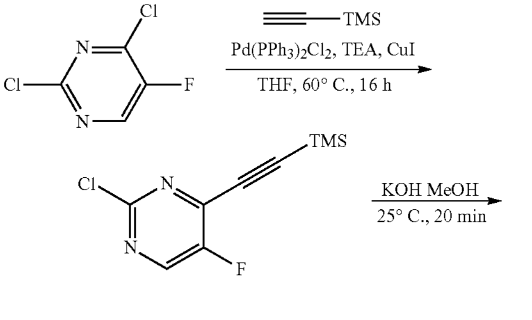

-continued

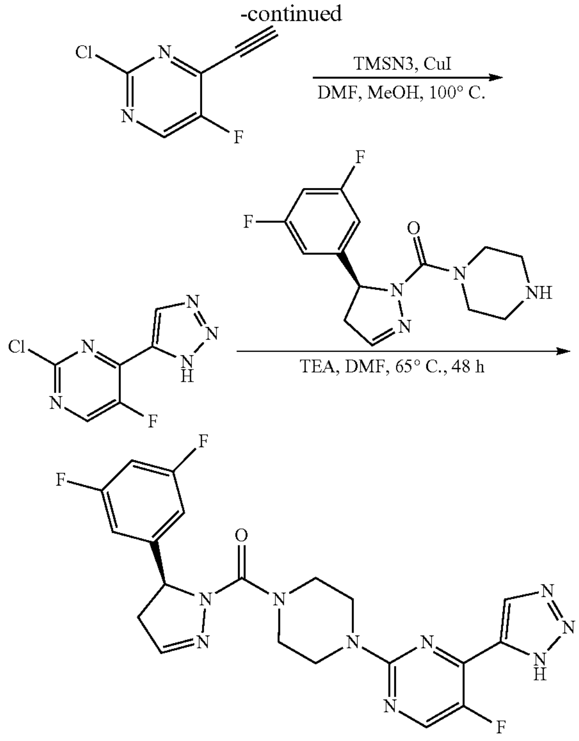

Step 1. 2,4-dichloro-5-fluoropyrimidine (1.699 g, 0.01 moL), $Pd(PPh_3)_2Cl_2$ (176.3 mg, 0.25 mmoL), CuI (128 mg, 0.66 mmoL) and TEA (2.057 g, 0.02 moL) were dissolved 100 mL THF. Let it stir at 60° C. under nitrogen for 30 mins. Then ethynyltrimethylsilane (500 mg, 5.09 mmoL) in 25 mL THF was added slowly to the mixture and let it stir at 60° C. for 16 hrs. The solvent was evaporated to dryness and purified by column chromatography (PE/EA=10/1) to give 0.92 g of 2-chloro-5-fluoro-4-((trimethylsilyl)ethynyl)pyrimidine as a light-yellow solid. Yield: 79.2%. LC-MS (m/z) 229.2 $[M+H]^+$.

Step 2. 2-chloro-5-fluoro-4-((trimethylsilyl)ethynyl)pyrimidine (670 mg, 2.94 mmoL) was dissolved in 5 mL MeOH. 114 ul KOH in MeOH (35 mg KOH in 5 mL MeOH) was added. Let it stir at r.t for 20 mins. The solvent was evaporated to dryness and purified by column chromatography (PE/EA=6/1) to give 0.32 g of 2-chloro-4-ethynyl-5-fluoropyrimidine as a white solid. Yield: quantitative.

Step 3. 2-chloro-4-ethynyl-5-fluoropyrimidine (220 mg, 1.41 mmoL) and TMSN3 (242 mg, 2.1 mmoL), CuI (13.2 mg, 0.07 mmoL) were dissolved in 5 mL DMF/MeOH (9/1) solution. Let it stir at 100° C. for 4 hrs. The solvent was evaporated to dryness and purified by Prep-TLC (DCM/MeOH=12/1) to give 0.14 g of 2-chloro-5-fluoro-4-(1H-1,2,3-triazol-5-yl)pyrimidine as a brown solid. Yield: 49%. LC-MS (m/z) 200.1 $[M+H]^+$.

Step 4. The titled compound 8 was prepared in 16.1% yield from 2-chloro-5-fluoro-4-(1H-1,2,3-triazol-5-yl)pyrimidine and (S)-(5-(3,5-difluorophenyl)-4,5-dihydro-1H-pyrazol-1-yl)(piperazin-1-yl)methanone according to the procedure outlined for compound 7. Mass (ESI): m/z calcd for $C_{20}H_{18}F_3N_9O$ 457.4, found 458.3 $[M+H]^+$. $^1H$ NMR (400 MHz, $CDCl_3$) δ (ppm): δ 8.33 (d, J=2.4 Hz, 1H), 8.28 (d, J=2.0 Hz, 1H), 6.80-6.85 (m, 3H), 6.65-6.69 (m, 1H), 5.36 (t, J=10.4 Hz, 1H), 3.91-3.95 (m, 2H), 3.76-3.87 (m, 4H), 3.61-3.68 (m, 2H), 3.32 (ddd, J=1.2, 12.0, 12.8 Hz, 1H), 2.68 (ddd, J=0.8, 9.6, 10.4 Hz, 1H).

Compound 9: methyl (5)-5-(2-(4-(5-(3,5-difluorophenyl)-4,5-dihydro-1H-pyrazole-1-carbonyl)piperazin-1-yl)pyrimidin-4-yl)-1H-pyrrole-3-carboxylate

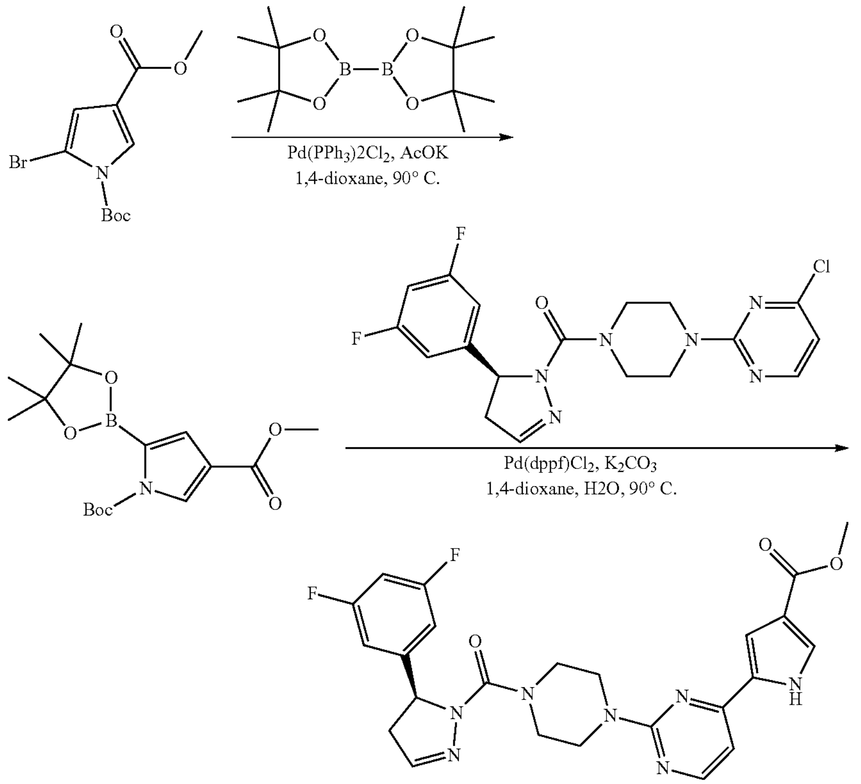

Step 1. 1-(tert-butyl) 3-methyl 5-bromo-1H-pyrrole-1,3-dicarboxylate (614 mg, 2.026 mmoL) and 4,4,4',4',5,5,5',5'-octamethyl-2,2'-bi(1,3,2-dioxaborolane) (1.029 g, 4.05 mmoL) were dissolved in 20 mL 1,4-dioxane. KOAc (380.7 mg, 4.054 mmoL) and $Pd(PPh_3)_2Cl_2$ (66.7 mg, 0.095 mmoL) were added. Let it stir at 90° C. for 16 hrs. The solvent was evaporated to dryness and purified by column chromatography (PE/EA=4/1) to give 1.01 g 1-(tert-butyl) 3-methyl 5-(4,4,5,5-tetramethyl-1,3,2-dioxaborolan-2-yl)-1H-pyrrole-1,3-dicarboxylate as brown oil. Yield: 87.5%. LC-MS (m/z) 270.2 $[M+H]^+$.

Step 2. 1-(tert-butyl) 3-methyl 5-(4,4,5,5-tetramethyl-1,3,2-dioxaborolan-2-yl)-1H-pyrrole-1,3-dicarboxylate (39.6 mg, 0.147 mmoL) and (S)-(4-(4-chloropyrimidin-2-yl)piperazin-1-yl)(5-(3,5-difluorophenyl)-4,5-dihydro-1H-pyrazol-1-yl)methanone (60 mg, 0.147 mmoL), $K_2CO_3$ (41 mg, 0.294 mmoL) and $Pd(dppf)Cl_2$ (10.7 mg, 0.014 mmoL) were dissolved in 3 mL 1,4-dioxane/$H_2O$ (3/1). Let it stir at 90° C. for 16 hrs. The solvent was evaporated to dryness and purified by column chromatography (PE/EA=1/3) to give 35 mg of compound 9 as a white solid. Yield: 47.9%. Mass (ESI): m/z calcd for $C_{24}H_{23}F_2N_7O_3$ 495.5, found 496.4 $[M+H]^+$. $^1H$ NMR (400 MHz, $CDCl_3$) δ (ppm): δ 9.68 (brs, 1H), 8.28-8.32 (m, 1H), 7.55 (s, 1H), 7.21 (s, 1H), 6.80-6.87 (m, 3H), 6.75-6.79 (m, 1H), 6.66-6.74 (m, 1H), 5.35 (t, J=10.4 Hz, 1H), 3.92-4.05 (m, 2H), 3.74-3.91 (m, 7H), 3.60-3.70 (m, 2H), 3.33 (dd, J=12.4, 18.4 Hz, 1H), 2.70 (dd, J=9.6, 18.4 Hz, 1H).

Compound 10: (S)-5-(2-(4-(5-(3,5-difluorophenyl)-4,5-dihydro-1H-pyrazole-1-carbonyl)piperazin-1-yl) pyrimidin-4-yl)-1H-pyrrole-3-carboxamide

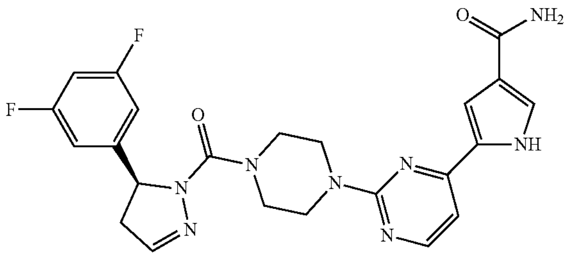 [SMILES: NC(=O)c1c[nH]c(-c2ccnc(N3CCN(C(=O)N4N=CC[C@H]4c4cc(F)cc(F)c4)CC3)n2)c1]

The titled compound 10 was prepared in 16% yield from ammonium hydroxide and (S)-5-(2-(4-(5-(3,5-difluorophenyl)-4,5-dihydro-1H-pyrazole-1-carbonyl) piperazin-1-yl) pyrimidin-4-yl)-1H-pyrrole-3-carbonyl chloride according to the procedure outlined for compound 92. Mass (ESI): m/z calcd for $C_{23}H_{22}F_2N_8O_2$ 480.5, found 481.3 $[M+H]^+$. $^1H$ NMR (400 MHz, $CDCl_3$) δ (ppm): δ 9.69 (brs, 1H), 8.29 (d, J=5.2 Hz, 1H), 7.49-7.50 (m, 1H), 7.02-7.03 (m, 1H), 6.82-6.86 (m, 3H), 6.70-6.76 (m, 2H), 5.32-5.37 (m, 1H), 3.95-4.00 (m, 2H), 3.77-3.89 (m, 4H), 3.61-3.69 (m, 2H), 3.33 (ddd, J=1.2, 12.0, 13.2 Hz, 1H), 2.69 (ddd, J=1.2, 10.0, 11.2 Hz, 1H).

Compound 11: (S)-1-(2-(4-(5-phenyl-4,5-dihydro-1H-pyrazole-1-carbonyl)piperazin-1-yl)pyrimidin-4-yl)-1H-pyrazole-4-carboxamide

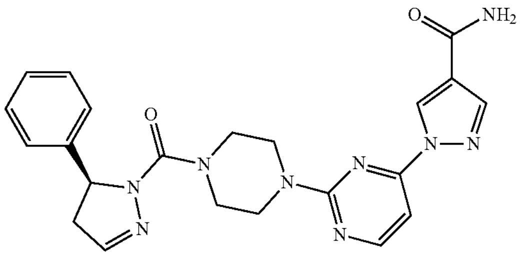 [SMILES: NC(=O)c1cnn(-c2ccnc(N3CCN(C(=O)N4N=CC[C@H]4c4ccccc4)CC3)n2)c1]

The titled compound 11 was prepared in analogous manner to the preparation of 10, as grey solid in 39.1% yield. LC-MS (m/z) 446.4 ($M+H^+$) $^1H$ NMR (400 MHz, DMSO-$d_6$) δ 9.26 (s, 1H), 8.51 (d, J=5.2 Hz, 1H), 8.17 (s, 1H), 7.91 (brs, 1H), 7.37-7.19 (m, 6H), 7.09 (d, J=5.2 Hz, 2H), 5.25 (t, J=10.4 Hz, 1H), 3.94-3.51 (m, 8H), 3.44-3.36 (m, 1H), 2.69-2.54 (m, 1H).

Compound 12: methyl (S)-5-(2-(4-(5-(3,5-difluorophenyl)-4,5-dihydro-1H-pyrazole-1-carbonyl)piperazin-1-yl)-5-fluoropyrimidin-4-yl)-1H-pyrrole-3-carboxylate

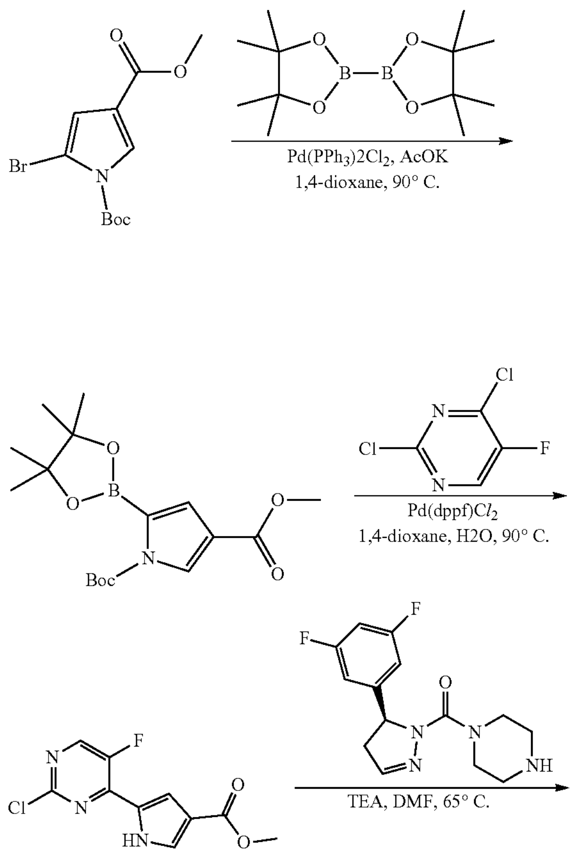

-continued

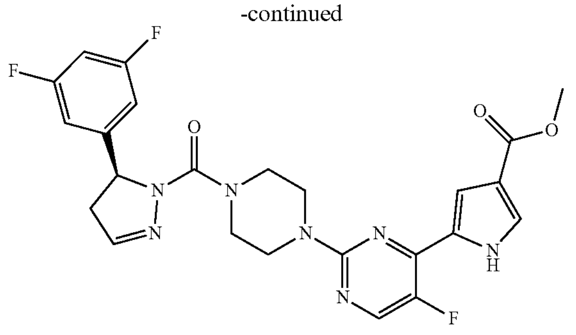

The titled compound 12 was prepared in 11.5% yield from methyl 5-(2-chloro-5-fluoropyrimidin-4-yl)-1H-pyrrole-3-carboxylate and (S)-(5-(3,5-difluorophenyl)-4,5-dihydro-1H-pyrazol-1-yl)(piperazin-1-yl)methanone according to the procedure outlined for 7. Mass (ESI): m/z calcd for $C_{24}H_{22}F_3N_7O_3$ 513.5, found 514.4 $[M+H]^+$. $^1H$ NMR (400 MHz, $CDCl_3$) δ (ppm): δ 9.73 (brs, 1H), 8.19 (d, J=2.8 Hz, 1H), 7.59 (dd, J=1.2, 2.8 Hz, 1H), 7.40-7.42 (m, 1H), 6.80-6.85 (m, 3H), 6.66-6.72 (m, 1H), 5.33 (dd, J=10.0, 11.6 Hz, 1H), 3.87-3.92 (m, 5H), 3.75-3.82 (m, 4H), 3.62-3.48 (m, 2H), 3.32 (ddd, J=2.0, 12.0, 13.6 Hz, 1H), 2.69 (ddd, J=1.6, 9.6, 11.2 Hz, 1H).

Compound 13: (S)-(5-(3,5-difluorophenyl)-4,5-dihydro-1H-pyrazol-1-yl)(4-(5-fluoro-4-(3-methyl-1H-pyrazol-4-yl)pyrimidin-2-yl)piperazin-1-yl)methanone

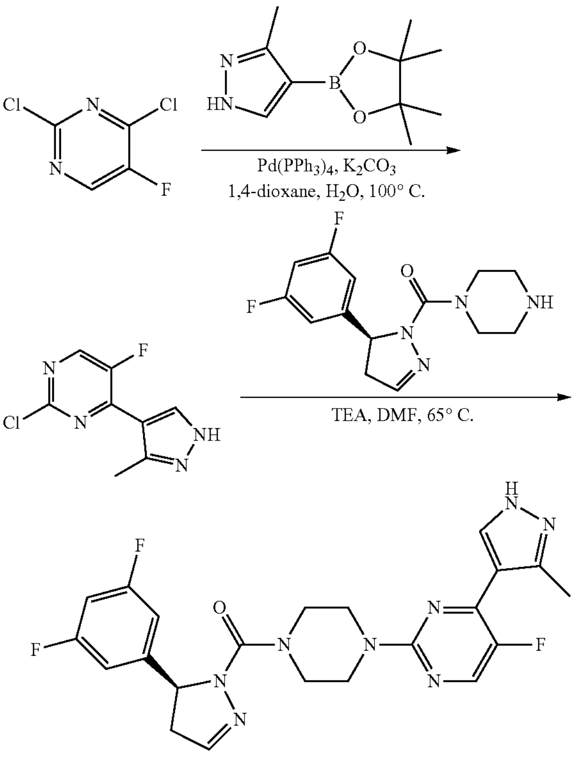

The titled compound 13 was prepared in 9% yield from 2-chloro-5-fluoro-4-(3-methyl-1H-pyrazol-4-yl)pyrimidine and (S)-(5-(3,5-difluorophenyl)-4,5-dihydro-1H-pyrazol-1-yl)(piperazin-1-yl)methanone according to the procedure outlined for 7. Mass (ESI): m/z calcd for $C_{22}H_{21}F_3N_8O$ 476.5, found 477.4 $[M+H]^+$. $^1H$ NMR (400 MHz, $CDCl_3$) δ (ppm): δ 8.09-8.31 (m, 2H), 6.82-6.86 (m, 3H), 6.69-6.72 (m, 1H), 5.35 (t, J=11.6 Hz, 1H), 3.88-3.96 (m, 2H), 3.76-3.85 (m, 4H), 3.59-3.72 (m, 2H), 3.32 (dd, J=12.0, 18.4 Hz, 1H), 2.66-2.79 (m, 4H).

Compound 14: (S)-(5-(3,5-difluorophenyl)-4,5-dihydro-1H-pyrazol-1-yl)(4-(4-(1,3-dimethyl-1H-pyrazol-4-yl)-5-fluoropyrimidin-2-yl)piperazin-1-yl)methanone

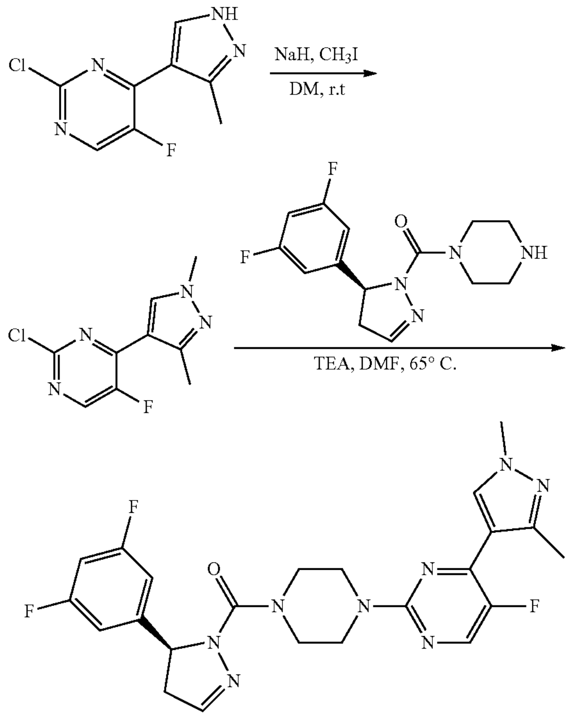

Step 1. 2-chloro-5-fluoro-4-(3-methyl-1H-pyrazol-4-yl)pyrimidine (50 mg, 0.236 mmoL) was dissolved in 3 mL DMF. NaH (28 mg, 0.699 mmoL) was added in portions at 0° C. Let it stir at 0° C. for 30 min. $CH_3I$ (67 mg, 0.472 mmoL) was added. Let it stir at r.t for 30 min. Water was added and extracted with EtOAc (10 mL×3). Dried with $Na_2SO_4$, filtered, and evaporated to dryness to give 64 mg 2-chloro-4-(1,3-dimethyl-1H-pyrazol-4-yl)-5-fluoropyrimidine as light-yellow solid. The crude product was used directly for next step without further purification. LC-MS (m/z) 227.2 $[M+H]^+$.

Step 2. The above residue and (S)-(5-(3,5-difluorophenyl)-4,5-dihydro-1H-pyrazol-1-yl)(piperazin-1-yl)methanone (83 mg, 0.282 mmoL) were dissolved in 9 mL DMF. Let it stir at 65° C. for 32 hrs. The solvent was evaporated to dryness and purified by Prep-TLC (PE/EA=1/2) to give 5 mg of 14 as a light-yellow solid. Yield: 4.4%. Mass (ESI): m/z calcd for $C_{23}H_{23}F_3N_8O$ 484.5, found 485.4 $[M+H]^+$.

$^1H$ NMR (400 MHz, $CDCl_3$) δ (ppm): δ 8.16 (d, J=3.6 Hz, 1H), 7.19 (d, J=4.0 Hz, 1H), 6.80-6.86 (m, 3H), 6.67-6.72 (m, 1H), 5.34 (dd, J=10.4, 11.2 Hz, 1H), 3.86-3.90 (m, 5H), 3.74-3.81 (m, 4H), 3.60-3.68 (m, 2H), 3.32 (ddd, J=1.6, 11.6, 18.4 Hz, 1H), 2.62-2.73 (m, 4H).

Compound 15: (5)-3-(1-(4-(4-(4-chloro-1-methyl-1H-pyrazol-5-yl)-5-fluoropyrimidin-2-yl)piperazine-1-carbonyl)-4,5-dihydro-1H-pyrazol-5-yl)-5-fluorobenzonitrile

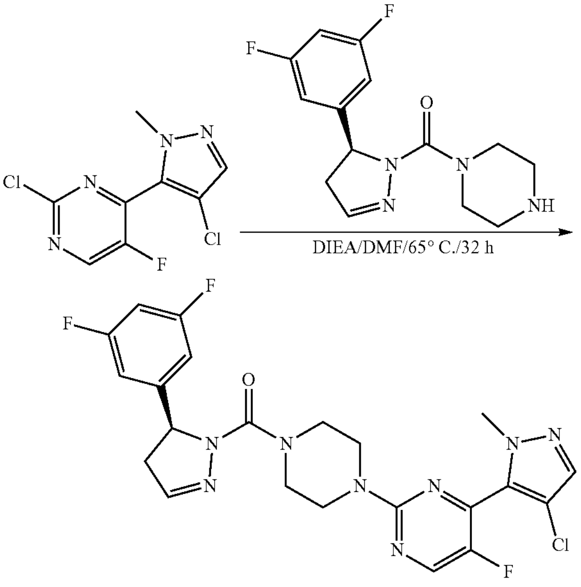

The titled compound 15 as a brown solid was prepared in 33.3% yield from 2-chloro-4-(4-chloro-1-methyl-1H-pyrazol-5-yl)-5-fluoropyrimidine and (S)-3-fluoro-5-(1-(piperazine-1-carbonyl)-4,5-dihydro-1H-pyrazol-5-yl)benzonitrile in analogous manner to the preparation of compound 14. $^1H$ NMR (400 MHz, $CDCl_3$) δ 8.37 (d, J=1.6 Hz, 1H), 7.51 (s, 1H), 7.42 (t, J=1.2 Hz, 1H), 7.30-7.26 (m, 1H), 7.25-7.20 (m, 1H), 6.89 (t, J=1.2 Hz, 1H), 5.37 (dd, J=11.6, 10.0 Hz, 1H), 3.95 (s, 3H), 3.94-3.86 (m, 2H), 3.85-3.73 (m, 4H), 3.70-3.60 (m, 2H), 3.36 (ddd, J=18.4, 11.6, 1.6 Hz, 1H), 2.69 (ddd, J=18.4, 10.0, 1.6 Hz, 1H). LC-MS (m/z): 512.8 $[M+H]^+$.

Compound 16: (S)-1-(2-(4-(5-(3-cyano-5-fluorophenyl)-4,5-dihydro-1H-pyrazole-1-carbonyl)piperazin-1-yl)-5-fluoropyrimidin-4-yl)-4-methyl-1H-imidazole-2-carbonitrile

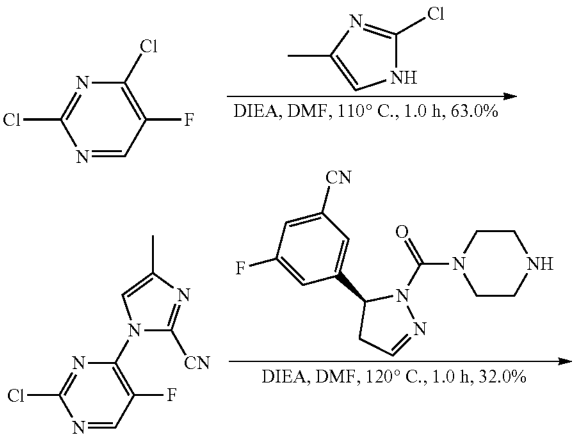

-continued

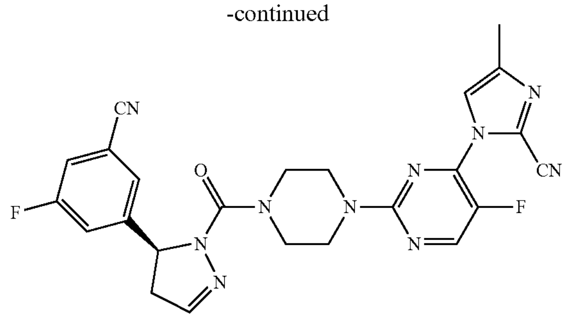

The titled compound 16 was prepared in 32.0% yield as white solid from 1-(2-chloro-5-fluoropyrimidin-4-yl)-4-methyl-1H-imidazole-2-carbonitrile (90 mg, 0.38 mmol) and (S)-3-fluoro-5-(1-(piperazine-1-carbonyl)-4,5-dihydro-1H-pyrazol-5-yl)benzonitrile (100 mg, 0.33 mmol), DIEA (200 mg, 1.45 mmol), DMF (5 mL) in analogous manner to the preparation of 14. LC-MS (m/z) 503.4 ($M+H^+$)$^1$H NMR (400 MHz, DMSO-$d_6$) δ 8.71 (d, J=3.2 Hz, 1H), 7.80 (dd, J=3.2, 1.2 Hz, 1H), 7.68 (ddd, J=8.6, 2.4, 1.2 Hz, 1H), 7.62-7.57 (m, 1H), 7.52-7.44 (m, 1H), 7.06 (d, J=1.6 Hz, 1H), 5.22 (t, J=10.8 Hz, 1H), 3.83-3.42 (m, 8H), 3.32-3.22 (m, 1H), 2.64 (ddd, J=18.4, 10.0, 1.6 Hz, 1H), 2.18 (d, J=1.2 Hz, 3H).

Compound 17: (S)-1-(2-(4-(5-(3-fluorophenyl)-4,5-dihydro-1H-pyrazole-1-carbonyl)piperazin-1-yl) pyrimidin-4-yl)-1H-pyrazole-4-carboxamide

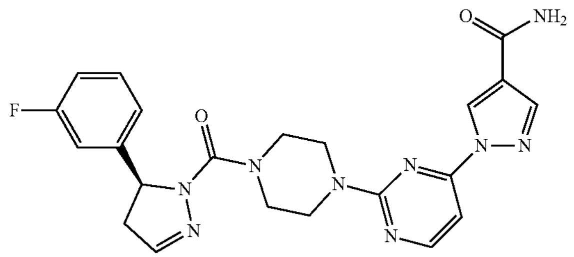 [SMILES: NC(=O)c1cnn(-c2ccnc(N3CCN(C(=O)N4N=CC[C@H]4c4cccc(F)c4)CC3)n2)c1]

The titled compound 17 was prepared in 17.0% yield as white solid in analogous manner to the preparation of 10. LC-MS (m/z) 464.4 ($M+H^+$)$^1$H NMR (400 MHz, DMSO-$d_6$) δ 9.21 (s, 1H), 8.51 (dd, J=5.2, 1.2 Hz, 1H), 8.15 (d, J=0.8 Hz, 1H), 7.84 (brs, 1H), 7.43-7.33 (m, 1H), 7.30 (brs, 1H), 7.15-7.03 (m, 5H), 5.26 (dd, J=11.6, 9.8 Hz, 1H), 3.93-3.51 (m, 8H), 3.43-3.35 (m, 1H), 2.68-2.59 (m, 1H).

Compound 18: (S)-2-(4-(2-(4-(5-(3,5-difluorophenyl)-4,5-dihydro-1H-pyrazole-1-carbonyl)piperazin-1-yl)-5-fluoropyrimidin-4-yl)-3-methyl-1H-pyrazol-1-yl)acetamide

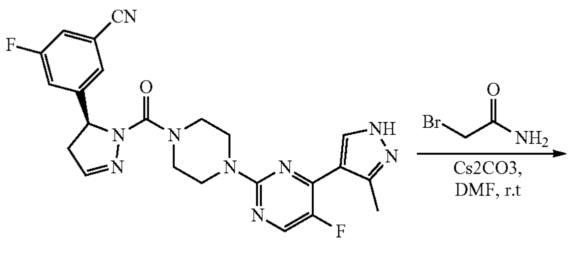

-continued

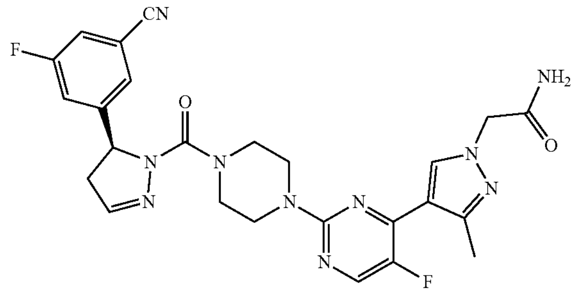

(S)-(5-(3,5-difluorophenyl)-4,5-dihydro-1H-pyrazol-1-yl)(4-(5-fluoro-4-(3-methyl-1H-pyrazol-4-yl)pyrimidin-2-yl)piperazin-1-yl)methanone (55 mg, 0.117 mmoL), 2-bromoacetamide (17.7 mg, 0.128 mmoL) and $Cs_2CO_3$ (76 mg, 0.234 mmoL) were mixed in 2 mL DMF. Let it stir at r.t for 16 hrs. Water was added to the solution and extracted with EtOAc (10 mL×3). The solvent was washed with brine. Filtered and evaporated to dryness and purified by Prep-HPLC to give 3 mg of 18 as a white solid. Yield: 4.9%. Mass (ESI): m/z calcd for $C_{24}H_{24}F_3N_9O_2$ 527.5, found 528.6 $[M+H]^+$. $^1$H NMR (400 MHz, $CDCl_3$) δ (ppm): δ 8.19 (d, J=3.2 Hz, 1H), 8.07 (d, J=3.2 Hz, 1H), 6.81-6.86 (m, 3H), 6.67-6.72 (m, 1H), 6.36 (brs, 1H), 5.59 (brs, 1H), 5.35 (t, J=10.8 Hz, 1H), 4.80 (s, 2H), 3.86-3.94 (m, 2H), 3.79 (q, J=7.2 Hz, 4H), 3.61-3.69 (m, 2H), 3.32 (ddd, J=2.0, 12.0, 13.6 Hz, 1H), 2.69 (ddd, J=1.6, 10.0, 11.2 Hz, 1H), 2.65 (s, 3H).

Compound 19: (S)-(5-(3,5-difluorophenyl)-4,5-dihydro-1H-pyrazol-1-yl)(4-(5-fluoro-2',6'-dimethoxy-[4,4'-bipyrimidin]-2-yl)piperazin-1-yl)methanone

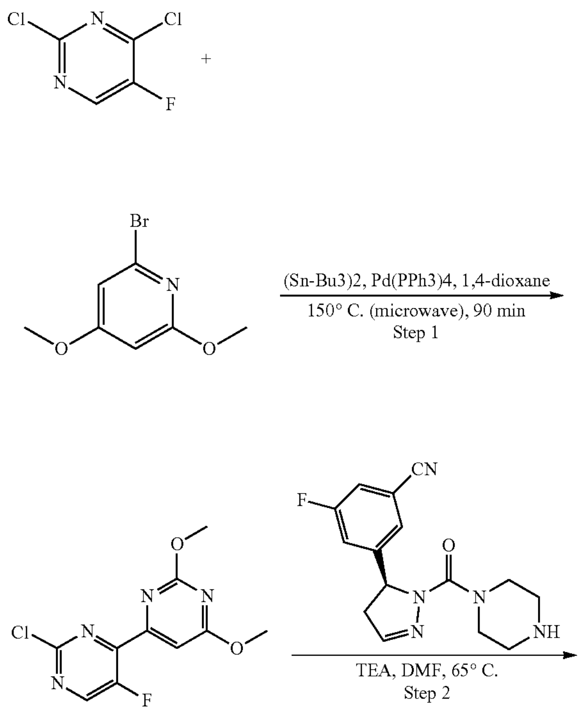

-continued

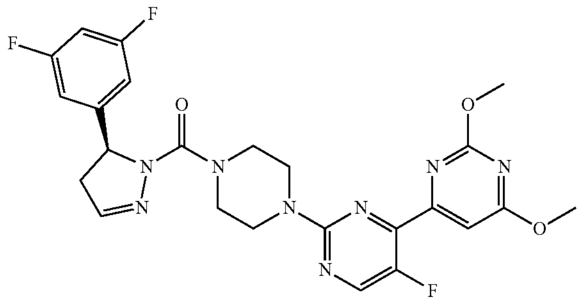

Step 1. 2,4-dichloro-5-fluoropyrimidine (1.14 g, 6.82 mmoL), 4-bromo-2,6-dimethoxypyrimidine (1.5 g, 6.84 mmoL) and $(Sn\text{-}Bu_3)_2$ (3.984 g, 6.87 mmoL) were dissolved in 17.5 mL. It was bubbled with $N_2$ for 5 min. Then $Pd(PPh_3)_4$ (528 mg, 0.342 mmoL) was added. Let it stir at 150° C. under microwave for 90 min. The solvent was evaporated to dryness and purified by column chromatography (PE/EA=4/1) to give 240 mg of 2-chloro-5-fluoro-2',6'-dimethoxy-4,4'-bipyrimidine as white solid. Yield: 19.5%. LC-MS (m/z) 271.2 $[M+H]^+$.

Step 2. 2-chloro-5-fluoro-2',6'-dimethoxy-4,4'-bipyrimidine (101 mg, 0.374 mmoL) and S)-(5-(3,5-difluorophenyl)-4,5-dihydro-1H-pyrazol-1-yl)(piperazin-1-yl) ethenone (100 mg, 0.34 mmoL) and 60 µl TEA were dissolved in 13 mL DMF. Let it stir at 65° C. for 32 hrs. Water was added to the solution and extracted with EtOAc (10 mL×3). The solvent was washed with brine. Filtered and evaporated to dryness and purified by Prep-TLC (PE/EA=1/1.2) to give 42 mg of 19 as a white solid. Yield: 21.4%. Mass (ESI): m/z calcd for $C_{24}H_{23}F_3N_8O_3$ 528.5, found 529.4 $[M+H]^+$. $^1H$ NMR (400 MHz, $CDCl_3$) δ (ppm): δ 8.35-8.36 (m, 1H), 7.1-7.33 (m, 1H), 6.80-6.88 (m, 3H), 6.69-6.72 (m, 1H), 5.30-5.37 (m, 1H), 4.40 (s, 6H), 3.88-3.96 (m, 2H), 3.75-3.84 (m, 4H), 3.60-3.70 (m, 2H), 3.27-3.40 (m, 1H), 2.64-2.75 (m, 1H).

Compound 20: (S)-(5-(3,5-difluorophenyl)-4,5-dihydro-1H-pyrazol-1-yl)(4-(5-fluoro-4-(5-iodo-1H-1,2,3-triazol-4-yl)pyrimidin-2-yl)piperazin-1-yl) methanone

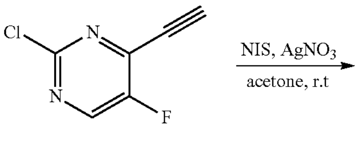

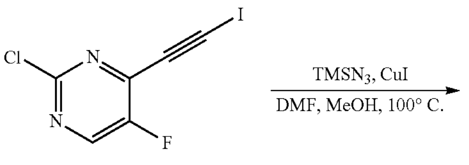

-continued

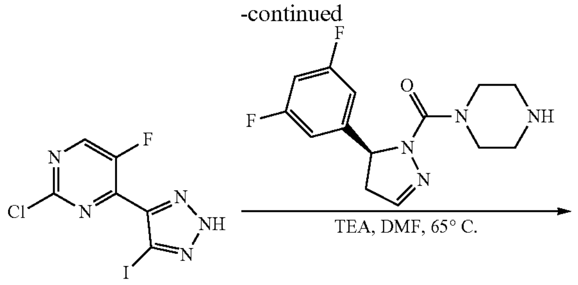

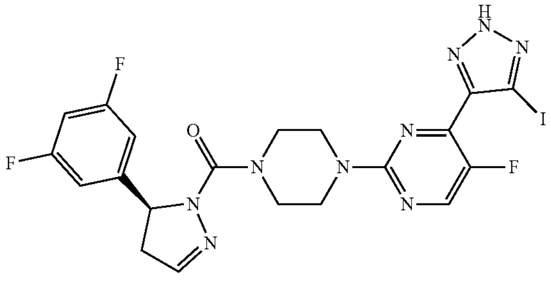

Step 1. 2-chloro-4-ethynyl-5-fluoropyrimidine (186 mg, 1.192 mmoL), NIS (318 mg, 1.413 mmoL) and $AgNO_3$ (20 mg, 0.118 mmoL) were suspended in 10.5 mL acetone. Let it stir at r.t for 2 hrs. The reaction mixture was filtered and evaporated to dryness. The residue was redissolved with EtOAc (30 mL) and washed with sat. $NH_4Cl$ solution, sat. $Na_2S_2O_3$ solution and water. Dried with $Na_2SO_4$, filtered and evaporated to dryness to give 340 mg of 2-chloro-5-fluoro-4-(iodoethynyl)pyrimidine as a white solid. Yield: quantitative. It was used for next step without further purification. LC-MS (m/z) 283.3 $[M+H]^+$.

Step 2. 2-chloro-5-fluoro-4-(iodoethynyl)pyrimidine (220 mg, 0.78 mmoL) and $TMSN_3$ (134.8 mg, 1.17 mmoL), CuI (11 mg, 0.058 mmoL) were dissolved in 5 mL DMF/MeOH (9/1) solution. Let it stir at 100° C. for 2 hrs. The solvent was evaporated to dryness and purified by Prep-TLC (DCM/MeOH=12/1) to give 20 mg of 2-chloro-5-fluoro-4-(5-iodo-2H-1,2,3-triazol-4-yl)pyrimidine as a brown solid. Yield: 7.9%. LC-MS (m/z) 326.2 $[M+H]^+$.

Step 3. The titled compound 20 was prepared in 5% yield from 2-chloro-5-fluoro-4-(5-iodo-2H-1,2,3-triazol-4-yl)pyrimidine and (S)-(5-(3,5-difluorophenyl)-4,5-dihydro-1H-pyrazol-1-yl)(piperazin-1-yl)methanone according to the procedure outlined for 7. Mass (ESI): m/z calcd for $C_{20}H_{17}F_3IN_9O$ 583.3, found 584.4 $[M+H]^+$. $^1H$ NMR (400 MHz, $CDCl_3$) δ (ppm): δ 8.36 (d, J=2.8 Hz, 1H), 6.80-6.89 (m, 3H), 6.67-6.72 (m, 1H), 5.36 (t, J=10.0, 1H), 3.99-4.05 (m, 2H), 3.89-3.94 (m, 2H), 3.78-3.84 (m, 2H), 3.64-3.70 (m, 2H), 3.33 (ddd, J=2.0, 12.0, 13.6 Hz, 1H), 2.69 (ddd, J=1.6, 9.6, 11.2 Hz, 1H).

Compound 21: (S)-5-(2-(4-(5-(3,5-difluorophenyl)-4,5-dihydro-1H-pyrazole-1-carbonyl)piperazin-1-yl)-5-fluoropyrimidin-4-yl)-1H-pyrrole-3-carboxylic acid

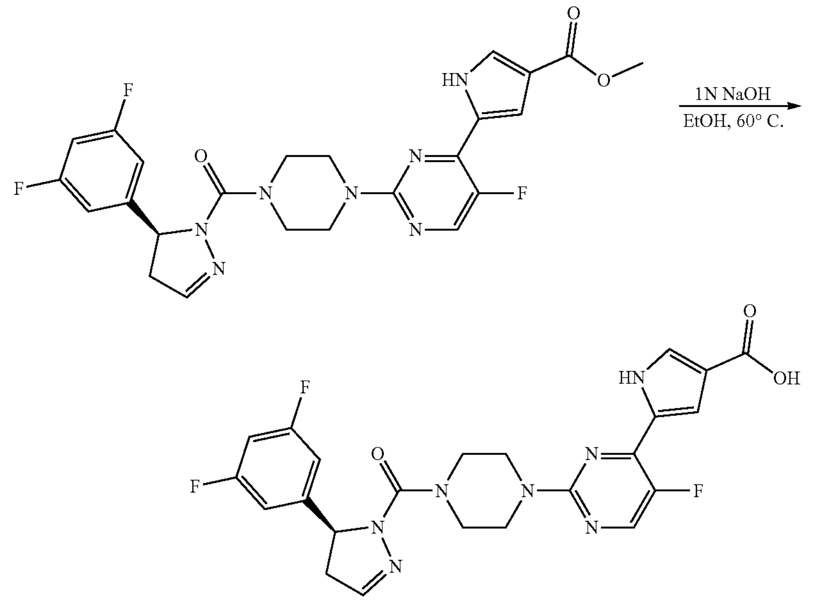

The titled compound 21 was prepared in 86.2% yield from methyl (S)-5-(2-(4-(5-(3,5-difluorophenyl)-4,5-dihydro-1H-pyrazole-1-carbonyl)piperazin-1-yl)-5-fluoropyrimidin-4-yl)-1H-pyrrole-3-carboxylate according to the procedure outlined for 10. Mass (ESI): m/z calcd for $C_{23}H_{20}F_3N_7O_3$ 499.5, found 500.4 $[M+H]^+$. $^1H$ NMR (400 MHz, $CDCl_3$) δ (ppm): δ 8.20-8.22 (m, 1H), 7.60-7.65 (m, 1H), 7.39-7.41 (m, 1H), 6.87-6.92 (m, 2H), 6.77-6.80 (m, 2H), 6.67-6.69 (m, 1H), 5.25-5.31 (m, 1H), 4.08-4.19 (m, 2H), 3.96-4.04 (m, 2H), 3.78-3.92 (m, 2H), 3.66-3.74 (m, 2H), 3.28-3.32 (m, 1H), 2.66-2.72 (m, 1H).

Compound 22: (S)-3-fluoro-5-(1-(4-(5-fluoro-4-(1H-pyrazol-3-yl)pyrimidin-2-yl)piperazine-1-carbonyl)-4,5-dihydro-1H-pyrazol-5-yl)benzonitrile

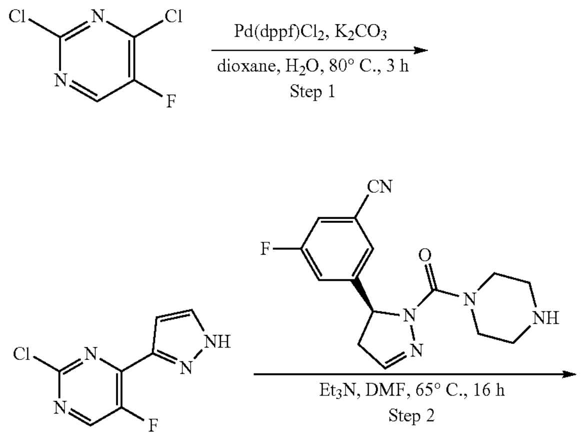

-continued

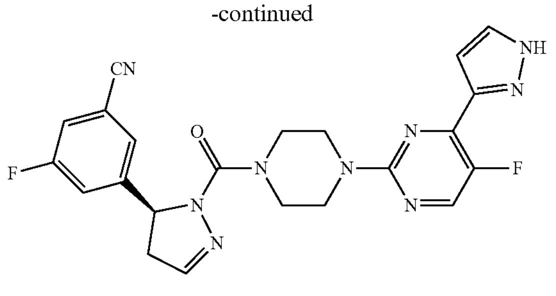

The titled compound 22 was prepared in analogous manner to the preparation of compound 7. $^1H$ NMR (400 MHz, $CDCl_3$) δ 8.31 (d, J=2.4 Hz, 1H), 7.92-7.64 (m, 1H), 7.42-7.41 (m, 1H), 7.33-7.20 (m, 2H), 7.00-6.97 (m, 1H), 6.91-8.89 (m, 1H), 5.33 (dd, J=10, 11.2 Hz, 1H), 4.02-3.50 (m, 8H), 3.36 (ddd, J=18.2, 11.7, 1.8 Hz, 1H), 2.70 (ddd, J=18.2, 10.0, 1.6 Hz, 1H).

Compound 23: (S)-(5-(3,5-difluorophenyl)-4,5-dihydro-1H-pyrazol-1-yl)(4-(5-fluoro-4-(5-methyl-1H-tetrazol-1-yl)pyrimidin-2-yl)piperazin-1-yl)methanone

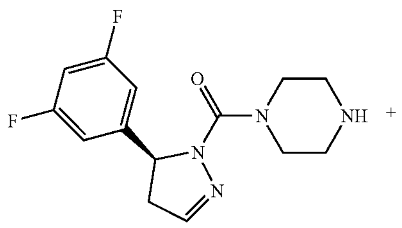

-continued

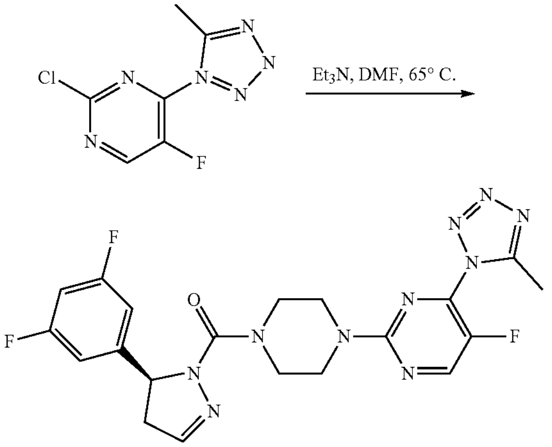

The titled compound 23 was prepared in analogous manner to the preparation of 7 $^1H$ NMR (400 MHz, $CDCl_3$) δ 8.52 (d, J=2.4 Hz, 1H), 6.90-6.75 (m, 3H), 6.74-6.55 (m, 1H), 5.33 (dd, J=10, 12 Hz, 1H), 3.97-3.56 (m, 8H), 3.33 (ddd, J=18.3, 11.8, 1.8 Hz, 1H), 2.80 (s, 3H), 2.70 (ddd, J=18.2, 10.0, 1.6 Hz, 1H).

Compound 24: (S)-(4-(4-(3-chloro-1H-1,2,4-triazol-1-yl)-5-fluoropyrimidin-2-yl)piperazin-1-yl)(5-(3,5-difluorophenyl)-4,5-dihydro-1H-pyrazol-1-yl)methanone

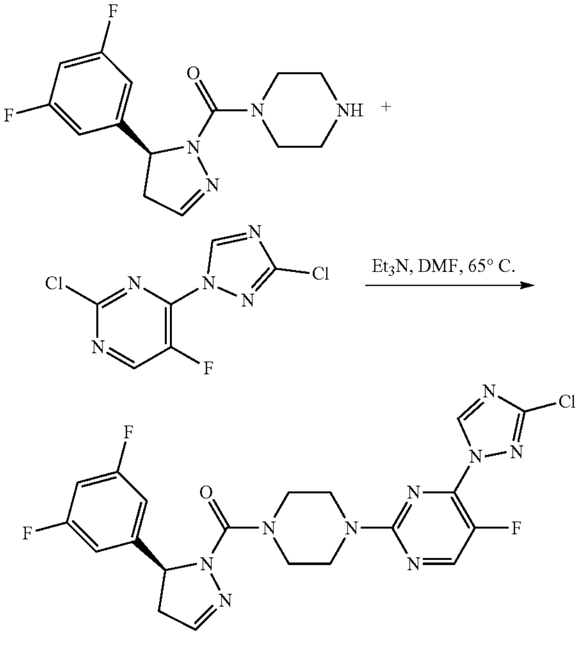

The titled compound 24 was prepared in analogous manner to the preparation of compound 7. $^1H$ NMR (400 MHz, $CDCl_3$) δ 8.93 (s, 1H), 8.43 (d, J=3.2 Hz, 1H), 6.96-6.75 (m, 3H), 6.70 (m, 1H), 5.33 (dd, J=9.6, 11.2 Hz, 1H), 4.02-3.53 (m, 8H), 3.33 (ddd, J=18.2, 11.7, 1.7 Hz, 1H), 2.70 (ddd, J=18.3, 9.7, 1.5 Hz, 1H).

Compound 25: (S)-(5-(3,5-difluorophenyl)-4,5-dihydro-1H-pyrazol-1-yl)(4-(5-fluoro-4-(6-hydroxypyridin-3-yl)pyrimidin-2-yl)piperazin-1-yl)methanone

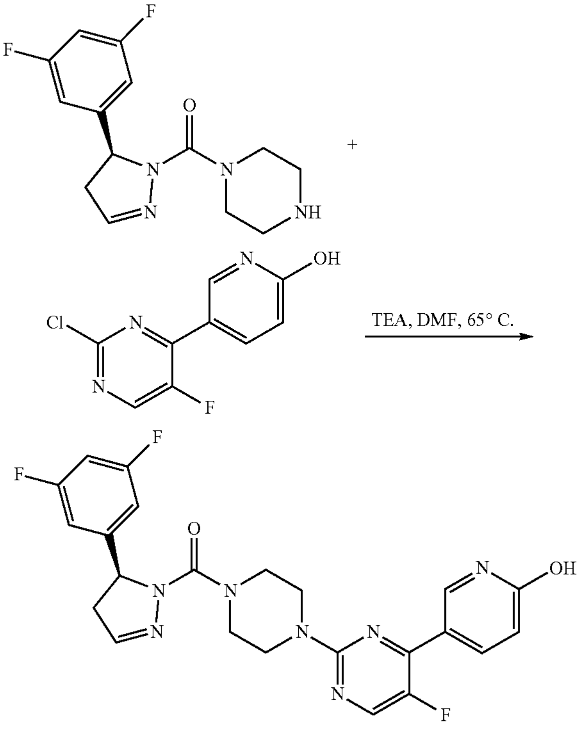

The titled compound 91 was prepared in analogous manner to the preparation of compound 7. $^1H$ NMR (400 MHz, $CDCl_3$) δ 13.14 (brs, 1H), 8.39-8.02 (m, 3H), 6.87-6.53 (m, 5H), 5.33 (dd, J=10, 11.6 Hz, 1H), 4.00-3.40 (m, 8H), 3.32-3.09 (m, 1H), 2.74 (m, 1H).

Compound 26: (S)-(5-(5-fluoropyridin-3-yl)-4,5-dihydro-1H-pyrazol-1-yl)(4-(4-(5-methyl-1H-tetrazol-1-yl)pyrimidin-2-yl)piperazin-1-yl)methanone

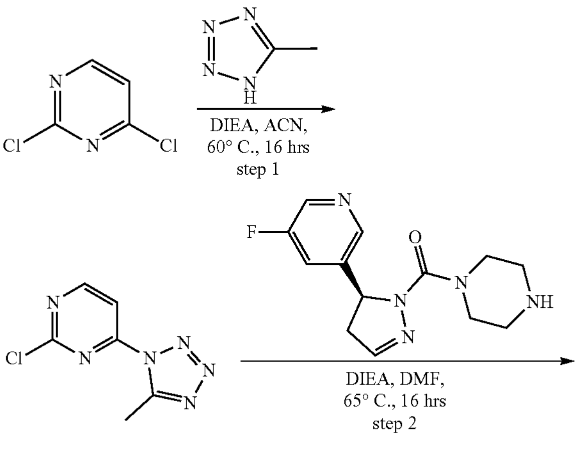

-continued

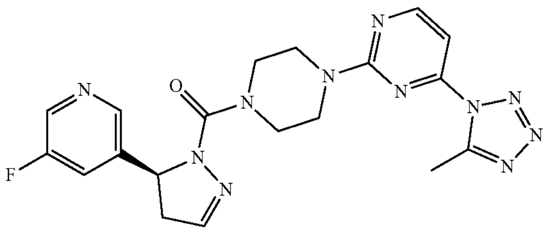

The titled compound 26 as a light-yellow solid was prepared in 41.1% yield from 4-chloro-2-(5-methyl-1H-tetrazol-1-yl)pyrimidine and (S)-(5-(5-fluoropyridin-3-yl)-4,5-dihydro-1H-pyrazol-1-yl)(piperazin-1-yl)methanone in analogous manner to the preparation of compound 7. 1H NMR (400 MHz, Chloroform-d) δ 8.57 (s, 1H), 8.55 (d, J=5.2 Hz, 1H), 8.48 (d, J=2.8 Hz, 1H), 7.67 (dt, J=8.4, 2.4 Hz, 1H), 7.25 (d, J=5.2 Hz, 1H), 6.96 (t, J=1.6 Hz, 1H), 5.47 (dd, J=11.2, 10.6 Hz, 1H), 4.02-3.91 (m, 2H), 3.89-3.75 (m, 4H), 3.74-3.63 (m, 2H), 3.44 (ddd, J=18.4, 11.6, 1.6 Hz, 1H), 2.97 (s, 3H), 2.80 (ddd, J=18.4, 10.0, 1.6 Hz, 1H). LC-MS (m/z): 438.3 [M+H]+.

Compound 27: (S)-(5-(3,5-difluorophenyl)-4,5-dihydro-1H-pyrazol-1-yl)(4-(5-fluoro-4-(1-methyl-1H-pyrazol-3-yl)pyrimidin-2-yl)piperazin-1-yl)methanone

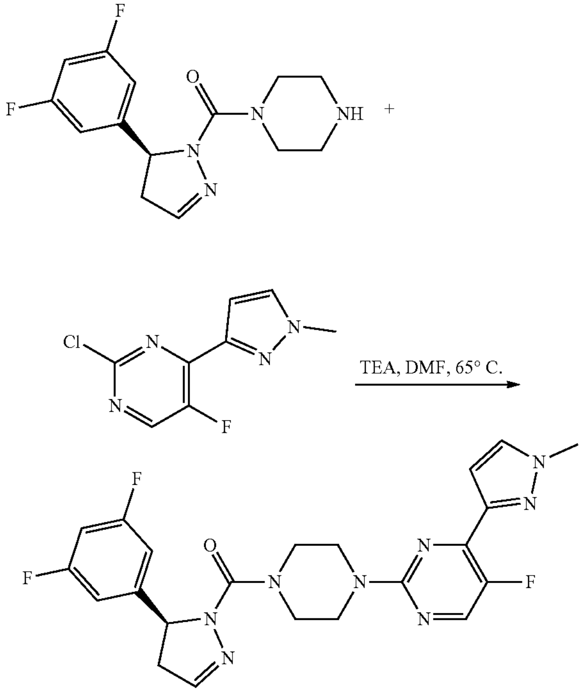

The titled compound 27 was prepared in analogous manner to the preparation of compound 7. $^{1}H$ NMR (400 MHz, $CDCl_3$) δ 8.29 (d, J=2.9 Hz, 1H), 7.56-7.57 (m, 1H), 6.87 (ddd, J=16.2, 6.2, 4.0 Hz, 4H), 6.72-6.66 (m, 1H), 5.35 (dd, J=13.4, 8.1 Hz, 1H), 4.28 (s, 3H), 4.03-3.54 (m, 8H), 3.38-3.29 (m, 1H), 2.69 (ddd, J=18.4, 9.9, 1.5 Hz, 1H).

Compound 28: (S)-(5-(3,5-difluorophenyl)-4,5-dihydro-1H-pyrazol-1-yl)(4-(5-fluoro-4-(1-methyl-1H-pyrazol-5-yl)pyrimidin-2-yl)piperazin-1-yl)methanone

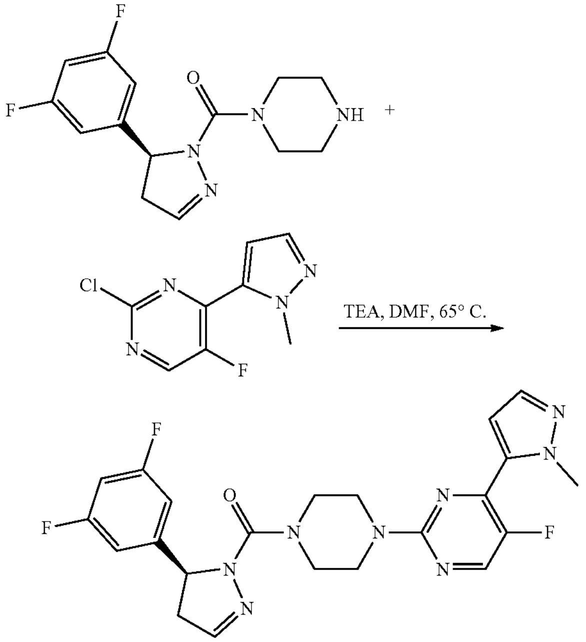

The titled compound 28 was prepared in analogous manner to the preparation of compound 7. $^{1}H$ NMR (400 MHz, $CDCl_3$) δ 8.35-8.12 (m, 1H), 7.58-7.52 (m, 1H), 7.00-6.77 (m, 4H), 6.74-6.66 (m, 1H), 5.36-5.31 (m, 1H), 4.04 (s, 3H), 3.99-3.56 (m, 8H), 3.37-3.25 (m, 1H), 2.74-7.64 (m, 1H).

Compound 29: (S)-2-(3-(2-(4-(5-(3,5-difluorophenyl)-4,5-dihydro-1H-pyrazole-1-carbonyl)piperazin-1-yl)-5-fluoropyrimidin-4-yl)-1H-pyrazol-1-yl)acetamide

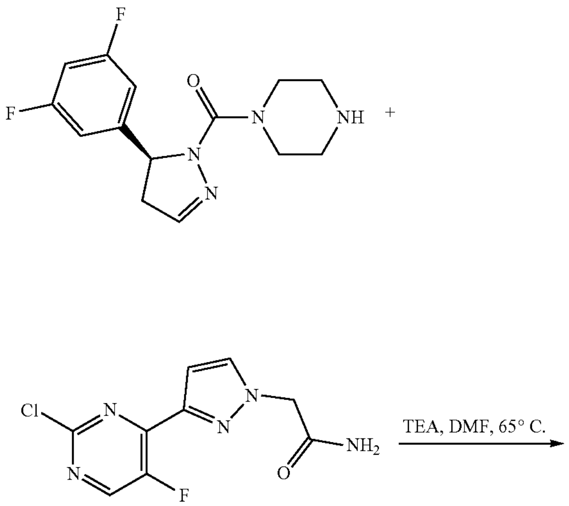

-continued

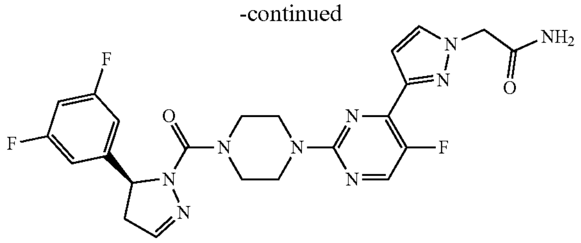

The titled compound 29 was prepared in analogous manner to the preparation of compound 7. $^1H$ NMR (400 MHz, $CDCl_3$) δ 8.41-8.02 (m, 1H), 7.69-7.41 (m, 1H), 7.25-6.98 (m, 3H), 6.95-6.48 (m, 2H), 5.36-5.31 (m, 1H), 4.95 (s, 2H), 4.09-3.46 (m, 8H), 3.32 (dd, J=17.4, 12.7 Hz, 1H), 2.69 (dd, J=19.1, 10.8 Hz, 1H).

Compound 30: (S)-(5-(3,5-difluorophenyl)-4,5-dihydro-1H-pyrazol-1-yl)(4-(5-fluoro-4-(5-methyl-1H-1,2,3-triazol-4-yl)pyrimidin-2-yl)piperazin-1-yl)methanone

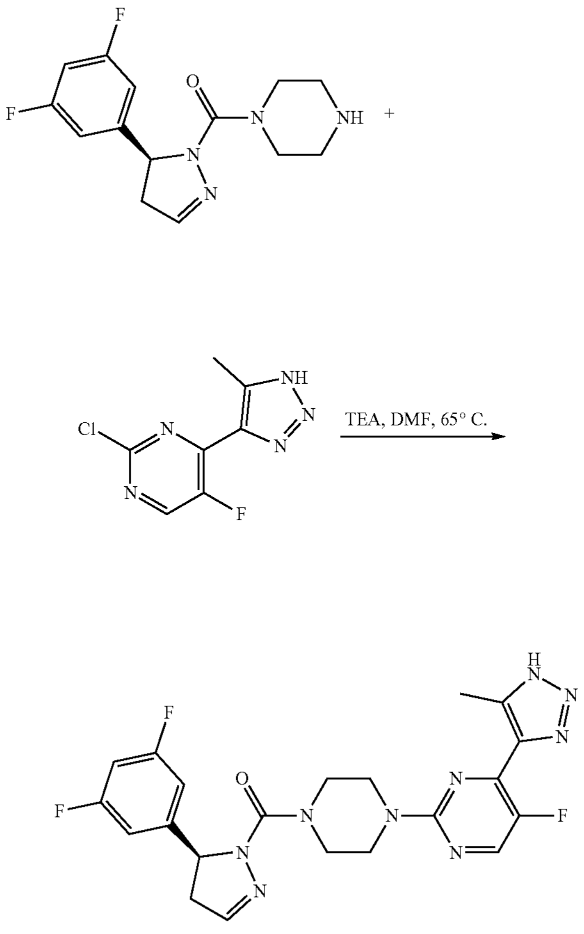

The titled compound 30 was prepared in analogous manner to the preparation of compound 7. $^1H$ NMR (400 MHz, $CDCl_3$) δ 8.34 (d, J=4 Hz, 1H), 6.92-6.77 (m, 5H), 6.74-6.62 (m, 1H), 5.37-5.32 (m, 1H), 4.04-3.51 (m, 8H), 3.39-3.26 (m, 1H), 2.74-2.68 (m, 1H), 2.67 (s, 3H).

Compound 31: (S)-2-(4-(2-(4-(5-(3,5-difluorophenyl)-4,5-dihydro-1H-pyrazole-1-carbonyl)piperazin-1-yl)-5-fluoropyrimidin-4-yl)-5-methyl-1H-1,2,3-triazol-1-yl)acetamide

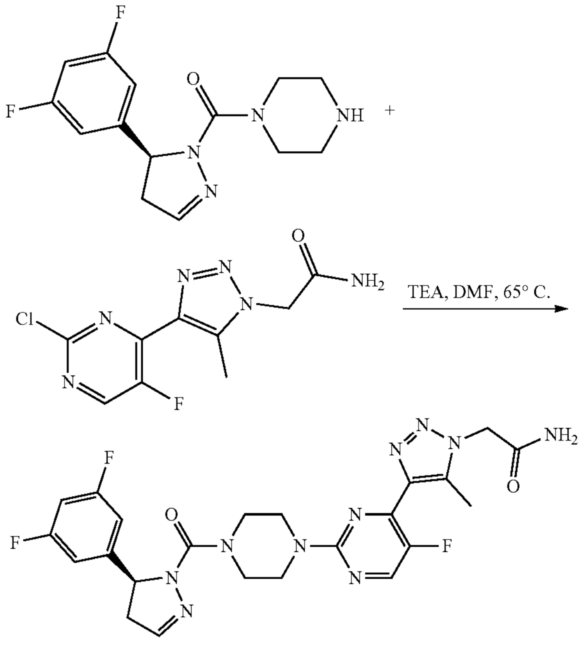

The titled compound 31 was prepared in analogous manner to the preparation of compound 7. $^1H$ NMR (400 MHz, $CDCl_3$) δ 8.33 (d, J=4 Hz, 1H), 6.72-6.67 (m, 3H), 6.86-8.81 (m, 1H), 5.42-5.25 (m, 1H), 5.17 (s, 2H), 3.92-3.64 (m, 8H), 3.36-3.29 (m, 1H), 2.73-2.67 (m, 1H), 2.67 (s, 3H).

Compound 32: (S)-2-(4-(2-(4-(5-(3,5-difluorophenyl)-4,5-dihydro-1H-pyrazole-1-carbonyl)piperazin-1-yl)-5-fluoropyrimidin-4-yl)-5-methyl-2H-1,2,3-triazol-2-yl)acetamide

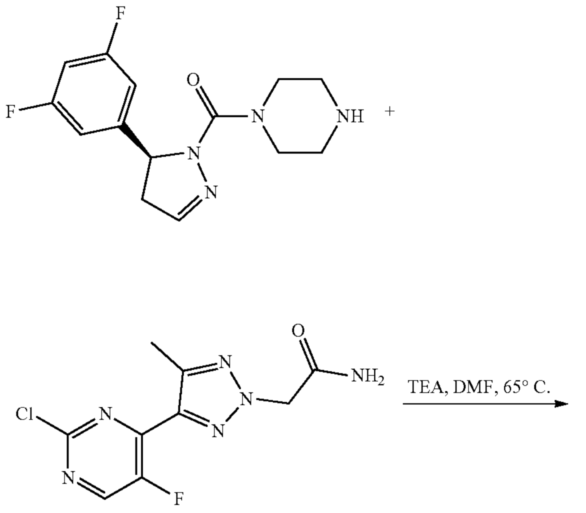

-continued

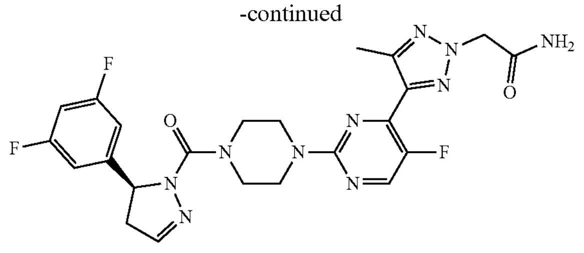

The titled compound 32 was prepared in analogous manner to the preparation of compound 7. $^1$H NMR (400 MHz, $CDCl_3$) δ 8.34 (d, J=4.0 Hz, 1H), 6.90-6.77 (m, 3H), 6.72-6.67 (m, 1H), 5.42-5.25 (m, 1H), 5.07 (s, 2H), 3.92-3.64 (m, 8H), 3.36-3.29 (m, 1H), 2.73-2.67 (m, 1H), 2.67 (s, 3H).

Compound 33: (S)-(4-(4-(1H-pyrazol-3-yl)pyrimidin-2-yl)piperazin-1-yl)(5-(3,5-difluorophenyl)-4,5-dihydro-1H-pyrazol-1-yl)methanone

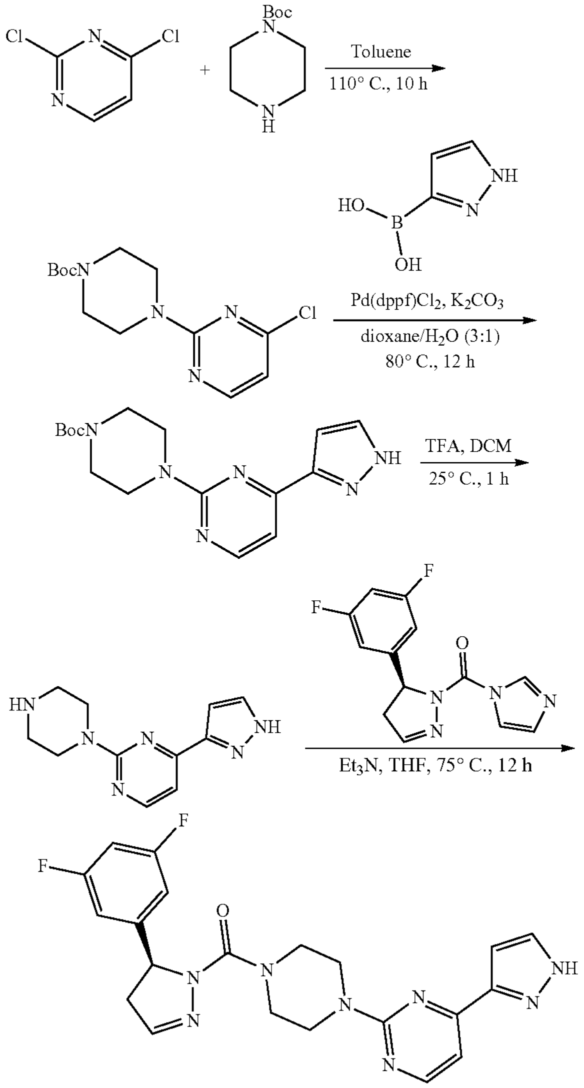

Step 1: To a solution of 2,4-dichloropyrimidine (10 g, 67.1 mmol) in toluene (80 mL) was added tert-butyl piperazine-1-carboxylate (12.5 g, 67.1 mmol). The reaction mixture was stirred at 110° C. for 10 h. The crude was purified by Flash chromatography. tert-butyl 4-(4-chloropyrimidin-2-yl)piperazine-1-carboxylate was obtained (4.2 g) as a white solid, Yield: 20.9%. LC-MS (m/z) 299.1 ($M+H^+$).

Step 2: To a solution of tert-butyl 4-(4-chloropyrimidin-2-yl)piperazine-1-carboxylate (1 g, 3.35 mmol) in dioxane (20 mL) and $H_2O$ (6 mL) was added (1H-pyrazol-3-yl) boronic acid (412 mg, 3.68 mmol), Pd(dppf)$Cl_2$ (246 mg, 0.034 mmol) and $K_2CO_3$ (926 mg, 6.7 mmol). The reaction mixture was stirred at 80° C. for 12 h under Ar. The crude was purified by Flash chromatography. tert-butyl 4-(4-(1H-pyrazol-3-yl)pyrimidin-2-yl)piperazine-1-carboxylate (640 mg) as a white solid, Yield: 57.9%. LC-MS (m/z) 331.1 ($M+H^+$).

Step 3: To a solution of tert-butyl 4-(4-(1H-pyrazol-3-yl) pyrimidin-2-yl)piperazine-1-carboxylate (200 mg, 605.3 umol) in DCM (5 mL) was added TFA (5 mL). The reaction mixture was stirred at 25° C. for 1 h. The crude was concentrated under vacuum and used to next step directly. LC-MS (m/z) 231.1 ($M+H^+$).

Step 4: To a solution of (S)-(5-(3,5-difluorophenyl)-4,5-dihydro-1H-pyrazol-1-yl)(1H-imidazol-1-yl)methanone (100 mg, 362 umol) in THF (6 mL) was added 2-(piperazin-1-yl)-4-(1H-pyrazol-3-yl)pyrimidine (84 mg, 362 umol) and $Et_3N$ (2 mL). The reaction mixture was stirred at 75° C. for 12 h. The crude was purified by Flash chromatography. The titled compound 33 was obtained (43 mg) as a white solid, Yield: 27.1%. LC-MS (m/z) 439.1 ($M+H^+$). $^1$H NMR (400 MHz, $CDCl_3$) δ 8.37 (dd, J=5.1, 1.1 Hz, 1H), 7.64 (s, 1H), 7.42-7.41 (m, 1H), 7.34-7.21 (m, 2H), 6.94 (dd, J=5.0, 1.1 Hz, 1H), 6.92-6.82 (m, 2H), 5.37 (t, J=10.8 Hz, 1H), 4.04-3.60 (m, 8H), 3.35 (ddt, J=18.2, 11.7, 1.4 Hz, 1H), 2.68 (ddt, J=18.2, 10.0, 1.4 Hz, 1H).

Compound 34: (5)-3-(1-(4-(4-(1H-pyrazol-3-yl) pyrimidin-2-yl)piperazine-1-carbonyl)-4,5-dihydro-1H-pyrazol-5-yl)-5-fluorobenzonitrile

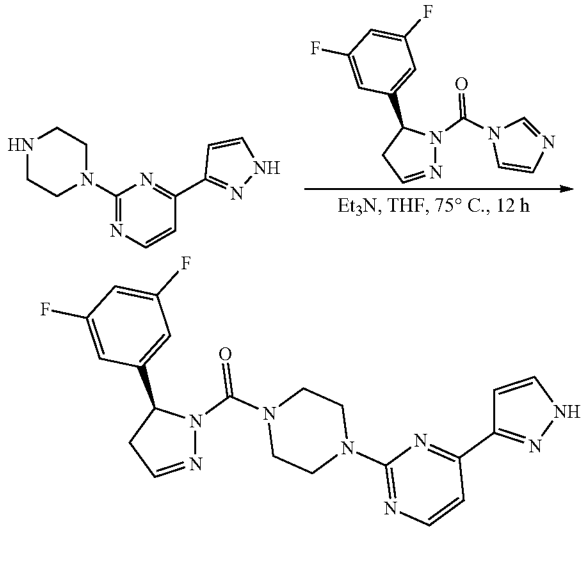

The titled compound 34 was prepared in 35.2% yield from 2-(piperazin-1-yl)-4-(1H-pyrazol-3-yl)pyrimidine according to the procedure outlined for compound 33. LC-MS (m/z) 446.1 (M+H$^+$). $^1$H NMR (400 MHz, $CDCl_3$) δ 8.30 (dd, J=5.1, 1.1 Hz, 1H), 7.58 (s, 1H), 7.34 (t, J=1.4 Hz, 1H), 7.27-7.14 (m, 2H), 6.88 (dd, J=5.0, 1.1 Hz, 1H), 6.85-6.76 (m, 2H), 5.31 (t, J=10.8 Hz, 1H), 3.97-3.53 (m, 8H), 3.28 (ddt, J=18.2, 11.7, 1.4 Hz, 1H), 2.62 (ddt, J=18.2, 10.0, 1.4 Hz, 1H).

Compound 35: (S)-(4-(4-(1H-pyrazol-3-yl)pyrimidin-2-yl)piperazin-1-yl)(5-(3-fluorophenyl)-4,5-dihydro-1H-pyrazol-1-yl)methanone

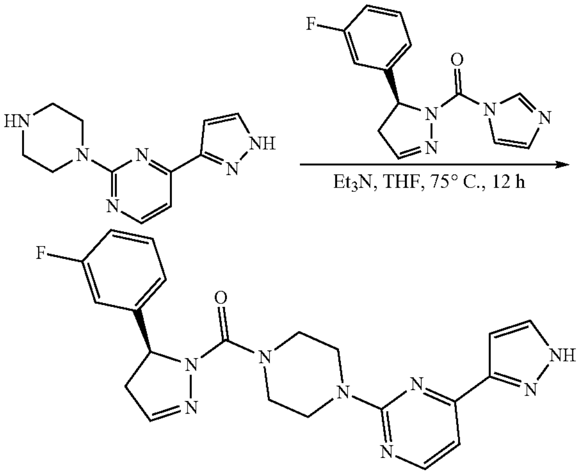

The titled compound 35 was prepared in 32.7% yield from 2-(piperazin-1-yl)-4-(1H-pyrazol-3-yl)pyrimidine prepared in analogous manner to the preparation of compound 33. LC-MS (m/z) 421.1 (M+H$^+$). $^1$H NMR (400 MHz, DMSO-$d_6$) δ 8.34 (d, J=5.2, 1H), 7.62 (d, J=2.2 Hz, 1H), 7.32 (td, J=8.0, 5.9 Hz, 1H), 7.19-7.07 (m, 2H), 7.03-6.94 (m, 2H), 6.93-6.87 (m, 2H), 5.41-5.30 (m, 1H), 4.04-3.61 (m, 8H), 3.37 (ddd, J=18.3, 11.7, 1.8 Hz, 1H), 2.72 (ddd, J=18.3, 9.8, 1.7 Hz, 1H).

Compound 36: (S)-(4-(4-(1H-pyrazol-3-yl)pyrimidin-2-yl)piperazin-1-yl)(5-(5-fluoropyridin-3-yl)-4,5-dihydro-1H-pyrazol-1-yl)methanone

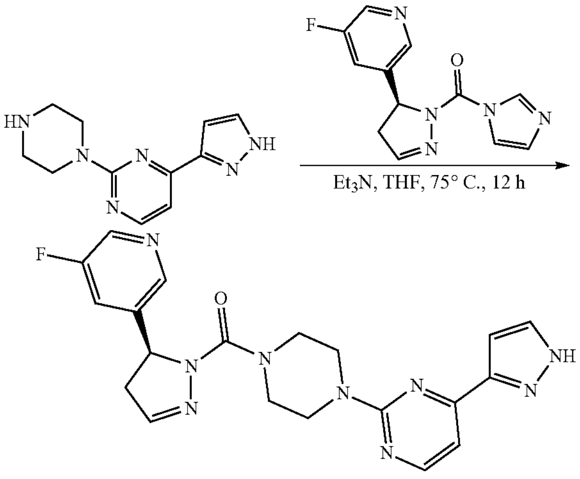

The titled compound 36 was prepared in 26.2% yield from 2-(piperazin-1-yl)-4-(1H-pyrazol-3-yl)pyrimidine prepared in analogous manner to the preparation of compound 33. LC-MS (m/z) 422.1 (M+H$^+$). $^1$H NMR (400 MHz, DMSO-$d_6$) δ 8.43 (s, 1H), 8.39-8.31 (m, 2H), 7.60 (dd, J=2.2, 0.6 Hz, 1H), 7.41 (dt, J=9.3, 2.3 Hz, 1H), 7.11 (dd, J=5.2, 0.6 Hz, 1H), 7.04-6.95 (m, 1H), 6.89 (dd, J=2.3, 0.6 Hz, 1H), 5.46-5.35 (m, 1H), 4.04-3.60 (m, 8H), 3.49-3.36 (m, 1H), 2.84-2.71 (m, 1H).

Compound 37: (S)-3-(1-(4-(4-(1H-pyrazol-3-yl)pyrimidin-2-yl)piperazine-1-carbonyl)-4,5-dihydro-1H-pyrazol-5-yl)benzonitrile

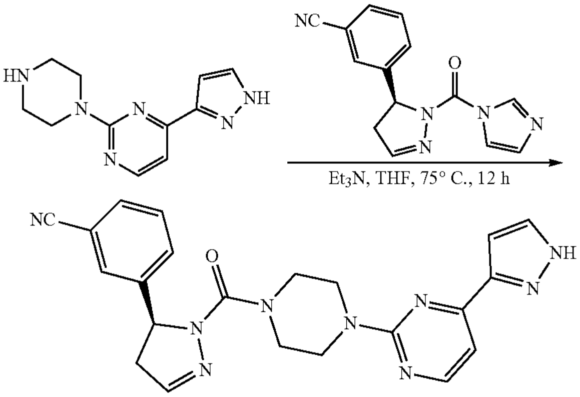

The titled compound 37 was prepared in 28.6% yield from 2-(piperazin-1-yl) (1H-pyrazol-3-yl)pyrimidine prepared in analogous manner to the preparation of 33. LC-MS (m/z) 428.1 (M+H$^+$). $^1$H NMR (400 MHz, $CDCl_3$) δ 8.28 (dt, J=5.2, 0.6 Hz, 1H), 7.57-7.45 (m, 4H), 7.38 (t, J=7.7 Hz, 1H), 6.99 (d, J=5.1 Hz, 1H), 6.85-6.78 (m, 2H), 5.31 (dd, J=11.7, 10.0 Hz, 1H), 3.99-3.53 (m, 8H), 3.29 (ddd, J=18.4, 11.7, 1.8 Hz, 1H), 2.63 (ddd, J=18.2, 10.1, 1.6 Hz, 1H).

Compound 38: (S)-5-(1-(4-(4-(1H-pyrazol-3-yl)pyrimidin-2-yl)piperazine-1-carbonyl)-4,5-dihydro-1H-pyrazol-5-yl)nicotinonitrile

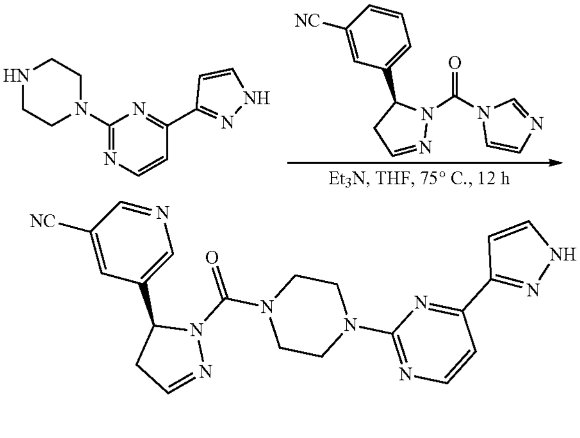

The titled compound 38 was prepared in 22.5% yield from 2-(piperazin-1-yl)-4-(1H-pyrazol-3-yl)pyrimidine prepared in analogous manner to the preparation of compound 33.

LC-MS (m/z) 429.1 (M+H+). $^{1}$H NMR (400 MHz, $CDCl_3$) δ 8.82 (d, J=2.2 Hz, 1H), 8.79 (d, J=2.0 Hz, 1H), 8.34 (d, J=5.1 Hz, 1H), 8.04 (t, J=2.1 Hz, 1H), 7.62 (d, J=2.2 Hz, 1H), 7.12 (d, J=5.1 Hz, 1H), 7.05-7.01 (m, 1H), 6.89 (d, J=2.2 Hz, 1H), 5.46-5.37 (m, 1H), 4.09-3.62 (m, 8H), 3.45 (ddd, J=18.3, 10.2, 1.6 Hz, 1H), 2.80 (ddd, J=18.3, 10.2, 1.6 Hz, 1H).

Compound 39: (S)-(4-(4-(1H-pyrazol-3-yl)pyrimidin-2-yl)piperazin-1-yl)(5-phenyl-4,5-dihydro-1H-pyrazol-1-yl)methanone

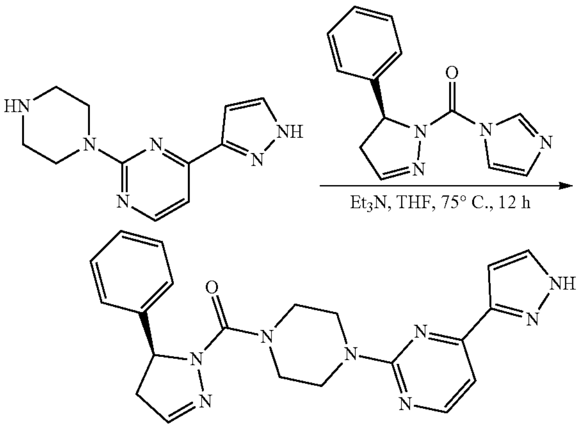

The titled compound 39 was prepared in 29.2% yield from 2-(piperazin-1-yl)-4-(1H-pyrazol-3-yl)pyrimidine prepared in analogous manner to the preparation of compound 33. LC-MS (m/z) 403.1 (M+H+). $^{1}$H NMR (400 MHz, $CDCl_3$) δ 8.27 (dd, J=5.1, 0.6 Hz, 1H), 7.53 (d, J=2.2 Hz, 1H), 7.30-7.14 (m, 5H), 7.02 (d, J=5.1 Hz, 1H), 6.82 (q, J=1.9 Hz, 2H), 5.33-5.24 (m, 1H), 3.97-3.51 (m, 8H), 3.34-3.21 (m, 1H), 2.73-2.62 (m, 1H).

Compound 40: (S)-(5-(3,5-difluorophenyl)-4,5-dihydro-1H-pyrazol-1-yl)(4-(5-fluoro-4-(1-methyl-1H-1,2,3-triazol-4-yl)pyrimidin-2-yl)piperazin-1-yl)methanone

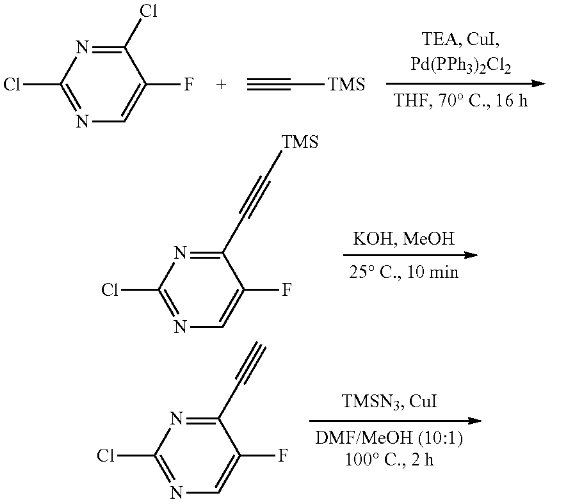

-continued

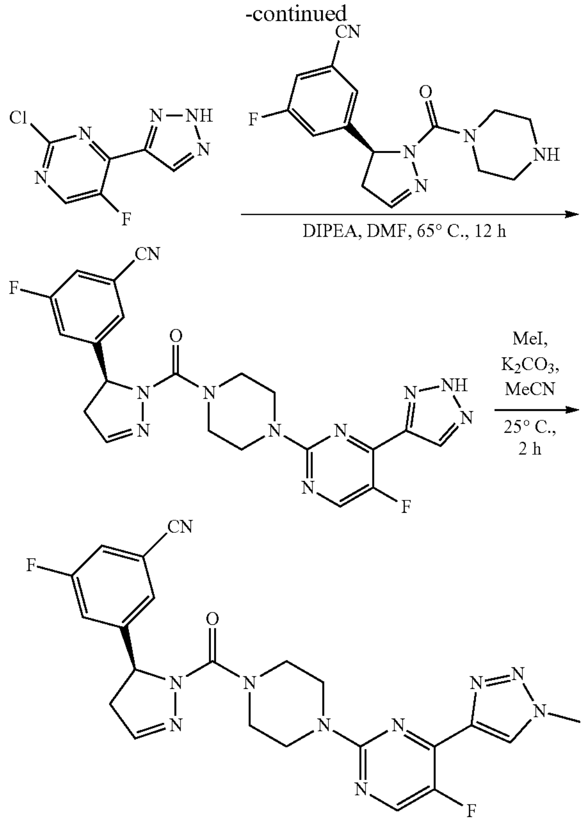

Step 1: To a solution of 2,4-dichloro-5-fluoropyrimidine (10 g, 59.9 mmol) in THF (200 mL) was added $Et_3N$ (24.2 g, 239.6 mmol), CuI (1.48 g, 7.79 mmol), $Pd(PPh_3)_2Cl_2$ (2.1 g, 2.99 mmol) and ethynyltrimethylsilane (2.94 g, 29.4 mmol) under Ar. The reaction mixture was stirred at 70° C. for 16 h under Ar. The crude was purified by Flash chromatography. 2-chloro-5-fluoro-4-((trimethylsilyl)ethynyl)pyrimidine (5 g) was obtained as a light-yellow oil, Yield: 36.5%. LC-MS (m/z) 229.1 (M+H+).

Step 2: To a solution of 2-chloro-5-fluoro-4-((trimethylsilyl)ethynyl)pyrimidine (5 g, 21.86 mmol) in MeOH (70 mL) was added KOH (62 mg, 1.09 mmol). The reaction mixture was stirred at 25° C. for 10 min. The crude was purified by Flash chromatography. 2-chloro-4-ethynyl-5-fluoropyrimidine (2.9 g) was obtained as a light-yellow oil, Yield: 84.7%. LC-MS (m/z) 156.9 (M+H+).

Step 3: To a solution of 2-chloro-4-ethynyl-5-fluoropyrimidine (2 g, 12.78 mmol) in DMF (30 mL) and MeOH (3 mL) was added CuI (243 mg, 128 mmol) and $TMSN_3$ (4.42 g, 38.33 mmol) under Ar. The reaction mixture was stirred at 100° C. for 2 h under Ar. The crude was purified by Flash chromatography. 2-chloro-5-fluoro-4-(2H-1,2,3-triazol-4-yl)pyrimidine (1.2 g) was obtained as a light-yellow solid, Yield: 47.1%. LC-MS (m/z) 200.1 (M+H+).

Step 4: To a solution of (S)-3-fluoro-5-(1-(piperazine-1-carbonyl)-4,5-dihydro-1H-pyrazol-5-yl)benzonitrile (1 g, 3.32 mmol) in DMF (10 mL) was added DIPEA (1.72 g, 13.27 mmol) and 2-chloro-5-fluoro-4-(2H-1,2,3-triazol-4-yl)pyrimidine (660 mg, 3.32 mmol). The reaction mixture was stirred at 65° C. for 12 h. The crude was purified by Flash chromatography. (S) fluoro-5-(1-(4-(5-fluoro-4-(2H-1,2,3-triazol-4-yl)pyrimidin-2-yl)piperazine-1-carbonyl)-4,5-dihydro-1H-pyrazol-5-yl)benzonitrile (1.1 g) was obtained as a white solid, Yield: 71.6%. LC-MS (m/z) 465.1 (M+H+).

Step 5:

To a solution of (S)-3-fluoro-5-(1-(4-(5-fluoro-4-(2H-1,2,3-triazol-4-yl)pyrimidin-2-yl)piperazine-1-carbonyl)-4,5-dihydro-1H-pyrazol-5-yl)benzonitrile (0.8 g, 1.73 mmol) in MeCN (20 mL) was added $K_2CO_3$ (595 mg, 4.31 mmol) and MeI (269 mg, 1.9 mmol). The reaction mixture was stirred at 25° C. for 2 h. The crude was purified by Pre-HPLC. (S)-3-fluoro-5-(1-(4-(5-fluoro-4-(1-methyl-1H-1,2,3-triazol-4-yl)pyrimidin-2-yl)piperazine-1-carbonyl)-4,5-dihydro-1H-pyrazol-5-yl)benzonitrile (126 mg) was obtained as a white solid, Yield: 15.3%. LC-MS (m/z) 479.1 ($M+H^+$).

$^1$H NMR (400 MHz, DMSO-$d_6$) δ 8.76 (d, J=1.5 Hz, 1H), 8.54 (d, J=2.9 Hz, 1H), 7.74 (ddd, J=8.5, 2.6, 1.4 Hz, 1H), 7.65 (s, 1H), 7.53 (ddd, J=9.8, 2.5, 1.4 Hz, 1H), 7.12 (s, 1H), 5.29 (dd, J=11.5, 10.2 Hz, 1H), 4.14 (s, 3H), 3.87-3.58 (m, 6H), 3.41-3.33 (m, 2H), 3.37 (ddd, J=18.3, 11.6, 1.9 Hz, 1H), 2.71 (ddd, J=18.3, 10.2, 1.6 Hz, 1H).

Compound 41: (S)-(5-(3,5-difluorophenyl)-4,5-dihydro-1H-pyrazol-1-yl)(4-(5-fluoro-4-(1-methyl-1H-1,2,3-triazol-5-yl)pyrimidin-2-yl)piperazin-1-yl)methanone

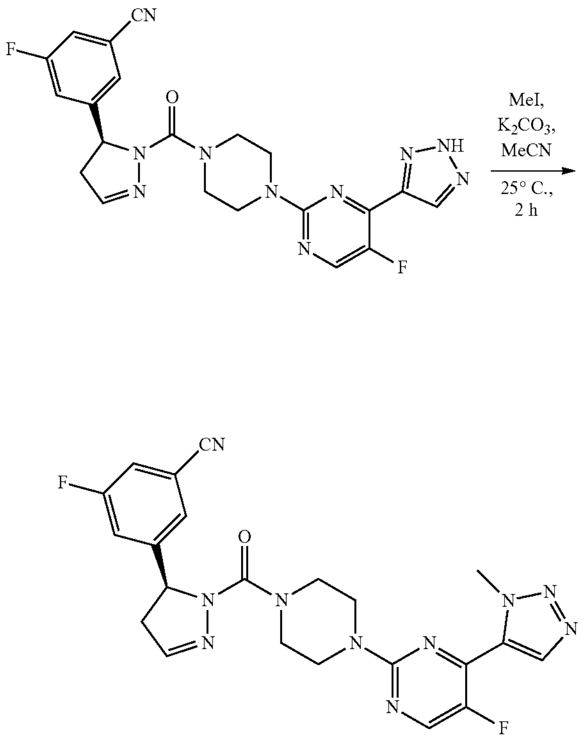

The titled compound 41 was prepared in 32.2% yield from (S)-3-fluoro-5-(1-(4-(5-fluoro-4-(2H-1,2,3-triazol-4-yl)pyrimidin-2-yl)piperazine-1-carbonyl)-4,5-dihydro-1H-pyrazol-5-yl)benzonitrile according to the procedure outlined for compound 40. LC-MS (m/z) 479.1 ($M+H^+$). $^1$H NMR (400 MHz, DMSO-$d_6$) δ 8.65 (d, J=2.6 Hz, 1H), 8.26 (d, J=4.0 Hz, 1H), 7.74 (ddd, J=8.5, 2.6, 1.3 Hz, 1H), 7.65 (s, 1H), 7.53 (ddd, J=9.8, 2.5, 1.4 Hz, 1H), 7.12 (s, 1H), 5.29 (dd, J=11.5, 10.1 Hz, 1H), 4.38 (s, 3H), 3.84-3.65 (m, 6H), 3.60-3.54 (m, 2H), 3.37 (ddd, J=18.3, 11.6, 1.8 Hz, 1H), 2.70 (ddd, J=18.3, 10.1, 1.6 Hz, 1H).

Compound 42: (S)-(5-(3,5-difluorophenyl)-4,5-dihydro-1H-pyrazol-1-yl)(4-(5-fluoro-4-(2-methyl-2H-1,2,3-triazol-4-yl)pyrimidin-2-yl)piperazin-1-yl)methanone

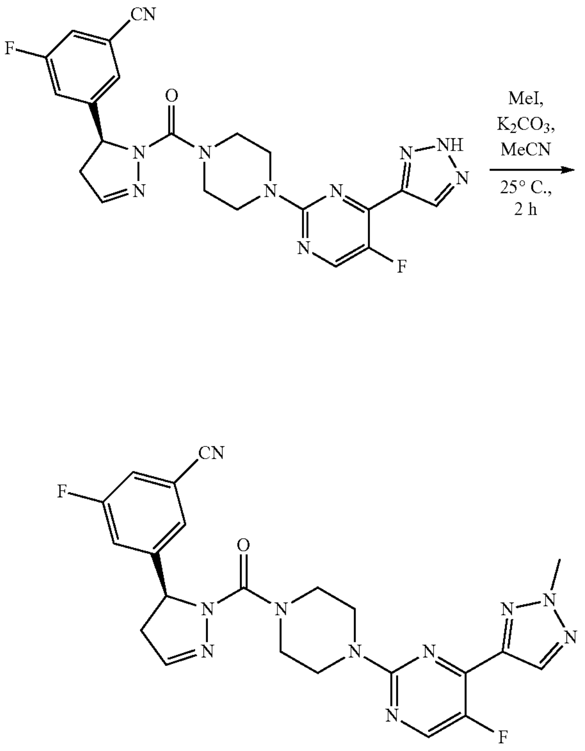

The titled compound 42 was prepared in 17.2% yield from (S)-3-fluoro-5-(1-(4-(5-fluoro-4-(2H-1,2,3-triazol-4-yl)pyrimidin-2-yl)piperazine-1-carbonyl)-4,5-dihydro-1H-pyrazol-5-yl)benzonitrile according to the procedure outlined for compound 40. LC-MS (m/z) 479.1 ($M+H^+$). $^1$H NMR (400 MHz, DMSO-$d_6$) δ 8.57 (d, J=2.8 Hz, 1H), 8.35 (d, J=1.2 Hz, 1H), 7.74 (ddd, J=8.5, 2.5, 1.3 Hz, 1H), 7.65 (s, 1H), 7.57-7.49 (m, 1H), 7.12 (s, 1H), 5.29 (dd, J=11.5, 10.1 Hz, 1H), 4.27 (s, 3H), 3.84-3.63 (m, 6H), 3.57-3.52 (m, 2H), 3.36 (ddd, J=18.3, 11.6, 1.8 Hz, 1H), 2.71 (ddd, J=18.3, 10.1, 1.6 Hz, 1H).

Compound 43: (S)-(5-(3,5-difluorophenyl)-4,5-dihydro-1H-pyrazol-1-yl)(4-(5-fluoro-4-(2-methyl-2H-1,2,3-triazol-4-yl)pyrimidin-2-yl)piperazin-1-yl)methanone

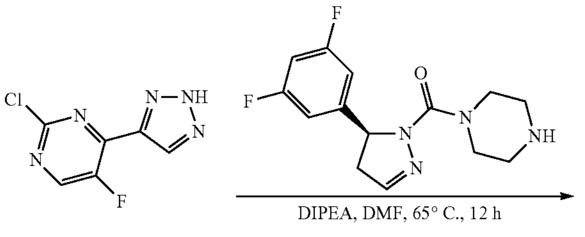

-continued

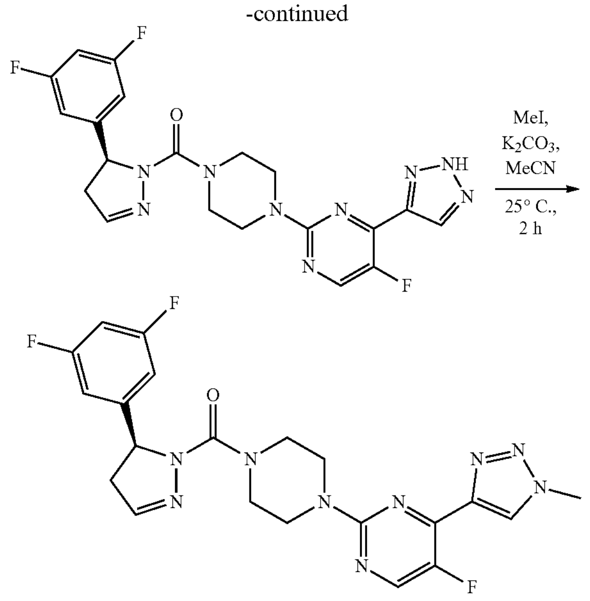

The titled compound 43 was prepared in analogous manner to the preparation of compound 40. $^1H$ NMR (400 MHz, $CDCl_3$) δ (ppm): δ 8.30 (d, J=2.4 Hz, 1H), 8.15 (d, J=2.0 Hz, 1H), 6.80-6.85 (m, 3H), 6.67-6.71 (m, 1H), 5.33 (dd, J=10.0, 11.6 Hz, 1H), 4.21 (s, 3H), 3.93-3.99 (m, 2H), 3.76-3.88 (m, 4H), 3.62-3.68 (m, 2H), 3.32 (ddd, J=2.0, 12.0, 13.6 Hz, 1H), 2.69 (ddd, J=1.6, 10.0, 11.6 Hz, 1H). Mass (ESI): m/z calcd for $C_{21}H_{20}F_3N_9O$ 471.5, found 472.4 $[M+H]^+$.

Compound 44: (S)-(5-(3,5-difluorophenyl)-4,5-dihydro-1H-pyrazol-1-yl)(4-(5-fluoro-4-(1-methyl-1H-1,2,3-triazol-5-yl)pyrimidin-2-yl)piperazin-1-yl) methanone

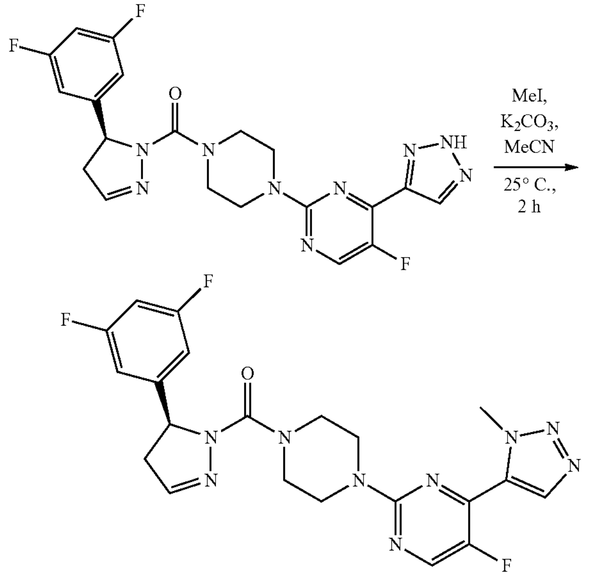

The titled compound 44 was prepared in analogous manner to the preparation of compound 40. $^1H$ NMR (400 MHz, $CDCl_3$) δ (ppm): δ 8.35 (d, J=2.4 Hz, 1H), 8.25 (d, J=4.4 Hz, 1H), 6.79-6.89 (m, 3H), 6.68-6.72 (m, 1H), 5.35 (t, J=10.8, 1H), 4.47 (s, 3H), 3.88-3.94 (m, 2H), 3.76-3.84 (m, 4H), 3.62-3.70 (m, 2H), 3.33 (ddd, J=2.0, 12.0, 14.0 Hz, 1H), 2.70 (ddd, J=1.6, 9.6, 11.6 Hz, 1H). Mass (ESI): m/z calcd for $C_{21}H_{20}F_3N_9O$ 471.5, found 472.3 $[M+H]^+$.

Compound 45: (S)-(5-(3,5-difluorophenyl)-4,5-dihydro-1H-pyrazol-1-yl)(4-(5-fluoro-4-(1-methyl-1H-1,2,3-triazol-4-yl)pyrimidin-2-yl)piperazin-1-yl) methanone

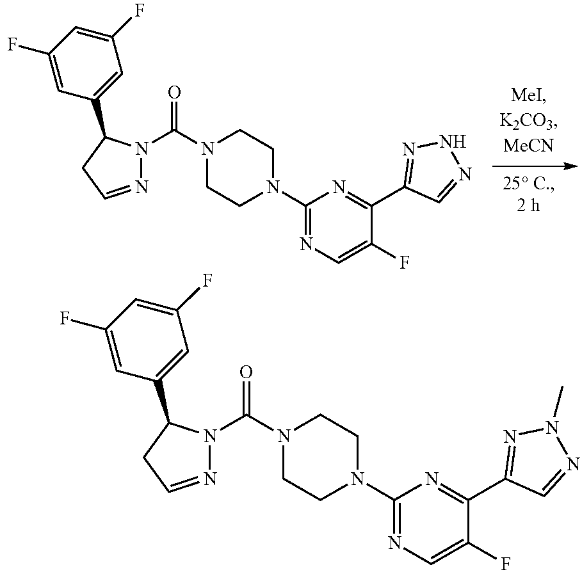

The titled compound 45 was prepared in analogous manner to the preparation of compound 40. $^1H$ NMR (400 MHz, $CDCl_3$) δ (ppm): δ 8.31 (d, J=2.8 Hz, 1H), 8.16 (d, J=2.0 Hz, 1H), 6.80-6.86 (m, 3H), 6.67-6.72 (m, 1H), 5.34 (dd, J=10.0, 11.6, 1H), 4.32 (s, 3H), 3.90-3.97 (m, 2H), 3.76-3.86 (m, 4H), 3.62-3.69 (m, 2H), 3.32 (ddd, J=1.6, 11.6, 13.6 Hz, 1H), 2.69 (ddd, J=1.6, 10.0, 11.6 Hz, 1H).

Compound 46: (S)-(5-(3,5-difluorophenyl)-4,5-dihydro-1H-pyrazol-1-yl)(4-(4-(3,5-dimethyl-4H-1,2,4-triazol-4-yl)-5-fluoropyrimidin-2-yl)piperazin-1-yl)methanone

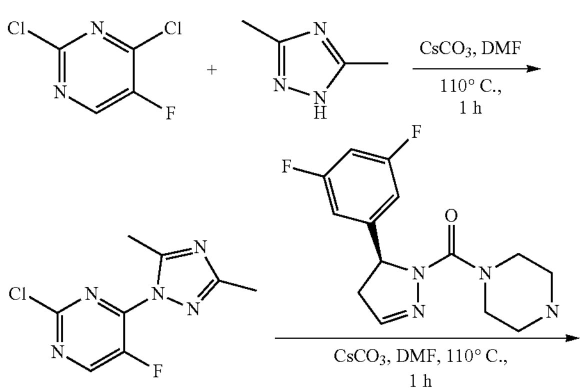

-continued

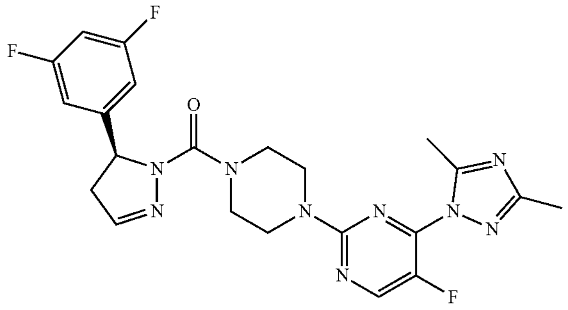

Step 1: To a solution of 2,4-dichloro-5-fluoropyrimidine (5 g, 29.95 mmol) in DMF (40 mL) was added 3,5-dimethyl-1H-1,2,4-triazole (3 g, 30.84 mmol) and $CsCO_3$ (11.6 g, 59.89 mmol). The reaction mixture was stirred at 110° C. for 1 h. The mixture was purified by Flash chromatography. 2-chloro-4-(3,5-dimethyl-1H-1,2,4-triazol-1-yl)-5-fluoropyrimidine was obtained as a white solid (6.1 g, 89.5%). LC-MS (m/z) 228.1 ($M+H^+$).

Step 2: To a solution of 2-chloro-4-(3,5-dimethyl-1H-1,2,4-triazol-1-yl)-5-fluoropyrimidine (86 mg, 373.8 umol) in DMF (5 mL) was added (S)-(5-(3,5-difluorophenyl)-4,5-dihydro-1H-pyrazol-1-yl)(piperazin-1-yl)methanone (100 mg, 339.8 umol) and $CsCO_3$ (132 mg, 629.6 umol). The reaction mixture was stirred at 110° C. for 1 h. The mixture was purified by Flash chromatography. The titled compound 46 (86 mg) was obtained as a white solid, Yield: 48.6%. LC-MS (m/z) 486.1 ($M+H^+$). $^1H$ NMR (400 MHz, $CDCl_3$) δ (ppm): δ 8.38 (s, 1H), 6.90-6.56 (m, 4H), 5.35-5.28 (m, 1H), 3.98-3.50 (m, 8H), 3.41-3.18 (m, 1H), 2.82-2.57 (m, 4H), 2.42 (s, 3H).

Compound 47: (S)-3-(1-(4-(4-(3,5-dimethyl-1H-1,2,4-triazol-1-yl)-5-fluoropyrimidin-2-yl)piperazine-1-carbonyl)-4,5-dihydro-1H-pyrazol-5-yl)-5-fluorobenzonitrile

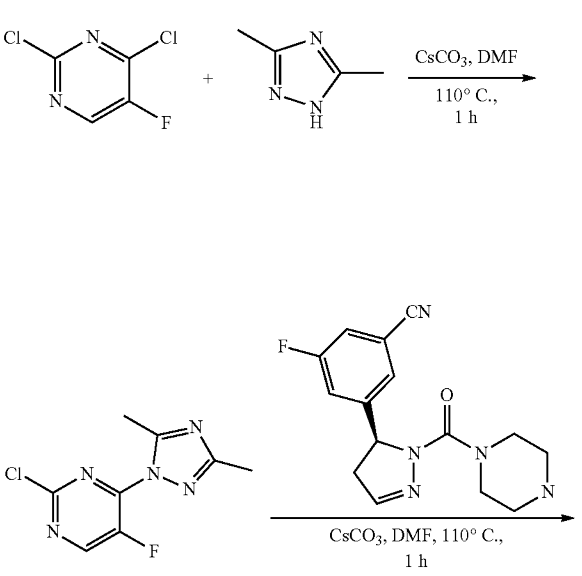

-continued

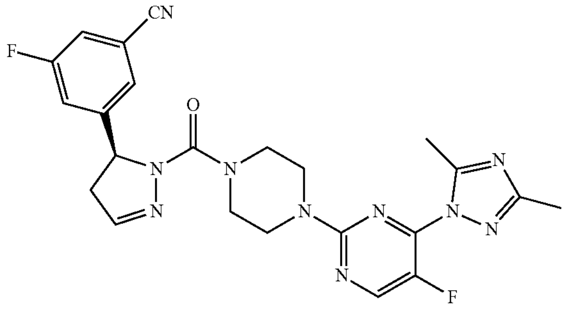

The titled compound 47 was prepared according to the procedure outlined for compound 46. LC-MS (m/z) 493.1 ($M+H^+$).

$^1H$ NMR (400 MHz, $CDCl_3$) δ (ppm): δ 8.28 (d, J=1.0 Hz, 1H), 7.11 (m, 3H), 6.74 (s, 1H), 5.21 (t, J=10.8 Hz, 1H), 3.82-3.40 (m, 9H), 3.21 (m, 1H), 2.65-2.46 (m, 4H), 2.32 (s, 3H).

Compound 48: (S)-3-fluoro-5-(1-(4-(5-fluoro-4-(6-hydroxypyridin-3-yl)pyrimidin-2-yl)piperazine-1-carbonyl)-4,5-dihydro-1H-pyrazol-5-yl)benzonitrile

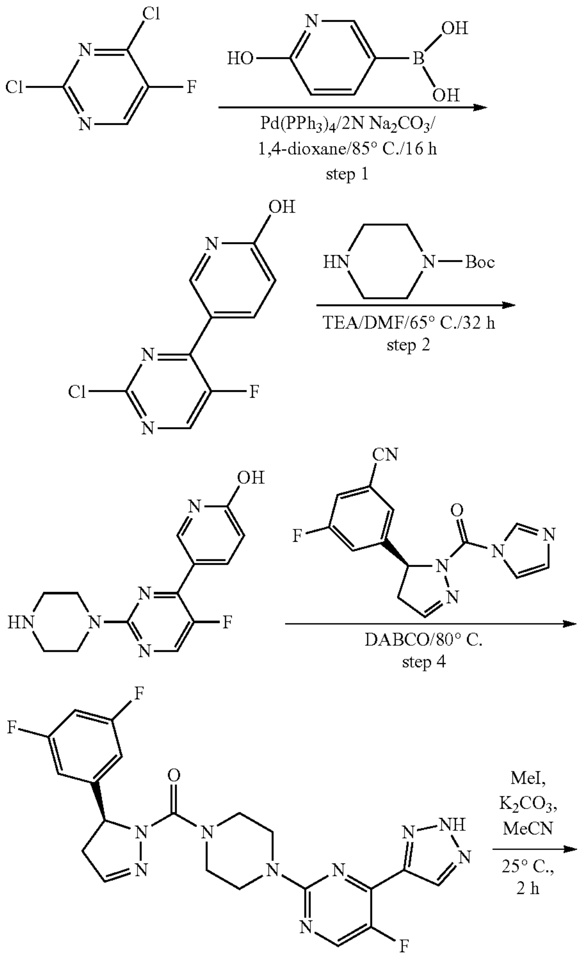

-continued

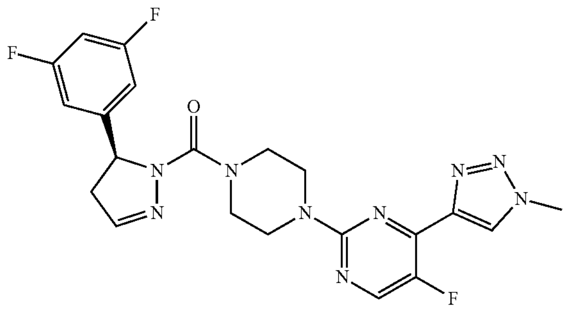

Step1: 2,4-dichloro-5-fluoropyrimidine (697 mg, 4.20 mmol) and (6-hydroxypyridin-3-yl)boronic acid (700 mg, 5.04 mmol) and $Pd(PPh_3)_4$ (485 mg, 0.42 mmol) were dissolved in 10 mL 1,4-dioxane. 2N $Na_2CO_3$ (6.25 ml) was added. Let it stir at 85° C. for 16 hrs. The solvent was evaporated to dryness and purified by column chromatography (EA) to give 800 mg 5-(2-chloro-5-fluoropyrimidin-4-yl)pyridin-2-ol as light-yellow solid. Yield: 84.6%. LC-MS (m/z): 256.3 $[M+H]^+$.

Step2: tert-butyl piperazine-1-carboxylate (447 mg, 2.5 mmol) and 5-(2-chloro-5-fluoropyrimidin-4-yl)pyridin-2-ol (450 mg, 2 mmol) were dissolved in 10 mL DMF. 0.5 mL DIEA was added. Let it stir at 65° C. for 16 hrs. Water was added to the reaction and extracted with EtOAc (30 mL×3). The organic layers were combined and evaporated to dryness and purified by prep-TLC (DCM/MeOH=12/1) to give 350 mg tert-butyl 4-(5-fluoro-4-(6-hydroxypyridin-3-yl)pyrimidin-2-yl)piperazine-1-carboxylate as brown solid. Yield: 46.7%. LC-MS (m/z): 376.2 $[M+H]^+$.

Step 3 and 4: tert-butyl 4-(5-fluoro-4-(6-hydroxypyridin-3-yl)pyrimidin-2-yl)piperazine-1-carboxylate (92 mg, 0.245 mmol) was dissolved in 3 mL DCM. 2 mL of TFA/DCM (1/1) was added to the solution at 0° C. Let it stir at r.t for 1 h. The solvent was evaporated to dryness and used for next step without further purification. LC-MS (m/z): 276.3 $[M+H]^+$.

The above residue and (S)-3-(1-(1H-imidazole-1-carbonyl)-4,5-dihydro-1H-pyrazol-5-yl)-5-fluorobenzonitrile (69.4 mg, 0.245 mmol) and DABCO (110 mg, 0.98 mmol) were mixed in 3 mL THF. It was evaporated to dryness and directly lighted with 100 W filament lamp for 2 hrs. The solid was purified by prep-TLC (DCM/MeOH=14/1) to give 35 mg of (S)-3-fluoro-5-(1-(4-(5-fluoro-4-(6-hydroxypyridin-3-yl)pyrimidin-2-yl)piperazine-1-carbonyl)-4,5-dihydro-1H-pyrazol-5-yl)benzonitrile as light-yellow solid. Total yield for two steps: 29.1%. $^1H$ NMR (400 MHz, $CDCl_3$) δ (ppm): 8.35 (d, J=2.8 Hz, 1H), 8.33-8.30 (m, 1H), 8.23 (d, J=3.6 Hz, 1H), 7.42 (t, J=1.2 Hz, 1H), 7.29 (s, 1H), 6.89 (t, J=1.6 Hz, 1H), 6.73-6.69 (m, 1H), 5.37 (dd, J=11.2, 10.4 Hz, 1H), 3.96-3.86 (m, 2H), 3.84-3.75 (m, 4H), 3.69-3.62 (m, 2H), 3.36 (ddd, J=18.4, 12.0, 1.6 Hz, 1H), 2.70 (ddd, J=18.4, 10.0, 1.6 Hz, 1H). LC-MS (m/z): 491.3 $[M+H]^+$.

Compound 49: (S)-(5-(3,5-difluorophenyl)-4,5-dihydro-1H-pyrazol-1-yl)(4-(5-fluoro-2',4',6'-trimethoxy-[4,5'-bipyrimidin]-2-yl)piperazin-1-yl)methanone

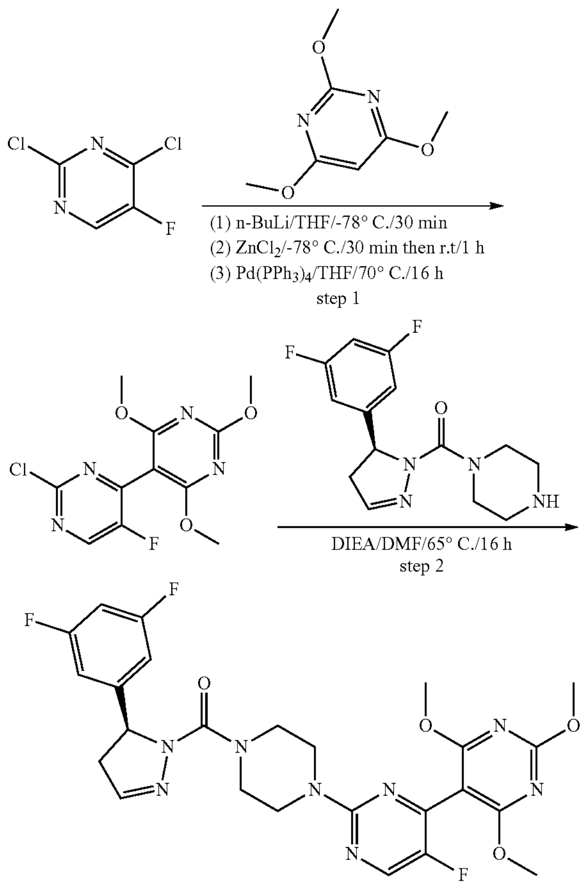

Step 1: 2,4,6-trimethoxypyrimidine (1 g, 5.88 mmol) was dissolved in 20 ml THF. n-BuLi (2.85 ml, 6.84 mmol, 2.4 M in hexane) was added slowly to the solution at −78° C. Let it stir at −78° C. for 30 mins. Then the solution of $ZnCl_2$ (6.3 ml, 6.3 mmol, 1M in THF) was added dropwise at −78° C. Let it stir at −78° C. for 30 mins and then warmed to room temperature and stirred at room temperature for 1 h. 2,4-dichloro-5-fluoropyrimidine (286 mg, 1.71 mmol) and $Pd(PPh_3)_4$ (224 mg, 0.194 mmol) in 6 ml THF were added to the solution in one portion. Let it stir at 70° C. for 16 hrs. Water was added to quench the reaction and extracted with EtOAc (60 ml×3). The solvent was evaporated to dryness and purified by column chromatography (PE/EA=85/15) to give 160 mg 2-chloro-5-fluoro-2',4',6'-trimethoxy-4,5'-bipyrimidine as a light-yellow solid. Yield: 31.2%. LC-MS (m/z): 301.4 $[M+H]^+$.

Step 2: 2-chloro-5-fluoro-2',4',6'-trimethoxy-4,5'-bipyrimidine (28 mg, 0.093 mmol) and (S)-(5-(3,5-difluorophenyl)-4,5-dihydro-1H-pyrazol-1-yl)(piperazin-1-yl)methanone (25 mg, 0.085 mmol) were dissolved in 2 mL DMF. 0.2 mL DIEA was added. Let it stir at 65° C. for 32 hrs. Water was added to the reaction and extracted with EtOAc (50 mL×3). The organic layers were combined and evaporated to dryness and purified by column chromatography (PE/EA=1/3) to give 17 mg of (S)-(5-(3,5-difluorophenyl)-4,5-dihydro-1H-pyrazol-1-yl)(4-(5-fluoro-2',4',6'-trimethoxy-[4,5'-bipyrimidin]-2-yl)piperazin-1-yl)methanone as a white solid. Yield: 36.2%. $^1$H NMR (400 MHz, $CDCl_3$) δ (ppm): 8.20 (d, J=1.2 Hz, 1H), 6.85-6.80 (m, 2H), 6.69 (tt, J=8.8, 2.0 Hz, 1H), 5.33 (dd, J=11.6, 10.0 Hz, 1H), 4.02 (s, 3H), 3.94 (s, 6H), 3.91-3.82 (m, 2H), 3.81-3.71 (m, 4H), 3.67-3.58 (m, 2H), 3.31 (ddd, J=18.4, 12.0, 2.0 Hz, 1H), 2.67 (ddd, J=18.4, 10.0, 1.6 Hz, 1H). LC-MS (m/z): 559.3 $[M+H]^+$.

Compound 50: (S)-3-fluoro-5-(1-(4-(5-fluoro-2',6'-dihydroxy-[4,4'-bipyrimidin]-2-yl)piperazine-1-carbonyl)-4,5-dihydro-1H-pyrazol-5-yl)benzonitrile

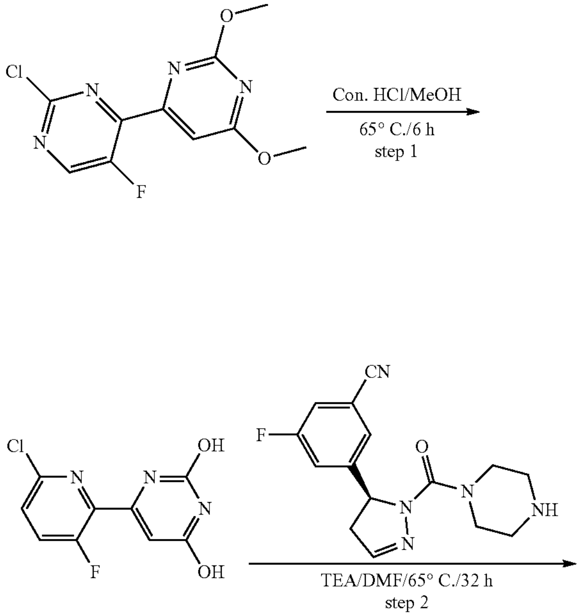

-continued

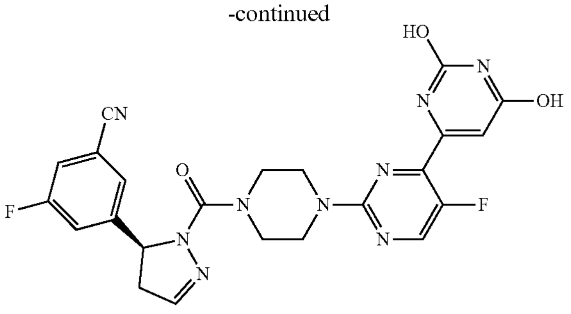

Step 1:2-chloro-5-fluoro-2',6'-dimethoxy-4,4'-bipyrimidine (80 mg, 0.296 mmol) was dissolved in 2 mL MeOH. 0.3 mL of con. HCl was added to the solution. Let it stir at 60° C. for 10 hrs. The solvent was evaporated to dryness and purified by recrystallization (EA/PE) to give 60 mg 2'-chloro-5'-fluoro-[4,4'-bipyrimidine]-2,6-diol as white solid. Yield: 83.8%. LC-MS (m/z): 243.2 $[M+H]^+$.

Step 2: 2'-chloro-5'-fluoro-[4,4'-bipyrimidine]-2,6-diol (60 mg, 0.199 mmol) and (S)-3-fluoro-5-(1-(piperazine-1-carbonyl)-4,5-dihydro-1H-pyrazol-5-yl)benzonitrile (47.8 mg, 0.198 mmol) were dissolved in 2 mL DMF. 0.2 mL DIEA was added to the solution. Let it stir at 65° C. for 32 hrs. 1 mL water was added to the solution and extracted with EtOAc (10 mL×3). The organic layers were combined and evaporated to dryness and purified by prep-TLC (DCM/MeOH=14/1) to give 50 mg of (S)-3-fluoro-5-(1-(4-(5-fluoro-2',6'-dihydroxy-[4,4'-bipyrimidin]-2-yl)piperazine-1-carbonyl)-4,5-dihydro-1H-pyrazol-5-yl)benzonitrile as brown solid. Yield: 51.5%. $^1$H NMR (400 MHz, $CDCl_3$) δ (ppm): 9.00 (s, 1H), 8.43 (d, J=2.8 Hz, 1H), 8.40 (s, 1H), 7.42 (t, J=1.6 Hz, 1H), 6.92 (t, J=1.6 Hz, 1H), 6.64 (t, J=2.0 Hz, 1H), 5.37 (dd, J=11.2, 10.4 Hz, 1H), 3.99-3.86 (m, 2H), 3.85-3.75 (m, 4H), 3.72-3.62 (m, 2H), 3.37 (ddd, J=18.4, 11.6, 1.6 Hz, 1H), 2.72 (ddd, J=18.4, 10.0, 1.6 Hz, 1H). LC-MS (m/z): 508.3 $[M+H]^+$.

Compound 51: (S)-3-fluoro-5-(1-(4-(5-fluoro-1',3'-dimethyl-2',6'-dioxo-1',2',3',6'-tetrahydro-[4,4'-bipyrimidin]-2-yl)piperazine-1-carbonyl)-4,5-dihydro-1H-pyrazol-5-yl)benzonitrile

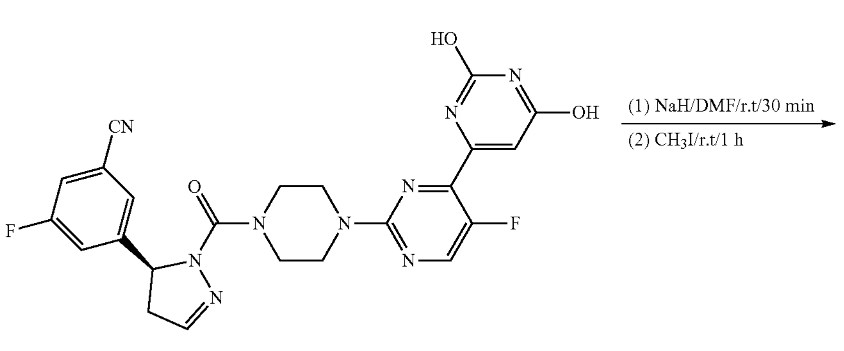

-continued

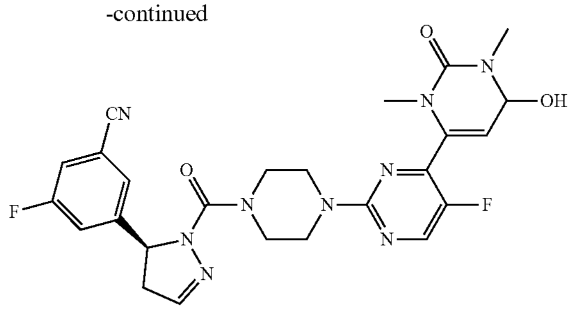

(S)-3-fluoro-5-(1-(4-(5-fluoro-2',6'-dihydroxy-[4,4'-bipyrimidin]-2-yl)piperazine-1-carbonyl)-4,5-dihydro-1H-pyrazol-5-yl)benzonitrile (25 mg, 0.049 mmol) was dissolved in 2 mL DMF. NaH (6 mg, 0.15 mmol) was added at r.t. Let stir at r.t for 30 min. Then $CH_3I$ (0.05 mL) was added. Let stir at r.t for 1 h. Water was added to quench the reaction and extracted with EtOAc (5 mL×3). The organic layers were combined and evaporated to dryness and purified by prep-TLC (PE/EA=1/3) to give 6 mg of (S)-3-fluoro-5-(1-(4-(5-fluoro-1',3'-dimethyl-2',6'-dioxo-1',2',3',6'-tetrahydro-[4,4'-bipyrimidin]-2-yl)piperazine-1-carbonyl)-4,5-dihydro-1H-pyrazol-5-yl)benzonitrile as light-yellow solid. Yield: 22.8%. $^1H$ NMR (400 MHz, $CDCl_3$) δ (ppm): 8.38 (d, J=1.2 Hz, 1H), 7.41 (t, J=1.2 Hz, 1H), 7.29 (s, 1H), 6.89 (s, 1H), 5.87 (s, 1H), 5.37 (d, J=11.2, 10.4 Hz, 1H), 3.90-3.85 (m, 2H), 3.81-3.74 (m, 4H), 3.68-3.60 (m, 2H), 3.41 (s, 3H), 3.34 (ddd, J=18.4, 11.6, 1.6 Hz, 1H), 3.31 (s, 3H), 2.70 (ddd, J=18.4, 10.0, 1.6 Hz, 1H). LC-MS (m/z): 508.3 $[M+H]^+$.

Compound 52: (S)-(5-(3,5-difluorophenyl)-4,5-dihydro-1H-pyrazol-1-yl)(4-(5-fluoro-4-(1H-pyrazol-4-yl)pyrimidin-2-yl)piperazin-1-yl)methanone

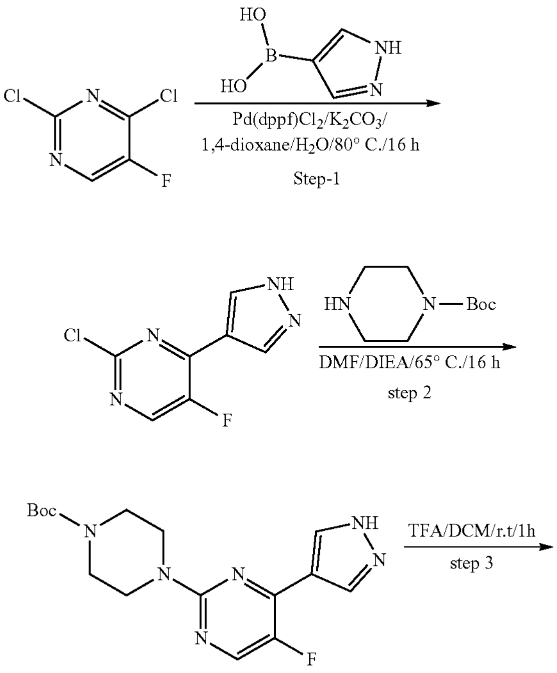

-continued

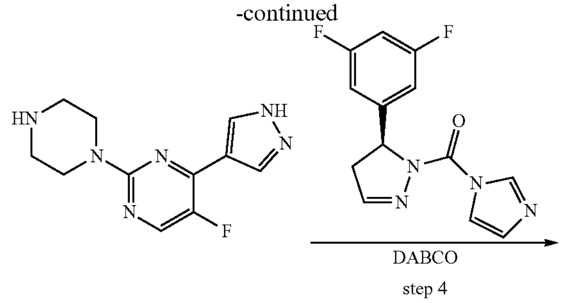

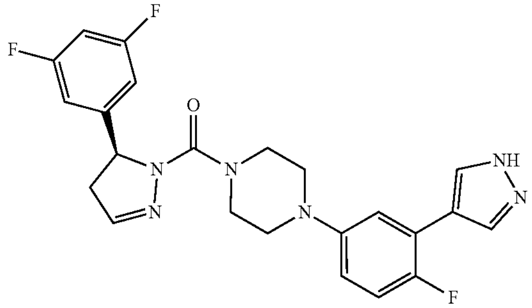

Step 1: 2,4-dichloro-5-fluoropyrimidine (6.74 g, 40.6 mmol) and (1H-pyrazol-4-yl)boronic acid (5 g, 44.7 mmol) and $K_2CO_3$ (11.2 g, 81.16 mmol) were mixed in 120 mL 1,4-dioxane/$H_2O$ (3/1). Pd(dppf)$Cl_2$ (2.97 g, 4.06 mmol) was added. Let it stir at 85° C. for 16 hrs. The solvent was evaporated to dryness and purified by column chromatography (PE/EA=3/1) to give 3.28 g 2-chloro-5-fluoro-4-(1H-pyrazol-4-yl)pyrimidine as orange oil. Yield: 40.8%. LC-MS (m/z): 199.3 $[M+H]^+$.

Step 2: tert-butyl piperazine-1-carboxylate (960 mg, 5.15 mmol) and 2-chloro-5-fluoro-4-(1H-pyrazol-4-yl)pyrimidine (1 g, 5.05 mmol) were dissolved in 23 mL DMF. 1 mL DIEA was added. Let it stir at 65° C. for 32 hrs. Water was added to the reaction and extracted with EtOAc (50 mL×3). The organic layers were combined and evaporated to dryness and purified by column chromatography (PE/EA=1/2) to give 800 mg tert-butyl 4-(5-fluoro-4-(1H-pyrazol yl)pyrimidin-2-yl)piperazine-1-carboxylate as yellow oil. Yield: 45.5%. LC-MS (m/z): 349.3 $[M+H]^+$.

Step 3 and step 4: tert-butyl 4-(5-fluoro-4-(1H-pyrazol-4-yl)pyrimidin-2-yl)piperazine-1-carboxylate (400 mg, 1.15 mmol) was dissolved in 5 mL DCM. 3 mL of TFA/DCM (1/1) was added to the solution at 0° C. Let it stir at r.t for 1 h. The solvent was evaporated to dryness to give 650 mg 5-fluoro-2-(piperazin-1-yl)-4-(1H-pyrazol-4-yl)pyrimidine as brown oil and it was used for next step without further purification. LC-MS (m/z): 249.2 $[M+H]^+$.

The above residue (325 mg, 1.305 mmol) and (S)-(5-(3,5-difluorophenyl)-4,5-dihydro-1H-pyrazol-1-yl)(1H-imidazol-1-yl)methanone (317.4 mg, 1.146 mmol) and DABCO (514.2 mg, 4.584 mmol) were mixed in 8 mL THF. It was evaporated to dryness and directly lighted with 100 W filament lamp for 1 h. The solid was purified by prep-TLC (PE/EA=1/3) to give 42 mg of (S)-(5-(3,5-difluorophenyl)-4,5-dihydro-1H-pyrazol-1-yl)(4-(5-fluoro-4-(1H-pyrazol-4-yl)pyrimidin-2-yl)piperazin-1-yl)methanone as white solid. Yield: 8%. $^1$H NMR (400 MHz, $CDCl_3$) δ (ppm): 8.31 (s, 1H), 8.24-8.22 (m, 1H), 6.86-6.81 (m, 3H), 6.70 (tt, J=11.2, 2.0 Hz, 1H)), 5.34 (dd, J=11.6, 10.0 Hz, 1H), 4.02-3.89 (m, 2H), 3.89-3.75 (m, 4H), 3.71-3.61 (m, 2H), 3.33 (ddd, J=18.4, 12.0, 2.0 Hz, 1H), 2.70 (ddd, J=18.4, 9.6, 1.6 Hz, 1H). LC-MS (m/z): 457.5 $[M+H]^+$.

Compound 53: (S)-2-(4-(2-(4-(5-(3,5-difluorophenyl)-4,5-dihydro-1H-pyrazole-1-carbonyl)piperazin-1-yl)-5-fluoropyrimidin-4-yl)-1H-pyrazol-1-yl)acetamide

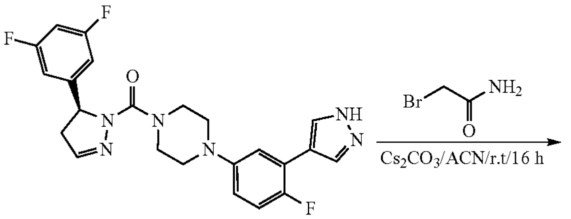

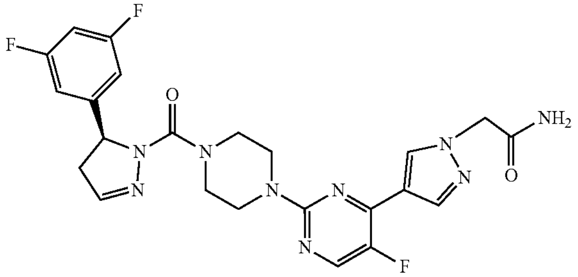

(S)-(5-(3,5-difluorophenyl)-4,5-dihydro-1H-pyrazol-1-yl)(4-(5-fluoro-4-(1H-pyrazol-4-yl)pyrimidin-2-yl)piperazin-1-yl)methanone (100 mg, 0.219 mmol) and 2-bromoacetamide (33.3 mg, 0,241 mmol) and $Cs_2CO_3$ (144 mg, 0.439 mmol) were mixed in 2 mL $CH_3CN$. Let it stir at room temperature for 16 hrs. The solvent was evaporated to dryness and purified by column chromatography (DCM/MeOH=17/3) to give 21 mg of (S)-2-(4-(2-(4-(5-(3,5-difluorophenyl)-4,5-dihydro-1H-pyrazole-1-carbonyl)piperazin-1-yl)-5-fluoropyrimidin-4-yl)-1H-pyrazol-1-yl) acetamide as white solid. Yield: 18.6%. $^1$H NMR (400 MHz, $CDCl_3$) δ (ppm): 8.27 (d, J=0.8 Hz, 1H), 8.22 (d, J=2.8 Hz, 1H), 8.18 (d, J=1.2 Hz, 1H), 6.88-6.80 (m, 2H), 6.70 (tt, J=8.8, 2.4 Hz, 1H), 6.23 (brs, 1H), 5.52 (brs, 1H), 5.34 (dd, J=11.2, 10.0 Hz, 1H), 4.89 (s, 2H), 3.99-3.90 (m, 2H), 3.86-3.77 (m, 4H), 3.72-3.61 (m, 2H), 3.33 (ddd, J=18.4, 12.0, 2.0 Hz, 1H), 2.70 (ddd, J=18.3, 10.0, 1.6 Hz, 1H). LC-MS (m/z): 514.3 $[M+H]^+$.

Compound 54: (S)-3-fluoro-5-(1-(4-(5-fluoro-4-(1H-pyrazol-4-yl)pyrimidin yl)piperazine-1-carbonyl)-4,5-dihydro-1H-pyrazol-5-yl)benzonitrile

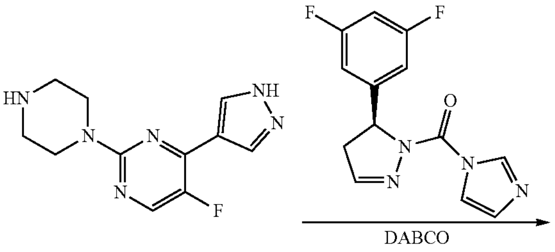

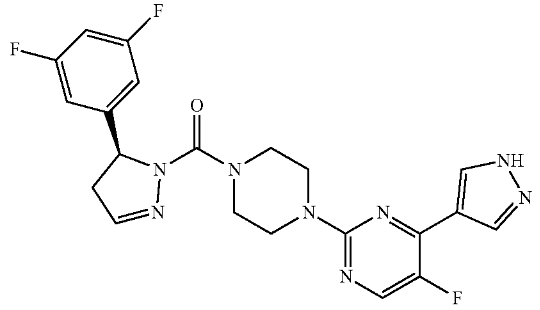

5-fluoro-2-(piperazin-1-yl)-4-(1H-pyrazol-4-yl)pyrimidine (325 mg, 1.305 mmol) and (S)-3-(1-(1H-imidazole-1-carbonyl)-4,5-dihydro-1H-pyrazol-5-yl)-5-fluorobenzonitrile (325.5 mg, 1.146 mmol) and DABCO (514.2 mg, 4.584 mmol) were mixed in 8 mL THF. It was evaporated to dryness and directly lighted with 100 W filament lamp for 1 h. The solid was purified by prep-TLC (PE/EA=1/3) to give 152 mg of (S)-3-fluoro-5-(1-(4-(5-fluoro-4-(1H-pyrazol-4-yl)pyrimidin-2-yl)piperazine-1-carbonyl)-4,5-dihydro-1H-pyrazol-5-yl)benzonitrile as light-yellow solid. Yield: 28.6%. $^1$H NMR (400 MHz, $CDCl_3$) δ (ppm): 8.35-8.27 (m, 2H), 8.23 (d, J=2.8 Hz, 1H), 7.42 (t, J=1.2 Hz, 1H), 7.29 (s, 1H), 6.90 (t, J=1.6 Hz, 1H), 5.37 (dd, J=11.6, 10.0 Hz, 1H), 4.00-3.92 (m, 2H), 3.90-3.75 (m, 4H), 3.70-3.64 (m, 2H), 3.36 (ddd, J=18.4, 11.6, 2.0 Hz, 1H), 2.70 (ddd, J=18.4, 10.0, 1.6 Hz, 1H). LC-MS (m/z): 464.3 $[M+H]^+$.

Compound 55: (S)-(5-(3,5-difluorophenyl)-4,5-dihydro-1H-pyrazol-1-yl)(4-(4-(2,4-dimethylthiazol-5-yl)-5-fluoropyrimidin-2-yl)piperazin-1-yl)methanone

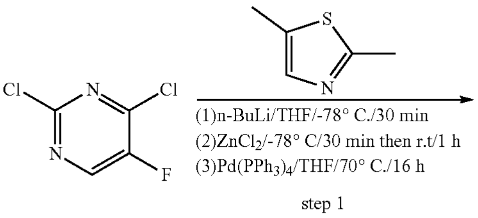

-continued

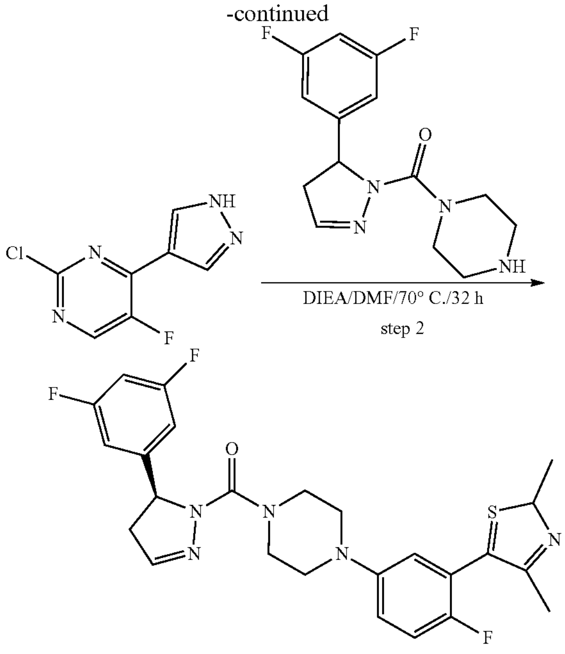

Step 1: 2,5-dimethylthiazole (300 mg, 2.65 mmol) was dissolved in 10 ml THF. n-BuLi (1.3255 ml, 3.18 mmol, 2.4 M in hexane) was added slowly to the solution at −78° C. Let it stir at −78° C. for 30 mins. Then the solution of $ZnCl_2$ (2.91 ml, 2.91 mmol, 1M in THF) was added dropwise at −78° C. Let it stir at −78° C. for 30 mins and then warmed to room temperature and stirred at room temperature for 1 h. 2,4-dichloro-5-fluoropyrimidine (310 mg, 1.856 mmol) and $Pd(PPh_3)_4$ (152 mg, 0.13 mmol) in 6 ml THF were added to the solution in one portion. Let it stir at 70° C. for 16 hrs. Water was added to quench the reaction and extracted with EtOAc (30 ml×3). The solvent was evaporated to dryness and purified by column chromatography (PE/EA=85/15) to give 75 mg 5-(2-chloro-5-fluoropyrimidin-4-yl)-2,4-dimethylthiazole as orange solid. Yield: 16.6%. LC-MS (m/z): 244.3 $[M+H]^+$.

Step 2: The titled compound 55 as a light-yellow solid was prepared in 35.2% yield from 5-(2-chloro-5-fluoropyrimidin-4-yl)-2,4-dimethylthiazole and (S)-(5-(3,5-difluorophenyl)-4,5-dihydro-1H-pyrazol-1-yl)(piperazin-1-yl) methanone according to the procedure outlined for compound 7. $^1H$ NMR (400 MHz, $CDCl_3$) δ (ppm): 8.24 (d, J=2.4 Hz, 1H), 6.94-6.78 (m, 2H), 6.69 (t, J=8.8 Hz, 1H), 5.34 (t, J=10.4 Hz, 1H), 3.95-3.85 (m, 2H), 3.83-3.73 (m, 4H), 3.69-3.59 (m, 2H), 3.32 (dd, J=18.0 12.8 Hz, 1H), 2.73 (s, 3H), 2.72-2.61 (m, 4H). LC-MS (m/z): 502.4 $[M+H]^+$.

Compound 56: (S)-(5-(3,5-difluorophenyl)-4,5-dihydro-1H-pyrazol-1-yl)(4-(5-fluoro-4-(2-methylthiazol-5-yl)pyrimidin-2-yl)piperazin-1-yl)methanone

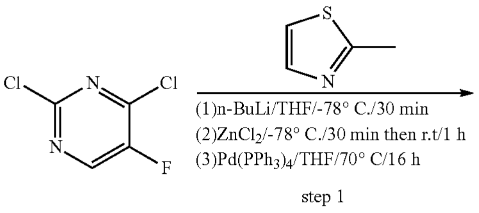

-continued

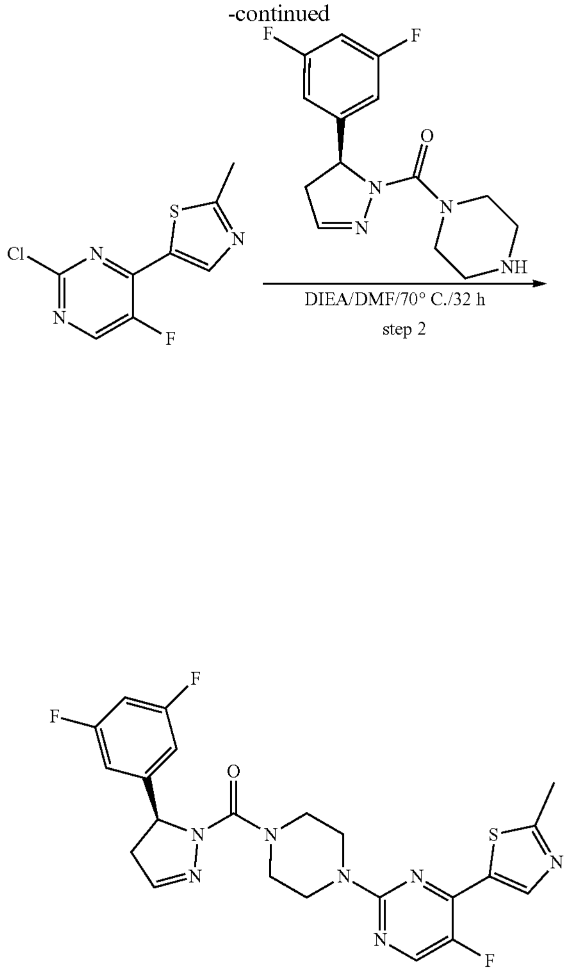

Step 1: 2-methylthiazole (300 mg, 3.03 mmol) was dissolved in 10 ml THF. n-BuLi (1.388 ml, 3.33 mmol, 0.4 M in hexane) was added slowly to the solution at −78° C. Let it stir at −78° C. for 30 mins. Then the solution of $ZnCl_2$ (3.3 ml, 3.3 mmol, 1M in THF) was added dropwise at −78° C. Let it stir at −78° C. for 30 mins and then warmed to room temperature and stirred at room temperature for 1 h. 2,4-dichloro-5-fluoropyrimidine (354.2 mg, 2.12 mmol) and $Pd(PPh_3)_4$ (175 mg, 0.152 mmol) in 6 ml THF were added to the solution in one portion. Let it stir at 70° C. for 16 hrs. Water was added to quench the reaction and extracted with EtOAc (30 ml×3). The solvent was evaporated to dryness and purified by column chromatography (PE/EA=1/1) to give 328 mg 5-(2-chloro-5-fluoropyrimidin-4-yl)-2-methylthiazole as grey solid. Yield: 67.6%. LC-MS (m/z): 230.4 $[M+H]^+$.

Step 2: The titled compound 56 as a light-yellow solid was prepared in 70% yield from 5-(2-chloro-5-fluoropyrimidin-4-yl)-2-methylthiazole and (S)-(5-(3,5-difluorophenyl)-4,5-dihydro-1H-pyrazol-1-yl)(piperazin-1-yl)methanone according to the procedure outlined for compound 7. $^1H$ NMR (400 MHz, $CDCl_3$) δ (ppm): 8.32 (d, J=2.0 Hz, 1H), 8.24 (d, J=2.8 Hz, 1H), 6.86-6.81 (m, 2H), 6.70 (dt, J=8.8, 2.4 Hz, 1H), 5.34 (dd, J=11.6, 10.0 Hz, 1H), 3.93-3.84 (m, 2H), 3.78 (q, J=7.6 Hz, 4H), 3.68-3.58 (m, 2H), 3.32 (ddd, J=18.4, 11.6, 1.6 Hz, 1H), 2.77 (s, 3H), 2.69 (ddd, J=18.4, 10.0, 1.6 Hz, 1H). LC-MS (m/z): 488.3 $[M+H]^+$.

Compound 57: (S)-3-fluoro-5-(1-(4-(5-fluoro-4-(2-methylthiazol-5-yl)pyrimidin-2-yl)piperazine-1-carbonyl)-4,5-dihydro-1H-pyrazol-5-yl)benzonitrile

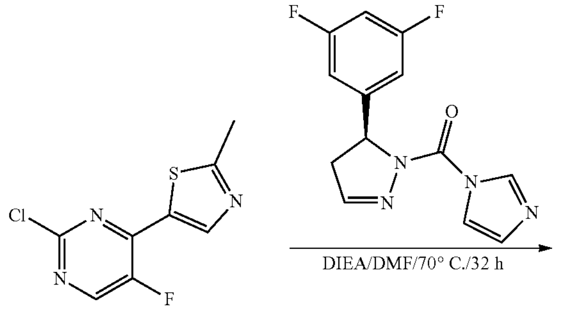

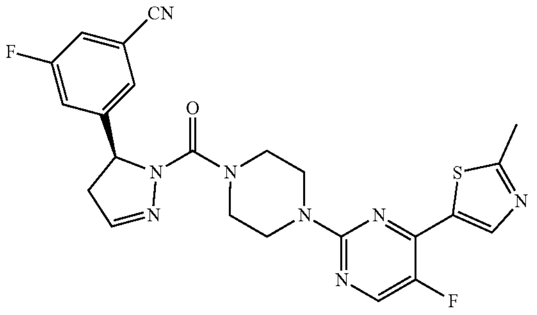

The titled compound 57 as a brown solid was prepared in 42.1% yield from 5-(2-chloro-5-fluoropyrimidin-4-yl)-2-methylthiazole and (S)-3-fluoro-5-(1-(piperazine-1-carbonyl)-4,5-dihydro-1H-pyrazol-5-yl)benzonitrile according to the procedure outlined for compound 56. $^1$H NMR (400 MHz, $CDCl_3$) δ 8.32 (d, J=1.6 Hz, 1H), 8.25 (d, J=2.8 Hz, 1H), 7.42 (t, J=1.6 Hz, 1H), 7.37-7.28 (m, 2H), 6.89 (t, J=1.6 Hz, 1H), 5.37 (dd, J=11.2, 10.4 Hz, 1H), 3.92-3.84 (m, 2H), 3.82-3.72 (m, 4H), 3.69-3.60 (m, 2H), 3.36 (ddd, J=18.4, 11.6, 1.6 Hz, 1H), 2.77 (s, 3H), 2.69 (ddd, J=18.4, 10.0, 1.6 Hz, 1H). LC-MS (m/z): 495.4 $[M+H]^+$.

Compound 58: (S)-(5-(3,5-difluorophenyl)-4,5-dihydro-1H-pyrazol-1-yl)(4-(5-fluoro-4-(1,3,5-trimethyl-1H-pyrazol-4-yl)pyrimidin-2-yl)piperazin-1-yl)methanone

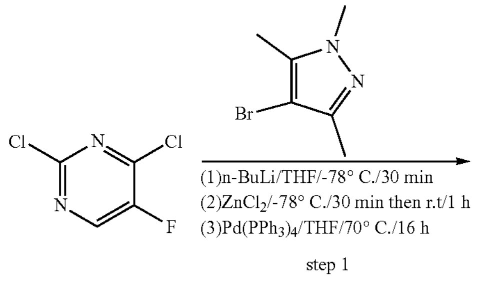

-continued

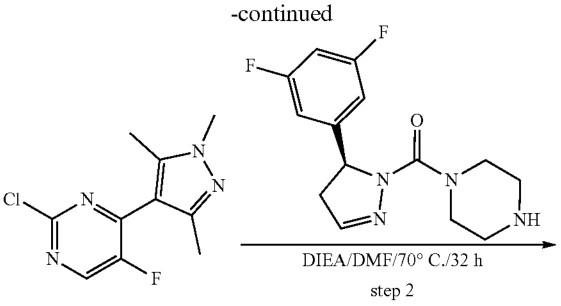

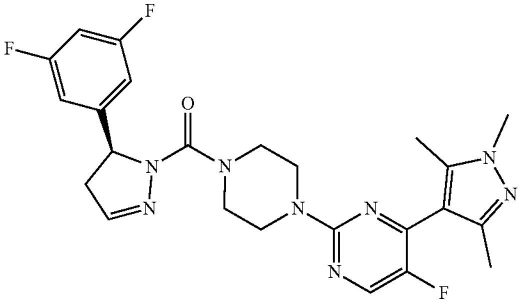

Step 1: 4-bromo-1,3,5-trimethyl-1H-pyrazole (500 mg, 2.64 mmol) was dissolved in 10 ml THF. n-BuLi (1.323 ml, 3.168 mmol, 2.4 M in hexane) was added slowly to the solution at −78° C. Let it stir at −78° C. for 30 mins. Then the solution of $ZnCl_2$ (2.91 ml, 2.91 mmol, 1M in THF) was added dropwise at −78° C. Let it stir at −78° C. for 30 mins and then warmed to room temperature and stirred at room temperature for 1 h. 2,4-dichloro-5-fluoropyrimidine (397.6 mg, 2.38 mmol) and $Pd(PPh_3)_4$ (305.8 mg, 0.265 mmol) in 6 ml THF were added to the solution in one portion. Let it stir at 70° C. for 16 hrs. Water was added to quench the reaction and extracted with EtOAc (40 ml×3). The solvent was evaporated to dryness and purified by column chromatography (PE/EA=2/1) to give 300 mg of 2-chloro-5-fluoro-4-(1,3,5-trimethyl-1H-pyrazol-4-yl)pyrimidine as white solid. Yield: 52.5%. LC-MS (m/z): 241.3 $[M+H]^+$.

Step 2: The titled compound as a light-yellow solid was prepared in 20.7% yield from 2-chloro-5-fluoro-4-(1,3,5-trimethyl-1H-pyrazol-4-yl)pyrimidine and (S)-(5-(3,5-difluorophenyl)-4,5-dihydro-1H-pyrazol-1-yl)(piperazin-1-yl) methanone according to the procedure outlined for compound 7. $^1$H NMR (400 MHz, $CDCl_3$) δ (ppm): 8.22 (d, J=2.4 Hz, 1H), 6.86-6.81 (m, 2H), 6.69 (tt, J=8.8, 2.4 Hz, 1H), 5.33 (dd, J=11.2, 10.0 Hz, 1H), 3.95-3.84 (m, 2H), 3.82-3.72 (m, 7H), 3.68-3.60 (m, 2H), 3.32 (ddd, J=18.4, 12.0, 1.6 Hz, 1H), 2.69 (ddd, J=18.4, 10.0, 1.6 Hz, 1H), 2.33 (d, J=1.6 Hz, 6H). LC-MS (m/z): 499.3 $[M+H]^+$.

Compound 59: (S)-3-fluoro-5-(1-(4-(5-fluoro-4-(5-methyl-1H-tetrazol-1-yl)pyrimidin-2-yl)piperazine-1-carbonyl)-4,5-dihydro-1H-pyrazol-5-yl)benzonitrile

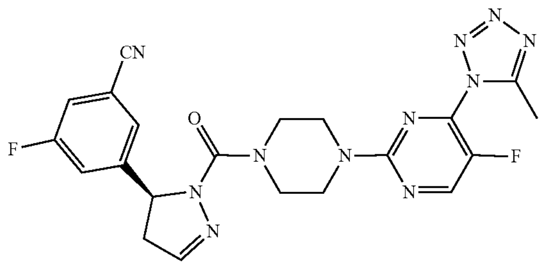

The titled compound 59 was prepared according to the procedure outlined for compound 56. LC-MS (m/z): 480.5 $[M+H]^+$.

Compound 60: (S)-(5-(3,5-difluorophenyl)-4,5-dihydro-1H-pyrazol-1-yl)(4-(5-fluoro-4-(1-(2-hydroxyethyl)-1H-pyrazol-4-yl)pyrimidin-2-yl)piperazin-1-yl)methanone

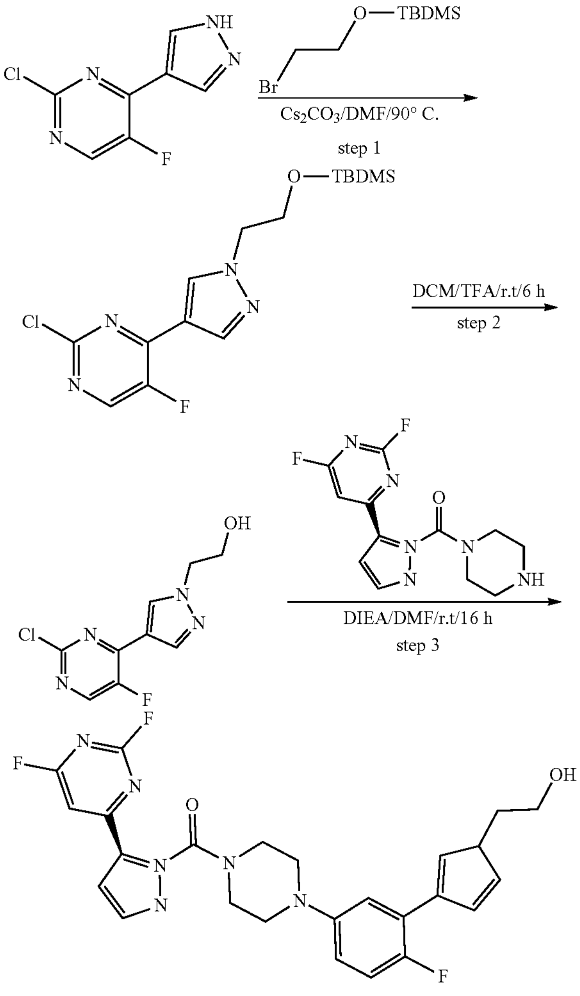

Step 1: 2-chloro-5-fluoro-4-(1H-pyrazol-4-yl)pyrimidine (400 mg, 2.02 mmol) and (2-bromoethoxy)(tert-butyl)dimethylsilane (531.6 mg, 2.22 mmol) were dissolved in 5 ml DMF. $Cs_2CO_3$ (1.313 g, 4.04 mmol) was added. Let it stir at room temperature for 16 hrs. Water was added to the reaction and extracted with EtOAc (40 mL×3). The organic layers were combined and evaporated to dryness and purified by column chromatography (PE/EA=17/3) to give 100 mg 4-(1-(2-((tert-butyldimethylsilyl)oxy)ethyl)-1H-pyrazol-4-yl)-2-chloro-5-fluoropyrimidine as white solid. Yield: 13.9%. LC-MS (m/z): 357.6$[M+H]^+$.

Step 2 and Step 3: 4-(1-(2-((tert-butyldimethylsilyl)oxy)ethyl)-1H-pyrazol-4-yl)-2-chloro-5-fluoropyrimidine (40 mg, 0.11 mmol) was dissolved in 2 ml DCM. 1 ml TFA was added slowly to the solution at 0° C. Then let it stir at r.t for 6 hrs. The solvent was evaporated to dryness and used for next step without further purification. LC-MS (m/z): 257.6 $[M+H]^+$. The above residue was dissolved in 2 ml of DMF. (S)-(5-(3,5-difluorophenyl)-4,5-dihydro-1H-pyrazol-1-yl)(piperazin-1-yl)methanone (44 mg, 0.15 mmol) and 0.2 ml DIEA were added to the solution The solvent was evaporated to dryness and purified by prep-HPLC to give 15 mg of (S)-(5-(3,5-difluorophenyl)-4,5-dihydro-1H-pyrazol-1-yl)(4-(5-fluoro-4-(1-(2-hydroxyethyl)-1H-pyrazol-4-yl)pyrimidin-2-yl)piperazin-1-yl)methanone as a brown oil. Yield of two steps: 27.3%. $^1H$ NMR (400 MHz, $CDCl_3$) δ (ppm): 8.18 (d, J=2.8 Hz, 1H), 8.12 (d, J=0.8 Hz, 1H), 6.90-6.79 (m, 3H), 6.69 (tt, J=8.8, 2.4 Hz, 1H), 5.34 (dd, J=11.6, 10.0 Hz, 1H), 4.32 (t, J=4.8 Hz, 2H), 4.05 (t, J=4.8 Hz, 2H), 3.94-3.85 (m, 2H), 3.82-3.77 (m, 2H), 3.69-3.60 (m, 4H), 3.32 (ddd, J=18.4, 11.6, 1.6 Hz, 1H), 2.69 (ddd, J=18.4, 10.0, 1.6 Hz, 1H). LC-MS (m/z): 501.4$[M+H]^+$.

Compound 61: (S)-(5-(3,5-difluorophenyl)-4,5-dihydro-1H-pyrazol-1-yl)(4-(4-(1,4-dimethyl-1H-pyrazol-5-yl)-5-fluoropyrimidin-2-yl)piperazin-1-yl)methanone

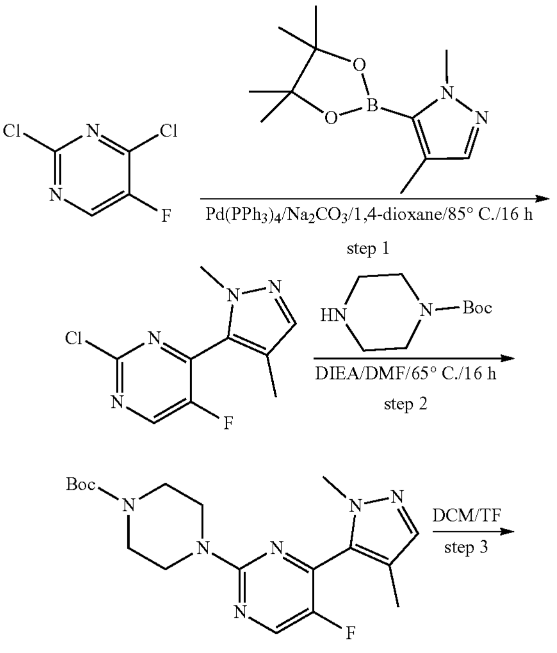

-continued

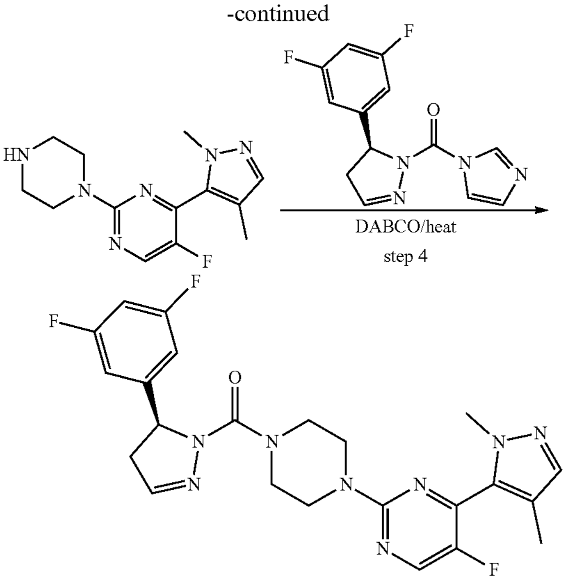

Step 1: 2,4-dichloro-5-fluoropyrimidine (300 mg, 1.796 mmol) and 1,4-dimethyl-5-(4,4,5,5-tetramethyl-1,3,2-dioxaborolan-2-yl)-1H-pyrazole (399 mg, 1.797 mmol) and 2N $Na_2CO_3$ (2.69 ml, 5.38 mmol) were mixed in 5 mL 1,4-dioxane. $Pd(PPh_3)_4$ (207 mg, 0.179 mmol) was added. Let it stir at 85° C. for 16 hrs. The solvent was evaporated to dryness and purified by column chromatography (PE/EA=4/1) to give 140 mg 2-chloro-4-(1,4-dimethyl-1H-pyrazol-5-yl)-5-fluoropyrimidine as white solid. Yield: 34.5%. LC-MS (m/z): 227.5 $[M+H]^+$.

Step 2: tert-butyl piperazine-1-carboxylate (126.7 mg, 0.68 mmol) and 2-chloro-4-(1,4-dimethyl-1H-pyrazol-5-yl)-5-fluoropyrimidine (140 mg, 0.62 mmol) were dissolved in 4 mL DMF. 0.2 mL DIEA was added. Let it stir at 65° C. for 16 hrs. Water was added to the reaction and extracted with EtOAc (15 mL×3). The organic layers were combined and evaporated to dryness and purified by column chromatography (PE/EA=17/3) to give 213 mg tert-butyl 4-(4-(1,4-dimethyl-1H-pyrazol-5-yl)-5-fluoropyrimidin-2-yl)piperazine-1-carboxylate as brown oil. Yield: 91%. LC-MS (m/z): 377.3 $[M+H]^+$.

Step 3 and step 4: tert-butyl 4-(4-(1,4-dimethyl-1H-pyrazol-5-yl)-5-fluoropyrimidin-2-yl)piperazine-1-carboxylate (85 mg, 0.226 mmol) was dissolved in 3 mL DCM. 2 mL of TFA/DCM (1/1) was added to the solution at 0° C. Let it stir at r.t for 1 h. The solvent was evaporated to dryness and used for next step without further purification. LC-MS (m/z): 277.4 $[M+H]^+$.

The above residue and (S)-(5-(3,5-difluorophenyl)-4,5-dihydro-1H-pyrazol-1-yl)(1H-imidazol-1-yl)methanone (68.6 mg, 0.248 mmol) and DABCO (101.4 mg, 0.904 mmol) were mixed in 3 mL of THF. It was evaporated to dryness and directly lighted with 100 W filament lamp for 3 hrs. The solid was purified by prep-TLC (PE/EA=1/3) to give 60 mg of (S)-(5-(3,5-difluorophenyl)-4,5-dihydro-1H-pyrazol-1-yl)(4-(4-(1,4-dimethyl-1H-pyrazol-5-yl)-5-fluoropyrimidin-2-yl)piperazin-1-yl)methanone as white solid. Yield of two steps: 54.8%. $^1H$ NMR (400 MHz, $CDCl_3$) δ (ppm): 8.32 (s, 1H), 7.37 (s, 1H), 6.97-6.74 (m, 3H), 6.69 (t, J=8.4 Hz, 1H), 5.33 (t, J=10.8 Hz, 1H), 3.93 (s, 3H), 3.91-3.85 (m, 2H), 3.84-3.71 (m, 4H), 3.69-3.56 (m, 2H), 3.32 (dd, J=18.4, 12.0 Hz, 1H), 2.69 (dd, J=18.0, 10.0 Hz, 1H), 2.08 (s, 3H). LC-MS (m/z): 485.3 $[M+H]^+$.

Compound 62: (S)-3-(1-(4-(4-(1,4-dimethyl-1H-pyrazol-5-yl)-5-fluoropyrimidin-2-yl)piperazine-1-carbonyl)-4,5-dihydro-1H-pyrazol-5-yl)-5-fluorobenzonitrile

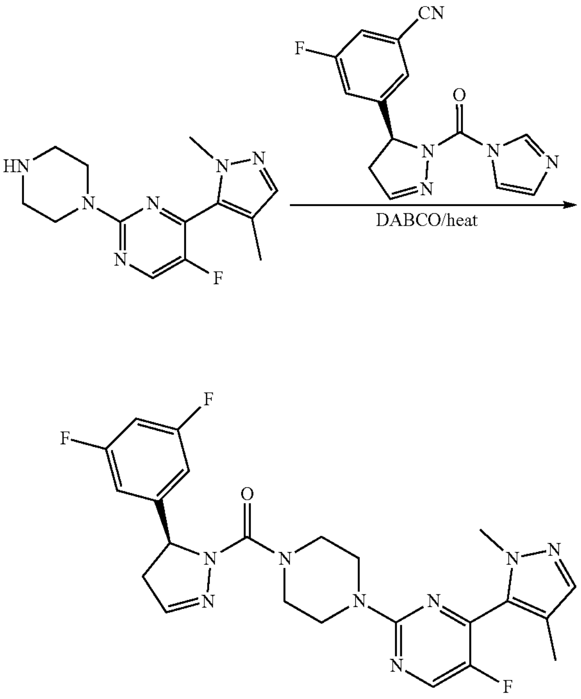

The titled compound 62 as a light-yellow solid was prepared in 51.8% yield from 4-(1,4-dimethyl-1H-pyrazol-5-yl)-5-fluoro-2-(piperazin-1-yl)pyrimidine of trifluoroacetic acid salt and (S)-3-(1-(1H-imidazole-1-carbonyl)-4,5-dihydro-1H-pyrazol-5-yl)-5-fluorobenzonitrile according to the procedure outlined for compound 61. $^1H$ NMR (400 MHz, $CDCl_3$) δ (ppm): 8.33 (d, J=2.0 Hz, 1H), 7.42 (t, J=1.6 Hz, 1H), 7.38 (s, 1H), 7.28 (dd, J=5.2, 1.2 Hz, 1H), 6.89 (t, J=1.6 Hz, 1H), 5.37 (dd, J=11.65, 10.4 Hz, 1H), 3.94 (s, 3H), 3.92-3.86 (m, 2H), 3.83-3.74 (m, 4H), 3.69-3.59 (m, 2H), 3.35 (ddd, J=18.4, 11.6, 1.6 Hz, 1H), 2.69 (ddd, J=18.4, 10.0, 1.6 Hz, 1H), 2.08 (d, J=2.4 Hz, 3H). LC-MS (m/z): 492.4 $[M+H]^+$.

Compound 63: (S)-(5-(3,5-difluorophenyl)-4,5-dihydro-1H-pyrazol-1-yl)(4-(5-fluoro-4-(5-methyl-1,3,4-thiadiazol-2-yl)pyrimidin-2-yl)piperazin-1-yl)methanone

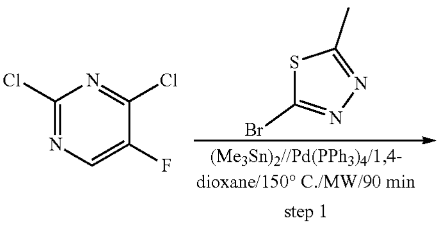

-continued

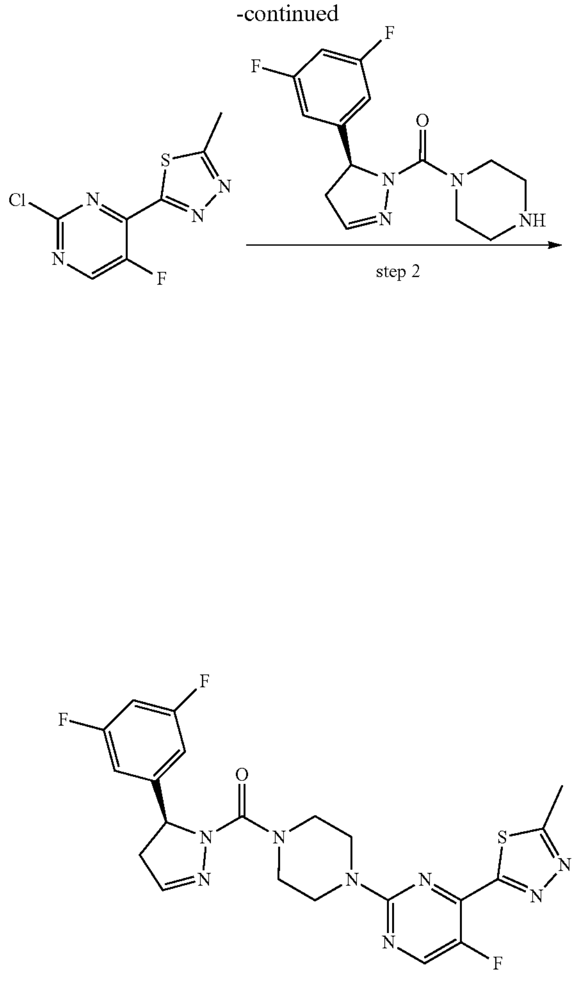

Step 1: 2,4-dichloro-5-fluoropyrimidine (200 mg, 1.197 mmol), 2-bromo-5-methyl-1,3,4-thiadiazole (214.8 mg, 1.197 mmol), 1,1,1,2,2,2-hexamethyldistannane (392 mg, 1.196 mmol) and $Pd(PPh_3)_4$ (68.8 mg, 0.06 mmol) were mixed in 8 ml 1,4-dioxane. Let it stir at 150° C. under microwave for 90 mins. The solvent was evaporated to dryness and purified by prep-TLC (PE/EA=1/1) to give 79 mg 2-(2-chloro-5-fluoropyrimidin-4-yl)-5-methyl-1,3,4-thiadiazole as brown oil. Yield: 25.4%. LC-MS (m/z): 231.4 $[M+H]^+$.

Step 2: 2-(2-chloro-5-fluoropyrimidin-4-yl)-5-methyl-1,3,4-thiadiazole (40 mg, 0.173 mmol) (S)-(5-(3,5-difluorophenyl)-4,5-dihydro-1H-pyrazol-1-yl)(piperazin-1-yl)methanone (50.9 mg, 0.173 mmol) were dissolved in 3 ml DMF. 0.2 ml DIEA was added. Let it stir at 70° C. for 32 hrs. Water was added to the reaction and extracted with EtOAc (10 mL×3). The organic layers were combined and evaporated to dryness and purified by column chromatography (PE/EA=1/2) to give 12 mg of (S)-(5-(3,5-difluorophenyl)-4,5-dihydro-1H-pyrazol-1-yl)(4-(5-fluoro-4-(5-methyl-1,3,4-thiadiazol-2-yl)pyrimidin-2-yl)piperazin-1-yl)methanone as a brown solid. Yield: 14.2%. $^1H$ NMR (400 MHz, $CDCl_3$) δ (ppm): 8.43 (d, J=2.4 Hz, 1H), 6.86 (t, J=1.6 Hz, 1H), 6.82 (dd, J=8.8, 2.4 Hz, 1H), 6.69 (tt, J=8.8, 2.0 Hz, 1H), 5.34 (dd, J=11.6, 9.6 Hz, 1H), 3.94-3.86 (m, 2H), 3.84-3.73 (m, 4H), 3.70-3.61 (m, 2H), 3.33 (ddd, J=18.4, 11.6, 1.6 Hz, 1H), 2.85 (s, 3H), 2.69 (ddd, J=18.4, 10.0, 1.6 Hz, 1H). LC-MS (m/z): 489.3 $[M+H]^+$.

Compound 64: (S)-3-fluoro-5-(1-(4-(5-fluoro-4-(5-methyl-1,3,4-thiadiazol-2-yl)pyrimidin-2-yl)piperazine-1-carbonyl)-4,5-dihydro-1H-pyrazol-5-yl)benzonitrile

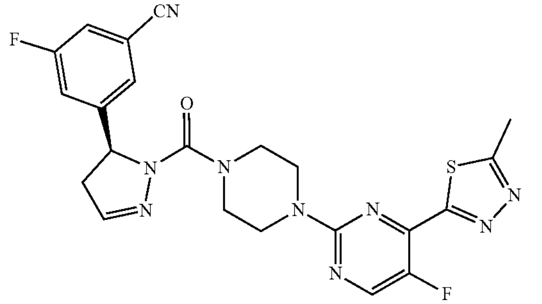 [SMILES: Cc1nnc(-c2nc(N3CCN(C(=O)N4N=CC[C@H]4c4cc(F)cc(C#N)c4)CC3)ncc2F)s1]

The titled compound 64 as a brown solid was prepared in 25.5% yield from 2-(2-chloro fluoropyrimidin-4-yl)-5-methyl-1,3,4-thiadiazole and (S)-3-fluoro-5-(1-(piperazine-1-carbonyl)-4,5-dihydro-1H-pyrazol-5-yl)benzonitrile according to the procedure outlined for compound 63. $^1H$ NMR (400 MHz, $CDCl_3$) δ 8.44 (d, J=2.4 Hz, 1H), 7.42 (t, J=1.6 Hz, 1H), 7.31-7.27 (m, 2H), 6.90 (t, J=1.6 Hz, 1H), 5.38 (dd, J=11.6, 10.4 Hz, 1H), 3.96-3.86 (m, 2H), 3.85-3.73 (m, 4H), 3.70-3.61 (m, 2H), 3.37 (ddd, J=18.4, 11.6, 1.6 Hz, 1H), 2.86 (s, 3H), 2.70 (ddd, J=18.4, 10.0, 1.6 Hz, 1H). LC-MS (m/z): 496.4 $[M+H]^+$.

Compound 65: (S)-(5-(3,5-difluorophenyl)-4,5-dihydro-1H-pyrazol-1-yl)(4-(5-fluoro-4-(1-methyl-1H-1,2,4-triazol-5-yl)pyrimidin-2-yl)piperazin-1-yl)methanone

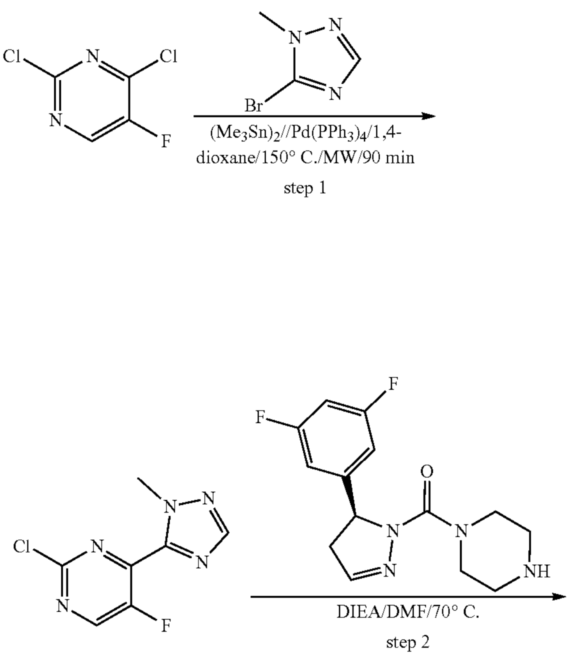

-continued

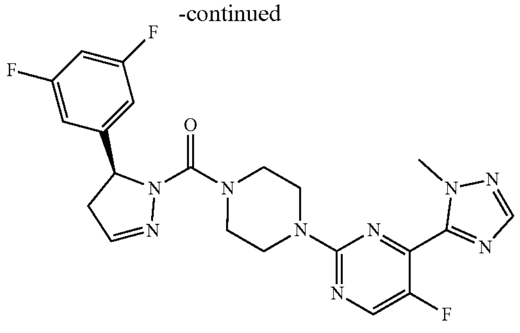

Step 1: 2,4-dichloro-5-fluoropyrimidine (300 mg, 1.796 mmol), 5-bromo-1-methyl-1H-1,2,4-triazole (291 mg, 1.796 mmol), 1,1,1,2,2,2-hexamethyldistannane (588.5 mg, 1.796 mmol) and $Pd(PPh_3)_4$ (103.8 mg, 0.317 mmol) were mixed in 8 ml 1,4-dioxane. Let it stir at 150° C. under microwave for 90 mins. The solvent was evaporated to dryness and purified by prep-TLC (PE/EA=4/1) to give 28 mg 2-chloro-5-fluoro-4-(1-methyl-1H-1,2,4-triazol-5-yl)pyrimidine as light-yellow solid. Yield: 7.3%. LC-MS (m/z): 214.4 $[M+H]^+$.

Step 2: 2-chloro-5-fluoro-4-(1-methyl-1H-1,2,4-triazol-5-yl)pyrimidine (28 mg, 0.131 mmol) (S)-(5-(3,5-difluorophenyl)-4,5-dihydro-1H-pyrazol-1-yl)(piperazin-1-yl)methanone (38.5 mg, 0.131 mmol) were dissolved in 3 ml DMF. 0.2 ml DIEA was added. Let it stir at 70° C. for 32 hrs. Water was added to the reaction and extracted with EtOAc (10 mL×3). The organic layers were combined and evaporated to dryness and purified by column chromatography (PE/EA=1/2) to give 16 mg of (S)-(5-(3,5-difluorophenyl)-4,5-dihydro-1H-pyrazol-1-yl)(4-(5-fluoro-4-(1-methyl-1H-1,2,4-triazol-5-yl)pyrimidin-2-yl)piperazin-1-yl)methanone as brown solid. Yield: 25.9%. $^1H$ NMR (400 MHz, $CDCl_3$) δ (ppm): 8.42 (d, J=2.4 Hz, 1H), 8.04 (s, 1H), 6.86 (t, J=1.6 Hz, 1H), 6.83-6.81 (m, 1H), 6.69 (tt, J=8.8, 2.0 Hz, 1H), 5.33 (dd, J=11.6, 10.0 Hz, 1H), 4.24 (s, 3H), 3.95-3.85 (m, 2H), 3.83-3.74 (m, 4H), 3.70-3.61 (m, 2H), 3.32 (ddd, J=18.4, 11.6, 1.6 Hz, 1H), 2.69 (ddd, J=18.4, 10.0, 1.6 Hz, 1H). LC-MS (m/z): 472.3 $[M+H]^+$.

Compound 66: (S)-3-fluoro-5-(1-(4-(5-fluoro-4-(1-methyl-1H-1,2,4-triazol-5-yl)pyrimidin-2-yl)piperazine-1-carbonyl)-4,5-dihydro-1H-pyrazol-5-yl)benzonitrile

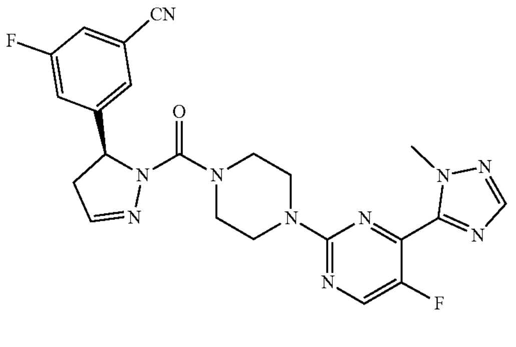 [SMILES: Cn1ncnc1-c1nc(N2CCN(C(=O)N3N=CC[C@H]3c3cc(F)cc(C#N)c3)CC2)ncc1F]

The titled compound 66 as a light-yellow solid was prepared in 17.9% yield from 2-chloro-5-fluoro-4-(1-methyl-1H-1,2,4-triazol-5-yl)pyrimidine and (S)-3-fluoro-5-(1-(piperazine-1-carbonyl)-4,5-dihydro-1H-pyrazol-5-yl)

benzonitrile according to the procedure outlined for compound 65. $^1H$ NMR (400 MHz, $CDCl_3$) δ 8.43 (d, J=2.4 Hz, 1H), 8.05 (s, 1H), 7.42 (t, J=1.6 Hz, 1H), 7.30-7.25 (m, 2H), 6.90 (t, J=1.6 Hz, 1H), 5.37 (dd, J=11.6, 10.4 Hz, 1H), 4.24 (s, 3H), 3.95-3.86 (m, 2H), 3.85-3.74 (m, 4H), 3.72-3.60 (m, 2H), 3.37 (ddd, J=18.4, 12.0, 2.0 Hz, 1H), 2.70 (ddd, J=18.4, 10.0, 1.6 Hz, 1H). LC-MS (m/z): 479.3 $[M+H]^+$.

Compound 67: (S)-5-(2-(4-(5-(3-cyano-5-fluorophenyl)-4,5-dihydro-1H-pyrazole-1-carbonyl)piperazin-1-yl)-5-fluoropyrimidin-4-yl)-1-methyl-1H-pyrazole-4-carbonitrile

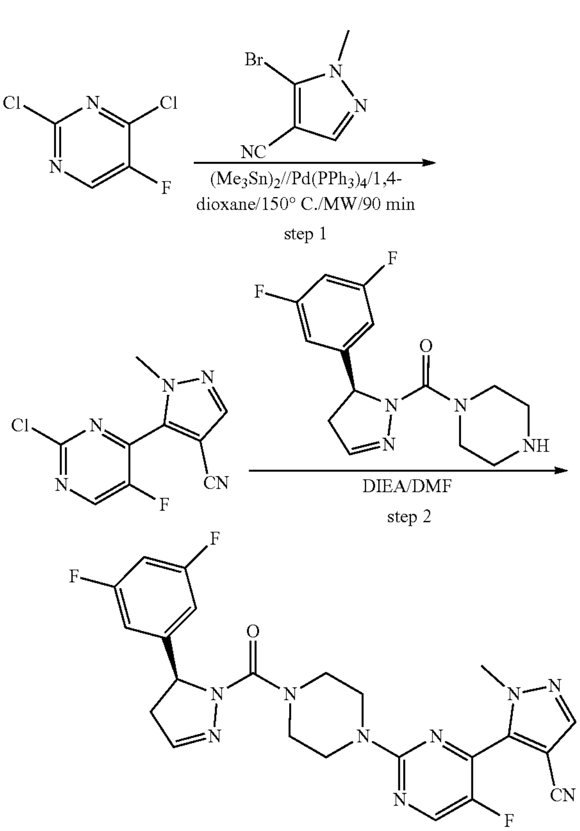

Step 1: 2,4-dichloro-5-fluoropyrimidine (673 mg, 4.03 mmol), 5-bromo-1-methyl-1H-pyrazole-4-carbonitrile (750 mg, 4.03 mmol), 1,1,1,2,2,2-hexamethyldistannane (1.318 g, 4.03 mmol) and $Pd(PPh_3)_4$ (232.9 mg, 0.2 mmol) were mixed in 20 ml 1,4-dioxane. Let it stir at 150° C. under microwave for 90 mins. The solvent was evaporated to dryness and purified by prep-TLC (PE/EA=3/1) to give 150 mg of 5-(2-chloro-5-fluoropyrimidin-4-yl)-1-methyl-1H-pyrazole-4-carbonitrile as light-yellow solid. Yield: 15.6%. LC-MS (m/z): 238.3 $[M+H]^+$.

Step 2: 5-(2-chloro-5-fluoropyrimidin-4-yl)-1-methyl-1H-pyrazole-4-carbonitrile (60 mg, 0.252 mmol) and (S)-(5-(3,5-difluorophenyl)-4,5-dihydro-1H-pyrazol-1-yl)(piperazin-1-yl)methanone (76 mg, 0.252 mmol) were dissolved in 3 ml DMF. 0.2 ml DIEA was added. Let it stir at 70° C. for 32 hrs. Water was added to the reaction and extracted with EtOAc (10 mL×3). The organic layers were combined and evaporated to dryness and purified by column chromatography (PE/EA=1/3) to give 10 mg of (S)-5-(2-(4-(5-(3-cyano-5-fluorophenyl)-4,5-dihydro-1H-pyrazole-1-carbonyl)piperazin-1-yl)-5-fluoropyrimidin-4-yl)-1-methyl-1H-pyrazole-4-carbonitrile as a brown solid. Yield: 7.9%. $^1$H NMR (400 MHz, $CDCl_3$) δ 8.43 (d, J=1.6 Hz, 1H), 7.88 (s, 1H), 7.41 (t, J=1.6 Hz, 1H), 7.30-7.27 (m, 1H), 7.25-7.23 (m, 1H), 6.89 (t, J=1.6 Hz, 1H), 5.37 (dd, J=11.6, 10.4 Hz, 1H), 4.04 (d, J=1.2 Hz, 3H), 3.97-3.87 (m, 2H), 3.83-3.74 (m, 4H), 3.71-3.61 (m, 2H), 3.36 (ddd, J=18.4, 11.6, 1.6 Hz, 1H), 2.69 (ddd, J=18.4, 10.0, 1.6 Hz, 1H). LC-MS (m/z): 503.2 $[M+H]^+$.

Compound 68: (S)-(4-(4-(4-chloro-1-methyl-1H-pyrazol-5-yl)-5-fluoropyrimidin-2-yl)piperazin-1-yl)(5-(3,5-difluorophenyl)-4,5-dihydro-1H-pyrazol-1-yl)methanone

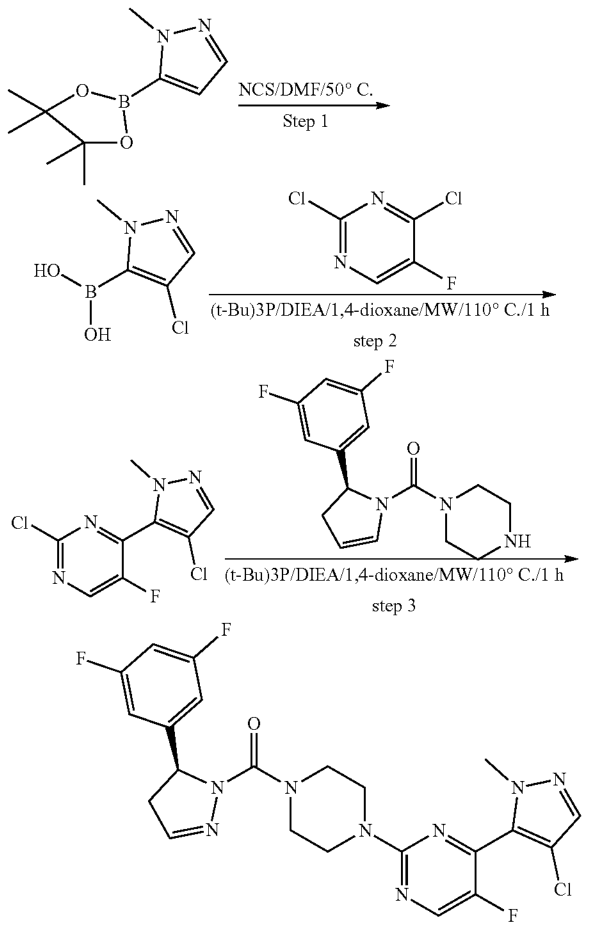

Step 1: 1-methyl-5-(4,4,5,5-tetramethyl-1,3,2-dioxaborolan-2-yl)-1H-pyrazole (3.1 g, 14.899 mmol) was dissolved in 40 ml DMF. Let it stir at 50° C. for 8 hrs. Water was added to the reaction and extracted with EtOAc (60 mL×3). The organic layers were combined and evaporated to dryness and purified by column chromatography (PE/EA=2/1) to give 2.14 g (4-chloro-1-methyl-1H-pyrazol-5-yl)boronic acid as white solid. Yield: 89.8%. LC-MS (m/z): 161.2 $[M+H]^+$.

Step 2: 2,4-dichloro-5-fluoropyrimidine (191.6 mg, 1.198 mmol) and (4-chloro-1-methyl-1H-pyrazol-5-yl)boronic acid (200 mg, 1.198 mmol) and $(t-BuP)_2Pd$ (61.2 mg, 0.12 mmol) and 0.2 ml DIEA were mixed in 8 ml 1,4-dioxane/$H_2O$ (5/1). The solvent was stirred under microwave at 110° C. for 1 h. The solvent was evaporated to dryness and purified by prep-TLC (PE/EA=7/1) to give 80 mg 2-chloro-4-(4-chloro-1-methyl-1H-pyrazol-5-yl)-5-fluoropyrimidine as light-yellow solid. Yield: 27%. LC-MS (m/z): 248.2 $[M+H]^+$.

Step 3: 2-chloro-4-(4-chloro-1-methyl-1H-pyrazol-5-yl)-5-fluoropyrimidine (35 mg, 0.142 mmol) and (S)-(5-(3,5-difluorophenyl)-4,5-dihydro-1H-pyrazol-1-yl)(piperazin yl)methanone (41.7 mg, 0.142 mmol) were dissolved in 3 ml DMF. 0.2 ml DIEA was added. Let it stir at 70° C. for 32 hrs. Water was added to the reaction and extracted with EtOAc (10 mL×3). The organic layers were combined and evaporated to dryness and purified by column chromatography (PE/EA=1/2) to give 35 mg of (S)-(4-(4-(4-chloro-1-methyl-1H-pyrazol yl)-5-fluoropyrimidin-2-yl)piperazin-1-yl)(5-(3,5-difluorophenyl)-4,5-dihydro-1H-pyrazol yl)methanone as a brown solid. Yield: 48.9%. $^1$H NMR (400 MHz, $CDCl_3$) δ (ppm): 8.37 (d, J=2.0 Hz, 1H), 7.51 (s, 1H), 6.86 (t, J=1.6 Hz, 1H), 6.84-6.81 (m, 1H), 6.70 (tt, J=8.8, 2.4 Hz, 1H), 5.34 (dd, J=11.6, 10.0 Hz, 1H), 3.95 (s, 3H), 3.93-3.86 (m, 2H), 3.84-3.75 (m, 4H), 3.69-3.61 (m, 2H), 3.32 (ddd, J=18.4, 11.6, 1.6 Hz, 1H), 2.69 (ddd, J=18.4, 10.0, 1.6 Hz, 1H). LC-MS (m/z): 505.6 $[M+H]^+$.

Compound 69: (S)-3-fluoro-5-(1-(4-(5-fluoro-4-(1-methyl-1H-pyrazol-5-yl)pyrimidin-2-yl)piperazine-1-carbonyl)-4,5-dihydro-1H-pyrazol-5-yl)benzonitrile

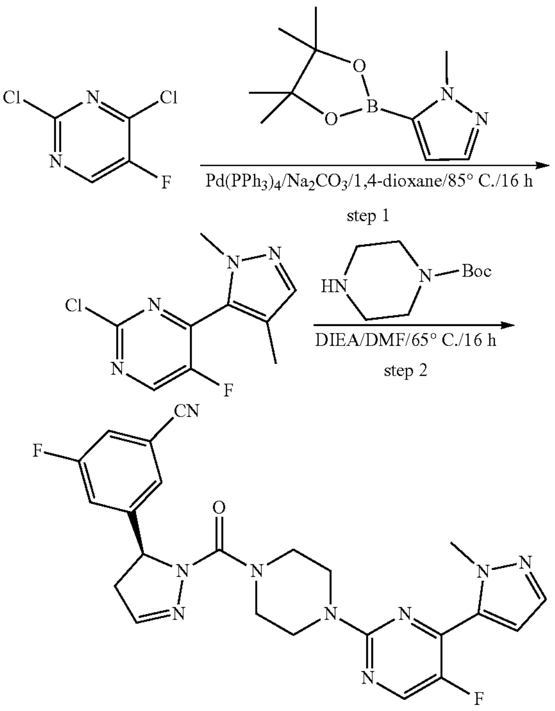

Step 1: 2,4-dichloro-5-fluoropyrimidine (400 mg, 2.395 mmol) and 1-methyl-5-(4,4,5,5-tetramethyl-1,3,2-dioxaborolan-2-yl)-1H-pyrazole (498 mg, 2.393 mmol) and 2N $Na_2CO_3$ (3.95 ml, 7.18 mmol) were mixed in 8 mL 1,4-dioxane. $Pd(PPh_3)_4$ (276.88 mg, 0.24 mmol) was added. Let it stir at 85° C. for 16 hrs. The solvent was evaporated to dryness and purified by column chromatography (PE/EA=3/

1) to give 228 mg 2-chloro-5-fluoro-4-(1-methyl-1H-pyrazol-5-yl)pyrimidine as white solid. Yield: 44.9%. LC-MS (m/z): 213.4 $[M+H]^+$.

Step 2: 2-chloro-5-fluoro-4-(1-methyl-1H-pyrazol-5-yl) pyrimidine (120 mg, 0.563 mmol) (S)-(5-(3,5-difluorophenyl)-4,5-dihydro-1H-pyrazol-1-yl)(piperazin-1-yl)methanone (165.6 mg, 0.563 mmol) were dissolved in 5 ml of DMF. 0.5 ml of DIEA was added. Let it stir at 70° C. for 32 hrs. Water was added to the reaction and extracted with EtOAc (30 mL×3). The organic layers were combined and evaporated to dryness and purified by Prep-HPLC to give 80 mg of (S)-3-fluoro-5-(1-(4-(5-fluoro-4-(1-methyl-1H-pyrazol-5-yl)pyrimidin-2-yl)piperazine-1-carbonyl)-4,5-dihydro-1H-pyrazol-5-yl)benzonitrile as a white solid. Yield: 30.2%. $^1H$ NMR (400 MHz, $CDCl_3$) δ (ppm): 8.30 (d, J=2.8 Hz, 1H), 7.57 (d, J=2.0 Hz, 1H), 7.42 (t, J=1.6 Hz, 1H), 7.30-7.27 (m, 1H), 6.92-6.88 (m, 2H), 5.37 (dd, J=11.6, 10.0 Hz, 1H), 4.28 (s, 3H), 3.96-3.85 (m, 2H), 3.85-3.74 (m, 4H), 3.72-3.59 (m, 2H), 3.36 (ddd, J=18.4, 11.6, 1.6 Hz, 1H), 2.70 (ddd, J=18.4, 10.0, 1.6 Hz, 1H). LC-MS (m/z): 471.3 $[M+H]^+$.

Compound 70: (S)-3-(1-(4-(4-(1,4-dimethyl-1H-1,2,3-triazol-5-yl)-5-fluoropyrimidin-2-yl)piperazine-1-carbonyl)-4,5-dihydro-1H-pyrazol-5-yl)-5-fluorobenzonitrile

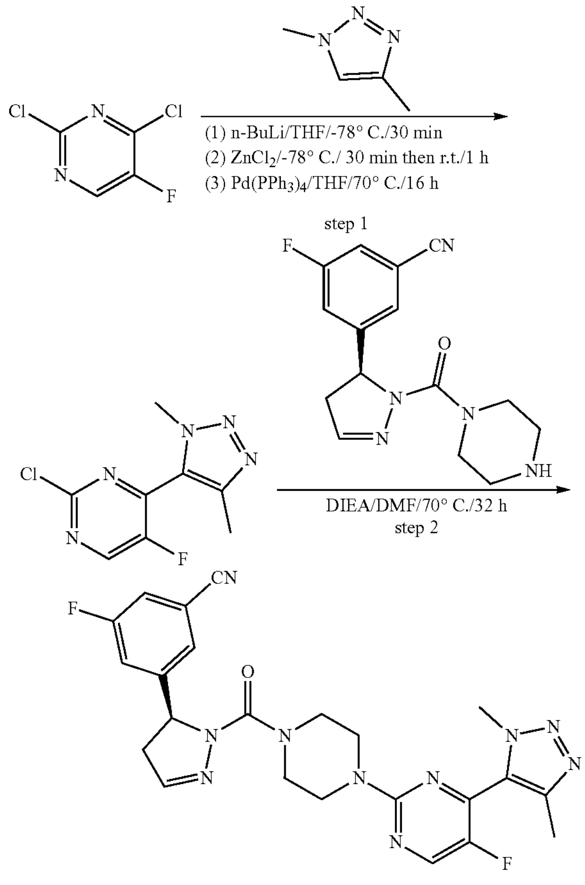

Step 1: 1,4-dimethyl-1H-1,2,3-triazole (350 mg, 3.60 mmol) was dissolved in 10 ml THF. n-BuLi (1.653 ml, 3.97 mmol, 2.4 M in hexane) was added slowly to the solution at −78° C. Let it stir at −78° C. for 30 mins. Then the solution of $ZnCl_2$ (3.97 ml, 3.97 mmol, 1M in THF) was added dropwise at −78° C. Let it stir at −78° C. for 30 mins and then warmed to room temperature and stirred at room temperature for 1 h. 2,4-dichloro-5-fluoropyrimidine (543 mg, 3.25 mmol) and $Pd(PPh_3)_4$ (417.1 mg, 0.36 mmol) in 10 ml THF were added to the solution in one portion. Let it stir at 70° C. for 16 hrs. Water was added to quench the reaction and extracted with EtOAc (40 ml×3). The solvent was evaporated to dryness and purified by column chromatography (PE/EA=4/1) to give 396 mg of 2-chloro-4-(1,4-dimethyl-1H-1,2,3-triazol-5-yl)-5-fluoropyrimidine as a light-yellow solid. Yield: 53.5%. LC-MS (m/z): 228.4 $[M+H]^+$.

Step 2: The titled compound 70 as a light-yellow solid was prepared in 31% yield from 2-chloro-4-(1,4-dimethyl-1H-1,2,3-triazol-5-yl)-5-fluoropyrimidine and (S)-3-fluoro-5-(1-(piperazine-1-carbonyl)-4,5-dihydro-1H-pyrazol-5-yl) benzonitrile according to the procedure outlined for compound 69. $^1H$ NMR (400 MHz, Chloroform-d) δ 8.37 (d, J=1.6 Hz, 1H), 7.41 (t, J=1.6 Hz, 1H), 7.29-7.27 (m, 1H), 7.25-7.24 (m, 1H), 6.89 (t, J=1.6 Hz, 1H), 5.37 (dd, J=11.6, 10.0 Hz, 1H), 4.15 (s, 3H), 3.94-3.84 (m, 2H), 3.84-3.73 (m, 4H), 3.70-3.60 (m, 2H), 3.36 (ddd, J=18.4, 11.6, 1.8 Hz, 1H), 2.70 (ddd, J=18.4, 10.0, 1.6 Hz, 1H), 2.40 (d, J=2.4 Hz, 3H). LC-MS (m/z): 493.3 $[M+H]^+$.

Compound 71: (S)-(5-(3,5-difluorophenyl)-4,5-dihydro-1H-pyrazol-1-yl)(4-(4-(1,4-dimethyl-1H-1,2,3-triazol-5-yl)-5-fluoropyrimidin-2-yl)piperazin-1-yl)methanone

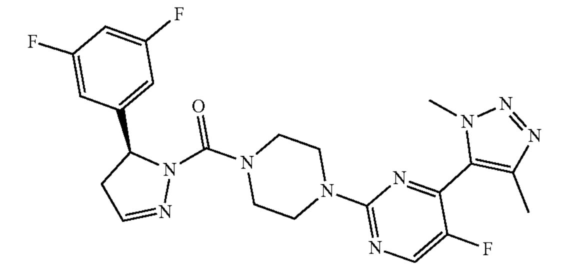 [SMILES: Cc1nnn(C)c1-c1nc(N2CCN(C(=O)N3N=CC[C@H]3c3cc(F)cc(F)c3)CC2)ncc1F]

The titled compound 71 as a light-yellow solid was prepared in 46.9% yield from 2-chloro-4-(1,4-dimethyl-1H-1,2,3-triazol-5-yl)-5-fluoropyrimidine and (S)-(5-(3,5-difluorophenyl)-4,5-dihydro-1H-pyrazol-1-yl)(piperazin-1-yl) methanone according to the procedure outlined for compound 70. $^1H$ NMR (300 MHz, Chloroform-d) δ 8.36 (d, J=1.8 Hz, 1H), 6.88-6.80 (m, 3H), 6.70 (tt, J=9.0, 2.4 Hz, 1H), 5.34 (dd, J=11.7, 10.2 Hz, 1H), 4.15 (s, 3H), 3.99-3.86 (m, 2H), 3.85-3.72 (m, 4H), 3.71-3.60 (m, 2H), 3.33 (ddd, J=18.3, 11.7, 1.8 Hz, 1H), 2.70 (ddd, J=18.3, 9.9, 1.5 Hz, 1H), 2.39 (d, J=2.4 Hz, 3H). LC-MS (m/z): 486.3 $[M+H]^+$.

Compound 72: (S)-3-fluoro-5-(1-(4-(5-fluoro-4-(3-(hydroxymethyl)-1-methyl-1H-1,2,4-triazol-5-yl) pyrimidin-2-yl)piperazine-1-carbonyl)-4,5-dihydro-1H-pyrazol-5-yl)benzonitrile

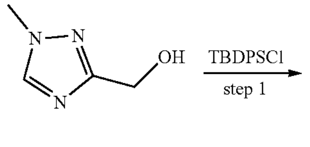

-continued

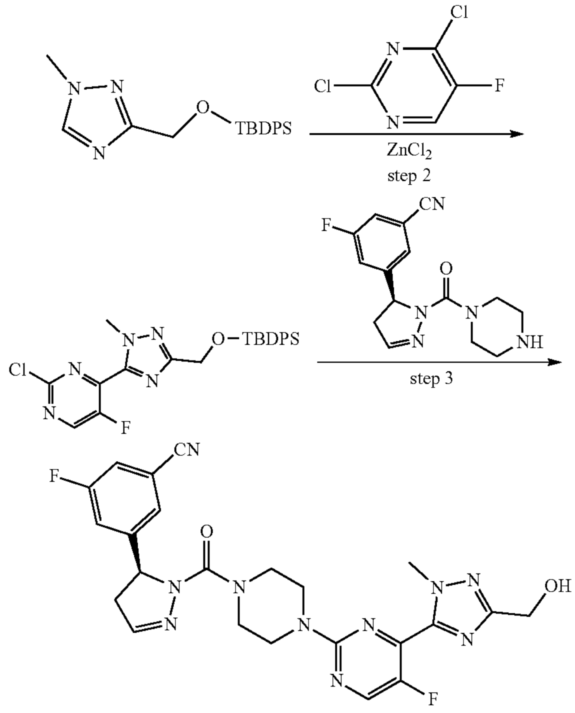

Step 1: (1-methyl-1H-1,2,4-triazol-3-yl)methanol (600 mg, 5.31 mmol), tert-butylchlorodiphenylsilane (1.605 g, 5.836 mmol) and imidazole (722 mg, 10.618 mmol) were mixed in 10 mL of DCM. Let it stir at room temperature for 16 hrs. The solvent was evaporated to dryness and purified by column chromatography (PE/EA=1/2 to give 1.6 g 3-(((tert-butyldiphenylsilyl)oxy)methyl)-1-methyl-1H-1,2,4-triazole as white solid. Yield: 85.7%. LC-MS (m/z): 352.3 $[M+H]^+$.

Step 2: 3-(((tert-butyldiphenylsilyl)oxy)methyl)-1-methyl-1H-1,2,4-triazole (300 mg, 0.852 mmol) was dissolved in 10 ml THF. n-BuLi (0.426 ml, 1.022 mmol, 2.4 M in hexane) was added slowly to the solution at −78° C. Let it stir at −78° C. for 30 mins. Then the solution of $ZnCl_2$ (0.852 ml, 0.852 mmol, 1M in THF) was added dropwise at −78° C. Let it stir at −78° C. for 30 mins and then warmed to room temperature and stirred at room temperature for 1 h. 2,4-dichloro-5-fluoropyrimidine (113.8 mg, 0.681 mmol) and $Pd(PPh_3)_4$ (98.5 mg, 0.078 mmol) in 6 ml THF were added to the solution in one portion. Let it stir at 70° C. for 16 hrs. Water was added to quench the reaction and extracted with EtOAc (30 ml×3). The solvent was evaporated to dryness and purified by column chromatography (PE/EA=2/1) to give 220 mg 4-(3-(((tert-butyldiphenylsilyl)oxy)methyl)-1-methyl-1H-1,2,4-triazol-5-yl)-2-chloro-5-fluoropyrimidine as light-yellow. Yield: 61%. LC-MS (m/z): 404.3 $[M+H-ph]^+$.

Step 3: The titled compound 72 as a light-yellow solid was prepared in 33.1% yield from 4-(3-(((tert-butyldiphenylsilyl)oxy)methyl)-1-methyl-1H-1,2,4-triazol-5-yl)-2-chloro-5-fluoropyrimidine and (S)-3-fluoro-5-(1-(piperazine-1-carbonyl)-4,5-dihydro-1H-pyrazol-5-yl)benzonitrile according to the procedure outlined for compound 7. $^1$H NMR (400 MHz, $CDCl_3$) δ 8.43 (d, J=2.4 Hz, 1H), 7.41 (t, J=1.6 Hz, 1H), 7.30-7.27 (m, 1H), 7.25-7.22 (m, 1H), 6.89 (t, J=1.6 Hz, 1H), 5.37 (dd, J=11.6, 10.2 Hz, 1H), 4.82 (s, 2H), 4.20 (s, 3H), 3.94-3.85 (m, 2H), 3.84-3.75 (m, 4H), 3.71-3.64 (m, 2H), 3.36 (ddd, J=18.4, 11.6, 1.6 Hz, 1H), 2.70 (ddd, J=18.4, 10.0, 1.6 Hz, 1H). LC-MS (m/z): 509.3 $[M+H]^+$.

Compound 73: ethyl (S)-4-(2-(4-(5-(3-cyano-5-fluorophenyl)-4,5-dihydro-1H-pyrazole-1-carbonyl)piperazin-1-yl)-5-fluoropyrimidin-4-yl)-5-methyl-1H-pyrazole-3-carboxylat

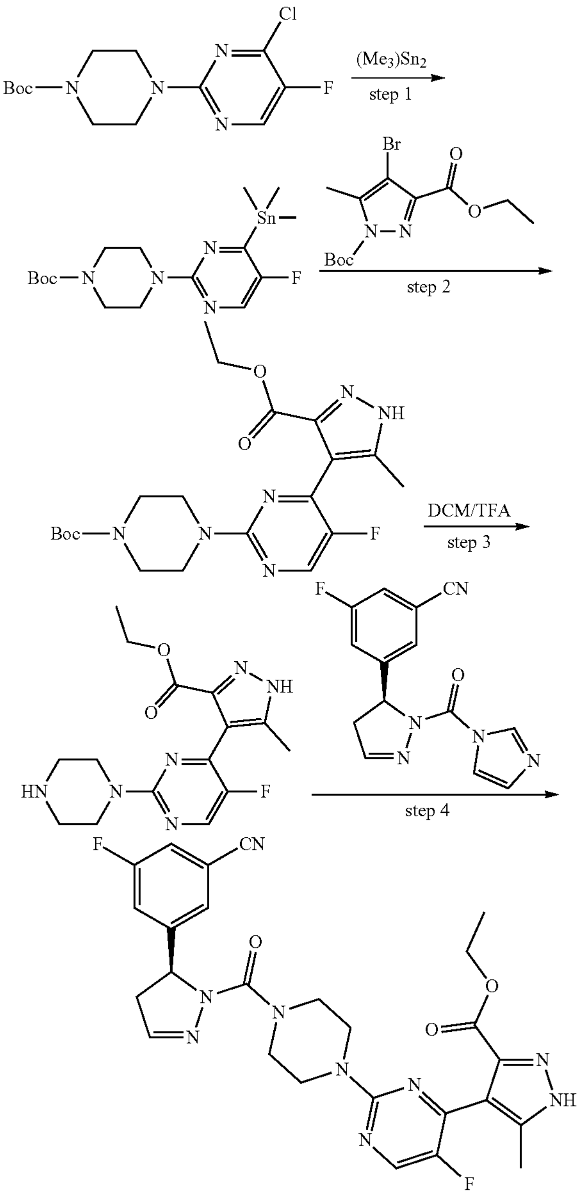

Step 1: Tert-butyl 4-(4-chloro-5-fluoropyrimidin-2-yl)piperazine-1-carboxylate (4 g, 12.658 mmol), 1,1,1,2,2,2-hexamethyldistannane (4.97 g, 15.17 mmol) and 1,1'-Bis(di-Tert-butyl 4-(4-chloro-5-fluoropyrimidin-2-yl)piperazine-1-carboxylate (4 g, 12.7 mmol), 1,1,1,2,2,2-hexamethyldistannane (4.97 g, 15.17 mmol) and 1,1'-Bis(di-tert-butylphosphino)ferrocene palladium dichloride (0.414 g, 0.633 mmol) were mixed in 25 ml 1,4-dioxane. Let it stir at 120° C. for 16 hrs. The solvent was evaporated to dryness and purified by column chromatography (PE/EA=2/1) to give 3 g tert-butyl 4-(5-fluoro-4-(trimethylstannyl)pyrimidin-2-yl)piperazine-1-carboxylate as white solid. Yield: 53.3%. LC-MS (m/z): 446.3 $[M+H]^+$.

Step 2: Tert-butyl 4-(5-fluoro-4-(trimethylstannyl)pyrimidin-2-yl)piperazine-1-carboxylate (2.4 g, 2.696 mmol) and 1-(tert-butyl) 3-ethyl 4-bromo-5-methyl-1H-pyrazole-1,3-dicarboxylate (1 g, 3.0 mmol) and $Pd(PPh_3)_4$ were mixed in 30 ml toluene. Let it stir at 120° C. for 48 hrs. The solvent was evaporated to dryness and purified by column chromatography (PE/EA=1/1) to give 240 mg of tert-butyl 4-(4-(3-(ethoxycarbonyl)-5-methyl-1H-pyrazol-4-yl)-5-fluoropyrimidin-2-yl)piperazine-1-carboxylate as brown oil. Yield: 20.5%. LC-MS (m/z): 435.4 $[M+H]^+$.

Step 3 and step 4: Tert-butyl 4-(4-(3-(ethoxycarbonyl)-5-methyl-1H-pyrazol-4-yl)-5-fluoropyrimidin-2-yl)piperazine-1-carboxylate (40 mg, 0.092 mmol) was dissolved in 3 mL DCM. 1 mL of TFA/DCM (1/1) was added to the solution at 0° C. Let it stir at r.t for 1 h. The solvent was evaporated to dryness and used for next step without further purification. LC-MS (m/z): 335.3 $[M+H]^+$.

The above residue and (S)-3-(1-(1H-imidazole-1-carbonyl)-4,5-dihydro-1H-pyrazol-5-yl)-5-fluorobenzonitrile (30 mg, 0.106 mmol) and DABCO (41 mg, 0.366 mmol) were mixed in 3 mL THF. It was evaporated to dryness and directly lighted with 100 W filament lamp for 3 hrs. The solid was purified by prep-HPLC to give 10 mg of ethyl (S)-4-(2-(4-(5-(3-cyano-5-fluorophenyl)-4,5-dihydro-1H-pyrazole-1-carbonyl)piperazin-1-yl)-5-fluoropyrimidin-4-yl)-5-methyl-1H-pyrazole-3-carboxylate as white solid. Yield of two steps: 19.8%. $^1H$ NMR (400 MHz, $CDCl_3$) δ 8.22 (d, J=1.6 Hz, 1H), 7.42 (t, J=1.6 Hz, 1H), 7.30-7.27 (m, 1H), 7.25-7.22 (m, 1H), 6.89 (t, J=1.6 Hz, 1H), 5.37 (dd, J=11.2, 10.4 Hz, 1H), 4.32 (q, J=7.2 Hz, 2H), 3.93-3.83 (m, 2H), 3.82-3.71 (m, 4H), 3.68-3.61 (m, 2H), 3.35 (ddd, J=18.4, 11.6, 1.6 Hz, 1H), 2.69 (ddd, J=18.4, 10.0, 1.6 Hz, 1H), 2.42 (s, 3H), 1.28 (t, J=7.2 Hz, 3H). LC-MS (m/z): 550.4 $[M+H]^+$.

Compound 74: (S)-3-fluoro-5-(1-(4-(5-fluoro-4-(3-(hydroxymethyl)-5-methyl-1H-pyrazol-4-yl)pyrimidin-2-yl)piperazine-1-carbonyl)-4,5-dihydro-1H-pyrazol-5-yl)benzonitrile

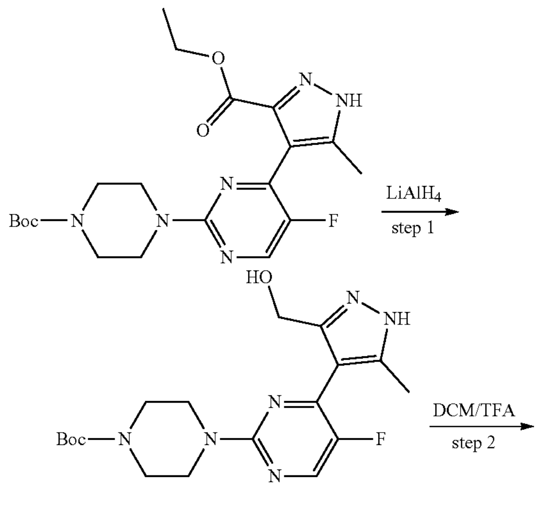

-continued

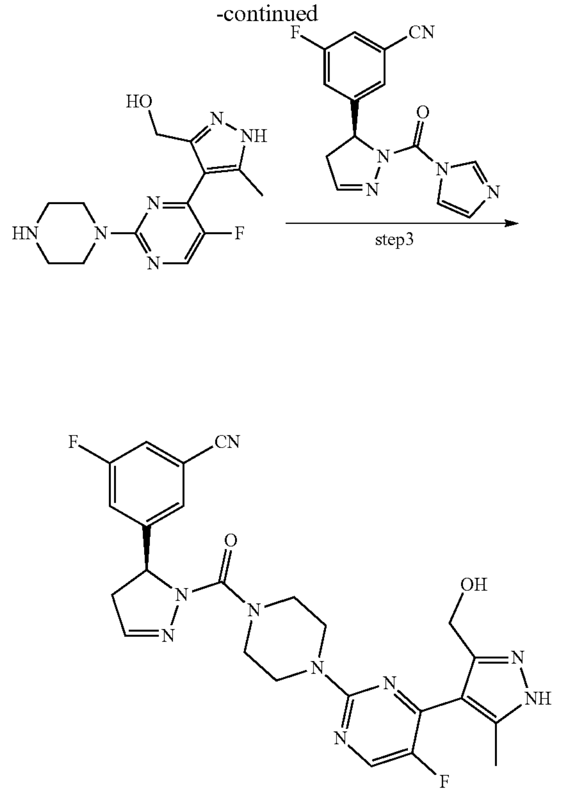

Step 1: 4-(4-(3-(ethoxycarbonyl)-5-methyl-1H-pyrazol-4-yl)-5-fluoropyrimidin-2-yl)piperazine-1-carboxylate (150 mg, 0.146 mmol) was dissolved in 4 ml THF. $LiAlH_4$ (0.6 ml, 0.6 mmol, 1 M in THF solution) was added slowly to the solution at 0° C. Let it stir at room temperature for 8 hrs. 0.6 ml $H_2O$ and 0.6 ml 1N NaOH solution was added to quench the reaction. The reaction mixture was filtered and the filtrate was evaporated to dryness to give 180 mg 4-(5-fluoro-4-(3-(hydroxymethyl)-5-methyl-1H-pyrazol-4-yl)pyrimidin-2-yl)piperazine-1-carboxylate as crude brown oil. It was used for next step without further purification. LC-MS (m/z): 393.4 $[M+H]^+$.

Step 2 and step 3: Tert-butyl 4-(5-fluoro-4-(3-(hydroxymethyl)-5-methyl-1H-pyrazol-4-yl)pyrimidin-2-yl)piperazine-1-carboxylate (180 mg, 0.459 mmol) was dissolved in 3 mL DCM. 2 mL of TFA/DCM (1/1) was added to the solution at 0° C. Let it stir at r.t for 1 h. The solvent was evaporated to dryness and used for next step without further purification. LC-MS (m/z): 293.5 $[M+H]^+$.

The above residue and (S)-3-(1-(1H-imidazole-1-carbonyl)-4,5-dihydro-1H-pyrazol-5-yl)-5-fluorobenzonitrile (75 mg, 0.265 mmol) and DABCO (150 mg, 1.339 mmol) were mixed in 3 mL THF. It was evaporated to dryness and directly lighted with 100 W filament lamp for 1 hr. The solid was purified by prep-HPLC to give 5 mg of (S)-3-fluoro-5-(1-(4-(5-fluoro-4-(3-(hydroxymethyl)-5-methyl-1H-pyrazol-4-yl)pyrimidin-2-yl)piperazine-1-carbonyl)-4,5-dihydro-1H-pyrazol-5-yl)benzonitrile as white solid. Yield of two steps: 3.7%. $^1H$ NMR (400 MHz, $CDCl_3$) δ 8.24 (s, 1H), 7.42 (s, 1H), 7.31-7.28 (m, 1H), 7.25-7.21 (m, 1H), 6.89 (s, 1H), 5.35 (dd, J=11.6, 10.4 Hz, 1H), 4.90-4.75 (m, 2H), 3.94-3.82 (m, 2H), 3.81-3.70 (m, 4H), 3.68-3.58 (m, 2H), 3.35 (ddd, J=18.4, 11.6, 1.6 Hz), 2.69 (ddd, J=18.4, 9.6, 1.6 Hz, 1H), 2.43 (s, 3H). LC-MS (m/z): 508.4 $[M+H]^+$.

Compound 75: (S)-3-fluoro-5-(1-(4-(5-fluoro-4-(5-methyl-1H-tetrazol-1-yl)pyrimidin yl)piperazine-1-carbonyl)-4,5-dihydro-1H-pyrazol-5-yl)benzonitrile

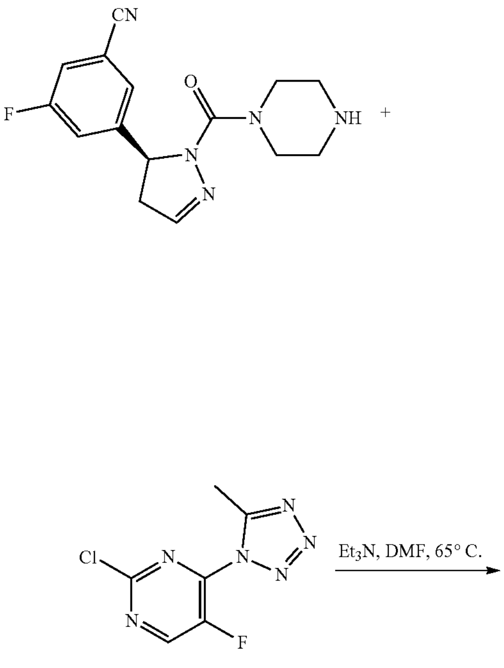

-continued

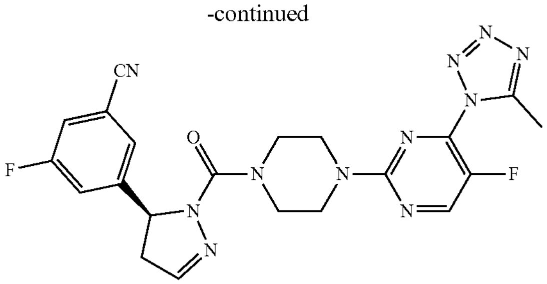

To a solution of (S)-3-fluoro-5-(1-(piperazine-1-carbonyl)-4,5-dihydro-1H-pyrazol-5-yl)benzonitrile (50 mg, 0.2 mmol) and 2-chloro-5-fluoro-4-(5-methyl-1H-tetrazol-1-yl)pyrimidine (43 mg, 0.2 mmol) in DMF (2 mL) was added $Et_3N$ (25 mg, 0.2 mmol). The mixture was stirred at 65° C. for overnight. The mixture was extracted with EA, washed with brine, dried ($Na_2SO_4$), and concentrated in vacuo. The crude product was purified by pre-TLC (petrol ether/EtOAc=1/1) to give the titled compound (31 mg, 38% yield) as a white solid. LCMS (ES, m/z): 480.2$[M+H]^+$. $^1H$ NMR (400 MHz, $CDCl_3$) δ 8.52 (d, J=2.0 Hz, 1H), 7.41 (t, J=1.4 Hz, 1H), 7.29-7.26 (m, 1H), 7.26-7.23 (m, 1H), 6.96-6.73 (m, 1H), 5.36 (dd, J=11.6, 10.1 Hz, 1H), 4.02-3.50 (m, 8H), 3.37 (ddd, J=18.3, 11.7, 1.8 Hz, 1H), 2.80 (s, 3H), 2.70 (ddd, J=18.3, 9.9, 1.6 Hz, 1H)

Compound 76: (S)-2-(3-(2-(4-(5-(3-cyano-5-fluorophenyl)-4,5-dihydro-1H-pyrazole-1-carbonyl)piperazin-1-yl)-5-fluoropyrimidin-4-yl)-1H-pyrazol-1-yl)acetamide

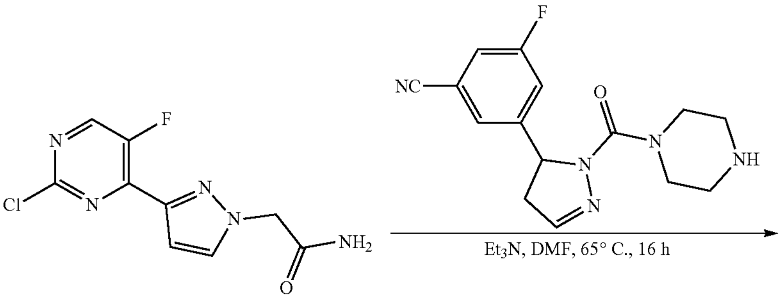

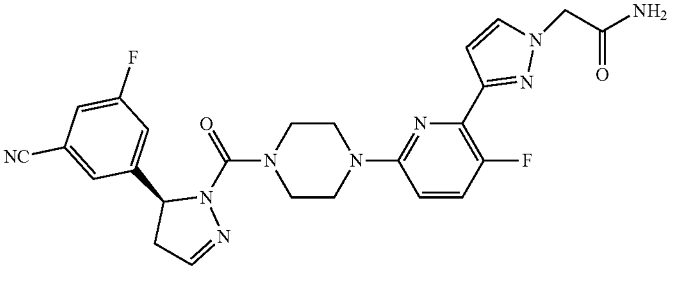

The titled compound 76 was prepared in analogous manner to the preparation of compound 7 (8 mg, 14% yield) as a white solid. LCMS (ES, m/z): 521.2[M+H]$^+$. $^1$H NMR (400 MHz, dmso) δ 8.47 (s, 1H), 7.83-7.44 (m, 3H), 7.29 (s, 1H), 7.09 (s, 1H), 6.90 (s, 1H), 5.28 (d, J=10.9 Hz, 1H), 4.88 (s, 2H), 3.82-3.49 (m, 8H), 3.36 (dd, J=17.4, 12.6 Hz, 1H), 2.59 (dd, J=18.3, 10.9 Hz, 1H).

Compound 77: (S)-2-(3-(5-fluoro-2-(4-(5-phenyl-4,5-dihydro-1H-pyrazole-1-carbonyl)piperazin-1-yl)pyrimidin-4-yl)-1H-pyrazol-1-yl)acetamideyl)acetamide

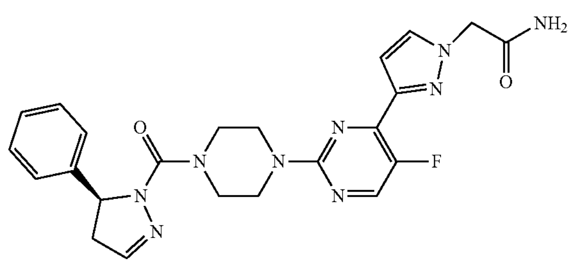 [SMILES: NC(=O)Cn1ccc(-c2nc(N3CCN(C(=O)N4N=CC[C@H]4c4ccccc4)CC3)ncc2F)n1]

The titled compound 77 was prepared in analogous manner to the preparation of compound 76 (9 mg, 16% yield) as a white solid. LCMS (ES, m/z): 478.2[M+H]$^+$. $^1$H NMR (400 MHz, dmso) δ 8.47 (d, J=3.2 Hz, 1H), 7.84 (d, J=2.3 Hz, 1H), 7.58 (s, 1H), 7.37-7.14 (m, 4H), 7.05 (s, 1H), 6.90 (s, 1H), 5.27-5.12 (m, 1H), 4.88 (s, 2H), 3.67 (m, 8H), 3.36 (dd, J=17.4, 12.6 Hz, 1H), 2.59 (dd, J=18.3, 10.9 Hz, 1H)

Compound 78 and 79: (S)-2-(4-(2-(4-(5-(3-cyano-5-fluorophenyl)-4,5-dihydro-1H-pyrazole-1-carbonyl)piperazin-1-yl)-5-fluoropyrimidin-4-yl)-5-methyl-2H-1,2,3-triazol-2-yl)acetamide and (S)-2-(4-(2-(4-(5-(3-cyano-5-fluorophenyl)-4,5-dihydro-1H-pyrazole-1-carbonyl)piperazin-1-yl)-5-fluoropyrimidin-4-yl)-5-methyl-1H-1,2,3-triazol-1-yl)acetamide

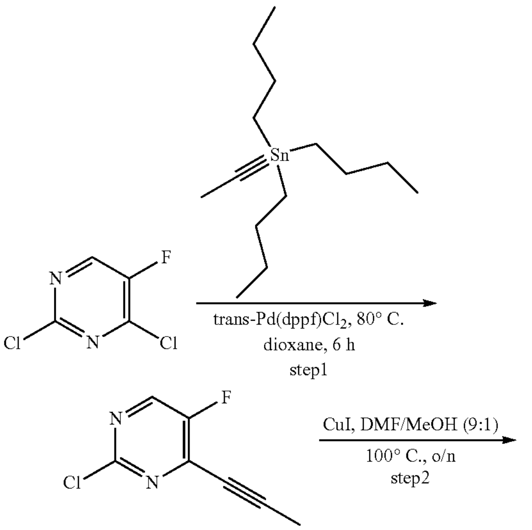

-continued

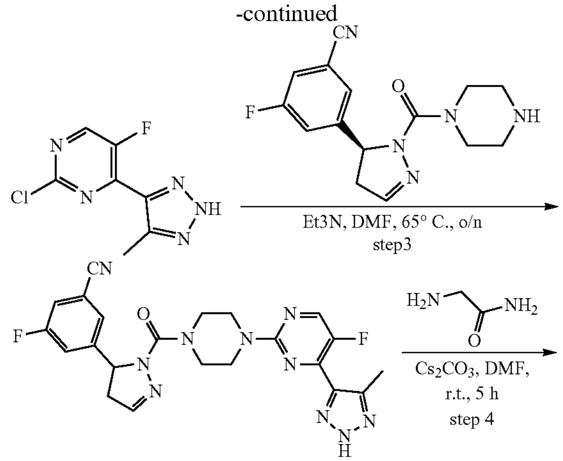

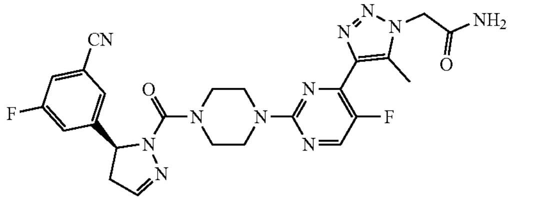

79 and

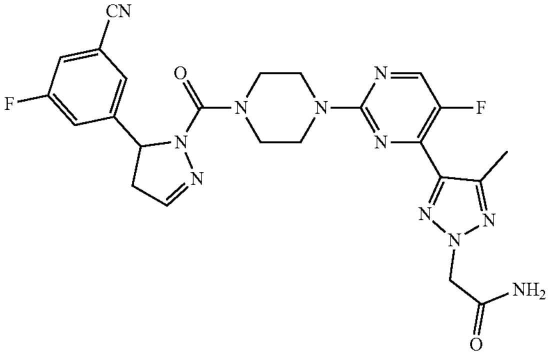

78

Step 1: To a solution of 2,4-dichloro-5-fluoropyrimidine (254 mg, 1.5 mmol) in dioxane (200 mL) was added tributyl(prop-1-yn-1-yl)stannane (500 mg, 1.52 mmol) and trans-Pd(dppf)$Cl_2$ (107 mg, 0.15 mmol) under $N_2$. The resulting mixture was stirred for 12 h at 80° C. After cooled to room temperature, the reaction mixture was concentrated under vacuum. The residue was purified by silica gel chromatography (eluting with ethyl acetate/petroleum ether=2:1) to afford 2-chloro-5-fluoro-4-(prop-1-yn-1-yl)pyrimidine as a white solid (234 mg, 46%). LCMS (ES, m/z): 171.0[M+H]+.

Step 2: To a solution of 2-chloro-5-fluoro-4-(prop-1-yn-1-yl)pyrimidine (234 mg, 1.4 mmol) in 10 mL DMF/MeOH (9:1) was added TMSN3 (238 mg, 2.0 mmol) and CuI (500 mg, 1.52 mmol) under N2. The resulting mixture was stirred for 12 h at 100° C., diluted with ethyl acetate (20 mL), washed with water (10 mL) and brine (10 mL), dried (Na2SO4), filtered, and concentrated. The residue was purified by silica gel chromatography (eluting with ethyl acetate/petroleum ether=1:1) to afford 2-chloro-5-fluoro-4-(5-methyl-2H-1,2,3-triazol-4-yl)pyrimidine as a white solid (62 mg, 21%). LCMS (ES, m/z): 214.6[M+H]+.

Step 3: To a solution of (S)-3-fluoro-5-(1-(piperazine-1-carbonyl)-4,5-dihydro-1H-pyrazol-5-yl)benzonitrile (53 mg, 0.25 mmol) and 2-chloro-5-fluoro-4-(5-methyl-2H-1,2,3-triazol-4-yl)pyrimidine (50 mg, 0.17 mmol) in DMF (5 mL) was added Et3N (25 mg, 0.24 mmol). The mixture was stirred at 65° C. for overnight. The mixture was extracted with EA, washed with brine, dried (Na2SO4), and concentrated in vacuo. The crude product was purified by pre-TLC (petrol ether/EtOAc=1/4) to give the titled compound (60 mg, 81% yield) as a white solid. LCMS (ES, m/z): 479.2 [M+H]+.

Step 4: (S)-3-fluoro-5-(1-(4-(5-fluoro-4-(5-methyl-2H-1,2,3-triazol-4-yl)pyrimidin-2-yl)piperazine-1-carbonyl)-4,5-dihydro-1H-pyrazol-5-yl)benzonitrile (25 mg, 0.10 mmol) in DMF (2 mL) was added 2-aminoacetamide (11 mg, 0.10 mmol) and Cs2CO3 (26 mg, 0.10 mmol). The mixture was stirred at room temperature for 5 h. The mixture was extracted with EA, washed with brine, dried (Na2SO4), and concentrated in vacuo. The crude product was purified by pre-TLC (DCM/MeOH=20/1) to give the titled compound (8.7 mg 23% yield and 2.1 mg 14% yield) as a white solid. LCMS (ES, m/z): 536.4[M+H]$^+$. compound 78: $^1$H NMR (400 MHz, cdcl3) δ 8.33 (d, J=2.7 Hz, 1H), 7.67 (dd, J=12.1, 6.9 Hz, 1H), 7.57-7.44 (m, 1H), 7.42 (s, 1H), 6.89 (s, 1H), 5.41-5.32 (m, 1H), 5.17 (s, 2H), 3.90 (dd, J=14.6, 7.7 Hz, 2H), 3.80 (d, J=9.5 Hz, 4H), 3.67 (dd, J=14.5, 7.9 Hz, 2H), 3.41-3.31 (m, 1H), 2.69 (dd, J=19.1, 10.7 Hz, 1H), 2.63 (s, 3H). compound 79: 1H NMR (400 MHz, cdcl3) δ 8.33 (d, J=2.7 Hz, 1H), 7.67 (dd, J=12.1, 6.9 Hz, 1H), 7.57-7.44 (m, 1H), 7.42 (s, 1H), 6.89 (s, 1H), 5.41-5.32 (m, 1H), 5.08 (s, 2H), 3.93-3.83 (m, 2H), 3.78 (d, J=9.9 Hz, 4H), 3.70-3.60 (m, 2H), 3.36 (dd, J=16.5, 11.9 Hz, 1H), 2.70 (dd, J=15.8, 7.4 Hz, 1H), 2.65 (d, J=13.1 Hz, 3H).

Compound 80: (S)-3-fluoro-5-(1-(4-(5-fluoro-4-(5-methyl-2H-1,2,3-triazol-4-yl)pyrimidin-2-yl)piperazine-1-carbonyl)-4,5-dihydro-1H-pyrazol-5-yl)benzonitrile

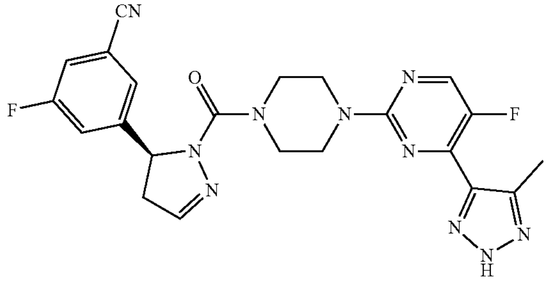 [SMILES: Cc1n[nH]nc1-c1nc(N2CCN(C(=O)N3N=CC[C@H]3c3cc(F)cc(C#N)c3)CC2)ncc1F]

The titled compound 80 (10 mg, 6% yield) as a white solid was prepared in analogous manner to the preparation of compound 78. LCMS (ES, m/z): 479.2[M+H]$^+$. $^1$H NMR (400 MHz, CDCl3) δ 8.36 (d, J=2.8 Hz, 1H), 7.43 (d, J=8.7 Hz, 1H), 7.30 (dd, J=9.2, 1.5 Hz, 1H), 7.27 (d, J=1.4 Hz, 1H), 6.91 (d, J=11.4 Hz, 1H), 5.45-5.31 (m, 1H), 3.94 (td, J=10.1, 6.4 Hz, 2H), 3.84 (dd, J=10.9, 8.1 Hz, 4H), 3.75-3.61 (m, 2H), 3.45-3.29 (m, 1H), 2.77-2.71 (m, 1H), 2.71-2.67 (m, 3H).

Compound 81: (S)-3-fluoro-5-(1-(4-(5-fluoro-4-(1H-pyrazol-3-yl)pyrimidin-2-yl)piperazine-1-carbonyl)-4,5-dihydro-1H-pyrazol-5-yl)benzonitrile

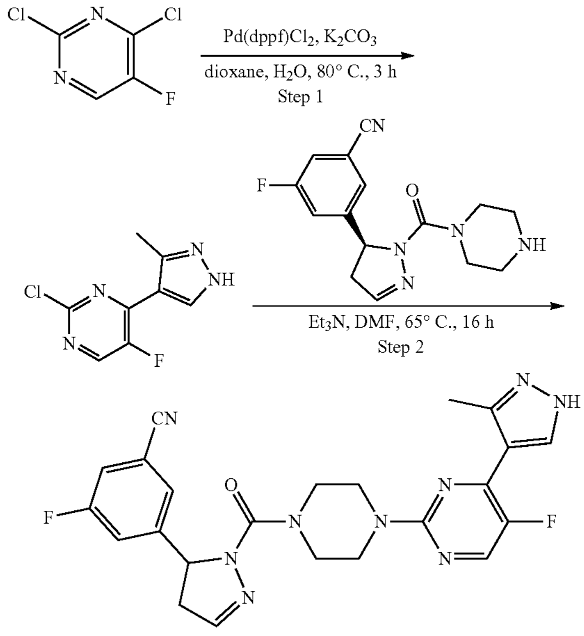

Step 1: To a solution 2,4-dichloro-5-fluoropyrimidine (1.0 g, 6.0 mmol) was dissolved in 10 mL of 1.4-dioxane/H2O (5:1) was (3-methyl-1H-pyrazol-4-yl)boronic acid (900 mg, 7.2 mmol), $K_2CO_3$ (1.65 g, 11.98 mmol) and Pd(dppf)$_2$Cl$_2$ (240 mg, 2.37 mmol) and were added to the above solution under nitrogen at room temperature. The mixture was stirred for 1.0 h at 80° C. The mixture was extracted with EA, washed with brine, dried (Na2SO4), and concentrated in vacuo. Purification by silica gel chromatography to give the titled compound (700 mg, 58%) as a white solid. (ES, m/s): 213.2 [M+H]+

Step 2: To a solution of (S)-3-fluoro-5-(1-(piperazine-1-carbonyl)-4,5-dihydro-1H-pyrazol-5-yl)benzonitrile (165 mg, 0.78 mmol) and 2-chloro-5-fluoro-4-(1H-pyrazol-3-yl) pyrimidine (258 mg, 0.86 mmol) in DMF (5 mL) was added Et3N (118 mg, 1.17 mmol). The mixture was stirred at 65° C. for overnight. The mixture was extracted with EA, washed with brine, dried (Na2SO4), and concentrated in vacuo. The crude product was purified by pre-TLC (petrol ether/EtOAc=1/1) to give the titled compound 81 (65 mg, 26% yield) as a off-white solid. LCMS (ES, m/z): 462.2 [M+H]+.

Compound 82: (S)-3-fluoro-5-(1-(4-(5-fluoro-4-(1H-pyrazol-3-yl)pyrimidin-2-yl)piperazine-1-carbonyl)-4,5-dihydro-1H-pyrazol-5-yl)benzonitrile

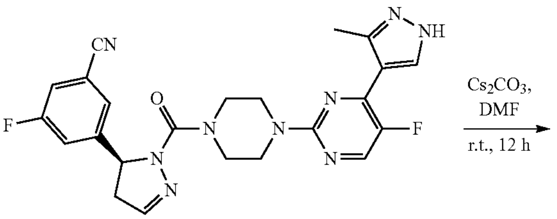

-continued

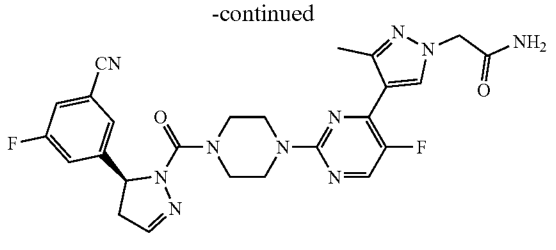

To a solution of (S)-3-fluoro-5-(1-(4-(5-fluoro-4-(3-methyl-1H-pyrazol-4-yl)pyrimidin-2-yl)piperazine-1-carbonyl)-4,5-dihydro-1H-pyrazol-5-yl)benzonitrile (30 mg, 0.06 mmol) and 2-bromoacetamide (13 mg, 0.09 mmol) in DMF (2 mL) was added Cs2CO3 (30 mg, 0.09 mmol). The mixture was stirred at room temperature for 16 h. The mixture was extracted with EA, washed with brine, dried (Na2SO4), and concentrated in vacuo. The crude product was purified by pre-HPLC to give the titled compound (2 mg, 6% yield) as a white solid. LCMS (ES, m/z): 535.2[M+H]+.

1H NMR (400 MHz, $CDCl_3$) δ 8.22 (d, J=3.1 Hz, 1H), 8.09 (d, J=3.1 Hz, 1H), 7.44 (s, 1H), 7.30 (d, J=12.1 Hz, 2H), 6.92 (s, 1H), 6.37 (brs, 1H), 5.58 (brs, 1H), 5.43-5.32 (m, 1H), 4.83 (s, 2H), 3.97-3.86 (m, 2H), 3.83 (t, J=9.0 Hz, 4H), 3.72-3.63 (m, 2H), 3.38 (dd, J=17.5, 12.6 Hz, 1H), 2.76-2.69 (m, 1H), 2.68 (s, 3H).

Compound 83: (S)-(5-(3,5-difluorophenyl)-4,5-dihydro-1H-pyrazol-1-yl)(4-(4-(1,3-dimethyl-1H-pyrazol-5-yl)-5-fluoropyrimidin-2-yl)piperazin-1-yl)methanone

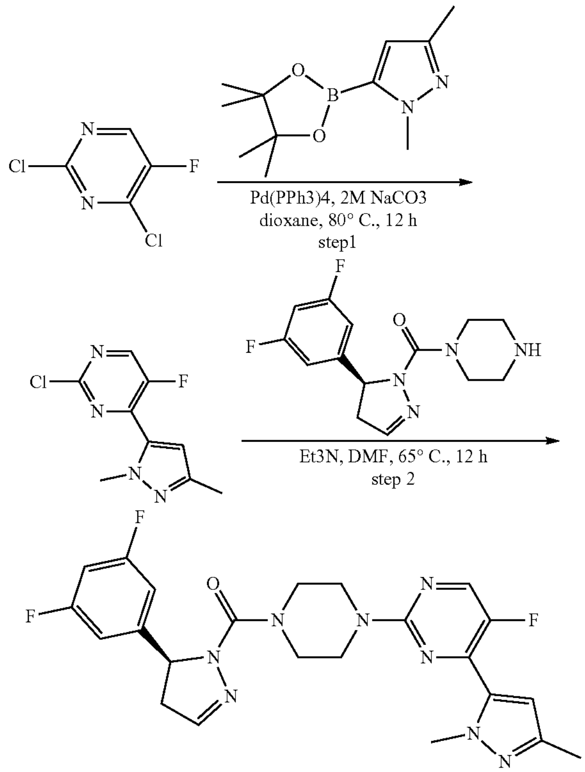

Step 1: To a solution 2,4-dichloro-5-fluoropyrimidine (200 mg, 1.19 mmol) was dissolved in 6 mL of 1.4-dioxane/H2O (5:1) was 1,3-dimethyl-5-(4,4,5,5-tetramethyl-1,3,2-dioxaborolan-2-yl)-1H-pyrazole (293 mg, 1.32 mmol), Na2CO3 (1.8 mL, 2M) and Pd(PPh3)4 (138 mg, 0.12 mmol) and were added to the above solution under nitrogen at room temperature. The mixture was stirred at 80° C. for overnight. The mixture was extracted with EA, washed with brine, dried (Na2SO4), and concentrated in vacuo. Purification by silica gel chromatography to give the titled compound (150 mg, 55%) as a white solid. (ES, m/s): 227.2 [M+H]+

Step 2: To a solution of 2-chloro-4-(1,3-dimethyl-1H-pyrazol-5-yl) fluoropyrimidine (50 mg, 0.31 mmol) and (S)-(5-(3,5-difluorophenyl)-4,5-dihydro-1H-pyrazol-1-yl)(piperazin-1-yl)methanone (60 mg, 0.28 mmol) in DMF (5 mL) was added Et3N (56 mg, 0.58 mmol). The mixture was stirred at 65° C. for overnight. The mixture was extracted with EA, washed with brine, dried (Na2SO4), and concentrated in vacuo. The crude product was purified by pre-TLC (petrol ether/EtOAc=1/1) to give the titled compound 83 (47 mg, 47% yield) as an off-white solid. LCMS (ES, m/z): 485.2$[M+H]^+$. $^1$H NMR (400 MHz, CDCl3) δ 8.20 (d, J=2.9 Hz, 1H), 6.81-6.69 (m, 3H), 6.66-6.58 (m, 2H), 5.27 (dd, J=11.6, 10.0 Hz, 1H), 4.13 (s, 3H), 3.87-3.79 (m, 2H), 3.76-3.66 (m, 4H), 3.62-3.52 (m, 2H), 3.26 (ddd, J=18.3, 11.7, 1.8 Hz, 1H), 2.62 (ddd, J=18.3, 9.9, 1.5 Hz, 1H), 2.24 (s, 3H).

Compound 84: (S)-3-(1-(4-(4-(1,3-dimethyl-1H-pyrazol-5-yl)-5-fluoropyrimidin-2-yl)piperazine-1-carbonyl)-4,5-dihydro-1H-pyrazol-5-yl)-5-fluorobenzonitrile

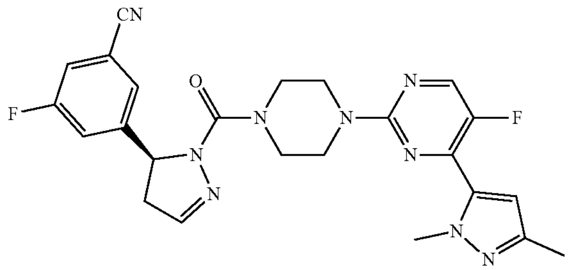 [SMILES: Cc1cc(-c2nc(N3CCN(C(=O)N4N=CC[C@H]4c4cc(F)cc(C#N)c4)CC3)ncc2F)n(C)n1]

The titled compound 84 was prepared in 22% yield as white solid in analogous manner to the preparation of compound 83 from (S)-3-(1-(4-(4-(1,3-dimethyl-1H-pyrazol-5-yl)-5-fluoropyrimidin-2-yl)piperazine-1-carbonyl)-4,5-dihydro-1H-pyrazol-5-yl)-5-fluorobenzonitrile (24 mg) LC-MS (m/z) 492.1 $(M+H^+)$$^1$H NMR (400 MHz, $CDCl_3$) δ 8.20 (d, J=2.9 Hz, 1H), 7.34 (s, 1H), 7.23-7.19 (m, 1H), 7.18-7.15 (m, 1H), 6.81 (s, 1H), 6.60 (d, J=4.3 Hz, 1H), 5.37-5.22 (m, 1H), 4.13 (s, 3H), 3.85-3.76 (m, 2H), 3.76-3.64 (m, 4H), 3.61-3.47 (m, 2H), 3.28 (ddd, J=18.3, 11.7, 1.7 Hz, 1H), 2.61 (ddd, J=18.3, 10.1, 1.5 Hz, 1H), 2.24 (s, 3H).

Compound 85: (S)-(4-(4-(1,3-dimethyl-1H-pyrazol-5-yl)-5-fluoropyrimidin-2-yl)piperazin-1-yl)(5-phenyl-4,5-dihydro-1H-pyrazol-1-yl)methanone

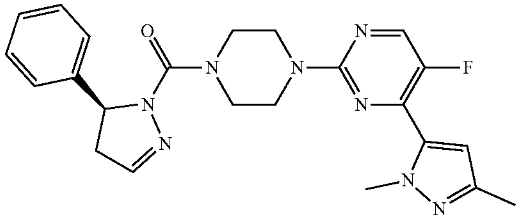 [SMILES: Cc1cc(-c2nc(N3CCN(C(=O)N4N=CC[C@H]4c4ccccc4)CC3)ncc2F)n(C)n1]

The titled compound 85 was prepare in 34% yield as white solid in analogous manner to the preparation of 83 from (S)-(4-(4-(1,3-dimethyl-1H-pyrazol-5-yl)-5-fluoropyrimidin-2-yl)piperazin-1-yl)(5-phenyl-4,5-dihydro-1H-pyrazol-1-yl)methanone (34 mg) LC-MS (m/z) 449.2 $(M+H^+)$ $^1H$ NMR (400 MHz, $CDCl_3$) δ 8.19 (d, J=2.9 Hz, 1H), 7.29-7.18 (m, 5H), 6.78 (t, J=1.6 Hz, 1H), 6.60 (d, J=4.4 Hz, 1H), 5.31 (dd, J=11.7, 9.8 Hz, 1H), 4.13 (s, 3H), 3.87-3.77 (m, 2H), 3.75-3.62 (m, 4H), 3.59-3.51 (m, 2H), 3.26 (ddd, J=18.3, 11.8, 1.8 Hz, 1H), 2.68 (ddd, J=18.3, 9.8, 1.6 Hz, 1H), 2.24 (s, 3H).

Compound 86: (S)-(4-(4-(1,3-dimethyl-1H-pyrazol-5-yl)-5-fluoropyrimidin yl)piperazin-1-yl)(5-(5-fluoropyridin-3-yl)-4,5-dihydro-1H-pyrazol-1-yl)methanone

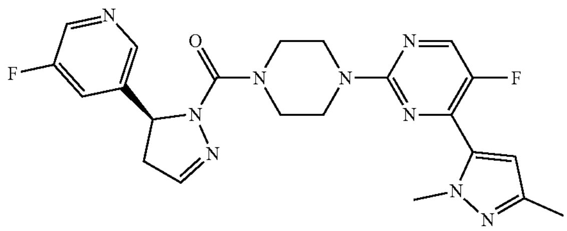 [SMILES: Cc1cc(-c2nc(N3CCN(C(=O)N4N=CC[C@H]4c4cncc(F)c4)CC3)ncc2F)n(C)n1]

The titled compound 86 was prepared as white solid in analogous manner to the preparation of 83 from (S)-(5-(5-fluoropyridin-3-yl)-4,5-dihydro-1H-pyrazol-1-yl)(piperazin-1-yl)methanone LCMS (ES, m/z): 468.2$[M+H]^+$.

Compound 87: (S)-3-(2-(4-(5-(3,5-difluorophenyl)-4,5-dihydro-1H-pyrazole-1-carbonyl)piperazin-1-yl)-5-fluoropyrimidin-4-yl)pyridin-2(1H)-one

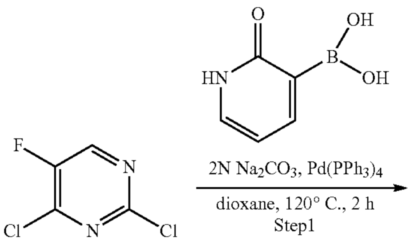

-continued

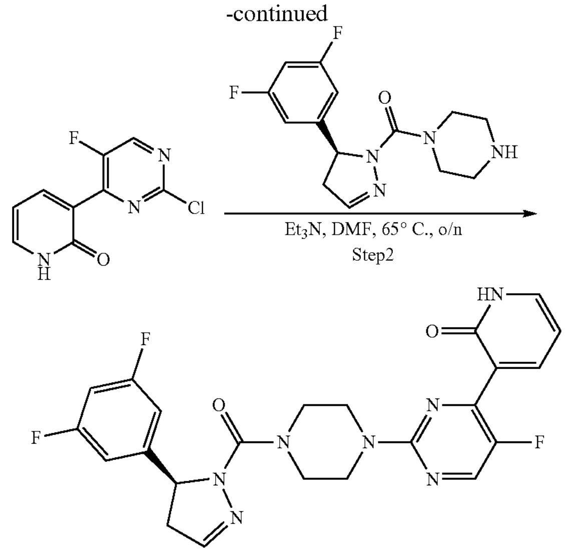

Step 1: 2,4-dichloro-5-fluoropyrimidine (300 mg, 1.80 mmol) and (2-oxo-1,2-dihydropyridin-3-yl)boronic acid (300 mg, 2.17 mmol) was dissolved in 5 mL of 1.4-dioxane was Na2CO3 (2.7 mL, 2N) and Pd(PPh3)4 (207 mg, 0.18 mmol) and were added to the above solution under nitrogen at room temperature. The mixture was stirred for 1.0 h at 80° C. The mixture was extracted with EA, washed with brine, dried (Na2SO4), and concentrated in vacuo. Purification by silica gel chromatography to give the titled compound (100 mg, 24%) as a white solid. LCMS (ES, m/s): 226.1[M+H]+

Step 2: (S)-(5-(3,5-difluorophenyl)-4,5-dihydro-1H-pyrazol-1-yl)(piperazin-1-yl)methanone (100 mg, 0.34 mmol) and 2-chloro-5-fluoro-4-(1H-pyrazol-3-yl)pyrimidine (84 mg, 0.37 mmol) in DMF (5 mL) was added Et3N (68 mg, 0.68 mmol). The mixture was stirred at 65° C. for overnight. The mixture was extracted with EA, washed with brine, dried (Na2SO4), and concentrated in vacuo. The crude product was purified by pre-TLC (petrol ether/EtOAc=5/1) to give the titled compound 87 (42 mg, 19% yield) as a white solid. LCMS (ES, m/z): 484.2 $[M+H]^+$. $^1H$ NMR (400 MHz, $CDCl_3$) δ 8.18 (d, J=2.1 Hz, 1H), 7.79 (d, J=5.1 Hz, 1H), 7.47 (dd, J=13.7, 5.8 Hz, 1H), 6.73 (ddd, J=18.7, 9.8, 4.6 Hz, 3H), 6.62 (tt, J=8.9, 2.3 Hz, 1H), 6.39 (t, J=6.6 Hz, 1H), 5.24 (dd, J=19.9, 9.9 Hz, 1H), 3.81 (td, J=10.1, 6.4 Hz, 2H), 3.76-3.63 (m, 4H), 3.56 (td, J=10.0, 6.3 Hz, 2H), 3.24 (ddd, J=18.2, 11.7, 1.8 Hz, 1H), 2.61 (ddd, J=18.2, 9.9, 1.5 Hz, 1H).

Compound 88: (S)-3-(2-(4-(5-(3,5-difluorophenyl)-4,5-dihydro-1H-pyrazole-1-carbonyl)piperazin-1-yl)-5-fluoropyrimidin-4-yl)-1-methylpyridin-2(1H)-one

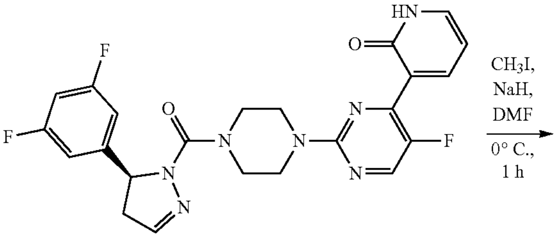

-continued

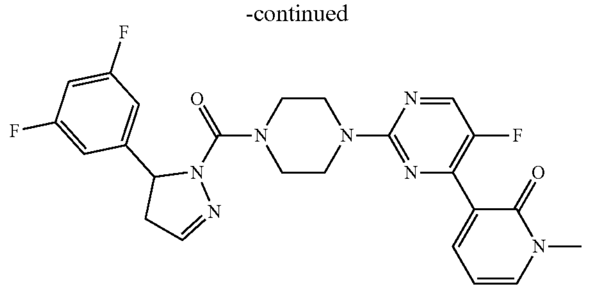

(S)-3-(2-(4-(5-(3,5-difluorophenyl)-4,5-dihydro-1H-pyrazole-1-carbonyl)piperazin-1-yl)-5-fluoropyrimidin-4-yl)pyridin-2(1H)-one (22 mg, 0.05 mmoL) was dissolved in 3 mL DMF. NaH (2 mg, 0.05 mmoL) was added in portions at 0° C. Let it stir at 0° C. for 30 min. $CH_3I$ (10 mg, 0.06 mmoL) was added. Let it stir at r.t for 30 min. Water was added and extracted with EtOAc (10 mL×3). Dried with $Na_2SO_4$, filtered, and evaporated to dryness to give 64 mg of 2-chloro-4-(1,3-dimethyl-1H-pyrazol-4-yl)-5-fluoropyrimidine as light-yellow solid. The crude product was purified by pre-TLC (petrol ether/EtOAc=1/5) to give the titled compound 88 (5.6 mg, 21% yield) as a white solid. LCMS (ES, m/z): 498.2 $[M+H]^+$. $^1$H NMR (400 MHz, $CDCl_3$) δ 8.16 (s, 1H), 7.71-7.52 (m, 1H), 7.44 (dd, J=21.9, 14.9 Hz, 2H), 6.82-6.67 (m, 2H), 6.68-6.48 (m, 1H), 6.23 (s, 1H), 5.34-5.11 (m, 1H), 3.82 (s, 2H), 3.77-3.63 (m, 4H), 3.56 (s, 5H), 3.23 (dd, J=17.6, 12.4 Hz, 1H), 2.60 (dd, J=18.2, 9.8 Hz, 1H).

Compound 89: (S)-5-(2-(4-(5-(3,5-difluorophenyl)-4,5-dihydro-1H-pyrazole-1-carbonyl)piperazin-1-yl)-5-fluoropyrimidin-4-yl)-1-methylpyridin-2(1H)-one

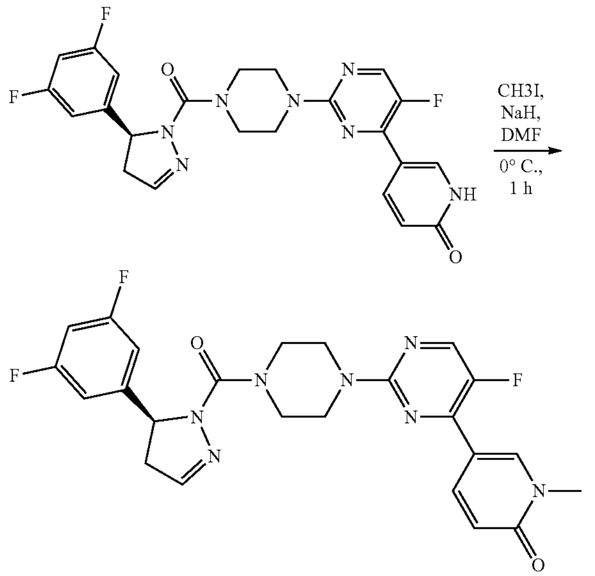

(S)-5-(2-(4-(5-(3,5-difluorophenyl)-4,5-dihydro-1H-pyrazole-1-carbonyl)piperazin-1-yl)-5-fluoropyrimidin-4-yl)-1-methylpyridin-2(1H)-one (20 mg, 0.05 mmoL) was dissolved in 3 mL DMF. NaH (2 mg, 0.05 mmoL) was added in portions at 0° C. Let it stir at 0° C. for 30 min. $CH_3I$ (10 mg, 0.06 mmoL) was added. Let it stir at r.t for 30 min. Water was added and extracted with EtOAc (10 mL×3). Dried with $Na_2SO_4$, filtered, and evaporated to dryness to give 64 mg of 2-chloro-4-(1,3-dimethyl-1H-pyrazol-4-yl)-5-fluoropyrimidine as light-yellow solid. The crude product was purified by pre-TLC (petrol ether/EtOAc=1/5) to give the titled compound 89 (5.0 mg, 18% yield) as a white solid. LCMS (ES, m/z): 498.2 $[M+H]^+$. $^1$H NMR (400 MHz, $CDCl_3$) δ 8.24-8.15 (m, 1H), 8.11 (dd, J=11.3, 3.2 Hz, 2H), 6.75 (dd, J=11.0, 5.0 Hz, 3H), 6.65-6.46 (m, 2H), 5.32-5.20 (m, 1H), 3.82 (dd, J=14.7, 8.0 Hz, 2H), 3.76-3.65 (m, 4H), 3.62-3.49 (m, 5H), 3.25 (ddd, J=18.4, 11.8, 1.8 Hz, 1H), 2.67-2.55 (m, 1H).

Compound 90: (S)-(5-(3,5-difluorophenyl)-4,5-dihydro-1H-pyrazol-1-yl)(4-(6-(3,5-dimethyl-1H-1,2,4-triazol-1-yl)pyrimidin-4-yl)piperazin-1-yl)methanone

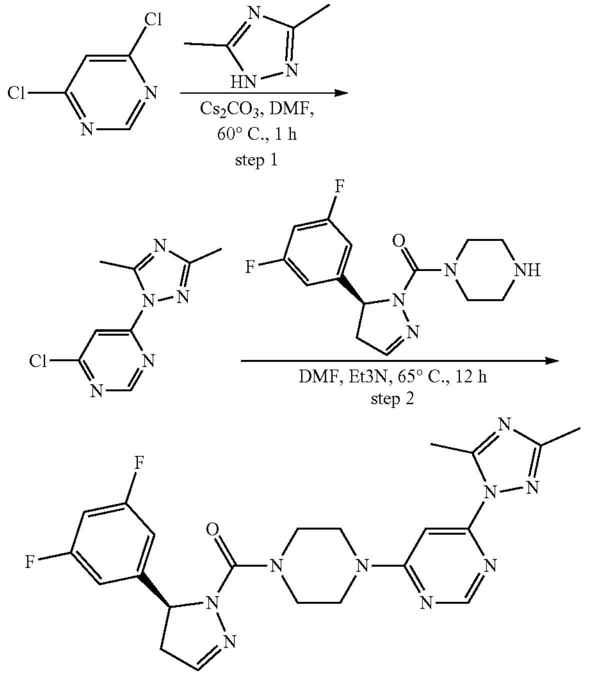

Step 1: 4,6-dichloropyrimidine (200 mg, 1.34 mmol) and 3,5-dimethyl-1H-1,2,4-triazole (105 mg, 0.17 mmol) in DMF (5 mL) was added $Cs_2CO_3$ (654 mg, 2.01 mmol). The mixture was stirred at 60° C. for 1 h. The mixture was extracted with EA, washed with brine, dried (Na2SO4), and concentrated in vacuo. The crude product was purified by pre-TLC (petrol ether/EtOAc=1/4) to give the titled compound (90 mg, 32% yield) as a white solid. LCMS (ES, m/z): 210.2[M+H]+.

Step 2: 4,6-dichloropyrimidine (90 mg, 0.43 mmol) and (S)-(5-(3,5-difluorophenyl)-4,5-dihydro-1H-pyrazol-1-yl)(piperazin-1-yl)methanone (138 mg, 0.47 mmol) in DMF (5 mL) was added $Et_3N$ (65 mg, 0.64 mmol). The mixture was stirred at 60° C. for 1 h. The mixture was extracted with EA, washed with brine, dried (Na2SO4), and concentrated in vacuo. The crude product was purified by pre-TLC (petrol ether/EtOAc=1/4) to give the titled compound 90 (76.9 mg, 32% yield) as a white solid. LCMS (ES, m/z): 468.2$[M+H]^+$. $^1$H NMR (400 MHz, $CDCl_3$) δ 8.42 (d, J=0.7 Hz, 1H), 6.94

(t, J=3.5 Hz, 1H), 6.80-6.70 (m, 3H), 6.63 (tt, J=8.8, 2.3 Hz, 1H), 5.25 (dd, J=11.6, 9.9 Hz, 1H), 3.85-3.69 (m, 4H), 3.69-3.54 (m, 4H), 3.26 (ddd, J=18.3, 11.7, 1.8 Hz, 1H), 2.79 (s, 3H), 2.63 (ddd, J=18.3, 9.8, 1.6 Hz, 1H), 2.32 (s, 3H).

Compound 91: methyl (5)-1-(2-(4-(5-(3,5-difluorophenyl)-4,5-dihydro-1H-pyrazole-1-carbonyl)piperazin-1-yl)-5-fluoropyrimidin-4-yl)-5-methyl-1H-pyrrole-3-carboxylate

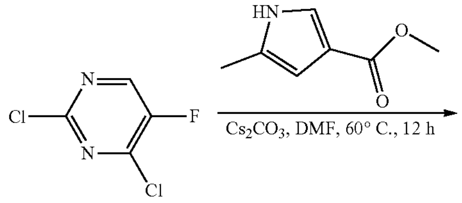

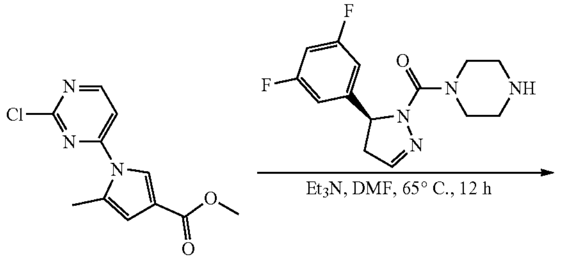

-continued

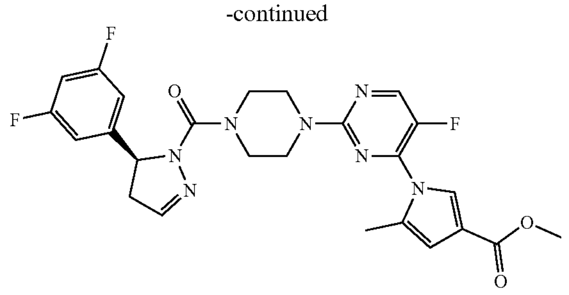

Step 1: 2,4-dichloro-5-fluoropyrimidine (200 mg, 1.20 mmol) and 5-methyl-1H-pyrrole-3-carboxylate (166 mg, 1.2 mmol) in DMF (5 mL) was added $Cs_2CO_3$ (584 mg, 1.79 mmol). The mixture was stirred at 60° C. for 12 h. The mixture was extracted with EA, washed with brine, dried (Na2SO4), and concentrated in vacuo. The crude product was purified by pre-TLC (petrol ether/EtOAc=1/4) to give the titled compound (181 mg, 60% yield) as a white solid. LCMS (ES, m/z): 252.2 $[M+H]^+$.

Step 2: methyl 1-(2-chloropyrimidin-4-yl)-5-methyl-1H-pyrrole-3-carboxylate (181 mg, 0.67 mmol) and (S)-(5-(3,5-difluorophenyl)-4,5-dihydro-1H-pyrazol-1-yl)(piperazin-1-yl)methanone (256 mg, 0.87 mmol) in DMF (5 mL) was added $Et_3N$ (102 mg, 1.01 mmol). The mixture was stirred at 60° C. for 12 h. The mixture was extracted with EA, washed with brine, dried ($Na_2SO_4$), and concentrated in vacuo. The crude product was purified by pre-TLC (petrol ether/EtOAc=1/4) to give the titled compound 91 (27.3 mg, 8% yield) as a white solid. LCMS (ES, m/z): 528.2 $[M+H]^+$.

Compound 92: (S)-1-(2-(4-(5-(3,5-difluorophenyl)-4,5-dihydro-1H-pyrazole-1-carbonyl)piperazin-1-yl)-5-fluoropyrimidin-4-yl)-5-methyl-1H-pyrrole-3-carboxamide

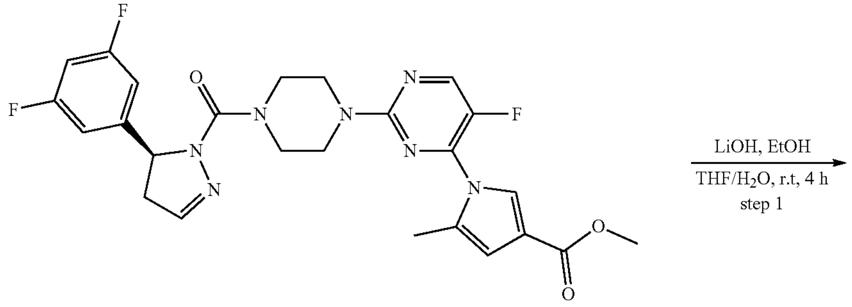

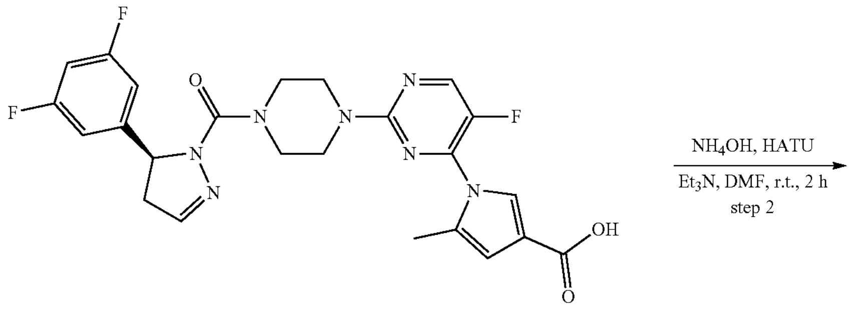

-continued

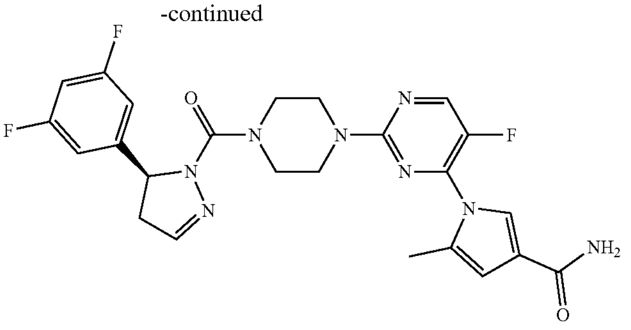

Step 1: methyl (S)-1-(2-(4-(5-(3,5-difluorophenyl)-4,5-dihydro-1H-pyrazole-1-carbonyl)piperazin-1-yl)-5-fluoro-pyrimidin-4-yl)-5-methyl-1H-pyrrole-3-carboxylate (80 mg, 0.15 mmol) in MeOH (5 mL) was added 1 N NaOH (1 mL). The reaction mixture was stirred at room temperature for overnight. 50 mg of (S)-1-(2-(4-(5-(3,5-difluorophenyl)-4,5-dihydro-1H-pyrazole-1-carbonyl)piperazin-1-yl)-5-fluoropyrimidin-4-yl)-5-methyl-1H-pyrrole-3-carboxylic acid was obtained as a white solid. Yield: 74%. LC-MS (m/z) 514.2 (M+H+).

Step 2: (S)-1-(2-(4-(5-(3,5-difluorophenyl)-4,5-dihydro-1H-pyrazole-1-carbonyl)piperazin-1-yl)-5-fluoropyrimidin-4-yl)-5-methyl-1H-pyrrole-3-carboxylic acid (50 mg, 0.10 mmol) in DMF (15 mL) was added $NH_4C1$ (17 mg, 0.3 mmol), HATU (111 mg, 0.3 mmol) and TAE (29 mg, 0.3 mmol). The reaction mixture was stirred at room temperature for 1 h. The mixture was extracted with EA, washed with brine, dried (Na2SO4), and concentrated in vacuo. The crude product was purified by pre-HPLC to give the titled compound 92 (12 mg, 24% yield) as a white solid. LCMS (ES, m/z): 513.2[M+H]$^+$. $^1$H NMR (400 MHz, $CDCl_3$) δ 8.35 (s, 1H), 7.68 (s, 1H), 6.79 (dd, J=36.2, 30.1 Hz, 4H), 6.35 (s, 1H), 5.33 (t, J=10.4 Hz, 1H), 3.98-3.52 (m, 8H), 3.37-3.21 (m, 1H), 2.69 (dd, J=18.3, 9.8 Hz, 1H), 2.40 (s, 3H).

Compound 93: (S)-(5-(3,5-difluorophenyl)-4,5-dihydro-1H-pyrazol-1-yl)(4-(4-(3,5-dimethyl-1H-pyrazol-4-yl)-5-fluoropyrimidin-2-yl)piperazin-1-yl) methanone

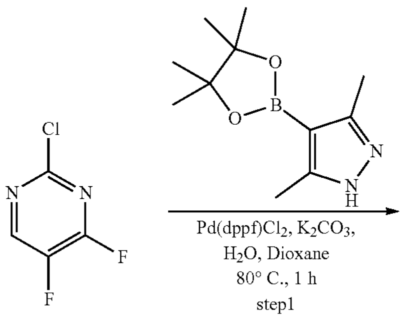

-continued

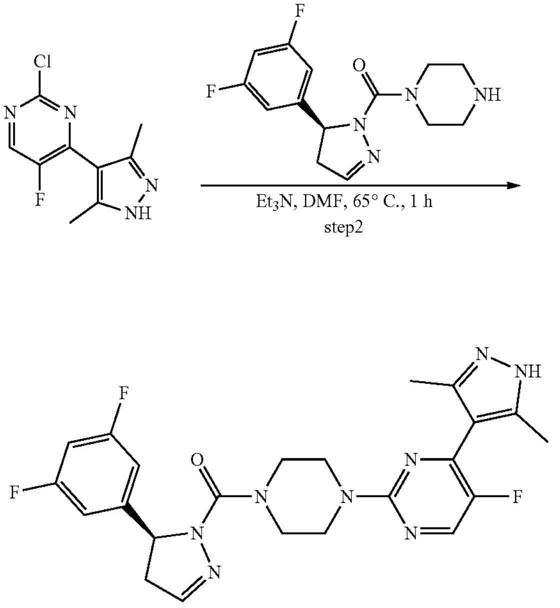

Step 1: 2,4-dichloro-5-fluoropyrimidine (500 mg, 2.99 mmol) and 3,5-dimethyl-4-(4,4,5,5-tetramethyl-1,3,2-dioxaborolan-2-yl)-1H-pyrazole (731 mg, 3.29 mmol) and K2CO3 (826 mg, 5.98 mmol) were mixed in 20 mL 1,4-dioxane/$H_2O$ (5:1). Pd(dppf)2Cl2 (219 mg, 0.30 mmol) was added. Let it stir at 85° C. for 16 hrs. The solvent was evaporated to dryness and purified by column chromatography (PE/EA=1/3) to give 300 mg crude 2-chloro-4-(3,5-dimethyl-1H-pyrazol-4-yl)-5-fluoropyrimidine as light yellow solid. LC-MS (m/z): 227.2 [M+H]+.

Step 2: (S)-(5-(3,5-difluorophenyl)-4,5-dihydro-1H-pyrazol-1-yl)(piperazin-1-yl)methanone (150 mg, 0.41 mmol) and 2-chloro-4-(3,5-dimethyl-1H-pyrazol-4-yl)-5-fluoropyrimidine (126 mg, 0.56 mmol) in DMF (5 mL) was added Et3N (68 mg, 0.68 mmol). The mixture was stirred at 65° C. for overnight. The mixture was extracted with EA, washed with brine, dried (Na2SO4), and concentrated in vacuo. The crude product was purified by pre-HPLC to give the titled compound 93 (10 mg, 4% yield) as a white solid. LCMS (ES, m/z): 485.2 [M+H]$^+$. $^1$H NMR (400 MHz, $CDCl_3$) δ 8.31 (dd, J=5.9, 1.9 Hz, 1H), 6.83 (ddd, J=13.8, 8.4, 3.7 Hz, 3H), 6.73-6.56 (m, 1H), 5.33 (dd, J=18.3, 8.3 Hz, 1H), 3.88 (dt, J=15.3, 7.5 Hz, 2H), 3.82-3.68 (m, 4H), 3.64 (dd, J=9.9, 6.9 Hz, 2H), 3.33 (ddd, J=18.3, 11.7, 1.7 Hz, 1H), 2.70 (ddd, J=18.3, 9.8, 1.5 Hz, 1H), 2.53 (d, J=1.5 Hz, 6H).

Compound 94: (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile

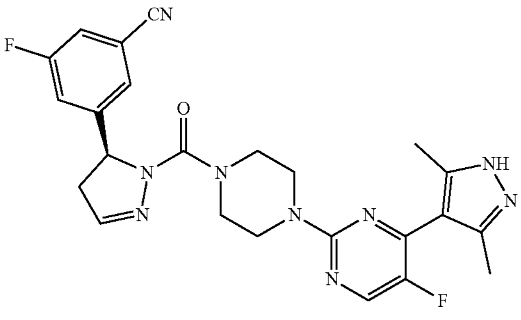 [SMILES: Cc1n[nH]c(C)c1-c1nc(N2CCN(C(=O)N3N=CC[C@H]3c3cc(F)cc(C#N)c3)CC2)ncc1F]

The titled compound 94 was prepared in 4% yield as white solid in analogous manner to the preparation of 93 from (S)-3-(1-(4-(4-(3,5-dimethyl-1H-pyrazol-4-yl)-5-fluoropyrimidin yl)piperazine-1-carbonyl)-4,5-dihydro-1H-pyrazol-5-yl)-5-fluorobenzonitrile. LC-MS (m/z) 492.2 (M+H+)

1H NMR (400 MHz, $CDCl_3$) δ 8.32 (dd, J=7.2, 1.9 Hz, 1H), 7.41 (d, J=1.3 Hz, 1H), 7.33-7.20 (m, 2H), 6.90 (s, 1H), 5.43-5.30 (m, 1H), 3.95-3.81 (m, 2H), 3.78 (d, J=10.0 Hz, 4H), 3.69-3.57 (m, 2H), 3.41-3.29 (m, 1H), 2.70 (dd, J=18.3, 10.0 Hz, 1H), 2.52 (d, J=1.5 Hz, 6H).

Compound 95: (S)-2-(2-(4-(5-(3,5-difluorophenyl)-4,5-dihydro-1H-pyrazole-1-carbonyl)piperazin-1-yl)-5-fluoropyrimidin-4-yl)-4,5-dimethyl-2,4-dihydro-3H-1,2,4-triazol-3-one

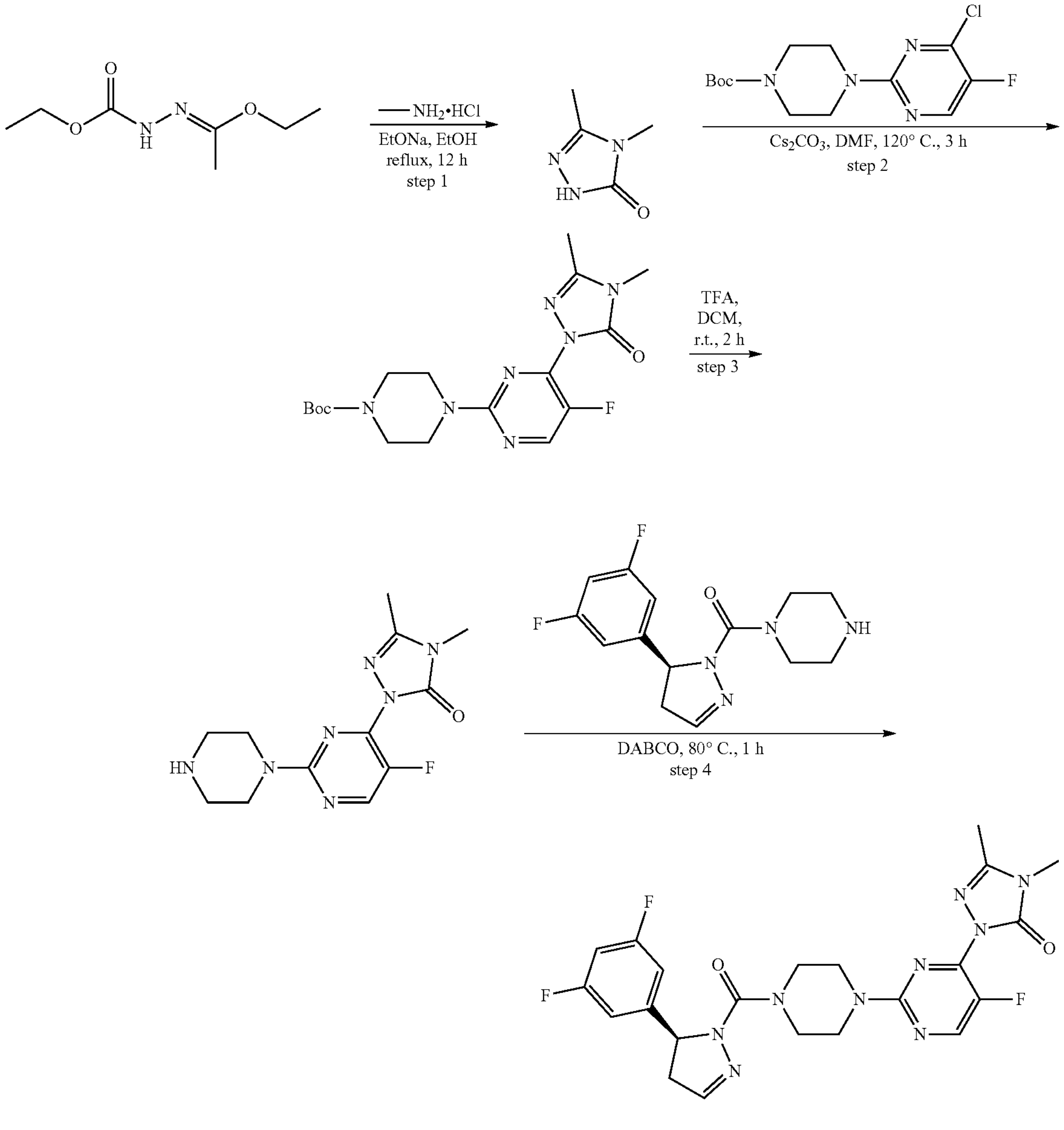

Step 1: methylamine hydrochloride (2.70 g, 40 mmol) was dissolved in absolute EtOH (200 mL) to which a suspension of sodium ethoxide (2.72 g, 40 mmol) in absolute EtOH (70 mL) was added and reaction was stirred for 5 min at room temperature. A solution of (E)-ethyl 2-(1-ethoxyethylidene)hydrazine carboxylate (3.48 g, 20 mmol) in absolute EtOH (50 mL) was added dropwise and reaction refluxed for 4 h. The reaction was then cooled to room temperature and filtered over a celite pad. The eluant was dried under reduced pressure and the resultant residue was recrystallised (through a hot filtration) from EtOAc to give the pure product. Isolated yield: 904 mg (40%, 20 mmol scale); White crystals (recrystallised from EtOAc); LCMS (ES, m/z): 114.1[M+H]$^+$.

Step 2: tert-butyl 4-(4-chloro-5-fluoropyrimidin-2-yl)piperazine-1-carboxylate (200 mg, 0.63 mmol) in DMF (20 mL) was added 4,5-dimethyl-2,4-dihydro-3H-1,2,4-triazol-3-one (100 mg, 0.75 mmol), $Cs_2CO_3$ (2.5 g, 7.62 mmol). The reaction was stirred at 120° C. for 3 h. Water was added and extracted with EA, washed with brine, dried with ($Na_2SO_4$). The resulting mixture was removed under vacuum and the crude product was purified by silica gel chromatography to give tert-butyl 4-(4-(3,4-dimethyl-5-oxo-4,5-dihydro-1H-1,2,4-triazol-1-yl) fluoropyrimidin-2-yl)piperazine-1-carboxylate. (281 mg, 41%) as yellow solid. LC-MS (m/z) 394.2 (M+H$^+$).

Step 3: tert-butyl 4-(4-(3,4-dimethyl-5-oxo-4,5-dihydro-1H-1,2,4-triazol-1-yl) fluoropyrimidin-2-yl)piperazine-1-carboxylate (281 mg, 0.71 mmol) was dissolved in 5 mL DCM. 1 mL of TFA/DCM (1/5) was added to the solution at 0° C. Let it stir at r.t for 1 h. The solvent was evaporated to dryness and used for next step without further purification. LC-MS (m/z): 294.2 [M+H]$^+$.

Step 4: The above residue and (S)-(5-(3,5-difluorophenyl)-4,5-dihydro-1H-pyrazol-1-yl)(piperazin-1-yl)methanone (100 mg, 0.36 mmol) and DABCO (61 mg, 0.55 mmol) were mixed in 3 mL THF. It was evaporated to dryness and directly lighted with 100 W filament lamp for 2 hrs. The solid was purified by prep-HPLC to give 48.8 mg of ((S)-2-(2-(4-(5-(3,5-difluorophenyl)-4,5-dihydro-1H-pyrazole-1-carbonyl)piperazin-1-yl)-5-fluoropyrimidin-4-yl)-4,5-dimethyl-2,4-dihydro-3H-1,2,4-triazol-3-one as white solid. Total yield for two steps: 14%. LC-MS (m/z): 502.2 [M+H]$^+$. $^1$H NMR (400 MHz, $CDCl_3$) δ 8.23 (d, J=2.6 Hz, 1H), 6.80-6.71 (m, 3H), 6.62 (tt, J=8.9, 2.3 Hz, 1H), 5.26 (dd, J=11.5, 10.0 Hz, 1H), 3.86-3.76 (m, 2H), 3.70 (tdd, J=9.7, 7.2, 2.8 Hz, 4H), 3.60-3.50 (m, 2H), 3.29-3.19 (m, 1H), 3.22 (s, 3H), 2.61 (ddd, J=18.3, 9.9, 1.6 Hz, 1H), 2.26 (s, 3H).

Compound 96: (S)-3-(1-(4-(4-(3,4-dimethyl-5-oxo-4,5-dihydro-1H-1,2,4-triazol-1-yl)-5-fluoropyrimidin-2-yl)piperazine-1-carbonyl)-4,5-dihydro-1H-pyrazol-5-yl)-5-fluorobenzonitrile

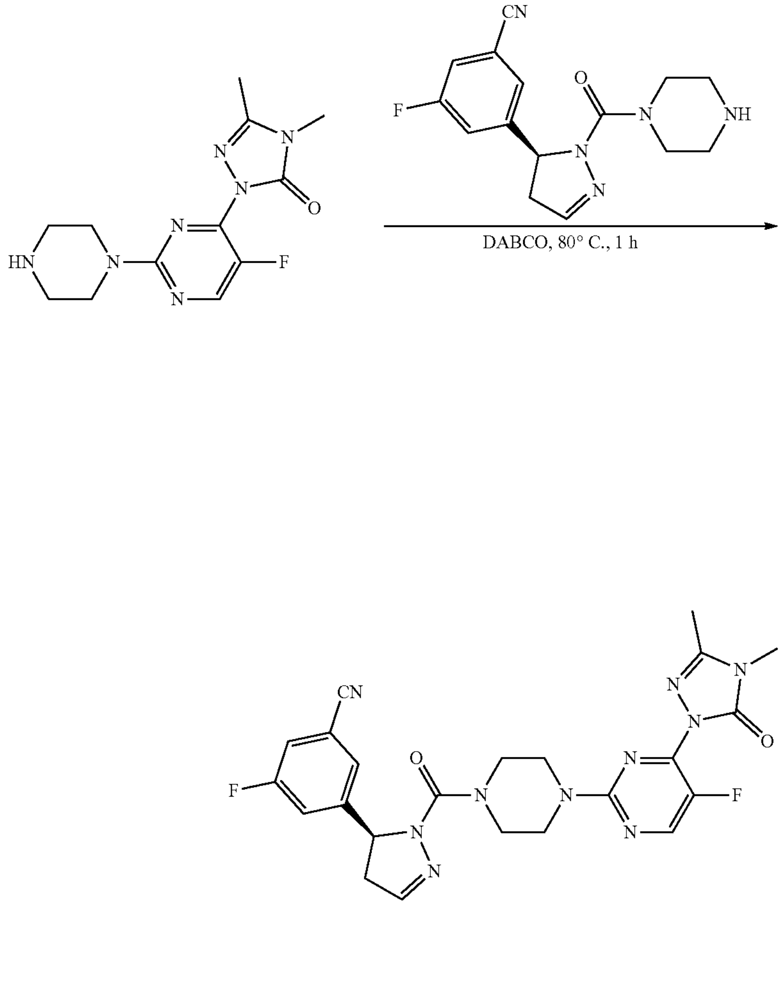

2-(5-fluoro-2-(piperazin-1-yl)pyrimidin-4-yl)-4,5-dimethyl-2,4-dihydro-3H-1,2,4-triazol-3-one (124 mg, 0.42 mmol) and (S)-3-(1-(1H-imidazole-1-carbonyl)-4,5-dihydro-1H-pyrazol-5-yl)-5-fluorobenzonitrile (100 mg, 0.35 mmol) and DABCO (60 mg, 0.55 mmol) were mixed in 2 mL THF. It was evaporated to dryness and directly lighted with 100 W filament lamp for 1 h. The solid was purified by prep-HPLC to give 150 mg of (S)-3-fluoro-5-(1-(4-(5-fluoro-4-(1H-pyrazol-4-yl)pyrimidin-2-yl)piperazine-1-carbonyl)-4,5-dihydro-1H-pyrazol-5-yl)benzonitrile as light-yellow solid. Yield: 28%. LC-MS (m/z): 509.2 $[M+H]^+$. $^1H$ NMR (400 MHz, $CDCl_3$) δ 8.24 (d, J=2.6 Hz, 1H), 7.34 (d, J=1.3 Hz, 1H), 7.22-7.17 (m, 2H), 6.80 (t, J=1.5 Hz, 1H), 5.29 (dd, J=11.3, 10.4 Hz, 1H), 3.85-3.76 (m, 2H), 3.70 (qd, J=7.0, 3.5 Hz, 4H), 3.59-3.50 (m, 2H), 3.28 (ddd, J=18.2, 11.7, 1.8 Hz, 1H), 3.22 (s, 3H), 2.61 (ddd, J=18.2, 10.1, 1.5 Hz, 1H), 2.26 (s, 3H).

Compound 97: (S)-3-(1-(4-(4-(4-ethyl-3-methyl-5-oxo-4,5-dihydro-1H-1,2,4-triazol-1-yl)-5-fluoropyrimidin-2-yl)piperazine-1-carbonyl)-4,5-dihydro-1H-pyrazol-5-yl)-5-fluorobenzonitrile

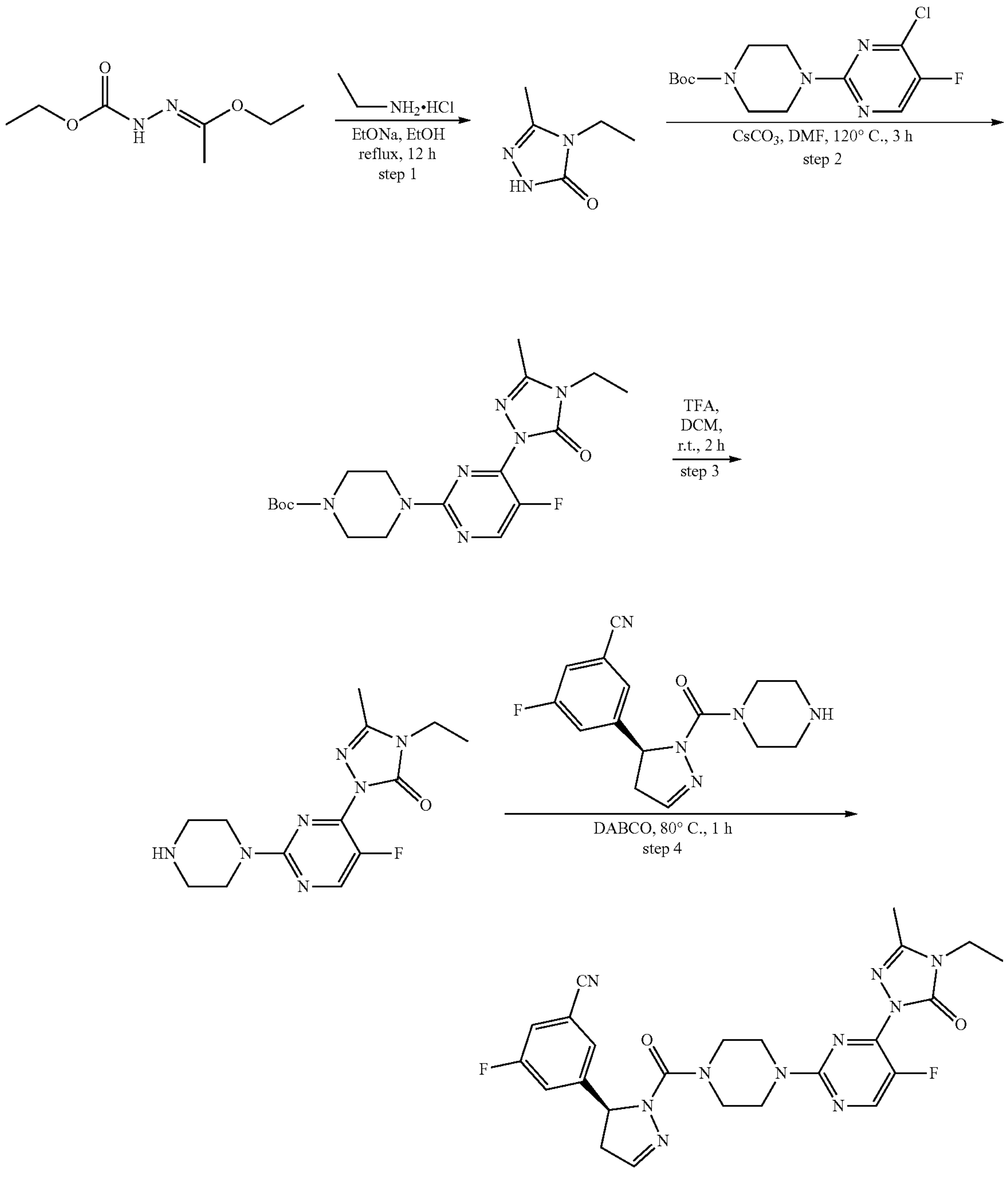

Step 1: Ethanamine hydrochloride (2.0 g, 10 mmol) was dissolved in absolute EtOH (200 mL) to which a suspension of sodium ethoxide (1.33 g, 19.5 mmol) in absolute EtOH (70 mL) was added and reaction was stirred for 5 min at room temperature. A solution of (E)-ethyl 2-(1-ethoxyethylidene)hydrazine carboxylate (1.6 g, 19.5 mmol) in absolute EtOH (50 mL) was added dropwise and reaction refluxed for 4 h. The reaction was then cooled to room temperature and filtered over a celite pad. The eluant was dried under reduced pressure and the resultant residue was recrystallised (through a hot filtration) from EtOAc to give the pure product. Isolated yield: 183 mg (10%); White crystals (recrystallised from EtOAc); LCMS (ES, m/z): 128.1[M+H]$^+$.

Step 2: tert-butyl 4-(4-chloro-5-fluoropyrimidin-2-yl)piperazine-1-carboxylate (300 mg, 0.95 mmol) in DMF (20 mL) was added 4-ethyl-5-methyl-2,4-dihydro-3H-1,2,4-triazol-3-one (128 mg, 1.42 mmol), $Cs_2CO_3$ (462 mg, 1.42 mmol). The reaction was stirred at 120° C. for 3 h. Water was added and extracted with EA, washed with brine, dried with ($Na_2SO_4$). The resulting mixture was removed under vacuum and the crude product was purified by silica gel chromatography to give tert-butyl 4-(4-(4-ethyl-3-methyl-5-oxo-4,5-dihydro-1H-1,2,4-triazol-1-yl)-5-fluoropyrimidin-2-yl)piperazine-1-carboxylate. (300 mg, 77%) as yellow solid. LC-MS (m/z) 408.2 (M+H$^+$).

Step 3: tert-butyl 4-(4-(4-ethyl-3-methyl-5-oxo-4,5-dihydro-1H-1,2,4-triazol-1-yl)-5-fluoropyrimidin-2-yl)piperazine-1-carboxylate (300 mg, 0.73 mmol) was dissolved in 5 mL DCM. 1 mL of TFA/DCM (1/5) was added to the solution at 0° C. Let it stir at r.t for 1 h. The solvent was evaporated to dryness and used for next step without further purification. LC-MS (m/z): 308.2 [M+H]$^+$.

Step 4: The above residue and 4-ethyl-2-(5-fluoro-2-(piperazin-1-yl)pyrimidin-4-yl)-5-methyl-2,4-dihydro-3H-1,2,4-triazol-3-one (260 mg, 0.84 mmol) and DABCO (53 mg, 1.06 mmol) were mixed in 3 mL THF. It was evaporated to dryness and directly lighted with 100 W filament lamp for 2 hrs. The solid was purified by prep-HPLC to give 20 mg of (S)-3-(1-(4-(4-(4-ethyl-3-methyl-5-oxo-4,5-dihydro-1H-1,2,4-triazol-1-yl)-5-fluoropyrimidin-2-yl)piperazine-1-carbonyl)-4,5-dihydro-1H-pyrazol-5-yl)-5-fluorobenzonitrile as white solid. Total yield for two steps: 6%. LC-MS (m/z): 523.2 [M+H]$^+$. $^1$H NMR (400 MHz, $CDCl_3$) δ 8.24 (d, J=2.7 Hz, 1H), 7.34 (s, 1H), 7.26-7.11 (m, 2H), 6.80 (s, 1H), 5.36-5.21 (m, 1H), 3.89-3.77 (m, 2H), 3.77-3.60 (m, 6H), 3.61-3.48 (m, 2H), 3.28 (ddd, J=18.2, 11.7, 1.7 Hz, 1H), 2.62 (ddd, J=18.2, 10.0, 1.5 Hz, 1H), 2.28 (s, 3H), 1.26 (q, J=7.4 Hz, 3H).

Compound 98: (S)-2-(2-(4-(5-(3,5-difluorophenyl)-4,5-dihydro-1H-pyrazole-1-carbonyl)piperazin-1-yl)-5-fluoropyrimidin-4-yl)-4-ethyl-5-methyl-2,4-dihydro-3H-1,2,4-triazol-3-one

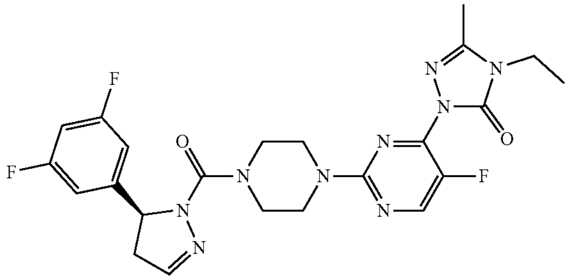 [SMILES: CCn1c(C)nn(-c2nc(N3CCN(C(=O)N4N=CC[C@H]4c4cc(F)cc(F)c4)CC3)ncc2F)c1=O]

The titled compound 98 was prepare in 8% yield as white solid in analogous manner to the preparation of 97 from (S)-2-(2-(4-(5-(3,5-difluorophenyl)-4,5-dihydro-1H-pyrazole-1-carbonyl)piperazin-1-yl)-5-fluoropyrimidin-4-yl)-4-ethyl-5-methyl-2,4-dihydro-3H-1,2,4-triazol-3-one (25 mg). LC-MS (m/z) 516.2 (M+H$^+$)$^1$H NMR (400 MHz, $CDCl_3$) δ 8.23 (d, J=2.7 Hz, 1H), 6.79-6.69 (m, 3H), 6.69-6.53 (m, 1H), 5.26 (dd, J=11.4, 10.1 Hz, 1H), 3.86-3.77 (m, 2H), 3.70 (tdd, J=14.4, 9.2, 5.0 Hz, 6H), 3.60-3.51 (m, 2H), 3.24 (ddd, J=18.2, 11.7, 1.7 Hz, 1H), 2.61 (ddd, J=18.3, 9.9, 1.5 Hz, 1H), 2.27 (s, 3H), 1.27 (t, J=7.2 Hz, 3H).

Compound 99: (S)-5-(1-(4-(4-(5-methyl-1H-tetrazol-1-yl)pyrimidin-2-yl)piperazine-1-carbonyl)-4,5-dihydro-1H-pyrazol-5-yl)nicotinonitrile

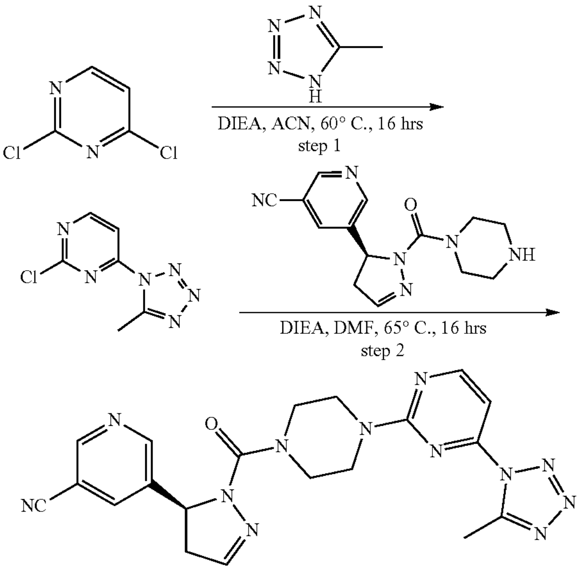

The titled compound 99 as a light-yellow solid was prepared in 20.7% yield from 2-chloro-4-(5-methyl-1H-tetrazol-1-yl)pyrimidine and (S)-5-(1-(piperazine-1-carbonyl)-4,5-dihydro-1H-pyrazol-5-yl)nicotinonitrile in analogous manner to the preparation of compound 7. 1H NMR (400 MHz, Chloroform-d) δ 8.83 (s, 2H), 8.56 (d, J=5.2 Hz, 1H), 8.00 (t, J=2.0 Hz, 1H), 7.26 (t, J=2.8 Hz, 1H), 6.98 (t, J=1.6 Hz, 1H), 5.46 (dd, J=11.6, 10.0 Hz, 1H), 4.01-3.91 m, 2H), 3.90-3.76 (m, 4H), 3.73-3.63 (m, 2H), 3.44 (ddd, J=18.4, 11.6, 2.0 Hz, 1H), 2.98 (s, 3H), 2.78 (ddd, J=18.4, 10.0, 1.6 Hz, 1H). LC-MS (m/z): 445.3 [M+H]+

Compound 100: (S)-(5-(3,5-difluorophenyl)-4,5-dihydro-1H-pyrazol-1-yl)(4-(4-(3,5-dimethyl-1H-1,2,4-triazol-1-yl)pyrimidin-2-yl)piperazin-1-yl)methanone

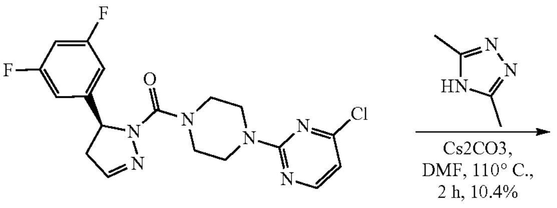

-continued

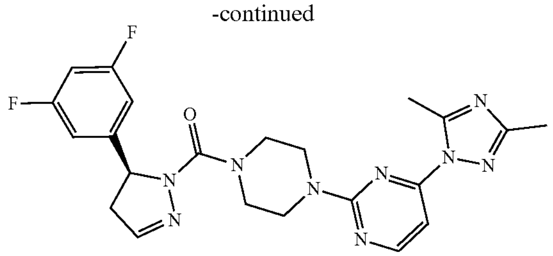

Step 1: To a solution of (S)-(4-(4-chloropyrimidin-2-yl)piperazin-1-yl)(5-(3,5-difluorophenyl)-4,5-dihydro-1H-pyrazol-1-yl)methanone (30 mg, 0.07 mmol) in DMF (20 mL) was added 3,5-dimethyl-4H-1,2,4-triazole (14 mg, 0.14 mmol), $Cs_2CO_3$ (48 mg, 0.14 mmol) at 30° C. The reaction was stirred at 110° C. for 2.0 h. Water was added and extracted with EA, washed with brine, dried with ($Na_2SO_4$). The resulting mixture was removed under vacuum and the crude product was purified by silica gel chromatography to give (S)-(5-(3,5-difluorophenyl)-4,5-dihydro-1H-pyrazol-1-yl)(4-(4-(3,5-dimethyl-1H-1,2,4-triazol-1-yl)pyrimidin-2-yl)piperazin-1-yl)methanone (4.0 mg, 10.4%) as a white solid. LC-MS (m/z) 468.4 ($M+H^+$). $^1H$ NMR (400 MHz, DMSO-$d_6$) δ 8.50 (d, J=5.2 Hz, 1H), 7.15-7.11 (m, 1H), 7.11-7.08 (m, 1H), 7.03-7.01 (m, 2H), 7.01-6.99 (m, 1H), 5.26 (dd, J=11.6, 10.0 Hz, 1H), 3.88-3.53 (m, 8H), 3.49-3.42 (m, 1H), 2.79 (s, 3H), 2.65 (ddd, J=18.4, 10.0, 1.6 Hz, 1H), 2.29 (s, 3H).

Compound 101: (5)-1-(2-(4-(5-(3,5-difluorophenyl)-4,5-dihydro-1H-pyrazole-1-carbonyl)piperazin-1-yl)-5-fluoropyrimidin-4-yl)-1H-pyrazole-4-carboxamide

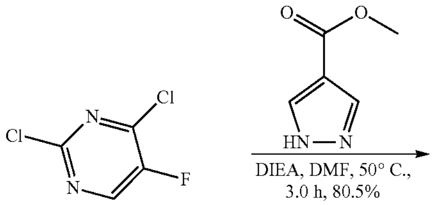

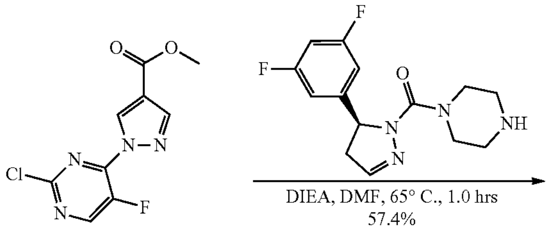

-continued

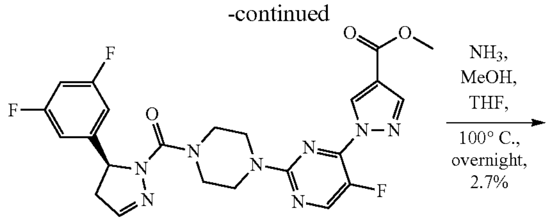

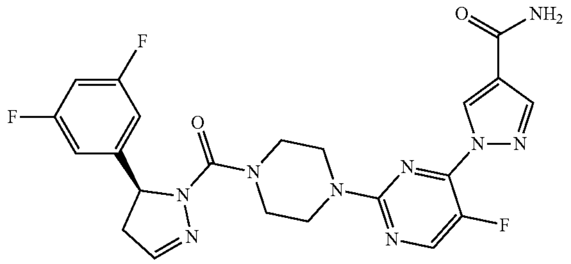

Step 1: To a solution of 2,4-dichloro-5-fluoropyrimidine (1.0 g, 5.98 mmol) in DMF (20 mL) was added methyl 1H-pyrazole-4-carboxylate (950 mg, 7.53 mmol), DIEA (1.54 g, 11.93 mmol) at 30° C. The reaction was stirred at 50° C. for 3.0 h. Water was added and extracted with EA, washed with brine, dried with ($Na_2SO_4$). The resulting mixture was removed under vacuum and the crude product was purified by silica gel chromatography to give methyl 1-(2-chloro-5-fluoropyrimidin-4-yl)-1H-pyrazole-4-carboxylate. (1.2 g, 85.5%) as grey solid. LC-MS (m/z) 257.6 ($M+H^+$).

Step 2: To a solution of methyl 1-(2-chloro-5-fluoropyrimidin-4-yl)-1H-pyrazole-4-carboxylate (130 mg, 0.51 mmol) in DMF (3 mL) was added (S)-(5-(3,5-difluorophenyl)-4,5-dihydro-1H-pyrazol-1-yl)(piperazin-1-yl)methanone (100 mg, 0.34 mmol), DIEA (87 mg, 0.67 mmol) at 30° C. The reaction was stirred at 65° C. for 1.0 h. Water was added and extracted with EA, washed with brine, dried with ($Na_2SO_4$). The resulting mixture was removed under vacuum and the crude product was purified by silica gel chromatography to give methyl (S)-1-(2-(4-(5-(3,5-difluorophenyl)-4,5-dihydro-1H-pyrazole-1-carbonyl)piperazin-1-yl)-5-fluoropyrimidin-4-yl)-1H-pyrazole-4-carboxylate. (100 mg, 57.4%) as yellow oil. LC-MS (m/z) 515.4 ($M+H^+$).

Step 3: To a solution of methyl (S)-1-(2-(4-(5-(3,5-difluorophenyl)-4,5-dihydro-1H-pyrazole-1-carbonyl)piperazin-1-yl)-5-fluoropyrimidin-4-yl)-1H-pyrazole-4-carboxylate (100 mg, 0.19 mmol) in MeOH (10 mL) and THF (10 mL) was added $NH_3$ (23 w % in $H_2O$)(2 mL) at 30° C. The reaction was stirred at 100° C. for 1 overnight. Water was added and extracted with EA, washed with brine, dried with ($Na_2SO_4$). The resulting mixture was removed under vacuum and the crude product was purified by silica gel chromatography to give (S)-1-(2-(4-(5-(3,5-difluorophenyl)-4,5-dihydro-1H-pyrazole-1-carbonyl)piperazin-1-yl)-5-fluoropyrimidin-4-yl)-1H-pyrazole-4-carboxamide (2.7 mg, 2.7%) as a white solid. LC-MS (m/z) 500.4 ($M+H^+$).

Compound 102: (S)-1-(2-(4-(5-(3-cyano-5-fluorophenyl)-4,5-dihydro-1H-pyrazole-1-carbonyl)piperazin-1-yl)pyrimidin-4-yl)-1H-pyrazole-4-carboxamide

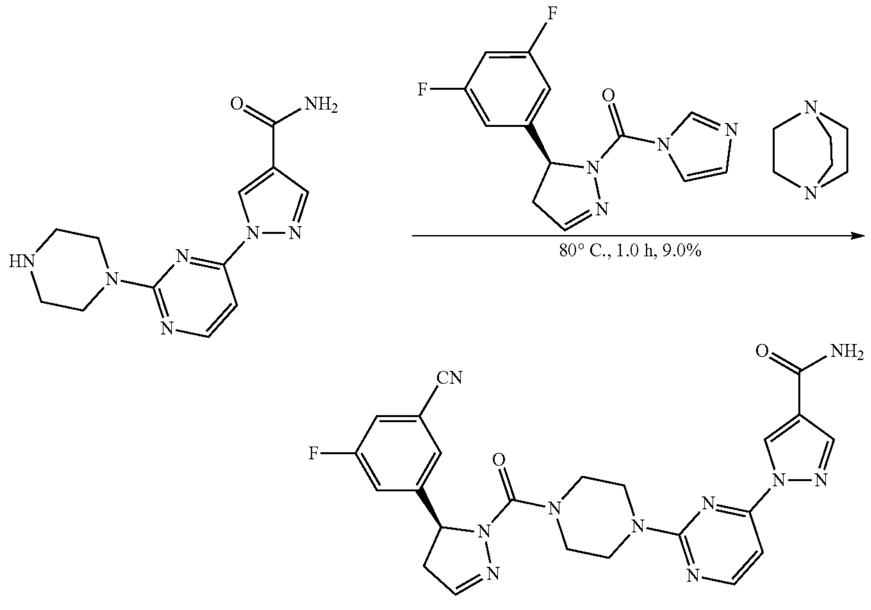

The titled compound 102 was prepared in 9.0% yield as white solid from ((S)-3-(1-(1H-imidazole-1-carbonyl)-4,5-dihydro-1H-pyrazol-5-yl)-5-fluorobenzonitrile (20 mg, 0.07 mmol) and 1-(2-(piperazin-1-yl)pyrimidin-4-yl)-1H-pyrazole-4-carboxamide (30 mg, crude) according to the procedure outlined for compound 95. LC-MS (m/z) 489.4 $(M+H^+)$ $^1$H NMR (400 MHz, DMSO-$d_6$) δ 9.21 (brs, 1H), 8.51 (d, J=5.2 Hz, 1H), 8.16 (s, 1H), 7.85 (s, 1H), 7.78-7.72 (m, 1H), 7.65 (s, 1H), 7.53 (d, J=9.6 Hz, 1H), 7.31 (s, 1H), 7.14-7.06 (m, 2H), 5.30 (t, J=10.8 Hz, 1H), 3.94-3.52 (m, 8H), 3.42-3.35 (m, 1H), 2.72 (dd, J=18.6, 10.8 Hz, 1H).

Compound 103: (S)-(5-(3-fluorophenyl)-4,5-dihydro-1H-pyrazol-1-yl)(4-(4-(5-(trifluoromethyl)-1H-tetrazol-1-yl)pyrimidin-2-yl)piperazin-1-yl)methanone

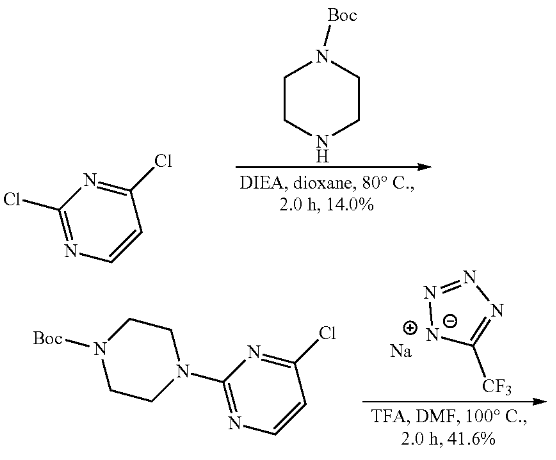

-continued

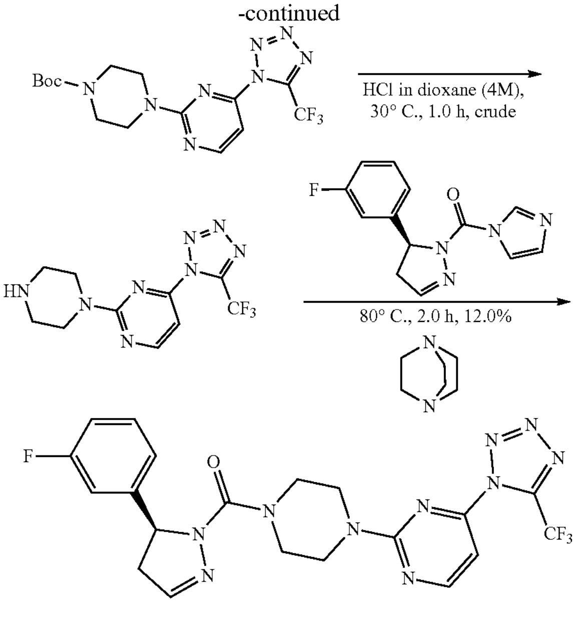

Step 1: To a solution of 2,4-dichloropyrimidine (5.0 g, 33.56 mmol) in dioxane (100 mL) was added tert-butyl piperazine-1-carboxylate (7.48 g, 40.00 mmol), DIEA (8.65 g, 67.05 mmol) at 30° C. The reaction was stirred at 80° C. for 2.0 h. Water was added and extracted with EA, washed with brine, dried with ($Na_2SO_4$). The resulting mixture was removed under vacuum and the crude product was purified by silica gel chromatography to give tert-butyl 4-(4-chloropyrimidin-2-yl)piperazine-1-carboxylate. (1.4 g, 14.0%) as yellow solid. LC-MS (m/z) 299.6 $(M+H^+)$.

Step 2: To a solution of tert-butyl 4-(4-chloropyrimidin-2-yl)piperazine-1-carboxylate (900 mg, 3.01 mmol) in DMF (20 mL) was added 5-(trifluoromethyl)-1H-tetrazole, sodium salt (1.0 g, crude), TFA (1.8 mL) at 30° C. The reaction was stirred at 100° C. for 2.0 h. Water was added and extracted with EA, washed with brine, dried with ($Na_2SO_4$). The resulting mixture was removed under vacuum and the crude product was purified by silica gel chromatography to give tert-butyl 4-(4-(5-(trifluoromethyl)-1H-tetrazol-1-yl)pyrimidin-2-yl)piperazine-1-carboxylate. (500 mg, 41.6%) as yellow solid. LC-MS (m/z) 401.4 ($M+H^+$).

Step 3: To a solution of tert-butyl 4-(4-(5-(trifluoromethyl)-1H-tetrazol-1-yl)pyrimidin-2-yl)piperazine-1-carboxylate (500 mg, 1.25 mmol) in dioxane (5 mL) was added HCl (4M in dioxane)(20 mL) at 30° C. The reaction was stirred at 30° C. for 1.0 h. The resulting mixture was removed under vacuum and the crude product without purified was used to the next step reaction. 2-(piperazin-1-yl)-4-(5-(trifluoromethyl)-1H-tetrazol-1-yl)pyrimidine hydrochloride. (600 mg, crude) as grey solid. LC-MS (m/z) 301.4 ($M+H^+$).

Step 4: To a solution of 2-(piperazin-1-yl)-4-(5-(trifluoromethyl)-1H-tetrazol-1-yl)pyrimidine hydrochloride (100 mg, crude) in THF (20 mL) was added 1,4-diazabicyclo [2.2.2]octane (300 mg, 2.67 mmol), (S)-(5-(3-fluorophenyl)-4,5-dihydro-1H-pyrazol-1-yl)(1H-imidazol-1-yl) methanone (60 mg, 0.23 mmol) at 30° C. The solvent was removed under vacuum and the reaction mixture was stand at 80° C. for 2.0 h. The crude product was purified by silica gel chromatography to give (S)-(5-(3-fluorophenyl)-4,5-dihydro-1H-pyrazol-1-yl)(4-(4-(5-(trifluoromethyl)-1H-tetrazol-1-yl)pyrimidin-2-yl)piperazin-1-yl)methanone (14.7 mg, 12.0%) as a yellow solid. LC-MS (m/z) 491.4 ($M+H^+$).

Compound 104: (S)-(5-phenyl-4,5-dihydro-1H-pyrazol-1-yl)(4-(4-(5-(trifluoromethyl)-1H-tetrazol-1-yl)pyrimidin-2-yl)piperazin-1-yl)methanone

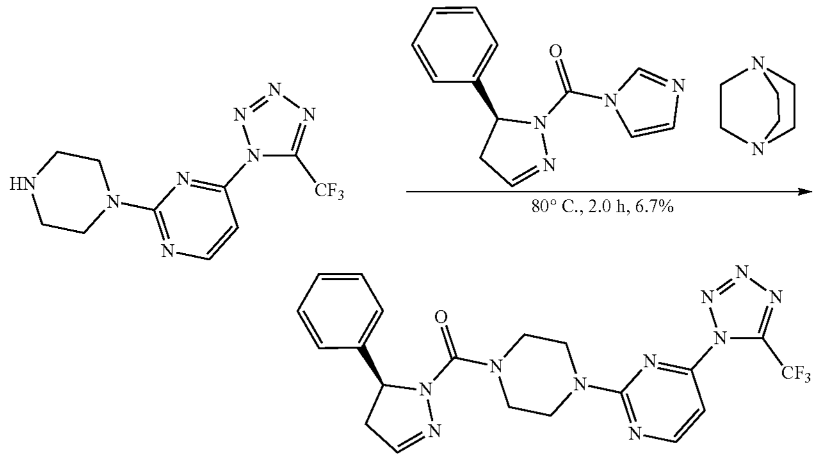

The titled compound 104 was prepare in 6.7% yield as yellow solid from (S)-(1H-imidazol-1-yl)(5-phenyl-4,5-dihydro-1H-pyrazol-1-yl)methanone (60 mg, 0.25 mmol) and 2-(piperazin-1-yl)-4-(5-(trifluoromethyl)-1H-tetrazol-1-yl) pyrimidine (100 mg, crude) in analogous manner to the preparation of compound 103. LC-MS (m/z) 473.4 ($M+H^+$)

Compound 105: (S)-(5-(3,5-difluorophenyl)-4,5-dihydro-1H-pyrazol-1-yl)(4-(5-fluoro-4-(4-(trifluoromethyl)-1H-1,2,3-triazol-5-yl)pyrimidin-2-yl)piperazin yl)methanone

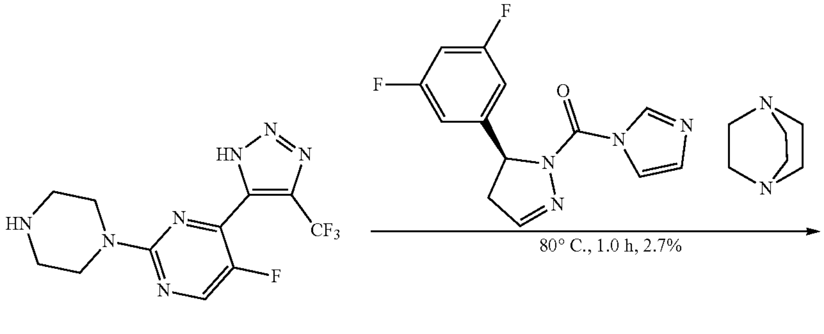

-continued

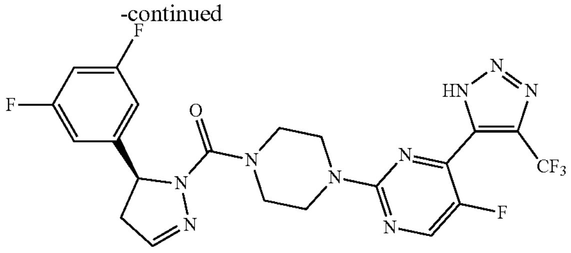

The titled compound 105 was prepare in 2.7% yield as yellow solid from (S)-(5-(3,5-difluorophenyl)-4,5-dihydro-1H-pyrazol-1-yl)(1H-imidazol-1-yl)methanone (100 mg, 0.36 mmol) and 5-fluoro-2-(piperazin-1-yl)-4-(4-(trifluoromethyl)-1H-1,2,3-triazol-5-yl)pyrimidine (150 mg, crude) in analogous manner to the preparation of compound 103. LC-MS (m/z) 526.4 ($M+H^+$)$^1$H NMR (400 MHz, DMSO-$d_6$) δ 8.41 (d, J=2.8 Hz, 1H), 7.14-7.04 (m, 2H), 7.01-6.91 (m, 2H), 5.22 (dd, J=11.6, 10.0 Hz, 1H), 3.52-3.18 (m, 9H), 2.62 (ddd, J=18.4, 10.0, 1.6 Hz, 1H).

Compound 106: (S)-1-(2-(4-(5-(3-cyanophenyl)-4,5-dihydro-1H-pyrazole-1-carbonyl)piperazin-1-yl) pyrimidin-4-yl)-1H-pyrazole-4-carboxamide

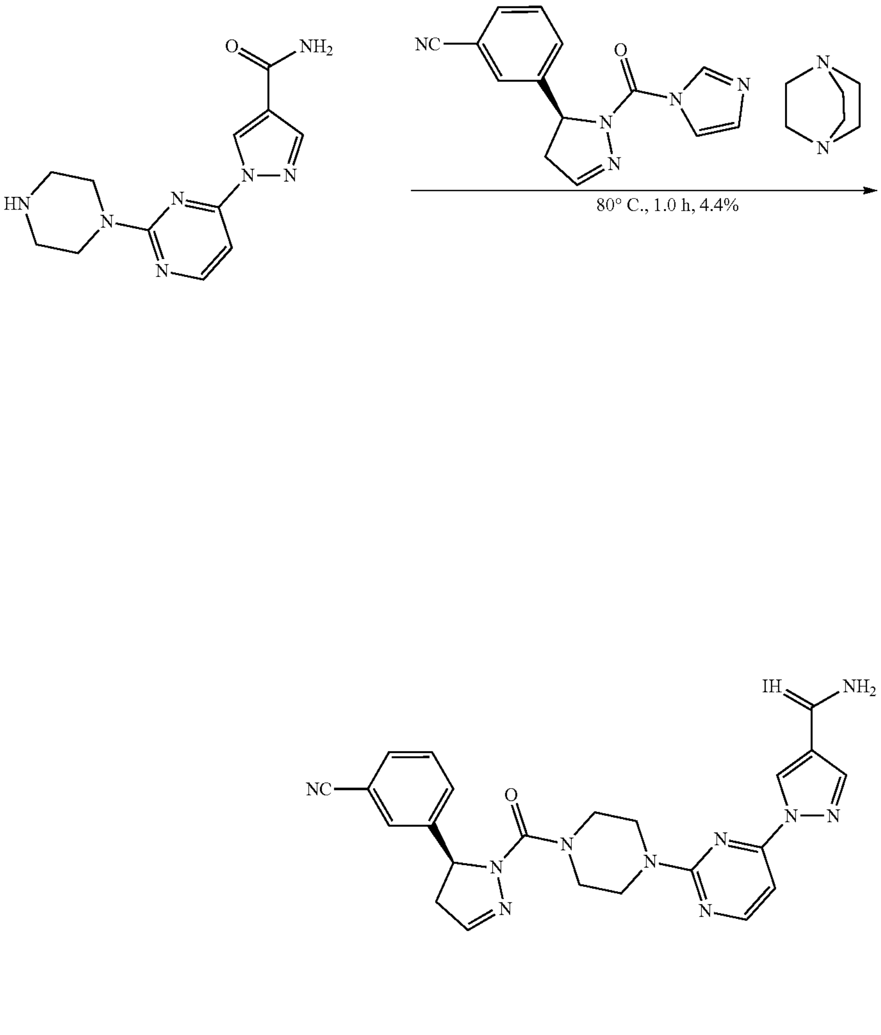

The titled compound 106 was prepared in 4.4% yield as white solid from (S)-3-(1-(1H-imidazole-1-carbonyl)-4,5-dihydro-1H-pyrazol-5-yl)benzonitrile (20 mg, 0.07 mmol) and 1-(2-(piperazin-1-yl)pyrimidin-4-yl)-1H-pyrazole-4-carboxamide (30 mg, crude) in analogous manner to the preparation of compound 103. LC-MS (m/z) 471.6 ($M+H^+$) $^1H$ NMR (400 MHz, DMSO-$d_6$) δ 9.21 (s, 1H), 8.51 (d, J=5.2 Hz, 1H), 8.16 (s, 1H), 7.85 (brs, 1H), 7.77-7.71 (m, 2H), 7.63 (d, J=7.6 Hz, 1H), 7.56 (t, J=8.4 Hz, 1H), 7.31 (brs, 1H), 7.14-7.07 (m, 2H), 5.30 (dd, J=11.6, 10.0 Hz, 1H), 3.95-3.51 (m, 8H), 3.44-3.37 (m, 1H), 2.74-2.64 (m, 1H).

Compound 107: (S)-1-(2-(4-(5-(3-cyano-5-fluorophenyl)-4,5-dihydro-1H-pyrazole-1-carbonyl)piperazin-1-yl)-5-fluoropyrimidin-4-yl)-1H-pyrazole-4-carboxamide

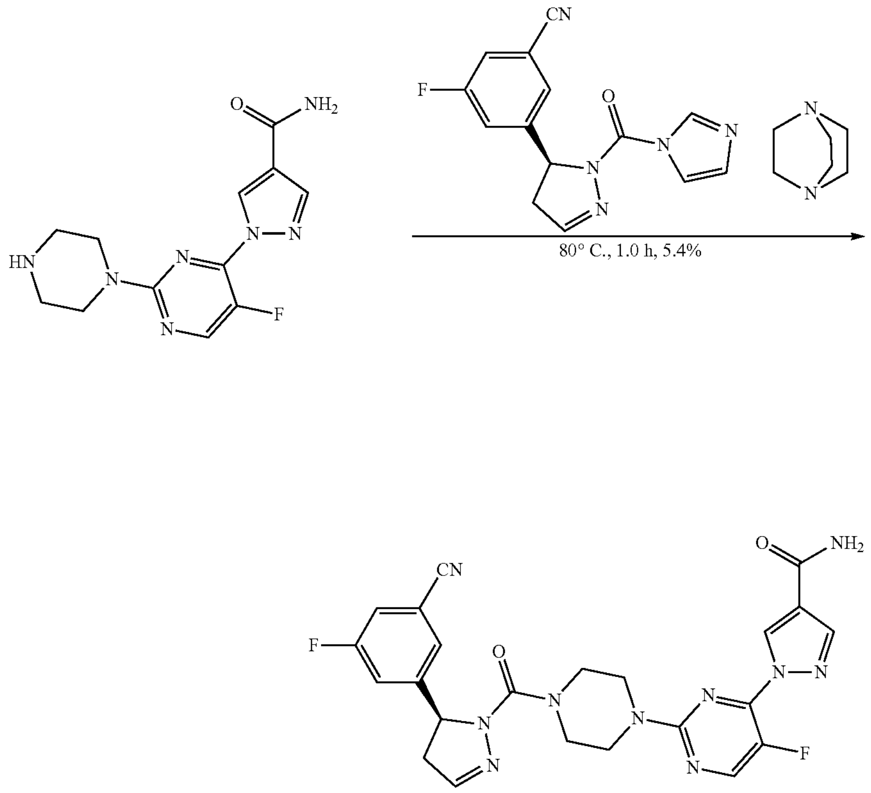

The titled compound 107 was prepare in 5.4% yield as white solid from (S)-3-(1-(1H-imidazole-1-carbonyl)-4,5-dihydro-1H-pyrazol-5-yl)-5-fluorobenzonitrile (20 mg, 0.08 mmol) and 1-(5-fluoro-2-(piperazin-1-yl)pyrimidin-4-yl)-1H-pyrazole-4-carboxamide (30 mg, crude) in analogous manner to the preparation of 103. LC-MS (m/z) 507.4 ($M+H^+$)

$^1H$ NMR (400 MHz, DMSO-$d_6$) δ 9.14 (d, J=2.8 Hz, 1H), 8.65 (d, J=3.2 Hz, 1H), 8.21 (d, J=2.8 Hz, 1H), 7.88 (brs, 1H), 7.78-7.71 (m, 1H), 7.66-7.62 (m, 1H), 7.56-7.49 (m, 1H), 7.34 (brs, 1H), 7.12 (s, 1H), 5.29 (t, J=10.8 Hz, 1H), 3.91-3.52 (m, 8H), 3.44-3.33 (m, 1H), 2.71 (dd, J=18.8, 10.8 Hz, 1H).

Compound 108: (S)-(5-(3,5-difluorophenyl)-4,5-dihydro-1H-pyrazol-1-yl)(4-(4-(3,5-dimethylisoxazol-4-yl)-5-fluoropyrimidin-2-yl)piperazin-1-yl)methanone

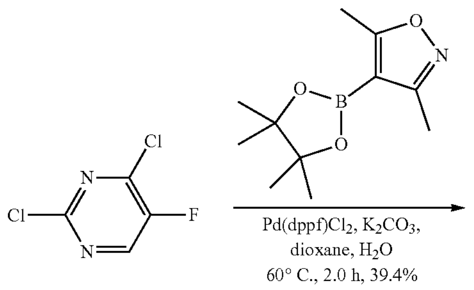

-continued

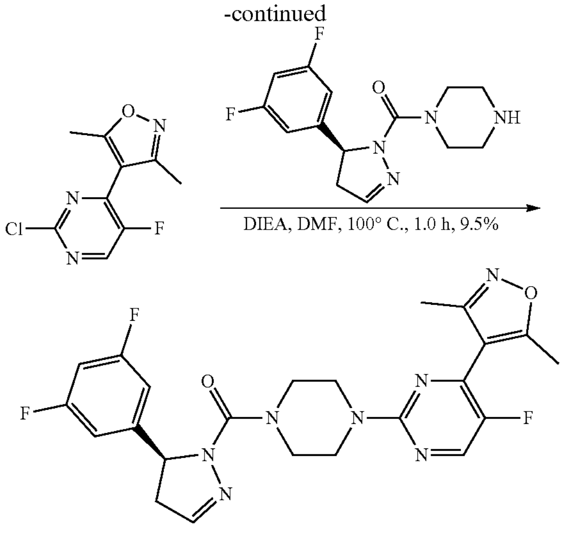

Step 1: To a solution of 2,4-dichloro-5-fluoropyrimidine (334 mg, 2.00 mmol) in dioxane (12 mL) and $H_2O$ (3 mL) was added 3,5-dimethyl-4-(4,4,5,5-tetramethyl-1,3,2-dioxaborolan-2-yl)isoxazole (448 mg, 2.00 mmol), Pd(dppf)$Cl_2$ (146 mg, 0.20 mmol), $K_2CO_3$ (276 mg, 2.00 mmol) at 30° C. under Ar. The reaction was stirred at 60° C. for 2.0 h. The solvent was removed under vacuum and the crude product was purified by silica gel chromatography to give 4-(2-chloro-5-fluoropyrimidin-4-yl)-3,5-dimethylisoxazole (180 mg, 39.4%) as a white solid. LC-MS (m/z) 228.6 ($M+H^+$).

Step 2: To a solution of 4-(2-chloro-5-fluoropyrimidin-4-yl)-3,5-dimethylisoxazole (25 mg, 0.11 mmol) in DMF (10 mL) was added (S)-(5-(3,5-difluorophenyl)-4,5-dihydro-1H-pyrazol-1-yl)(piperazin-1-yl)methanone (29 mg, 0.10 mmol) and DIEA (60 mg, 0.46 mmol) at 30° C. The reaction mixture was stirred at 120° C. for 1.0 h. Water was added and extracted with EA, washed with brine, dried with ($Na_2SO_4$). The resulting mixture was removed under vacuum and the crude product was purified by silica gel chromatography to give (S)-(5-(3,5-difluorophenyl)-4,5-dihydro-1H-pyrazol-1-yl)(4-(4-(3,5-dimethylisoxazol-4-yl)-5-fluoropyrimidin-2-yl)piperazin-1-yl)methanone (4.7 mg, 9.5%) as a white solid. LC-MS (m/z) 486.4 ($M+H^+$). $^1H$ NMR (400 MHz, DMSO-$d_6$) δ 8.55 (d, J=2.4 Hz, 1H), 7.15-7.05 (m, 2H), 7.01-6.94 (m, 2H), 5.28-5.18 (m, 1H), 3.79-3.48 (m, 8H), 3.35-3.30 (m, 1H), 2.66-2.58 (m, 1H), 2.45 (d, J=2.4 Hz, 3H), 2.28 (d, J=1.2 Hz, 3H).

Compound 109: (S)-1-(2-(4-(5-(3-cyanophenyl)-4,5-dihydro-1H-pyrazole-1-carbonyl)piperazin-1-yl)-5-fluoropyrimidin-4-yl)-1H-pyrazole-4-carboxamide

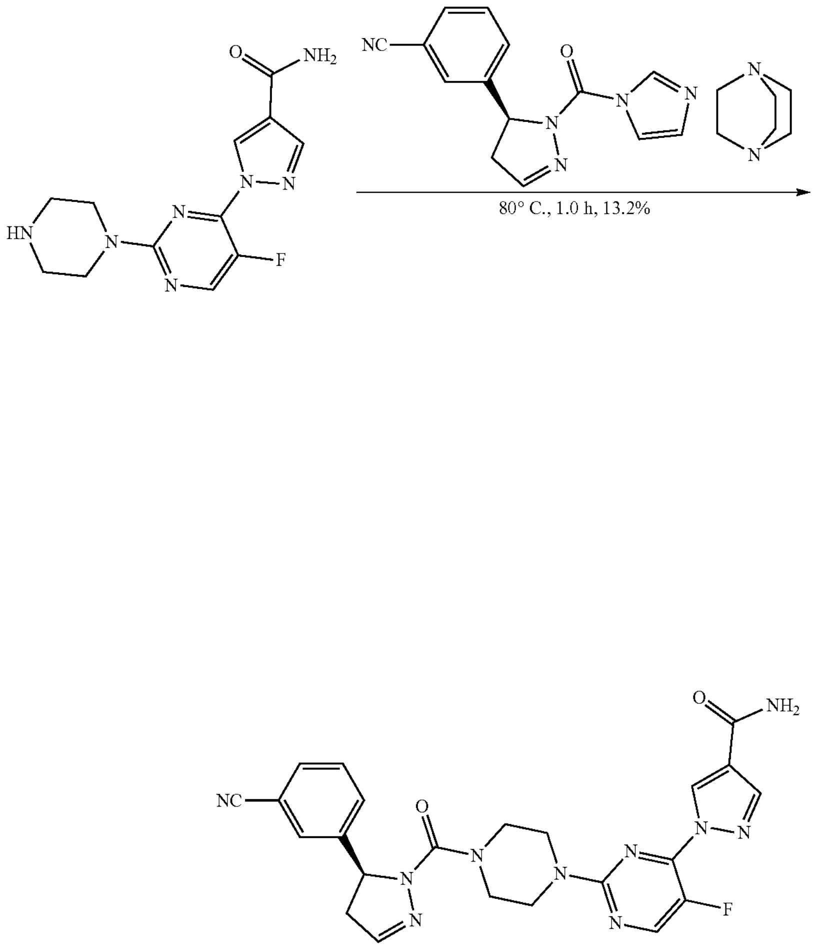

The titled compound 109 was prepare in 13.2% yield as white solid from (S)-3-(1-(1H-imidazole-1-carbonyl)-4,5-dihydro-1H-pyrazol-5-yl)benzonitrile (20 mg, 0.08 mmol) and 1-(5-fluoro-2-(piperazin-1-yl)pyrimidin-4-yl)-1H-pyrazole-4-carboxamide (30 mg, crude) in analogous manner to the preparation of compound 103. LC-MS (m/z) 489.4 $(M+H^+)$ $^1H$ NMR (400 MHz, DMSO-$d_6$) δ 9.12 (d, J=0.8 Hz, 1H), 8.64 (d, J=4.0 Hz, 1H), 8.19 (d, J=0.8 Hz, 1H), 7.86 (brs, 1H), 7.73-7.67 (m, 1H), 7.61 (dt, J=8.0, 1.6 Hz, 1H), 7.56-7.49 (m, 2H), 7.32 (brs, 1H), 7.10-7.08 (m, 1H), 5.31-5.22 (m, 1H), 3.85-3.50 (m, 8H), 3.45-3.36 (m, 1H), 2.70-2.62 (m, 1H).

Compound 110: (S)-1-(5-fluoro-2-(4-(5-(3-fluorophenyl)-4,5-dihydro-1H-pyrazole-1-carbonyl)piperazin-1-yl)pyrimidin-4-yl)-1H-pyrazole-4-carboxamide

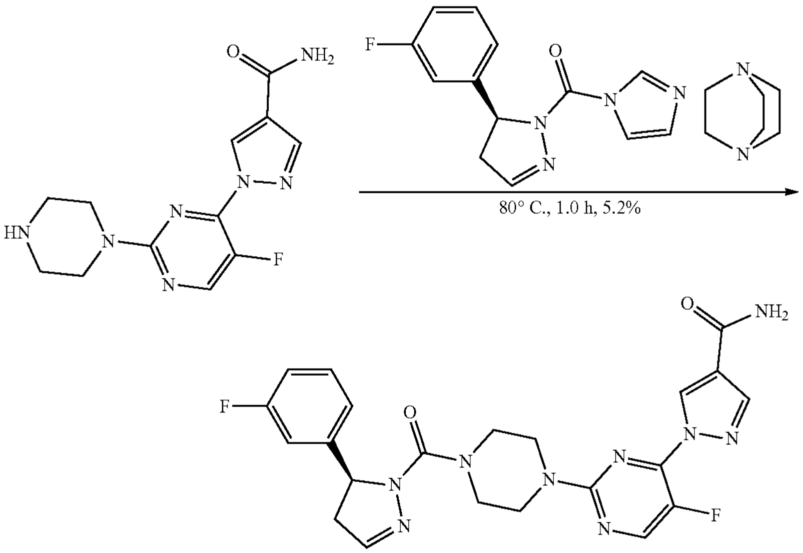

The titled compound 110 was prepared in 5.2% yield as white solid from (S)-(5-(3-fluorophenyl)-4,5-dihydro-1H-pyrazol-1-yl)(1H-imidazol-1-yl)methanone (20 mg, 0.08 mmol) and 1-(5-fluoro-2-(piperazin-1-yl)pyrimidin-4-yl)-1H-pyrazole-4-carboxamide (30 mg, crude) in analogous manner to the preparation of compound 103. LC-MS (m/z) 482.4 $(M+H^+)$ $^1H$ NMR (400 MHz, DMSO-$d_6$) δ 9.14 (m, 1H), 8.65 (dd, J=4.0, 0.8 Hz, 1H), 8.21 (d, J=0.8 Hz, 1H), 7.88 (brs, 1H), 7.41-7.30 (m, 2H), 7.14-7.02 (m, 4H), 5.29-5.22 (m, 1H), 3.87-3.51 (m, 8H), 3.42-3.35 (m, 1H), 2.68-2.58 (m, 1H).

Compound 111: (S)-1-(5-fluoro-2-(4-(5-phenyl-4,5-dihydro-1H-pyrazole-1-carbonyl)piperazin-1-yl)pyrimidin-4-yl)-1H-pyrazole-4-carboxamide

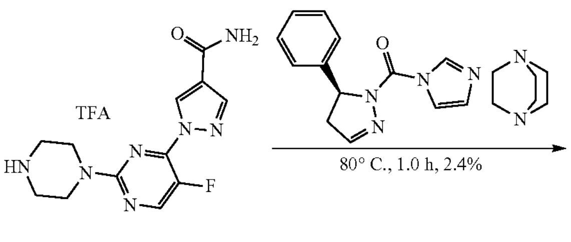

-continued

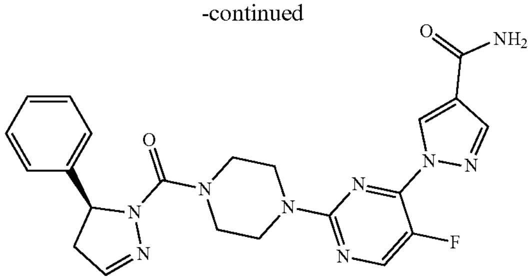

The titled compound 111 was prepared in 2.4% yield as white solid from (S)-(1H-imidazol-1-yl)(5-phenyl-4,5-dihydro-1H-pyrazol-1-yl)methanone (20 mg, 0.08 mmol) and 1-(5-fluoro-2-(piperazin-1-yl)pyrimidin-4-yl)-1H-pyrazole-4-carboxamide (30 mg, crude) in analogous manner to the preparation of compound 103. LC-MS (m/z) 464.4 $(M+H^+)$ $^1H$ NMR (400 MHz, DMSO-$d_6$) δ 9.13 (d, J=0.8 Hz, 1H), 8.64 (d, J=4.0 Hz, 1H), 8.19 (d, J=0.8 Hz, 1H), 7.86 (brs, 1H), 7.35-7.28 (m, 3H), 7.26-7.19 (m, 3H), 7.09-7.03 (m, 1H), 5.23 (dd, J=11.6, 9.6 Hz, 1H), 3.87-3.47 (m, 8H), 3.41-3.35 (m, 1H), 2.59 (ddd, J=18.4, 9.6, 1.6 Hz, 1H).

Compound 112: (S)-3-fluoro-5-(1-(4-(5-fluoro-4-(1H-imidazol-2-yl)pyrimidin-2-yl)piperazine-1-carbonyl)-4,5-dihydro-1H-pyrazol-5-yl)benzonitrile

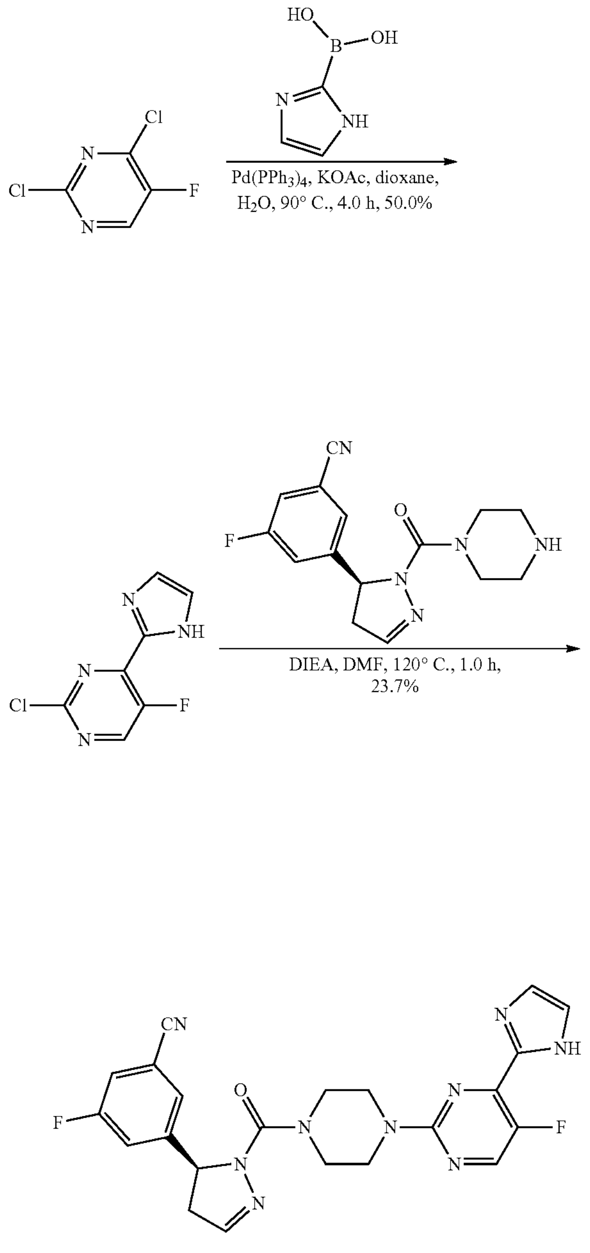

The titled compound 112 was prepared in 23.7% yield as white solid from 2-chloro-5-fluoro-4-(1H-imidazol-2-yl)pyrimidine (30 mg, 0.15 mmol) and (S)-3-fluoro-5-(1-(piperazine-1-carbonyl)-4,5-dihydro-1H-pyrazol-5-yl)benzonitrile (40 mg, 0.13 mmol), DIEA (100 mg, 0.77 mmol), DMF (3 mL) in analogous manner to the preparation of compound 7. LC-MS (m/z) 464.4 ($M+H^+$)$^1$H NMR (400 MHz, DMSO-$d_6$) δ 8.67-8.63 (m, 1H), 8.50-8.47 (m, 1H), 7.93-7.89 (m, 1H), 7.77-7.72 (m, 1H), 7.67-7.61 (m, 1H), 7.56-7.49 (m, 1H), 7.21-7.15 (m, 1H), 7.14-7.09 (m, 1H), 5.29 (t, J=10.8 Hz, 1H), 3.86-3.51 (m, 8H), 3.41-3.35 (m, 1H), 2.77-2.65 (m, 1H).

Compound 113: (S)-(5-(3,5-difluorophenyl)-4,5-dihydro-1H-pyrazol-1-yl)(4-(6-(1,4-dimethyl-1H-pyrazol-5-yl)-5-fluoropyridin-2-yl)piperazin-1-yl)methanone

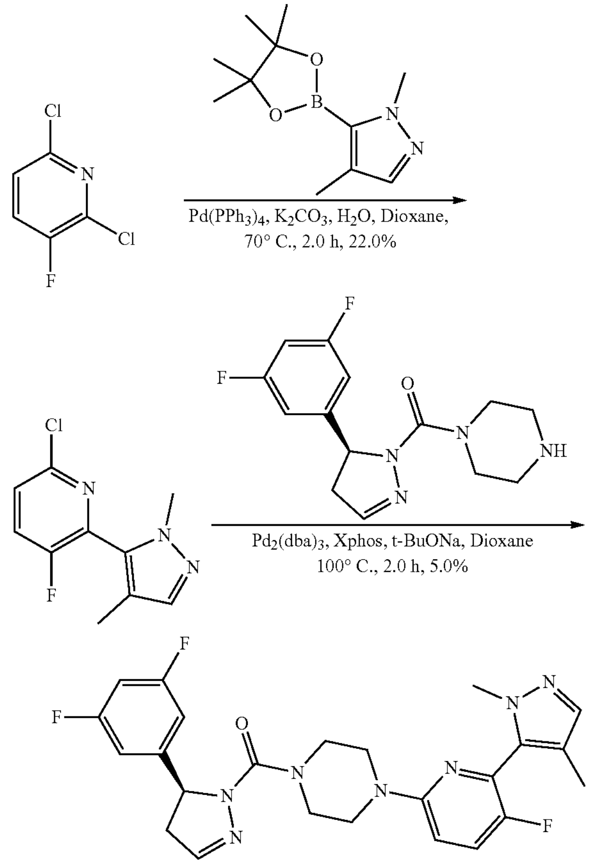

Step 1: To a solution of 2,6-dichloro-3-fluoropyridine (168 mg, 1.00 mmol) in dioxane (20 mL) and $H_2O$ (5 mL) was added 1,4-dimethyl-5-(4,4,5,5-tetramethyl-1,3,2-dioxaborolan-2-yl)-1H-pyrazole (222 mg, 1.00 mmol), $Pd(PPh_3)_4$ (115 mg, 0.10 mmol), $K_2CO_3$ (256 mg, 2.00 mmol) at 30° C. under Ar. The reaction was stirred at 70° C. for 2.0 h. The solvent was removed under vacuum and the crude product was purified by silica gel chromatography to give 6-chloro-2-(1,4-dimethyl-1H-pyrazol-5-yl)-3-fluoropyridine (50 mg, 22.0%) as a white solid. LC-MS (m/z) 226.5 ($M+H^+$).

Step 2: To a solution of 6-chloro-2-(1,4-dimethyl-1H-pyrazol-5-yl)-3-fluoropyridine (40 mg, 0.17 mmol) in dioxane (10 mL) was added (S)-(5-(3,5-difluorophenyl)-4,5-dihydro-1H-pyrazol-1-yl)(piperazin-1-yl)methanone (52 mg, 0.17 mmol) and $Pd_2(dba)_3$ (16 mg, 0.02 mmol), Xphos (16 mg, 0.04 mmol), t-BuONa (28 mg, 0.30 mmol) at 30° C. under Ar. The reaction mixture was stirred at 100° C. for 2.0 h. The solvent was removed under vacuum and the crude product was purified by silica gel chromatography to give (S)-(5-(3,5-difluorophenyl)-4,5-dihydro-1H-pyrazol-1-yl)(4-(6-(1,4-dimethyl-1H-pyrazol-5-yl)-5-fluoropyridin-2-yl)piperazin-1-yl)methanone (4.3 mg, 5.0%) as a white solid. LC-MS (m/z) 484.5 ($M+H^+$). $^1$H NMR (400 MHz, DMSO-$d_6$) δ 7.70 (t, J=9.2 Hz, 1H), 7.34 (s, 1H), 7.16-7.08 (m, 2H), 7.05-6.98 (m, 3H), 5.26 (t, J=10.8 Hz, 1H), 3.77 (s, 3H), 3.75-3.43 (m, 8H), 3.41-3.35 (m, 1H), 2.77-2.65 (m, 1H), 1.96 (d, J=2.0 Hz, 3H).

Compound 114: (S)-(5-(3,5-difluorophenyl)-4,5-dihydro-1H-pyrazol-1-yl)(4-(4-(1,4-dimethyl-1H-pyrazol-5-yl)-5-fluoropyridin-2-yl)piperazin-1-yl) methanone

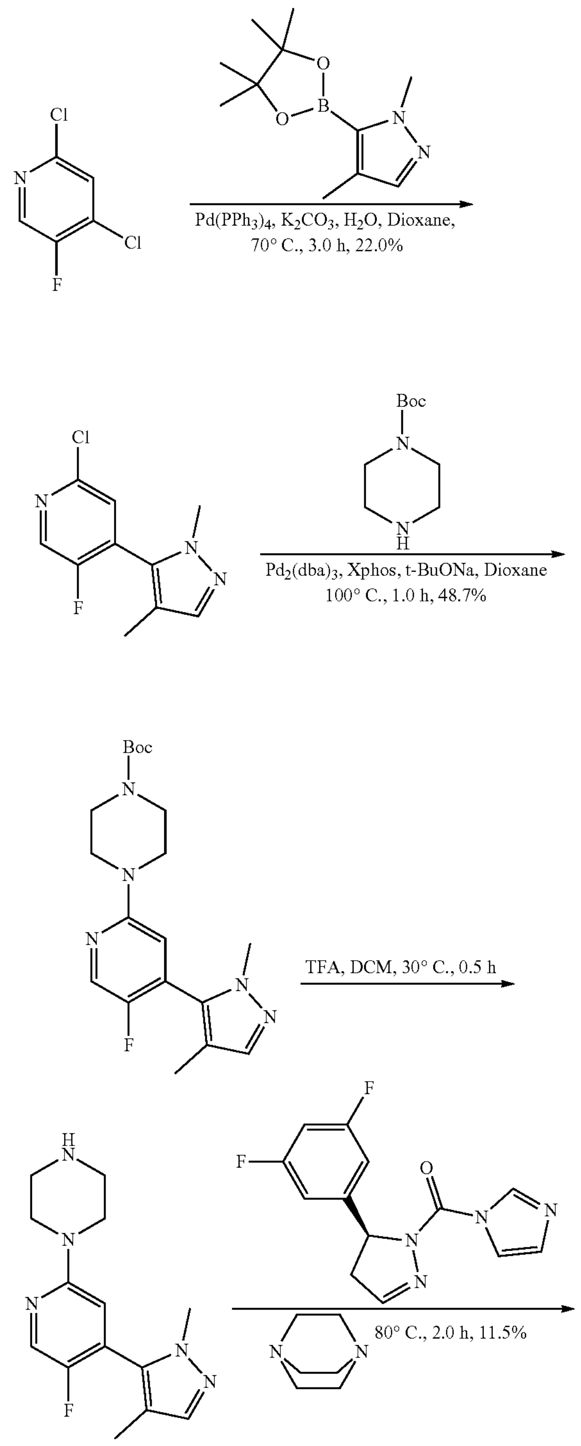

-continued

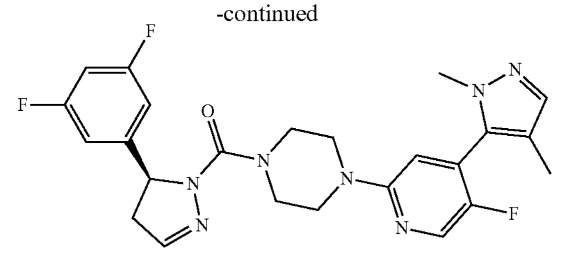

Step 1: To a solution of 2,4-dichloro-5-fluoropyridine (210 mg, 1.00 mmol) in dioxane (20 mL) and $H_2O$ (5 mL) was added 1,4-dimethyl-5-(4,4,5,5-tetramethyl-1,3,2-dioxaborolan-2-yl)-1H-pyrazole (222 mg, 1.00 mmol), $Pd(PPh_3)_4$ (115 mg, 0.10 mmol), $K_2CO_3$ (256 mg, 2.00 mmol) at 30° C. under Ar. The reaction was stirred at 70° C. for 3.0 h. The solvent was removed under vacuum and the crude product was purified by silica gel chromatography to give 2-chloro-4-(1,4-dimethyl-1H-pyrazol-5-yl)-5-fluoropyridine (50 mg, 22.0%) as a white solid. LC-MS (m/z) 226.5 ($M+H^+$).

Step 2: To a solution of 2-chloro-4-(1,4-dimethyl-1H-pyrazol-5-yl)-5-fluoropyridine (50 mg, 0.22 mmol) in dioxane (2 mL) was added tert-butyl piperazine-1-carboxylate (60 mg, 0.32 mmol), $Pd_2(dba)_3$ (40 mg, 0.04 mmol), Xphos (40 mg, 0.08 mmol), t-BuONa (40 mg, 0.41 mmol) at 30° C. under Ar. The reaction was stirred at 100° C. for 1.0 h. The solvent was removed under vacuum and the crude product was purified by silica gel chromatography to give tert-butyl 4-(4-(1,4-dimethyl-1H-pyrazol-5-yl)-5-fluoropyridin-2-yl)piperazine-1-carboxylate (40 mg, 48.7%) as a yellow oil. LC-MS (m/z) 376.4 ($M+H^+$).

Step 3: To a solution of tert-butyl 4-(4-(1,4-dimethyl-1H-pyrazol-5-yl)-5-fluoropyridin-2-yl)piperazine-1-carboxylate (40 mg, 0.10 mmol) in DCM (5 mL) was added TFA (2 mL) at 30° C. The reaction was stirred at 30° C. for 0.5 h. The solvent was removed under vacuum and the crude product (60 mg, crude) as a yellow oil was used to next step reaction. LC-MS (m/z) 276.4 ($M+H^+$).

Step 4: Prepared of (S)-(5-(3,5-difluorophenyl)-4,5-dihydro-1H-pyrazol-1-yl)(4-(4-(1,4-dimethyl-1H-pyrazol-5-yl)-5-fluoropyridin-2-yl)piperazin-1-yl)methanone To a solution of 2,2,2-trifluoroacetaldehyde compound with 1-(4-(1,4-dimethyl-1H-pyrazol-5-yl) fluoropyridin-2-yl)piperazine (1:1) (60 mg, crude) in THF (20 mL) was added 1,4-diazabicyclo[2.2.2]octane (32 mg, 0.28 mmol), (S)-(5-(3,5-difluorophenyl)-4,5-dihydro-1H-pyrazol-1-yl)(1H-imidazol-1-yl)methanone (40 mg, 0.14 mmol) at 30° C. The solvent was removed under vacuum and the reaction mixture was stand at 70° C. for 3.0 h. The crude product was purified by silica gel chromatography to give (S)-(5-(3,5-difluorophenyl)-4,5-dihydro-1H-pyrazol-1-yl)(4-(4-(1,4-dimethyl-1H-pyrazol-5-yl)-5-fluoropyridin-2-yl)piperazin-1-yl) methanone (8 mg, 11.5%) as a white solid. LC-MS (m/z) 484.5 ($M+H^+$). $^1H$ NMR (400 MHz, DMSO-$d_6$) δ 8.28 (s, 1H), 7.39 (s, 1H), 7.16-7.06 (m, 2H), 7.03-6.96 (m, 2H), 6.89 (d, J=4.8 Hz, 1H), 5.25 (dd, J=11.6, 10.0 Hz, 1H), 3.69 (s, 3H), 3.59-3.43 (m, 8H), 3.40-3.35 (m, 1H), 2.66-2.60 (m, 1H), 1.94 (s, 3H).

Compound 115: (S)-(5-(3,5-difluorophenyl)-4,5-dihydro-1H-pyrazol-1-yl)(4-(6-(1,3-dimethyl-1H-pyrazol-5-yl)-5-fluoropyridin-2-yl)piperazin-1-yl) methanone

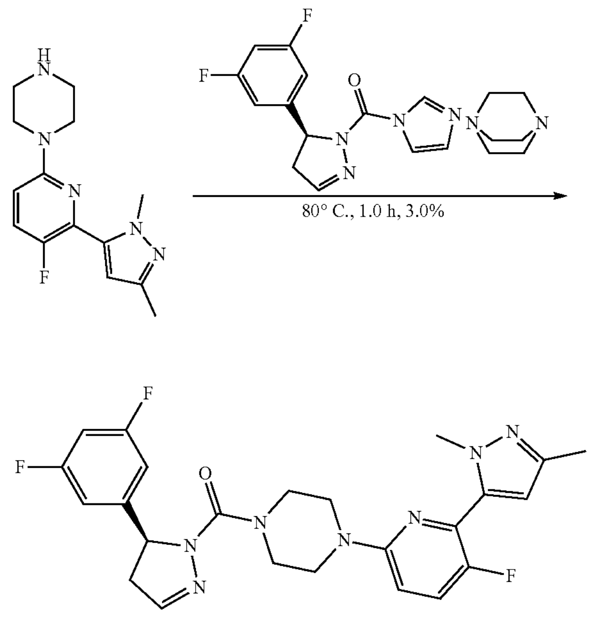

The titled compound 115 was prepared in 3.0% yield as white solid from 1-(6-(1,3-dimethyl-1H-pyrazol-5-yl)-5-fluoropyridin-2-yl)piperazine (1:1) (60 mg, crude) and (S)-(5-(3,5-difluorophenyl)-4,5-dihydro-1H-pyrazol-1-yl)(1H-imidazol-1-yl)methanone (50 mg, 0.18 mmol), 1,4-diazabicyclo[2.2.2]octane (100 mg, 0.89 mmol) in analogous manner to the preparation of 114. LC-MS (m/z) 484.5 ($M+H^+$). $^1H$ NMR (400 MHz, DMSO-$d_6$) δ 8.23 (d, J=1.6 Hz, 1H), 7.13-7.06 (m, 2H), 7.01-6.94 (m, 2H), 6.87 (d, J=4.8 Hz, 1H), 6.26 (s, 1H), 5.23 (dd, J=11.6, 10.0 Hz, 1H), 3.69 (d, J=1.2 Hz, 3H), 3.67-3.41 (m, 8H), 3.38-3.32 (m, 1H), 2.66-2.58 (m, 1H), 2.16 (s, 3H).

Compound 116: (S)-(5-(3,5-difluorophenyl)-4,5-dihydro-1H-pyrazol-1-yl)(4-(4-(1,3-dimethyl-1H-pyrazol-5-yl)-5-fluoropyridin-2-yl)piperazin-1-yl) methanone

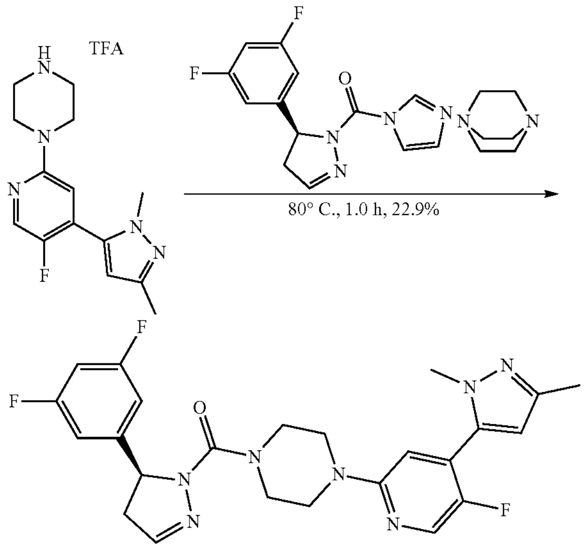

The titled compound 116 was prepared in 22.9% yield as white solid from 2,2,2-trifluoroacetaldehyde compound with 1-(4-(1,3-dimethyl-1H-pyrazol-5-yl)-5-fluoropyridin-2-yl) piperazine (1:1) (110 mg, crude) and (S)-(5-(3,5-difluorophenyl)-4,5-dihydro-1H-pyrazol-1-yl)(1H-imidazol-1-yl) methanone (100 mg, 0.36 mmol), 1,4-diazabicyclo[2.2.2] octane (200 mg, 1.78 mmol) in analogous manner to the preparation of 114. LC-MS (m/z) 484.5 ($M+H^+$). $^1H$ NMR (400 MHz, DMSO-$d_6$) δ 7.65 (t, J=9.6 Hz, 1H), 7.10 (d, J=9.2 Hz, 2H), 7.02-6.90 (m, 3H), 6.44-6.39 (m, 1H), 5.25 (t, J=10.8 Hz, 1H), 3.99 (d, J=2.8 Hz, 3H), 3.75-3.44 (m, 8H), 3.38-3.32 (m, 1H), 2.64 (dd, J=18.4, 9.2 Hz, 1H), 2.18 (s, 3H).

Compound 117: (S)-(5-(3,5-difluorophenyl)-4,5-dihydro-1H-pyrazol-1-yl)(4-(4-(1-ethyl-3,5-dimethyl-1H-pyrazol-4-yl)-5-fluoropyrimidin-2-yl)piperazin-1-yl)methanone

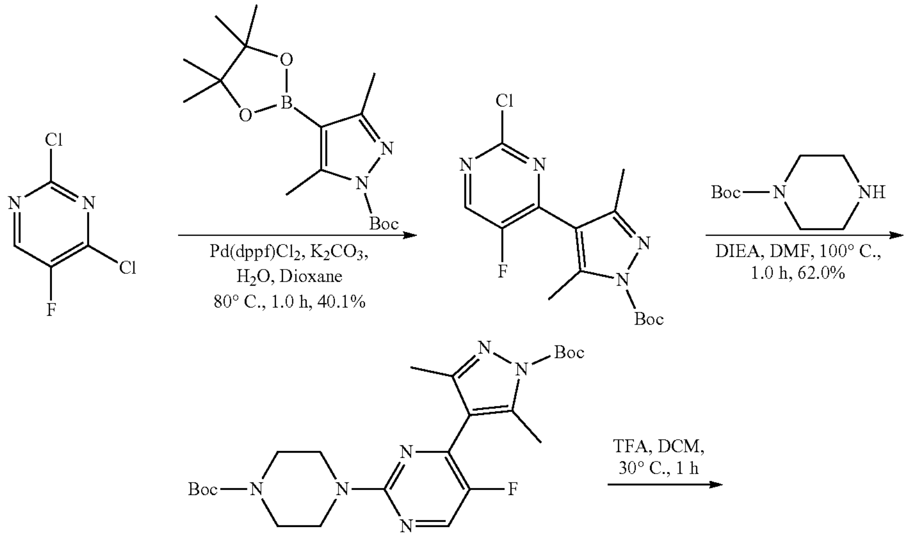

-continued

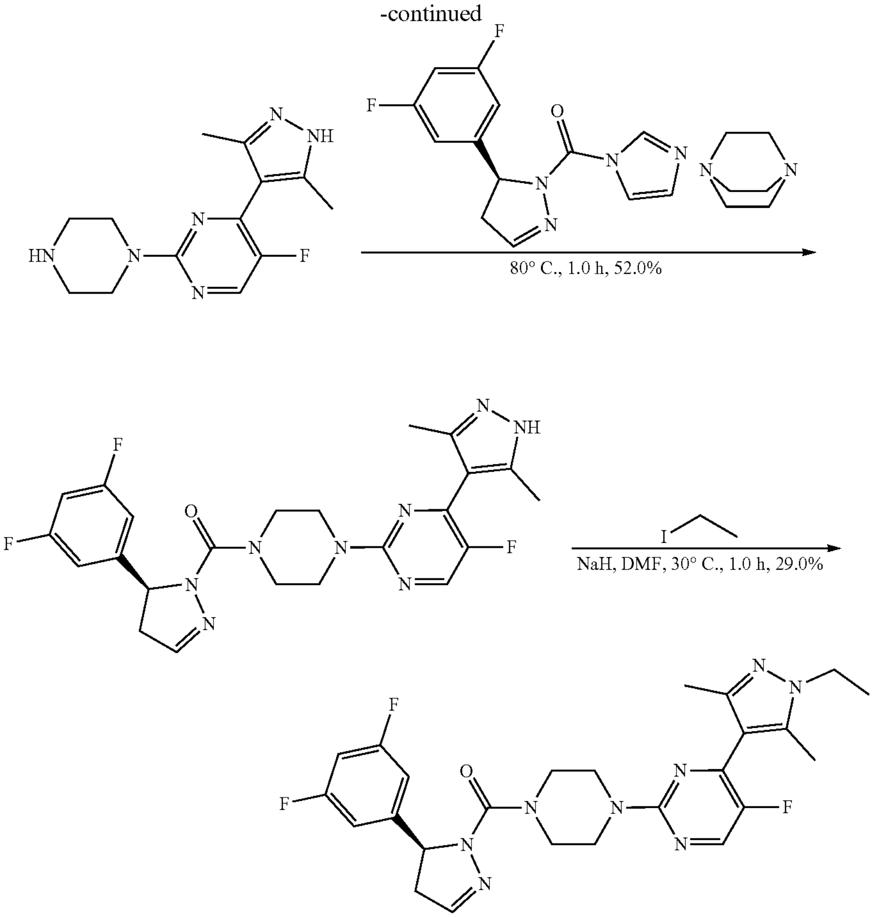

Step 1~4: (S)-(5-(3,5-difluorophenyl)-4,5-dihydro-1H-pyrazol-1-yl)(4-(4-(3,5-dimethyl-1H-pyrazol-4-yl)-5-fluoropyrimidin-2-yl)piperazin-1-yl)methanone was prepared in 52.0% yield as white solid from 4-(3,5-dimethyl-1H-pyrazol-4-yl)-5-fluoro-2-(piperazin yl)pyrimidine (300 mg, crude) and (S)-(5-(3,5-difluorophenyl)-4,5-dihydro-1H-pyrazol yl)(1H-imidazol-1-yl)methanone (116 mg, 0.41 mmol), 1,4-diazabicyclo[2.2.2]octane (300 mg, 2.67 mmol) in analogous manner to the preparation of 114. LC-MS (m/z) 484.5 ($M+H^+$)

Step 5: To a solution of (S)-(5-(3,5-difluorophenyl)-4,5-dihydro-1H-pyrazol-1-yl)(4-(4-(3,5-dimethyl-1H-pyrazol-4-yl)-5-fluoropyrimidin-2-yl)piperazin-1-yl)methanone. (30 mg, 0.06 mmol) in DMF (3 mL) was added NaH (10 mg, 60% in mineral oil), iodoethane (50 mg, 0.32 mmol) at 30° C. The solvent was removed under vacuum and the reaction mixture was stand at 30° C. for 1.0 h. Water was added and extracted with EA, washed with brine, dried with ($Na_2SO_4$). The resulting mixture was removed under vacuum. The crude product was purified by silica gel chromatography to give (S)-(5-(3,5-difluorophenyl)-4,5-dihydro-1H-pyrazol-1-yl)(4-(4-(1-ethyl-3,5-dimethyl-1H-pyrazol-4-yl)-5-fluoropyrimidin-2-yl)piperazin-1-yl)methanone (9.0 mg, 29.0%) as a white solid. LC-MS (m/z) 513.4 ($M+H^+$). $^1H$ NMR (400 MHz, DMSO-$d_6$) δ 8.44 (d, J=2.4 Hz, 1H), 7.16-7.08 (m, 2H), 7.06-6.97 (m, 2H), 5.31-5.21 (m, 1H), 4.06 (q, J=7.2 Hz, 2H), 3.80-3.61 (m, 8H), 3.56-3.51 (m, 1H), 2.71-2.59 (m, 1H), 2.29 (d, J=1.8 Hz, 3H), 2.18 (d, J=1.8 Hz, 3H), 1.32 (t, J=7.2 Hz, 3H).

Compound 118: (S)-(5-(3,5-difluorophenyl)-4,5-dihydro-1H-pyrazol-1-yl)(4-(5-fluoro-4-(1-(2-hydroxyethyl)-3,5-dimethyl-1H-pyrazol-4-yl)pyrimidin-2-yl)piperazin-1-yl)methanone

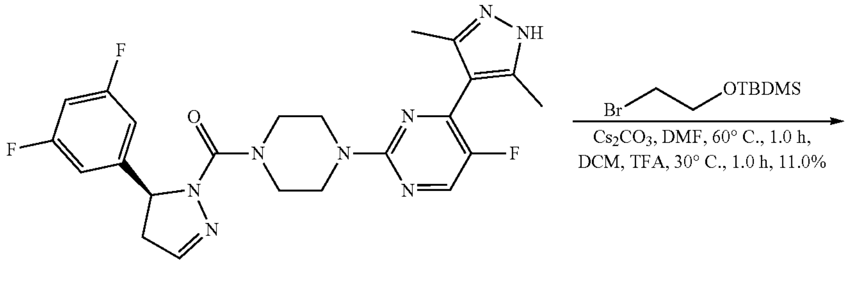

-continued

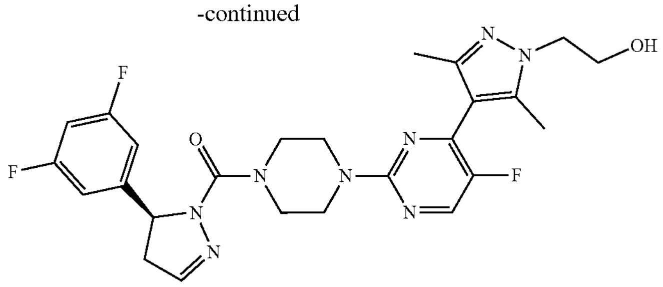

The titled compound 118 was prepared in 11.0% yield as white solid from (S)-(5-(3,5-difluorophenyl)-4,5-dihydro-1H-pyrazol-1-yl)(4-(4-(3,5-dimethyl-1H-pyrazol-4-yl)-5-fluoropyrimidin-2-yl)piperazin-1-yl)methanone (80 mg, 0.16 mmol) and (2-bromoethoxy)(tert-butyl)dimethylsilane (54 mg, 0.22 mmol) in analogous manner to the preparation of compound 59. LC-MS (m/z) 529.6 $(M+H^+)$ $^1H$ NMR (400 MHz, DMSO-$d_6$) δ 8.45 (d, J=2.4 Hz, 1H), 7.15-7.08 (m, 2H), 7.03-6.98 (m, 2H), 5.31-5.22 (m, 1H), 4.07 (t, J=5.6 Hz, 2H), 3.81-3.50 (m, 8H), 3.57-3.49 (m, 2H), 3.42-3.30 (m, 1H), 2.68-2.59 (m, 1H), 2.30 (d, J=2.0 Hz, 3H), 2.19 (d, J=1.6 Hz, 3H).

Compound 119: (S)-2-(4-(2-(4-(5-(3,5-difluorophenyl)-4,5-dihydro-1H-pyrazole-1-carbonyl)piperazin-1-yl)-5-fluoropyrimidin-4-yl)-3,5-dimethyl-1H-pyrazol-1-yl)acetamide

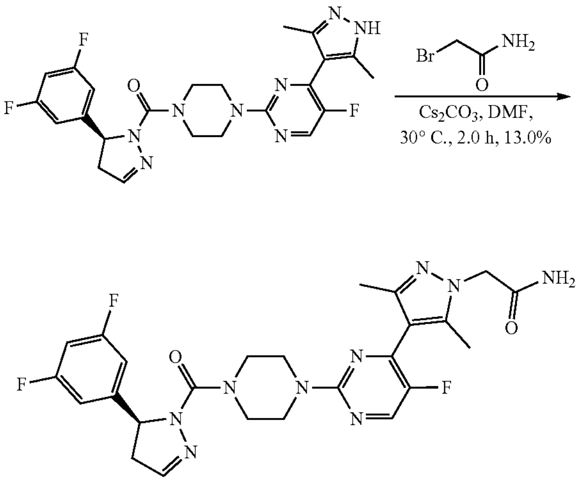

The titled compound 119 was prepared in 13.0% yield as white solid from (S)-(5-(3,5-difluorophenyl)-4,5-dihydro-1H-pyrazol-1-yl)(4-(4-(3,5-dimethyl-1H-pyrazol-4-yl)-5-fluoropyrimidin-2-yl)piperazin-1-yl)methanone (80 mg, 0.16 mmol) and 2-bromoacetamide (50 mg, 0.36 mmol), $Cs_2CO_3$ (105 mg, 0.32 mmol), DMF (5 mL) in analogous manner to the preparation of compound 59. LC-MS (m/z) 542.6 $(M+H^+)$ $^1H$ NMR (400 MHz, DMSO-$d_6$) δ 8.46 (d, J=2.4 Hz, 1H), 7.61 (brs, 1H), 7.29 (brs, 1H), 7.15-7.08 (m, 2H), 7.04-6.97 (m, 2H), 5.26 (dd, J=11.6, 10.0 Hz, 1H), 4.72 (s, 2H), 3.82-3.49 (m, 8H), 3.42-3.36 (m, 1H), 2.71-2.59 (m, 1H), 2.24 (d, J=2.0 Hz, 3H), 2.18 (d, J=1.6 Hz, 3H).

Compound 120: (S)-(5-(3,5-difluorophenyl)-4,5-dihydro-1H-pyrazol-1-yl)(4-(5-fluoro-4-(1-(2-methoxyethyl)-3,5-dimethyl-1H-pyrazol-4-yl)pyrimidin-2-yl)piperazin-1-yl)methanone

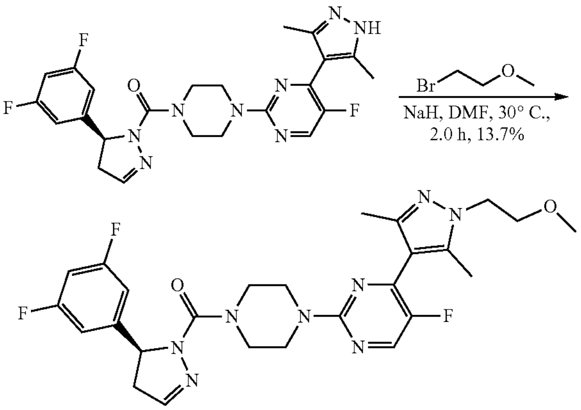

The titled compound 120 was prepared in 13.7% yield as white solid from (S)-(5-(3,5-difluorophenyl)-4,5-dihydro-1H-pyrazol-1-yl)(4-(4-(3,5-dimethyl-1H-pyrazol-4-yl)-5-fluoropyrimidin-2-yl)piperazin-1-yl)methanone (30 mg, 0.06 mmol) and 1-bromo-2-methoxyethane (50 mg, 0.35 mmol), NaH (10 mg, 60% in mineral oil), DMF (3 mL) according to the procedure outlined for compound 59. LC-MS (m/z) 543.6 $(M+H^+)$ $^1H$ NMR (400 MHz, DMSO-$d_6$) δ 8.45 (d, J=2.4 Hz, 1H), 7.17-7.07 (m, 2H), 7.05-6.96 (m, 2H), 5.26 (dd, J=11.6, 10.0 Hz, 1H), 4.18 (t, J=5.2 Hz, 2H), 3.82-3.49 (m, 8H), 3.41-3.35 (m, 1H), 3.24 (s, 3H), 2.71-2.59 (m, 1H), 2.28 (d, J=2.0 Hz, 3H), 2.19 (d, J=1.6 Hz, 3H).

Compound 121: (S)-(4-(4-(1-(cyclopropylmethyl)-3,5-dimethyl-1H-pyrazol-4-yl) fluoropyrimidin-2-yl) piperazin-1-yl)(5-(3,5-difluorophenyl)-4,5-dihydro-1H-pyrazol-1-yl)methanone

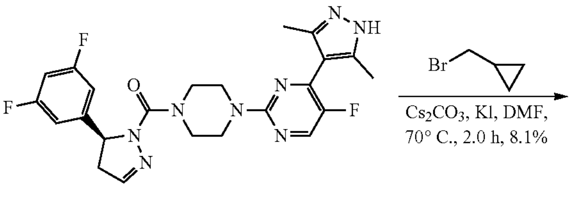

-continued

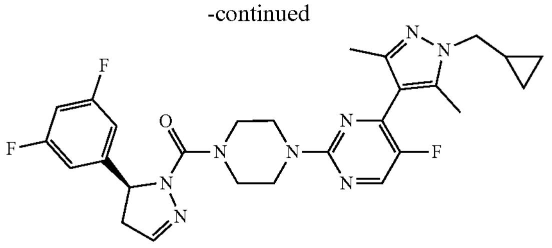

The titled compound 121 was prepared in 8.1% yield as white solid from (S)-(5-(3,5-difluorophenyl)-4,5-dihydro-1H-pyrazol-1-yl)(4-(4-(3,5-dimethyl-1H-pyrazol-4-yl)-5-fluoropyrimidin-2-yl)piperazin-1-yl)methanone (30 mg, 0.06 mmol) and (bromomethyl)cyclopropane (50 mg, 0.37 mmol), $Cs_2CO_3$ (108 mg, 0.32 mmol), KI (16 mg, 0.10 mmol) DMF (3 mL) according to the procedure outlined for compound 59. LC-MS (m/z) 539.4 ($M+H^+$)

Compound 122: (S)-(5-(3,5-difluorophenyl)-4,5-dihydro-1H-pyrazol-1-yl)(4-(4-(3,5-dimethyl-1-((tetrahydro-2H-pyran-4-yl)methyl)-1H-pyrazol-4-yl)-5-fluoropyrimidin-2-yl)piperazin-1-yl)methanone

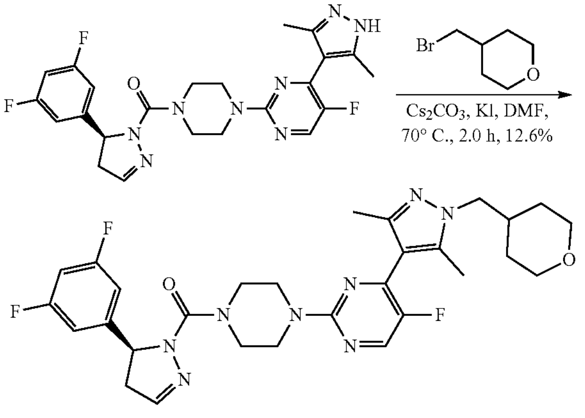

The titled compound 227 was prepare in 12.6% yield as white solid from (S)-(5-(3,5-difluorophenyl)-4,5-dihydro-1H-pyrazol-1-yl)(4-(4-(3,5-dimethyl-1H-pyrazol-4-yl)-5-fluoropyrimidin-2-yl)piperazin-1-yl)methanone (30 mg, 0.06 mmol) and 4-(bromomethyl)tetrahydro-2H-pyran (50 mg, 0.28 mmol), $Cs_2CO_3$ (108 mg, 0.32 mmol), KI (16 mg, 0.10 mmol) DMF (3 mL) according to the procedure outlined for compound 59. LC-MS (m/z) 583.6 ($M+H^+$)$^1$H NMR (400 MHz, DMSO-$d_6$) δ 8.45 (d, J=2.4 Hz, 1H), 7.17-7.07 (m, 2H), 7.05-6.96 (m, 2H), 5.28 (d, J=10.8 Hz, 1H), 3.92 (d, J=7.2 Hz, 2H), 3.88-3.49 (m, 12H), 3.41-3.35 (m, 1H), 2.71-2.59 (m, 1H), 2.29 (d, J=2.0 Hz, 3H), 2.19 (d, J=1.6 Hz, 3H), 2.10-2.06 (m, 1H), 1.48-1.39 (m, 1H), 1.30-1.22 (m, 1H), 1.16-1.13 (m, 2H).

Compound 123: (S)-2-(4-(2-(4-(5-(3-cyano-5-fluorophenyl)-4,5-dihydro-1H-pyrazole-1-carbonyl)piperazin-1-yl)-5-fluoropyrimidin-4-yl)-3,5-dimethyl-1H-pyrazol-1-yl)acetamide

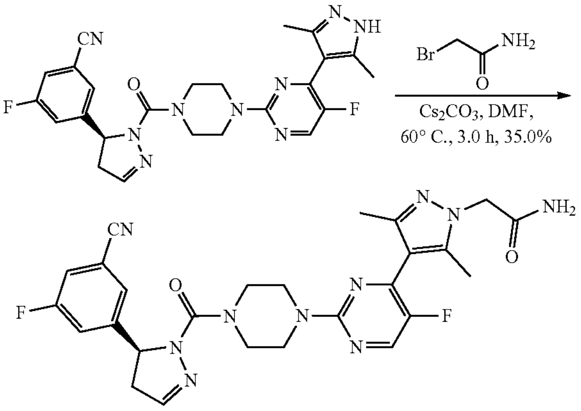

The titled compound 123 was prepared in 35.0% yield as white solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (70 mg, 0.14 mmol) and 2-bromoacetamide (40 mg, 0.28 mmol), $Cs_2CO_3$ (92 mg, 0.28 mmol), DMF (3 mL) according to the procedure outlined for compound 59. LC-MS (m/z) 549.6 ($M+H^+$)$^1$H NMR (400 MHz, DMSO-$d_6$) δ 8.45 (d, J=2.4 Hz, 1H), 7.78-7.70 (m, 1H), 7.65 (t, J=1.6 Hz, 1H), 7.60 (brs, 1H), 7.53 (dt, J=9.6, 2.0 Hz, 1H), 7.28 (brs, 1H), 7.11 (d, J=1.6 Hz, 1H), 5.28 (t, J=10.8 Hz, 1H), 4.71 (s, 2H), 3.82-3.50 (m, 8H), 3.42-3.34 (m, 1H), 2.71-2.59 (m, 1H), 2.23 (d, J=2.0 Hz, 3H), 2.17 (d, J=1.6 Hz, 3H).

Compound 124: (S)-3-fluoro-5-(1-(4-(5-fluoro-4-(1-(2-hydroxyethyl)-3,5-dimethyl-1H-pyrazol-4-yl)pyrimidin-2-yl)piperazine-1-carbonyl)-4,5-dihydro-1H-pyrazol-5-yl)benzonitrile

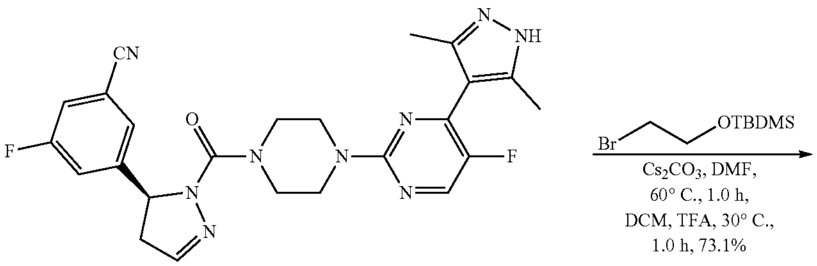

-continued

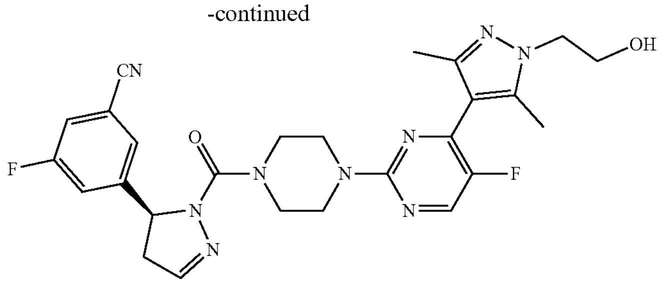

The titled compound 124 was prepare in 73.1% yield as white solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (70 mg, 0.14 mmol) and (2-bromoethoxy)(tert-butyl)dimethylsilane (54 mg, 0.22 mmol), $Cs_2CO_3$ (108 mg, 0.32 mmol), DMF (5 mL) according to the procedure outlined for compound 59. LC-MS (m/z) 536.4 ($M+H^+$)$^1$H NMR (400 MHz, DMSO-$d_6$) δ 8.43 (d, J=2.4 Hz, 1H), 7.76-7.71 (m, 1H), 7.64 (t, J=1.6 Hz, 1H), 7.52 (dt, J=9.6, 2.0 Hz, 1H), 7.11 (d, J=1.6 Hz, 1H), 5.28 (t, J=10.8 Hz, 1H), 4.92 (t, J=5.2 Hz, 1H), 4.05 (t, J=5.6 Hz, 2H), 3.79-3.60 (m, 8H), 3.57-3.48 (m, 2H), 3.42-3.34 (m, 1H), 2.75-2.63 (m, 1H), 2.29 (d, J=2.0 Hz, 3H), 2.18 (d, J=1.6 Hz, 3H).

Compound 125: (S)-1-(2-(4-(5-(3-cyano-5-fluorophenyl)-4,5-dihydro-1H-pyrazole-1-carbonyl)piperazin-1-yl)-5-fluoropyrimidin-4-yl)-1H-1,2,4-triazole-3-carbonitrile

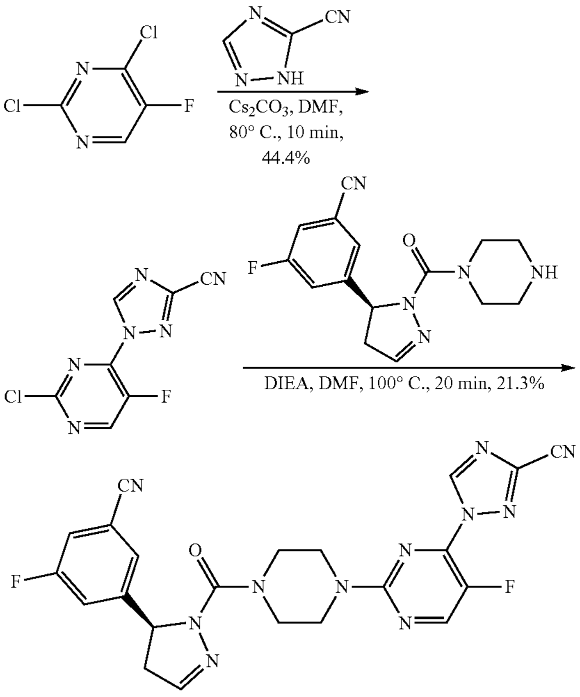

Step 1: To a solution of 2,4-dichloro-5-fluoropyrimidine (334 mg, 2.00 mmol) in DMF (5 mL) was added 1H-1,2,4-triazole-5-carbonitrile (188 mg, 2.00 mmol) $Cs_2CO_3$ (1.3 g, 4.00 mmol) at 30° C. under Ar. The reaction was stirred at 80° C. for 10 minute. Water was added and extracted with EA, washed with brine, dried with ($Na_2SO_4$). The resulting mixture was removed under vacuum and the crude product was purified by silica gel chromatography to give 1-(2-chloro-5-fluoropyrimidin-4-yl)-1H-1,2,4-triazole-3-carbonitrile (200 mg, 44.4%) as a light yellow solid. LC-MS (m/z) 225.4 ($M+H^+$).

Step 2: To a solution of 1-(2-chloro-5-fluoropyrimidin-4-yl)-1H-1,2,4-triazole-3-carbonitrile (60 mg, 0.26 mmol) in DMF (3 mL) was added (S)-3-fluoro-5-(1-(piperazine-1-carbonyl)-4,5-dihydro-1H-pyrazol-5-yl)benzonitrile (80 mg, 0.26 mmol), DIEA (100 mg, 0.77 mmol) at 30° C. under Ar. The reaction was stirred at 100° C. for 20 minute. Water was added and extracted with EA, washed with brine, dried with ($Na_2SO_4$). The resulting mixture was removed under vacuum and the crude product was purified by silica gel chromatography to give the titled compound 5 (28 mg, 21.3%) as a white solid. LC-MS (m/z) 490.4 ($M+H^+$). $^1$H NMR (400 MHz, DMSO-$d_6$) δ 9.61 (s, 1H), 8.76 (d, J=3.6 Hz, 1H), 7.76 (ddd, J=8.4, 2.8, 1.2 Hz, 1H), 7.68-7.63 (m, 1H), 7.54 (dt, J=9.6, 2.0 Hz, 1H), 7.13 (d, J=1.6 Hz, 1H), 5.30 (dd, J=11.6, 10.0 Hz, 1H), 3.89-3.51 (m, 8H), 3.44-3.35 (m, 1H), 2.78-2.66 (m, 1H).

Compound 126: (S)-3-(1-(4-(4-(3-chloro-1H-1,2,4-triazol-1-yl)-5-fluoropyrimidin yl)piperazine-1-carbonyl)-4,5-dihydro-1H-pyrazol-5-yl)-5-fluorobenzonitrile

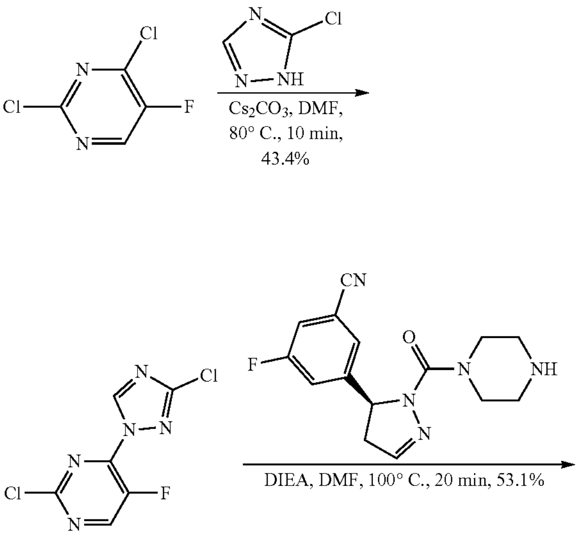

-continued

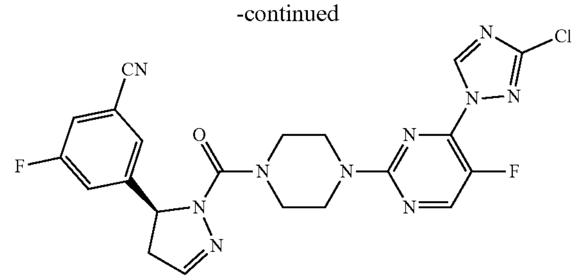

The titled compound 126 was prepared in 53.1% yield as white solid from 2-chloro-4-(3-chloro-1H-1,2,4-triazol-1-yl)-5-fluoropyrimidine (62 mg, 0.26 mmol) and (S)-3-fluoro-5-(1-(piperazine-1-carbonyl)-4,5-dihydro-1H-pyrazol-5-yl)benzonitrile (80 mg, 0.26 mmol), DIEA (100 mg, 0.77 mmol), DMF (3 mL) according to the procedure outlined for compound 125. LC-MS (m/z) 499.6 $(M+H^+)$ $^1H$ NMR (400 MHz, DMSO-$d_6$) δ 9.88 (s, 1H), 8.83 (d, J=3.2 Hz, 1H), 7.76 (ddd, J=8.4, 2.8, 1.2 Hz, 1H), 7.66 (t, J=1.6 Hz, 1H), 7.58-7.50 (m, 1H), 7.17-7.11 (m, 1H), 5.30 (t, J=10.8 Hz, 1H), 3.92-3.53 (m, 8H), 3.42-3.36 (m, 1H), 2.78-2.66 (m, 1H).

Compound 127: (S)-1-(2-(4-(5-(3-cyano-5-fluorophenyl)-4,5-dihydro-1H-pyrazole-1-carbonyl)piperazin-1-yl)-5-fluoropyrimidin-4-yl)-1H-pyrazole-4-carbonitrile

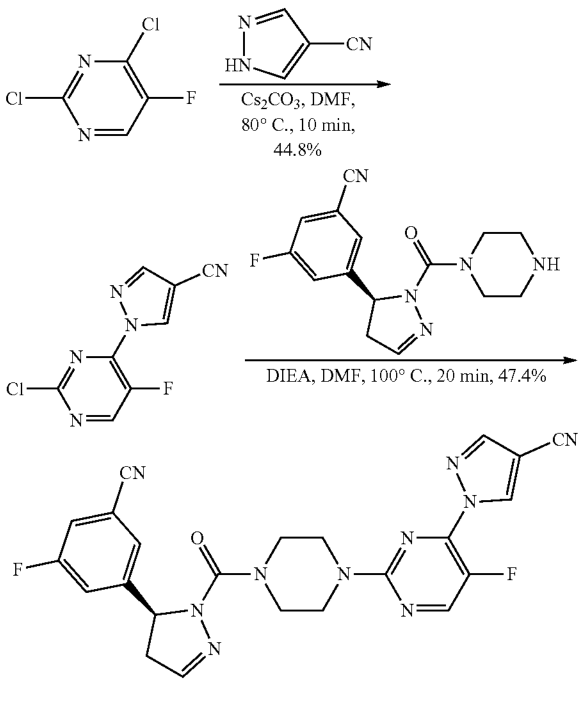

The titled compound 127 was prepared in 47.4% yield as white solid from 1-(2-chloro fluoropyrimidin-4-yl)-1H-pyrazole-4-carbonitrile (60 mg, 0.27 mmol) and (S)-3-fluoro-5-(1-(piperazine-1-carbonyl)-4,5-dihydro-1H-pyrazol-5-yl)benzonitrile (80 mg, 0.26 mmol), DIEA (100 mg, 0.77 mmol), DMF (3 mL) according to the procedure outlined for compound 125. LC-MS (m/z) 489.4 $(M+H^+)$ $^1H$ NMR (400 MHz, DMSO-$d_6$) δ 9.60 (s, 1H), 8.72 (d, J=4.0

Hz, 1H), 8.49 (s, 1H), 7.80-7.72 (m, 1H), 7.65 (t, J=1.6 Hz, 1H), 7.58-7.50 (m, 1H), 7.13 (d, J=1.6 Hz, 1H), 5.30 (dd, J=11.6, 10.0 Hz, 1H), 3.90-3.51 (m, 8H), 3.43-3.36 (m, 1H), 2.78-2.66 (m, 1H).

Compound 128: (S)-1-(2-(4-(5-(3-cyano-5-fluorophenyl)-4,5-dihydro-1H-pyrazole-1-carbonyl)piperazin-1-yl)-5-fluoropyrimidin-4-yl)-1H-pyrazole-3-carbonitrile

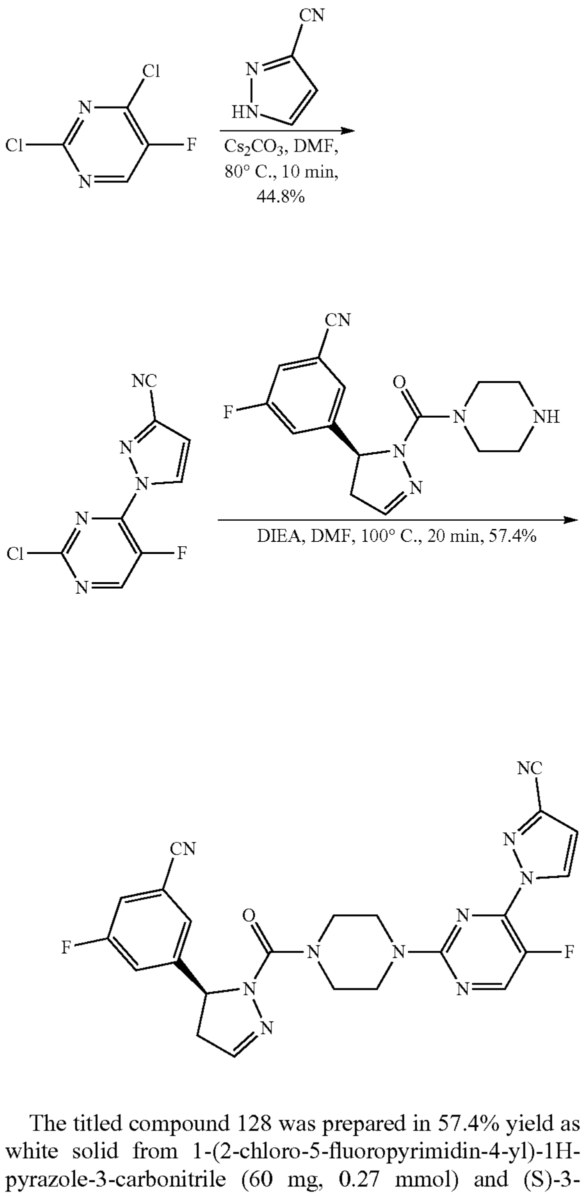

The titled compound 128 was prepared in 57.4% yield as white solid from 1-(2-chloro-5-fluoropyrimidin-4-yl)-1H-pyrazole-3-carbonitrile (60 mg, 0.27 mmol) and (S)-3-fluoro-5-(1-(piperazine-1-carbonyl)-4,5-dihydro-1H-pyrazol-5-yl)benzonitrile (80 mg, 0.26 mmol), DIEA (100 mg, 0.77 mmol), DMF (3 mL) according to the procedure outlined for compound 125. LC-MS (m/z) 489.4 $(M+H^+)$ $^1H$ NMR (400 MHz, DMSO-$d_6$) δ 8.96 (d, J=2.8 Hz, 1H), 8.75 (d, J=3.6 Hz, 1H), 7.76 (ddd, J=8.4, 2.8, 1.2 Hz, 1H), 7.65 (t, J=1.6 Hz, 1H), 7.58-7.50 (m, 1H), 7.35 (d, J=2.8 Hz, 1H), 7.13 (d, J=1.6 Hz, 1H), 5.30 (dd, J=11.6, 10.0 Hz, 1H), 3.88-3.52 (m, 8H), 3.42-3.34 (m, 1H), 2.78-2.66 (m, 1H).

Compound 129: ethyl (S)-1-(2-(4-(5-(3-cyano-5-fluorophenyl)-4,5-dihydro-1H-pyrazole-1-carbonyl)piperazin-1-yl)-5-fluoropyrimidin-4-yl)-5-methyl-1H-1,2,4-triazole-3-carboxylate

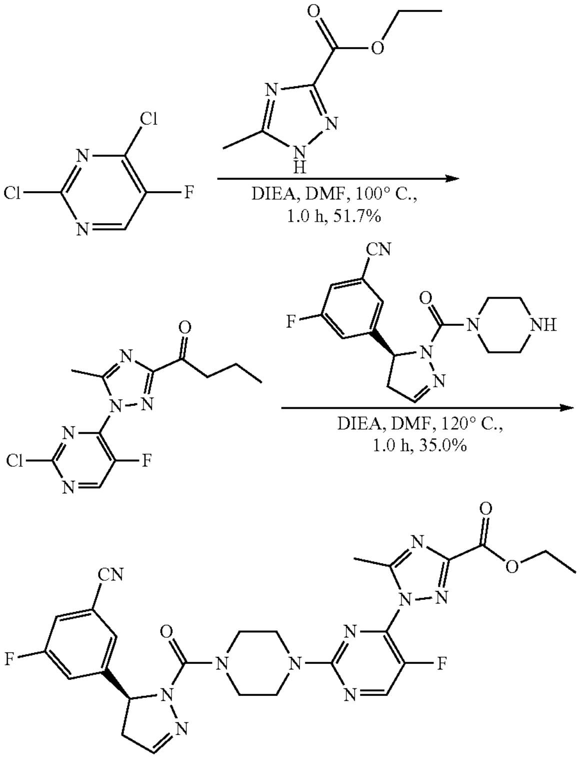

The titled compound 129 was prepared in 35.0% yield as white solid from ethyl 1-(2-chloro-5-fluoropyrimidin-4-yl)-5-methyl-1H-1,2,4-triazole-3-carboxylate (30 mg, 0.10 mmol) and (S)-3-fluoro-5-(1-(piperazine-1-carbonyl)-4,5-dihydro-1H-pyrazol-5-yl)benzonitrile (40 mg, 0.13 mmol), DIEA (100 mg, 0.77 mmol), DMF (3 mL) in analogous manner to the preparation of 125. LC-MS (m/z) 551.6 $(M+H^+)$ $^1$H NMR (400 MHz, DMSO-$d_6$) δ 8.80 (d, J=2.8 Hz, 1H), 7.74 (ddd, J=8.4, 2.4, 1.2 Hz, 1H), 7.64 (t, J=1.6 Hz, 1H), 7.52 (dt, J=9.6, 2.0 Hz, 1H), 7.12 (d, J=1.6 Hz, 1H), 5.28 (t, J=10.8 Hz, 1H), 4.35 (q, J=7.2 Hz, 2H), 3.82-3.52 (m, 8H), 3.42-3.35 (m, 1H), 2.75-2.66 (m, 4H), 1.31 (t, J=7.2 Hz, 3H).

Compound 130: (S)-3-(1-(4-(4-(3,5-dimethyl-1H-1,2,4-triazol-1-yl)-1,3,5-triazin-2-yl)piperazine-1-carbonyl)-4,5-dihydro-1H-pyrazol-5-yl)-5-fluorobenzonitrile

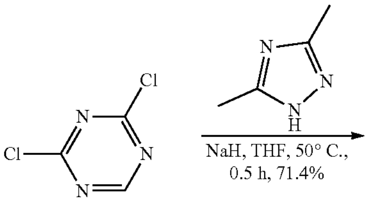

-continued

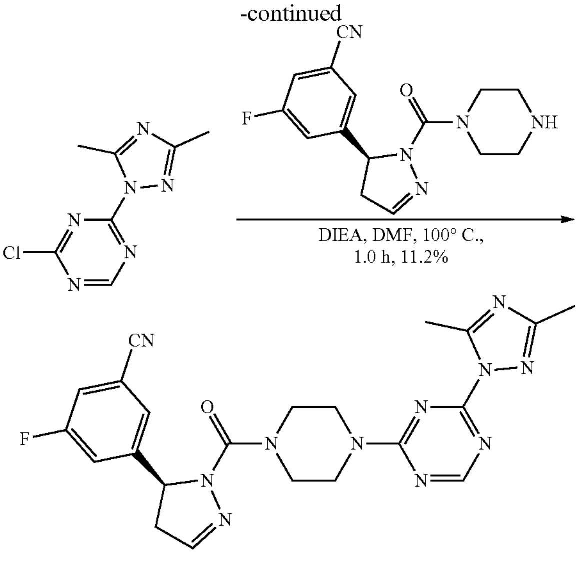

The titled compound 130 was prepare in 11.2% yield as yellow solid from 2-chloro-4-(3,5-dimethyl-1H-1,2,4-triazol-1-yl)-1,3,5-triazine (50 mg, crude) and (S)-3-fluoro-5-(1-(piperazine-1-carbonyl)-4,5-dihydro-1H-pyrazol-5-yl)benzonitrile (50 mg, 0.16 mmol), DIEA (60 mg, 0.46 mmol), DMF (4 mL) in analogous manner to the preparation of 125. LC-MS (m/z) 476.4 $(M+H^+)$ $^1$H NMR (400 MHz, DMSO-$d_6$) δ 8.70 (s, 1H), 7.80-7.72 (m, 1H), 7.66 (d, J=1.6 Hz, 1H), 7.55 (dt, J=9.6, 2.0 Hz, 1H), 7.14 (d, J=1.6 Hz, 1H), 5.30 (t, J=10.8 Hz, 1H), 3.97-3.52 (m, 8H), 3.42-3.35 (m, 1H), 2.75 (s, 3H), 2.74-2.66 (m, 1H), 2.29 (s, 3H).

Compound 131: (S)-3-(1-(4-(4-(4-amino-3,5-dimethyl-1H-pyrazol-1-yl)-5-fluoropyrimidin-2-yl)piperazine-1-carbonyl)-4,5-dihydro-1H-pyrazol-5-yl)-5-fluorobenzonitrile

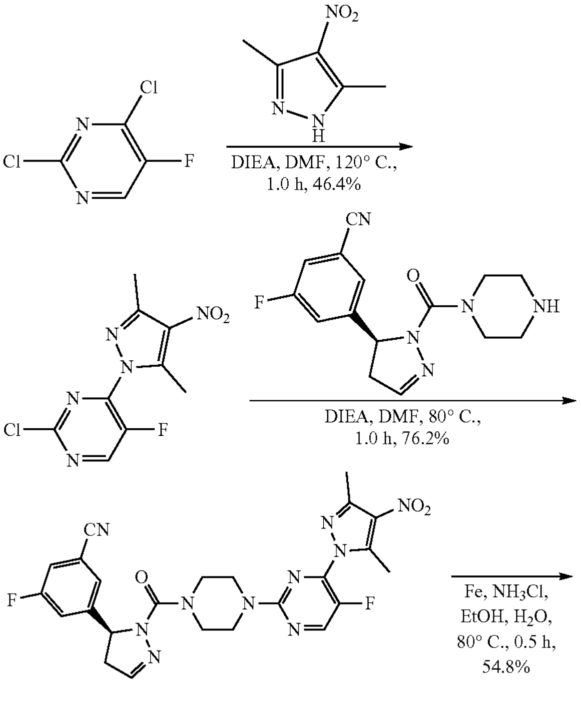

-continued

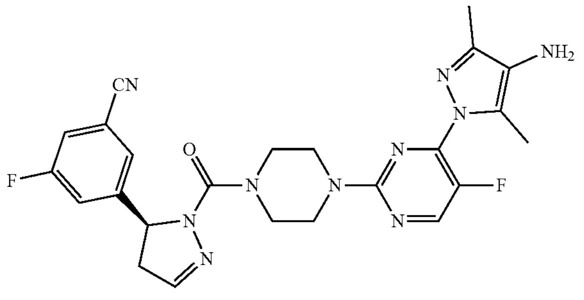

Step 1: To a solution of 2,4-dichloro-5-fluoropyrimidine (334 mg, 2.00 mmol) in DMF (5 mL) was added 3,5-dimethyl-4-nitro-1H-pyrazole (280 mg, 2.00 mmol) DIEA (516 mg, 4.00 mmol) at 30° C. The reaction was stirred at 120° C. for 1.0 h. Water was added and extracted with EA, washed with brine, dried with ($Na_2SO_4$). The resulting mixture was removed under vacuum and the crude product was purified by silica gel chromatography to give 2-chloro-4-(3,5-dimethyl-4-nitro-1H-pyrazol-1-yl)-5-fluoropyrimidine (250 mg, 44.4%) as a yellow solid. LC-MS (m/z) 272.6 ($M+H^+$).

Step 2: To a solution of 2-chloro-4-(3,5-dimethyl-4-nitro-1H-pyrazol-1-yl)-5-fluoropyrimidine (100 mg, 0.37 mmol) in DMF (4 mL) was added (S)-3-fluoro-5-(1-(piperazine-1-carbonyl)-4,5-dihydro-1H-pyrazol-5-yl)benzonitrile (110 mg, 0.36 mmol), DIEA (190 mg, 1.47 mmol) at 30° C. The reaction was stirred at 80° C. for 1.0 h. Water was added and extracted with EA, washed with brine, dried with ($Na_2SO_4$). The resulting mixture was removed under vacuum and the crude product was purified by silica gel chromatography to give (S)-3-(1-(4-(4-(3,5-dimethyl-4-nitro-1H-pyrazol-1-yl)-5-fluoropyrimidin-2-yl)piperazine-1-carbonyl)-4,5-dihydro-1H-pyrazol-5-yl)-5-fluorobenzonitrile (150 mg, 76.2%) as a yellow solid. LC-MS (m/z) 537.6 ($M+H^+$).

Step 3: To a solution of (S)-3-(1-(4-(4-(3,5-dimethyl-4-nitro-1H-pyrazol-1-yl) fluoropyrimidin-2-yl)piperazine-1-carbonyl)-4,5-dihydro-1H-pyrazol-5-yl) fluorobenzonitrile (120 mg, 0.22 mmol) in EtOH (6 mL) and $H_2O$ (2 mL) was added $NH_3Cl$ (53 mg, 1.00 mmol), Fe(112 mg, 2.00 mmol) at 30° C. The reaction was stirred at 80° C. for 0.5 h. Water was added and extracted with EA, washed with brine, dried with ($Na_2SO_4$). The resulting mixture was removed under vacuum and the crude product was purified by silica gel chromatography to give (S)-3-(1-(4-(4-(4-amino-3,5-dimethyl-1H-pyrazol-1-yl)-5-fluoropyrimidin-2-yl)piperazine-1-carbonyl)-4,5-dihydro-1H-pyrazol-5-yl)-5-fluorobenzonitrile (62 mg, 54.8%) as a light yellow solid. LC-MS (m/z) 507.4 ($M+H^+$). $^1H$ NMR (400 MHz, DMSO-$d_6$) δ 8.45 (d, J=4.0 Hz, 1H), 7.75 (ddd, J=8.4, 2.4, 1.2 Hz, 1H), 7.65 (t, J=1.6 Hz, 1H), 7.57-7.50 (m, 1H), 7.12 (d, J=1.6 Hz, 1H), 5.29 (t, J=10.8 Hz, 1H), 4.03 (brs, 1H), 3.77-3.52 (m, 8H), 3.41-3.34 (m, 1H), 2.76-2.65 (m, 1H), 2.38 (s, 3H), 2.10 (s, 3H).

Compound 132: 3-((5S)-1-(4-(4-(3,5-dimethyl-1-((tetrahydrofuran-3-yl)methyl)-1H-pyrazol-4-yl)-5-fluoropyrimidin-2-yl)piperazine-1-carbonyl)-4,5-dihydro-1H-pyrazol-5-yl)-5-fluorobenzonitrile

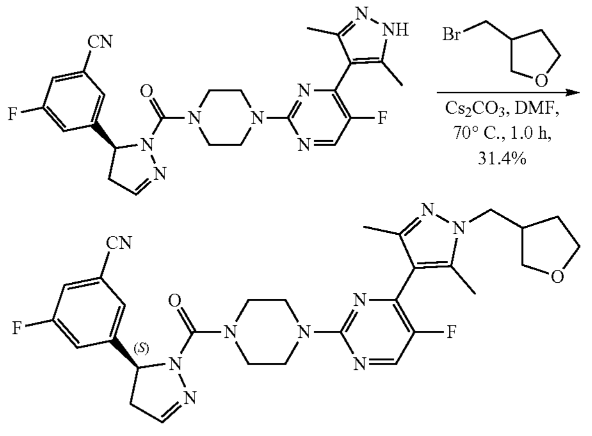

The titled compound 132 was prepared in 31.4% yield as white solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (100 mg, 0.20 mmol) and 3-(bromomethyl)tetrahydrofuran (50 mg, 0.30 mmol), $Cs_2CO_3$ (131 mg, 0.40 mmol), DMF (5 mL) in analogous manner to the preparation of compound 59. LC-MS (m/z) 576.4 ($M+H^+$)

$^1H$ NMR (400 MHz, DMSO-$d_6$) δ 8.44 (d, J=2.4 Hz, 1H), 7.75 (ddd, J=8.4, 2.4, 1.2 Hz, 1H), 7.65 (t, J=1.6 Hz, 1H), 7.53 (dt, J=9.6, 2.0 Hz, 1H), 7.11 (d, J=1.6 Hz, 1H), 5.28 (t, J=10.8 Hz, 1H), 4.07-3.93 (m, 2H), 3.83-3.46 (m, 12H), 3.47-3.39 (m, 1H), 3.31 (s, 2H), 2.75-2.65 (m, 2H), 2.29 (d, J=2.0 Hz, 3H), 2.18 (d, J=1.6 Hz, 3H), 2.01-1.87 (m, 1H), 1.67-1.60 (m, 1H).

Compound 133: 3-((S)-1-(4-(4-(3,5-dimethyl-1-(((R)-oxiran-2-yl)methyl)-1H-pyrazol-4-yl)-5-fluoropyrimidin-2-yl)piperazine-1-carbonyl)-4,5-dihydro-1H-pyrazol-5-yl) fluorobenzonitrile

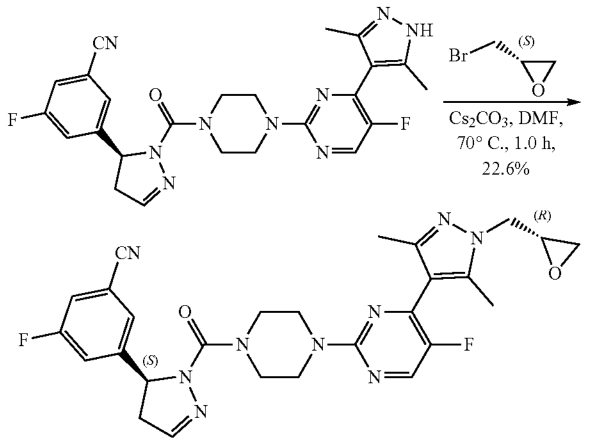

The titled compound 133 was prepared in 22.6% yield as white solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (100 mg, 0.20 mmol) and (S)-2-(bromomethyl)oxirane (50 mg, 0.36 mmol), $Cs_2CO_3$ (131 mg, 0.40 mmol), DMF (5 mL) in analogous manner to the preparation of 59. LC-MS (m/z) 548.6 $(M+H^+)$ $^1H$ NMR (400 MHz, DMSO-$d_6$) δ 8.46 (d, J=2.4 Hz, 1H), 7.75 (ddd, J=8.4, 2.4, 1.2 Hz, 1H), 7.68-7.63 (m, 1H), 7.54 (dt, J=9.6, 2.0 Hz, 1H), 7.15-7.09 (m, 1H), 5.29 (t, J=10.8 Hz, 1H), 4.38 (dd, J=15.2, 3.6 Hz, 1H), 4.12 (dd, J=15.2, 6.0 Hz, 1H), 3.81-3.50 (m, 8H), 3.43-3.34 (m, 1H), 3.32-3.30 (m, 1H), 2.81 (dd, J=5.2, 4.0 Hz, 1H), 2.76-2.64 (m, 1H), 2.59 (dd, J=5.2, 2.4 Hz, 1H), 2.29 (d, J=2.0 Hz, 3H), 2.20 (d, J=1.6 Hz, 3H).

Compound 134: 3-((S)-1-(4-(4-(3,5-dimethyl-1-(((S)-oxiran-2-yl)methyl)-1H-pyrazol-4-yl)-5-fluoropyrimidin-2-yl)piperazine-1-carbonyl)-4,5-dihydro-1H-pyrazol-5-yl)-5-fluorobenzonitrile

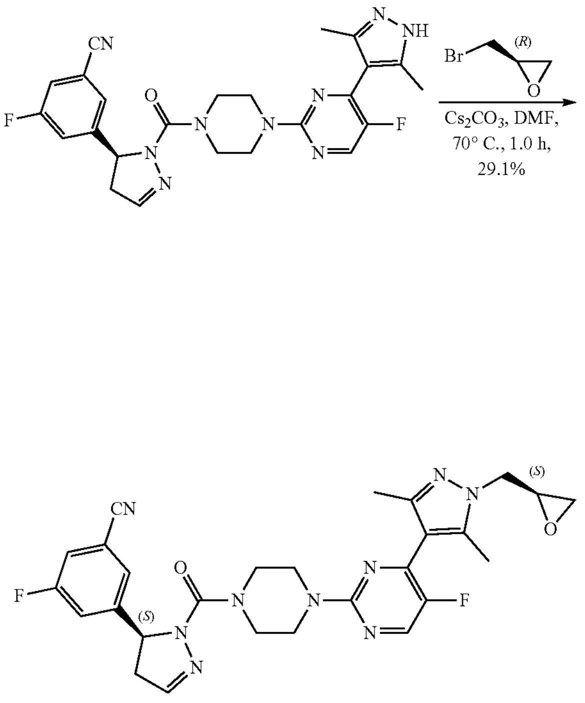

The titled compound 134 was prepared in 29.1% yield as white solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (100 mg, 0.20 mmol) and (R)-2-(bromomethyl)oxirane (50 mg, 0.36 mmol), $Cs_2CO_3$ (131 mg, 0.40 mmol), DMF (5 mL) in analogous manner to the preparation of 59. LC-MS (m/z) 548.6 $(M+H^+)$ $^1H$ NMR (400 MHz, DMSO-$d_6$) δ 8.44 (d, J=2.4 Hz, 1H), 7.74 (ddd, J=8.4, 2.4, 1.2 Hz, 1H), 7.64 (d, J=1.6 Hz, 1H), 7.52 (dt, J=10.0, 2.0 Hz, 1H), 7.10 (d, J=1.6 Hz, 1H), 5.28 (t, J=10.8 Hz, 1H), 4.36 (dd, J=15.2, 3.6 Hz, 1H), 4.10 (dd, J=15.2, 6.0 Hz, 1H), 3.80-3.48 (m, 8H), 3.42-3.35 (m, 1H), 3.32-3.30 (m, 1H), 2.81 (dd, J=5.2, 4.0 Hz, 1H), 2.73-2.64 (m, 1H), 2.58 (dd, J=5.2, 2.4 Hz, 1H), 2.28 (dd, J=5.2, 2.0 Hz, 3H), 2.18 (d, J=1.6 Hz, 3H).

Compound 135: (S)-3-(1-(4-(4-(3,5-dimethyl-1-(oxetan-3-ylmethyl)-1H-pyrazol-4-yl)-5-fluoropyrimidin-2-yl)piperazine-1-carbonyl)-4,5-dihydro-1H-pyrazol-5-yl) fluorobenzonitrile

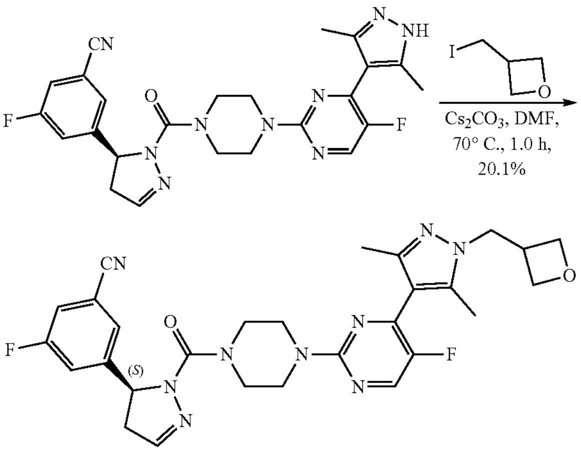

The titled compound 135 was prepared in 29.1% yield as white solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (100 mg, 0.20 mmol) and 3-(iodomethyl)oxetane (60 mg, 0.30 mmol), $Cs_2CO_3$ (131 mg, 0.40 mmol), DMF (5 mL) in analogous manner to the preparation of 59. LC-MS (m/z) 562.4 $(M+H^+)$ $^1H$ NMR (400 MHz, DMSO-$d_6$) δ 8.45 (d, J=2.4 Hz, 1H), 7.75 (ddd, J=8.4, 2.4, 1.2 Hz, 1H), 7.65 (t, J=1.6 Hz, 1H), 7.53 (dt, J=9.6, 2.0 Hz, 1H), 7.15-7.09 (m, 1H), 5.29 (t, J=10.8 Hz, 1H), 4.66 (dd, J=7.6, 6.0 Hz, 2H), 4.45 (t, J=6.0 Hz, 2H), 4.33 (d, J=7.2 Hz, 2H), 3.81-3.49 (m, 8H), 3.47-3.39 (m, 1H), 3.38-3.34 (m, 1H), 2.76-2.67 (m, 1H), 2.30 (d, J=2.0 Hz, 3H), 2.17 (d, J=1.6 Hz, 3H).

Compound 137: 3-((58)-1-(4-(4-(3,5-dimethyl-1-((tetrahydro-2H-pyran-2-yl)methyl)-1H-pyrazol-4-yl)-5-fluoropyrimidin-2-yl)piperazine-1-carbonyl)-4,5-dihydro-1H-pyrazol-5-yl)-5-fluorobenzonitrile

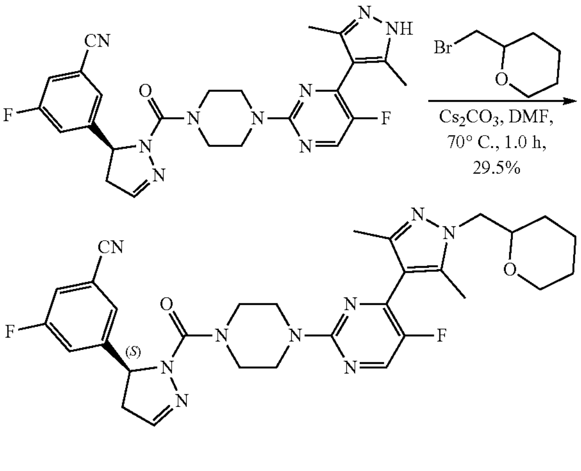

The titled compound 137 was prepared in 29.5% yield as white solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (100 mg, 0.20 mmol) and 2-(bromomethyl)tetrahydro-2H-pyran (50 mg, 0.28 mmol), $Cs_2CO_3$ (131 mg, 0.40 mmol), DMF (5 mL) in analogous manner to the preparation of 117. LC-MS (m/z) 590.4 $(M+H^+)$ $^1$H NMR (400 MHz, DMSO-$d_6$) δ 8.43 (d, J=2.4 Hz, 1H), 7.74 (ddd, J=8.4, 2.4, 1.2 Hz, 1H), 7.65-7.63 (m, 1H), 7.52 (dt, J=9.6, 2.0 Hz, 1H), 7.10 (d, J=1.6 Hz, 1H), 5.28 (t, J=10.8 Hz, 1H), 4.07-3.92 (m, 2H), 3.85-3.48 (m, 10H), 3.40-3.20 (m, 2H), 2.74-2.64 (m, 1H), 2.26 (d, J=2.0 Hz, 3H), 2.17 (d, J=1.6 Hz, 3H), 1.82-1.73 (m, 1H), 1.63-1.55 (m, 1H), 1.47-1.37 (m, 3H), 1.28-1.17 (m, 1H).

Compound 138: (S)-3-(1-(4-(4-(3,5-dimethyl-1-(2-(tetrahydro-2H-pyran-4-yl)ethyl)-1H-pyrazol-4-yl)-5-fluoropyrimidin-2-yl)piperazine-1-carbonyl)-4,5-dihydro-1H-pyrazol-5-yl)-5-fluorobenzonitrile

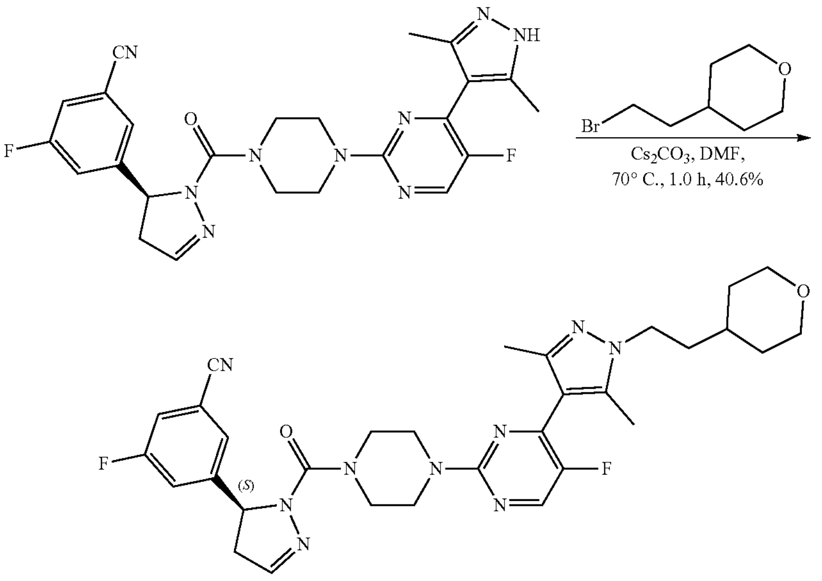

The titled compound 138 was prepared in 40.6% yield as white solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (100 mg, 0.20 mmol) and 4-(2-bromoethyl)tetrahydro-2H-pyran (60 mg, 0.31 mmol), $Cs_2CO_3$ (131 mg, 0.40 mmol), DMF (5 mL) in analogous manner to the preparation of 59. LC-MS (m/z) 604.4 $(M+H^+)$ $^1$H NMR (400 MHz, DMSO-$d_6$) δ 8.44 (d, J=2.4 Hz, 1H), 7.75 (ddd, J=8.4, 2.4, 1.2 Hz, 1H), 7.65 (t, J=1.6 Hz, 1H), 7.57-7.49 (m, 1H), 7.12 (d, J=1.6 Hz, 1H), 5.29 (t, J=10.8 Hz, 1H), 4.12-4.01 (m, 2H), 3.87-3.43 (m, 8H), 3.43-3.35 (m, 1H), 3.30-3.23 (m, 3H), 2.76-2.67 (m, 1H), 2.29 (d, J=2.0 Hz, 3H), 2.18 (d, J=1.6 Hz, 3H), 1.70-1.59 (m, 4H), 1.58-1.50 (m, 2H), 1.27-1.14 (m, 2H).

Compound 136: (S)-3-(1-(4-(4-(1-(cyanomethyl)-3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile

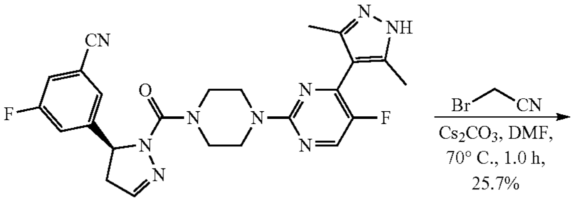

-continued

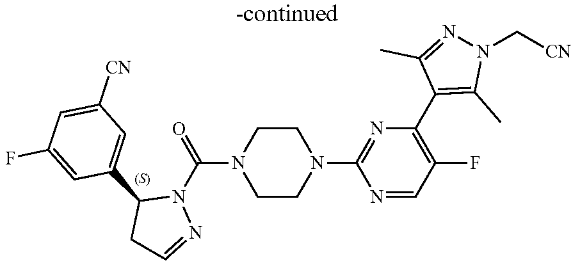

The titled compound 136 was prepared in 25.7% yield as brown solid from (S)-3-(1-(4-(4-(3,5-dimethyl-1H-pyrazol-4-yl)-5-fluoropyrimidin-2-yl)piperazine-1-carbonyl)-4,5-dihydro-1H-pyrazol-5-yl)-5-fluorobenzonitrile (100 mg, 0.20 mmol) and 2-bromoacetonitrile (50 mg, 0.42 mmol), $Cs_2CO_3$ (131 mg, 0.40 mmol), DMF (5 mL) in analogous manner to the preparation of 59. LC-MS (m/z) 531.6 $(M+H^+)$ $^1$H NMR (400 MHz, DMSO-$d_6$) δ 8.49 (d, J=2.4 Hz, 1H), 7.75 (ddd, J=8.4, 2.4, 1.2 Hz, 1H), 7.65 (d, J=1.6 Hz, 1H), 7.53 (dt, J=9.6, 2.0 Hz, 1H), 7.12 (d, J=1.6 Hz, 1H), 5.46 (s, 2H), 5.29 (t, J=10.8 Hz, 1H), 3.81-3.50 (m, 8H), 3.43-3.35 (m, 1H), 2.76-2.64 (m, 1H), 2.35 (d, J=2.0 Hz, 3H), 2.21 (d, J=1.6 Hz, 3H).

Compound 139: (S)-1-(2-(4-(5-(3-cyano-5-fluorophenyl)-4,5-dihydro-1H-pyrazole-1-carbonyl)piperazin-1-yl)-5-fluoropyrimidin-4-yl)-5-methyl-1H-1,2,4-triazole-3-carbonitrile

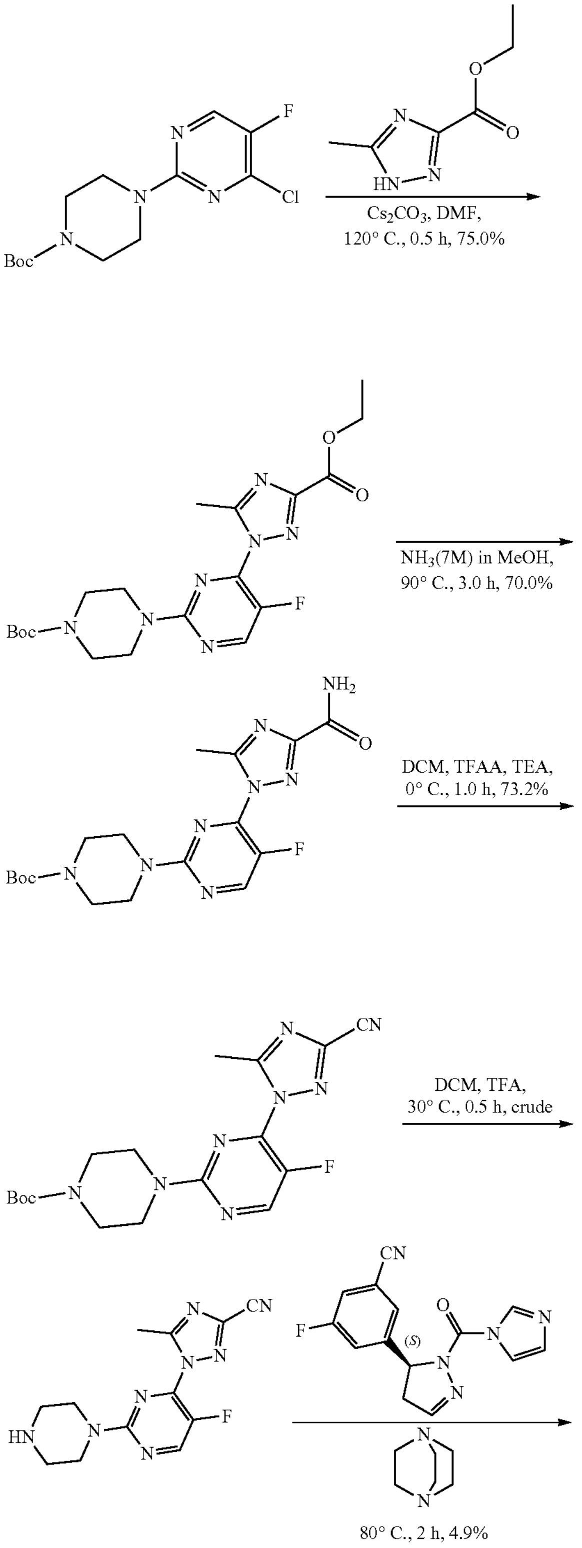

-continued

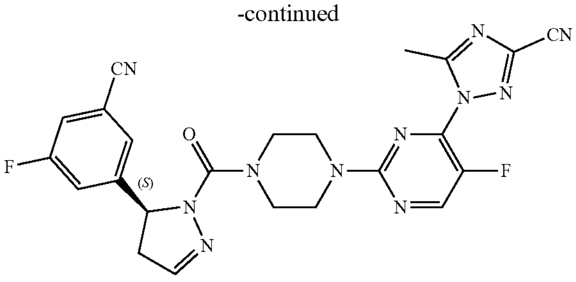

Step 1: To a solution of tert-butyl 4-(4-chloro-5-fluoropyrimidin-2-yl)piperazine-1-carboxylate (1.2 g, 3.79 mmol) in DMF (20 mL) was added ethyl 5-methyl-1H-1,2,4-triazole-3-carboxylate (600 mg, 3.87 mmol), $Cs_2CO_3$ (2.5 g, 7.62 mmol) at 30° C. under Ar. The reaction was stirred at 120° C. for 0.5 h. Water was added and extracted with EA, washed with brine, dried with ($Na_2SO_4$). The resulting mixture was removed under vacuum and the crude product was purified by silica gel chromatography to give tert-butyl 4-(4-(3-(ethoxycarbonyl)-5-methyl-1H-1,2,4-triazol-1-yl)-5-fluoropyrimidin-2-yl)piperazine-1-carboxylate. (1.2 g, 75.0%) as yellow oil. LC-MS (m/z) 436.4 ($M+H^+$).

Step 2: To a solution of tert-butyl 4-(4-(3-(ethoxycarbonyl)-5-methyl-1H-1,2,4-triazol-1-yl)-5-fluoropyrimidin-2-yl)piperazine-1-carboxylate (1.1 g, 2.52 mmol) in MeOH (10 mL) was added $NH_3$ (7M in MeOH) (20 mL) at 30° C. The reaction was stirred at 90° C. for 3.0 h. The solvent was removed under vacuum and the crude product was purified by silica gel chromatography to give tert-butyl 4-(4-(3-carbamoyl-5-methyl-1H-1,2,4-triazol-1-yl)-5-fluoropyrimidin-2-yl)piperazine-1-carboxylate (700 mg, 70.0%) as a white solid. LC-MS (m/z) 407.4 ($M+H^+$).

Step 3: To a solution of tert-butyl 4-(4-(3-carbamoyl-5-methyl-1H-1,2,4-triazol-1-yl) fluoropyrimidin-2-yl)piperazine-1-carboxylate (200 mg, 0.49 mmol) in DCM (5 mL) was added TEA (149 mg, 1.47 mmol), TFAA (206 mg, 0.98 mmol) at 0° C. under Ar. The reaction was stirred at 0° C. for 1.0 h. Water was added and extracted with EA, washed with brine, dried with ($Na_2SO_4$). The resulting mixture was removed under vacuum and the crude product was purified by silica gel chromatography to give tert-butyl 4-(4-(3-cyano-5-methyl-1H-1,2,4-triazol-1-yl)-5-fluoropyrimidin-2-yl)piperazine-1-carboxylate (140 mg, 73.2%) as a colorless oil. LC-MS (m/z) 389.4 ($M+H^+$).

Step 4: To a solution of tert-butyl 4-(4-(3-cyano-5-methyl-1H-1,2,4-triazol-1-yl)-5-fluoropyrimidin-2-yl)piperazine-1-carboxylate (140 mg, 0.36 mmol) in DCM (5 mL) was added TFA (20 mL) at 30° C. The reaction was stirred at 30° C. for 0.5 h. The solvent was removed under vacuum and the crude product without purified was used to next step reaction (200 mg, crude) as a brown oil. LC-MS (m/z) 289.4 ($M+H^+$).

Step 5: To a solution of 1-(5-fluoro-2-(piperazin-1-yl) pyrimidin-4-yl)-5-methyl-1H-1,2,4-triazole-3-carbonitrile compound with 2,2,2-trifluoro-1l3-ethan-1-one (1:1) (200 mg, crude) in THF (20 mL) was added 1,4-diazabicyclo [2.2.2]octane (150 mg, 1.34 mmol), (S)-3-(1-(1H-imidazole-1-carbonyl)-4,5-dihydro-1H-pyrazol-5-yl)-5-fluorobenzonitrile (60 mg, 0.21 mmol) at 30° C. The solvent was removed under vacuum and the reaction mixture was stand at 80° C. for 2.0 h. The crude product was purified by silica gel chromatography to give (S)-1-(2-(4-(5-(3-cyano-5-fluorophenyl)-4,5-dihydro-1H-pyrazole-1-carbonyl)piperazin-1-yl)-5-fluoropyrimidin-4-yl)-5-methyl-1H-1,2,4-triazole- 3-carbonitrile (12.0 mg, 4.9%) as a white solid. LC-MS (m/z) 504.4 ($M+H^+$). $^1H$ NMR (400 MHz, DMSO-$d_6$) δ 8.85 (d, J=2.6 Hz, 1H), 7.76 (ddd, J=8.4, 2.4, 1.2 Hz, 1H), 7.65 (t, J=1.6 Hz, 1H), 7.54 (dt, J=9.6, 2.0 Hz, 1H), 7.13 (d, J=1.6 Hz, 1H), 5.29 (dd, J=11.6, 10.0 Hz, 1H), 3.85-3.53 (m, 8H), 3.43-3.35 (m, 1H), 2.76 (s, 3H), 2.75-2.65 (m, 2H)
Compound 140: (S)-3-fluoro-5-(1-(4-(5-fluoro-4-(4-methyl-5-oxo-4,5-dihydro-1H-1,2,4-triazol-1-yl)pyrimidin-2-yl)piperazine-1-carbonyl)-4,5-dihydro-1H-pyrazol-5-yl)benzonitrile
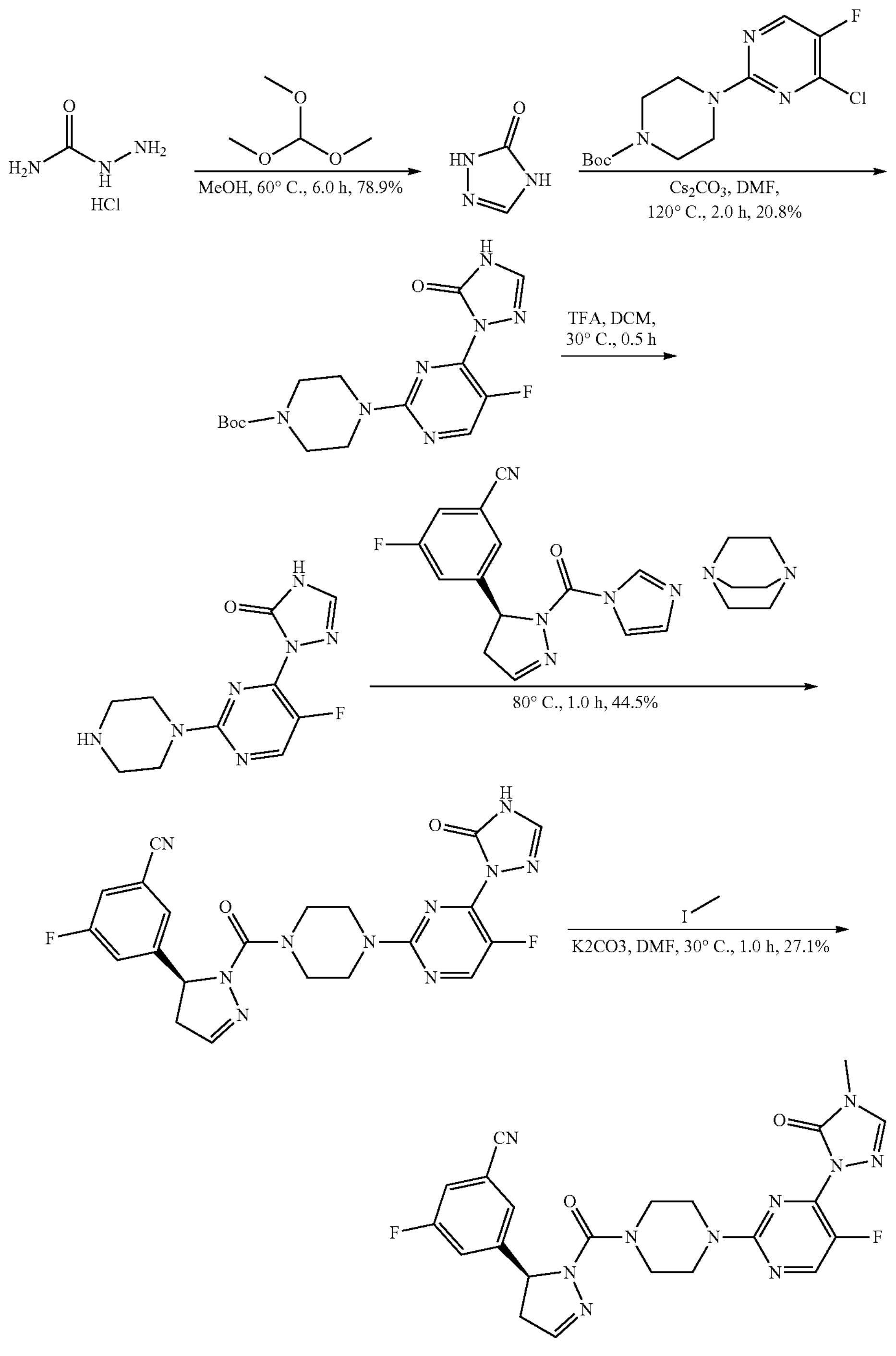

The titled compound 140 was prepared in 27.1% yield as white solid from (S)-3-fluoro-5-(1-(4-(5-fluoro-4-(5-oxo-4,5-dihydro-1H-1,2,4-triazol-1-yl)pyrimidin-2-yl)piperazine-1-carbonyl)-4,5-dihydro-1H-pyrazol-5-yl)benzonitrile (70 mg, 0.15 mmol) and iodomethane (140 mg, 1.00 mmol), $K_2CO_3$ (500 mg, 1.32 mmol), DMF (8 mL) in analogous manner to the preparation of 139. LC-MS (m/z) 495.4 $(M+H^+)$ $^1H$ NMR (400 MHz, DMSO-$d_6$) δ 8.68 (d, J=2.4 Hz, 1H), 8.39 (s, 1H), 7.75 (ddd, J=8.4, 2.4, 1.2 Hz, 1H), 7.65 (t, J=1.6 Hz, 1H), 7.53 (dt, J=9.6, 2.0 Hz, 1H), 7.12 (d, J=1.6 Hz, 1H), 5.28 (t, J=10.8 Hz, 1H), 3.81-3.49 (m, 8H), 3.40-3.34 (m, 4H), 2.76-2.67 (m, 1H).

Compound 141: (S)-3-fluoro-5-(1-(4-(5-fluoro-4-(5-hydroxy-3-methyl-1H-pyrazol-1-yl)pyrimidin-2-yl)piperazine-1-carbonyl)-4,5-dihydro-1H-pyrazol-5-yl)benzonitrile

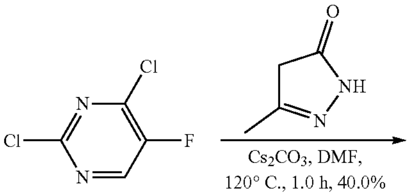

-continued

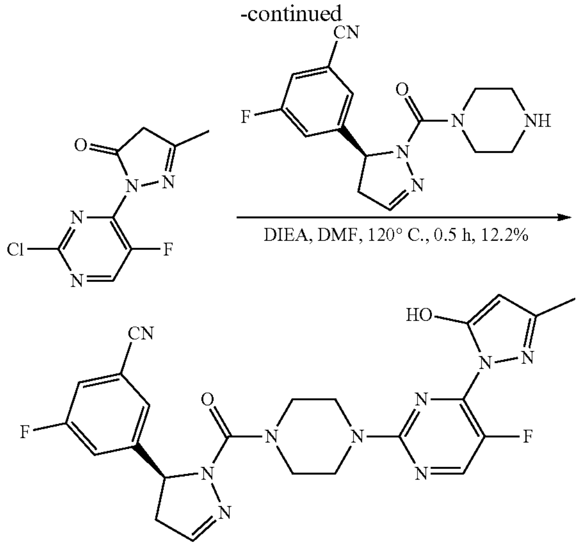

The titled compound 141 was prepared in 12.2% yield as light yellow solid from 2-(2-chloro-5-fluoropyrimidin-4-yl)-5-methyl-2,4-dihydro-3H-pyrazol-3-one (100 mg, crude) and (S)-3-fluoro-5-(1-(piperazine-1-carbonyl)-4,5-dihydro-1H-pyrazol-5-yl)benzonitrile (50 mg, 0.17 mmol), DIEA (100 mg, 0.77 mmol), DMF (5 mL) according to the procedure outlined for compound 125. LC-MS (m/z) 494.4 $(M+H^+)$ $^1H$ NMR (400 MHz, DMSO-$d_6$) δ 10.48 (brs, 1H), 8.51 (d, J=4.0 Hz, 1H), 7.75 (ddd, J=8.4, 2.4, 1.2 Hz, 1H), 7.65 (t, J=1.6 Hz, 1H), 7.53 (dt, J=9.6, 2.0 Hz, 1H), 7.12 (d, J=1.6 Hz, 1H), 5.77 (s, 1H), 5.34-5.24 (m, 1H), 3.78-3.51 (m, 8H), 3.41-3.35 (m, 1H), 2.76-2.64 (m, 1H), 2.49 (s, 3H).

Compound 142: (S)—N-(1-(2-(4-(5-(3-cyano-5-fluorophenyl)-4,5-dihydro-1H-pyrazole-1-carbonyl)piperazin-1-yl)-5-fluoropyrimidin-4-yl)-3,5-dimethyl-1H-pyrazol-4-yl)acetamide

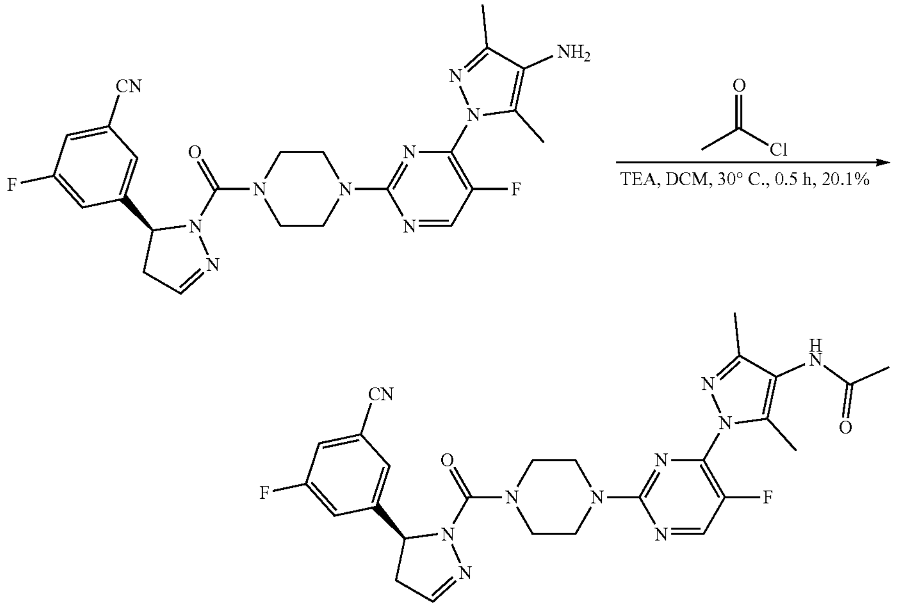

To a solution of (S)-3-(1-(4-(4-(4-amino-3,5-dimethyl-1H-pyrazol-1-yl)-5-fluoropyrimidin-2-yl)piperazine-1-carbonyl)-4,5-dihydro-1H-pyrazol-5-yl)-5-fluorobenzonitrile (100 mg, 0.48 mmol) in DCM (5 mL) was added TEA (0.5 mL), acetyl chloride (40 mg, 0.50 mmol) at 30° C. The reaction was stirred at 30° C. for 0.5 h. Water was added and extracted with EA, washed with brine, dried with ($Na_2SO_4$). The resulting mixture was removed under vacuum and the crude product was purified by silica gel chromatography to give (S)—N-(1-(2-(4-(5-(3-cyano-5-fluorophenyl)-4,5-dihydro-1H-pyrazole-1-carbonyl)piperazin-1-yl)-5-fluoropyrimidin-4-yl)-3,5-dimethyl-1H-pyrazol-4-yl)acetamide (21.7 mg, 20.1%) a white solid. LC-MS (m/z) 549.4 ($M+H^+$). $^1H$ NMR (400 MHz, DMSO-$d_6$) δ 9.24 (brs, 1H), 8.59 (d, J=3.6 Hz, 1H), 7.74 (ddd, J=8.4, 2.4, 1.2 Hz, 1H), 7.64 (t, J=1.6 Hz, 1H), 7.52 (dt, J=9.6, 2.0 Hz, 1H), 7.11 (d, J=1.6 Hz, 1H), 5.28 (t, J=10.8 Hz, 1H), 3.78-3.49 (m, 8H), 3.40-3.34 (m, 1H), 2.75-2.63 (m, 1H), 2.30 (s, 3H), 2.06 (s, 3H), 2.02 (s, 3H).

Compound 143: (S)-(4-(4-(3-amino-1,4-dimethyl-1H-pyrazol-5-yl)pyrimidin yl)piperazin-1-yl)(5-(3,5-difluorophenyl)-4,5-dihydro-1H-pyrazol-1-yl)methanone

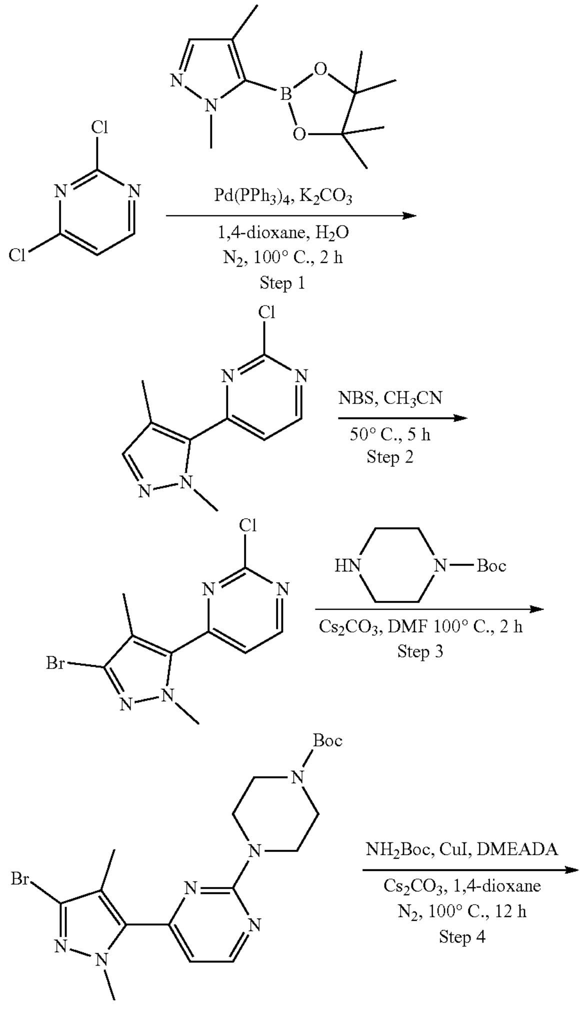

-continued

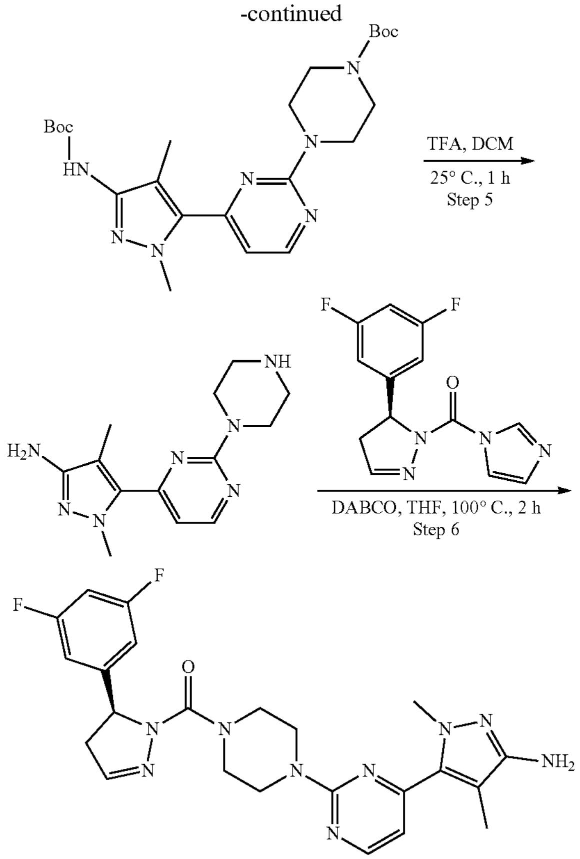

Step 1: 2,4-dichloropyrimidine (1450 mg, 10 mmol), 1,4-dimethyl-5-(4,4,5,5-tetramethyl-1,3,2-dioxaborolan-2-yl)-1H-pyrazole (2220 mg, 10 mmol), $Pd(PPh_3)_4$ (578 mg, 0.5 mmol), $K_2CO_3$ (4150 mg, 30 mmol) was added to a solution of $H_2O$ (4 mL) in 1,4-dioxane (20 mL) under $N_2$ and the whole reaction mixture was stirred at 100° C. for 2 hours. After the mixture was concentrated and further purification by silica gel chromatography to give 2-chloro-4-(1,4-dimethyl-1H-pyrazol-5-yl)pyrimidine (887 mg, 42.4%) as a clear oil. LC-MS (m/z) 209.1 ($M+H^+$).

Step 2: 2-chloro-4-(1,4-dimethyl-1H-pyrazol-5-yl)pyrimidine (832 mg, 4 mmol), NBS (784 mg, 4.4 mmol) in $CH_3CN$ (15 mL) and the whole reaction mixture was stirred at 50° C. for 5 hours. After the mixture was concentrated and further purification by silica gel chromatography to give 4-(3-bromo-1,4-dimethyl-1H-pyrazol-5-yl)-2-chloropyrimidine (720 mg, 62.7%) as a white solid. LC-MS (m/z) 287.0 ($M+H^+$).

Step 3: 4-(3-bromo-1,4-dimethyl-1H-pyrazol-5-yl)-2-chloropyrimidine (604 mg, 2.1 mmol), tert-butyl piperazine-1-carboxylate (430 mg, 2.3 mmol), $Cs_2CO_3$ (1370 mg, 4.2 mmol) in DMF (10 mL) and the whole reaction mixture was stirred at 100° C. for 2 hours. After the mixture was concentrated and further purification by silica gel chromatography to give tert-butyl 4-(4-(3-bromo-1,4-dimethyl-1H-pyrazol-5-yl)pyrimidin-2-yl)piperazine-1-carboxylate (930 mg, 99.9%) as a white solid. LC-MS (m/z) 437.2 ($M+H^+$).

Step 4: tert-butyl 4-(4-(3-bromo-1,4-dimethyl-1H-pyrazol-5-yl)pyrimidin-2-yl)piperazine carboxylate (930 mg, 2.13 mmol), $NH_2Boc$ (374 mg, 3.19 mmol), CuI (610 mg, 3.19 mmol), DMEDA (281 mg, 3.19 mmol) was added to a solution of $Cs_2CO_3$ (2082 mg, 6.39 mmol), in 1,4-dioxane (15 mL) under $N_2$ and the whole reaction mixture was stirred at 100° C. for 12 hours. After the mixture was concentrated and further purification by silica gel chromatography to give tert-butyl 4-(4-(3-((tert-butoxycarbonyl)amino)-1,4-dimethyl-1H-pyrazol-5-yl)pyrimidin-2-yl)piperazine-1-carboxylate (392 mg, 38.9%) as a white solid. LC-MS (m/z) 474.4 ($M+H^+$).

Step 5: tert-butyl 4-(4-(3-((tert-butoxycarbonyl)amino)-1,4-dimethyl-1H-pyrazol-5-yl)pyrimidin-2-yl)piperazine-1-carboxylate (310 mg, 0.63 mmol) was dissolved in 10 mL of DCM, trifluoroacetic acid (719 mg, 6.3 mmol) was added, the mixture was stirred at 25° C. for 1 hour. Concentrated to give the desired product 1,4-dimethyl-5-(2-(piperazin-1-yl)pyrimidin-4-yl)-1H-pyrazol-3-amine, which was used for next step without further purification.

Step 6: 1,4-dimethyl-5-(2-(piperazin-1-yl)pyrimidin-4-yl)-1H-pyrazol-3-amine (113 mg, 0.41 mmol), (S)-(5-(3,5-difluorophenyl)-4,5-dihydro-1H-pyrazol-1-yl)(1H-imidazol-1-yl)methanone (102 mg, 0.37 mmol) and 1,4-diazabicyclo[2.2.2]octane (459 mg, 4.15 mmol) were dissolved in THF (10 mL). Concentrated in vacuo and the whole reaction mixture was stirred at 100° C. for 2 hours. The mixture was extracted with EA, washed with brine, dried ($Na_2SO_4$), and concentrated in vacuo. Purification by prep-HPLC to give the titled compound 143 (58 mg, 32.5%) as a yellow solid. $^1H$ NMR (300 MHz, Chloroform-d) δ 8.40 (dd, J=5.1, 1.7 Hz, 1H), 6.95-6.50 (m, 5H), 5.34 (dd, J=11.7, 9.9 Hz, 1H), 4.08-3.55 (m, 11H), 3.39-3.28 (m, 1H), 2.73-2.62 (m, 1H), 2.47 (s, 2H), 2.03 (d, J=1.7 Hz, 3H). LC-MS (m/z) 482.3 ($M+H^+$).

Compound 144: (S)-3-fluoro-5-(1-(4-(5-fluoro-4-(3-(hydroxymethyl)-5-methyl-1H-1,2,4-triazol-1-yl)pyrimidin-2-yl)piperazine-1-carbonyl)-4,5-dihydro-1H-pyrazol-5-yl)benzonitrile

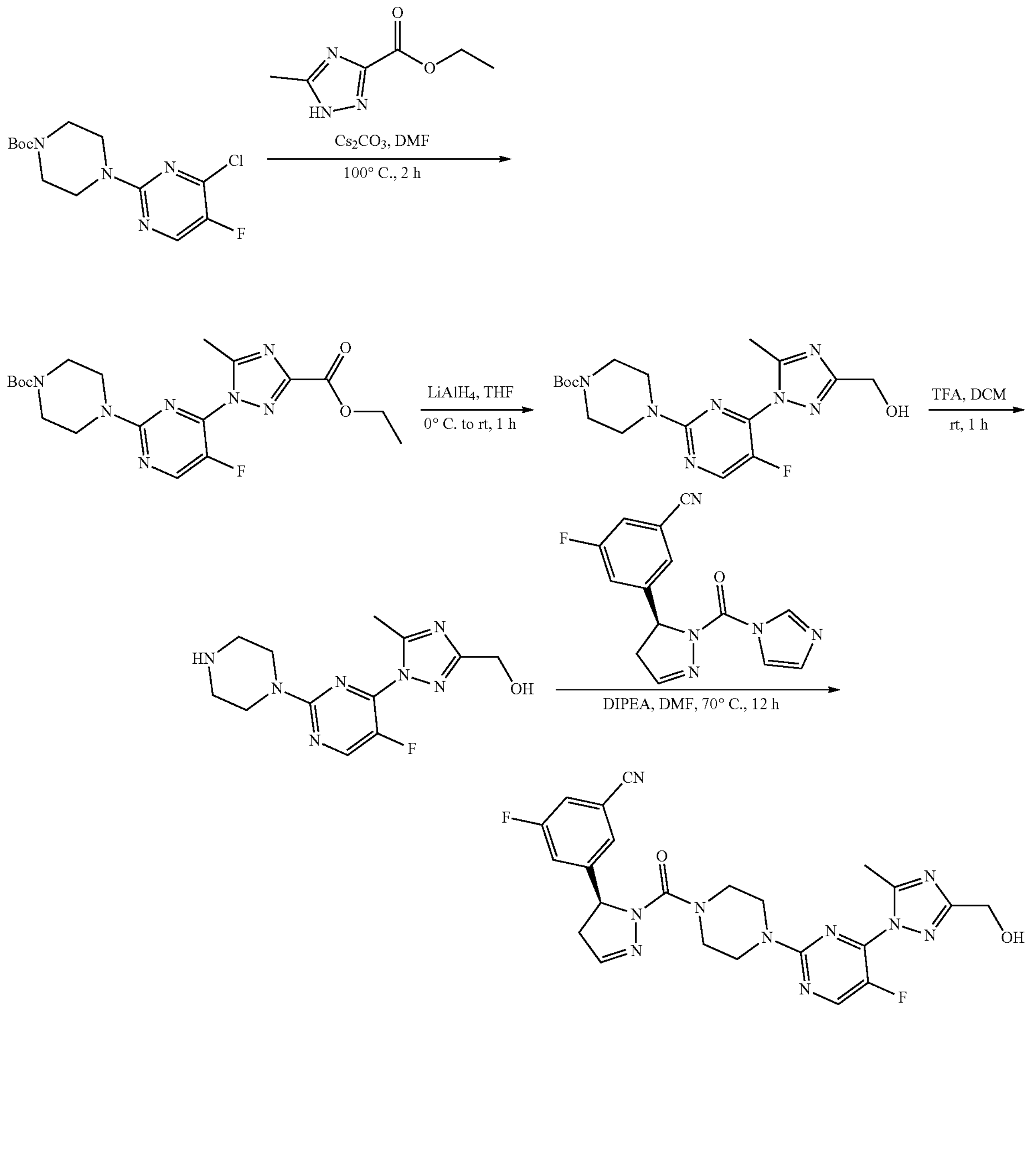

Step 1: To a solution of tert-butyl 4-(4-chloro-5-fluoropyrimidin-2-yl)piperazine-1-carboxylate (2 g, 6.31 mmol) in DMF (15 mL) was added ethyl 5-methyl-1H-1,2,4-triazole-3-carboxylate (980 mg, 6.31 mmol) and $CsCO_3$ (2.44 g, 12.6 mmol). The reaction mixture was stirred at 100° C. for 2 h. The crude was purified by column chromatography on silica gel. tert-butyl 4-(4-(3-(ethoxycarbonyl)-5-methyl-1H-1,2,4-triazol-1-yl)-5-fluoropyrimidin-2-yl)piperazine carboxylate (2.1 g, 76%) was obtained as a white solid MS (m/z): 436.1 $[M+H]^+$.

Step 2: To a solution of tert-butyl 4-(4-(3-(ethoxycarbonyl)-5-methyl-1H-1,2,4-triazol-1-yl)-5-fluoropyrimidin-2-yl)piperazine-1-carboxylate (200 mg, 459.3 umol) in THF (10 mL) was added $LiAlH_4$ (0.5 mL, 505.2 umol) under Ar at 0° C. The reaction mixture was stirred at rt for 1 h. The crude was purified by column chromatography on silica gel. tert-butyl 4-(5-fluoro-4-(3-(hydroxymethyl)-5-methyl-1H-1,2,4-triazol-1-yl)pyrimidin-2-yl)piperazine-1-carboxylate (100 mg, 55%) was obtained as a white solid MS (m/z): 394.1 $[M+H]^+$.

Step 3: To a solution of tert-butyl 4-(5-fluoro-4-(3-(hydroxymethyl)-5-methyl-1H-1,2,4-triazol-1-yl)pyrimidin-2-yl)piperazine-1-carboxylate (100 mg, 254.2 umol) in DCM (3 mL) was added TFA (3 mL). The reaction mixture was stirred at rt for 1 h. The solvent was concentrated under vacuum. The crude was used to next step directly MS (m/z): 294.2 $[M+H]^+$.

Step 4: To a solution of (S)-3-(1-(1H-imidazole-1-carbonyl)-4,5-dihydro-1H-pyrazol-5-yl)-5-fluorobenzonitrile (65 mg, 229.5 umol) in THF (5 mL) was added (1-(5-fluoro-2-(piperazin-1-yl)pyrimidin-4-yl)-5-methyl-1H-1,2,4-triazol-3-yl)methanol (75 mg, 254.9 umol) and DIPEA (98 mg, 764.9 umol). The reaction mixture was stirred at 70° C. for 12 h. The crude was purified by Pre-HPLC. Compound 144 (13 mg, 11%) was obtained as a light-yellow solid. MS (m/z): 509.1 $[M+H]^+$. $^1H$ NMR (400 MHz, DMSO-d6) δ 8.73 (d, J=2.9 Hz, 1H), 7.75 (ddd, J=8.5, 2.5, 1.3 Hz, 1H), 7.65 (t, J=1.4 Hz, 1H), 7.53 (ddd, J=9.8, 2.6, 1.5 Hz, 1H), 7.12 (d, J=1.7 Hz, 1H), 5.29 (t, J=10.8 Hz, 1H), 4.46 (s, 2H), 3.87-3.50 (m, 8H), 3.37 (ddd, J=18.3, 11.6, 1.9 Hz, 1H), 2.74-2.67 (m, 1H), 2.65 (s, 3H).

Compound 145: (4-(2-(1,4-dimethyl-1H-pyrazol-5-yl)-5-fluoropyrimidin-4-yl)piperazin-1-yl)(5-(5-methylthiazol-2-yl)-4,5-dihydro-1H-pyrazol-1-yl)methanone

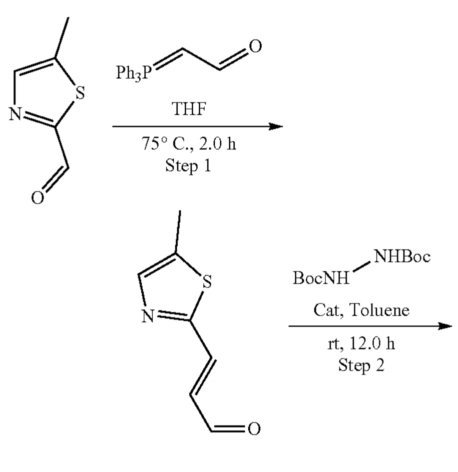

-continued

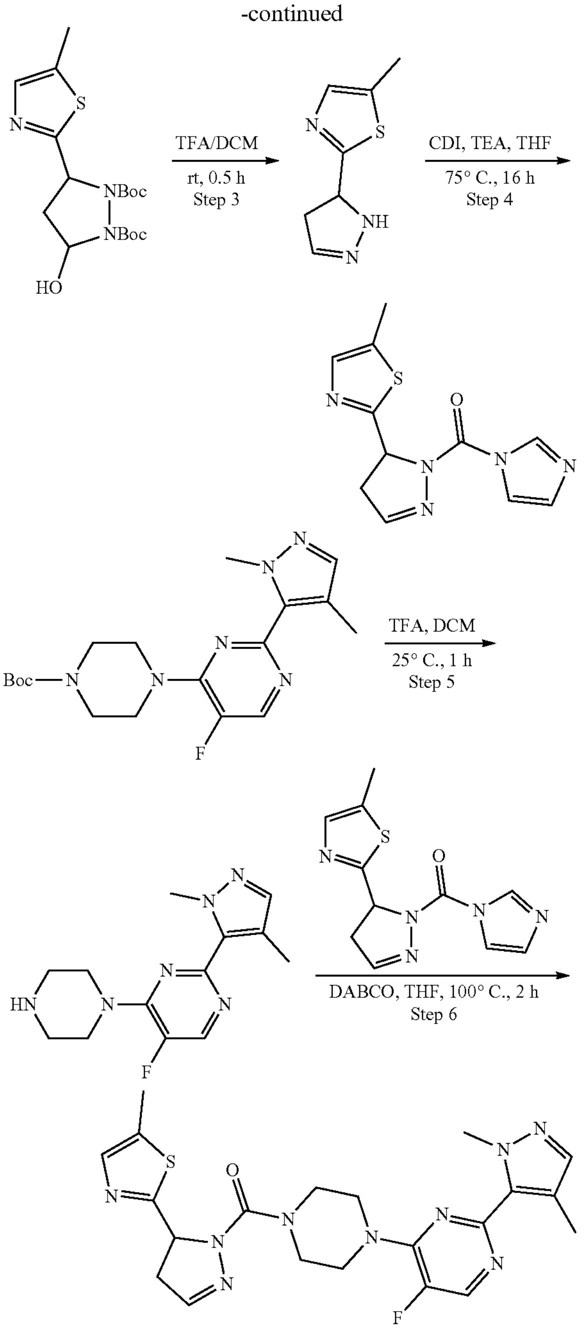

Step 1: Synthesis of (E)-3-(5-methylthiazol-2-yl)acrylaldehyde

To a stirred solution of 5-methylthiazole-2-carbaldehyde (1 g, 7.86 mmol) and 2-(triphenyl-15-phosphaneylidene) acetaldehyde (2.87 g, 9.44 mmol) in THF (15 mL) at room temperature. The resulting mixture was stirred for additional 2 h at 75° C. The mixture was allowed to cool down to room temperature. The resulting mixture was concentrated under reduced pressure. The residue was purified by silica gel column chromatography, eluted with (PE:EtOAc) (1:1) to afford (E)-3-(5-methylthiazol-2-yl)acrylaldehyde (1.2 g, 99.6%) as a brown yellow oil. MS (m/z): 154.2 $[M+H]^+$.

Step 2: Synthesis of di-tert-butyl 3-hydroxy-5-(5-methylthiazol-2-yl)pyrazolidine-1,2-dicarboxylate To a stirred solution of (E)-3-(5-methylthiazol-2-yl)acrylaldehyde (1 g, 6.54 mmol) and di-tert-butyl hydrazine-1,2-dicarboxylate (2.3 g, 9.80 mmol) in toluene (20 mL) was added (5)-2-(diphenyl((trimethylsilyl)oxy)methyl)pyrrolidine (489 mg, 1.50 mmol) at room temperature. The resulting mixture was stirred for additional 12 h at room temperature. The resulting mixture was concentrated under reduced pressure. The residue was purified by silica gel column chromatography, eluted with (PE:EtOAc) (1:1) to afford di-tert-butyl 3-hydroxy-5-(5-methylthiazol-2-yl)pyrazolidine-1,2-dicarboxylate (2.2 g, 87.4%) as a brown yellow solid. MS (m/z): 386.4 $[M+H]^+$.

Step 3: Synthesis of 2-(4,5-dihydro-1H-pyrazol-5-yl)-5-methylthiazole

To a stirred solution of di-tert-butyl 3-hydroxy-5-(5-methylthiazol-2-yl)pyrazolidine-1,2-dicarboxylate (2.2 g, 5.71 mmol) in DCM (8 mL) was added TFA (5 mL) at room temperature. The resulting mixture was stirred for additional 0.5 h at room temperature. The resulting mixture was concentrated under reduced pressure to afford 2-(4,5-dihydro-1H-pyrazol-5-yl)-5-methylthiazole (0.95 g, 99.5%) as a yellow oil. MS (m/z): 168.2 $[M+H]^+$.

Step 4: Synthesis of (1H-imidazol-1-yl)(5-(5-methylthiazol-2-yl)-4,5-dihydro-1H-pyrazol-1-yl)methanone To a stirred solution of 2-(4,5-dihydro-1H-pyrazol-5-yl)-5-methylthiazole (0.95 g, 5.68 mmol) and CDI (4.60 g, 28.40 mmol) in THF (20 mL) was added TEA (1.72 g, 17.06 mmol) at room temperature under $N_2$ atmosphere. The resulting mixture was stirred for additional 16 h at 75° C. The mixture was allowed to cool down to room temperature. The resulting mixture was concentrated under reduced pressure. The residue was purified by silica gel column chromatography, eluted with (PE:EtOAc) (1:2) to afford (1H-imidazol-1-yl)(5-(5-methylthiazol-2-yl)-4,5-dihydro-1H-pyrazol-1-yl)methanone (0.8 g, 53.8%) as a brown yellow oil. MS (m/z): 262.3 $[M+H]^+$.

Step 5 and 6

The titled compound 145 was prepared in 7.5% yield according to the procedure outlined for compound 143. $^1$H NMR (400 MHz, Chloroform-d) δ 8.19 (d, J=6.3 Hz, 1H), 7.36 (q, J=1.2 Hz, 1H), 7.33 (d, J=0.7 Hz, 1H), 6.91 (t, J=1.7 Hz, 1H), 5.70 (t, J=10.4 Hz, 1H), 4.14 (s, 3H), 3.95-3.89 (m, 2H), 3.87-3.78 (m, 4H), 3.75-3.64 (m, 2H), 3.32 (dd, J=10.5, 1.7 Hz, 2H), 2.42 (d, J=1.2 Hz, 3H), 2.28 (s, 3H). LC-MS (m/z) 470.3 $(M+H^+)$.

The following intermediates used for the preparation of compounds 145, 151, 156 to 162, 212 to 217, 223 to 224, 231, 239 to 242, 291 to 294, 296, 298 to 299, 316 to 319 were synthesized using the methods analogous to the preparation of (1H-imidazol-1-yl)(5-(5-methylthiazol-2-yl)-4,5-dihydro-1H-pyrazol-1-yl)methanone as described above.

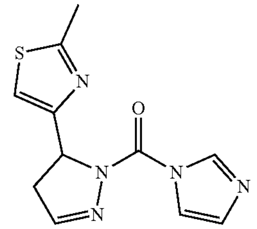

(1H-imidazol-1-yl)(5-(2-methylthiazol-4-yl)-2,5-dihydro-1H-pyrazol-1-yl)methanone

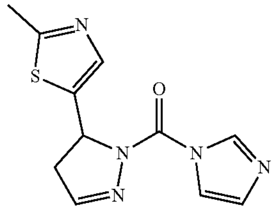

(1H-imidazol-1-yl)(5-(2-methylthiazol-5-yl)-2,5-dihydro-1H-pyrazol-1-yl)methanone

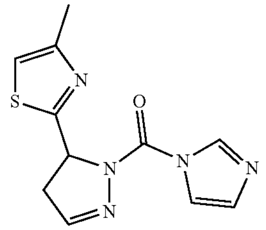

(1H-imidazol-1-yl)(5-(4-methylthiazol-2-yl)-4,5-dihydro-1H-pyrazol-1-yl)methanone

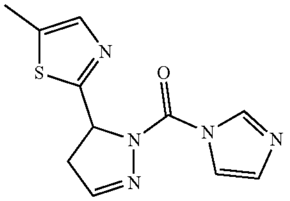

(1H-imidazol-1-yl)(5-(5-methylthiazol-2-yl)-4,5-dihydro-1H-pyrazol-1-yl)methanone

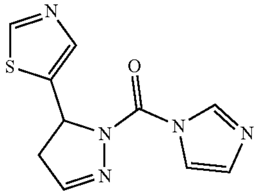

(1H-imidazol-1-yl)(5-(thiazol-5-yl)-4,5-dihydro-1H-pyrazol-1-yl)methanone

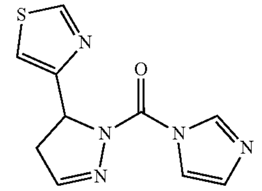

(1H-imidazol-1-yl)(5-(thiazol-4-yl)-4,5-dihydro-1H-pyrazol-1-yl)methanone

Compound 146: 3-((S)-1-((2S,6R)-4-(4-(3,5-dimethyl-1H-1,2,4-triazol-1-yl)-5-fluoropyrimidin-2-yl)-2,6-dimethylpiperazine-1-carbonyl)-4,5-dihydro-1H-pyrazol-5-yl)-5-fluorobenzonitrile

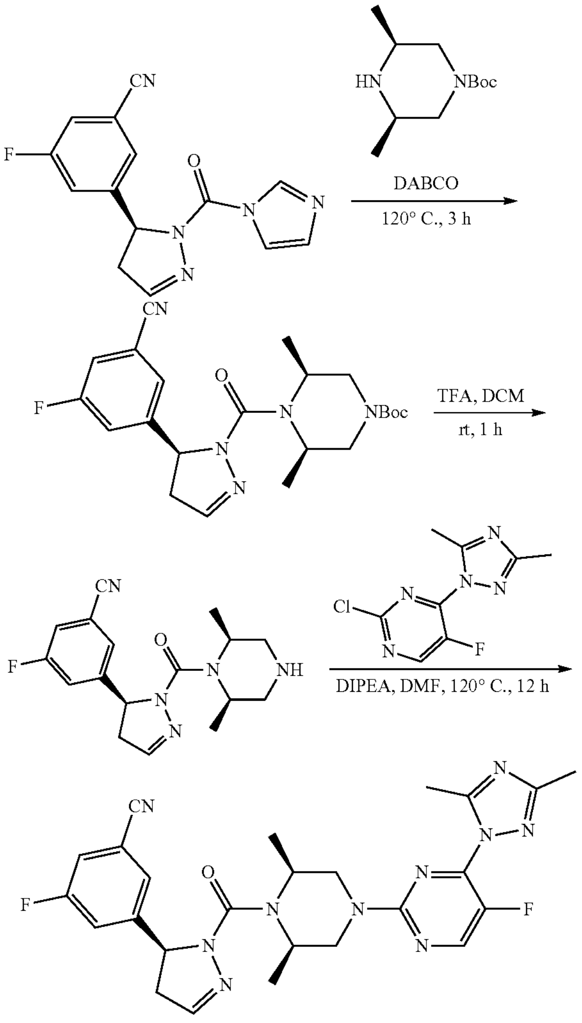

Step 1: (S)-3-(1-(1H-imidazole-1-carbonyl)-4,5-dihydro-1H-pyrazol-5-yl)-5-fluorobenzonitrile (1 g, 3.53 mmol) and tert-butyl (3R,5S)-3,5-dimethylpiperazine-1-carboxylate (1.52 g, 7.06 mmol) were dissolved in THF (10 mL), evaporated to dryness and heated for 3 h at 120° C. The crude was purified by column chromatography on silica gel. tert-butyl(3R,5S)-4-((S)-5-(3-cyano-5-fluorophenyl)-4,5-dihydro-1H-pyrazole-1-carbonyl)-3,5-dimethylpiperazine carboxylate (50 mg, 3%) was obtained as a off-white solid MS (m/z): 430.2 $[M+H]^+$.

Step 2: To a solution of tert-butyl (3R,5S)-4-((S)-5-(3-cyano-5-fluorophenyl)-4,5-dihydro-1H-pyrazole-1-carbonyl)-3,5-dimethylpiperazine-1-carboxylate (50 mg, 116.4 umol) in DCM (3 mL) was added TFA (3 mL). The reaction mixture was stirred at rt for 1 h. The solvent was concentrated under vacuum. The crude was used to next step directly MS (m/z): 330.2 $[M+H]^+$.

Step 3: To a solution of 3-((S)-1-((2S,6R)-2,6-dimethylpiperazine-1-carbonyl)-4,5-dihydro-1H-pyrazol-5-yl)-5-fluorobenzonitrile (20 mg, 60.7 umol) in DMF (2 mL) was added 2-chloro-4-(3,5-dimethyl-1H-1,2,4-triazol-1-yl)-5-fluoropyrimidine (14 mg, 60.7 umol) and DIPEA (40 mg, 303.6 umol). The reaction mixture was stirred at 120° C. for 12 h. The crude was purified by Pre-HPLC. 3-((S)-1-((2S,6R)-4-(4-(3,5-dimethyl-1H-1,2,4-triazol-1-yl)-5-fluoropyrimidin-2-yl)-2,6-dimethylpiperazine-1-carbonyl)-4,5-dihydro-1H-pyrazol-5-yl)-5-fluorobenzonitrile (2 mg, 6%) was obtained as a white solid MS (m/z): 521.2 $[M+H]^+$. $^1H$ NMR (400 MHz, DMSO-d6) δ 8.74 (d, J=3.1 Hz, 1H), 7.90-7.80 (m, 2H), 7.74-7.71 (m, 1H), 7.32 (d, J=8.2 Hz, 1H), 5.33 (q, J=7.8 Hz, 1H), 4.59-4.44 (m, 1H), 4.34-4.27 (m, 1H), 3.73-3.63 (m, 2H), 3.33-3.08 (m, 2H), 2.69 (s, 3H), 2.36 (s, 3H), 1.34 (s, 3H), 1.31 (s, 3H).

Compound 147: (S)-3-fluoro-5-(1-(4-(4-(5-methyl-3-(trifluoromethyl)-1H-1,2,4-triazol-1-yl)pyrimidin-2-yl)piperazine-1-carbonyl)-4,5-dihydro-1H-pyrazol-5-yl)benzonitrile

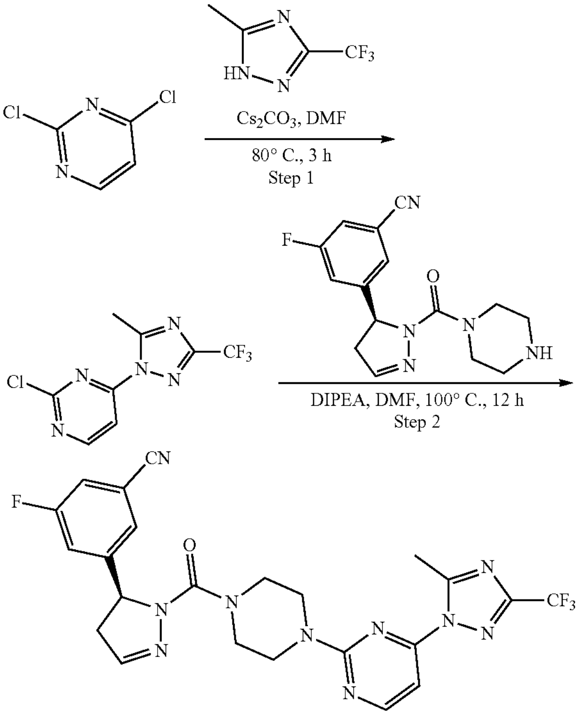

Step 1: To a solution of 2,4-dichloropyrimidine (300 mg, 2.01 mmol) in DMF (5 mL) was added 5-methyl-3-(trifluoromethyl)-1H-1,2,4-triazole (305 mg, 2.01 mmol) and $CsCO_3$ (777 mg, 4.03 mmol). The reaction mixture was stirred at 80° C. for 3 h. The crude was purified by column chromatography on silica gel. 2-chloro-4-(5-methyl-3-(trifluoromethyl)-1H-1,2,4-triazol-1-yl)pyrimidine (150 mg, 28%) was obtained as a white solid MS (m/z): 264.0 $[M+H]^+$.

Step 2: To a solution of (S)-3-fluoro-5-(1-(piperazine-1-carbonyl)-4,5-dihydro-1H-pyrazol-5-yl)benzonitrile (100 mg, 331.9 umol) in DMF (4 mL) was added 2-chloro-4-(5-methyl-3-(trifluoromethyl)-1H-1,2,4-triazol-1-yl)pyrimidine (70 mg, 331.9 umol) and DIPEA (129 mg, 995.6 umol). The reaction mixture was stirred at 100° C. for 12 h. The crude was purified by Pre-HPLC. (S)-3-fluoro-5-(1-(4-(4-(5-methyl-3-(trifluoromethyl)-1H-1,2,4-triazol-1-yl)pyrimidin-2-yl)piperazine-1-carbonyl)-4,5-dihydro-1H-pyrazol-5-yl)benzonitrile (22 mg, 13%) was obtained as a white solid MS (m/z): 529.1[M+H]$^+$. $^1$H NMR (400 MHz, DMSO-d6) δ 8.59 (d, J=5.3 Hz, 1H), 7.74 (ddd, J=8.4, 2.6, 1.3 Hz, 1H), 7.66 (t, J=1.5 Hz, 1H), 7.54 (ddd, J=9.7, 2.5, 1.4 Hz, 1H), 7.13 (d, J=1.7 Hz, 1H), 7.07 (d, J=5.3 Hz, 1H), 5.30 (dd, J=11.5, 10.1 Hz, 1H), 3.93-3.52 (m, 8H), 3.38 (ddd, J=18.3, 11.6, 1.9 Hz, 1H), 2.91 (s, 3H), 2.71 (ddd, J=18.3, 10.1, 1.6 Hz, 1H).
Compound 148: 1-(2-(4-((S)-5-(3-cyano-5-fluorophenyl)-4,5-dihydro-1H-pyrazole-1-carbonyl)piperazin-1-yl)-5-fluoropyrimidin-4-yl)-2-methyl-1H-imidazole-5-carbonitrile
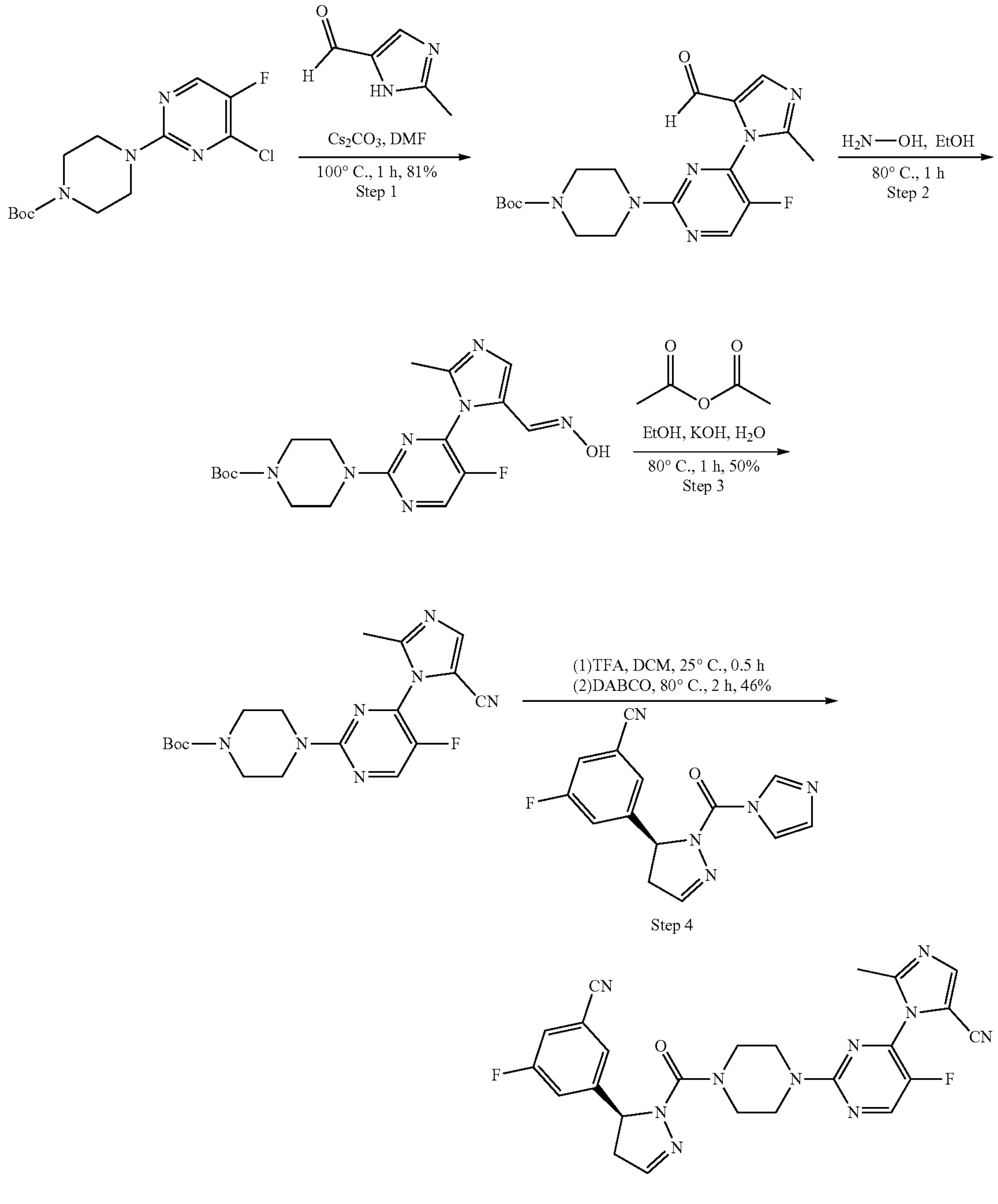

Step 1: tert-butyl 4-(4-chloro-5-fluoropyrimidin-2-yl)piperazine-1-carboxylate (1.0 g, 3.16 mmol), 2-methyl-1H-imidazole-5-carbaldehyde (500 mg, 4.54 mmol), and $Cs_2CO_3$ (2.0 g, 6.09 mmol) in DMF (20 mL) under $N_2$ and the whole reaction mixture was stirred at 100° C. for 1.0 hours. The mixture was concentrated in vacuo to give tert-butyl 4-(5-fluoro-4-(5-formyl-2-methyl-1H-imidazol-1-yl)pyrimidin-2-yl)piperazine-1-carboxylate (1.0 g, 81%) as a yellow oil. MS (m/z): 391.4 $[M+H]^+$.

Step 2: tert-butyl 4-(5-fluoro-4-(5-formyl-2-methyl-1H-imidazol-1-yl)pyrimidin-2-yl)piperazine-1-carboxylate (200 mg, 0.51 mmol), and hydroxylamine (50 mg, 0.81 mmol) were in EtOH (10 mL) under $N_2$ and the whole reaction mixture was stirred at 80° C. for 1 hours. The mixture was concentrated in vacuo to give tert-butyl (E)-4-(5-fluoro-4-(5-((hydroxyimino)methyl)-2-methyl-1H-imidazol-1-yl)pyrimidin-2-yl)piperazine-1-carboxylate (250 mg, crude) as a yellow solid and used into next step reaction without purification. MS (m/z): 406.4 $[M+H]^+$.

Step 3: Tert-butyl (E)-4-(5-fluoro-4-(5-((hydroxyimino)methyl)-2-methyl-1H-imidazol-1-yl)pyrimidin-2-yl)piperazine-1-carboxylate (250 mg, crude), (S)-3-(1-(1H-imidazole-1-carbonyl)-4,5-dihydro-1H-pyrazol-5-yl)-5-fluorobenzonitrile (50 mg, 0.17 mmol), and DABCO (300 mg, 2.67 mmol) were in THF (10 mL) under $N_2$. The solvent was removed under vacuum and the reaction mixture was stand at 80° C. for 2.0 h. The mixture was extracted with EA, washed with brine, dried ($Na_2SO_4$), and concentrated in vacuo. Purification by silica gel chromatography to give compound 148 (57 mg, 46.0%) as a white solid. MS (m/z): 503.4 $[M+H]^+$. $^1H$ NMR (400 MHz, DMSO-$d_6$) δ 8.78 (d, J=2.4 Hz, 1H), 8.51 (d, J=2.8 Hz, 1H), 7.75 (ddd, J=8.4, 2.4, 1.6 Hz, 1H), 7.64 (d, J=1.6 Hz, 1H), 7.53 (dt, J=9.6, 2.0 Hz, 1H), 7.12 (d, J=1.6 Hz, 1H), 5.29 (t, J=10.8 Hz, 1H), 3.82-3.51 (m, 8H), 3.43-3.36 (m, 1H), 3.34 (s, 3H), 2.76-2.67 (m, 1H).

Compound 149: (S)-(5-(3,5-difluorophenyl)-4,5-dihydro-1H-pyrazol-1-yl)(4-(2-(1,4-dimethyl-1H-pyrazol-5-yl)-5-fluoropyridin-4-yl)piperazin-1-yl)methanone

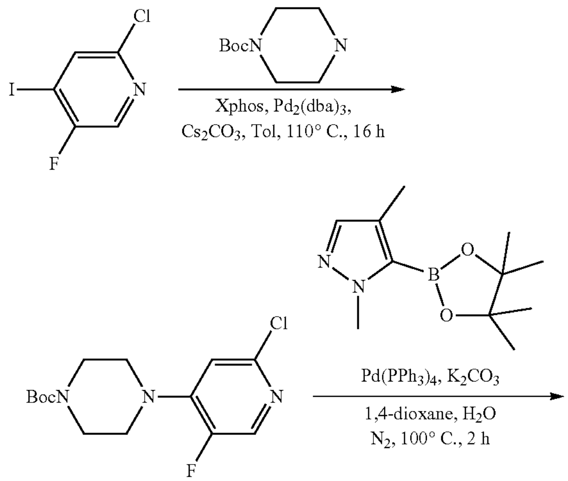

-continued

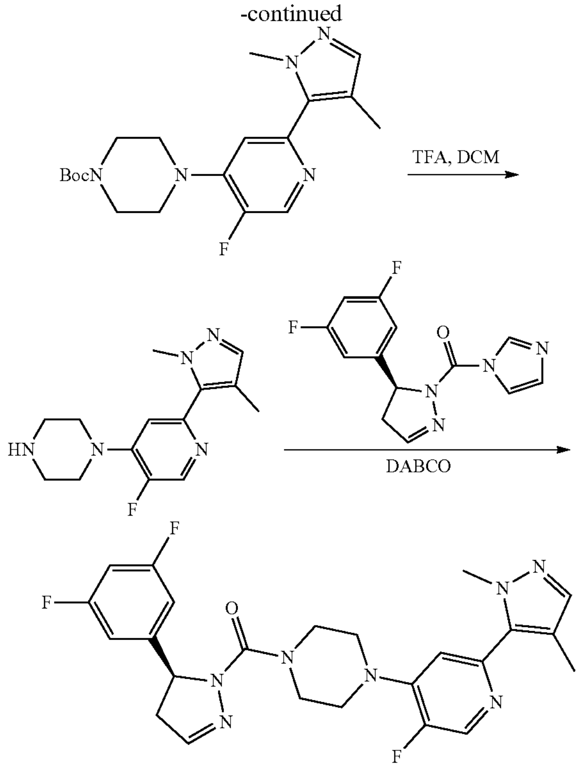

Step 1: 2-chloro-5-fluoro-4-iodopyridine (1.84 g, 7.16 mmoL) and tert-butyl piperazine-1-carboxylate (2.0 g, 10.7 mmoL), $Pd_2(dba)_3$ (655 mg), Xphos (341 mg) and $Cs_2CO_3$ (3.49 g, 10.74 mmoL) were mixed in 30 mL toluene. Let it stir at 110° C. for 16 h. The solvent was evaporated to dryness and purified by chromatography (PE/EA=4/1) to give 1.5 g brown oil. Yield: 66.4%. LC-MS (m/z): 316.4 $[M+H]^+$.

Step 2 and 3 and 4:

The titled compound 149 was prepared in 24.3% yield as a white solid from according to the procedure outlined for compound 143. $^1H$ NMR (400 MHz, Chloroform-d) δ 8.34 (d, J=5.2 Hz, 1H), 7.34 (d, J=0.6 Hz, 1H), 6.91-6.76 (m, 4H), 6.70 (tt, J=8.9, 2.3 Hz, 1H), 5.33 (dd, J=11.7, 9.7 Hz, 1H), 3.93 (s, 3H), 3.88 (ddd, J=13.4, 7.1, 3.2 Hz, 2H), 3.74 (ddd, J=13.3, 6.6, 3.2 Hz, 2H), 3.44-3.36 (m, 2H), 3.36-3.25 (m, 3H), 2.70 (ddd, J=18.3, 9.7, 1.6 Hz, 1H), 2.11 (s, 3H). Mass (m/z): 484.3$[M+H]^+$.

Compound 150: (S)-3-fluoro-5-(1-(4-(5-methoxy-4-(1-methyl-1H-1,2,4-triazol-5-yl)pyrimidin-2-yl)piperazine-1-carbonyl)-4,5-dihydro-1H-pyrazol-5-yl)benzonitrile

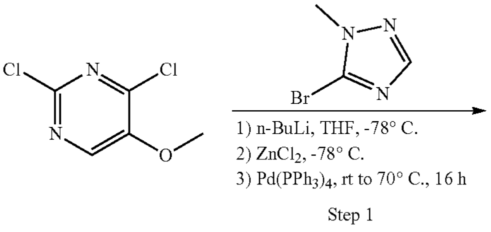

-continued

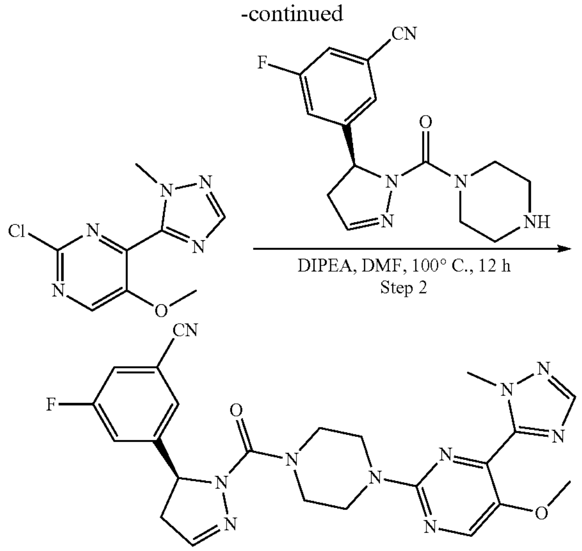

Step 1: To a solution of 5-bromo-1-methyl-1H-1,2,4-triazole (1.13 g, 6.98 mmol) in THF (80 mL) was added n-BuLi (3.4 mL, 8.38 mmol) at −78° C. under Ar. The reaction mixture was stirred at −78° C. for 0.5 h. Then $ZnCl_2$ (7.7 mL, 7.68 mmol) was added to the reaction mixture under −78° C. The reaction mixture was added at −78° C. for 0.5 h. 2,4-dichloro methoxypyrimidine (1 g, 5.59 mmol) and $Pd(PPh_3)_4$ (807 mg, 6.98 mmol) was added to the reaction mixture and the reaction mixture was stirred at 70° C. for 16 h. The crude was purified by column chromatography on silica gel. 2-chloro-5-methoxy-4-(1-methyl-1H-1,2,4-triazol yl)pyrimidine (600 mg, 48%) was obtained as a white solid MS (m/z): 226.0 $[M+H]^+$.

Step 2: To a solution of (S)-3-fluoro-5-(1-(piperazine-1-carbonyl)-4,5-dihydro-1H-pyrazol yl)benzonitrile (80 mg, 265.5 umol) in DMF (3 mL) was added 2-chloro-5-methoxy-4-(1-methyl-1H-1,2,4-triazol-5-yl)pyrimidine (60 mg, 265.5 umol) and DIPEA (172 mg, 1.33 mmol). The reaction mixture was stirred at 100 for 12 h. The crude was purified by Pre-HPLC. (S)-3-fluoro-5-(1-(4-(5-methoxy-4-(1-methyl-1H-1,2,4-triazol-5-yl)pyrimidin-2-yl)piperazine-1-carbonyl)-4,5-dihydro-1H-pyrazol-5-yl)benzonitrile (9 mg, 7%) was obtained as a white solid MS (m/z): 491.1 $[M+H]^+$.

Compound 151: (S)-5-(5-fluoro-2-(4-(5-(5-methylthiazol-2-yl)-4,5-dihydro-1H-pyrazole-1-carbonyl)piperazin-1-yl)pyrimidin-4-yl)-1-methyl-1H-1,2,4-triazole-3-carbonitrile

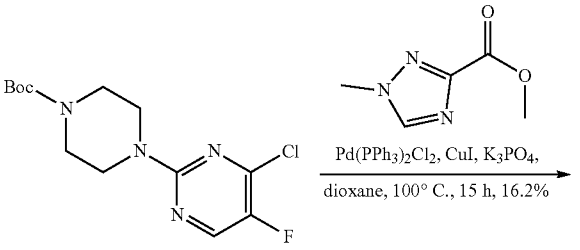

-continued

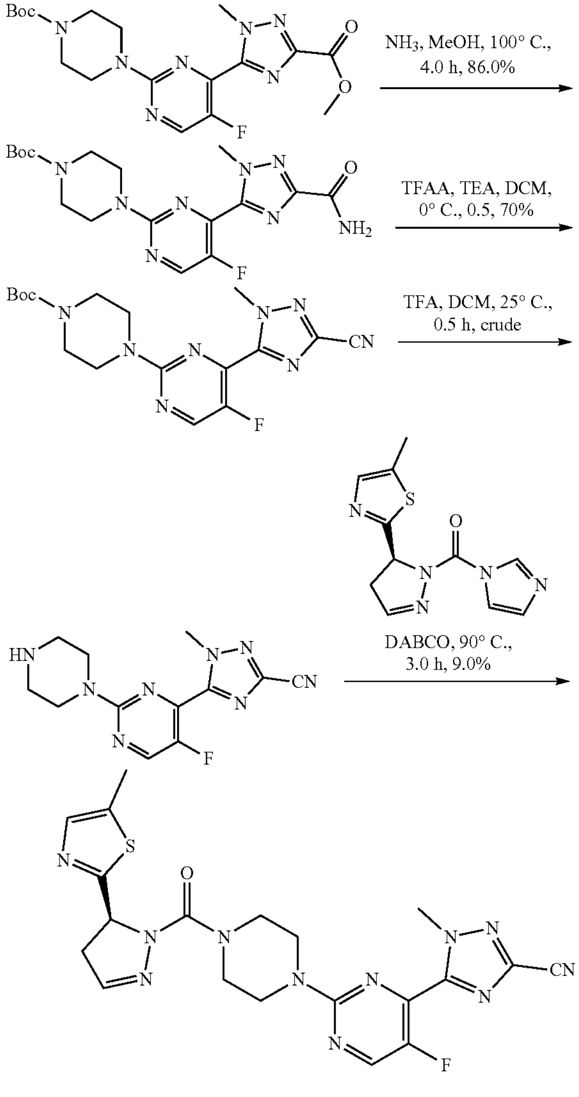

Step 1: tert-butyl 4-(4-chloro-5-fluoropyrimidin-2-yl)piperazine-1-carboxylate (2.8 g, 12.96 mmol), CuI (4.0 g, 21.05 mmol), methyl 1-methyl-1H-1,2,4-triazole-3-carboxylate (2.0 g, 14.08 mmol), $Pd(PPh_3)_2Cl_2$ (3.0 g, 4.28 mmol), $K_3PO_4$ (6.0 g, 28.30 mmol) were in dioxane (200 mL) under $N_2$ and the whole reaction mixture was stirred at 100° C. for 15 hours. The mixture was extracted with EA, washed with brine, dried ($Na_2SO_4$), and concentrated in vacuo. Purification by silica gel chromatography to give tert-butyl 4-(5-fluoro-4-(3-(methoxycarbonyl)-1-methyl-1H-1,2,4-triazol-5-yl)pyrimidin-2-yl)piperazine-1-car (600 mg, 16.2%) as a yellow solid. MS (m/z): 422.2 $[M+H]^+$.

Step 2: tert-butyl 4-(5-fluoro-4-(3-(methoxycarbonyl)-1-methyl-1H-1,2,4-triazol-5-yl)pyrimidin-2-yl)piperazine-1-car (600 mg, 1.42 mmol) was in $NH_3$ in MeOH (10 mL, 7M) under $N_2$ and the whole reaction mixture was stirred at 100° C. for 4.0 hours. The mixture was extracted with EA, washed with brine, dried ($Na_2SO_4$), and concentrated in vacuo. Purification by silica gel chromatography to give tert-butyl 4-(4-(3-carbamoyl-1-methyl-1H-1,2,4-triazol-5-yl)-5-fluoropyrimidin-2-yl)piperazine-1-carboxylate (500 mg, 86.0%) as a yellow solid. MS (m/z): 407.2 $[M+H]^+$.

Step 3: tert-butyl 4-(4-(3-carbamoyl-1-methyl-1H-1,2,4-triazol-5-yl)-5-fluoropyrimidin yl)piperazine-1-carboxylate (300 mg, 0.71 mmol), TFAA (310 mg, 1.47 mmol), TEA (223 mg, 2.20 mmol) were in DCM (10 mL) under $N_2$ and the whole reaction mixture was stirred at 0° C. for 0.5 hours. The mixture was extracted with EA, washed with brine, dried ($Na_2SO_4$), and concentrated in vacuo. Purification by silica gel chromatography to give tert-butyl 4-(4-(3-cyano-1-methyl-1H-1,2,4-triazol-5-yl)-5-fluoropyrimidin-2-yl) piperazine-1-carboxylate (200 mg, 70.0%) as a yellow oil. MS (m/z): 389.2 $[M+H]^+$.

Step 4: tert-butyl 4-(4-(3-cyano-1-methyl-1H-1,2,4-triazol-5-yl)-5-fluoropyrimidin-2-yl)piperazine-1-carboxylate (200 mg, 0.51 mmol), TFA (2 mL) were in DCM (5 mL) under $N_2$ and the whole reaction mixture was stirred at 25° C. for 0.5 hours. The mixture was concentrated in vacuo to give 5-(5-fluoro-2-(piperazin-1-yl)pyrimidin-4-yl)-1-methyl-1H-1,2,4-triazole-3-carbonitrile (300 mg, crude) as a brown oil and used into next step reaction without purification. MS (m/z): 289.2 $[M+H]^+$.

Step 5: 5-(5-fluoro-2-(piperazin-1-yl)pyrimidin-4-yl)-1-methyl-1H-1,2,4-triazole-3-carbonitrile (300 mg, crude), (S)-(1H-imidazol-1-yl)(5-(5-methylthiazol-2-yl)-4,5-dihydro-1H-pyrazol-1-yl)methanone (30 mg, 0.11 mmol), and DABCO (200 mg, 1.78 mmol) were in THF (10 mL) under $N_2$. The solvent was removed under vacuum and the reaction mixture was stand at 90° C. for 3.0 h. The mixture was extracted with EA, washed with brine, dried ($Na_2SO_4$), and concentrated in vacuo. Purification by silica gel chromatography to give compound 151 (5.0 mg, 9.0%) as a white solid. MS (m/z): 482.2 $[M+H]^+$. $^1H$ NMR (400 MHz, Chloroform-d) δ 8.47 (d, J=2.0 Hz, 1H), 7.37 (s, 1H), 6.90 (d, J=1.6 Hz, 1H), 5.71 (t, J=10.4 Hz, 1H), 4.29 (s, 3H), 3.95-3.62 (m, 8H), 3.33 (d, J=10.4 Hz, 2H), 2.43 (s, 3H).

Compound 152: (S)-3-(1-(4-(4-(5-acetyl-1-methyl-1,4,5,6-tetrahydropyrrolo[3,4-c]pyrazol-3-yl)-5-fluoropyrimidin-2-yl)piperazine-1-carbonyl)-4,5-dihydro-1H-pyrazol-5-yl)-5-fluorobenzonitrile

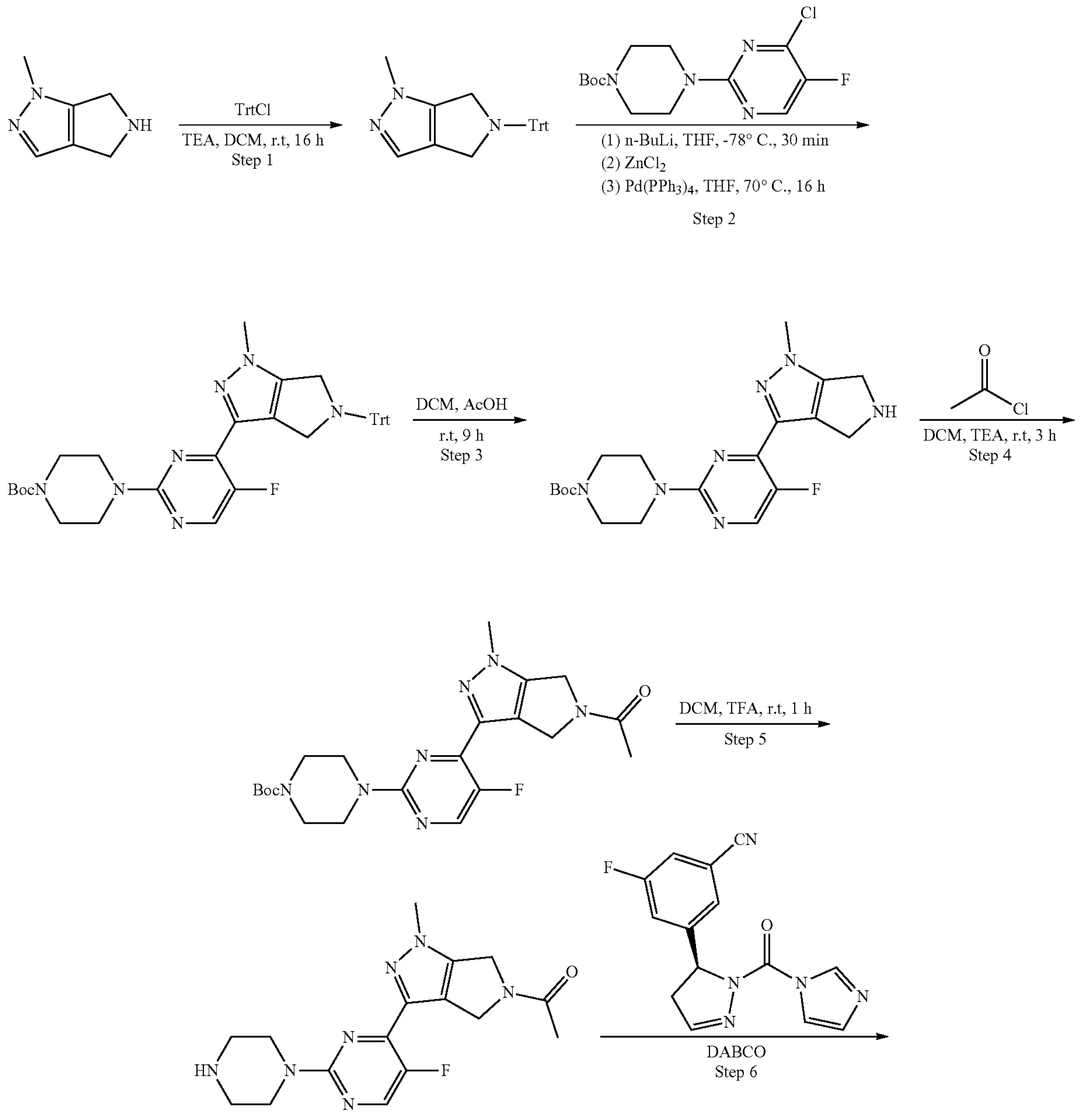

-continued

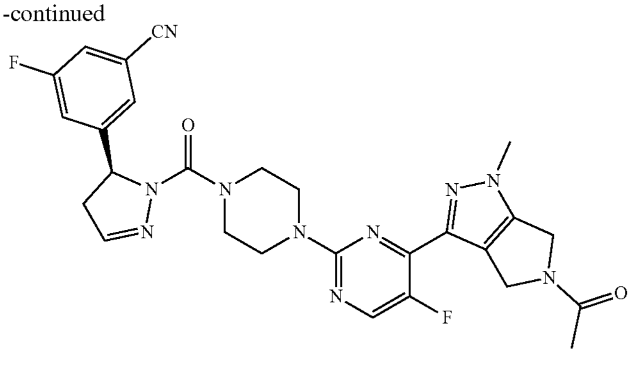

Step 1: Synthesis of 1-methyl-5-trityl-1,4,5,6-tetrahydropyrrolo[3,4-c]pyrazole 1-methyl-1,4,5,6-tetrahydropyrrolo[3,4-c]pyrazole hydrogen chloride (0.487 g, 3.063 mmol), triphenylMethyl chloride (0.974 g, 3.493 mmol) and TEA (0.3 mL) were mixed in 5 mL DCM. Let it stir at room temperature for 16 h. The solvent was evaporated to dryness and purified by column chromatography (PE/EA=1/1) to give 540 mg white solid. Yield: 48.2%. LC-MS (m/z): 366.4 $[M+H]^+$.

Step 2: Synthesis of tert-butyl 4-(5-fluoro-4-(1-methyl-5-trityl-1,4,5,6-tetrahydropyrrolo[3,4-c]pyrazol-3-yl)pyrimidin-2-yl)piperazine-1-carboxylate 1-methyl-5-trityl-1,4,5,6-tetrahydropyrrolo[3,4-c]pyrazole (560 mg, 1.53 mmol) was dissolved in 15 mL THF. n-BuLi (0.765 mL, 1.836 mmol) was added dropwise to the solution at −78° C. Let it stir at −78° C. for 30 min. Then $ZnCl_2$ solution (1.68 mL, 1.68 mmoL) was added slowly to the solution at −78° C. Let it stir at −78° C. for 30 min.

Then let it stir at room temperature for 1 h. Tert-butyl 4-(4-chloro-5-fluoropyrimidin-2-yl)piperazine-1-carboxylate (386.8 mg, 1.22 mmoL) and $Pd(PPh_3)_4$ (176.8 mg, 0.153 mmoL) in 5 mL THF was added. Let it stir at 70° C. for 16 h. The solvent was evaporated to dryness and purified by column chromatography (PE/EA=3/1) to give 250 mg light-yellow solid. Yield: 31.7%. LC-MS (m/z): 404.4 $[M+H-Trt]^+$.

Step 3: Synthesis of tert-butyl 4-(5-fluoro-4-(1-methyl-1,4,5,6-tetrahydropyrrolo[3,4-c]pyrazol-3-yl)pyrimidin-2-yl)piperazine-1-carboxylate Tert-butyl 4-(5-fluoro-4-(1-methyl-5-trityl-1,4,5,6-tetrahydropyrrolo[3,4-c]pyrazol-3-yl)pyrimidin-2-yl)piperazine-1-carboxylate (125 mg, 0.193 mmoL) was dissolved in 5 mL DCM. 3 mL AcOH was added. Let it stir at r.t for 9 h. The solution was neutralized with sat. $Na_2CO_3$ solution and extracted with DCM (15 mL×3). Dried with $Na_2SO_4$, filtered and evaporated to dryness to give 139 mg crude product as brown oil. LC-MS (m/z): 404.3 $[M+H]^+$.

Step 4: Synthesis of tert-butyl 4-(4-(5-acetyl-1-methyl-1,4,5,6-tetrahydropyrrolo[3,4-c]pyrazol-3-yl)-5-fluoropyrimidin-2-yl)piperazine-1-carboxylate The above oil (139 mg) was dissolved in 3 mL DCM. 0.3 mL TEA was added. Acetyl chloride (37.3 mg, 0.379 mmoL) was added. Let it stir at r.t for 3 h. The solvent was evaporated to dryness and purified by column chromatography (EA) to give 99 mg light-yellow oil. Total yield of step 3 and 4: quantitative. LC-MS (m/z): 446.4 $[M+H]^+$.

Step 5: Synthesis of 1-(3-(5-fluoro-2-(piperazin-1-yl)pyrimidin-4-yl)-1-methyl-4,6-dihydropyrrolo[3,4-c]pyrazol-5(1H)-yl)ethan-1-one Tert-butyl 4-(4-(5-acetyl-1-methyl-1,4,5,6-tetrahydropyrrolo[3,4-c]pyrazol-3-yl) fluoropyrimidin-2-yl)piperazine-1-carboxylate (99 mg, 0.222 mmoL) was dissolved in 2 mL DCM. 2 mL DCM/TFA (1/1) was added slowly to the solution at 0° C. Let it stir at r.t for 1 h. The solvent was evaporated to dryness to give 75 mg crude product as brown oil. It was used for next step without further purification. LC-MS (m/z): 346.4 $[M+H]^+$.

Step 6: Synthesis of (5)-3-(1-(4-(4-(5-acetyl-1-methyl-1,4,5,6-tetrahydropyrrolo[3,4-c]pyrazol-3-yl)-5-fluoropyrimidin-2-yl)piperazine-1-carbonyl)-4,5-dihydro-1H-pyrazol-5-yl)-5-fluorobenzonitrile The above oil (75 mg) and (S)-3-(1-(1H-imidazole-1-carbonyl)-4,5-dihydro-1H-pyrazol-5-yl)-5-fluorobenzonitrile (62.8 mg 0.222 mmoL) and DABCO (100 mg, 0.893 mmoL) were mixed in 2 mL THF. Let it evaporated to dryness and irradiated under 125 W incandescent lamp for 1 h. The mixture was purified by prep-HPLC to give 25 mg off-white solid. Yield: 20.1%. LC-MS (m/z): 561.4 $[M+H]^+$. $^1H$ NMR (400 MHz, $CDCl_3$) δ 8.22-8.18 (m, 1H), 7.41 (s, 1H), 7.36 (d, J=11.6 Hz, 1H), 7.29-7.27 (m, 1H), 6.91-6.87 (m, 1H), 5.39-5.31 (m, 1H), 5.29-5.24 (m, 2H), 4.70-4.52 (m, 4H), 3.82-3.74 (m, 2H), 3.74-3.62 (m, 5H), 3.62-3.54 (m, 2H), 3.35 (ddd, J=18.4, 11.6, 1.6 Hz, 1H), 2.69 (ddd, J=18.4, 10.0, 1.6 Hz, 1H), 2.16 (s, 3H).

Compound 153: (S)-3-(1-(4-(4-(3-amino-1,4-dimethyl-1H-pyrazol-5-yl)-5-fluoropyrimidin-2-yl)piperazine-1-carbonyl)-4,5-dihydro-1H-pyrazol-5-yl)-5-fluorobenzonitrile

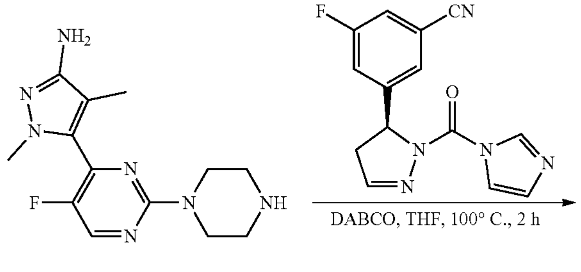

-continued

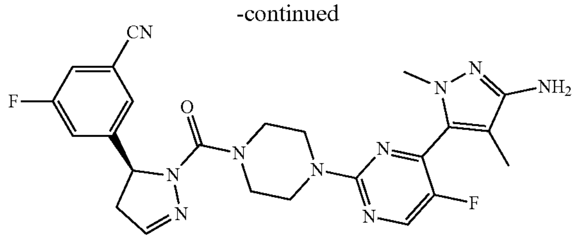

The titled compound 153 was prepared in 53.2% yield according to the procedure outlined for compound 143. $^1H$ NMR (300 MHz, Chloroform-d) δ 8.39 (t, J=1.6 Hz, 1H), 7.41 (d, J=1.7 Hz, 1H), 7.27 (d, J=4.8 Hz, 2H), 6.90 (d, J=1.6 Hz, 1H), 5.37 (t, J=10.8 Hz, 1H), 3.93-3.33 (m, 14H), 2.70 (ddd, J=18.2, 10.1, 1.7 Hz, 1H), 1.93 (s, 3H). LC-MS (m/z) 507.4 ($M+H^+$).

Compound 154: (S)-3-(1-(4-(4-(3-amino-1,4-dimethyl-1H-pyrazol-5-yl)pyrimidin-2-yl)piperazine-1-carbonyl)-4,5-dihydro-1H-pyrazol-5-yl)-5-fluorobenzonitrile

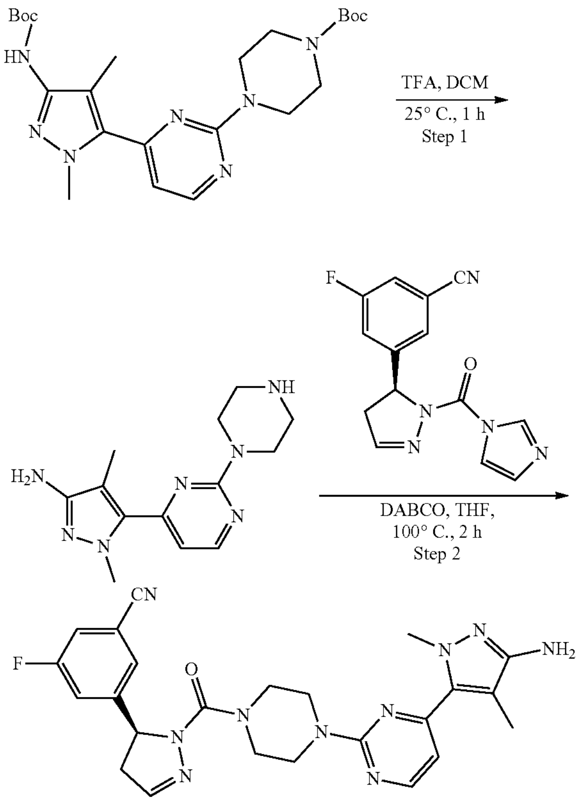

The titled compound 154 was prepared in 49.3% yield according to the procedure outlined for compound 143. $^1H$ NMR (300 MHz, Chloroform-d) δ 8.52 (d, J=4.7 Hz, 1H), 7.41 (s, 1H), 7.28 (d, J=4.4 Hz, 2H), 6.92 (s, 1H), 6.65 (d, J=4.8 Hz, 1H), 5.37 (t, J=10.8 Hz, 1H), 4.11-3.60 (m, 13H), 3.37 (ddd, J=18.3, 11.7, 2.0 Hz, 1H), 2.71 (dd, J=18.3, 9.9 Hz, 1H), 2.02 (d, J=2.7 Hz, 3H). LC-MS (m/z) 489.3 ($M+H^+$).

Compound 155: (S)-(4-(4-(3-amino-1,4-dimethyl-1H-pyrazol-5-yl)-5-fluoropyrimidin yl)piperazin-1-yl)(5-(3,5-difluorophenyl)-4,5-dihydro-1H-pyrazol-1-yl)methanone

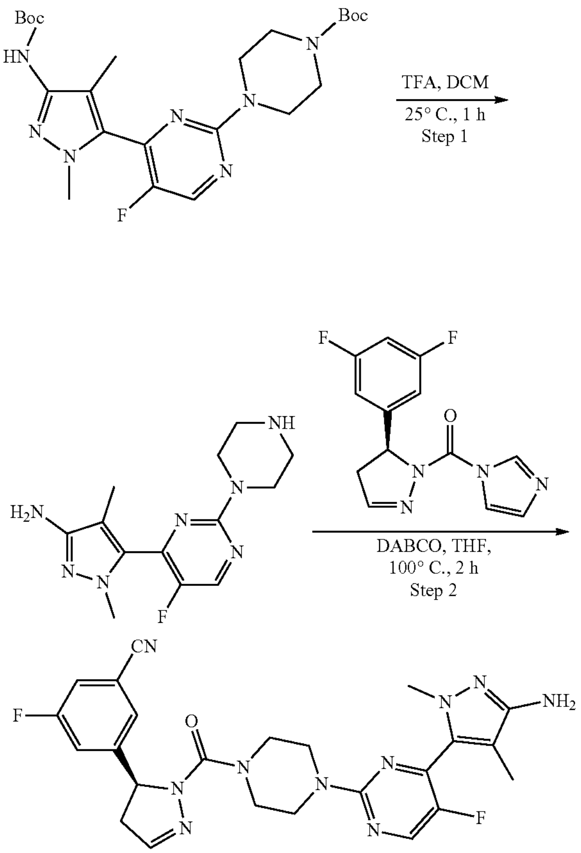

The titled compound 155 was prepared in 22.6% yield according to the procedure outlined for compound 143. $^1H$ NMR (300 MHz, Chloroform-d) δ 8.31 (d, J=2.0 Hz, 1H), 7.27 (s, 1H), 6.88-6.77 (m, 2H), 6.69 (tt, J=8.8, 2.3 Hz, 1H), 5.33 (dd, J=11.7, 9.9 Hz, 1H), 3.95-3.56 (m, 11H), 3.36-3.24 (m, 1H), 2.69 (ddd, J=18.3, 9.9, 1.7 Hz, 1H), 2.26 (s, 2H), 1.93 (s, 3H). LC-MS (m/z) 500.4 ($M+H^+$).

Compound 156: (4-(2-(1,4-dimethyl-1H-pyrazol-5-yl)-5-fluoropyridin-4-yl)piperazin-1-yl)(5-(2-methylthiazol-4-yl)-4,5-dihydro-1H-pyrazol-1-yl)methanone

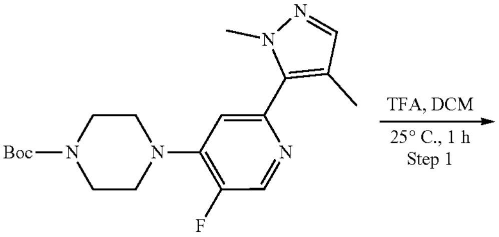

-continued

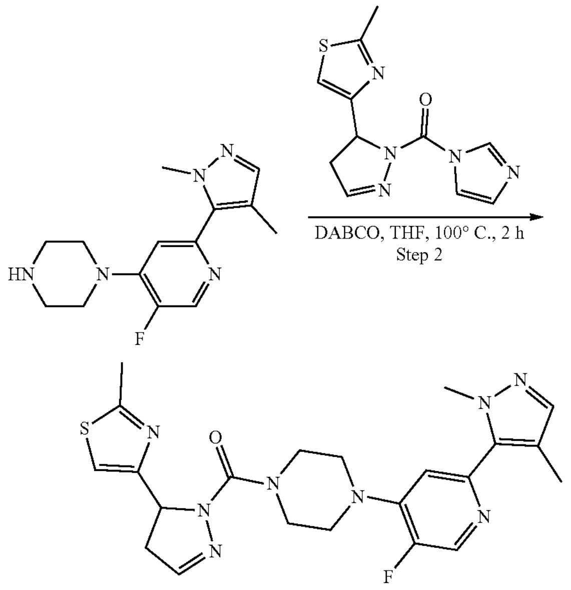

The titled compound 156 was prepared in 30.2% yield as a white solid according to the procedure outlined for compound 143. $^{1}$H NMR (400 MHz, Chloroform-d) δ 8.36 (d, J=5.6 Hz, 1H), 7.36 (s, 1H), 7.07 (d, J=0.5 Hz, 1H), 6.90 (t, J=1.7 Hz, 1H), 6.79 (d, J=7.4 Hz, 1H), 5.50 (dd, J=11.4, 9.9 Hz, 1H), 3.94 (s, 3H), 3.91-3.83 (m, 2H), 3.72 (ddd, J=13.3, 6.6, 3.0 Hz, 2H), 3.41 (d, J=33.8 Hz, 4H), 3.29-3.13 (m, 2H), 2.69 (s, 3H), 2.11 (d, J=0.6 Hz, 3H). LC-MS (m/z) 469.3 (M+H$^{+}$).

Compound 157: (4-(2-(1,4-dimethyl-1H-pyrazol-5-yl)-5-fluoropyridin-4-yl)piperazin-1-yl)(5-(4-methylthiazol-2-yl)-4,5-dihydro-1H-pyrazol-1-yl)methanone

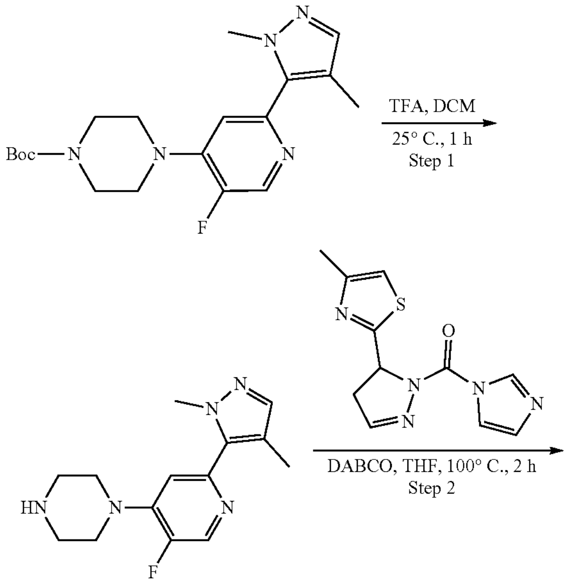

-continued

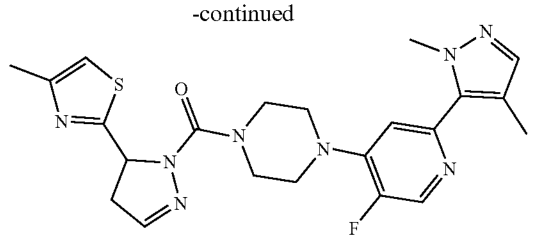

The titled compound 157 was prepared in 20.5% yield according to the procedure outlined for compound 143. $^{1}$H NMR (400 MHz, Chloroform-d) δ 8.36 (d, J=5.5 Hz, 1H), 7.36 (d, J=0.7 Hz, 1H), 6.90 (t, J=1.7 Hz, 1H), 6.83-6.75 (m, 2H), 5.75 (dd, J=11.8, 9.2 Hz, 1H), 3.94 (s, 5H), 3.77 (ddd, J=13.4, 6.7, 3.2 Hz, 2H), 3.51-3.32 (m, 5H), 3.24 (ddd, J=18.4, 9.3, 1.7 Hz, 1H), 2.42 (d, J=1.0 Hz, 3H), 2.12 (d, J=0.6 Hz, 3H). LC-MS (m/z) 469.3 (M+H$^{+}$).

Compound 158: (4-(2-(1,4-dimethyl-1H-pyrazol-5-yl)-5-fluoropyrimidin-4-yl)piperazin yl)(5-(2-methylthiazol-4-yl)-4,5-dihydro-1H-pyrazol-1-yl)methanone

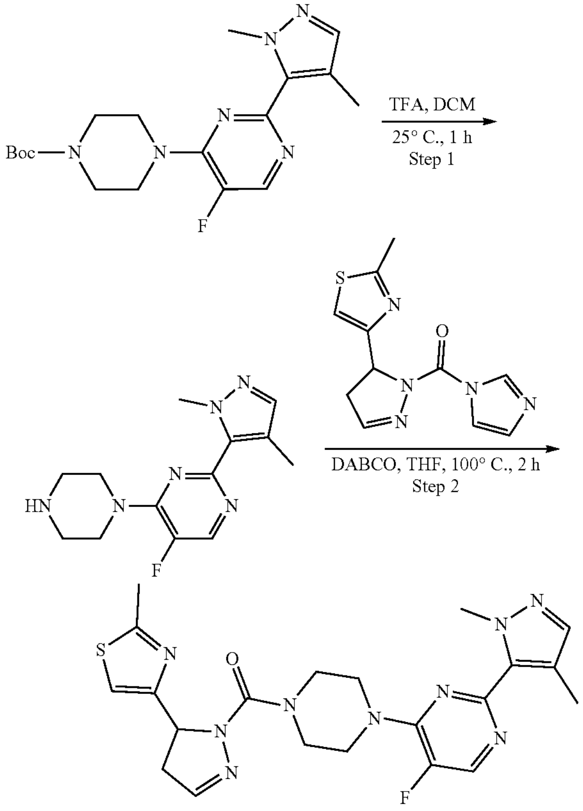

The titled compound 158 was prepared in 17.7% yield according to the procedure outlined for compound 143. $^{1}$H NMR (400 MHz, Chloroform-d) δ 8.18 (d, J=6.3 Hz, 1H), 7.33 (s, 1H), 7.07 (s, 1H), 6.90 (t, J=1.7 Hz, 1H), 5.50 (dd, J=11.4, 9.9 Hz, 1H), 4.14 (s, 3H), 3.94-3.87 (m, 2H), 3.87-3.77 (m, 4H), 3.71-3.61 (m, 2H), 3.28-3.12 (m, 2H), 2.68 (s, 3H), 2.28 (s, 3H). LC-MS (m/z) 470.3 (M+H$^{+}$).

Compound 159: (4-(2-(1,4-dimethyl-1H-pyrazol-5-yl)-5-fluoropyrimidin-4-yl)piperazin-1-yl)(5-(thiazol-5-yl)-4,5-dihydro-1H-pyrazol-1-yl)methanone

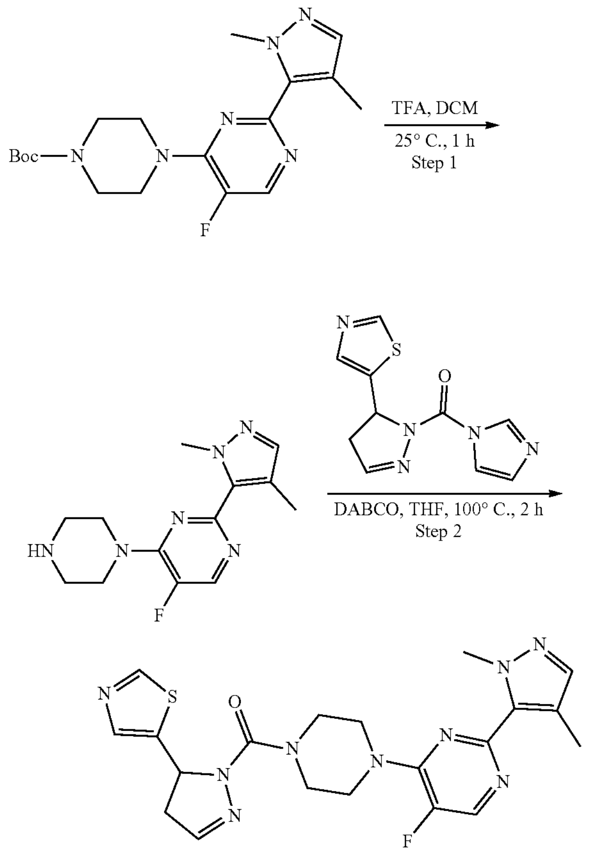

The titled compound 159 was prepared in 13.2% yield according to the procedure outlined for compound 143. $^1$H NMR (400 MHz, Chloroform-d) δ 8.71 (d, J=0.7 Hz, 1H), 8.18 (d, J=6.3 Hz, 1H), 7.84 (d, J=0.7 Hz, 1H), 7.31 (d, J=0.7 Hz, 1H), 6.91 (t, J=1.7 Hz, 1H), 5.70 (dd, J=11.4, 10.0 Hz, 1H), 4.12 (s, 3H), 3.95-3.86 (m, 2H), 3.85-3.75 (m, 4H), 3.69-3.58 (m, 2H), 3.38 (ddd, J=18.3, 11.5, 1.8 Hz, 1H), 2.88 (ddd, J=18.2, 10.0, 1.6 Hz, 1H), 2.26 (s, 3H). LC-MS (m/z) 456.3 (M+H$^+$).

Compound 160: (4-(2-(1,4-dimethyl-1H-pyrazol-5-yl)-5-fluoropyrimidin-4-yl)piperazin-1-yl)(5-(thiazol-4-yl)-4,5-dihydro-1H-pyrazol-1-yl)methanone

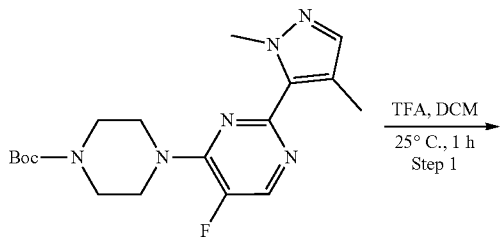

-continued

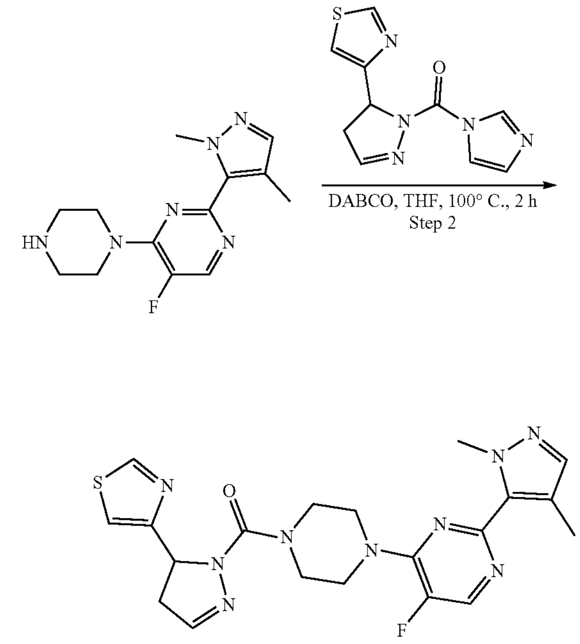

The titled compound 160 was prepared in 13.2% yield according to the procedure outlined for compound 143. $^1$H NMR (400 MHz, Chloroform-d) δ 8.77 (d, J=2.1 Hz, 1H), 8.18 (d, J=6.4 Hz, 1H), 7.33 (dd, J=6.6, 1.4 Hz, 2H), 6.92 (t, J=1.7 Hz, 1H), 5.63 (dd, J=11.3, 9.7 Hz, 1H), 4.13 (s, 3H), 3.95-3.86 (m, 2H), 3.86-3.75 (m, 4H), 3.72-3.60 (m, 2H), 3.34-3.16 (m, 2H), 2.27 (d, J=0.6 Hz, 3H). LC-MS (m/z) 456.2 (M+H$^+$).

Compound 161: (4-(2-(1,4-dimethyl-1H-pyrazol-5-yl)-5-fluoropyrimidin-4-yl)piperazin yl)(5-(4-methylthiazol-2-yl)-4,5-dihydro-1H-pyrazol-1-yl)methanone

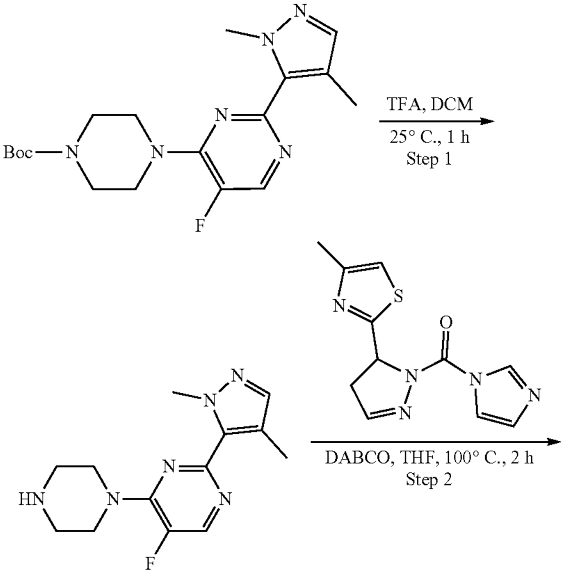

-continued

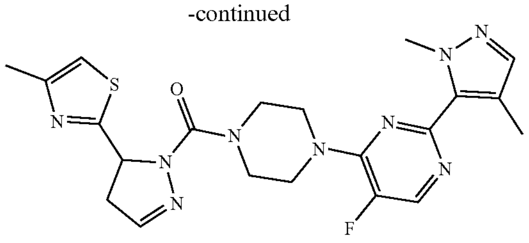

The titled compound 161 was prepared in 12.1% yield according to the procedure outlined for compound 143. $^{1}H$ NMR (400 MHz, Chloroform-d) δ 8.20 (d, J=6.3 Hz, 1H), 7.34 (d, J=0.8 Hz, 1H), 6.91 (t, J=1.7 Hz, 1H), 6.82 (q, J=1.0 Hz, 1H), 5.76 (dd, J=11.8, 9.3 Hz, 1H), 4.15 (s, 3H), 3.98-3.66 (m, 8H), 3.43-3.18 (m, 2H), 2.43 (d, J=1.0 Hz, 3H), 2.29 (d, J=0.5 Hz, 3H). LC-MS (m/z) 470.3 ($M+H^{+}$).

Compound 162: (4-(2-(1,4-dimethyl-1H-pyrazol-5-yl)-5-fluoropyrimidin-4-yl)piperazin-1-yl)(5-(2-methylthiazol-5-yl)-4,5-dihydro-1H-pyrazol-1-yl) methanone

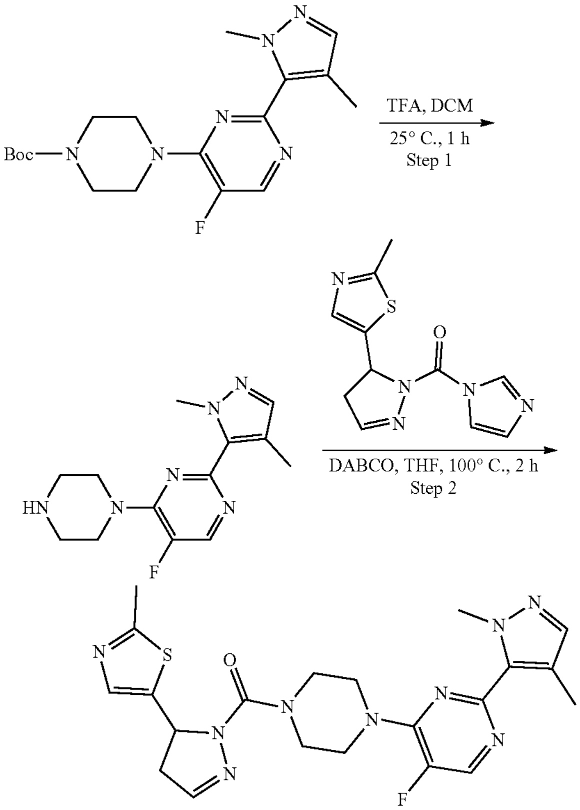

The titled compound 162 was prepared in 25.9% yield according to the procedure outlined for compound 143. $^{1}H$ NMR (400 MHz, Chloroform-d) δ 8.20 (d, J=6.3 Hz, 1H), 7.57 (s, 1H), 7.34 (s, 1H), 6.93-6.87 (m, 1H), 5.62 (t, J=10.7 Hz, 1H), 4.14 (s, 3H), 3.95-3.85 (m, 2H), 3.84-3.75 (m, 4H), 3.65 (dd, J=10.3, 6.8 Hz, 2H), 3.34 (ddd, J=18.2, 11.5, 1.8 Hz, 1H), 2.93-2.82 (m, 1H), 2.65 (s, 3H), 2.29 (s, 3H). LC-MS (m/z) 470.3 ($M+H^{+}$).

Compound 163: (S)-3-fluoro-5-(1-(4-(5-fluoro-4-(3-(hydroxymethyl)-5-methyl-1H-pyrazol-4-yl)pyrimidin-2-yl)piperazine-1-carbonyl)-4,5-dihydro-1H-pyrazol-5-yl)benzonitrile

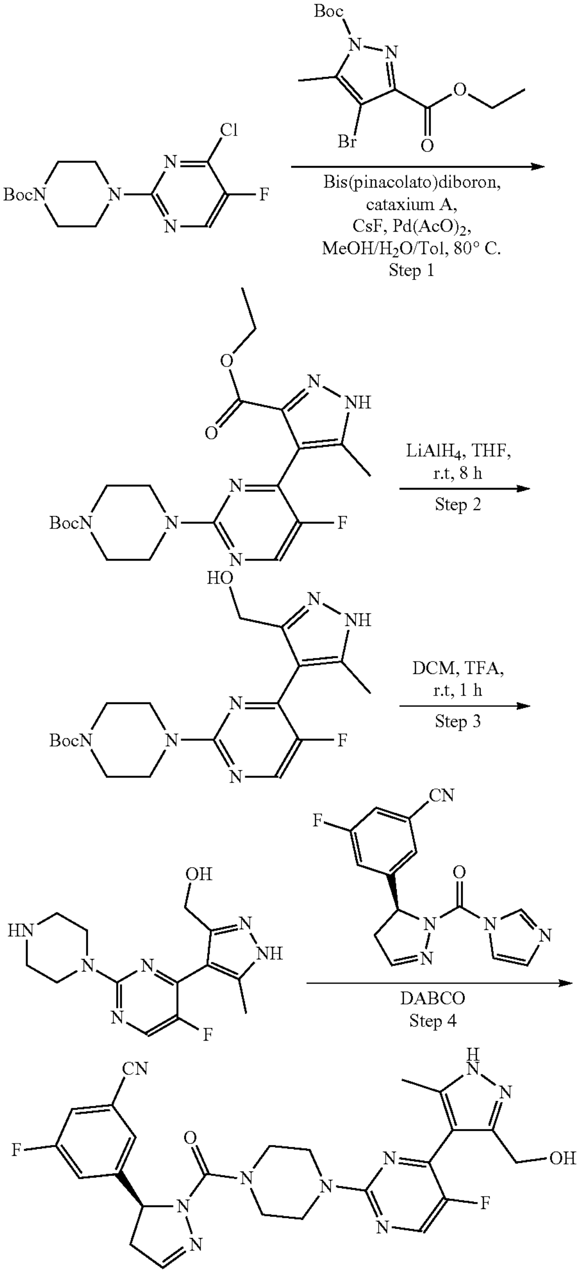

Step 1: Synthesis of tert-butyl 4-(4-(3-(ethoxycarbonyl)-5-methyl-1H-pyrazol-4-yl) fluoropyrimidin-2-yl)piperazine-1-carboxylate Tert-butyl 4-(4-chloro-5-fluoropyrimidin-2-yl)piperazine-1-carboxylate (316 mg, 1 mmoL), 1-(tert-butyl) 3-ethyl 4-bromo-5-methyl-1H-pyrazole-1,3-dicarboxylate (390 mg, 1.175 mmoL), cataxium A (72 mg, 0.2 mmoL), bis(pinacolato)diboron (380 mg, 3.534 mmoL), CsF (789.88 mg, 5.2 mmoL) and $Pd(AcO)_2$ (22.4 mg, 0.1 mmoL) were mixed in 15 mL MeOH/$H_2O$ (9/1). Let it stir at 60° C. for 3 h. Then another part of cataxium A (36 mg, 0.1 mmoL) and $Pd(AcO)_2$ (11 mg, 0.05 mmoL) in 2 mL toluene were added. Let it stir at 80° C. for 16 h. The solvent was evaporated to dryness and purified by column chromatography (PE/EA=3/1) to give 180 mg light-yellow oil. Yield: 41.3%. LC-MS (m/z): 435.4 $[M+H]^+$.

Step 2: Synthesis of tert-butyl 4-(5-fluoro-4-(3-(hydroxymethyl)-5-methyl-1H-pyrazol-4-yl)pyrimidin-2-yl)piperazine-1-carboxylate Tert-butyl 4-(4-(3-(ethoxycarbonyl)-5-methyl-1H-pyrazol-4-yl)-5-fluoropyrimidin-2-yl)piperazine-1-carboxylate (150 mg, 0.346 mmoL) was dissolved in 4 mL THF. $LiAlH_4$ (1M in THF solution, 0.6 mL, 0.6 mmoL) was added slowly to the solution at 0° C. Let it stir at r.t for 8 h. 0.6 mL $H_2O$ and 0.6 mL 1N NaOH was added to quench the reaction. It was filtered with celite. The filtrate was evaporated to dryness to give 180 mg brown oil crude product and used for next step without further purification.

Step 3 and Step 4

The titled compound 163 was prepared as white solid in a yield of 3.7% according to the procedure outlined for compound 152. LC-MS (m/z): 508.3 $[M+H]^+$. $^1H$ NMR (400 MHz, $CDCl_3$) δ 8.24 (s, 1H), 7.52-7.42 (m, 2H), 7.28 (s, 1H), 6.89 (s, 1H), 5.43-5.26 (m, 2H), 5.18-4.92 (m, 2H), 4.85-4.40 (m, 3H), 3.91-3.81 (m, 2H), 3.76 (s, 3H), 3.68-3.59 (m, 2H), 3.35 (ddd, J=18.4, 11.6, 1.6 Hz, 1H), 2.69 (ddd, J=18.4, 10.0, 1.6 Hz, 1H).

Compound 164: (S)-3-fluoro-5-(1-(4-(5-fluoro-4-(4-methyl-2-oxo-1,2-dihydropyridin-3-yl)pyrimidin-2-yl)piperazine-1-carbonyl)-4,5-dihydro-1H-pyrazol-5-yl)benzonitrile

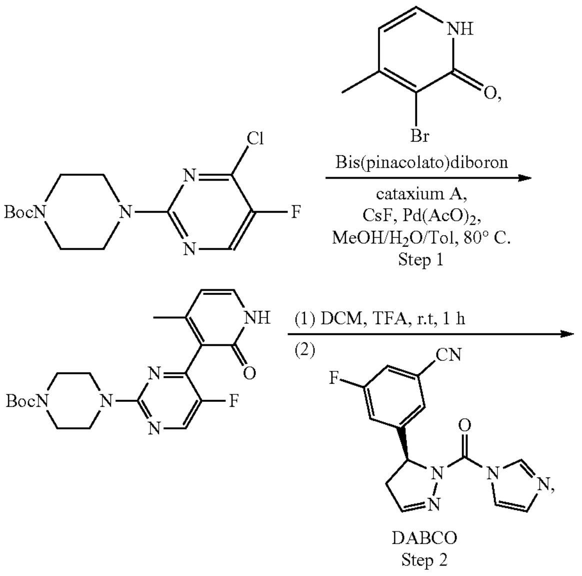

-continued

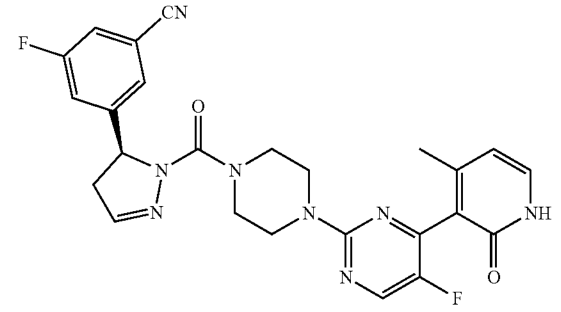

The titled compound 164 was prepared as white solid in a yield of 40.8% according to the procedure outlined for compound 152. LC-MS (m/z): 505.3 $[M+H]^+$.

Compound 165: (S)-3-fluoro-5-(1-(4-(5-fluoro-4-(3-(hydroxymethyl)-1,5-dimethyl-1H-pyrazol-4-yl)pyrimidin-2-yl)piperazine-1-carbonyl)-4,5-dihydro-1H-pyrazol-5-yl)benzonitrile

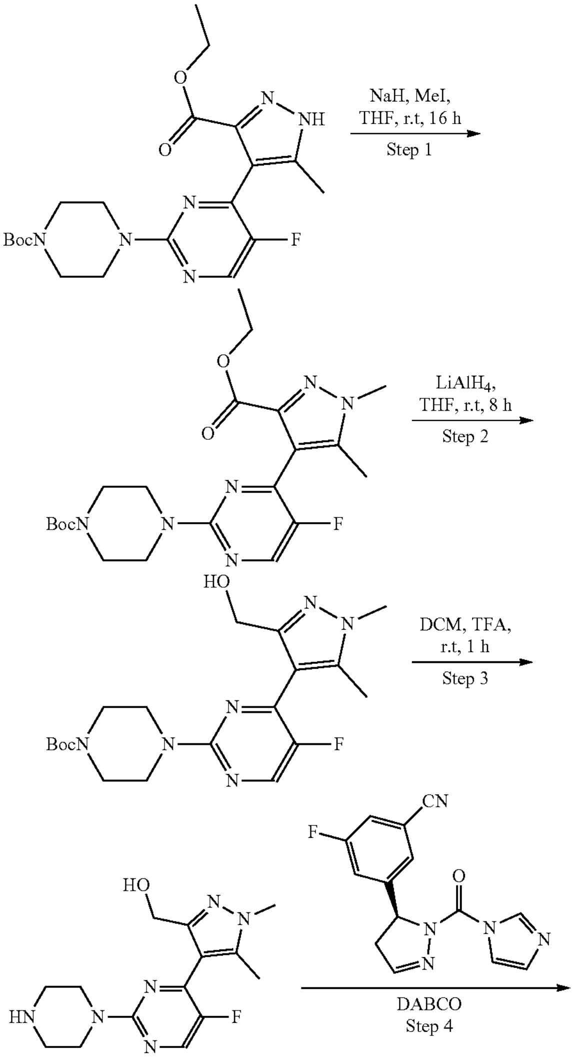

-continued

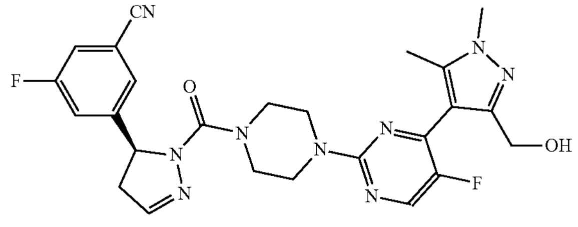

Step 1: Synthesis of tert-butyl 4-(4-(3-(ethoxycarbonyl)-1,5-dimethyl-1H-pyrazol-4-yl)-5-fluoropyrimidin-2-yl)piperazine-1-carboxylate Tert-butyl 4-(4-(3-(ethoxycarbonyl)-5-methyl-1H-pyrazol-4-yl)-5-fluoropyrimidin-2-yl)piperazine-1-carboxylate (140 mg, 0.322 mmoL) was dissolved in 3 mL THF. NaH (28 mg, 0.7 mmoL) was added in portions at 0° C. Let it stir at r.t for 16 h. Water was added and extracted with EtOAc (15 mL×3). Dried with $Na_2SO_4$, filtered and evaporated to dryness to give 70 mg brown oil. Yield: 48.6%. LC-MS (m/z): 449.4 $[M+H]^+$.

Step 2 and Step 3 and Step 4

The titled compound 165 was prepared as white solid in a yield of 6.4% according to the procedure outlined for compound 152. LC-MS (m/z): 522.3 $[M+H]^+$.

Compound 166: (S)-3-(1-(4-(5-chloro-4-(1-methyl-1H-1,2,4-triazol-5-yl)pyrimidin-2-yl)piperazine-1-carbonyl)-4,5-dihydro-1H-pyrazol-5-yl)-5-fluorobenzonitrile

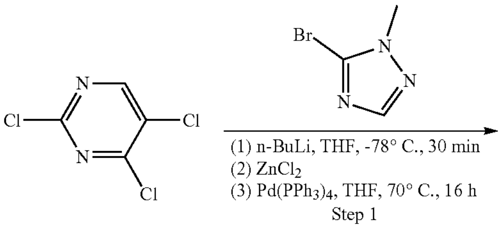

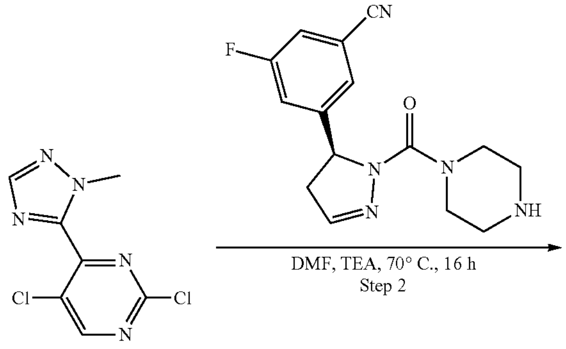

-continued

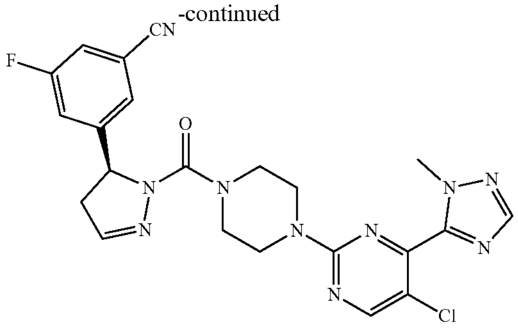

Step 1: Synthesis of 2,5-dichloro-4-(1-methyl-1H-1,2,4-triazol-5-yl)pyrimidine

The synthesis procedure was similar to that of tert-butyl 4-(5-fluoro-4-(1-methyl-5-trityl-1,4,5,6-tetrahydropyrrolo[3,4-c]pyrazol-3-yl)pyrimidin-2-yl)piperazine-1-carboxylate. 44 mg white solid was obtained. Yield: 48.6%. LC-MS (m/z): 231.4 $[M+H]^+$.

Step 2: Synthesis of (S)-3-(1-(4-(5-chloro-4-(1-methyl-1H-1,2,4-triazol-5-yl)pyrimidin-2-yl)piperazine-1-carbonyl)-4,5-dihydro-1H-pyrazol-5-yl)-5-fluorobenzonitrile 2,5-dichloro-4-(1-methyl-1H-1,2,4-triazol-5-yl)pyrimidine (44 mg, 0.1932 mmoL) and (S)-3-fluoro-5-(1-(piperazine-1-carbonyl)-4,5-dihydro-1H-pyrazol-5-yl)benzonitrile (56.5 mg, 0.188 mmoL) were dissolved in 2 mL DMF. 0.2 mL TEA was added. Let it stir at 70° C. for 16 h. Water was added and extracted with EtOAc (15 mL×3). Dried with $Na_2SO_4$, filtered and evaporated to dryness and purified by column chromatography (PE/EA=1/3) to give 40 mg light-yellow solid. Yield: 43%. LC-MS (m/z): 495.4 $[M+H]^+$.

Compound 167: (S)-3-(1-(4-(4-(1-ethyl-1H-1,2,4-triazol-5-yl)-5-fluoropyrimidin-2-yl)piperazine-1-carbonyl)-4,5-dihydro-1H-pyrazol-5-yl)-5-fluorobenzonitrile

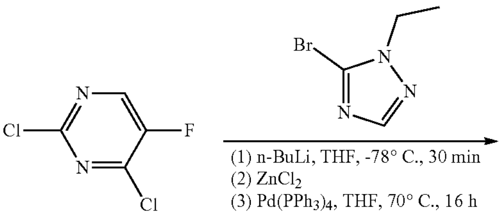

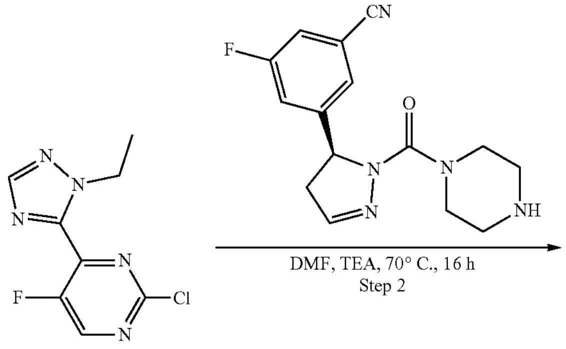

-continued

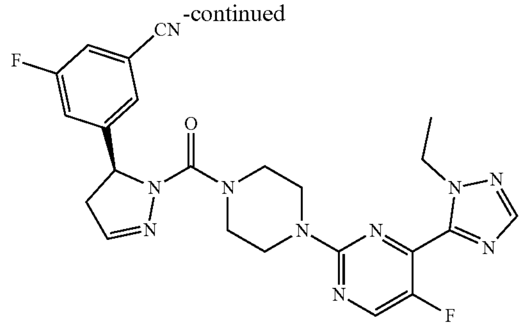

The titled compound 167 was prepared as light-yellow solid in a yield of 25.6% according to the procedure outlined for compound 166. LC-MS (m/z): 493.3 $[M+H]^+$. $^1H$ NMR (300 MHz, $CDCl_3$) δ 8.43 (d, J=2.1 Hz, 1H), 8.06 (s, 1H), 7.77-7.63 (m, 1H), 7.57-7.40 (m, 2H), 6.90 (s, 1H), 5.45-5.30 (m, 1H), 4.63 (q, J=7.2 Hz, 2H), 4.01-3.52 (m, 8H), 3.37 (dd, J=17.6, 12.4 Hz, 1H), 2.70 (dd, J=17.6, 10.0 Hz, 1H), 1.53 (t, J=7.2 Hz, 3H).

Compound 168: (S)-3-(1-(4-(5-chloro-4-(1-ethyl-1H-1,2,4-triazol-5-yl)pyrimidin-2-yl)piperazine-1-carbonyl)-4,5-dihydro-1H-pyrazol-5-yl)-5-fluorobenzonitrile

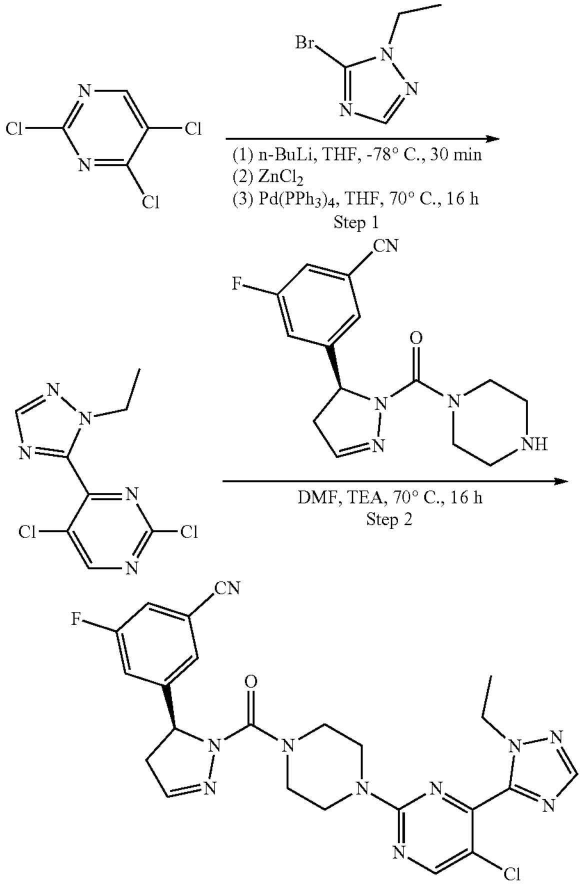

The titled compound 168 was prepared as light-yellow solid in a yield of 32.4% according to the procedure outlined for compound 166. LC-MS (m/z): 509.4 $[M+H]^+$. $^1H$ NMR (300 MHz, $CDCl_3$) δ 8.45 (s, 1H), 8.04 (s, 1H), 7.41 (s, 1H), 7.28 (s, 2H), 6.89 (s, 1H), 5.36 (t, J=10.8 Hz, 1H), 4.37 (q, J=7.2 Hz, 2H), 4.00-3.55 (m, 8H), 3.36 (dd, J=18.3, 11.7 Hz, 1H), 2.69 (dd, J=18.2, 10.0 Hz, 1H), 1.50 (t, J=7.2 Hz, 3H).

Compound 169: (S)-3-fluoro-5-(1-(4-(4-(3-(fluoromethyl)-1-methyl-1H-1,2,4-triazol-5-yl)pyrimidin-2-yl)piperazine-1-carbonyl)-4,5-dihydro-1H-pyrazol-5-yl)benzonitrile

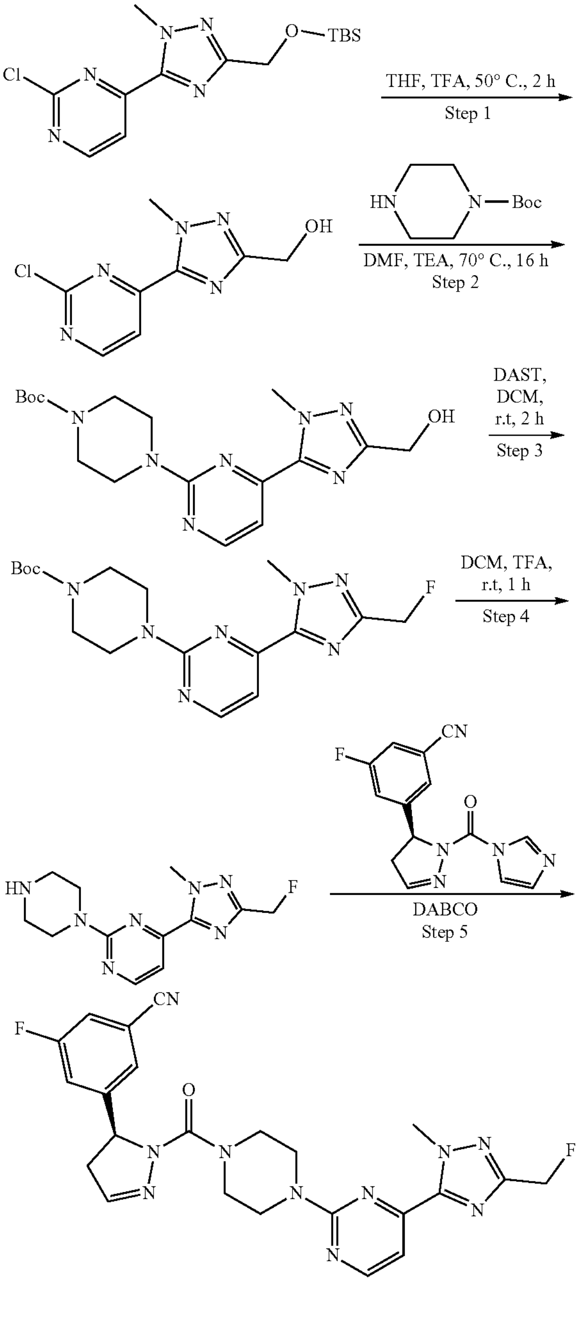

Step 1: Synthesis of (5-(2-chloropyrimidin-4-yl)-1-methyl-1H-1,2,4-triazol-3-yl)methanol 4-(3-(((tert-butyldimethylsilyl)oxy)methyl)-1-methyl-1H-1,2,4-triazol-5-yl) chloropyrimidine (150 mg, 0.442 mmoL) was dissolved in 3 mL THF. 2 mL TFA was added. Let it stir at 50° C. for 2 h. The solvent was evaporated to dryness and used for next step without further purification. LC-MS (m/z): 226.4 [M+H]+.

Step 2: Synthesis of tert-butyl 4-(4-(3-(hydroxymethyl)-1-methyl-1H-1,2,4-triazol-5-yl)pyrimidin-2-yl)piperazine-1-carboxylate The above residue and tert-butyl piperazine-1-carboxylate (90.7 mg, 0.487 mmoL) and TEA (0.2 mL) were dissolved in 3 mL DMF. Let it stir at 70° C. for 16 h. The solvent was evaporated to dryness and purified by column chromatography (EA) to give 120 mg light-yellow solid. Total yield: 72.7%. LC-MS (m/z): 376.4 [M+H]+.

Step 3: Synthesis of tert-butyl 4-(4-(3-(fluoromethyl)-1-methyl-1H-1,2,4-triazol-5-yl)pyrimidin-2-yl)piperazine-1-carboxylate Tert-butyl 4-(4-(3-(hydroxymethyl)-1-methyl-1H-1,2,4-triazol-5-yl)pyrimidin-2-yl)piperazine-1-carboxylate (120 mg, 0.32 mmoL) was dissolved in 3 mL DCM. DAST (101.5 mg, 0.63 mmoL) was added at 0° C. Let it stir at r.t for 2 h. The solvent was evaporated to dryness and purified by prep-TLC (PE/EA=1/5) to give 118 mg light-yellow solid. Total yield: 97.8%. LC-MS (m/z): 378.4 [M+H]+.

Step 4 and Step 5

The titled compound 169 was prepared as light-yellow solid in a yield of 22.7% according to the procedure outlined for compound 152. LC-MS (m/z): 493.4 [M+H]+. $^1$H NMR (300 MHz, $CDCl_3$) δ 8.51 (s, 1H), 7.42 (s, 2H), 7.28 (s, 2H), 6.90 (s, 1H), 5.52 (s, 1H), 5.45-5.31 (m, 2H), 4.37 (s, 3H), 4.11-3.54 (m, 8H), 3.37 (dd, J=17.4, 10.8 Hz, 1H), 2.70 (dd, J=17.4, 10.2 Hz, 1H)

Compound 170: (S)-3-fluoro-5-(1-(4-(5-fluoro-4-(3-(fluoromethyl)-1-methyl-1H-1,2,4-triazol-5-yl)pyrimidin-2-yl)piperazine-1-carbonyl)-4,5-dihydro-1H-pyrazol-5-yl)benzonitrile

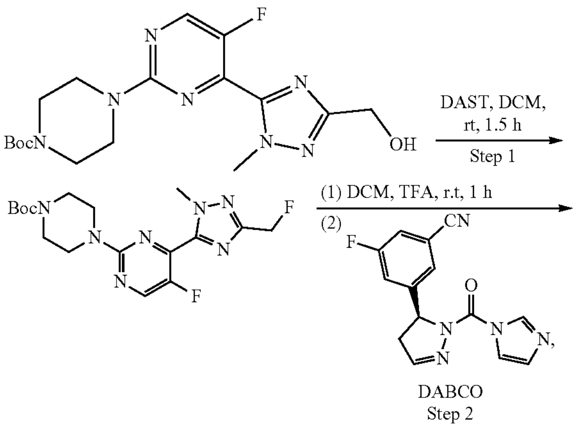

-continued

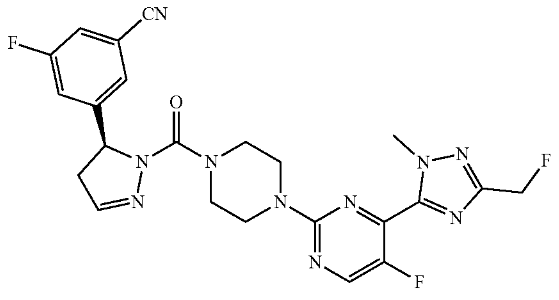

The titled compound 170 was prepared as light-yellow solid in a yield of 28.7% according to the procedure outlined for compound 152. LC-MS (m/z): 511.3 [M+H]+. $^1$H NMR (300 MHz, $CDCl_3$) δ 8.44 (d, J=2.1 Hz, 1H), 7.42 (s, 1H), 7.33-7.27 (m, 2H), 6.90 (s, 1H), 5.57 (s, 1H), 5.41 (s, 1H), 5.35 (d, J=10.8 Hz, 1H), 4.23 (s, 3H), 3.96-3.74 (m, 6H), 3.71-3.63 (m, 2H), 3.37 (ddd, J=18.3, 11.7, 1.5 Hz, 1H), 2.70 (ddd, J=18.3, 10.0, 1.2 Hz, 1H).

Compound 171: (S)-3-fluoro-5-(1-(4-(4-(3-(hydroxymethyl)-1-methyl-1H-1,2,4-triazol-5-yl)pyrimidin-2-yl)piperazine-1-carbonyl)-4,5-dihydro-1H-pyrazol-5-yl)benzonitrile

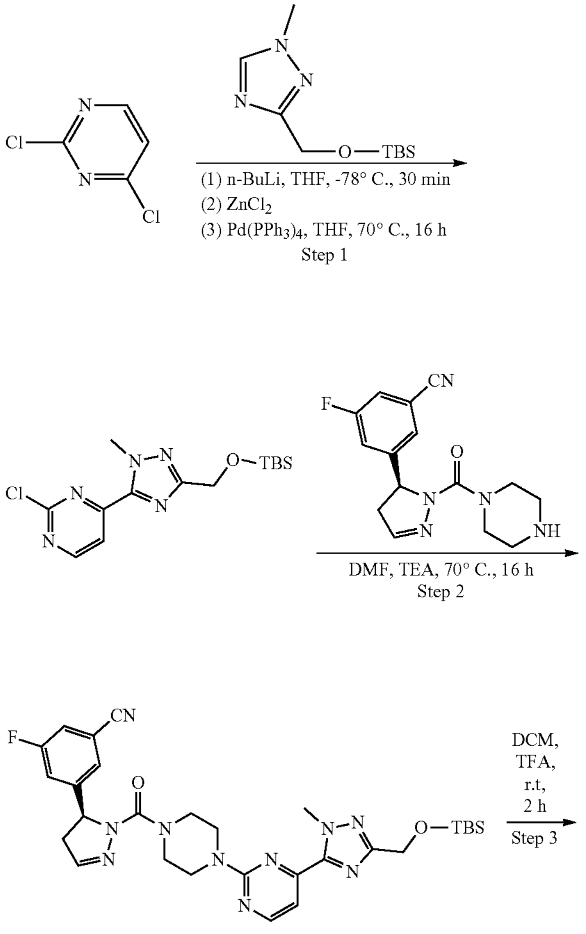

-continued

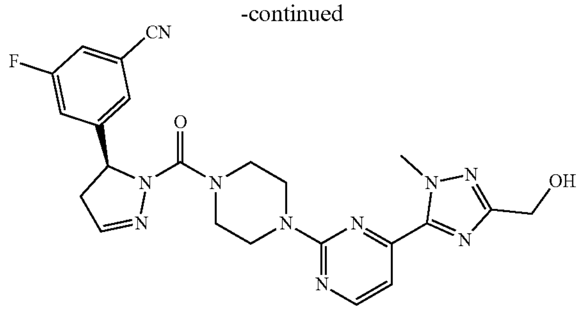

Step 1 and 2

The synthesis procedure was similar to that of 166. 77 mg (S)-3-(1-(4-(4-(3-(((tert-butyldimethylsilyl)oxy)methyl)-1-methyl-1H-1,2,4-triazol-5-yl)pyrimidin-2-yl)piperazine-1-carbonyl)-4,5-dihydro-1H-pyrazol-5-yl)-5-fluorobenzonitrile was obtained as light-yellow oil. Yield: 54.9%. LC-MS (m/z): 605.4 $[M+H]^+$.

Step 3: Synthesis of (5)-3-fluoro-5-(1-(4-(4-(3-(hydroxymethyl)-1-methyl-1H-1,2,4-triazol-5-yl)pyrimidin-2-yl)piperazine-1-carbonyl)-4,5-dihydro-1H-pyrazol-5-yl)benzonitrile (S)-3-(1-(4-(4-(3-(((tert-butyldimethylsilyl)oxy)methyl)-1-methyl-1H-1,2,4-triazol-5-yl)pyrimidin-2-yl)piperazine-1-carbonyl)-4,5-dihydro-1H-pyrazol-5-yl)-5-fluorobenzonitrile (77 mg, 0.127 mmoL) was dissolved in 2 mL DCM. 2 mL DCM/TFA (1/1) was added slowly to the solution at 0° C. Let it stir at r.t for 2 h. The solvent was evaporated to dryness and purified by prep-TLC (DCM/MeOH=12/1) to give 40 mg white solid. Yield: 64.3%. LC-MS (m/z): 491.4 $[M+H]^+$. $^1H$ NMR (300 MHz, $CDCl_3$) δ 8.51 (d, J=4.8 Hz, 1H), 7.42 (s, 1H), 7.39 (d, J=5.4 Hz, 1H), 7.32-7.27 (m, 1H), 6.91 (s, 1H), 5.44-5.32 (m, 1H), 4.80 (s, 2H), 4.35 (s, 3H), 4.03-3.62 (m, 8H), 3.37 (ddd, J=18.3, 11.7, 1.5 Hz, 1H), 2.70 (ddd, J=18.3, 10.0, 1.2 Hz, 1H).

Compound 172: (S)-3-fluoro-5-(1-(4-(5-fluoro-6-(5-methyl-1,3,4-thiadiazol-2-yl)pyridin-2-yl)piperazine-1-carbonyl)-4,5-dihydro-1H-pyrazol-5-yl)benzonitrile

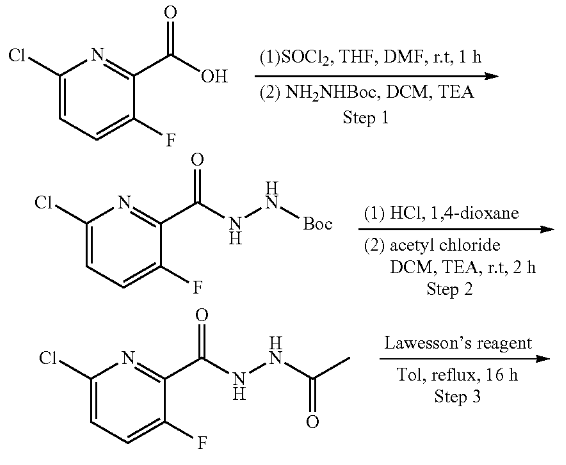

-continued

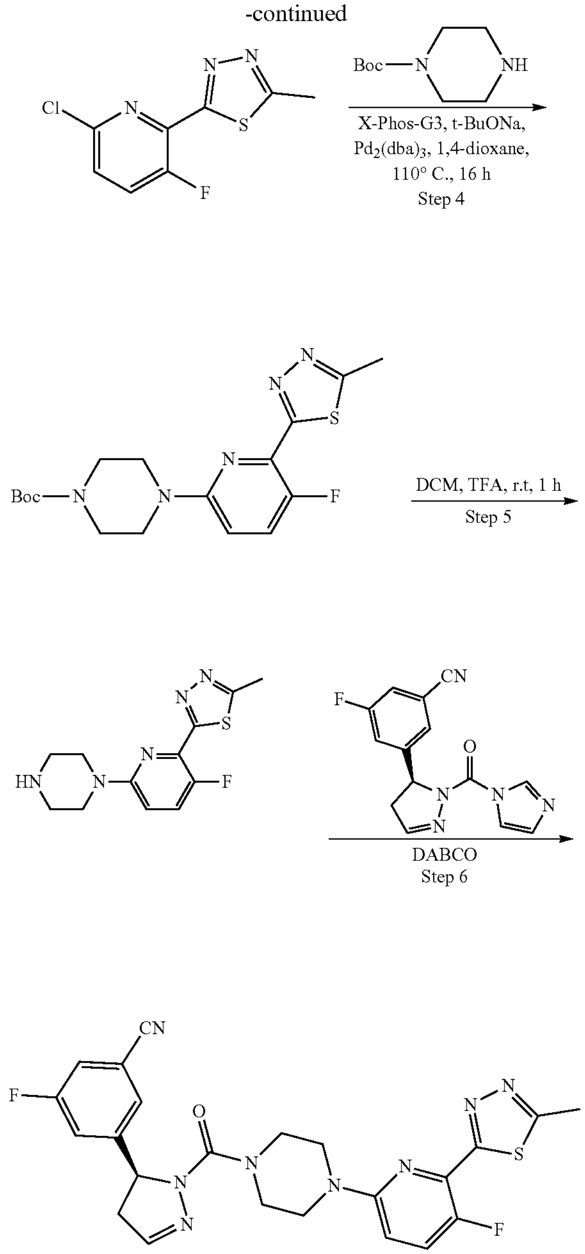

Step 1: Synthesis of tert-butyl 2-(6-chloro-3-fluoropicolinoyl)hydrazine-1-carboxylate 6-chloro-3-fluoropicolinic acid (500 mg, 2.841 mmoL) was dissolved in 5 mL THF. DMF (1 drop) was added. $SOCl_2$ (1 mL) was added. Let it stir at r.t for 1 h. The solvent was evaporated to dryness and used for next step without further purification.

The above residue in 4 mL DCM was added slowly to the solution of tert-butyl hydrazinecarboxylate (412.5 mg, 3.125 mmoL) and TEA (574 mg, 5.683 mmoL) in 5 mL DCM at 0° C. Let it stir at r.t for 16 h. The solvent was evaporated to dryness and redissolved with DCM and washed with water. Dried with $Na_2SO_4$, filtered and evaporated to dryness and used for next step without further purification. LC-MS (m/z): 290.4 $[M+H]^+$.

Step 2: Synthesis of N'-acetyl-6-chloro-3-fluoropicolinohydrazide

The above residue was dissolved in 4 mL DCM. 10 mL HCl/1,4-dioxane was added. Let it stir at r.t for 1 h. The solid was filtered and washed with PE to give 550 mg 6-chloro-3-fluoropicolinohydrazide as white solid. Yield for 3 steps: 84.9%. It was used for next step without further purification. LC-MS (m/z): 190.4 $[M+H]^+$.

The hydrogen chloride salt of 6-chloro-3-fluoropicolinohydrazide (550 mg) was mixed in 8 mL DCM. TEA (1 mL) was added. Acetyl chloride (209.2 mg, 2.665 mmoL) was added. Let it stir at r.t for 1.5 h. The solvent was evaporated to dryness to give 700 mg crude brown solid and it was used for next step without further purification. LC-MS (m/z): 232.3 $[M+H]^+$.

Step 3: Synthesis of 2-(6-chloro-3-fluoropyridin-2-yl)-5-methyl-1,3,4-thiadiazole N'-acetyl-6-chloro-3-fluoropicolinohydrazide (700 mg, crude) and Lawesson's Reagent (836.5 mg, 2.068 mmoL) were mixed in 10 mL toluene. Let it stir at 110° C. for 16 h. The solvent was evaporated to dryness and purified by prep-TLC (PE/EA=3/2) to give 95 mg yellow solid. Yield: 20.1%. LC-MS (m/z): 230.3 $[M+H]^+$.

Step 4: Synthesis of tert-butyl 4-(5-fluoro-6-(5-methyl-1,3,4-thiadiazol-2-yl)pyridin yl)piperazine-1-carboxylate 2-(6-chloro-3-fluoropyridin-2-yl)-5-methyl-1,3,4-thiadiazole (95 mg, 0.415 mmoL), tert-butyl piperazine-1-carboxylate (85 mg, 0.457 mmoL), X-phos-G3 (70.2 mg, 0.816 mmoL), t-BuONa (50 mg, 0.52 mmoL) and $Pd_2(dba)_3$ (38 mg, 0.042 mmoL) were mixed in 5 mL 1,4-dioxane. Let it stir at 110° C. for 16 h. The solvent was evaporated to dryness and purified by prep-TLC (PE/EA=2/3) to give 35 mg orange solid. Yield: 22.2%. LC-MS (m/z): 380.3 $[M+H]^+$.

Step 5 and 6

The titled compound 172 was prepared as light-yellow solid in a yield of 88.1% according to the procedure outlined for compound 166. LC-MS (m/z): 495.3 $[M+H]^+$. $^1H$ NMR (400 MHz, $CDCl_3$) δ 7.46 (t, J=9.2 Hz, 1H), 7.43-7.39 (m, 1H), 7.30-7.26 (m, 2H), 6.89 (t, J=1.5 Hz, 1H), 6.76-6.71 (m, 1H), 5.37 (dd, J=11.6, 10.1 Hz, 1H), 3.89-3.79 (m, 2H), 3.74-3.61 (m, 4H), 3.57-3.47 (m, 2H), 3.36 (ddd, J=18.3, 11.7, 1.8 Hz, 1H), 2.82 (s, 3H), 2.70 (ddd, J=18.2, 9.9, 1.5 Hz, 1H).

Compound 173: (S)-(4-(5-fluoro-6-(5-methyl-1,3,4-thiadiazol-2-yl)pyridin-2-yl)piperazin-1-yl)(5-(5-fluoropyridin-3-yl)-4,5-dihydro-1H-pyrazol-1-yl)methanone

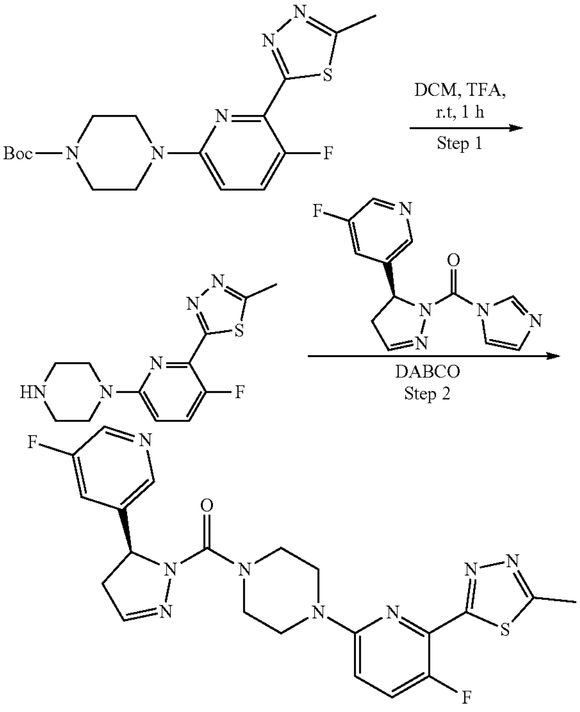

The titled compound 173 was prepared as light-yellow solid in a yield of 69.4% according to the procedure outlined for compound 166. LC-MS (m/z): 471.3 $[M+H]^+$. $^1H$ NMR (400 MHz, $CDCl_3$) δ 8.43 (s, 1H), 8.39 (d, J=2.0 Hz, 1H), 7.46 (t, J=9.2 Hz, 1H), 7.38-7.31 (m, 1H), 6.91 (t, J=1.6 Hz, 1H), 6.74 (dd, J=9.2, 2.8 Hz, 1H), 5.45-5.37 (m, 1H), 3.88-3.79 (m, 2H), 3.73-3.60 (m, 4H), 3.56-3.48 (m, 2H), 3.38 (ddd, J=18.4, 11.6, 1.6 Hz, 1H), 2.82 (s, 3H), 2.77 (ddd, J=18.4, 10.0, 1.6 Hz, 1H).

Compound 174: (S)-(4-(5-fluoro-4-(3-(hydroxymethyl)-1-methyl-1H-1,2,4-triazol-5-yl)pyrimidin-2-yl)piperazin-1-yl)(5-(5-fluoropyridin-3-yl)-4,5-dihydro-1H-pyrazol-1-yl)methanone

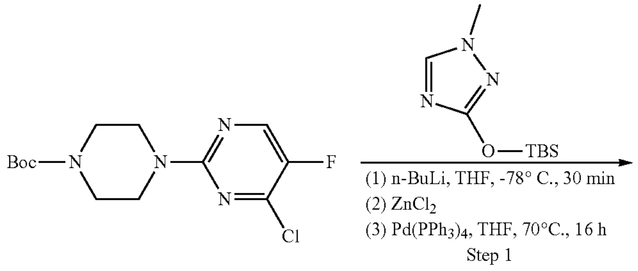

-continued

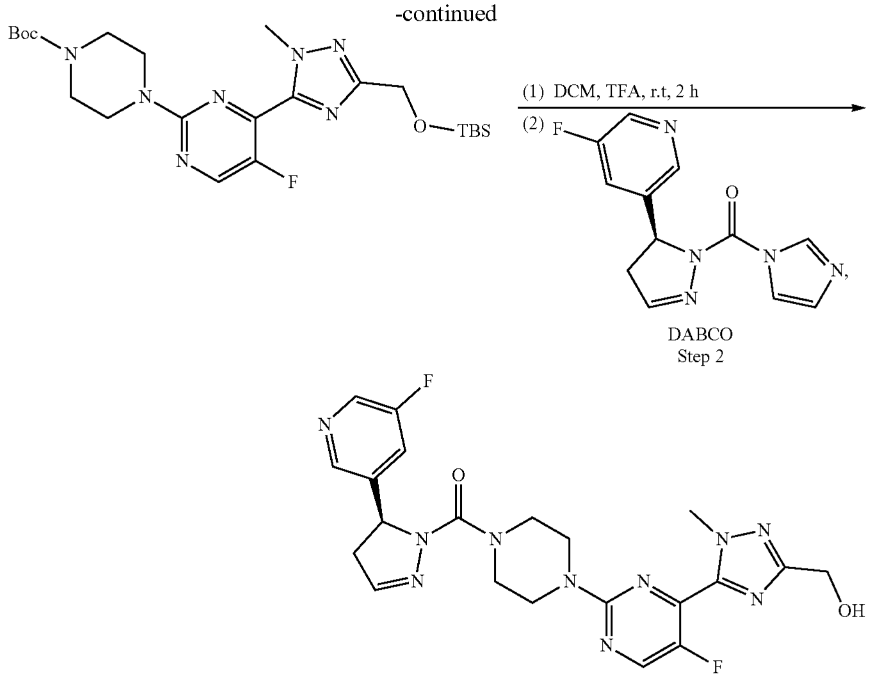

Step 1: Synthesis of tert-butyl 4-(4-(3-(((tert-butyldimethylsilyl)oxy)methyl)-1-methyl-1H-1,2,4-triazol-5-yl)-5-fluoropyrimidin-2-yl)piperazine-1-carboxylate The synthesis procedure was similar to that of tert-butyl 4-(5-fluoro-4-(1-methyl-5-trityl-1,4,5,6-tetrahydropyrrolo[3,4-c]pyrazol-3-yl)pyrimidin-2-yl)piperazine-1-carboxylate. 42 mg light-yellow oil was obtained. Yield: 3.5%. LC-MS (m/z): 508.3 $[M+H]^+$.

Step 2 and 3

The titled compound 174 was prepared as light-yellow solid in a yield of 22.5% according to the procedure outlined for compound 166. LC-MS (m/z): 485.3 $[M+H]^+$. $^1H$ NMR (300 MHz, $CDCl_3$) δ 8.48-8.34 (m, 3H), 7.39-7.30 (m, 1H), 6.91 (s, 1H), 5.41 (t, J=10.8 Hz, 1H), 4.82 (s, 2H), 4.19 (s, 3H), 3.92-3.61 (m, 8H), 3.38 (ddd, J=18.2, 11.8, 1.7 Hz, 1H), 2.75 (ddd, J=18.3, 10.1, 1.5 Hz, 1H).

Compound 175: (S)-(5-(3,5-difluorophenyl)-4,5-dihydro-1H-pyrazol-1-yl)(4-(3-fluoro-6-(1-methyl-1H-1,2,4-triazol-5-yl)pyridin-2-yl)piperazin-1-yl)methanone

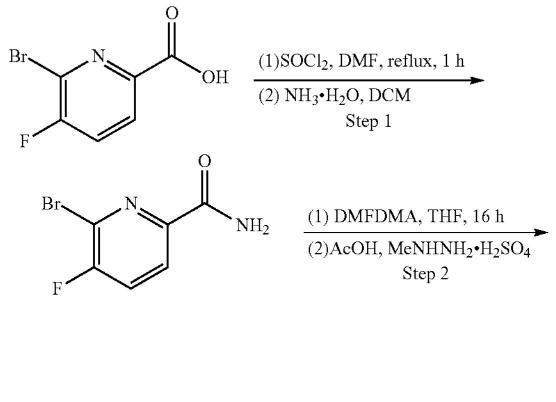

-continued

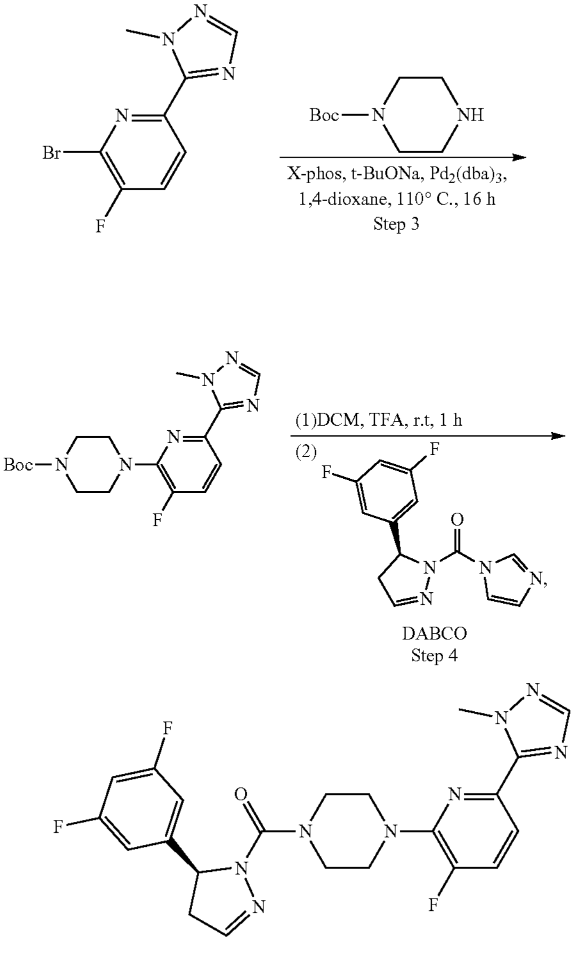

Step 1: Synthesis of 6-bromo-5-fluoropicolinamide

The synthesis procedure was similar to that of tert-butyl 2-(6-chloro-3-fluoropicolinoyl)hydrazine-1-carboxylate. 650 mg light-yellow oil was obtained. Yield: 83.8%. LC-MS (m/z): 220.3 $[M+H]^+$.

Step 2: Synthesis of 2-bromo-3-fluoro-6-(1-methyl-1H-1,2,4-triazol-5-yl)pyridine 6-bromo-5-fluoropicolinamide (650 mg, 2.968 mmoL) was dissolved in 10 mL THF. 2 mL DMFDMA was added. Let it stir at r.t for 16 h. The solvent was evaporated to dryness and used for next step without further purification.

The above solid and methylhydrazine sulfate (1.13 g, 7.8 mmoL) were mixed in 10 mL AcOH. Let it stir at 90° C. for 16 h. The mixture was neutralized with $K_2CO_3$. Extracted with EA (20 mL×3). The solvent was evaporated to dryness and purified by prep-TLC (PE/EA=1/1) to give 330 mg white solid. Yield: 54.2%. LC-MS (m/z): 258.3 $[M+H]^+$.

Step 3 and 4

The titled compound 175 was prepared as light-yellow solid in a yield of 44% according to the procedure outlined for compound 166. LC-MS (m/z): 471.3 $[M+H]^+$. $^1H$ NMR (400 MHz, $CDCl_3$) δ 7.92 (s, 1H), 7.81-7.75 (m, 1H), 7.40 (dd, J=12.4, 8.2 Hz, 1H), 6.87-6.81 (m, 3H), 6.73-6.66 (m, 1H), 5.35 (dd, J=11.6, 10.0 Hz, 1H), 4.34 (s, 3H), 3.92-3.86 (m, 2H), 3.76-3.71 (m, 2H), 3.64-3.46 (m, 4H), 3.33 (ddd, J=18.3, 11.8, 1.8 Hz, 1H), 2.70 (ddd, J=18.3, 9.9, 1.6 Hz, 1H).

Compound 176: (S)-3-fluoro-5-(1-(4-(3-fluoro-6-(1-methyl-1H-1,2,4-triazol-5-yl)pyridin-2-yl)piperazine-1-carbonyl)-4,5-dihydro-1H-pyrazol-5-yl)benzonitrile

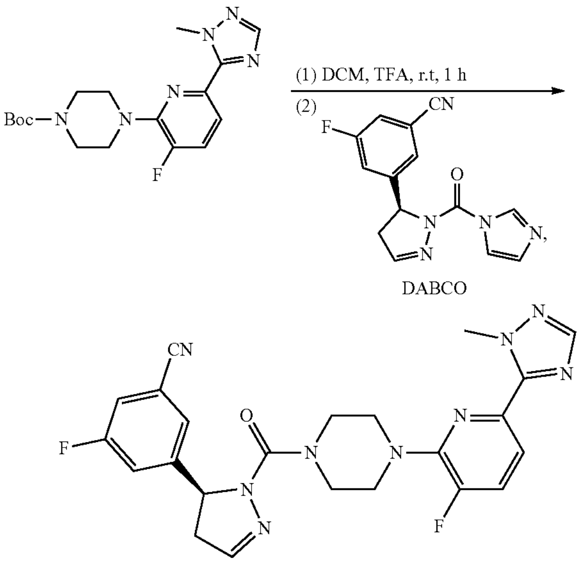

The titled compound 176 was prepared as light-yellow solid in a yield of 69.4% according to the procedure outlined for compound 166. LC-MS (m/z): 478.3 $[M+H]^+$. $^1H$ NMR (400 MHz, $CDCl_3$) δ 7.93 (s, 1H), 7.79 (dd, J=8.2, 2.9 Hz, 1H), 7.45-7.38 (m, 2H), 7.31-7.26 (m, 2H), 6.90 (t, J=1.7 Hz, 1H), 5.38 (dd, J=11.6, 10.1 Hz, 1H), 4.34 (s, 3H), 3.93-3.84 (m, 2H), 3.76-3.71 (m, 2H), 3.64-3.48 (m, 4H), 3.37 (ddd, J=18.3, 11.7, 1.8 Hz, 1H), 2.70 (ddd, J=18.3, 10.0, 1.6 Hz, 1H).

Compound 177: (S)-3-fluoro-5-(1-(4-(3-fluoro-6-(1-methyl-1H-1,2,4-triazol-3-yl)pyridin-2-yl)piperazine-1-carbonyl)-4,5-dihydro-1H-pyrazol-5-yl)benzonitrile

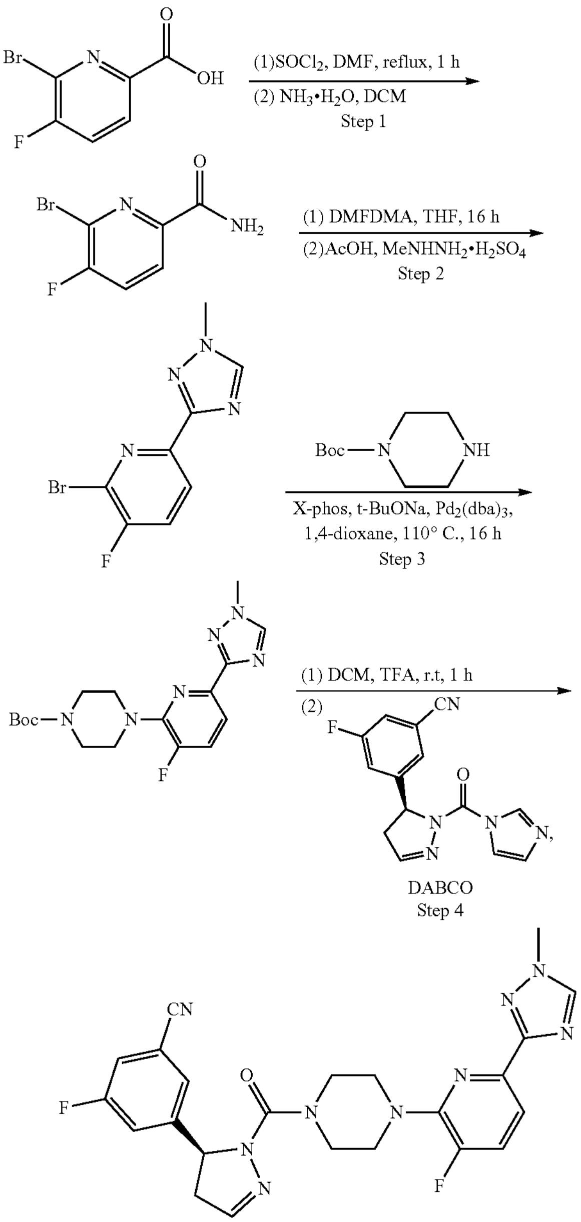

The titled compound 177 was prepared as light-yellow solid in a yield of 57.8% according to the procedure outlined for compound 166. LC-MS (m/z): 478.4 $[M+H]^+$. $^1H$ NMR (400 MHz, $CDCl_3$) δ 8.14 (s, 1H), 7.61 (dd, J=8.1, 2.9 Hz, 1H), 7.42 (t, J=1.4 Hz, 1H), 7.33 (dd, J=12.6, 8.1 Hz, 1H), 7.30-7.25 (m, 2H), 6.86 (t, J=1.6 Hz, 1H), 5.40-5.31 (m, 1H), 4.00 (s, 3H), 3.91-3.80 (m, 2H), 3.75-3.54 (m, 6H), 3.34 (ddd, J=18.2, 11.7, 1.8 Hz, 1H), 2.68 (ddd, J=18.2, 10.2, 1.6 Hz, 1H).

Compound 178: (S)-(5-(3,5-difluorophenyl)-4,5-dihydro-1H-pyrazol-1-yl)(4-(4-(4,5-dimethyl-4H-1,2,4-triazol-3-yl)-5-fluoropyrimidin-2-yl)piperazin-1-yl)methanone

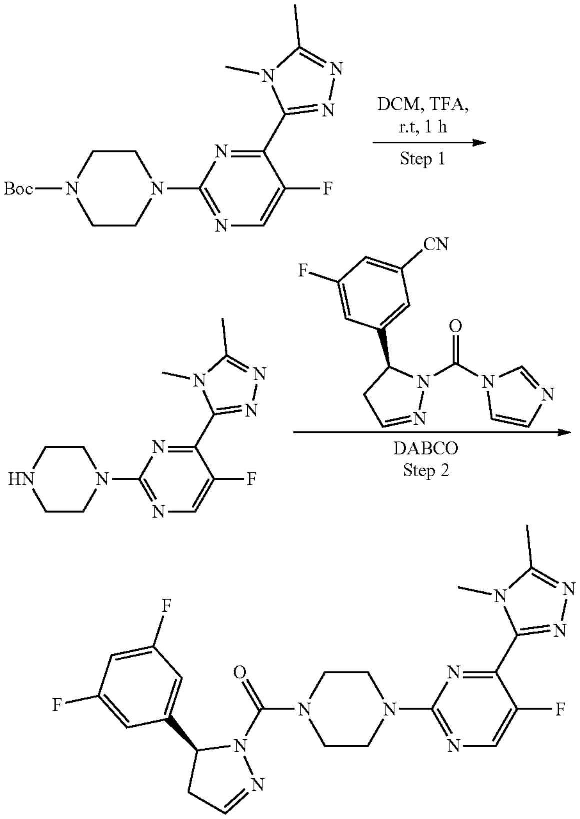

The titled compound 178 was prepared as yellow solid in a yield of 39.5% according to the procedure outlined for compound 166. LC-MS (m/z): 486.4 $[M+H]^+$. $^1H$ NMR (400 MHz, $CDCl_3$) δ 8.46 (d, J=2.0 Hz, 1H), 6.87 (t, J=1.6 Hz, 1H), 6.85-6.79 (m, 2H), 6.70 (tt, J=8.9, 2.3 Hz, 1H), 5.34 (dd, J=11.7, 9.8 Hz, 1H), 3.93 (s, 3H), 3.91-3.85 (m, 2H), 3.84-3.74 (m, 4H), 3.69-3.61 (m, 2H), 3.34 (ddd, J=18.4, 11.8, 1.8 Hz, 1H), 2.75-2.66 (m, 4H).

Compound 179: (S)-3-(1-(4-(4-(4,5-dimethyl-4H-1,2,4-triazol-3-yl)-5-fluoropyrimidin-2-yl)piperazine-1-carbonyl)-4,5-dihydro-1H-pyrazol-5-yl)-5-fluorobenzonitrile

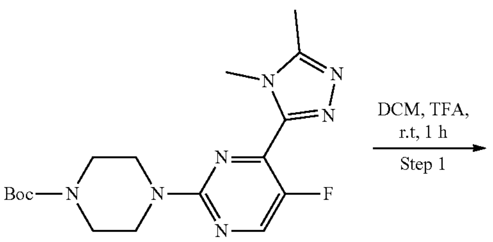

-continued

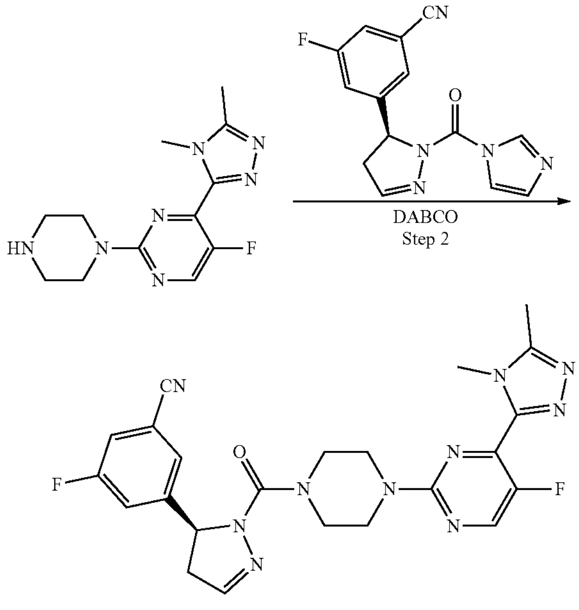

The titled compound 179 was prepared as yellow solid in a yield of 47.5% according to the procedure outlined for compound 166. LC-MS (m/z): 493.4 $[M+H]^+$. $^1H$ NMR (400 MHz, $cdcl_3$) δ 8.45 (d, J=2.0 Hz, 1H), 7.41 (t, J=1.4 Hz, 1H), 7.30-7.26 (m, 2H), 6.90 (t, J=1.6 Hz, 1H), 5.37 (dd, J=11.6, 10.0 Hz, 1H), 3.97-3.85 (m, 5H), 3.83-3.73 (m, 4H), 3.72-3.61 (m, 2H), 3.37 (ddd, J=18.3, 11.7, 1.8 Hz, 1H), 2.75-2.64 (m, 4H).

Compound 180: (S)-2-(2-(4-(5-(3,5-difluorophenyl)-4,5-dihydro-1H-pyrazole-1-carbonyl)piperazin-1-yl)-5-fluoropyrimidin-4-yl)-4-ethyl-5-methyl-2,4-dihydro-3H-1,2,4-triazol-3-one

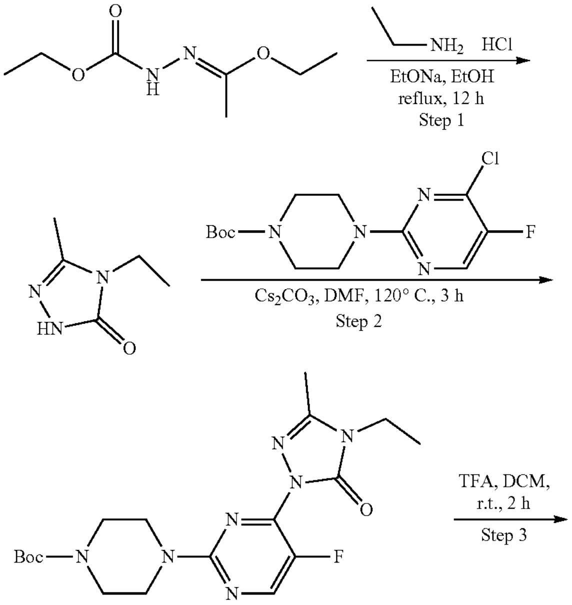

-continued

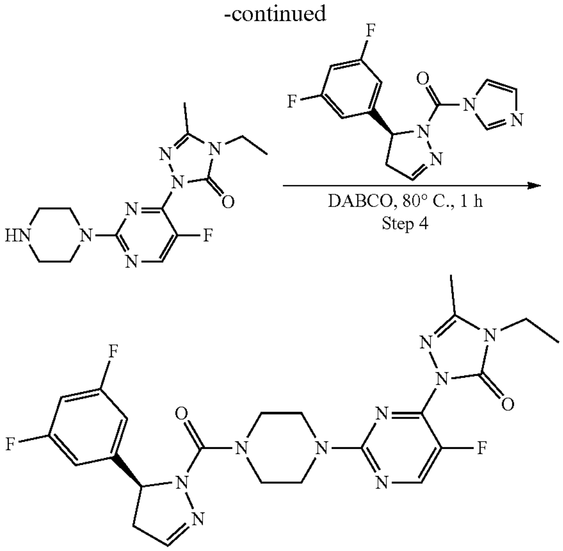

Step 1: 4-ethyl-5-methyl-2,4-dihydro-3H-1,2,4-triazol-3-one

Ethanamine hydrochloride (2.0 g, 10 mmol) was dissolved in absolute EtOH (200 mL) to which a suspension of sodium ethoxide (1.33 g, 19.5 mmol) in absolute EtOH (70 mL) was added and reaction was stirred for 5 min at room temperature. A solution of (E)-ethyl 2-(1-ethoxyethylidene) hydrazine carboxylate (1.6 g, 19.5 mmol) in absolute EtOH (50 mL) was added dropwise and reaction refluxed for 4 h. The reaction was then cooled to room temperature and filtered over a celite pad. The eluant was dried under reduced pressure and the resultant residue was recrystallised (through a hot filtration) from EtOAc to give the pure product. Isolated yield: 183 mg (10%); White crystals (re-crystallised from EtOAc); LCMS (ES, m/z): 128.1[M+H]$^+$.

Step 2: tert-butyl 4-(4-(4-ethyl-3-methyl-5-oxo-4,5-dihydro-1H-1,2,4-triazol-1-yl)-5-fluoropyrimidin-2-yl)piperazine-1-carboxylate Tert-butyl 4-(4-chloro-5-fluoropyrimidin-2-yl)piperazine-1-carboxylate (300 mg, 0.95 mmol) in DMF (20 mL) was added 4-ethyl-5-methyl-2,4-dihydro-3H-1,2,4-triazol-3-one (128 mg, 1.42 mmol), $Cs_2CO_3$ (462 mg, 1.42 mmol). The reaction was stirred at 120° C. for 3 h. Water was added and extracted with EA, washed with brine, dried with ($Na_2SO_4$). The resulting mixture was removed under vacuum and the crude product was purified by silica gel chromatography to give 300 mg tert-butyl 4-(4-(4-ethyl-3-methyl-5-oxo-4,5-dihydro-1H-1,2,4-triazol-1-yl)-5-fluoropyrimidin-2-yl)piperazine-1-carboxylate as yellow solid. Yield: 77%. LC-MS (m/z) 408.2 (M+H$^+$).

Step 3: 4-ethyl-2-(5-fluoro-2-(piperazin-1-yl)pyrimidin-4-yl)-5-methyl-2,4-dihydro-3H-1,2,4-triazol-3-one Tert-butyl 4-(4-(4-ethyl-3-methyl-5-oxo-4,5-dihydro-1H-1,2,4-triazol-1-yl)-5-fluoropyrimidin-2-yl)piperazine-1-carboxylate (300 mg, 0.73 mmol) was dissolved in 5 mL DCM. 1 mL of TFA/DCM (1/5) was added to the solution at 0° C. Let it stir at r.t for 1 h. The solvent was evaporated to dryness and used for next step without further purification. LC-MS (m/z): 308.2 [M+H]$^+$.

Step 4: (S)-3-(1-(4-(4-(4-ethyl-3-methyl-5-oxo-4,5-dihydro-1H-1,2,4-triazol-1-yl)-5-fluoropyrimidin-2-yl)piperazine-1-carbonyl)-4,5-dihydro-1H-pyrazol-5-yl)-5-fluorobenzonitrile The above residue and 4-ethyl-2-(5-fluoro-2-(piperazin-1-yl)pyrimidin-4-yl)-5-methyl-2,4-dihydro-3H-1,2,4-triazol-3-one (260 mg, 0.84 mmol) and DABCO (53 mg, 1.06 mmol) were mixed in 3 mL THF. It was evaporated to dryness and directly lighted with 100 W filament lamp for 2 hrs. The solid was purified by prep-HPLC to give 20 mg (S)-3-(1-(4-(4-(4-ethyl-3-methyl-5-oxo-4,5-dihydro-1H-1,2,4-triazol-1-yl)-5-fluoropyrimidin-2-yl)piperazine-1-carbonyl)-4,5-dihydro-1H-pyrazol-5-yl)-5-fluorobenzonitrile as white solid. Total yield for two steps: 6%. LC-MS (m/z): 516.5 [M+H]$^+$. $^1$H NMR (400 MHz, $CDCl_3$) δ 8.23 (d, J=2.7 Hz, 1H), 6.79-6.69 (m, 3H), 6.69-6.53 (m, 1H), 5.26 (dd, J=11.4, 10.1 Hz, 1H), 3.86-3.77 (m, 2H), 3.70 (tdd, J=14.4, 9.2, 5.0 Hz, 6H), 3.60-3.51 (m, 2H), 3.24 (ddd, J=18.2, 11.7, 1.7 Hz, 1H), 2.61 (ddd, J=18.3, 9.9, 1.5 Hz, 1H), 2.27 (s, 3H), 1.27 (t, J=7.2 Hz, 3H).

Compound 181: (S)-3-(1-(4-(4-(4-ethyl-3-methyl-5-oxo-4,5-dihydro-1H-1,2,4-triazol-1-yl)-5-fluoropyrimidin-2-yl)piperazine-1-carbonyl)-4,5-dihydro-1H-pyrazol-5-yl) fluorobenzonitrile

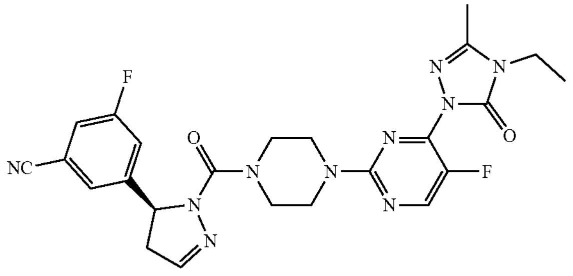 [SMILES: CCn1c(C)nn(-c2nc(N3CCN(C(=O)N4N=CC[C@H]4c4cc(F)cc(C#N)c4)CC3)ncc2F)c1=O]

The titled compound 181 was prepared in 8% yield as white solid according to the procedure outlined for compound 180. LC-MS (m/z) 523.3 (M+H)$^{+1}$H NMR (400 MHz, $CDCl_3$) δ 8.24 (d, J=2.7 Hz, 1H), 7.34 (s, 1H), 7.26-7.11 (m, 2H), 6.80 (s, 1H), 5.36-5.21 (m, 1H), 3.89-3.77 (m, 2H), 3.77-3.60 (m, 6H), 3.61-3.48 (m, 2H), 3.28 (ddd, J=18.2, 11.7, 1.7 Hz, 1H), 2.62 (ddd, J=18.2, 10.0, 1.5 Hz, 1H), 2.28 (s, 3H), 1.26 (q, J=7.4 Hz, 3H).

Compound 182: (S)-4-(2-(4-(5-(3,5-difluorophenyl)-4,5-dihydro-1H-pyrazole-1-carbonyl)piperazin-1-yl)-5-fluoropyrimidin-4-yl)-2-ethyl-5-methyl-2,4-dihydro-3H-1,2,4-triazol-3-one

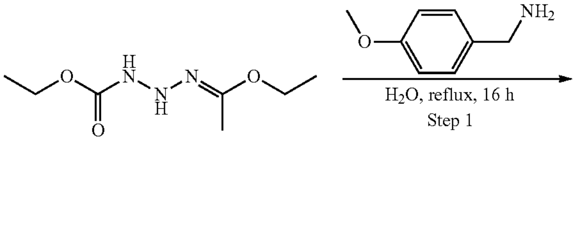

-continued

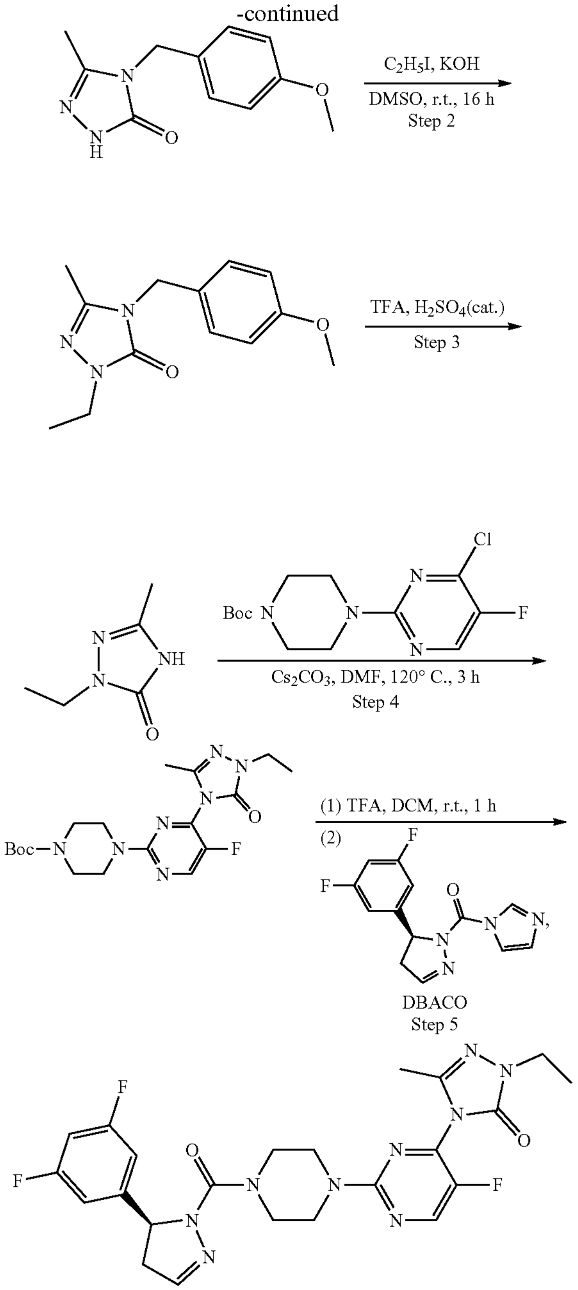

Step 1: A solution of ethyl (E)-3-(1-ethoxyethylidene) triazane-1-carboxylate (2.0 g, 0.01 mmol) in $H_2O$ (20 mL) was added (1.4 g, 0.01 mmol). The mixture reaction was stirred at 120° C. for 3 h and was then cooled to room temperature. The eluant was dried under reduced pressure and the resultant residue was recrystallised (through a hot filtration) from EtOAc to give titled compound 4-(4-methoxybenzyl)-5-methyl-2,4-dihydro-3H-1,2,4-triazol-3-one. Isolated yield: 1.54 g (67%); White crystals (recrystallised from EtOAc); LCMS (m/z): 220.1[M+H]$^+$.

Step 2: 4-(4-methoxybenzyl)-5-methyl-2,4-dihydro-3H-1,2,4-triazol-3-one (200 mg, 0.91 mmol) in DMSO (5 mL) was $CH_3I$ (213 mg, 1.37 mmol), KOH (154 mg, 2.7 mmol). The reaction was stirred at room temperature for overnight. Water was added and extracted with EA, washed with brine, dried with ($Na_2SO_4$). The resulting mixture was removed under vacuum and the crude product was purified by silica gel chromatography to give 2-ethyl-4-(4-methoxybenzyl)-5-methyl-2,4-dihydro-3H-1,2,4-triazol-3-one (200 mg, 89%) as yellow solid. LC-MS (m/z) 248.3 (M+H$^+$).

Step 3: 2-ethyl-4-(4-methoxybenzyl)-5-methyl-2,4-dihydro-3H-1,2,4-triazol-3-one (200 mg, 0.81 mmol) was dissolved in 5 mL TFA was added $H_2SO_4$ (cat.) Let it stir at 60° C. for 1 h. The solvent was evaporated to dryness and used for next step without further purification. LC-MS (m/z): 128.1 [M+H]$^+$.

Step 4: 2-ethyl-5-methyl-2,4-dihydro-3H-1,2,4-triazol-3-one (160 mg, 1.26 mmol) in DMF (20 mL) was added tert-butyl 4-(4-chloro-5-fluoropyrimidin-2-yl)piperazine-1-carboxylate (476 mg, 1.169 mmol), and $Cs_2CO_3$ (1.3 g, 3.98 mmol). The reaction was stirred at 120° C. for 3 h. Water was added and extracted with EA, washed with brine, dried with ($Na_2SO_4$). The resulting mixture was removed under vacuum and the crude product was purified by silica gel chromatography to give tert-butyl 4-(4-(1-ethyl-3-methyl-5-oxo-1,5-dihydro-4H-1,2,4-triazol-4-yl)-5-fluoropyrimidin-2-yl)piperazine-1-carboxylate (160 mg, 31%) as yellow solid. LC-MS (m/z) 408.2 (M+H$^+$).

Step 5: The above residue and (S)-(5-(3,5-difluorophenyl)-4,5-dihydro-1H-pyrazol-1-yl)(1H-imidazol-1-yl) methanone (130 mg, 0.47 mmol) and DABCO (53 mg, 1.06 mmol) were mixed in 3 mL THF. It was evaporated to dryness and directly lighted with 100 W filament lamp for 2 hrs. The solid was purified by prep-HPLC to give 15.9 mg titled compound as a white solid. Total yield for two steps: 8%. LC-MS (m/z): 516.2 [M+H]$^+$. $^1$H NMR (400 MHz, $CDCl_3$) δ 8.32 (d, J=1.7 Hz, 1H), 6.83-6.70 (m, 3H), 6.63 (tt, J=9.0, 2.4 Hz, 1H), 5.26 (dd, J=11.7, 9.8 Hz, 1H), 3.84-3.73 (m, 4H), 3.73-3.64 (m, 4H), 3.61-3.49 (m, 2H), 3.25 (ddd, J=18.3, 11.8, 1.9 Hz, 1H), 2.62 (ddd, J=18.3, 9.8, 1.6 Hz, 1H), 2.22 (s, 3H), 1.30 (t, J=7.2 Hz, 3H).

Compound 183: (S)-3-(1-(4-(4-(1-ethyl-3-methyl-5-oxo-1,5-dihydro-4H-1,2,4-triazol-4-yl)-5-fluoropyrimidin-2-yl)piperazine-1-carbonyl)-4,5-dihydro-1H-pyrazol-5-yl)-5-fluorobenzonitrile

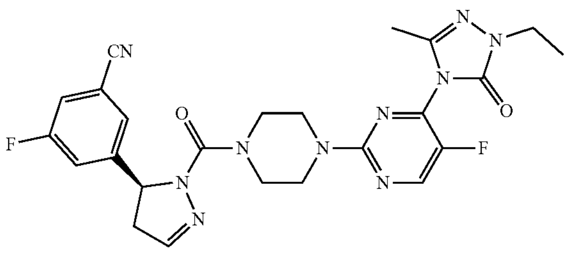 [SMILES: CCn1nc(C)n(-c2nc(N3CCN(C(=O)N4N=CC[C@H]4c4cc(F)cc(C#N)c4)CC3)ncc2F)c1=O]

The titled compound 183 was prepared in a yield of 11.5% according to the procedure outlined for compound 182. Mass (m/z) 523.2 [M+H]$^+$; $^1$H NMR (400 MHz, $CDCl_3$) δ 8.32 (d, J=1.7 Hz, 1H), 7.34 (d, J=1.5 Hz, 1H), 7.21 (dd, J=2.7, 1.5 Hz, 2H), 6.86-6.72 (m, 1H), 5.29 (dd, J=11.7, 10.0 Hz, 1H), 3.78 (dq, J=10.2, 7.2, 6.3 Hz, 4H), 3.74-3.62 (m, 4H), 3.61-3.44 (m, 2H), 3.29 (ddd, J=18.3, 11.7, 1.8 Hz, 1H), 2.62 (ddd, J=18.3, 10.0, 1.6 Hz, 1H), 2.22 (s, 3H), 1.30 (t, J=7.2 Hz, 3H).

Compound 184: (S)-3-fluoro-5-(1-(4-(5-fluoro-4-(2-methyl-5,6-dihydro-4H-pyrrolo[1,2-b]pyrazol-3-yl)pyrimidin-2-yl)piperazine-1-carbonyl)-4,5-dihydro-1H-pyrazol-5-yl)benzonitrile

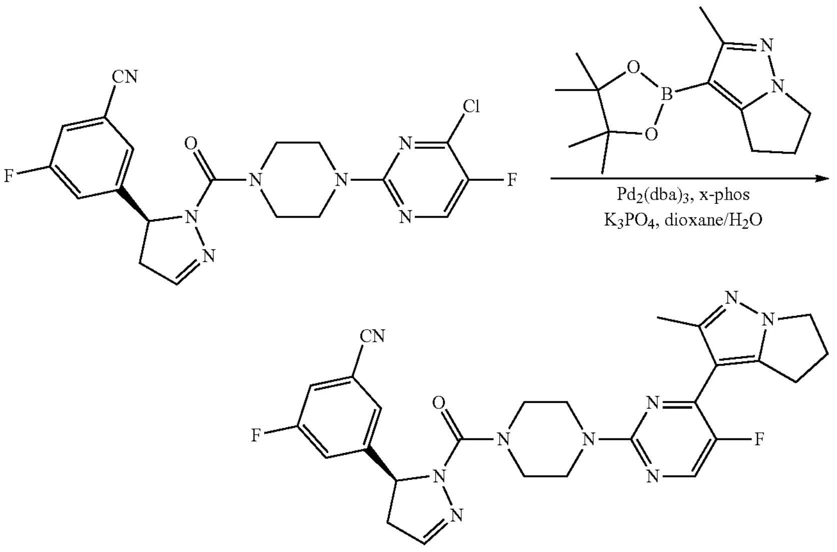

(S)-3-(1-(4-(4-chloro-5-fluoropyrimidin-2-yl)piperazine-1-carbonyl)-4,5-dihydro-1H-pyrazol-5-yl)-5-fluorobenzonitrile (388.6 mg, 0.49 mmol), 2-methyl-3-(4,4,5,5-tetramethyl-1,3,2-dioxaborolan-2-yl)-5,6-dihydro-4H-pyrrolo[1,2-b]pyrazole (181 mg, 0.73 mmol) X-Phos (23 mg, 0.05 mmol) and $Pd_2(dba)_3$ (45 mg, 0.05 mmol), $K_3PO_4$ (517 mg, 2.44 mmol) were placed in dioxane/$H_2O$ (10 mL). The mixture was stirred 100° C. for 2 h under $N_2$, the mixture was extracted with EA, washed with brine, dried ($Na_2SO_4$), and concentrated in vacuo. Purification by silica gel chromatography to give the titled compound (35 mg, yield: 13.8%) as a white solid. Mass (m/z) 518.2 $[M+H]^+$. $^1$HNMR (300 MHz, $CDCl_3$) δ 8.14 (t, J=2.5 Hz, 1H), 7.42 (d, J=1.7 Hz, 1H), 7.28 (d, J=8.0 Hz, 2H), 6.89 (d, J=1.9 Hz, 1H), 5.37 (t, J=10.9 Hz, 1H), 4.15 (q, J=7.8 Hz, 2H), 3.94-3.55 (m, 8H), 3.43-3.25 (m, 2H), 3.08 (td, J=7.4, 2.7 Hz, 2H), 2.77-2.65 (m, 1H), 2.66-2.57 (m, 1H), 2.56 (s, 3H).

Compound 185: (S)-(4-(4-chloro-5-(1,4-dimethyl-1H-pyrazol-5-yl)thiazol-2-yl)piperazin-1-yl)(5-(3,5-difluorophenyl)-4,5-dihydro-1H-pyrazol-1-yl)methanone

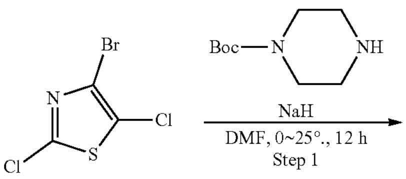

-continued

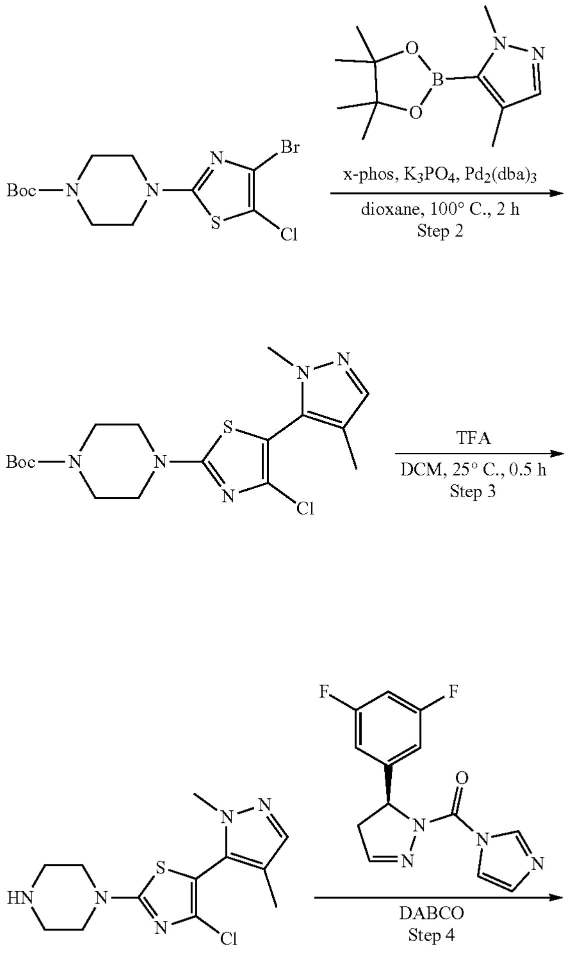

-continued

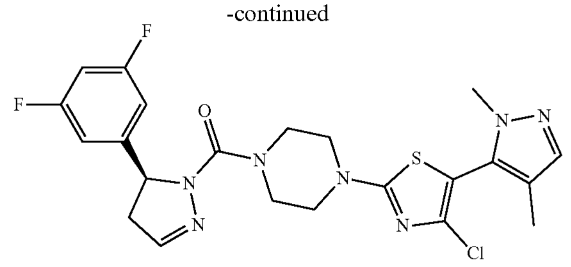

Step 1: 4-bromo-2,5-dichlorothiazole (1.0 g, 5.78 mmol) was dissolved in 10 ml of dry DMF, NaH (277 mg, 6.93 mmol) was added to the above solution at 0° C., the mixture was stirred for 30 min. Then tert-butyl piperazine-1-carboxylate (1.289 g, 6.93 mmol) was added to the above solution, the mixture was stirred for 12 h. The mixture was added water and extracted with EA, washed with brine, dried ($Na_2SO_4$), and concentrated in vacuo. Purification by silica gel chromatography to give the titled compound tert-butyl 4-(4-bromo-5-chlorothiazol yl)piperazine-1-carboxylate (526.5 mg, 23.8%) as a white solid. MS (m/z): 383.4 $[M+H]^+$.

Step 2: tert-butyl 4-(4-bromo-5-chlorothiazol-2-yl)piperazine-1-carboxylate (526.5 mg, 1.38 mmol), 1,4-dimethyl-5-(4,4,5,5-tetramethyl-1,3,2-dioxaborolan-2-yl)-1H-pyrazole (241 mg, 1.09 mmol), x-phos (65 mg, 0.13 mmol), $Pd_2(dba)_3$ (124 mg, 0.13 mmol), $K_3PO_4$ (5N, 5 mL) were placed in dioxane (10 mL). The mixture was stirred 100° C. for 12 h under $N_2$, The mixture was added water and extracted with DCM, washed with brine, dried ($Na_2SO_4$), and concentrated in vacuo. Purification by silica gel chromatography to give the titled compound tert-butyl 4-(4-chloro-5-(1,4-dimethyl-1H-pyrazol-5-yl)thiazol-2-yl)piperazine-1-carboxylate (45.4 mg, 8.3%) as a white solid. MS (m/z): 398.4 $[M+H]^+$.

Step 3 and 4:

The titled compound 185 was prepared in a yield of 17.7% as a white solid according to the procedure outlined for compound 143. Mass (m/z): 506.2 $[M+H]^+$.

Compound 186: ((S)-5-(3,5-difluorophenyl)-4,5-dihydro-1H-pyrazol-1-yl)(4-(5-fluoro-4-(5,6,7,7a-tetrahydro-4l4-pyrrolo[2,1-c][1,2,4]triazol-3-yl)pyrimidin-2-yl)piperazin-1-yl)methanone

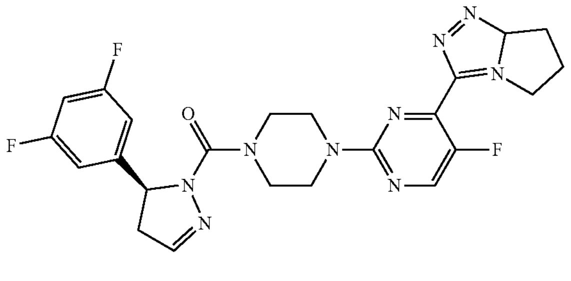

The titled compound 186 was prepared in a yield of 15.7% as a light-yellow solid according to the procedure outlined for compound 184. Mass (m/z) 499.2 $[M+H]^+$; $^1H$ NMR (400 MHz, $CDCl_3$) δ 8.37 (d, J=2.2 Hz, 1H), 7.34 (s, 1H), 7.23-7.20 (m, 1H), 6.84 (s, 1H), 5.31 (dd, J=11.5, 10.0 Hz, 1H), 4.30 (dd, J=36.2, 28.9 Hz, 5H), 3.70 (ddt, J=23.2, 16.2, 11.6 Hz, 7H), 3.31 (ddd, J=18.3, 11.7, 1.7 Hz, 1H), 3.16 (s, 2H), 2.85 (s, 2H), 2.64 (ddd, J=18.3, 9.9, 1.4 Hz, 1H).

Compound 187: (S)-(5-(3,5-difluorophenyl)-4,5-dihydro-1H-pyrazol-1-yl)(4-(5-fluoro-4-(5-methyl-1,3,4-oxadiazol-2-yl)pyrimidin-2-yl)piperazin-1-yl)methanone

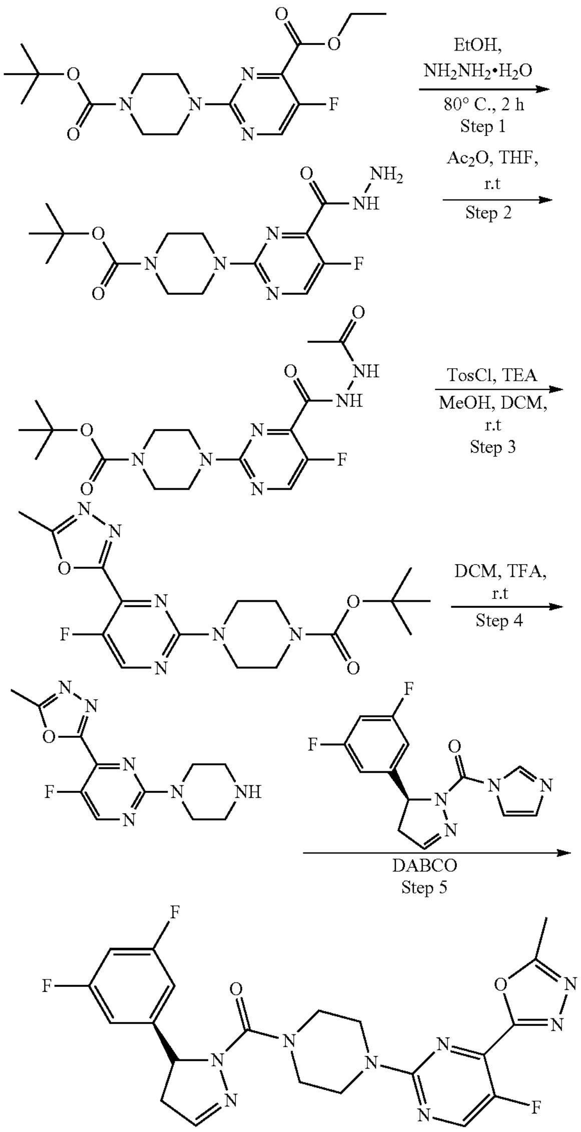

Step 1: ethyl 2-(4-(tert-butoxycarbonyl)piperazin-1-yl)-5-fluoropyrimidine-4-carboxylate (3.0 g, 8.7 mmol), in EtOH was added Hydrazine monohydrate (2.78 g, 87 mmol). The mixture was stirred 80° C. for 2 h under $N_2$ and concentrated under reduced pressure to give crude 3.0 g tert-butyl 4-(5-fluoro-4-(hydrazinecarbonyl)pyrimidin-2-yl)piperazine-1-carboxylate as s light yellow. Mass (m/z) 341.2 [M+H]+.

Step 2: tert-butyl 4-(5-fluoro-4-(hydrazinecarbonyl)pyrimidin-2-yl)piperazine-1-carboxylate (3.0 g, 8.82 mmol) in THF was added Acetic anhydride (3.4 mL). The mixture was stirred at room temperature for 2 h. The precipitate was filtered washed EA and dried on the filter to give 3.0 g tert-butyl 4-(4-(2-acetylhydrazine-1-carbonyl)-5-fluoropyrimidin-2-yl)piperazine-1-carboxylate as a yellow solid. Mass (m/z) 365.2 [M+H]+.

Step 3: To a solution of tert-butyl 4-(4-(2-acetylhydrazine-1-carbonyl)-5-fluoropyrimidin-2-yl)piperazine-1-carboxylate (2.0 g, 5.23 mmoL) in MeOH/DCM (1:1) was added Tosyl chloride and TEA (165 mg, 1.63 mmoL). The mixture reaction was stirred at room temperature for 5 h and concentrated in vacuo. Purification by column chromatography to give the titled compound tert-butyl 4-(5-fluoro-4-(5-methyl-1,3,4-oxadiazol-2-yl)pyrimidin-2-yl)piperazine-1-carboxylate (1.6 g, 84%). Mass (m/z) 365.2 $[M+H]^+$.

Step 4: tert-butyl 4-(5-fluoro-4-(5-methyl-1,3,4-oxadiazol-2-yl)pyrimidin-2-yl)piperazine-1-carboxylate (400 mg, 1.1 mmol) were dissolved in DCM (2 mL), TFA (1 ml) was added to the above solution, the mixture was stirred for 30 min. Concentrated to give the desired product 2-(5-fluoro-2-(piperazin-1-yl)pyrimidin-4-yl)-5-methyl-1,3,4-oxadiazole. MS (m/z): 265.2 $(M+H^+)$, which was used for next step without further purification.

Step 5: 2-(5-fluoro-2-(piperazin-1-yl)pyrimidin-4-yl)-5-methyl-1,3,4-oxadiazole (crude), (S)-(5-(3,5-difluorophenyl)-4,5-dihydro-1H-pyrazol-1-yl)(1H-imidazol-1-yl) methanone (200 mg, 1.32 mmol) were placed in THF (10 mL), TFA (1 ml) was added to the above solution. The mixture was stirred 12 h. The mixture was added water and extracted with EA, washed with brine, dried $(Na_2SO_4)$, and concentrated in vacuo. Purification by prep-HPLC to give the titled compound (72 mg, 13.8%) as a white solid. MS (m/z): 472.1 $(M+H^+)$. $^1$H NMR (400 MHz, $CDCl_3$) δ 8.46 (t, J=4.2 Hz, 1H), 7.42 (d, J=1.3 Hz, 1H), 7.31-7.22 (m, 2H), 6.90 (t, J=1.5 Hz, 1H), 5.46-5.23 (m, 1H), 3.96 (ddd, J=12.5, 6.7, 3.0 Hz, 2H), 3.89-3.73 (m, 4H), 3.66 (ddd, J=13.1, 6.7, 3.0 Hz, 2H), 3.37 (ddd, J=18.3, 11.7, 1.8 Hz, 1H), 2.75-2.66 (m, 1H), 2.69 (s, 3H).

Compound 188: (S)-3-fluoro-5-(1-(4-(5-fluoro-4-(5-methyl-1,3,4-oxadiazol-2-yl)pyrimidin-2-yl)piperazine-1-carbonyl)-4,5-dihydro-1H-pyrazol-5-yl)benzonitrile

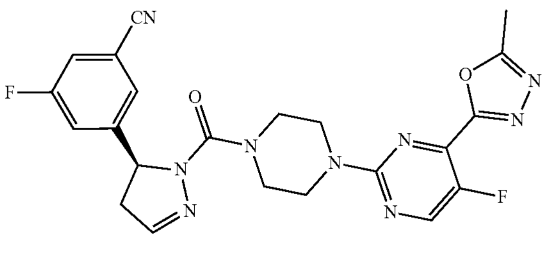 [SMILES: Cc1nnc(-c2nc(N3CCN(C(=O)N4N=CC[C@H]4c4cc(F)cc(C#N)c4)CC3)ncc2F)o1]

The titled compound 188 was prepared in a yield of 27.6% according to the procedure outlined for compound 187. Mass (m/z) 480.2 $[M+H]^+$; $^1$H NMR (400 MHz, $CDCl_3$) δ 8.46 (t, J=4.2 Hz, 1H), 7.42 (d, J=1.3 Hz, 1H), 7.34-7.25 (m, 2H), 6.90 (t, J=1.5 Hz, 1H), 5.36 (dt, J=26.8, 13.4 Hz, 1H), 4.04-3.90 (m, 2H), 3.90-3.72 (m, 4H), 3.66 (ddd, J=13.1, 6.7, 3.0 Hz, 2H), 3.37 (ddd, J=18.3, 11.7, 1.8 Hz, 1H), 2.75-2.66 (m, 1H), 2.69 (s, 3H).

Compound 189: (5-(3-chloropyridin-2-yl)-4,5-dihydro-1H-pyrazol-1-yl)(4-(4-(3,5-dimethyl-1H-1,2,4-triazol-1-yl)-5-fluoropyrimidin-2-yl)piperazin-1-yl)methanone

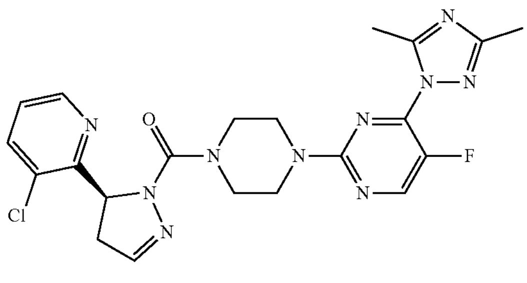 [SMILES: Cc1nc(C)n(-c2nc(N3CCN(C(=O)N4N=CC[C@H]4c4ncccc4Cl)CC3)ncc2F)n1]

The titled compound 189 was prepared in a yield of 10.4% according to the procedure outlined for compound 187. Mass (m/z) 485.2 $[M+H]^+$; $^1$H NMR (400 MHz, $CDCl_3$) δ 8.48 (dd, J=4.7, 1.5 Hz, 1H), 8.38 (t, J=2.3 Hz, 1H), 7.70 (dd, J=8.1, 1.5 Hz, 1H), 7.21-7.14 (m, 1H), 6.86 (t, J=1.6 Hz, 1H), 5.92 (dd, J=11.8, 9.1 Hz, 1H), 3.87-3.61 (m, 8H), 3.33 (ddd, J=18.0, 11.8, 1.8 Hz, 1H), 2.86 (ddd, J=18.0, 9.1, 1.6 Hz, 1H), 2.70 (s, 3H), 2.45 (s, 3H).

Compound 190: S)-1-(2-(4-(5-(3-cyano-5-fluorophenyl)-4,5-dihydro-1H-pyrazole-1-carbonyl)piperazin-1-yl)-5-fluoropyrimidin-4-yl)-5-methyl-1H-1,2,4-triazole-3-carboxylic acid

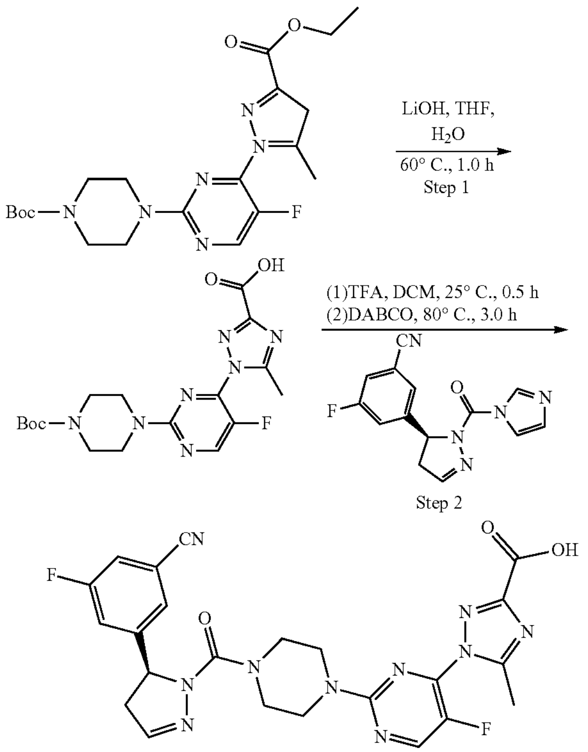

Step 1: tert-butyl 4-(4-(3-(ethoxycarbonyl)-5-methyl-1H-1,2,4-triazol-1-yl)-5-fluoropyrimidin-2-yl)piperazine-1-carboxylate (200 mg, 0.46 mmol), $LiOH{\cdot}H_2O$ (193 mg, 4.60 mmol) in THF (5 mL) and $H_2O$ (1 mL) under $N_2$ and the whole reaction mixture was stirred at 60° C. for 1.0 hours. The mixture was concentrated in vacuo to give 1-(2-(4-(tert-butoxycarbonyl)piperazin-1-yl)-5-fluoropyrimidin-4-yl)-5-methyl-1H-1,2,4-triazole-3-carboxylic acid (300 mg, crude) as a yellow solid and used into next step reaction without purification. MS (m/z): 406.4 $[M-H]^-$.

Step 2: 1-(2-(4-(tert-butoxycarbonyl)piperazin-1-yl)-5-fluoropyrimidin-4-yl)-5-methyl-1H-1,2,4-triazole-3-carboxylic acid (300 mg, crude), TFA (3 mL) were in DCM (5 mL) under $N_2$ and the whole reaction mixture was stirred at 25° C. for 0.5 hours. The mixture was concentrated in vacuo to give 1-(5-fluoro-2-(piperazin-1-yl)pyrimidin-4-yl)-5-methyl-1H-1,2,4-triazole carboxylic acid (200 mg, crude) as a yellow oil and used into next step reaction without purification. MS (m/z): 308.3 $[M+H]^+$.

The above residue (200 mg, crude), (S)-3-(1-(1H-imidazole-1-carbonyl)-4,5-dihydro-1H-pyrazol-5-yl)-5-fluorobenzonitrile (80 mg, 0.28 mmol), and DABCO (300 mg, 2.67 mmol) were in THF (10 mL) under $N_2$. The solvent was removed under vacuum and the reaction mixture was stand at 80° C. for 3.0 h. The mixture was extracted with EA, washed with brine, dried ($Na_2SO_4$), and concentrated in vacuo. Purification by silica gel chromatography to give compound 190 (12.8 mg, 20.0%) as a yellow solid. MS (m/z): 523.4 $[M+H]^+$. $^1H$ NMR (400 MHz, DMSO-$d_6$) δ 8.79 (d, J=2.8 Hz, 1H), 7.75 (ddd, J=8.4, 2.8, 1.6 Hz, 1H), 7.64 (d, J=1.6 Hz, 1H), 7.53 (dt, J=9.6, 2.0 Hz, 1H), 7.12 (d, J=1.6 Hz, 1H), 5.29 (t, J=10.8 Hz, 1H), 3.86-3.51 (m, 8H), 3.43-3.36 (m, 1H), 2.75-2.71 (m, 1H), 2.69 (s, 3H).

Compound 191: (S)-3-(1-(4-(4-(3,5-dimethyl-4-nitro-1H-pyrazol-1-yl)-5-fluoropyrimidin-2-yl)piperazine-1-carbonyl)-4,5-dihydro-1H-pyrazol-5-yl)-5-fluorobenzonitrile

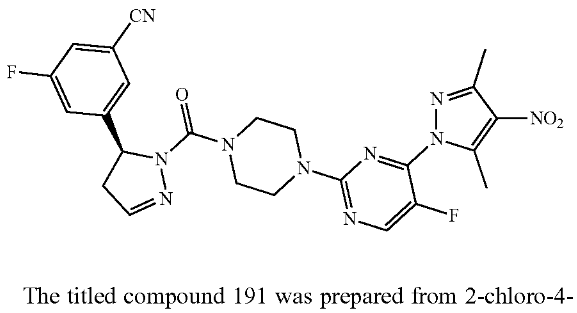

The titled compound 191 was prepared from 2-chloro-4-(3,5-dimethyl-4-nitro-1H-pyrazol-1-yl)-5-fluoropyrimidine in a yield of as a white solid 56.1% according to the procedure outlined for compound 166. Mass (m/z): 525.4 $[M+H]^+$. $^1H$ NMR (400 MHz, DMSO-$d_6$) δ 8.79 (d, J=2.4 Hz, 1H), 7.74 (ddd, J=8.4, 2.4, 1.2 Hz, 1H), 7.64 (d, J=1.6 Hz, 1H), 7.56-7.48 (m, 1H), 7.11 (d, J=1.6 Hz, 1H), 5.28 (t, J=10.8 Hz, 1H), 3.82-3.50 (m, 8H), 3.40-3.35 (m, 1H), 2.73 (s, 3H), 2.71-2.65 (m, 1H), 2.48 (s, 3H).

Compound 192: (S)—N-(1-(2-(4-(5-(3-cyano-5-fluorophenyl)-4,5-dihydro-1H-pyrazole-1-carbonyl)piperazin-1-yl)-5-fluoropyrimidin-4-yl)-3,5-dimethyl-1H-pyrazol-4-yl)cyclopropanecarboxamide

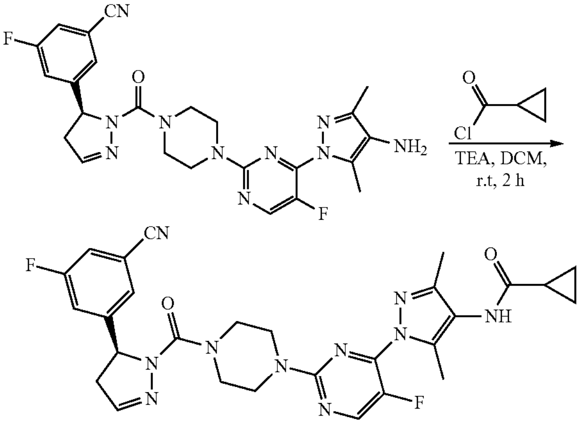

(S)-3-(1-(4-(4-(4-amino-3,5-dimethyl-1H-pyrazol-1-yl)-5-fluoropyrimidin-2-yl)piperazine-1-carbonyl)-4,5-dihydro-1H-pyrazol-5-yl)-5-fluorobenzonitrile (30 mg, 0.059 mmoL) was dissolved in 3 mL DCM. 0.2 ml TEA was added. Cyclopropanecarbonyl chloride (7.4 mg, 0.071 mmoL) was added. Let it stir at room temperature for 2 h. The solvent was evaporated to dryness and purified by $C_{18}$ column to give 20 mg compound 192 as a light yellow solid. Yield: 56.1%. Mass (m/z): 575.4 $[M+H]^+$. $^1H$ NMR (400 MHz, DMSO-$d_6$) δ 9.49 (s, 1H), 8.60 (d, J=3.2 Hz, 1H), 7.75 (ddd, J=8.4, 2.4, 1.2 Hz, 1H), 7.64 (t, J=1.6 Hz, 1H), 7.53 (dt, J=9.6, 2.4 Hz, 1H), 7.14-7.09 (m, 1H), 5.28 (t, J=10.8 Hz, 1H), 3.81-3.51 (m, 8H), 3.41-3.34 (m, 1H), 2.76-2.66 (m, 1H), 2.31 (s, 3H), 2.06 (s, 3H), 1.84-1.73 (m, 1H), 0.84-0.74 (m, 4H).

Compound 193: (S)—N-(1-(2-(4-(5-(3,5-difluorophenyl)-4,5-dihydro-1H-pyrazole-1-carbonyl)piperazin-1-yl)-5-fluoropyrimidin-4-yl)-3,5-dimethyl-1H-pyrazol-4-yl)acetamide

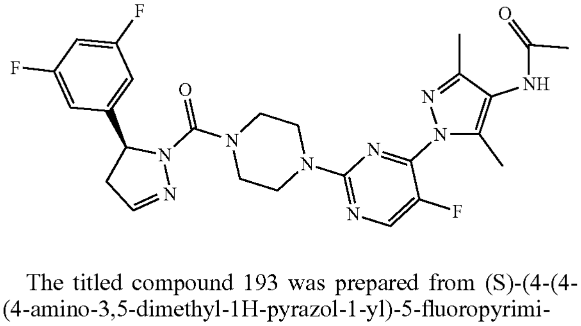

The titled compound 193 was prepared from (S)-(4-(4-(4-amino-3,5-dimethyl-1H-pyrazol-1-yl)-5-fluoropyrimidin-2-yl)piperazin-1-yl)(5-(3,5-difluorophenyl)-4,5-dihydro-1H-pyrazol-1-yl)methanone in 30.8% yield as light yellow solid according to the procedure outlined for compound 192. MS (m/z): 542.3 $[M+H]^+$. $^1H$ NMR (400 MHz, DMSO-$d_6$) δ 9.25 (s, 1H), 8.60 (d, J=3.6 Hz, 1H), 7.16-7.06 (m, 2H), 7.04-6.96 (m, 2H), 5.25 (dd, J=11.6, 10.0 Hz, 1H), 3.81-3.43 (m, 8H), 3.36 (ddd, J=18.4, 11.6, 2.0 Hz, 1H), 2.70-2.56 (m, 1H), 2.31 (s, 3H), 2.07 (s, 3H), 2.03 (s, 3H).

Compound 194: (S)—N-(1-(2-(4-(5-(3-cyano-5-fluorophenyl)-4,5-dihydro-1H-pyrazole-1-carbonyl)piperazin-1-yl)-5-fluoropyrimidin-4-yl)-3,5-dimethyl-1H-pyrazol-4-yl)ethanesulfonamide

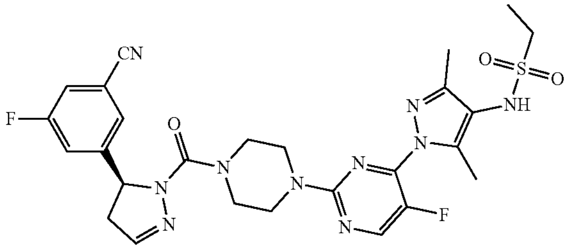 [SMILES: CCS(=O)(=O)Nc1c(C)nn(-c2nc(N3CCN(C(=O)N4N=CC[C@H]4c4cc(F)cc(C#N)c4)CC3)ncc2F)c1C]

The titled compound 194 was prepared in a yield of 7.0% as a light grey solid according to the procedure outlined for compound 192. Mass (m/z): 599.4 $[M+H]^+$. $^1H$ NMR (400 MHz, DMSO-$d_6$) δ 8.95 (s, 1H), 8.62 (d, J=3.6 Hz, 1H), 7.75 (ddd, J=8.4, 2.4, 1.2 Hz, 1H), 7.64 (d, J=1.6 Hz, 1H), 7.53 (dt, J=9.6, 2.0 Hz, 1H), 7.11 (d, J=1.6 Hz, 1H), 5.29 (t, J=10.8 Hz, 1H), 3.80-3.51 (m, 8H), 3.41-3.36 (m, 1H), 3.06 (q, J=7.2 Hz, 2H), 2.76-2.66 (m, 1H), 2.43 (s, 3H), 2.19 (s, 3H), 1.30 (t, J=7.2 Hz, 3H).

Compound 195: (S)—N-(1-(2-(4-(5-(3-cyano-5-fluorophenyl)-4,5-dihydro-1H-pyrazole-1-carbonyl)piperazin-1-yl)-5-fluoropyrimidin-4-yl)-3,5-dimethyl-1H-pyrazol-4-yl)-2-cyclopropylacetamide

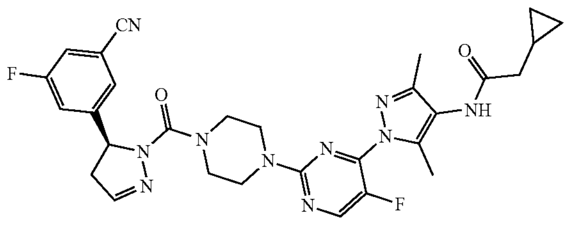 [SMILES: Cc1nn(-c2nc(N3CCN(C(=O)N4N=CC[C@H]4c4cc(F)cc(C#N)c4)CC3)ncc2F)c(C)c1NC(=O)CC1CC1]

The titled compound 195 was prepared in a yield of 19.0% as a white solid according to the procedure outlined for compound 192. Mass (m/z): 589.3 $[M+H]^+$. $^1H$ NMR (400 MHz, DMSO-$d_6$) δ 9.12 (s, 1H), 8.60 (d, J=3.6 Hz, 1H), 7.78-7.71 (m, 1H), 7.67-7.62 (m, 1H), 7.57-7.49 (m, 1H), 7.11 (d, J=1.7 Hz, 1H), 5.29 (t, J=10.8 Hz, 1H), 3.80-3.51 (m, 8H), 3.41-3.35 (m, 1H), 2.75-2.65 (m, 1H), 2.32 (s, 3H), 2.20 (d, J=7.2 Hz, 2H), 2.07 (s, 3H), 1.19-1.02 (m, 1H), 0.58-0.41 (m, 3H), 0.26-0.18 (m, 2H).

Compound 196: (S)-(5-(3,5-difluorophenyl)-4,5-dihydro-1H-pyrazol-1-yl)(4-(5-fluoro-4-(5-methyl-3-(trifluoromethyl)-1H-pyrazol-1-yl)pyrimidin-2-yl)piperazin-1-yl)methanone

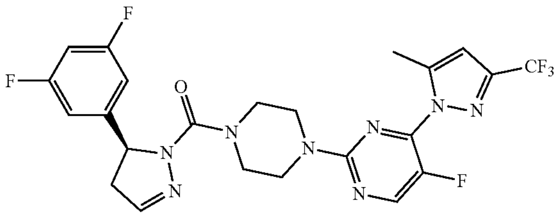 [SMILES: Cc1cc(C(F)(F)F)nn1-c1nc(N2CCN(C(=O)N3N=CC[C@H]3c3cc(F)cc(F)c3)CC2)ncc1F]

The titled compound 196 was prepared from (S)-(5-(3,5-difluorophenyl)-4,5-dihydro-1H-pyrazol-1-yl)(piperazin-1-yl)methanone in a yield of 49.0% as a white solid according to the procedure outlined for compound 147. Mass (m/z): 539.4 $[M+H]^{+1}H$ NMR (300 MHz, DMSO-$d_6$) δ 8.74 (d, J=2.8 Hz, 1H), 7.15-7.05 (m, 2H), 7.03-6.94 (m, 2H), 6.87 (s, 1H), 5.25 (dd, J=11.6, 10.0 Hz, 1H), 3.86-3.50 (m, 8H), 3.42-3.30 (m, 1H), 2.64 (ddd, J=18.4, 10.0, 1.6 Hz, 1H), 2.53 (s, 3H).

Compound 197: (S)-3-fluoro-5-(1-(4-(5-fluoro-4-(4-methyl-4H-1,2,4-triazol-3-yl)pyrimidin-2-yl)piperazine-1-carbonyl)-4,5-dihydro-1H-pyrazol-5-yl)benzonitrile

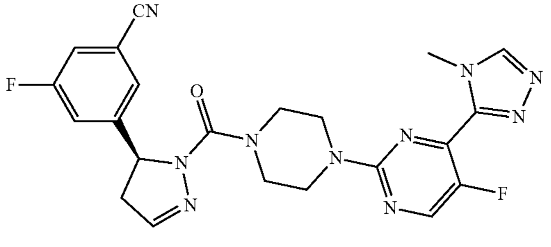 [SMILES: Cn1cnnc1-c1nc(N2CCN(C(=O)N3N=CC[C@H]3c3cc(F)cc(C#N)c3)CC2)ncc1F]

The titled compound 197 was prepared from (S)-3-(1-(1H-imidazole-1-carbonyl)-4,5-dihydro-1H-pyrazol-5-yl)-5-fluorobenzonitrile in a yield of 3.0% as a yellow solid according to the procedure outlined for compound 151. Mass (m/z): 578.4 $[M+H]^+$. $^1H$ NMR (300 MHz, DMSO-$d_6$) δ 8.73 (s, 1H), 8.68 (d, J=2.4 Hz, 1H), 7.81-7.73 (m, 2H), 7.65 (d, J=9.6 Hz, 1H), 7.33 (d, J=8.4 Hz, 1H), 5.19 (d, J=7.4 Hz, 1H), 3.93 (s, 3H), 3.77-3.68 (m, 8H), 3.55-3.44 (m, 1H), 2.75-2.62 (m, 1H).

Compound 198: (S)-(5-(3,5-difluorophenyl)-4,5-dihydro-1H-pyrazol-1-yl)(4-(4-(1,5-dimethyl-3-(trifluoromethyl)-1H-pyrazol-4-yl)-5-fluoropyrimidin-2-yl)piperazin-1-yl)methanone

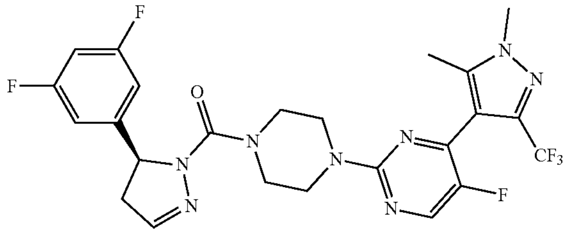 [SMILES: Cc1c(-c2nc(N3CCN(C(=O)N4N=CC[C@H]4c4cc(F)cc(F)c4)CC3)ncc2F)c(C(F)(F)F)nn1C]

The titled compound 198 was prepared from (S)-(5-(3,5-difluorophenyl)-4,5-dihydro-1H-pyrazol-1-yl)(1H-imidazol-1-yl)methanone in a yield of 14.0% as a white solid according to the procedure outlined for compound 151. Mass (m/z): 553.4 $[M+H]^+$. $^1H$ NMR (300 MHz, DMSO-$d_6$) δ 8.55 (d, J=2.0 Hz, 1H), 7.21-7.06 (m, 2H), 7.06-6.94 (m, 2H), 5.25 (t, J=10.8 Hz, 1H), 3.89 (s, 3H), 3.83-3.47 (m, 8H), 3.44-3.37 (m, 1H), 2.73-2.60 (m, 1H), 2.31 (s, 3H).

Compound 199: (S)-2-(2-(4-(5-(3,5-difluorophenyl)-4,5-dihydro-1H-pyrazole-1-carbonyl)piperazin-1-yl)-5-fluoropyrimidin-4-yl)-4-ethyl-2,4-dihydro-3H-1,2,4-triazol-3-one

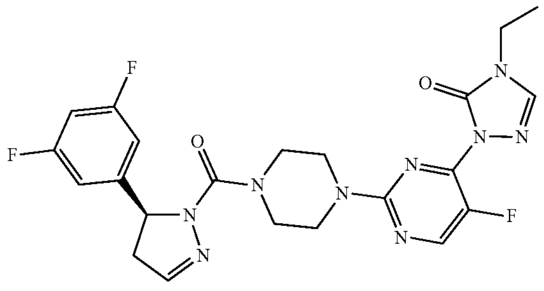 [SMILES: CCn1cnn(-c2nc(N3CCN(C(=O)N4N=CC[C@H]4c4cc(F)cc(F)c4)CC3)ncc2F)c1=O]

The titled compound 199 was prepared from (S)-(5-(3,5-difluorophenyl)-4,5-dihydro-1H-pyrazol-1-yl)(1H-imidazol-1-yl)methanone in a yield of 29.6% as a white solid according to the procedure outlined for compound 144. Mass (m/z): 502.4 $[M+H]^+$. $^1H$ NMR (300 MHz, DMSO-$d_6$) δ 8.68 (d, J=2.4 Hz, 1H), 8.40 (s, 1H), 7.19-7.05 (m, 2H), 7.07-6.94 (m, 2H), 5.25 (dd, J=11.6, 10.0 Hz, 1H), 3.84-3.47 (m, 10H), 3.44-3.34 (m, 1H), 2.65 (ddd, J=18.4, 10.0, 1.6 Hz, 1H), 1.25 (t, J=7.2 Hz, 3H).

Compound 200: (S)-3-(1-(4-(4-(4-ethyl-5-oxo-4,5-dihydro-1H-1,2,4-triazol-1-yl)-5-fluoropyrimidin-2-yl)piperazine-1-carbonyl)-4,5-dihydro-1H-pyrazol-5-yl)-5-fluorobenzonitrile

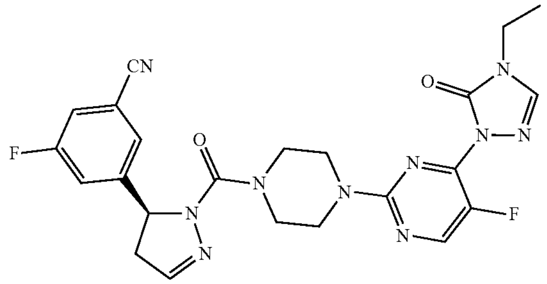 [SMILES: CCn1cnn(-c2nc(N3CCN(C(=O)N4N=CC[C@H]4c4cc(F)cc(C#N)c4)CC3)ncc2F)c1=O]

The titled compound 200 was prepared from (S)-3-fluoro-5-(1-(piperazine-1-carbonyl)-4,5-dihydro-1H-pyrazol-5-yl)benzonitrile in a yield of 21.3% as a white solid according to the procedure outlined for compound 144. Mass (m/z): 509.4 $[M+H]^+$. $^1H$ NMR (400 MHz, DMSO-$d_6$) δ 8.68 (d, J=2.4 Hz, 1H), 8.40 (s, 1H), 7.79-7.72 (m, 1H), 7.65 (s, 1H), 7.53 (d, J=9.6 Hz, 1H), 7.12 (s, 1H), 5.28 (t, J=10.8 Hz, 1H), 3.81-3.49 (m, 10H), 3.39-3.29 (m, 1H), 2.76-2.67 (m, 1H), 1.25 (t, J=7.2 Hz, 3H).

Compound 201: (S)-2-(2-(4-(5-(3,5-difluorophenyl)-4,5-dihydro-1H-pyrazole-1-carbonyl)piperazin-1-yl)-5-fluoropyrimidin-4-yl)-4-(2,2,2-trifluoroethyl)-2,4-dihydro-3H-1,2,4-triazol-3-one

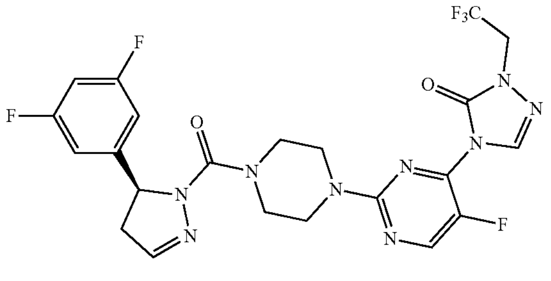 [SMILES: O=C(N1CCN(c2ncc(F)c(-n3cnn(CC(F)(F)F)c3=O)n2)CC1)N1N=CC[C@H]1c1cc(F)cc(F)c1]

The titled compound 201 was prepared from (S)-(5-(3,5-difluorophenyl)-4,5-dihydro-1H-pyrazol-1-yl)(1H-imidazol-1-yl)methanone in a yield of 10.5% as a light grey solid according to the procedure outlined for compound 144. Mass (m/z): 556.2 $[M+H]^+$. $^1H$ NMR (400 MHz, DMSO-$d_6$) δ 8.71 (d, J=2.4 Hz, 1H), 8.55 (s, 1H), 7.15-7.07 (m, 2H), 7.01-6.97 (m, 2H), 5.31-5.20 (m, 1H), 4.71 (q, J=9.2 Hz, 2H), 3.83-3.49 (m, 8H), 3.41-3.33 (m, 1H), 2.68-2.61 (m, 1H).

Compound 202: (S)-3-fluoro-5-(1-(4-(5-fluoro-4-(5-oxo-4-(2,2,2-trifluoroethyl)-4,5-dihydro-1H-1,2,4-triazol-1-yl)pyrimidin-2-yl)piperazine-1-carbonyl)-4,5-dihydro-1H-pyrazol-5-yl)benzonitrile

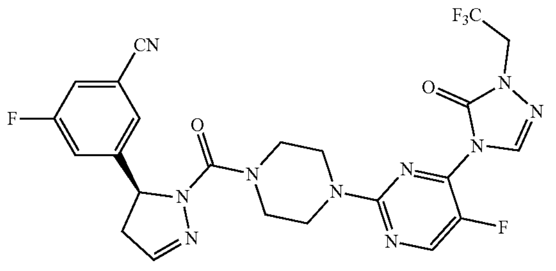 [SMILES: N#Cc1cc(F)cc([C@@H]2CC=NN2C(=O)N2CCN(c3ncc(F)c(-n4cnn(CC(F)(F)F)c4=O)n3)CC2)c1]

The titled compound 202 was prepared from (S)-3-fluoro-5-(1-(piperazine-1-carbonyl)-4,5-dihydro-1H-pyrazol-5-yl) benzonitrile in a yield of 21.3% as a white solid according to the procedure outlined for compound 144. Mass (m/z): 563.4 $[M+H]^+$. $^1H$ NMR (300 MHz, DMSO-$d_6$) δ 8.70 (d, J=2.4 Hz, 1H), 8.55 (s, 1H), 7.81-7.71 (m, 1H), 7.64 (d, J=1.6 Hz, 1H), 7.58-7.49 (m, 1H), 7.11 (d, J=1.6 Hz, 1H), 5.28 (t, J=10.8 Hz, 1H), 4.71 (q, J=9.2 Hz, 2H), 3.84-3.51 (m, 8H), 3.48-3.40 (m, 1H), 2.79-2.62 (m, 1H).

Compound 203: (S)-(5-(3,5-difluorophenyl)-4,5-dihydro-1H-pyrazol-1-yl)(4-(5-fluoro-4-(5-methyl-3-(trifluoromethyl)-1H-1,2,4-triazol-1-yl)pyrimidin-2-yl)piperazin-1-yl)methanone

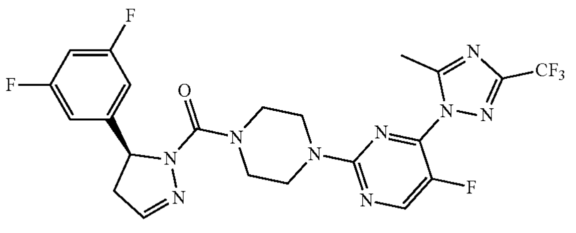

The titled compound 203 was prepared from (S)-(5-(3,5-difluorophenyl)-4,5-dihydro-1H-pyrazol-1-yl)(piperazin-1-yl)methanone in a yield of 44.1% as a light yellow solid according to the procedure outlined for compound 147. Mass (m/z): 540.4 $[M+H]^+$. $^1H$ NMR (301 MHz, DMSO-$d_6$) δ 8.82 (d, J=2.8 Hz, 1H), 7.17-7.06 (m, 2H), 7.01 (qd, J=6.4, 3.2 Hz, 2H), 5.26 (dd, J=11.6, 10.0 Hz, 1H), 3.88-3.51 (m, 8H), 3.45-3.37 (m, 1H), 2.75 (s, 3H), 2.65 (ddd, J=18.4, 10.0, 1.6 Hz, 1H).

Compound 204: (S)-3-(1-(4-(4-(3,5-dimethyl-4-(methylsulfonyl)-1H-pyrazol-1-yl)-5-fluoropyrimidin yl)piperazine-1-carbonyl)-4,5-dihydro-1H-pyrazol-5-yl)-5-fluorobenzonitrile

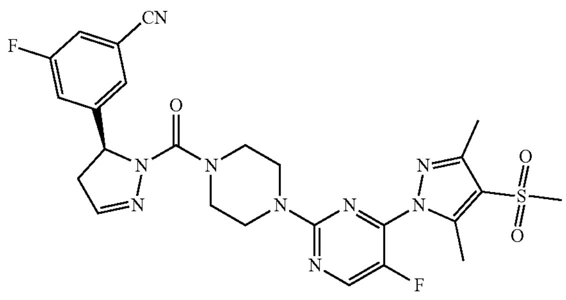 [SMILES: Cc1nn(-c2nc(N3CCN(C(=O)N4N=CC[C@H]4c4cc(F)cc(C#N)c4)CC3)ncc2F)c(C)c1S(C)(=O)=O]

The titled compound 204 was prepared from (S)-3-fluoro-5-(1-(piperazine-1-carbonyl)-4,5-dihydro-1H-pyrazol-5-yl) benzonitrile in a yield of 47.3% as a yellow solid according to the procedure outlined for compound 147. Mass (m/z): 570.3 $[M+H]^+$. $^1H$ NMR (400 MHz, Chloroform-d) δ 8.42 (d, J=2.4 Hz, 1H), 7.41 (d, J=1.6 Hz, 1H), 7.29-7.26 (m, 2H), 6.89 (t, J=1.6 Hz, 1H), 5.36 (dd, J=11.6, 10.0 Hz, 1H), 3.94-3.59 (m, 8H), 3.36 (ddd, J=18.4, 11.6, 1.6 Hz, 1H), 3.10 (s, 3H), 2.76-2.69 (m, 1H), 2.68 (s, 3H), 2.52 (s, 3H).

Compound 205: (S)-3-(1-(4-(4-(4-(ethylsulfonyl)-3,5-dimethyl-1H-pyrazol-1-yl)-5-fluoropyrimidin-2-yl)piperazine-1-carbonyl)-4,5-dihydro-1H-pyrazol-5-yl)-5-fluorobenzonitrile

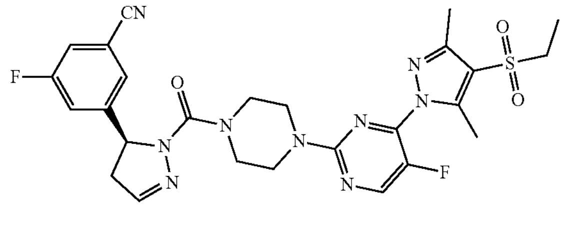 [SMILES: CCS(=O)(=O)c1c(C)nn(-c2nc(N3CCN(C(=O)N4N=CC[C@H]4c4cc(F)cc(C#N)c4)CC3)ncc2F)c1C]

The titled compound 205 was prepared from (S)-3-fluoro-5-(1-(piperazine-1-carbonyl)-4,5-dihydro-1H-pyrazol-5-yl) benzonitrile in a yield of 31.9% as an orange solid according to the procedure outlined for compound 147. Mass (m/z): 584.4 $[M+H]^+$. $^1H$ NMR (301 MHz, DMSO-$d_6$) δ 8.76 (d, J=2.4 Hz, 1H), 7.79-7.71 (m, 1H), 7.67-7.62 (m, 1H), 7.56-7.50 (m, 1H), 7.15-7.08 (m, 1H), 5.28 (t, J=10.8 Hz, 1H), 3.82-3.47 (m, 8H), 3.45-3.35 (m, 1H), 3.28 (d, J=7.2 Hz, 2H), 2.72 (dd, J=10.8, 7.6 Hz, 1H), 2.62 (s, 3H), 2.37 (s, 3H), 1.18 (t, J=7.2 Hz, 3H).

Compound 206: (S)-3-(1-(4-(4-(3,5-dimethyl-4-(methylsulfonyl)-1H-pyrazol-1-yl)pyrimidin-2-yl)piperazine-1-carbonyl)-4,5-dihydro-1H-pyrazol-5-yl)-5-fluorobenzonitrile

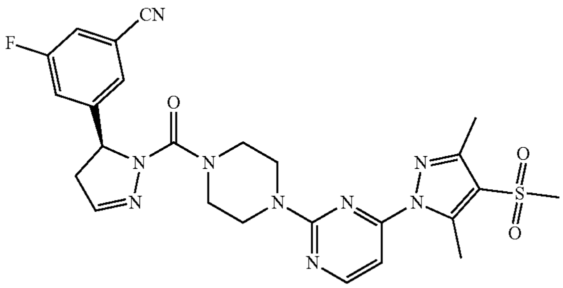 [SMILES: Cc1nn(-c2ccnc(N3CCN(C(=O)N4N=CC[C@H]4c4cc(F)cc(C#N)c4)CC3)n2)c(C)c1S(C)(=O)=O]

The titled compound 206 was prepared from (S)-3-fluoro-5-(1-(piperazine-1-carbonyl)-4,5-dihydro-1H-pyrazol-5-yl)benzonitrile in a yield of 42.6% as a yellow solid according to the procedure outlined for compound 147. Mass (m/z): 552.3 $[M+H]^+$. $^1$H NMR (400 MHz, Chloroform-d) δ 8.43 (d, J=5.2 Hz, 1H), 7.42 (d, J=1.6 Hz, 1H), 7.30-7.27 (m, 2H), 7.14 (d, J=5.2 Hz, 1H), 6.90 (s, 1H), 5.44-5.32 (m, 1H), 4.01-3.60 (m, 8H), 3.37 (dd, J=18.4, 11.6 Hz, 1H), 3.08 (s, 3H), 2.98 (s, 3H), 2.70 (dd, J=18.4, 10.4 Hz, 1H), 2.50 (s, 3H).

Compound 207: (S)-3-fluoro-5-(1-(4-(5-fluoro-4-(5-methyl-3-(trifluoromethyl)-1H-1,2,4-triazol-1-yl)pyrimidin-2-yl)piperazine-1-carbonyl)-4,5-dihydro-1H-pyrazol-5-yl)benzonitrile

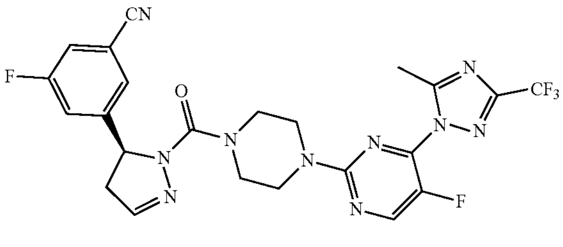 [SMILES: Cc1nc(C(F)(F)F)nn1-c1nc(N2CCN(C(=O)N3N=CC[C@H]3c3cc(F)cc(C#N)c3)CC2)ncc1F]

The titled compound 207 was prepared from (S)-3-fluoro-5-(1-(piperazine-1-carbonyl)-4,5-dihydro-1H-pyrazol-5-yl)benzonitrile in a yield of 45.8% as a yellow solid according to the procedure outlined for compound 147. Mass (m/z): 547.4 $[M+H]^+$. $^1$H NMR (300 MHz, DMSO-$d_6$) δ 8.83 (t, J=2.4 Hz, 1H), 7.75 (dt, J=8.4, 2.0 Hz, 1H), 7.65 (d, J=1.6 Hz, 1H), 7.53 (dt, J=9.6, 2.0 Hz, 1H), 7.12 (t, J=1.6 Hz, 1H), 5.29 (t, J=10.8 Hz, 1H), 3.87-3.50 (m, 8H), 3.43-3.36 (m, 1H), 2.75 (s, 3H), 2.72-2.63 (m, 1H).

Compound 208: (S)-3-(1-(4-(4-(3,5-dimethyl-1-(methylsulfonyl)-1H-pyrazol-4-yl)-5-fluoropyrimidin-2-yl)piperazine-1-carbonyl)-4,5-dihydro-1H-pyrazol-5-yl)-5-fluorobenzonitrile

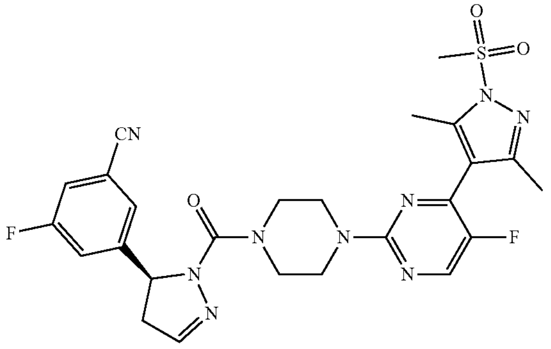 [SMILES: Cc1nn(S(C)(=O)=O)c(C)c1-c1nc(N2CCN(C(=O)N3N=CC[C@H]3c3cc(F)cc(C#N)c3)CC2)ncc1F]

The titled compound 208 was prepared from (S)-3-fluoro-5-(1-(piperazine-1-carbonyl)-4,5-dihydro-1H-pyrazol-5-yl)benzonitrile in a yield of 45.8% as a yellow solid according to the procedure outlined for compound 146. Mass (m/z): 547.4 $[M+H]^+$. $^1$H NMR (400 MHz, DMSO-$d_6$) δ 8.57 (d, J=2.0 Hz, 1H), 7.75 (ddd, J=8.4, 2.4, 1.6 Hz, 1H), 7.64 (d, J=1.6 Hz, 1H), 7.53 (dt, J=9.6, 2.0 Hz, 1H), 7.11 (d, J=1.6 Hz, 1H), 5.29 (t, J=10.8 Hz, 1H), 3.81-3.61 (m, 6H), 3.59 (s, 3H), 3.56-3.50 (m, 2H), 3.41-3.35 (m, 1H), 2.70 (ddd, J=18.4, 10.0, 1.6 Hz, 1H), 2.47 (d, J=2.0 Hz, 3H), 2.25 (s, 3H).

Compound 209: (4-(5-fluoro-4-(5-methyl-1,3,4-thiadiazol-2-yl)pyrimidin-2-yl)piperazin-1-yl)(5-(2-methyloxazol-4-yl)-4,5-dihydro-1H-pyrazol-1-yl)methanone

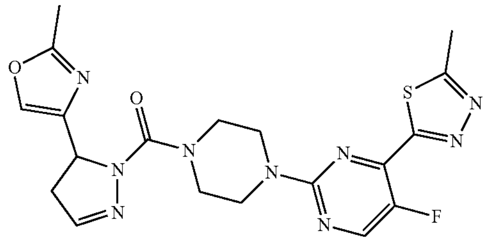 [SMILES: Cc1nc(C2CC=NN2C(=O)N2CCN(c3ncc(F)c(-c4nnc(C)s4)n3)CC2)co1]

The titled compound 209 was prepared in a yield of 1.4% as a yellow solid according to the procedure outlined for compound 166. Mass (m/z): 458.2$[M+H]^+$. $^1$H NMR (400 MHz, Chloroform-d) δ 8.42 (d, J=2.4 Hz, 1H), 7.55 (s, 1H), 6.89 (t, J=1.6 Hz, 1H), 5.36 (t, J=10.8 Hz, 1H), 3.93-3.53 (m, 8H), 3.24-3.07 (m, 2H), 2.86 (s, 3H), 2.43 (s, 3H).

Compound 210: 5-(3-chloropyridin-2-yl)-4,5-dihydro-1H-pyrazol-1-yl)(4-(5-fluoro-4-(5-methyl-1,3,4-thiadiazol-2-yl)pyrimidin-2-yl)piperazin-1-yl) methanone

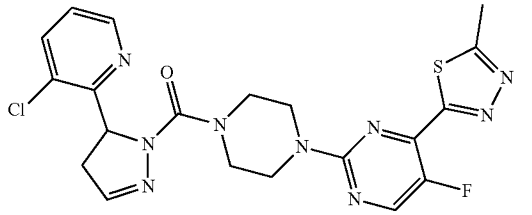 [SMILES: Cc1nnc(-c2nc(N3CCN(C(=O)N4N=CCC4c4ncccc4Cl)CC3)ncc2F)s1]

The titled compound 210 was prepared from (5-(3-chloropyridin-2-yl)-4,5-dihydro-1H-pyrazol-1-yl)(1H-imidazol-1-yl)methanone in a yield of 9.6% as a gold solid according to the procedure outlined for compound 166. Mass (m/z): 488.2[M+H]$^+$. $^1$H NMR (400 MHz, DMSO-$d_6$) δ 8.74 (d, J=2.8 Hz, 1H), 8.46 (dd, J=4.4, 1.6 Hz, 1H), 7.90 (dd, J=8.0, 1.6 Hz, 1H), 7.32 (dd, J=8.0, 4.8 Hz, 1H), 7.08-7.03 (m, 1H), 5.70 (dd, J=12.0, 8.0 Hz, 1H), 3.81-3.66 (m, 4H), 3.66-3.46 (m, 4H), 3.43-3.36 (m, 1H), 2.81 (s, 3H), 2.75-2.64 (m, 1H).

Compound 211: (4-(4-(3,5-dimethyl-1H-1,2,4-triazol-1-yl)-5-fluoropyrimidin-2-yl)piperazin-1-yl)(5-(2-methyloxazol-4-yl)-4,5-dihydro-1H-pyrazol-1-yl) methanone

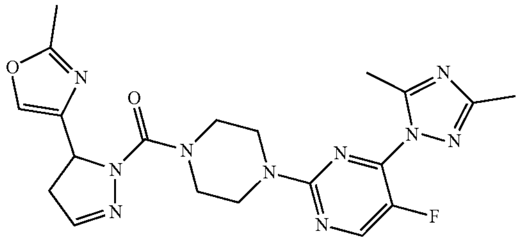 [SMILES: Cc1nc(C)n(-c2nc(N3CCN(C(=O)N4N=CCC4c4coc(C)n4)CC3)ncc2F)n1]

The titled compound 211 was prepared from (1H-imidazol-1-yl)(5-(2-methyloxazol-4-yl)-4,5-dihydro-1H-pyrazol-1-yl)methanone in a yield of 3.7% as a white solid according to the procedure outlined for compound 147. Mass (m/z): 455.2[M+H]$^+$. $^1$H NMR (400 MHz, Chloroform-d) δ 8.40 (d, J=2.4 Hz, 1H), 7.55 (s, 1H), 6.89 (t, J=1.6 Hz, 1H), 5.36 (t, J=10.8 Hz, 1H), 3.89-3.55 (m, 8H), 3.18-3.10 (m, 2H), 2.70 (s, 3H), 2.45 (s, 3H), 2.44 (s, 3H).

Compound 212: (4-(4-(3,5-dimethyl-1H-1,2,4-triazol-1-yl)-5-fluoropyrimidin-2-yl)piperazin-1-yl)(5-(thiazol-4-yl)-4,5-dihydro-1H-pyrazol-1-yl)methanone

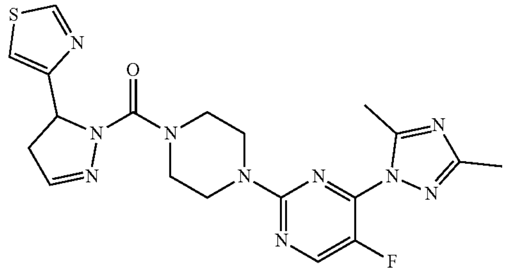 [SMILES: Cc1nc(C)n(-c2nc(N3CCN(C(=O)N4N=CCC4c4cscn4)CC3)ncc2F)n1]

The titled compound 212 was prepared from (1H-imidazol-1-yl)(5-(thiazol-4-yl)-4,5-dihydro-1H-pyrazol-1-yl) methanone in a yield of 6.2% as a white solid according to the procedure outlined for compound 147. Mass (m/z): 457.2[M+H]$^+$. $^1$H NMR (400 MHz, Chloroform-d) δ 8.82 (d, J=2.0 Hz, 1H), 8.41 (d, J=2.4 Hz, 1H), 7.35 (d, J=2.0 Hz, 1H), 6.93 (s, 1H), 5.68-5.58 (m, 1H), 3.90-3.56 (m, 8H), 3.34-3.13 (m, 2H), 2.72 (s, 3H), 2.47 (s, 3H).

Compound 213: (4-(4-(3,5-dimethyl-1H-1,2,4-triazol-1-yl)-5-fluoropyrimidin-2-yl)piperazin-1-yl)(5-(2-methylthiazol-4-yl)-4,5-dihydro-1H-pyrazol-1-yl) methanone

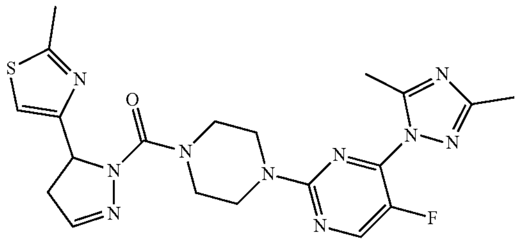 [SMILES: Cc1nc(C)n(-c2nc(N3CCN(C(=O)N4N=CCC4c4csc(C)n4)CC3)ncc2F)n1]

The titled compound 213 was prepared from (1H-imidazol-1-yl)(5-(2-methylthiazol-4-yl)-4,5-dihydro-1H-pyrazol-1-yl)methanone in a yield of 23.6% as a light yellow solid according to the procedure outlined for compound 147. Mass (m/z): 471.2[M+H]$^+$. $^1$H NMR (400 MHz, DMSO-$d_6$) δ 8.70 (d, J=3.2 Hz, 1H), 7.21 (s, 1H), 7.09 (d, J=1.6 Hz, 1H), 5.36 (dd, J=11.6, 9.2 Hz, 1H), 3.81-3.47 (m, 8H), 3.30-3.22 (m, 1H), 2.93-2.82 (m, 1H), 2.62-2.60 (m, 6H), 2.29 (s, 3H).

Compound 214: (4-(4-(3,5-dimethyl-1H-1,2,4-triazol-1-yl)-5-fluoropyrimidin-2-yl)piperazin-1-yl)(5-(2-methylthiazol-5-yl)-4,5-dihydro-1H-pyrazol-1-yl)methanone

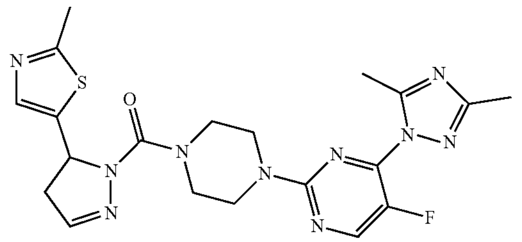 [SMILES: Cc1nc(C)n(-c2nc(N3CCN(C(=O)N4N=CCC4c4cnc(C)s4)CC3)ncc2F)n1]

The titled compound 214 was prepared from (1H-imidazol-1-yl)(5-(2-methylthiazol-5-yl)-4,5-dihydro-1H-pyrazol-1-yl)methanone in a yield of 17.3% as a yellow solid according to the procedure outlined for compound 147. Mass (m/z): 471.2[M+H]$^+$. $^1$H NMR (400 MHz, DMSO-$d_6$) δ 8.70 (d, J=3.2 Hz, 1H), 7.53 (s, 1H), 7.15 (d, J=1.6 Hz, 1H), 5.48 (t, J=10.4 Hz, 1H), 3.83-3.47 (m, 8H), 3.44-3.36 (m, 1H), 2.82 (ddd, J=18.4, 9.6, 1.6 Hz, 1H), 2.61 (s, 3H), 2.58 (s, 3H), 2.29 (s, 3H).

Compound 215: 4-(4-(3,5-dimethyl-1H-1,2,4-triazol-1-yl)-5-fluoropyrimidin-2-yl)piperazin-1-yl)(5-(4-methylthiazol-2-yl)-4,5-dihydro-1H-pyrazol-1-yl)methanone

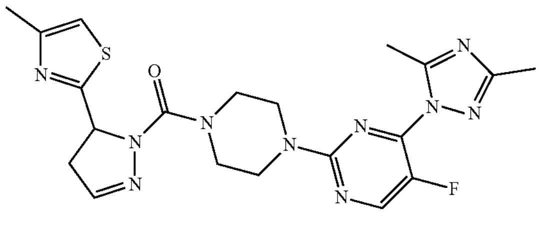

The titled compound 215 was prepared from (1H-imidazol-1-yl)(5-(4-methylthiazol-2-yl)-4,5-dihydro-1H-pyrazol yl)methanonein a yield of 14.1% as a yellow solid according to the procedure outlined for compound 147. Mass (m/z): 471.2[M+H]$^+$. $^1$HNMR (400 MHz, DMSO-$d_6$) δ 8.71 (d, J=3.2 Hz, 1H), 7.19-7.12 (m, 2H), 5.57 (dd, J=12.0, 9.2 Hz, 1H), 3.84-3.51 (m, 8H), 3.46-3.38 (m, 1H), 3.00 (dd, J=17.2, 9.2 Hz, 1H), 2.62 (s, 3H), 2.32 (d, J=1.2 Hz, 3H), 2.29 (s, 3H).

Compound 216: (4-(4-(3,5-dimethyl-1H-1,2,4-triazol-1-yl)-5-fluoropyrimidin-2-yl)piperazin-1-yl)(5-(5-methylthiazol-2-yl)-4,5-dihydro-1H-pyrazol-1-yl)methanone

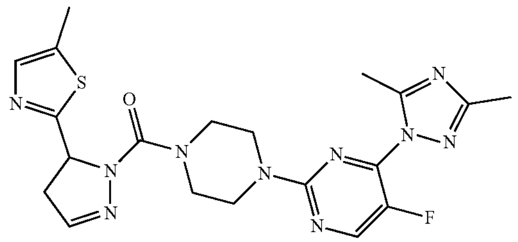 [SMILES: Cc1nc(C)n(-c2nc(N3CCN(C(=O)N4N=CCC4c4ncc(C)s4)CC3)ncc2F)n1]

The titled compound 216 was prepared from (1H-imidazol-1-yl)(5-(5-methylthiazol-2-yl)-4,5-dihydro-1H-pyrazol-1-yl)methanonein a yield of 17.0% as a light yellow solid according to the procedure outlined for compound 147. Mass (m/z): 471.2 [M+H]$^+$. $^1$H NMR (400 MHz, DMSO-$d_6$) δ 8.71 (d, J=3.2 Hz, 1H), 7.40 (q, J=1.2 Hz, 1H), 7.17-7.12 (m, 1H), 5.54 (dd, J=11.6, 9.2 Hz, 1H), 3.83-3.51 (m, 8H), 3.44-3.35 (m, 1H), 3.04 (ddd, J=18.4, 9.2, 1.6 Hz, 1H), 2.62 (s, 3H), 2.38 (d, J=1.2 Hz, 3H), 2.29 (s, 3H).

Compound 217: (4-(4-(3,5-dimethyl-1H-1,2,4-triazol-1-yl)-5-fluoropyrimidin-2-yl)piperazin-1-yl)(5-(thiazol-2-yl)-4,5-dihydro-1H-pyrazol-1-yl)methanone

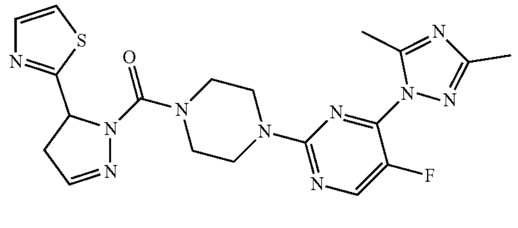 [SMILES: Cc1nc(C)n(-c2nc(N3CCN(C(=O)N4N=CCC4c4nccs4)CC3)ncc2F)n1]

The titled compound 217 was prepared from (1H-imidazol-1-yl)(5-(thiazol-2-yl)-4,5-dihydro-1H-pyrazol-1-yl)methanone in a yield of 13.1% as a yellow solid according to the procedure outlined for compound 147. Mass (m/z): 457.2[M+H]$^+$. $^1$HNMR (400 MHz, DMSO-$d_6$) δ 8.71 (d, J=3.2 Hz, 1H), 7.74 (d, J=3.2 Hz, 1H), 7.65 (d, J=3.2 Hz, 1H), 7.19-7.14 (m, 1H), 5.64 (dd, J=11.6, 9.0 Hz, 1H), 3.83-3.52 (m, 8H), 3.43 (ddd, J=18.4, 11.6, 1.8 Hz, 1H), 3.05 (ddd, J=18.4, 9.2, 1.6 Hz, 1H), 2.62 (s, 3H), 2.29 (s, 3H).

Compound 218: (S)-1-(4-(4-(5-(3,5-difluorophenyl)-4,5-dihydro-1H-pyrazole-1-carbonyl)piperazin-1-yl)-5-fluoropyrimidin-2-yl)-1H-pyrazole-4-carbonitrile

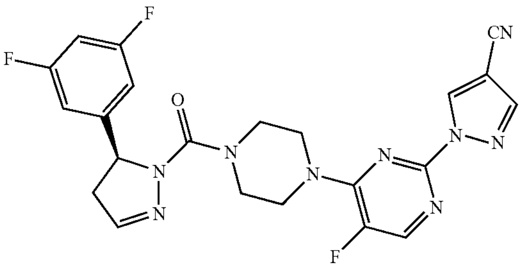 [SMILES: N#Cc1cnn(-c2ncc(F)c(N3CCN(C(=O)N4N=CC[C@H]4c4cc(F)cc(F)c4)CC3)n2)c1]

The titled compound 218 was prepared from (S)-(5-(3,5-difluorophenyl)-4,5-dihydro-1H-pyrazol-1-yl)(1H-imidazol-1-yl)methanone in a yield of 10.0% as a white solid according to the procedure outlined for compound 147. Mass (m/z): 482.2[M+H]$^+$. $^1$H NMR (400 MHz, DMSO-$d_6$) δ 9.44 (s, 1H), 8.39-8.31 (m, 2H), 7.17-7.06 (m, 2H), 7.05-6.94 (m, 2H), 5.26 (dd, J=11.6, 9.6 Hz, 1H), 3.94-3.77 (m, 4H), 3.73-3.56 (m, 4H), 3.37 (ddd, J=18.4, 11.6, 1.6 Hz, 1H), 2.65 (ddd, J=18.4, 9.6, 1.6 Hz, 1H).

Compound 219: (S)-1-(4-(4-(5-(3-cyano-5-fluorophenyl)-4,5-dihydro-1H-pyrazole-1-carbonyl)piperazin-1-yl)-5-fluoropyrimidin-2-yl)-1H-pyrazole-4-carbonitrile

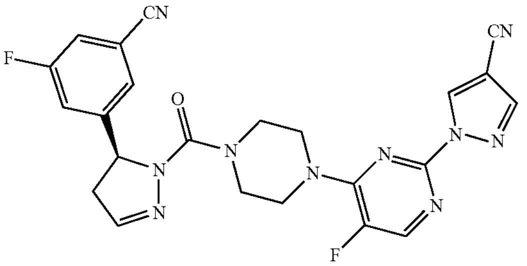 [SMILES: N#Cc1cc(F)cc([C@@H]2CC=NN2C(=O)N2CCN(c3nc(-n4cc(C#N)cn4)ncc3F)CC2)c1]

The titled compound 219 was prepared from (S)-3-(1-(1H-imidazole-1-carbonyl)-4,5-dihydro-1H-pyrazol-5-yl)-5-fluorobenzonitrile in a yield of 10.1% as a white solid according to the procedure outlined for compound 147. Mass (m/z): 489.2 [M+H]$^+$. $^1$H NMR (400 MHz, DMSO-$d_6$) δ 9.44 (s, 1H), 8.39-8.31 (m, 2H), 7.75 (dt, J=8.4, 2.0 Hz, 1H), 7.64 (d, J=1.6 Hz, 1H), 7.53 (dt, J=9.6, 2.0 Hz, 1H), 7.12 (d, J=1.6 Hz, 1H), 5.29 (dd, J=11.4, 10.0 Hz, 1H), 3.95-3.78 (m, 4H), 3.75-3.56 (m, 4H), 3.39-3.30 (m, 1H), 2.77-2.65 (m, 1H).

Compound 220: (4-(5-chloro-4-(3,5-dimethyl-1H-1,2,4-triazol-1-yl)pyrimidin-2-yl)piperazin-1-yl)(5-(3-chloropyridin-2-yl)-4,5-dihydro-1H-pyrazol-1-yl)methanone

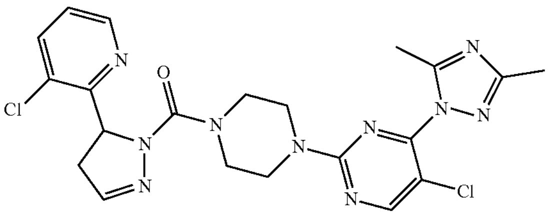 [SMILES: Cc1nc(C)n(-c2nc(N3CCN(C(=O)N4N=CCC4c4ncccc4Cl)CC3)ncc2Cl)n1]

The titled compound 220 was prepared from (5-(3-chloropyridin-2-yl)-4,5-dihydro-1H-pyrazol-1-yl)(1H-imidazol-1-yl)methanone in a yield of 21.3% as an orange solid according to the procedure outlined for compound 147. Mass (m/z): 501.2[M+H]$^+$. $^1$H NMR (400 MHz, DMSO-$d_6$) δ 8.69 (s, 1H), 8.46 (dd, J=4.4, 1.6 Hz, 1H), 7.90 (dd, J=8.0, 1.6 Hz, 1H), 7.33 (dd, J=8.0, 4.8 Hz, 1H), 7.07-7.03 (m, 1H), 5.70 (dd, J=12.0, 8.0 Hz, 1H), 3.73 (s, 4H), 3.65-3.47 (m, 4H), 3.44-3.36 (m, 1H), 2.73-2.65 (m, 1H), 2.48 (s, 3H), 2.28 (s, 3H).

Compound 221: ((5-(3-chloropyridin-2-yl)-4,5-dihydro-1H-pyrazol-1-yl)(4-(5-fluoro-4-(1-methyl-1H-1,2,4-triazol-5-yl)pyrimidin-2-yl)piperazin-1-yl)methanone

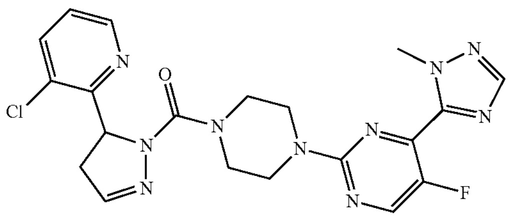 [SMILES: Cn1ncnc1-c1nc(N2CCN(C(=O)N3N=CCC3c3ncccc3Cl)CC2)ncc1F]

The titled compound 221 was prepared from (5-(3-chloropyridin-2-yl)-4,5-dihydro-1H-pyrazol-1-yl)(1H-imidazol-1-yl)methanone in a yield of 33.6% as a yellow solid according to the procedure outlined for compound 143. Mass (m/z): 471.2[M+H]$^+$. $^1$H NMR (400 MHz, DMSO-$d_6$) δ 8.70 (d, J=2.8 Hz, 1H), 8.46 (dd, J=4.4, 1.6 Hz, 1H), 8.16 (s, 1H), 7.90 (dd, J=8.1, 1.5 Hz, 1H), 7.33 (dd, J=8.0, 4.4 Hz, 1H), 7.08-6.99 (m, 1H), 5.70 (dd, J=12.0, 8.0 Hz, 1H), 4.15 (s, 3H), 3.81-3.67 (m, 4H), 3.67-3.48 (m, 4H), 3.45-3.37 (m, 1H), 2.73-2.65 (m, 1H).

Compound 222: (5-(3-chloropyridin-2-yl)-4,5-dihydro-1H-pyrazol-1-yl)(4-(3-fluoro-6-(1-methyl-1H-1,2,4-triazol-5-yl)pyridin-2-yl)piperazin-1-yl)methanone

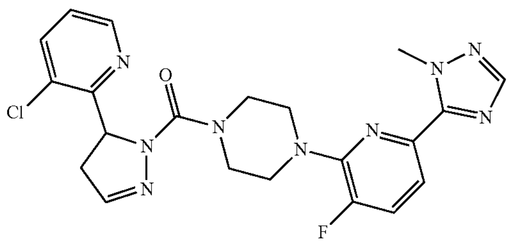 [SMILES: Cn1ncnc1-c1ccc(F)c(N2CCN(C(=O)N3N=CCC3c3ncccc3Cl)CC2)n1]

The titled compound 222 was prepared from (5-(3-chloropyridin-2-yl)-4,5-dihydro-1H-pyrazol-1-yl)(1H-imidazol-1-yl)methanone in a yield of 40.3% as an orange solid according to the procedure outlined for compound 175. Mass (m/z): 470.2[M+H]$^+$. $^1$H NMR (400 MHz, DMSO-$d_6$) δ 8.46 (dd, J=4.8, 1.6 Hz, 1H), 7.98 (s, 1H), 7.90 (dd, J=8.0, 1.6 Hz, 1H), 7.72 (dd, J=12.8, 8.0 Hz, 1H), 7.64 (dd, J=8.0, 3.2 Hz, 1H), 7.33 (dd, J=8.0, 4.4 Hz, 1H), 7.08-7.03 (m, 1H), 5.70 (dd, J=12.0, 8.0 Hz, 1H), 4.25 (s, 3H), 3.74-3.55 (m, 4H), 3.53-3.39 (m, 5H), 2.74-2.63 (m, 1H).

Compound 223: (4-(5-chloro-4-(3,5-dimethyl-1H-1,2,4-triazol-1-yl)pyrimidin-2-yl)piperazin-1-yl)(5-(2-methylthiazol-5-yl)-4,5-dihydro-1H-pyrazol-1-yl) methanone

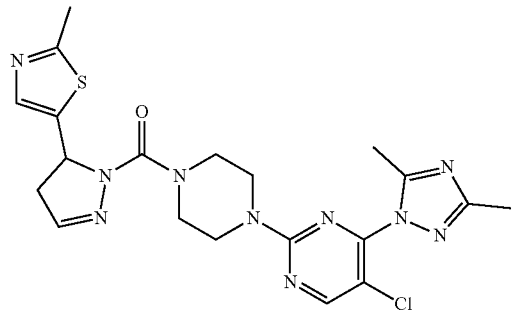 [SMILES: Cc1nc(C)n(-c2nc(N3CCN(C(=O)N4N=CCC4c4cnc(C)s4)CC3)ncc2Cl)n1]

The titled compound 223 was prepared from (1H-imidazol-1-yl)(5-(2-methylthiazol-5-yl)-4,5-dihydro-1H-pyrazol-1-yl)methanonein a yield of 20.1% as a light yellow solid according to the procedure outlined for compound 147. Mass (m/z): 487.2[M+H]$^+$. $^1$H NMR (400 MHz, Chloroform-d) δ 8.44 (s, 1H), 7.58 (s, 1H), 6.92-6.87 (m, 1H), 5.60 (dd, J=11.4, 10.0 Hz, 1H), 3.94-3.68 (m, 6H), 3.65-3.55 (m, 2H), 3.33 (ddd, J=18.0, 11.6, 1.6 Hz, 1H), 2.92-2.82 (m, 1H), 2.68 (s, 3H), 2.55 (s, 3H), 2.43 (s, 3H).

Compound 224: (4-(5-chloro-4-(3,5-dimethyl-1H-1,2,4-triazol-1-yl)pyrimidin-2-yl)piperazin-1-yl)(5-(2-methylthiazol-4-yl)-4,5-dihydro-1H-pyrazol-1-yl) methanone

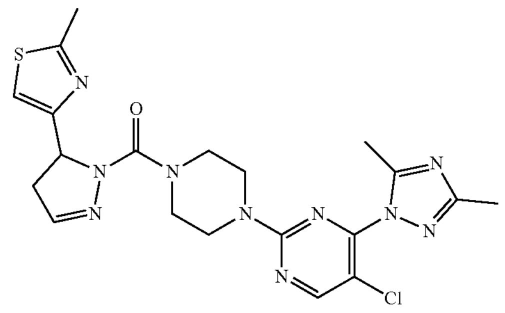 [SMILES: Cc1nc(C)n(-c2nc(N3CCN(C(=O)N4N=CCC4c4csc(C)n4)CC3)ncc2Cl)n1]

The titled compound 224 was prepared from (1H-imidazol-1-yl)(5-(2-methylthiazol-4-yl)-4,5-dihydro-1H-pyrazol-1-yl)methanonein a yield of 40.1% as a light yellow solid according to the procedure outlined for compound 147. Mass (m/z): 487.2[M+H]$^+$. $^1$H NMR (400 MHz, Chloroform-d) δ 8.46 (s, 1H), 7.09 (s, 1H), 6.90-6.88 (m, 1H), 5.50 (dd, J=11.6, 10.0 Hz, 1H), 3.95-3.67 (m, 6H), 3.65-3.55 (m, 2H), 3.24 (ddd, J=18.4, 11.6, 1.6 Hz, 1H), 3.13 (ddd, J=18.0, 10.0, 1.6 Hz, 1H), 2.71 (s, 3H), 2.60 (s, 3H), 2.47 (s, 3H).

Compound 225: 5-(2-(4-(5-(3,5-difluorophenyl)-4,5-dihydro-1H-pyrazole-1-carbonyl)piperazin-1-yl)-5-fluoropyrimidin-4-yl)-1-methyl-1H-1,2,4-triazole-3-carboxamide

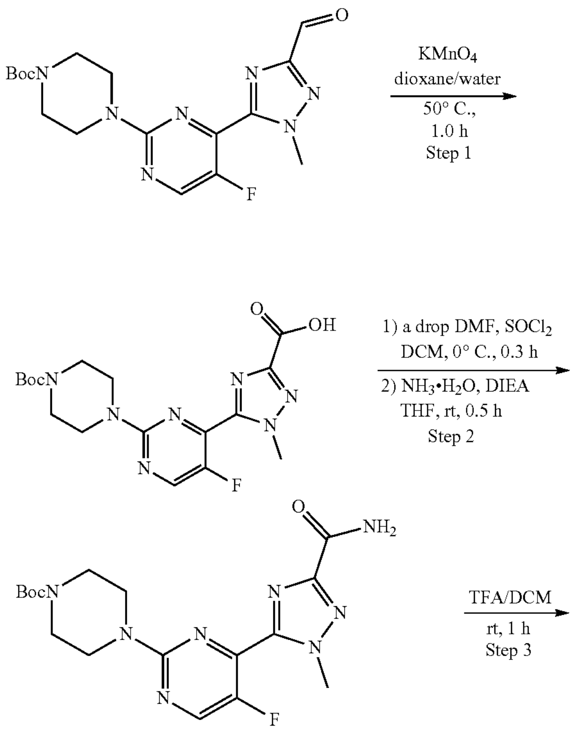

-continued

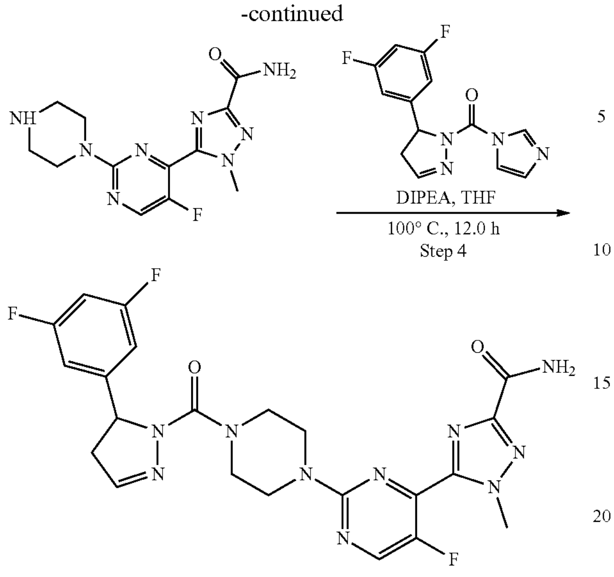

Step 1: Synthesis of 5-(2-(4-(tert-butoxycarbonyl) piperazin-1-yl)-5-fluoropyrimidin-4-yl)-1-methyl-1H-1,2,4-triazole-3-carboxylic acid To a stirred solution of tert-butyl 4-(5-fluoro-4-(3-formyl-1-methyl-1H-1,2,4-triazol-5-yl)pyrimidin-2-yl)piperazine-1-carboxylate (1.2 g, 3.07 mmol) in dioxane (5 mL) and water (5 mL) was added $KMnO_4$ (0.97 g, 6.14 mmol) at room temperature. The resulting mixture was stirred for additional 1 h at 50° C. The mixture was allowed to cool down to room temperature. The resulting mixture was filtered, the filter cake was washed with dioxane (3×1 mL). The filtrate was concentrated under reduced pressure to afford 5-(2-(4-(tert-butoxycarbonyl)piperazin-1-yl)-5-fluoropyrimidin-4-yl)-1-methyl-1H-1,2,4-triazole carboxylic acid (1.2 g, 96.0%) as a yellow solid. MS (m/z): 408.4 $[M+H]^+$.

Step 2: Synthesis of tert-butyl 4-(4-(3-carbamoyl-1-methyl-1H-1,2,4-triazol-5-yl) fluoropyrimidin-2-yl) piperazine-1-carboxylate To a stirred solution of 5-(2-(4-(tert-butoxycarbonyl)piperazin-1-yl)-5-fluoropyrimidin yl)-1-methyl-1H-1,2,4-triazole-3-carboxylic acid (1.2 g, 2.9 mmol) and a drop of DMF in DCM (15 mL) was added sulfurous dichloride (1.4 g, 11.8 mmol) at 0° C. The resulting mixture was stirred for additional 0.5 h at 0° C. A solution of ammonia hydrate (10 mL) and DIEA (5 mL) in DCM (15 mL) was then added dropwise over 30 min. The resulting mixture was concentrated under reduced pressure. The residue was purified by silica gel column chromatography, eluted with petroleum ether:ethyl acetate (PE:EtOAc) (1:1) to afford methyl tert-butyl 4-(4-(3-carbamoyl-1-methyl-1H-1,2,4-triazol-5-yl)-5-fluoropyrimidin-2-yl)piperazine-1-carboxylate (240 mg, 20.0%) as a yellow oil. MS (m/z): 407.4 $[M+H]^+$.

Step 3: Synthesis of 5-(5-fluoro-2-(piperazin-1-yl) pyrimidin-4-yl)-1-methyl-1H-1,2,4-triazole-3-carboxamide To a stirred solution of methyl tert-butyl 4-(4-(3-carbamoyl-1-methyl-1H-1,2,4-triazol-5-yl)-5-fluoropyrimidin-2-yl)piperazine-1-carboxylate (240 mg, 0.59 mmol) in TFA (5 mL) and DCM (5 mL) at room temperature. The resulting mixture was stirred for additional 0.5 h at 25° C. The resulting mixture was concentrated under reduced pressure to afford 5-(5-fluoro-2-(piperazin-1-yl)pyrimidin-4-yl)-1-methyl-1H-1,2,4-triazole-3-carboxamide (180 mg, 99.5%) as a brown yellow oil. LC-MS (m/z) 407.3$[M+H]^+$.

Step 4: Synthesis of 5-(2-(4-(5-(3,5-difluorophenyl)-4,5-dihydro-1H-pyrazole-1-carbonyl)piperazin-1-yl)-5-fluoropyrimidin-4-yl)-1-methyl-1H-1,2,4-triazole-3-carboxamide (Compound 225)

To a stirred solution of 5-(5-fluoro-2-(piperazin-1-yl) pyrimidin-4-yl)-1-methyl-1H-1,2,4-triazole-3-carboxamide (50 mg, 0.16 mmol) and (5-(3,5-difluorophenyl)-4,5-dihydro-1H-pyrazol-1-yl)(1H-imidazol-1-yl)methanone (45 mg, 0.16 mmol) in THF (2 mL) was added DIPEA (106 mg, 0.81 mmol) at room temperature. The resulting mixture was stirred for additional 12 h at 100° C. The resulting mixture was concentrated under reduced pressure. The residue was purified by Prep-HPLC to afford the titled Compound 225 (13 mg, 15.5%) as a light yellow solid. LC-MS (m/z): 514.4 $[M+H]^+$. $^1$HNMR (400 MHz, DMSO) δ 8.75 (d, J=2.4 Hz, 1H), 7.87 (s, 1H), 7.74-7.64 (m, 2H), 7.10 (d, J=1.9 Hz, 1H), 7.03-6.97 (m, 2H), 5.31-5.22 (m, 1H), 4.19 (s, 3H), 3.82-3.56 (m, 8H), 2.65 (ddd, J=18.4, 10.0, 1.6 Hz, 1H), 1.64 (dq, J=8.1, 6.5 Hz, 1H).

Compound 226: 5-(5-fluoro-2-(4-(5-(5-fluoropyridin-3-yl)-4,5-dihydro-1H-pyrazole-1-carbonyl)piperazin-1-yl)pyrimidin-4-yl)-1-methyl-1H-1,2,4-triazole-3-carboxamide

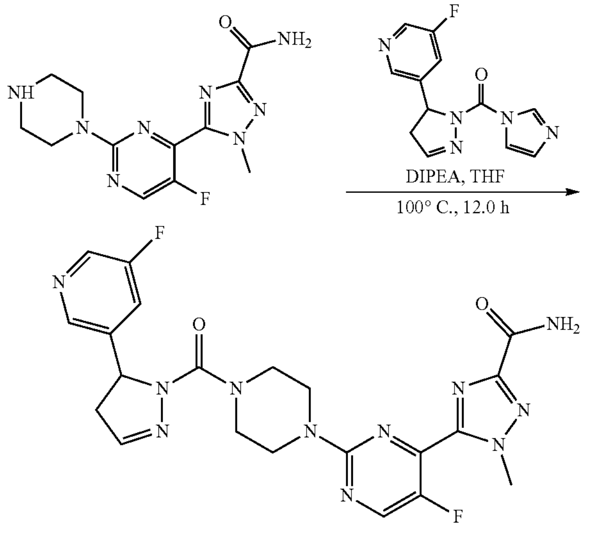

The titled compound 226 was prepared in a yield of 14.8% as a light yellow solid according to the procedure outlined for compound 225. LC-MS (m/z): 498.4 $[M+H]^+$. $^1$H NMR (400 MHz, DMSO) δ 8.74 (d, J=2.4 Hz, 1H), 8.48 (d, J=2.7 Hz, 1H), 8.42 (d, J=1.8 Hz, 1H), 7.87 (s, 1H), 7.72-7.61 (m, 2H), 7.16-7.13 (m, 1H), 5.31 (t, J=10.9 Hz, 1H), 4.19 (s, 3H), 3.85-3.53 (m, 8H), 3.14 (qd, J=7.4, 4.2 Hz, 1H), 2.81-2.70 (m, 1H).

Compound 227: (5-(3,5-difluorophenyl)-4,5-dihydro-1H-pyrazol-1-yl)(4-(5-fluoro-4-(3-(hydroxymethyl)-1-methyl-1H-1,2,4-triazol-5-yl)pyrimidin-2-yl)piperazin-1-yl)methanone

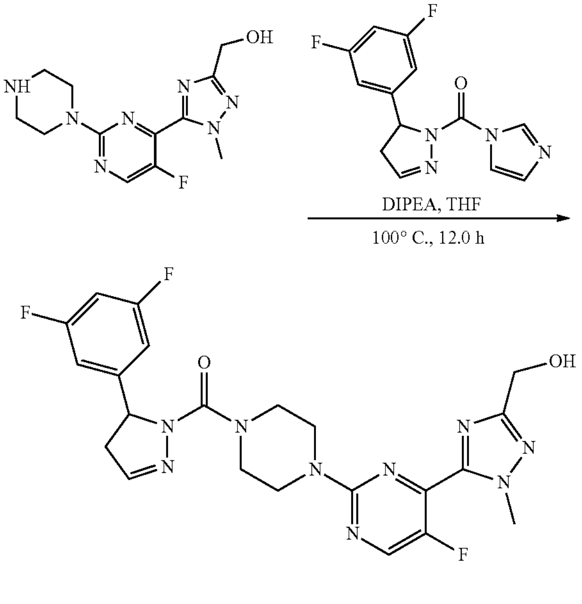

The titled compound 227 was prepared in a yield of 2.3% as a light yellow solid according to the procedure outlined for compound 225. LC-MS (m/z): 502.5 $[M+H]^+$. $^1H$ NMR (400 MHz, DMSO) δ 8.70 (d, J=2.5 Hz, 1H), 7.15-7.07 (m, 2H), 7.03-6.98 (m, 2H), 5.26 (dd, J=11.6, 9.9 Hz, 1H), 4.48 (s, 2H), 4.12 (s, 3H), 3.86-3.54 (m, 8H), 3.37 (ddd, J=18.3, 11.7, 1.8 Hz, 1H), 2.65 (ddd, J=18.3, 9.9, 1.5 Hz, 1H).

Compound 228: 5-(2-(4-(5-(3,5-difluorophenyl)-4,5-dihydro-1H-pyrazole-1-carbonyl)piperazin-1-yl)-5-fluoropyrimidin-4-yl)-1-methyl-1H-1,2,4-triazole-3-carbonitrile

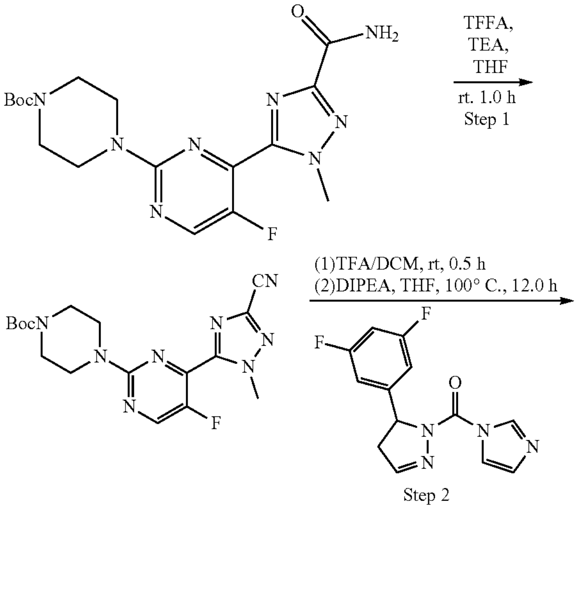

-continued

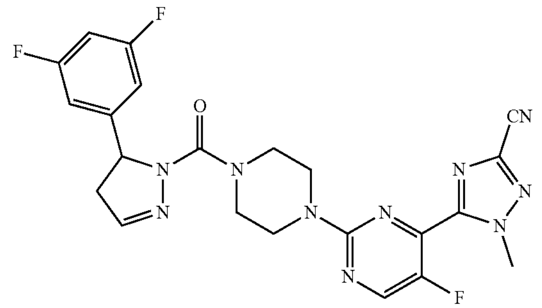

Step 1: Synthesis of tert-butyl 4-(4-(3-cyano-1-methyl-1H-1,2,4-triazol-5-yl)-5-fluoropyrimidin-2-yl)piperazine-1-carboxylate To a stirred solution of tert-butyl 4-(4-(3-carbamoyl-1-methyl-1H-1,2,4-triazol-5-yl) fluoropyrimidin-2-yl)piperazine-1-carboxylate (240 mg, 0.59 mmol) and TFFA (372 mg, 1.77 mmol) in THF (10 mL) was added TEA (239 mg, 2.36 mmol) at room temperature. The resulting mixture was stirred for additional 1.0 h at room temperature. The resulting mixture was concentrated under reduce pressure to afford tert-butyl 4-(4-(3-cyano-1-methyl-1H-1,2,4-triazol-5-yl)-5-fluoropyrimidin-2-yl)piperazine-1-carboxylate (170 mg, 85.1%) as a brown yellow oil. MS (m/z): 339.1 $[M+H]^+$.

Step 2

The titled compound 228 was prepared in a yield of 4.5% as a light yellow solid according to the procedure outlined for compound 225. LC-MS (m/z): 497.1 $[M+H]^+$. $^1H$ NMR (400 MHz, DMSO) δ 8.78 (d, J=2.5 Hz, 1H), 8.48 (d, J=2.8 Hz, 1H), 8.42 (d, J=1.9 Hz, 1H), 7.66 (dt, J=9.9, 2.3 Hz, 1H), 7.14 (d, J=1.8 Hz, 1H), 5.31 (t, J=10.9 Hz, 1H), 4.27 (s, 3H), 3.85-3.66 (m, 8H), 3.39 (ddd, J=18.3, 11.6, 1.9 Hz, 1H), 2.83-2.68 (m, 1H).

Compound 229: 5-(5-fluoro-2-(4-(5-(5-fluoropyridin-3-yl)-4,5-dihydro-1H-pyrazole-1-carbonyl)piperazin-1-yl)pyrimidin-4-yl)-1-methyl-1H-1,2,4-triazole-3-carbonitrile

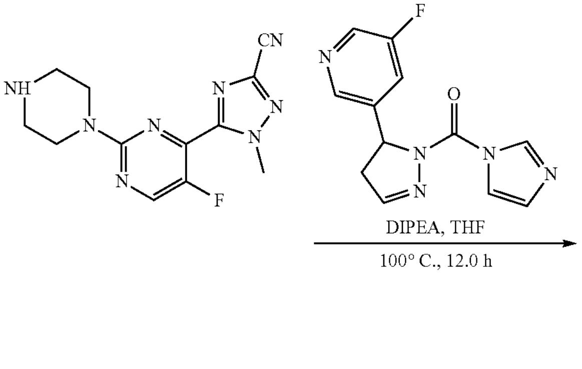

-continued

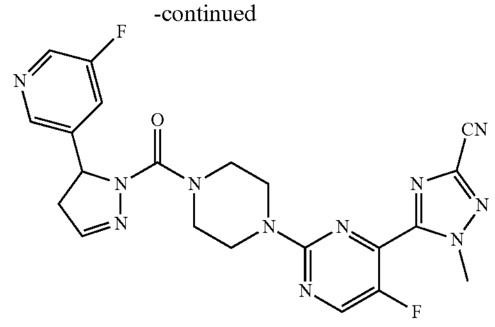

The titled compound 229 was prepared in a yield of 12.0% as a yellow solid according to the procedure outlined for compound 225. LC-MS (m/z): 480.1 $[M+H]^+$. $^1$H NMR (400 MHz, DMSO) δ 8.78 (d, J=2.5 Hz, 1H), 8.48 (d, J=2.8 Hz, 1H), 8.42 (d, J=1.9 Hz, 1H), 7.66 (dt, J=9.9, 2.3 Hz, 1H), 7.14 (d, J=1.8 Hz, 1H), 5.31 (t, J=10.9 Hz, 1H), 4.27 (s, 3H), 3.85-3.66 (m, 8H), 3.39 (ddd, J=18.3, 11.6, 1.9 Hz, 1H), 2.83-2.68 (m, 1H).

Compound 230: 5-(2-(4-(5-(3,5-difluorophenyl)-4,5-dihydro-1H-pyrazole-1-carbonyl)piperazin-1-yl)-5-fluoropyrimidin-4-yl)-1-methyl-1H-1,2,4-triazole-3-carboxylic acid

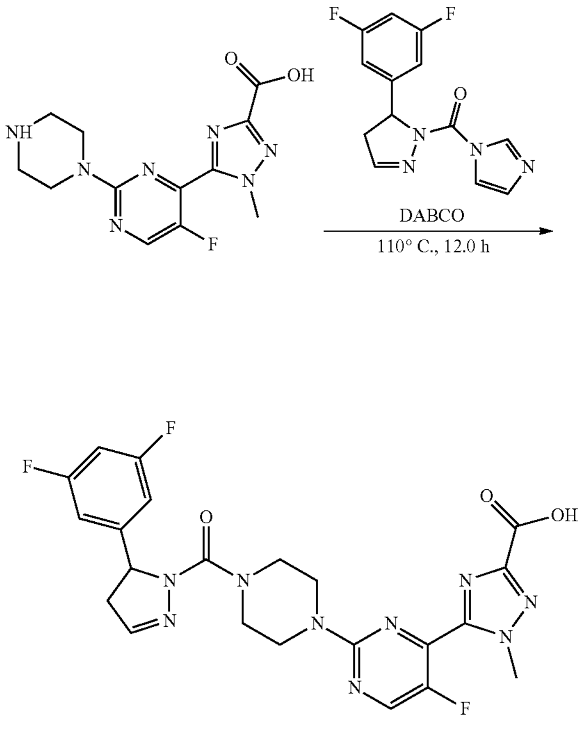

The titled compound 230 was prepared in a yield of 2.3% as an off-white solid according to the procedure outlined for compound 225. LC-MS (m/z): 516.41 $[M+H]^+$. $^1$H NMR (400 MHz, CDCl3) δ 8.39 (d, J=2.1 Hz, 1H), 6.83-6.71 (m, 3H), 6.67-6.59 (m, 1H), 5.31-5.23 (m, 1H), 4.26 (s, 3H), 3.93-3.78 (m, 3H), 3.73 (d, J=9.7 Hz, 3H), 3.65-3.54 (m, 2H), 3.30-3.23 (m, 1H), 2.68-2.60 (m, 1H).

Compound 231: (4-(4-(3,5-dimethyl-1H-1,2,4-triazol-1-yl)-5-fluoropyrimidin-2-yl)piperazin-1-yl)(5-(5-methylthiazol-2-yl)-4,5-dihydro-1H-pyrazol-1-yl)methanone

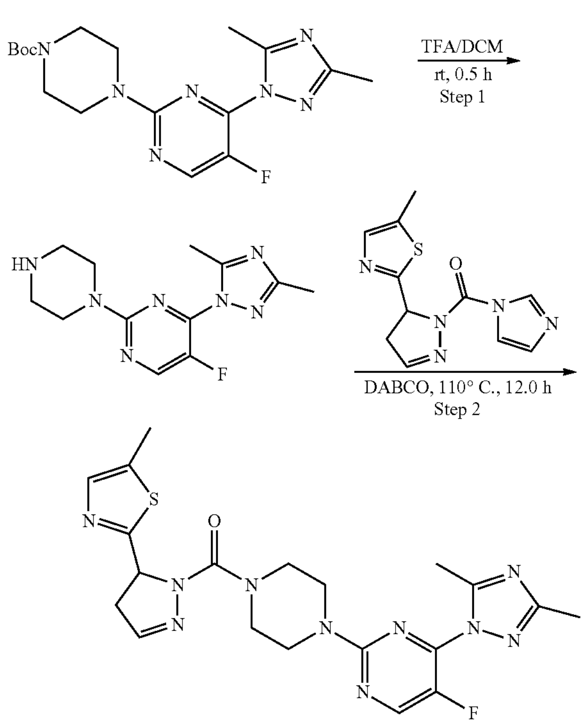

The titled compound 231 was prepared in a yield of 18.6% as an off-white solid according to the procedure outlined for compound 225. LC-MS (m/z): 471.5 $[M+H]^+$. $^1$H NMR (400 MHz, DMSO-D6) δ 8.66 (d, J=3.0 Hz, 1H), 7.36 (q, J=1.2 Hz, 1H), 7.11 (d, J=1.7 Hz, 1H), 5.50 (dd, J=11.8, 9.0 Hz, 1H), 3.82-3.46 (m, 9H), 3.01 (ddd, J=18.4, 9.0, 1.7 Hz, 1H), 2.58 (s, 3H), 2.35 (d, J=1.2 Hz, 3H), 2.25 (s, 3H).

Compound 232: (S)-(5-(3,5-difluorophenyl)-4,5-dihydro-1H-pyrazol-1-yl)(4-(6-(3,5-dimethyl-1H-1,2,4-triazol-1-yl)-3,5-difluoropyridin-2-yl)piperazin-1-yl)methanone

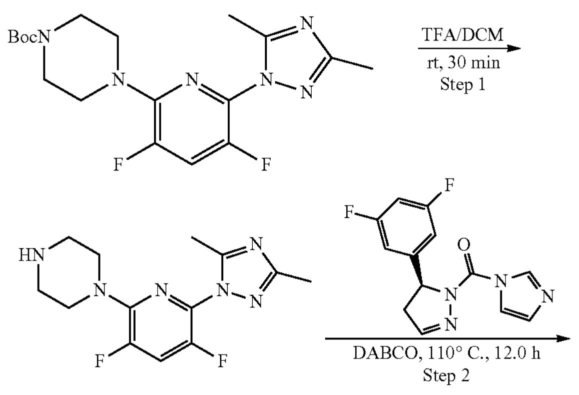

-continued

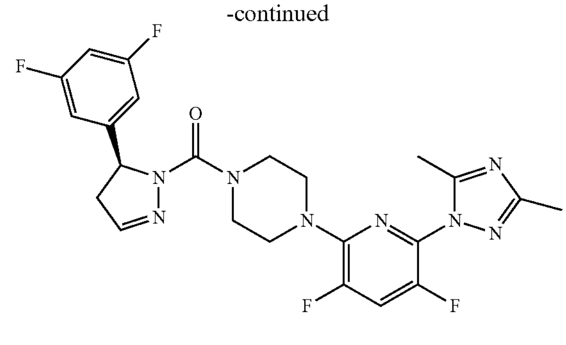

The titled compound 232 was prepared in a yield of 6.5% as an off-white solid according to the procedure outlined for compound 225. LC-MS (m/z): 503.4 $[M+H]^+$. $^1H$ NMR (400 MHz, DMSO-D6) δ 8.12 (dd, J=11.7, 8.8 Hz, 1H), 7.11-7.02 (m, 2H), 6.96 (qd, J=6.5, 3.3 Hz, 2H), 5.21 (dd, J=11.6, 9.9 Hz, 1H), 3.66 (ddd, J=13.0, 6.9, 3.3 Hz, 2H), 3.54 (ddd, J=13.0, 6.4, 3.4 Hz, 2H), 3.42-3.31 (m, 4H), 3.29-3.27 (m, 1H), 2.60 (ddd, J=18.4, 10.0, 1.7 Hz, 1H), 2.23 (s, 3H).

Compound 233: (S)-3-(1-(4-(6-(3,5-dimethyl-1H-1,2,4-triazol-1-yl)-3,5-difluoropyridin-2-yl)piperazine-1-carbonyl)-4,5-dihydro-1H-pyrazol-5-yl)-5-fluorobenzonitrile

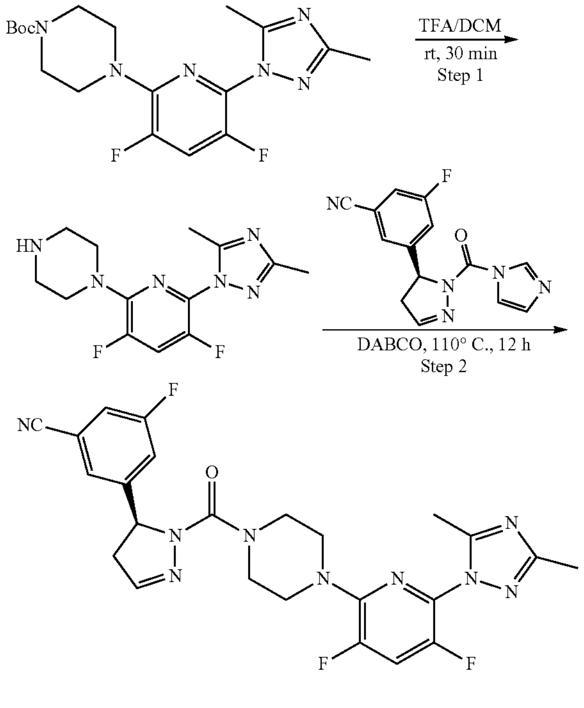

The titled compound 233 was prepared in a yield of 4.3% as an off-white solid according to the procedure outlined for compound 225. LC-MS (m/z): 510.5 $[M+H]^+$. $^1H$ NMR (400 MHz, DMSO-D6) δ 8.12 (dd, J=11.6, 8.9 Hz, 1H), 7.71 (ddd, J=8.6, 2.6, 1.4 Hz, 1H), 7.60 (t, J=1.5 Hz, 1H), 7.49 (ddd, J=9.8, 2.6, 1.5 Hz, 1H), 7.09-7.06 (m, 1H), 5.24 (dd, J=11.6, 10.1 Hz, 1H), 3.66 (ddd, J=13.1, 6.9, 3.3 Hz, 2H), 3.54 (ddd, J=13.0, 6.4, 3.4 Hz, 2H), 3.41-3.32 (m, 4H), 2.71-2.60 (m, 1H), 2.54 (d, J=1.8 Hz, 1H), 2.37 (s, 3H), 2.23 (s, 3H).

Compound 234: (S)-(4-(6-(3,5-dimethyl-1H-1,2,4-triazol-1-yl)-3,5-difluoropyridin-2-yl)piperazin-1-yl)(5-(5-fluoropyridin-3-yl)-4,5-dihydro-1H-pyrazol-1-yl)methanone

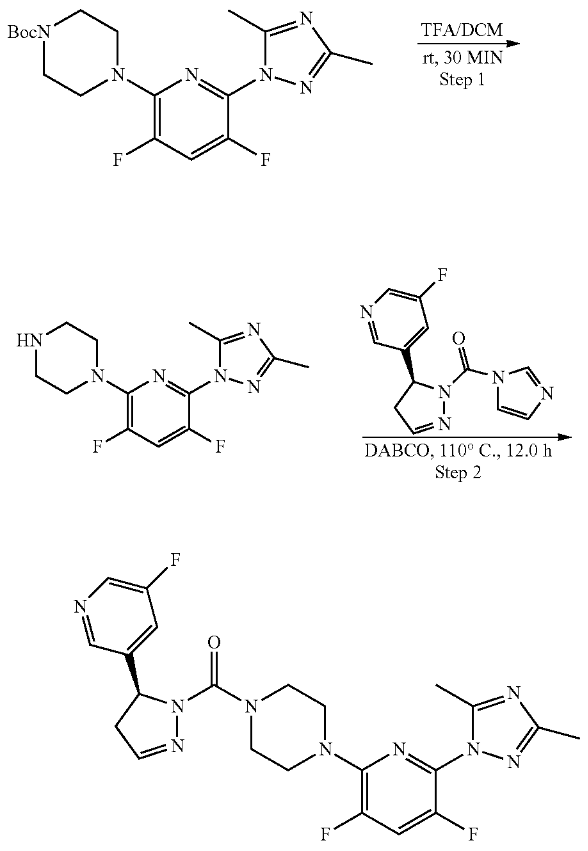

The titled compound 234 was prepared in a yield of 13.4% as a light yellow solid according to the procedure outlined for compound 225. LC-MS (m/z): 486.4 $[M+H]^+$. $^1H$ NMR (400 MHz, DMSO-D6) δ 8.45 (d, J=2.7 Hz, 1H), 8.38 (d, J=1.7 Hz, 1H), 8.12 (dd, J=11.6, 8.9 Hz, 1H), 7.62 (dq, J=9.8, 1.9 Hz, 1H), 7.09 (d, J=3.4 Hz, 1H), 5.26 (t, J=10.9 Hz, 1H), 3.65 (ddd, J=13.2, 6.9, 3.3 Hz, 2H), 3.53 (ddd, J=13.1, 6.5, 3.5 Hz, 2H), 3.37-3.29 (m, 4H), 2.70 (ddd, J=18.3, 10.2, 1.6 Hz, 1H), 2.49-2.48 (m, 1H), 2.37 (s, 3H), 2.23 (s, 3H).

Compound 235: (S)-(5-(3,5-difluorophenyl)-4,5-dihydro-1H-pyrazol-1-yl)(4-(5-fluoro-4-(3-methyl1H-1,2,4-triazol-1-yl)pyrimidin-2-yl)piperazin-1-yl)methanone

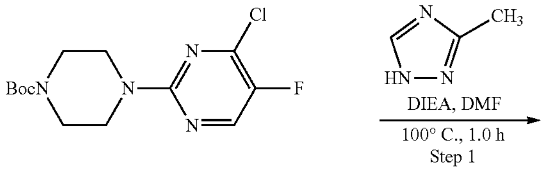

-continued

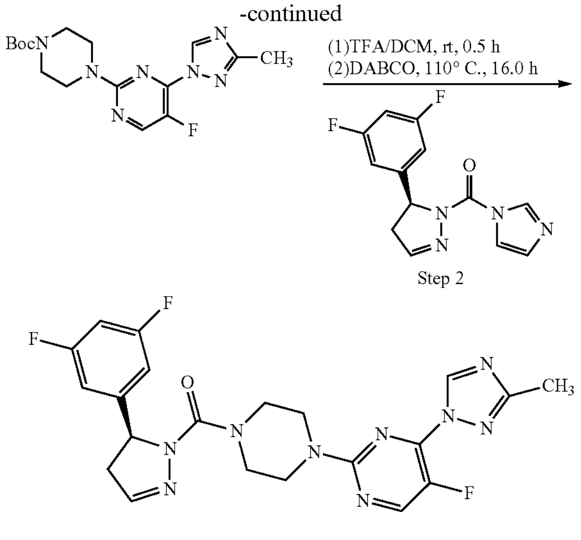

Step 1: Synthesis of tert-butyl 4-(5-fluoro-4-(3-methyl-1H-1,2,4-triazol-1-yl)pyrimidin-2-yl)piperazine-1-carboxylate To a stirred solution of tert-butyl 4-(4-chloro-5-fluoropyrimidin-2-yl)piperazine-1-carboxylate (1 g, 3.15 mmol) and 3-methyl-1H-1,2,4-triazole (288 mg, 3.47 mmol) in DMF (20 mL) were added DIEA (1.22 g, 9.45 mmol), $Cs_2CO_3$ (3.1 g, 9.45 mmol) at room temperature under $N_2$ atmosphere. The resulting mixture was stirred for additional 1 h at 100° C. The mixture was allowed to cool down to room temperature. The resulting mixture was filtered, the filter cake was washed with EA (3×15 mL). The filtrate was concentrated under reduce pressure. The residue was purified by reverse phase flash chromatography with the following conditions: Column: Spherical C18 40-60 um, 40 g; Mobile phase B: acetonitrile or ACN; Flow rate: 40 mL/min; Gradient: 35% B-50% B in 20 min; Detector: 254 nm. The fractions containing desired product were collected at 45% B and concentrated under reduce pressure to afford tert-butyl 4-(5-fluoro-4-(3-methyl-1H-1,2,4-triazol-1-yl)pyrimidin-2-yl) piperazine carboxylate (1.0 g, 69.4%) as an off-white solid. MS (m/z): 364.3 $[M+H]^+$.

Step 2 and 3

To a stirred solution of tert-butyl 4-(5-fluoro-4-(3-methyl-1H-1,2,4-triazol-1-yl)pyrimidin-2-yl)piperazine-1-carboxylate (300 mg, 0.83 mmol) in TFA (1 mL) and DCM (2 mL) at room temperature. The resulting mixture was stirred for additional 0.5 h at room temperature. The resulting mixture was concentrated under reduce pressure to afford 5-fluoro-4-(3-methyl-1H-1,2,4-triazol-1-yl)-2-(piperazin-1-yl)pyrimidine (140 mg, 64.4%) as a brown yellow oil. LC-MS (m/z) 264.3$[M+H]^+$.

To a 25 mL flask charged with 5-fluoro-4-(3-methyl-1H-1,2,4-triazol-1-yl)-2-(piperazin-1-yl)pyrimidine (70 mg, 0.27 mmol), (S)-(5-(3,5-difluorophenyl)-4,5-dihydro-1H-pyrazol-1-yl)(1H-imidazol-1-yl)methanone (88 mg, 0.32 mmol) and DABCO (302 mg, 2.71 mmo) at room temperature. The resulting mixture was stirred for additional 16 h at 110° C. The resulting mixture was diluted with water (10 mL) and EtOAc (10 mL). The mixture was acidified to pH 3-4 with 1 N hydrochloric acid or HCl. The resulting mixture was extracted with EtOAc (3×15 mL). The combined organic layers were washed with brine (30 mL), dried over anhydrous $Na_2SO_4$, after filtration, the filtrate was concentrated under reduce pressure. The residue was purified by reverse phase flash chromatography with the following conditions: Column: Spherical C18 40-60 um, 40 g; Mobile phase B: acetonitrile or ACN; Flow rate: 40 mL/min; Gradient: 35% B-50% B in 20 min; Detector: 254 nm. The fractions containing desired product were collected at 43% B and concentrated under reduce pressure to afford the titled 235 (23 mg, 18.3%) as a white solid. LC-MS (m/z): 472.4 $[M+H]^+$. $^1H$ NMR (400 MHz, DMSO-D6) δ 9.33 (s, 1H), 8.65 (d, J=3.6 Hz, 1H), 7.09-7.04 (m, 2H), 6.98-6.95 (m, 2H), 5.22 (dd, J=11.6, 9.9 Hz, 1H), 3.81-3.75 (m, 2H), 3.71 (dd, J=7.1, 3.5 Hz, 2H), 3.65-3.59 (m, 2H), 3.51 (dq, J=9.6, 3.3 Hz, 2H), 3.33 (ddt, J=18.3, 11.7, 1.6 Hz, 1H), 2.63-2.56 (m, 1H), 2.36 (s, 3H).

Compound 236: (S)-3-(1-(3-((2-(3,5-dimethylisoxazol-4-yl)-5-fluoropyridin-4-yl)oxy)azetidine-1-carbonyl)-4,5-dihydro-1H-pyrazol-5-yl)-5-fluorobenzonitrile

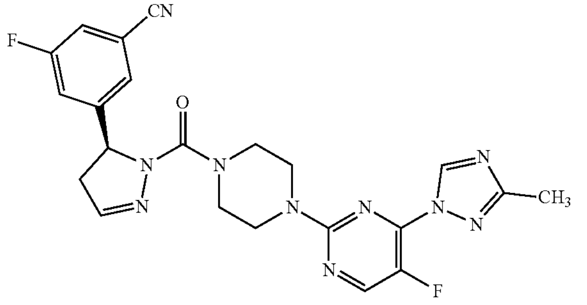 [SMILES: Cc1ncn(-c2nc(N3CCN(C(=O)N4N=CC[C@H]4c4cc(F)cc(C#N)c4)CC3)ncc2F)n1]

The titled compound 236 (16 mg, 12.5%) as a white solid according to the procedure outlined for compound 235. LC-MS (m/z): 479.4 $[M+H]^+$. $^1H$ NMR (400 MHz, DMSO-D6) δ 9.33 (s, 1H), 8.65 (dd, J=3.6, 1.1 Hz, 1H), 7.71 (ddt, J=8.6, 2.4, 1.1 Hz, 1H), 7.61 (t, J=1.5 Hz, 1H), 7.50 (ddd, J=9.8, 2.6, 1.4 Hz, 1H), 7.09 (d, J=1.7 Hz, 1H), 5.25 (dd, J=11.5, 10.2 Hz, 1H), 3.80-3.69 (m, 4H), 3.65-3.59 (m, 2H), 3.53-3.47 (m, 2H), 3.33 (ddd, J=18.2, 11.6, 1.8 Hz, 1H), 2.73-2.64 (m, 1H), 2.35 (s, 3H).

Compound 237: (5-(5-bromo-2,3-difluorophenyl)-4,5-dihydro-1H-pyrazol-1-yl)(4-(4-(3,5-dimethyl-1H-1,2,4-triazol-1-yl)-5-fluoropyrimidin-2-yl)piperazin-1-yl)methanone

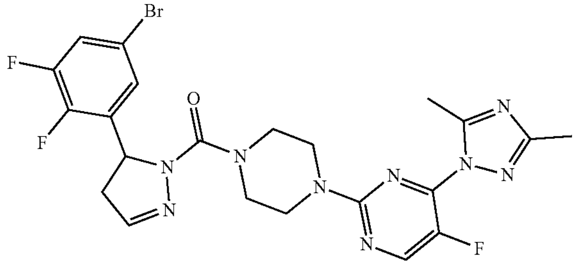 [SMILES: Cc1nc(C)n(-c2nc(N3CCN(C(=O)N4N=CCC4c4cc(Br)cc(F)c4F)CC3)ncc2F)n1]

The titled compound 237 (15 mg, 5.2%) as an off-white solid according to the procedure outlined for compound 235.

LC-MS (m/z): 565.3 $[M+H]^+$. $^1H$ NMR (400 MHz, DMSO-D6) δ 8.67 (d, J=3.1 Hz, 1H), 7.70 (ddd, J=9.6, 6.8, 2.4 Hz, 1H), 7.25 (dt, J=5.4, 2.1 Hz, 1H), 7.12 (d, J=3.4 Hz, 1H), 5.37 (dd, J=11.9, 9.5 Hz, 1H), 3.78-3.69 (m, 2H), 3.63 (ddt, J=12.4, 7.3, 4.4 Hz, 4H), 3.56-3.46 (m, 2H), 3.40-3.31 (m, 1H), 2.73 (ddd, J=18.3, 9.5, 1.7 Hz, 1H), 2.58 (s, 3H), 2.25 (s, 3H).

Compound 238: 3-(1-(4-(4-(3,5-dimethyl-1H-1,2,4-triazol-1-yl)-5-fluoropyrimidin-2-yl)piperazine-1-carbonyl)-4,5-dihydro-1H-pyrazol-5-yl)-4,5-difluorobenzonitrile

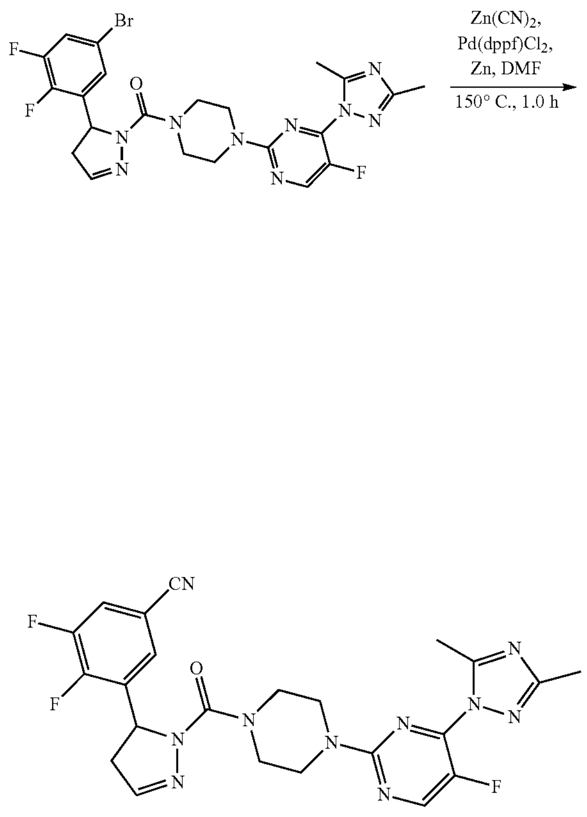

To a stirred solution of (5-(5-bromo-2,3-difluorophenyl)-4,5-dihydro-1H-pyrazol-1-yl)(4-(4-(3,5-dimethyl-1H-1,2,4-triazol-1-yl)-5-fluoropyrimidin-2-yl)piperazin-1-yl)methanone (50 mg, 0.09 mmol) and $Zn(CN)_2$ (20.84 mg, 0.18 mmol) in DMF (4 mL) were added Zn power (18 mg, 0.27 mmol), and $Pd(dppf)Cl_2$ (14 mg, 0.02 mmol) at room temperature under $N_2$ atmosphere. The resulting mixture was stirred for additional 1 h at 150° C. The mixture was allowed to cool down to room temperature. The resulting mixture was filtered, the filter cake was washed with EA (3×15 mL). The filtrate was concentrated under reduce pressure. The residue was purified by Prep-HPLC to afford the titled compound 238 (16 mg, 35.3%) as an off-white solid. LC-MS (m/z): 511.4 $[M+H]^+$. $^1H$ NMR (400 MHz, $CDCl_3$-d) δ 8.40 (d, J=2.6 Hz, 1H), 7.43-7.36 (m, 2H), 6.93-6.90 (m, 1H), 5.57 (dd, J=11.8, 9.9 Hz, 1H), 3.88 (dd, J=10.4, 6.9 Hz, 2H), 3.82-3.72 (m, 4H), 3.69-3.61 (m, 2H), 3.39 (ddt, J=18.2, 12.0, 1.2 Hz, 1H), 2.75-2.66 (m, 4H), 2.44 (s, 3H).

Compound 239: (R)-(4-(4-(3,5-dimethyl-1H-1,2,4-triazol-1-yl)-5-fluoropyrimidin yl)piperazin-1-yl)(5-(2-methylthiazol-5-yl)-4,5-dihydro-1H-pyrazol-1-yl)methanone

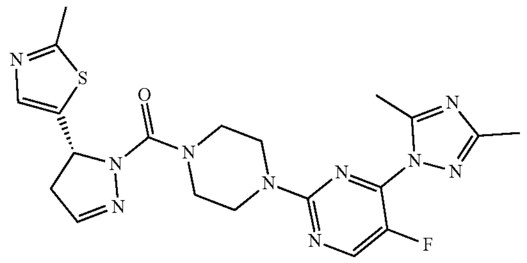 [SMILES: Cc1nc(C)n(-c2nc(N3CCN(C(=O)N4N=CC[C@@H]4c4cnc(C)s4)CC3)ncc2F)n1]

The titled compound 239 was prepared in a yield of 20% as an off-white solid according to the procedure outlined for compound 235 and separated by SFC. LC-MS (m/z): 471.3 $[M+H]^+$. $^1H$ NMR (400 MHz, $CDCl_3$) δ 8.40 (d, J=2.8 Hz, 1H), 7.58 (s, 1H), 6.90 (s, 1H), 5.60 (t, J=10.7 Hz, 1H), 3.92-3.82 (m, 2H), 3.80-3.69 (m, 4H), 3.67-3.56 (m, 2H), 3.34 (dd, J=18.3, 11.4 Hz, 1H), 2.88 (dd, J=18.3, 10.1 Hz, 1H), 2.69 (d, J=3.8 Hz, 6H), 2.44 (s, 3H). LC-MS (m/z): 471.4 $[M+H]^+$.

Compound 240: (S)-(4-(4-(3,5-dimethyl-1H-1,2,4-triazol-1-yl)-5-fluoropyrimidin-2-yl)piperazin-1-yl)(5-(2-methylthiazol-5-yl)-4,5-dihydro-1H-pyrazol-1-yl)methanone

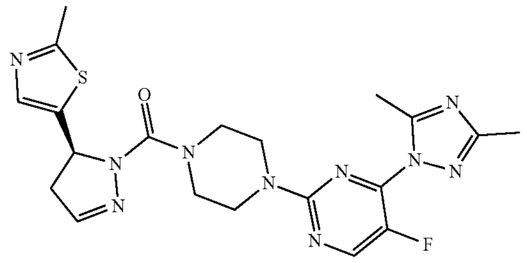 [SMILES: Cc1nc(C)n(-c2nc(N3CCN(C(=O)N4N=CC[C@H]4c4cnc(C)s4)CC3)ncc2F)n1]

The titled compound 240 was prepared in a yield of 18% as an off-white solid according to the procedure outlined for compound 235 and separated by SFC. LC-MS (m/z): 471.3 $[M+H]^+$. $^1H$ NMR (400 MHz, $CDCl_3$) δ 8.40 (s, 1H), 7.59 (s, 1H), 6.90 (s, 1H), 5.60 (t, J=10.8 Hz, 1H), 3.92-3.82 (m, 2H), 3.80-3.69 (m, 4H), 3.66-3.55 (m, 2H), 3.34 (dd, J=18.2, 11.5 Hz, 1H), 2.88 (dd, J=18.1, 10.1 Hz, 1H), 2.71 (s, 3H), 2.69 (s, 3H) 2.44 (d, J=2.6 Hz, 3H). LC-MS (m/z): 471.3 $[M+H]^+$.

Compound 241: (S)-(4-(4-(3,5-dimethyl-1H-1,2,4-triazol-1-yl)-5-fluoropyrimidin-2-yl)piperazin-1-yl)(5-(5-methylthiazol-2-yl)-4,5-dihydro-1H-pyrazol-1-yl)methanone

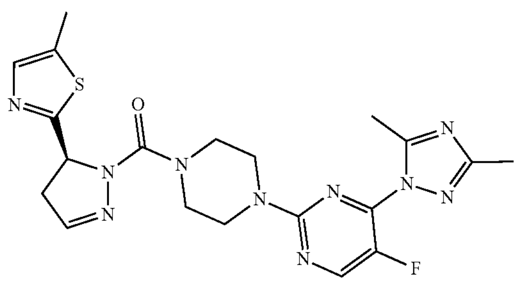 [SMILES: Cc1nc(C)n(-c2nc(N3CCN(C(=O)N4N=CC[C@H]4c4ncc(C)s4)CC3)ncc2F)n1]

The titled compound 241 was prepared in a yield of 18% as an off-white solid according to the procedure outlined for compound 235 and separated by SFC. LC-MS (m/z): 471.3 $[M+H]^+$. $^1H$ NMR (400 MHz, $CDCl_3$) δ 8.40 (d, J=2.8 Hz, 1H), 7.37 (s, 1H), 6.90 (s, 1H), 5.79-5.64 (m, 1H), 3.94-3.84 (m, 2H), 3.83-3.72 (m, 4H), 3.70-3.54 (m, 2H), 3.32 (d, J=10.4 Hz, 2H), 2.70 (s, 3H), 2.45 (s, 3H), 2.43 (s, 3H). LC-MS (m/z): 471.4 $[M+H]^+$.

Compound 242: (R)-(4-(4-(3,5-dimethyl-1H-1,2,4-triazol-1-yl)-5-fluoropyrimidin yl)piperazin-1-yl)(5-(5-methylthiazol-2-yl)-4,5-dihydro-1H-pyrazol-1-yl) methanone

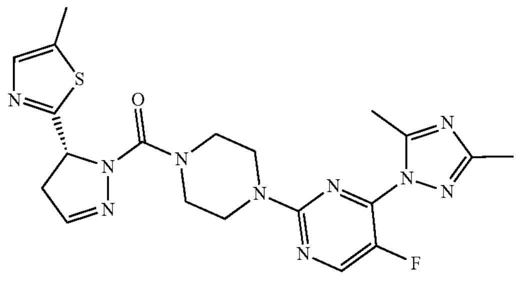 [SMILES: Cc1nc(C)n(-c2nc(N3CCN(C(=O)N4N=CC[C@@H]4c4ncc(C)s4)CC3)ncc2F)n1]

The titled compound 242 was prepared in a yield of 15% as an off-white solid according to the procedure outlined for compound 235 and separated by SFC. LC-MS (m/z): 471.3 $[M+H]^+$. $^1H$ NMR (400 MHz, $CDCl_3$) δ 8.40 (d, J=2.9 Hz, 1H), 7.37 (s, 1H), 6.90 (s, 1H), 5.71 (t, J=10.4 Hz, 1H), 3.93-3.59 (m, 8H), 3.32 (d, J=10.5 Hz, 2H), 2.69 (s, 3H), 2.44 (s, 3H), 2.42 (s, 3H). LC-MS (m/z): 471.4 $[M+H]^+$.

Compound 243: (S)-3-(1-(4-(4-(3,5-dimethyl-1H-1,2,4-triazol-1-yl)pyrimidin-2-yl)piperazine-1-carbonyl)-4,5-dihydro-1H-pyrazol-5-yl)-5-fluorobenzonitrile

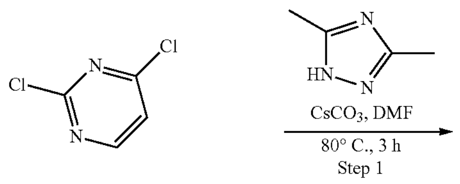

-continued

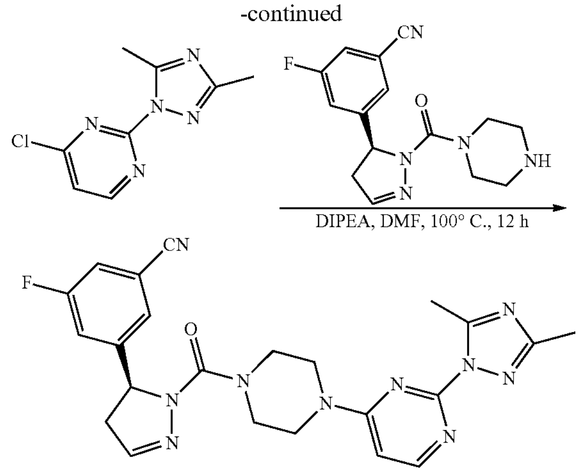

The titled compound 243 was prepared in 16% yield as a white solid according to the procedure outlined for compound 147. LC-MS (m/z) 475.1 $(M+H^+)$. $^1H$ NMR (400 MHz, DMSO-d6) δ 8.49 (d, J=5.4 Hz, 1H), 7.75 (ddd, J=8.5, 2.6, 1.4 Hz, 1H), 7.66 (t, J=1.5 Hz, 1H), 7.54 (ddd, J=9.8, 2.6, 1.5 Hz, 1H), 7.17-7.10 (m, 1H), 7.01 (d, J=5.4 Hz, 1H), 5.30 (dd, J=11.5, 10.2 Hz, 1H), 3.87-3.51 (m, 8H), 3.42-3.34 (m, 1H), 2.79 (s, 3H), 2.71 (ddd, J=18.3, 10.2, 1.6 Hz, 1H), 2.29 (s, 3H).

Compound 244: (S)-3-(1-(4-(2-(3,5-dimethyl-1H-1,2,4-triazol-1-yl)pyrimidin-4-yl)piperazine-1-carbonyl)-4,5-dihydro-1H-pyrazol-5-yl)-5-fluorobenzonitrile

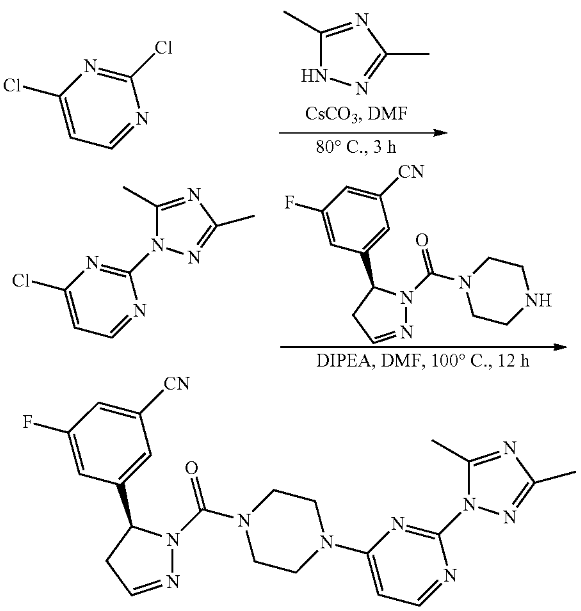

The titled compound 244 was prepared in 3% yield as a white solid according to the procedure outlined for compound 147. LC-MS (m/z) 475.1 $(M+H^+)$. $^1H$ NMR (400 MHz, DMSO-d6) δ 8.29 (d, J=6.1 Hz, 1H), 7.75 (ddd, J=8.5, 2.5, 1.3 Hz, 1H), 7.66 (t, J=1.5 Hz, 1H), 7.54 (ddd, J=9.7, 2.6, 1.5 Hz, 1H), 7.13 (d, J=1.7 Hz, 1H), 6.85 (d, J=6.2 Hz, 1H), 5.29 (dd, J=11.5, 10.1 Hz, 1H), 3.89-3.51 (m, 8H), 3.38 (ddd, J=18.4, 11.6, 1.9 Hz, 1H), 2.76-2.68 (m, 1H), 2.67 (s, 3H), 2.26 (s, 3H).

Compound 245: (S)-3-(1-(4-(4-(3-(difluoromethyl)-5-methyl-1H-1,2,4-triazol-1-yl)-5-fluoropyrimidin yl)piperazine-1-carbonyl)-4,5-dihydro-1H-pyrazol-5-yl)-5-fluorobenzonitrile

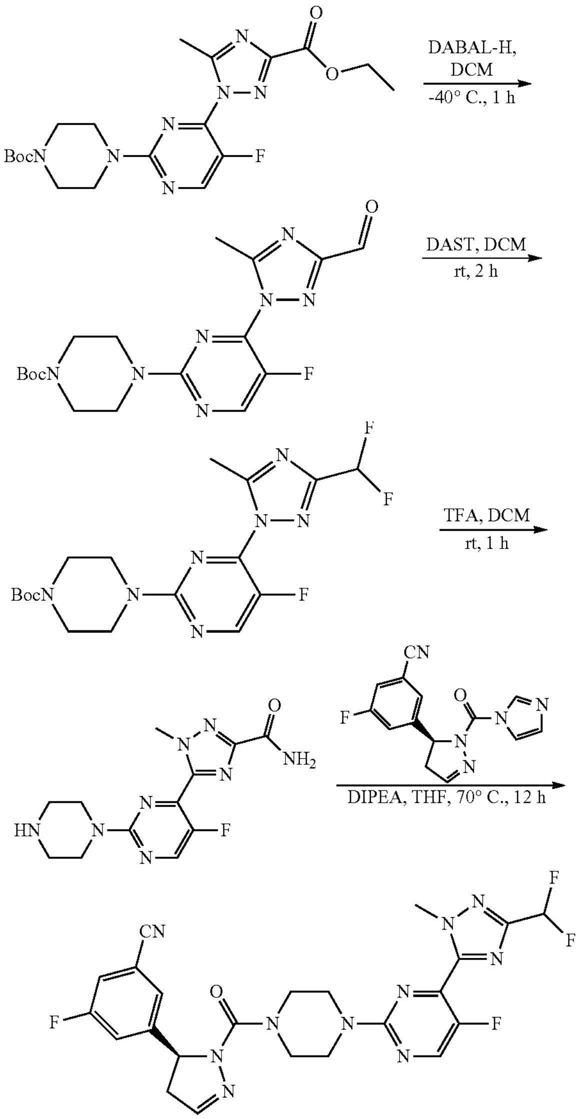

Step 1: To a solution of tert-butyl 4-(4-(3-(ethoxycarbonyl)-5-methyl-1H-1,2,4-triazol-1-yl)-5-fluoropyrimidin-2-yl)piperazine-1-carboxylate (200 mg, 459.3 umol) in DCM (10 mL) was added DABAL-H (0.5 mL, 505.2 umol) at −40° C. under Ar. The reaction mixture was stirred at −40° C. for 1 h. The crude was purified by column chromatography on silica gel. tert-butyl 4-(5-fluoro-4-(3-formyl-5-methyl-1H-1,2,4-triazol-1-yl)pyrimidin-2-yl)piperazine-1-carboxylate (103 mg, 57%) was obtained as a off-white solid MS (m/z): 392.1 $[M+H]^+$.

Step 2: To a solution of tert-butyl 4-(5-fluoro-4-(3-formyl-5-methyl-1H-1,2,4-triazol-1-yl)pyrimidin-2-yl)piperazine-1-carboxylate (100 mg, 255.5 umol) in DCM (3 mL) was added DAST (206 mg, 1.28 mmol) at 0° C. under Ar. The reaction mixture was stirred at rt for 2 h. The crude was purified by column chromatography on silica gel. tert-butyl 44443-(difluoromethyl)-5-methyl-1H-1,2,4-triazol-1-yl)-5-fluoropyrimidin-2-yl)piperazine-1-carboxylate (63 mg, 60%) was obtained as a white solid MS (m/z): 414.1 $[M+H]^+$.

Step 3: To a solution of tert-butyl 4-(4-(3-(difluoromethyl)-5-methyl-1H-1,2,4-triazol-1-yl)-5-fluoropyrimidin-2-yl)piperazine-1-carboxylate (50 mg, 120.9 umol) in DCM (3 mL) was added TFA (3 mL). The reaction mixture was stirred at rt for 1 h. The solvent was concentrated under vacuum. The crude was used to next step directly MS (m/z): 314.1 $[M+H]^+$.

Step 4: To a solution of (S)-3-(1-(1H-imidazole-1-carbonyl)-4,5-dihydro-1H-pyrazol-5-yl)-5-fluorobenzonitrile (35 mg, 123.6 umol) in THF (3 mL) was added 4-(3-(difluoromethyl)-5-methyl-1H-1,2,4-triazol-1-yl)-5-fluoro-2-(piperazin-1-yl)pyrimidine (38 mg, 123.6 umol) and DIPEA (80 mg, 617.8 umol). The reaction mixture was stirred at 70° C. for 12 h. The crude was purified by Pre-HPLC. (S)-3-(1-(4-(4-(3-(difluoromethyl)-5-methyl-1H-1,2,4-triazol-1-yl)-5-fluoropyrimidin-2-yl)piperazine-1-carbonyl)-4,5-dihydro-1H-pyrazol-5-yl)-5-fluorobenzonitrile (8 mg, 12%) was obtained as a white solid MS (m/z): 529.1 $[M+H]^+$. $^1$H NMR (400 MHz, DMSO-$d_6$) δ 8.79 (d, J=2.8 Hz, 1H), 7.75 (ddd, J=8.5, 2.6, 1.4 Hz, 1H), 7.65 (t, J=1.5 Hz, 1H), 7.58-7.48 (m, 1H), 7.34-7.01 (m, 2H), 5.29 (t, J=10.8 Hz, 1H), 3.85-3.50 (m, 8H), 3.39 (dd, J=11.6, 1.9 Hz, 1H), 2.72 (s, 3H), 2.68 (dd, J=10.2, 1.6 Hz, 1H).

Compound 246: (S)-3-(1-(4-(4-(3-(difluoromethyl)-5-methyl-1H-1,2,4-triazol-1-yl) fluoropyrimidin-2-yl)piperazine-1-carbonyl)-4,5-dihydro-1H-pyrazol-5-yl) fluorobenzonitrile

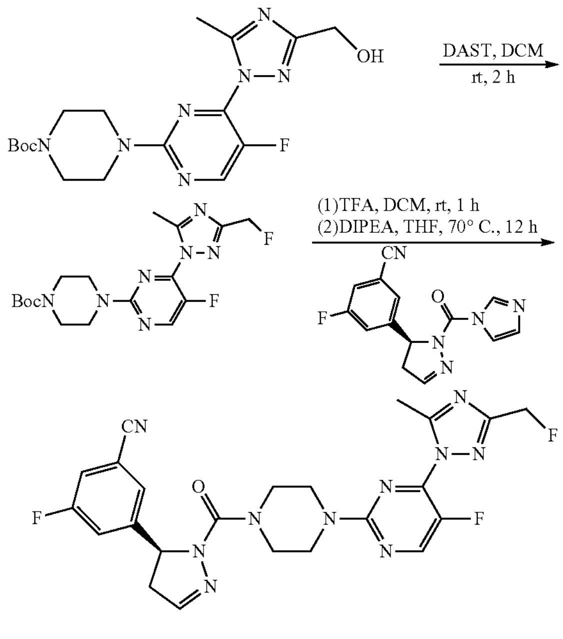

The titled compound 246 was prepared in 11% yield as a yellow solid according to the procedure outlined for compound 245. LC-MS (m/z) 511.1 $(M+H^+)$. $^1$H NMR (400

MHz, DMSO-d6) δ 8.76 (d, J=2.9 Hz, 1H), 7.75 (ddd, J=8.5, 2.5, 1.3 Hz, 1H), 7.65 (dt, J=3.0, 1.4 Hz, 1H), 7.59-7.49 (m, 1H), 7.12 (d, J=1.9 Hz, 1H), 5.50 (d, J=1.4 Hz, 1H), 5.38 (d, J=1.4 Hz, 1H), 5.29 (dd, J=12.5, 9.2 Hz, 1H), 3.83-3.52 (m, 8H), 3.41-3.36 (m, 1H), 2.74-2.61 (m, 1H), 2.69 (s, 3H).

Compound 247: (S)-3-(1-(4-(4-(3-(azetidine-1-carbonyl)-5-methyl-1H-1,2,4-triazol-1-yl)-5-fluoropyrimidin-2-yl)piperazine-1-carbonyl)-4,5-dihydro-1H-pyrazol-5-yl)-5-fluorobenzonitrile

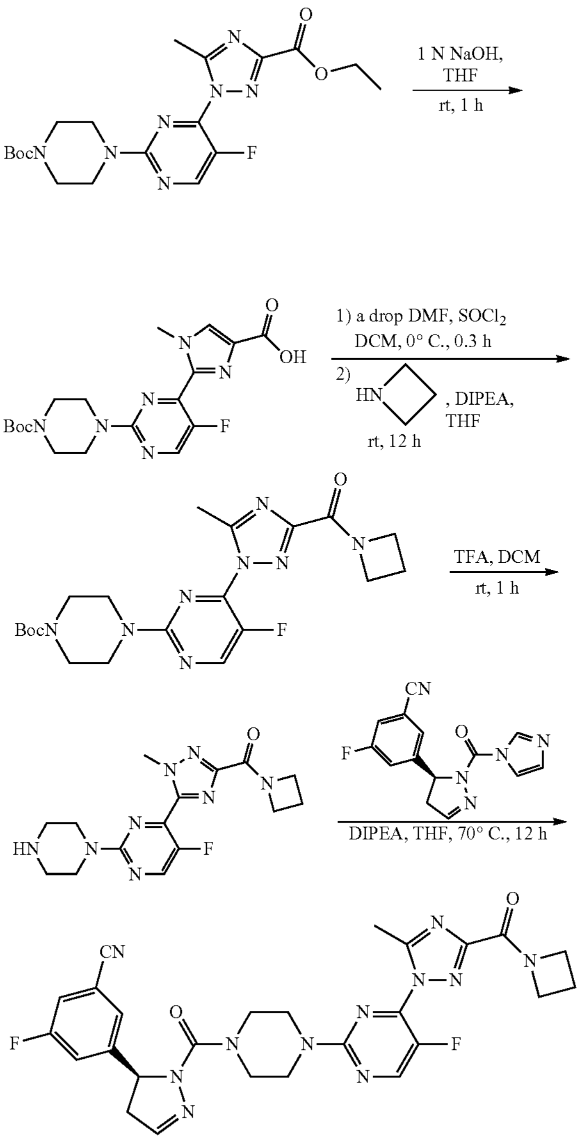

The titled compound 247 was prepared in 6% yield as a white solid according to the procedure outlined for compound 225. LC-MS (m/z): 562.2 (M+H$^+$). $^1$H NMR (400 MHz, DMSO-d6) δ 8.77 (d, J=2.9 Hz, 1H), 7.75 (ddd, J=8.5, 2.5, 1.3 Hz, 1H), 7.65 (d, J=1.5 Hz, 1H), 7.58-7.49 (m, 1H), 7.12 (d, J=1.7 Hz, 1H), 5.29 (t, J=10.9 Hz, 1H), 4.56-4.42 (m, 1H), 4.06 (t, J=7.7 Hz, 1H), 3.87-3.51 (m, 8H), 3.10 (qd, J=7.3, 4.8 Hz, 4H), 2.70 (s, 3H), 2.38-2.17 (m, 2H).

Compound 248: (S)-(4-(4-(3,5-dimethyl-1H-1,2,4-triazol-1-yl)-5-fluoropyrimidin-2-yl)piperazin-1-yl)(5-(5-fluoropyridin-3-yl)-4,5-dihydro-1H-pyrazol-1-yl)methanone

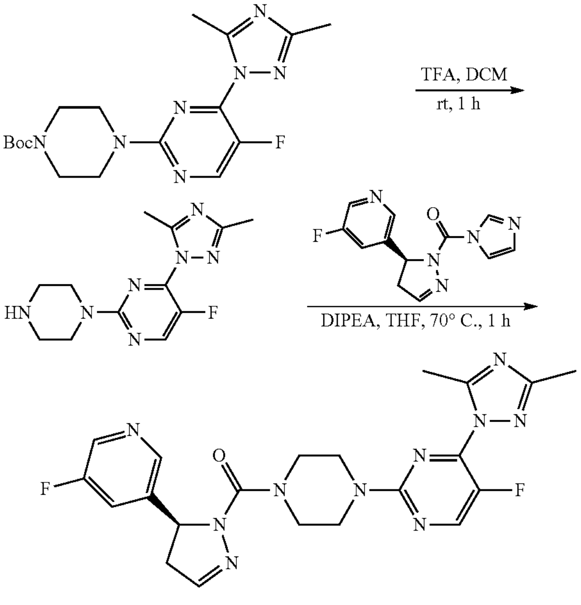

The titled compound 248 was prepared in 33% yield as a white solid according to the procedure outlined for compound 225 LC-MS (m/z) 469.1 (M+H$^+$). $^1$H NMR (400 MHz, Chloroform-d) δ 8.43-8.37 (m, 3H), 7.34 (dt, J=9.0, 2.3 Hz, 1H), 6.90 (t, J=1.7 Hz, 1H), 5.41 (dd, J=11.6, 10.2 Hz, 1H), 3.87-3.59 (m, 8H), 3.37 (ddd, J=18.3, 11.8, 1.8 Hz, 1H), 2.79-2.72 (m, 1H), 2.69 (s, 3H), 2.44 (s, 3H).

Compound 249: (S)-5-(2-(4-(5-(3-cyano-5-fluorophenyl)-4,5-dihydro-1H-pyrazole-1-carbonyl)piperazin-1-yl)-5-fluoropyrimidin-4-yl)-1-methyl-1H-1,2,4-triazole-3-carbonitrile

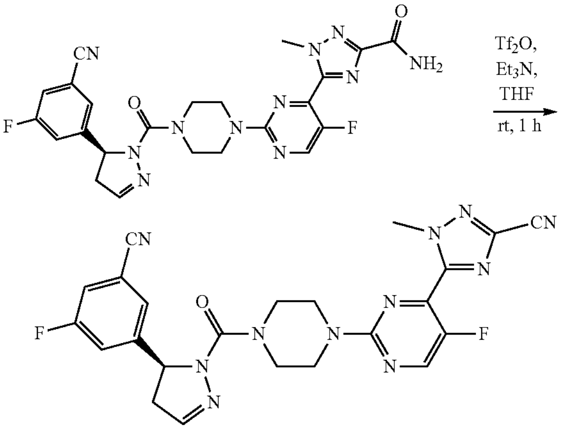

To a solution of (S)-5-(2-(4-(5-(3-cyano-5-fluorophenyl)-4,5-dihydro-1H-pyrazole-1-carbonyl)piperazin-1-yl)-5-fluoropyrimidin-4-yl)-1-methyl-1H-1,2,4-triazole-3-carboxamide (40 mg, 76.7 umol) in THF (2 mL) was added $Tf_2O$ (65 mg, 230.1 umol) and $Et_3N$ (40 mg, 383.5 umol) at 0° C. under Ar. The reaction mixture was stirred at rt for 1 h. The crude was purified by Pre-HPLC to give compound 249 (12 mg, 31%) was obtained as a white solid MS (m/z): 504.1 $[M+H]^+$. $^1H$ NMR (400 MHz, DMSO-d6) δ 9.52 (s, 1H), 8.78 (d, J=2.5 Hz, 1H), 7.74 (ddd, J=8.3, 2.5, 1.3 Hz, 1H), 7.65 (t, J=1.5 Hz, 1H), 7.53 (ddd, J=9.8, 2.5, 1.5 Hz, 1H), 5.38-5.30 (m, 1H), 3.84-3.86 (m, 8H), 3.42-3.37 (m, 1H), 3.36 (s, 3H), 2.71 (ddd, J=18.3, 10.1, 1.6 Hz, 1H).

Compound 250: (S)-(4-(5-fluoro-4-(3-(hydroxymethyl)-5-methyl-1H-1,2,4-triazol-1-yl)pyrimidin-2-yl)piperazin-1-yl)(5-(5-fluoropyridin-3-yl)-4,5-dihydro-1H-pyrazol-1-yl)methanone

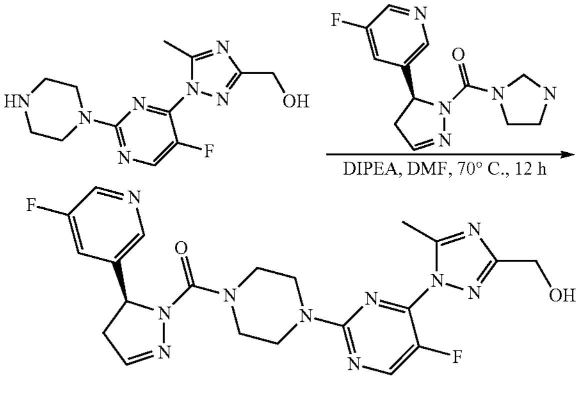

The titled compound 250 was prepared in 6% yield as a light-yellow solid according to the procedure outlined for compound 144. LC-MS (m/z) 485.1 $(M+H^+)$. $^1H$ NMR (400 MHz, DMSO-d6) δ 8.72 (d, J=3.0 Hz, 1H), 8.54-8.36 (m, 2H), 7.73-7.62 (m, 1H), 7.14 (d, J=1.7 Hz, 1H), 5.31 (t, J=10.9 Hz, 1H), 4.46 (s, 2H), 3.85-3.48 (m, 8H), 3.39 (ddd, J=18.3, 11.6, 1.9 Hz, 1H), 2.75 (ddd, J=18.3, 10.2, 1.6 Hz, 1H), 2.65 (s, 3H).

Compound 251: (S)-(5-(3,5-difluorophenyl)-4,5-dihydro-1H-pyrazol-1-yl)(4-(5-fluoro-4-(3-(hydroxymethyl)-5-methyl-1H-1,2,4-triazol-1-yl)pyrimidin-2-yl)piperazin yl)methanone

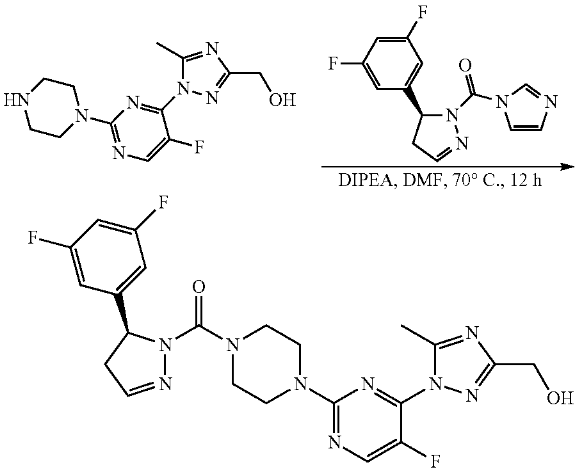

The titled compound 251 was prepared in 9% yield as a yellow solid according to the procedure outlined for compound 144. LC-MS (m/z) 502.1 $(M+H^+)$. $^1H$ NMR (400 MHz, DMSO-d6) δ 8.73 (d, J=2.9 Hz, 1H), 7.17-7.06 (m, 2H), 7.01 (ddd, J=8.4, 5.2, 2.4 Hz, 2H), 5.26 (dd, J=11.6, 9.9 Hz, 1H), 4.46 (d, J=5.7 Hz, 2H), 3.95-3.47 (m, 8H), 3.41-3.33 (m, 1H), 2.70-2.58 (m, 1H), 2.65 (s, 3H).

Compound 252: (S)-1-(2-(4-(5-(3,5-difluorophenyl)-4,5-dihydro-1H-pyrazole-1-carbonyl)piperazin-1-yl)-5-fluoropyrimidin-4-yl)-5-methyl-1H-1,2,4-triazole-3-carboxamide

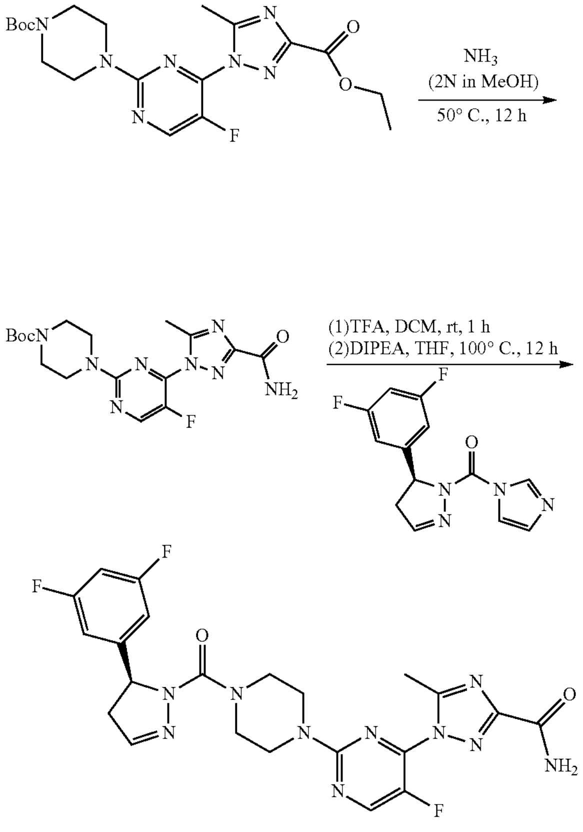

Step 1: To a solution of tert-butyl 4-(4-(3-(ethoxycarbonyl)-5-methyl-1H-1,2,4-triazol-1-yl)-5-fluoropyrimidin-2-yl)piperazine-1-carboxylate (300 mg, 688.9 umol) in MeOH (5 mL) was added $NH_3$ (5 mL, 2 N in MeOH). The reaction mixture was stirred at 50° C. for 12 h in a 25 mL of sealed tube. The crude was purified by column chromatography on silica gel. tert-butyl 4-(4-(3-carbamoyl-5-methyl-1H-1,2,4-triazol-1-yl)-5-fluoropyrimidin-2-yl)piperazine-1-carboxylate (200 mg, 71%) was obtained as a light-yellow solid MS (m/z): 407.1 $[M+H]^+$.

Step 2: The titled compound 252 was prepared in 15% yield as an off-white solid according to the procedure outlined for compound 225. MS (m/z): 515.1 $[M+H]^+$. $^1H$ NMR (400 MHz, DMSO-d6) δ 8.79 (d, J=2.7 Hz, 1H), 7.10 (qd, J=6.1, 5.3, 3.0 Hz, 2H), 7.05-6.93 (m, 2H), 5.26 (dd, J=11.6, 9.9 Hz, 1H), 3.89-3.48 (m, 8H), 3.37 (ddd, J=18.3, 11.7, 1.9 Hz, 1H), 2.69 (s, 3H), 2.76-2.59 (m, 1H).

Compound 253: (S)-1-(5-fluoro-2-(4-(5-(5-fluoro-pyridin-3-yl)-4,5-dihydro-1H-pyrazole-1-carbonyl)piperazin-1-yl)pyrimidin-4-yl)-5-methyl-1H-1,2,4-triazole-3-carboxamide

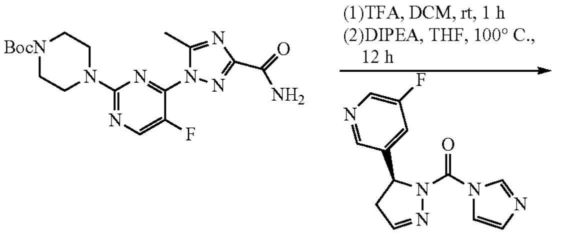

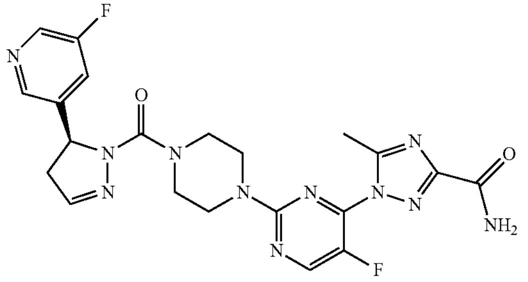

The titled compound 253 was prepared in 7% yield as a white solid according to the procedure outlined for compound 225. LC-MS (m/z) 498.1 (M+H$^+$). $^1$H NMR (400 MHz, DMSO-d6) δ 8.01-7.95 (m, 1H), 7.81-7.76 (m, 1H), 7.71-7.64 (m, 2H), 7.13-7.09 (m, 1H), 5.40-5.26 (m, 1H), 3.79-3.49 (m, 8H), 3.39 (dd, J=18.2, 11.7 Hz, 1H), 2.82-2.72 (m, 1H), 2.69 (s, 3H).

Compound 254: (S)-1-(2-(4-(5-(3,5-difluorophenyl)-4,5-dihydro-1H-pyrazole-1-carbonyl)piperazin-1-yl)-5-fluoropyrimidin-4-yl)-5-methyl-1H-1,2,4-triazole-3-carbonitrile

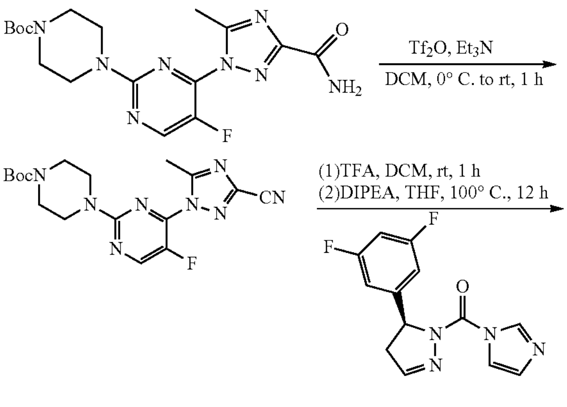

-continued

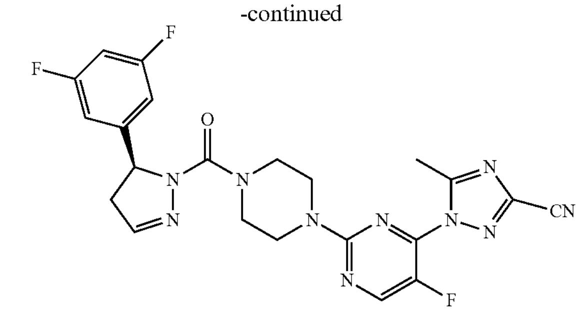

The titled compound 254 was prepared in 6% yield as a white solid according to the procedure outlined for compound 228. LC-MS (m/z) 497.1 (M+H$^+$).

Compound 255: (S)-1-(5-fluoro-2-(4-(5-(5-fluoro-pyridin-3-yl)-4,5-dihydro-1H-pyrazole-1-carbonyl)piperazin-1-yl)pyrimidin-4-yl)-5-methyl-1H-1,2,4-triazole-3-carbonitrile

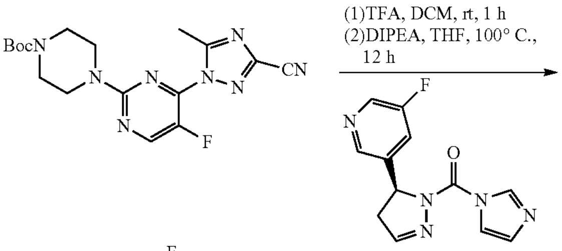

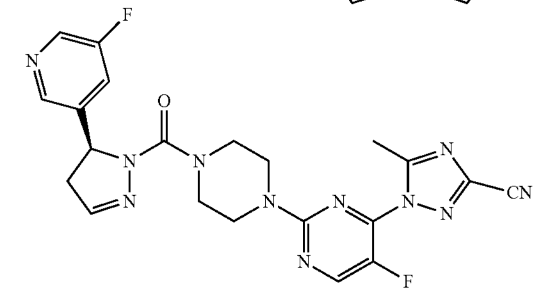

The titled compound 255 was prepared in 4% yield as a white solid according to the procedure outlined for compound 225. LC-MS (m/z) 480.1 (M+H$^+$).

Compound 256: (S)-5-(2-(4-(5-(3-cyano-5-fluoro-phenyl)-4,5-dihydro-1H-pyrazole-1-carbonyl)piperazin-1-yl)-5-fluoropyrimidin-4-yl)-1-methyl-1H-1,2,4-triazole-3-carboxamide

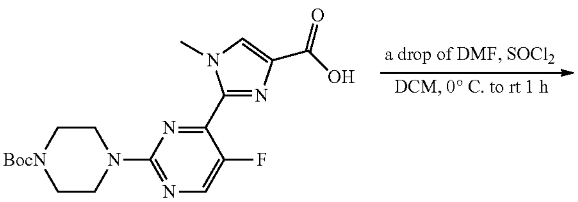

-continued

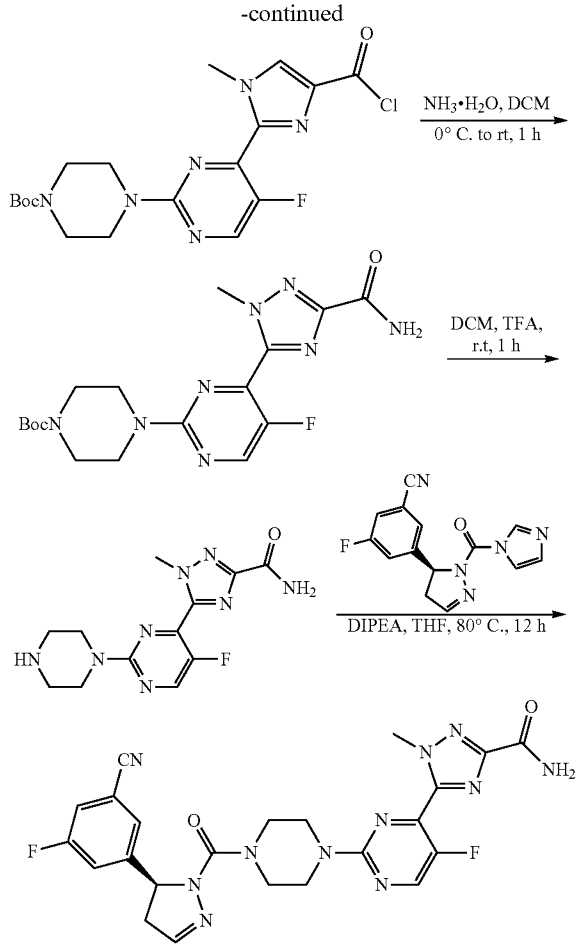

The titled compound 256 was prepared in 16% yield from 5-(2-(4-(tert-butoxycarbonyl)piperazin-1-yl)-5-fluoropyrimidin-4-yl)-1-methyl-1H-1,2,4-triazole carboxylic acid according to the procedure outlined for compound 225. LC-MS (m/z) 522.1 (M+H$^+$).

Compound 257: (S)-(5-(3,5-difluorophenyl)-4,5-dihydro-1H-pyrazol-1-yl)(4-(2-(3,5-dimethyl-1H-1,2,4-triazol-1-yl)-5-fluoropyrimidin-4-yl)piperazin-1-yl)methanone

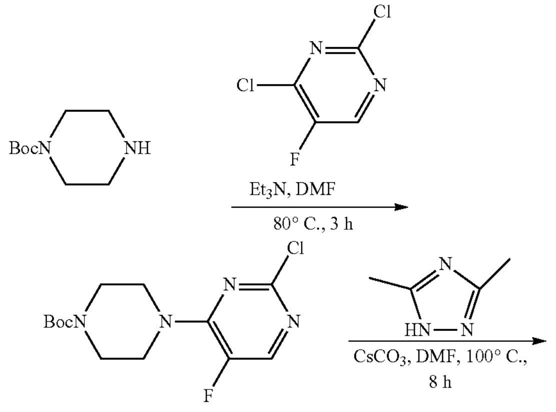

-continued

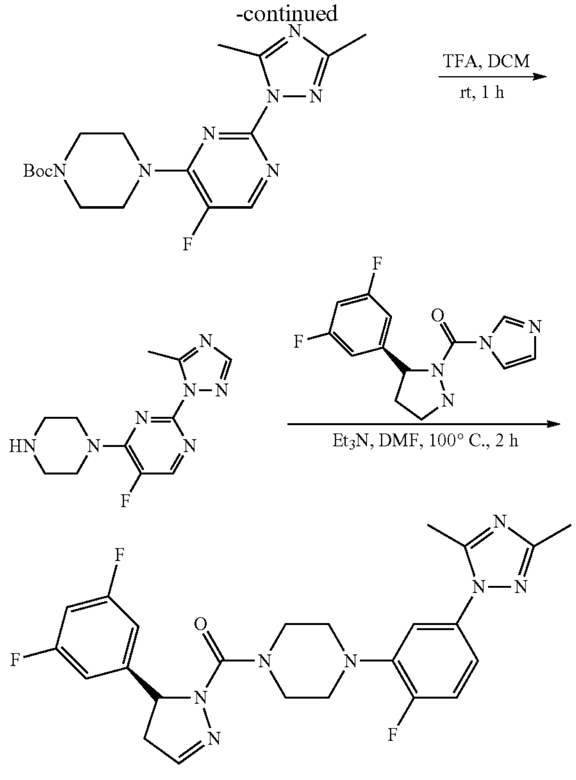

The titled compound 257 was prepared in 14% yield as a white solid according to the procedure outlined for compound 150. LC-MS (m/z) 486.1 (M+H$^+$). $^1$H NMR (400 MHz, $CDCl_3$) δ 8.19 (d, J=5.8 Hz, 1H), 6.89 (d, J=1.8 Hz, 1H), 6.87-6.77 (m, 2H), 6.71 (tt, J=8.8, 2.3 Hz, 1H), 5.33 (dd, J=11.7, 9.5 Hz, 1H), 4.07-3.66 (m, 8H), 3.36 (ddd, J=18.4, 11.7, 1.8 Hz, 1H), 2.92 (s, 3H), 2.72 (ddd, J=18.4, 9.5, 1.6 Hz, 1H), 2.52 (s, 3H).

Compound 258: (S)-3-(1-(4-(2-(3,5-dimethyl-1H-1,2,4-triazol-1-yl)-5-fluoropyrimidin-4-yl)piperazine-1-carbonyl)-4,5-dihydro-1H-pyrazol-5-yl)-5-fluorobenzonitrile

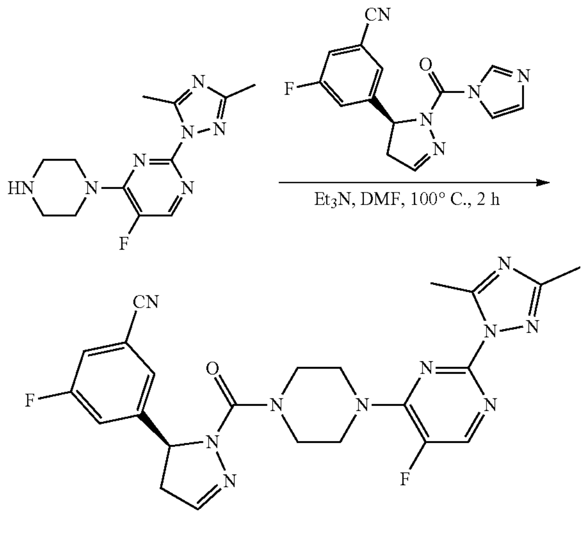

The titled compound 258 was prepared in 12% yield as a white solid according to the procedure outlined for compound 150. LC-MS (m/z) 493.1 ($M+H^+$). $^1H$ NMR (400 MHz, $CDCl_3$) δ 8.20 (d, J=5.7 Hz, 1H), 7.41 (t, J=1.5 Hz, 1H), 7.28 (dd, J=8.3, 1.5 Hz, 2H), 6.93 (t, J=1.7 Hz, 1H), 5.37 (dd, J=11.7, 9.7 Hz, 1H), 4.05-3.67 (m, 8H), 3.40 (ddd, J=18.4, 11.7, 1.9 Hz, 1H), 2.95 (s, 3H), 2.73 (ddd, J=18.4, 9.7, 1.6 Hz, 1H), 2.53 (s, 3H).

Compound 259: (S)-(4-(5-chloro-4-(3,5-dimethyl-1H-1,2,4-triazol-1-yl)pyrimidin-2-yl)piperazin-1-yl)(5-(3,5-difluorophenyl)-4,5-dihydro-1H-pyrazol-1-yl)methanone

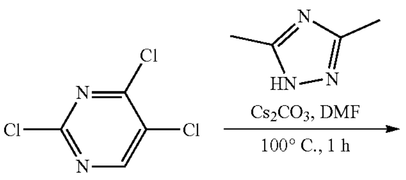

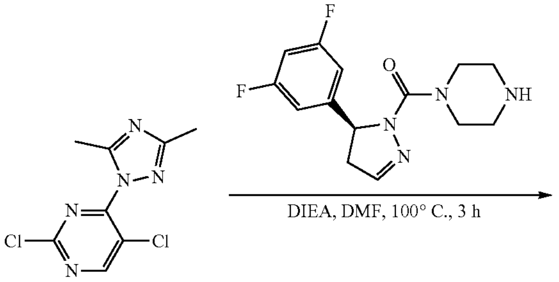

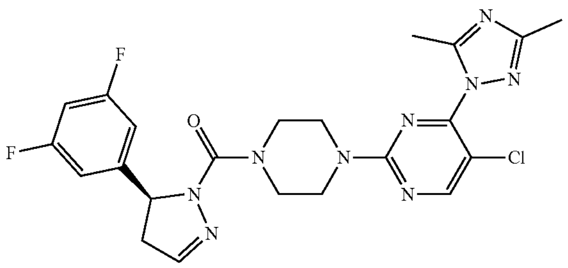

The titled compound 259 was prepared in 23% yield as a white solid according to the procedure outlined for compound 150. LC-MS (m/z) 502.1 ($M+H^+$). $^1H$ NMR (400 MHz, $CDCl_3$) δ 8.46 (s, 1H), 6.94-6.76 (m, 3H), 6.70 (tt, J=8.8, 2.3 Hz, 1H), 5.33 (dd, J=11.7, 9.8 Hz, 1H), 4.02-3.55 (m, 8H), 3.33 (ddd, J=18.3, 11.7, 1.8 Hz, 1H), 2.70 (ddd, J=18.3, 9.8, 1.7 Hz, 1H), 2.58 (s, 3H), 2.45 (s, 3H).

Compound 260: (S)-3-(1-(4-(5-chloro-4-(3,5-dimethyl-1H-1,2,4-triazol-1-yl)pyrimidin-2-yl)piperazine-1-carbonyl)-4,5-dihydro-1H-pyrazol-5-yl)-5-fluorobenzonitrile

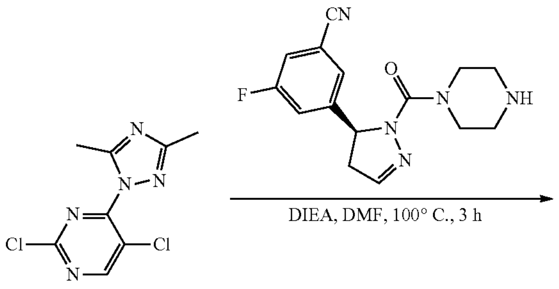

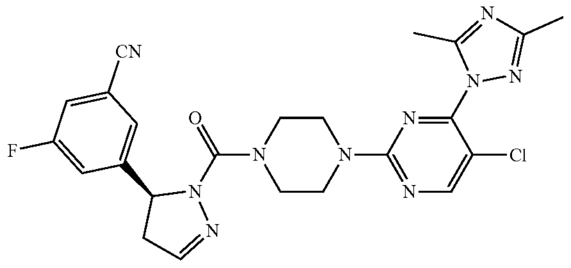

The titled compound 260 was prepared in 26% yield as a white solid according to the procedure outlined for compound 150. LC-MS (m/z) 509.1 ($M+H^+$).

Compound 261: (5-(3-chloropyridin-2-yl)-4,5-dihydro-1H-pyrazol-1-yl)(4-(2-(1,4-dimethyl-1H-pyrazol-5-yl)-5-fluoropyrimidin-4-yl)piperazin-1-yl)methanone

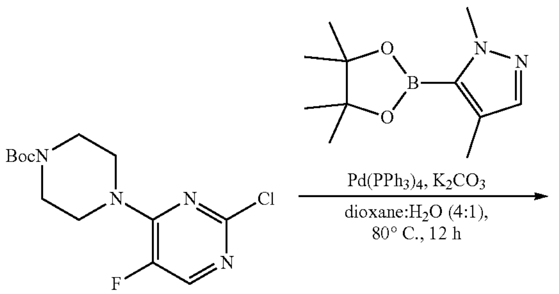

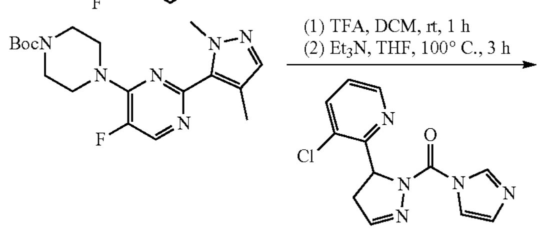

-continued

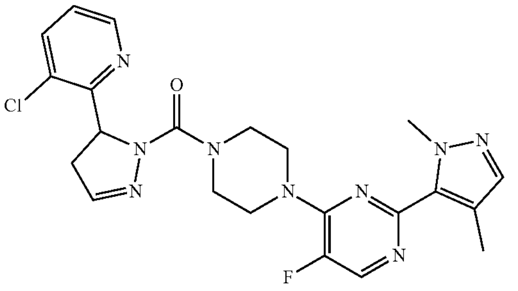

The titled compound 261 was prepared in 15% yield as a white solid according to the procedure outlined for compound 225. LC-MS (m/z) 484.1 (M+H$^+$).

Compound 262: (5-(3,5-difluorophenyl)-4,5-dihydro-1H-pyrazol-1-yl-5-d)(4-(4-(3,5-dimethyl-1H-1,2,4-triazol-1-yl)-5-fluoropyrimidin-2-yl)piperazin-1-yl)methanone

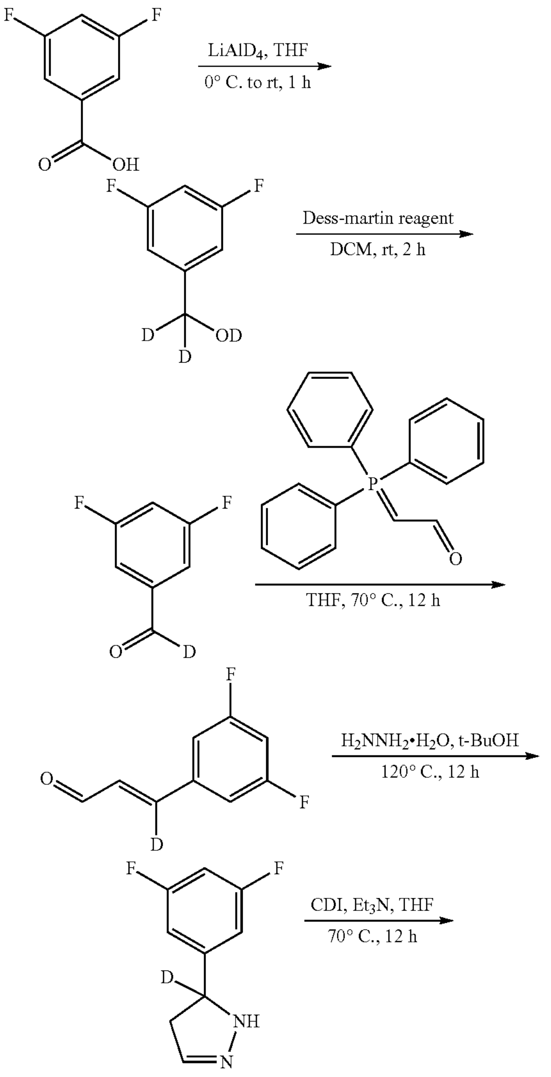

-continued

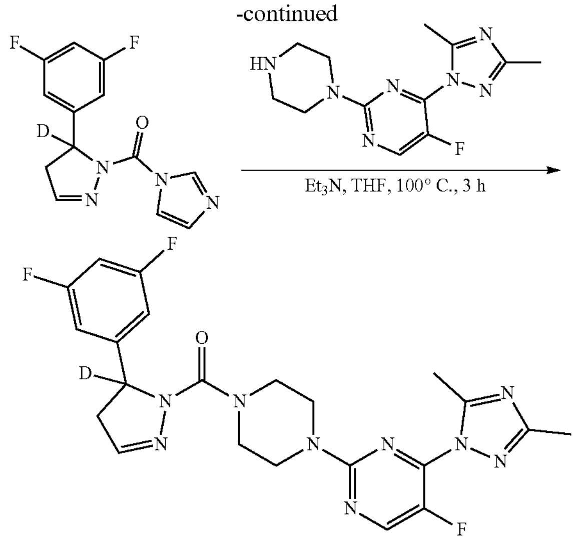

Step 1: To a solution of 3,5-difluorobenzoic acid (3 g, 18.97 mmol) in THF (50 mL) was added $LiAlD_4$ (956 mg, 22.8 mmol, dissolved in 20 mL THF) slowly at 0° C. under Ar. The reaction mixture was stirred at rt for 1 h. The crude was purified by column chromatography on silica gel. (3,5-difluorophenyl)methan-d2-ol-d (2.3 g, 82%) was obtained as a colorless oil MS (m/z): 148.1 [M+H]$^+$.

Step 2: To a solution of (3,5-difluorophenyl)methan-d2-ol-d (2.3 g, 15.6 mmol) in DCM (30 mL) was added Dess-martin reagent (13.3 g, 31.3 mmol). The reaction mixture was stirred at rt for 2 h. The crude was purified by column chromatography on silica gel. 3,5-difluorobenzaldehyde-d (1.3 g, 58%) was obtained as a colorless oil MS (m/z): 144.1 [M+H]$^+$.

Step 3: To a solution of 3,5-difluorobenzaldehyde-d (1.3 g, 9.08 mmol) in THF (20 mL) was added 2-(triphenyl-l5-phosphaneylidene)acetaldehyde (2.76 g, 9.08 mmol). The reaction mixture was stirred at 70° C. for 12 h. The crude was purified by column chromatography on silica gel. 3-(3,5-difluorophenyl)acrylaldehyde-3-d (1.1 g, 72%) was obtained as a off-white solid MS (m/z): 170.1 [M+H]$^+$.

Step 4: To a solution of $H_2NNH_2 \cdot H_2O$ (10 mL) in t-BuOH (40 mL) was added 3-(3,5-difluorophenyl)acrylaldehyde-3-d (1.1 g, 6.5 mmol, dissolved in 20 mL t-BuOH) slowly at 120° C. under Ar. The reaction mixture was stirred at 120° C. for 12 h. The crude was purified by column chromatography on silica gel. 5-(3,5-difluorophenyl)-4,5-dihydro-1H-pyrazole-5-d (0.8 g, 67%) was obtained as a light-yellow solid MS (m/z): 184.1 [M+H]$^+$.

Step 5: To a solution of 5-(3,5-difluorophenyl)-4,5-dihydro-1H-pyrazole-5-d (400 mg, 2.18 mmol) in THF (10 mL) was added CDI (355 mg, 2.18 mmol) and $Et_3N$ (663 mg, 6.55 mmol). The reaction mixture was stirred at 70° C. for 12 h. The crude was purified by column chromatography on silica gel. (5-(3,5-difluorophenyl)-4,5-dihydro-1H-pyrazol-1-yl-5-d)(1H-imidazol-1-yl)methanone (216 mg, 35%) was obtained as a light-yellow solid MS (m/z): 278.1 [M+H]$^+$.

Step 6: To a solution of (5-(3,5-difluorophenyl)-4,5-dihydro-1H-pyrazol-1-yl-5-d)(1H-imidazol-1-yl)methanone (30 mg, 108.2 umol) in THF (4 mL) was added 4-(3,5-dimethyl-1H-1,2,4-triazol-1-yl)-5-fluoro-2-(piperazin-1-yl)pyrimidine (30 mg, 108.2 umol) and $Et_3N$ (55 mg, 541.0 umol). The reaction mixture was stirred at 100° C. for 3 h. The crude was purified by Pre-HPLC. (5-(3,5-difluorophenyl)-4,5-dihydro-1H-pyrazol-1-yl-5-d)(4-(4-(3,5-dimethyl-1H-1,2,4-triazol-1-yl)-5-fluoropyrimidin-2-yl)piperazin-1-yl)methanone (9 mg, 17%) was obtained as a off-white solid MS (m/z): 487.2 [M+H]$^+$. $^1$H NMR (400 MHz, $CDCl_3$) δ 8.40 (d, J=2.62 Hz, 1H), 6.85-6.79 (m, 2H), 6.71-6.66 (m, 1H), 3.89-3.61 (m, 8H), 3.34-3.29 (m, 1H), 2.70 (s, 3H), 2.69-2.66 (m, 1H), 2.44 (s, 3H).

Compound 263: (5-(3-chloropyridin-2-yl)-4,5-dihydro-1H-pyrazol-1-yl)(4-(2-(3,5-dimethyl-1H-1,2,4-triazol-1-yl)-5-fluoropyrimidin-4-yl)piperazin-1-yl)methanone

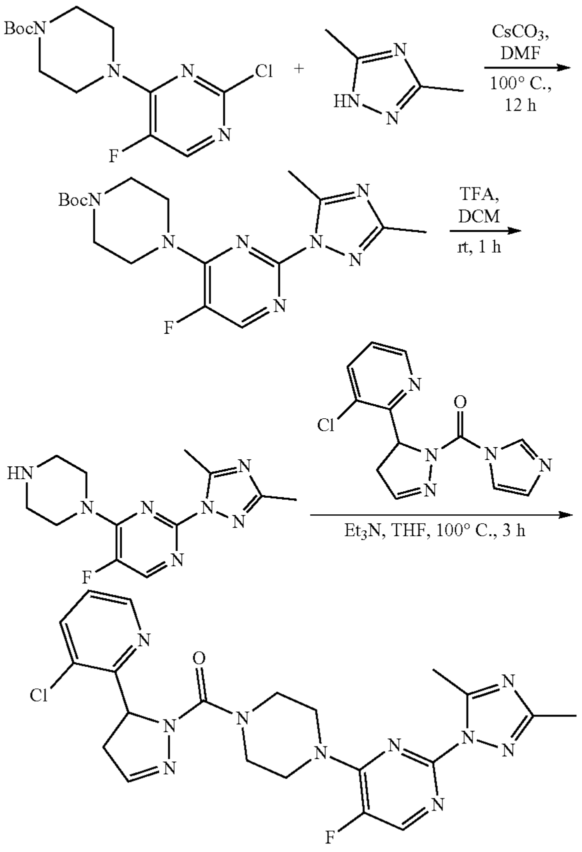

The titled compound 263 was prepared in 13% yield as a white solid according to the procedure outlined for compound 225. LC-MS (m/z) 485.1 (M+H$^+$).

Compound 264: (S)-(4-(4-(3,5-dimethyl-1H-1,2,4-triazol-1-yl)-5-fluoropyrimidin-2-yl)piperazin-1-yl)(5-(2,3,5-trifluorophenyl)-4,5-dihydro-1H-pyrazol-1-yl)methanone

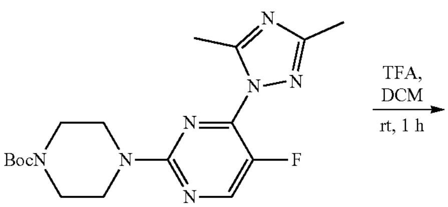

-continued

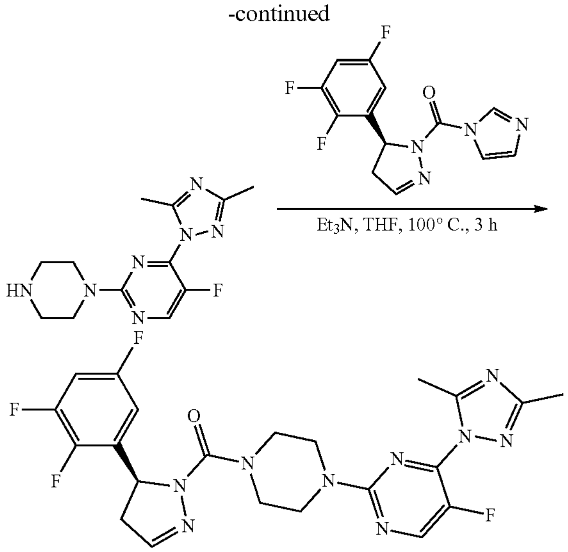

The titled compound 264 was prepared in 34% yield as a white solid according to the procedure outlined for compound 225. LC-MS (m/z) 504.1 (M+H$^+$). $^1$H NMR (400 MHz, $CDCl_3$) δ 8.58-8.41 (m, 1H), 7.12-7.65 (m, 3H), 5.70-5.51 (m, 1H), 4.15-3.64 (m, 8H), 3.42 (t, J=17.7 Hz), 3.34-3.29 (m, 1H), 2.69-2.66 (m, 1H), 2.83 (s, 3H), 2.55 (s, 3H).

Compound 265: (R)-(4-(4-(3,5-dimethyl-1H-1,2,4-triazol-1-yl)-5-fluoropyrimidin-2-yl)piperazin-1-yl)(5-(2,3,5-trifluorophenyl)-4,5-dihydro-1H-pyrazol-1-yl)methanone

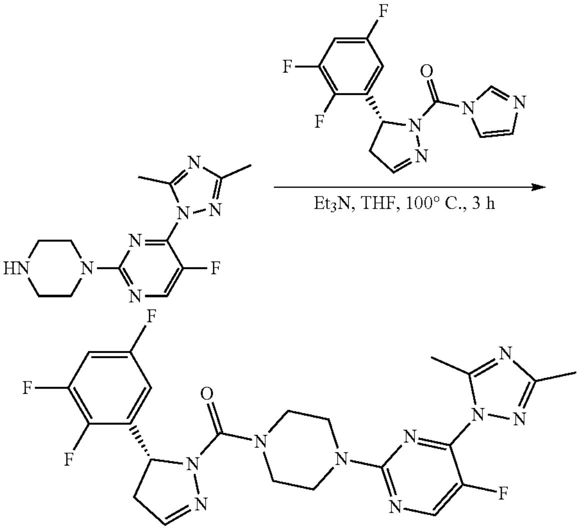

The titled compound 265 was prepared in 31% yield as a white solid according to the procedure outlined for compound 225. LC-MS (m/z) 504.1 (M+H$^+$). $^1$H NMR (400 MHz, $CDCl_3$) δ 8.58-8.41 (m, 1H), 7.12-7.65 (m, 3H), 5.70-5.51 (m, 1H), 4.15-3.64 (m, 8H), 3.42 (t, J=17.7 Hz), 3.34-3.29 (m, 1H), 2.69-2.66 (m, 1H), 2.83 (s, 3H), 2.55 (s, 3H).

Compound 266: (S)-3-(1-(4-(4-(1,4-dimethyl-1H-pyrazol-5-yl)-5-(hydroxymethyl)thiazol-2-yl)piperazine-1-carbonyl)-4,5-dihydro-1H-pyrazol-5-yl)-5-fluorobenzonitrile

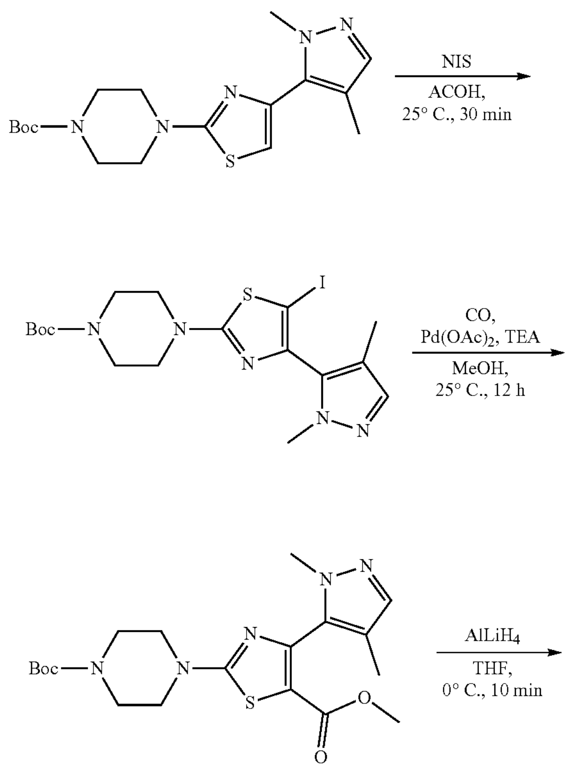

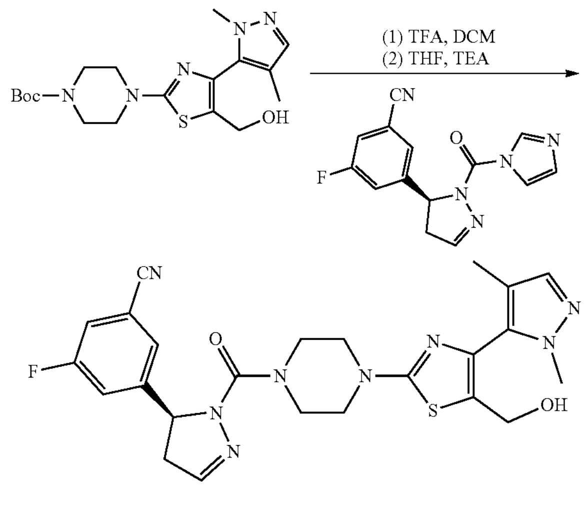

Step 1: Tert-butyl 4-(4-(1,4-dimethyl-1H-pyrazol-5-yl)thiazol-2-yl)piperazine-1-carboxylate (1 g, 2.75 mmol) was dissolved in 10 mL of acetic acid, NIS (618 mg, 2.75 mmol) was added, the mixture was stirred at r.t. for 30 min. Water was added and extracted with EA, washed with brine, dried ($Na_2SO_4$), and concentrated in vacuo. Purification by silica gel chromatography to give the compound tert-butyl 4-(4-(1,4-dimethyl-1H-pyrazol-5-yl)-5-iodothiazol-2-yl)piperazine-1-carboxylate (667 mg, 50%). MS (m/z): 489.2 ($M+H^+$).

Step 2: Tert-butyl 4-(4-(1,4-dimethyl-1H-pyrazol-5-yl)-5-iodothiazol-2-yl)piperazine-1-carboxylate (667 mg, 1.36 mmol), $Pd(OAc)_2$ (176 mg, 0.789 mmol), were dissolved in MeOH (15 mL), and stirred at 25° C. under CO (1 atm) for 12 h. The mixture was extracted with EA, washed with brine, dried ($Na_2SO_4$), and concentrated in vacuo to give the compound methyl 2-(4-(tert-butoxycarbonyl)piperazin-1-yl)-4-(1,4-dimethyl-1H-pyrazol-5-yl)thiazole-5-carboxylate (310 mg, crude). MS (m/z): 422.6 ($M+H^+$).

Step 3: Methyl 2-(4-(tert-butoxycarbonyl)piperazin-1-yl)-4-(1,4-dimethyl-1H-pyrazol-5-yl)thiazole-5-carboxylate (310 mg, 0.735 mmol) was dissolved in 10 ml of dry THF, $AlLiH_4$ (1M, 1 mL) was added to the above solution at 0° C., the mixture was stirred for 10 min at 0° C. Water was added and extracted with EA, washed with brine, dried ($Na_2SO_4$), and concentrated to dryness to give the desired product tert-butyl 4-(4-(1,4-dimethyl-1H-pyrazol-5-yl)-5-(hydroxymethyl)thiazol-2-yl)piperazine-1-carboxylate (150 mg, 51.8%) MS (m/z): 394.2 (M+H+).

Step 4 and 5:

The titled compound 266 was prepared in 32.6% yield as a white solid according to the procedure outlined for compound 225. $^1H$ NMR (400 MHz, Chloroform-d) δ 7.37 (s, 1H), 7.33 (t, J=1.5 Hz, 1H), 7.28 (s, 1H), 6.84 (d, J=1.7 Hz, 1H), 6.77 (s, 1H), 5.34-5.18 (m, 3H), 3.72 (s, 3H), 3.69-3.42 (m, 8H), 3.35-3.26 (m, 1H), 2.69-2.60 (m, 1H), 1.93 (s, 3H). LC-MS (m/z) 509.2 ($M+H^+$).

Compound 267: (S)-(5-(3,5-difluorophenyl)-4,5-dihydro-1H-pyrazol-1-yl)(4-(4-(1,4-dimethyl-1H-pyrazol-5-yl)-5-(hydroxymethyl)thiazol-2-yl)piperazin-1-yl)methanone

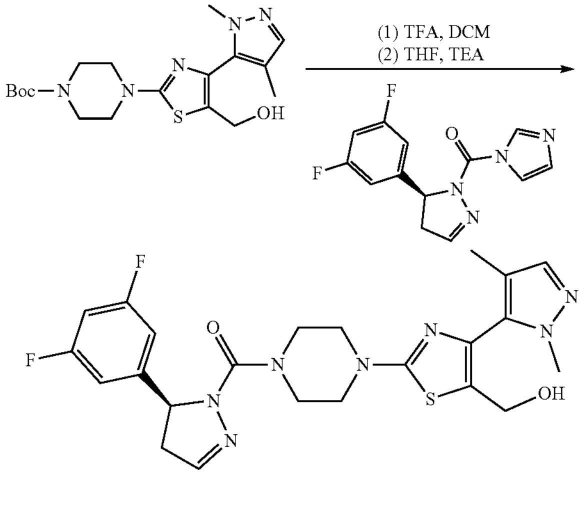

The titled compound 267 was prepared in 32.6% yield as a white solid according to the procedure outlined for compound 225. $^1H$ NMR (400 MHz, Chloroform-d) δ 7.38 (s, 1H), 7.31-7.26 (m, 1H), 6.82-6.76 (m, 1H), 6.73 (dt, J=6.5, 2.1 Hz, 1H), 6.63 (tt, J=8.8, 2.3 Hz, 1H), 5.29-5.17 (m, 3H), 3.82-3.38 (m, 8H), 3.73 (s, 3H) 3.27 (ddd, J=18.4, 11.8, 1.8 Hz, 1H), 2.64 (ddd, J=18.4, 9.5, 1.6 Hz, 1H), 1.93 (s, 3H). LC-MS (m/z) 502.2 ($M+H^+$).

Compound 268: (S)-3-(1-(4-(2-(1,4-dimethyl-1H-pyrazol-5-yl)-5-fluoropyrimidin-4-yl)piperazine-1-carbonyl)-4,5-dihydro-1H-pyrazol-5-yl)-5-fluorobenzonitrile

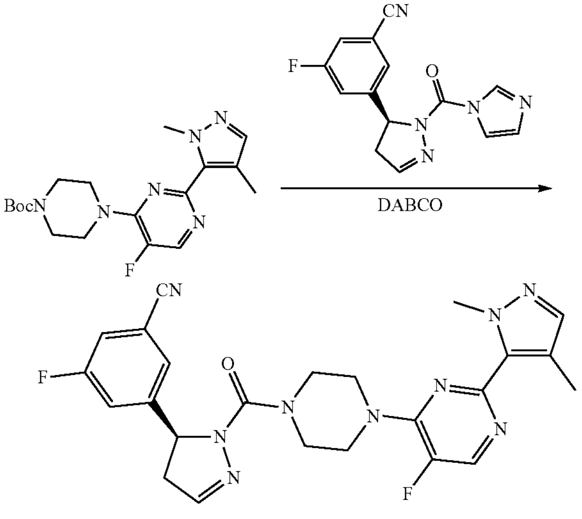

The titled compound 268 was prepared in 32.6% yield as a white solid according to the procedure outlined for compound 143. $^{1}$H NMR (400 MHz, Chloroform-d) δ 8.21 (d, J=6.3 Hz, 1H), 7.41 (t, J=1.5 Hz, 1H), 7.33 (d, J=0.6 Hz, 1H), 7.28 (dd, J=1.4, 0.8 Hz, 1H), 7.26-7.24 (m, 1H), 6.92-6.87 (m, 1H), 5.36 (dd, J=11.7, 10.0 Hz, 1H), 4.15 (s, 3H), 3.98-3.63 (m, 8H), 3.37 (ddd, J=18.3, 11.7, 1.8 Hz, 1H), 2.70 (ddd, J=18.3, 10.0, 1.6 Hz, 1H), 2.29 (d, J=0.6 Hz, 3H). Mass (m/z): 492.3[M+H]$^{+}$.

Compound 269: (S)-3-(1-(4-(2-(1,4-dimethyl-1H-pyrazol-5-yl)-5-fluoropyridin-4-yl)piperazine-1-carbonyl)-4,5-dihydro-1H-pyrazol-5-yl)-5-fluorobenzonitrile

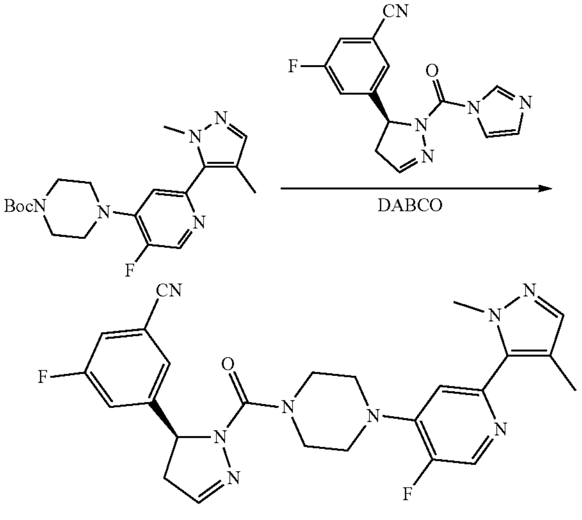

The titled compound 269 was prepared in 30.6% yield as a white solid according to the procedure outlined for compound 143. $^{1}$H NMR (400 MHz, Chloroform-d) δ 8.35 (d, J=5.2 Hz, 1H), 7.41 (t, J=1.5 Hz, 1H), 7.35 (d, J=0.7 Hz, 1H), 7.28 (d, J=1.4 Hz, 1H), 7.26-7.24 (m, 1H), 6.91-6.89 (m, 1H), 6.82 (d, J=7.4 Hz, 1H), 5.36 (dd, J=11.7, 9.9 Hz, 1H), 3.93 (s, 3H), 3.88 (ddd, J=13.4, 6.9, 3.2 Hz, 2H), 3.74 (ddd, J=13.1, 6.7, 3.2 Hz, 2H), 3.46-3.38 (m, 2H), 3.37-3.28 (m, 3H), 2.70 (ddd, J=18.3, 9.9, 1.6 Hz, 1H), 2.11 (s, 3H). Mass (m/z): 491.3[M+H]$^{+}$.

Compound 270: (4-(6-(1,4-dimethyl-1H-pyrazol-5-yl)-3-fluoropyridin-2-yl)piperazin-1-yl)(5-(2-methylthiazol-5-yl)-4,5-dihydro-1H-pyrazol-1-yl)methanone

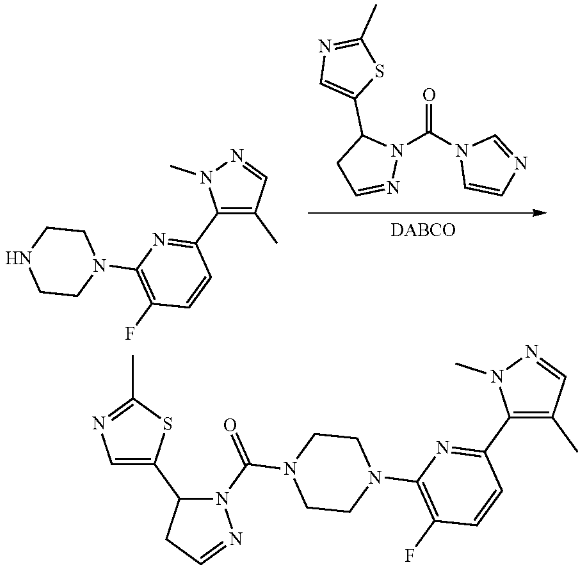

The titled compound 270 was prepared in 22.6% yield as a white solid according to the procedure outlined for compound 143. $^{1}$H NMR (400 MHz, Chloroform-d) δ 7.56 (s, 1H), 7.37-7.30 (m, 2H), 6.91-6.85 (m, 2H), 5.61 (dd, J=11.3, 10.3 Hz, 1H), 3.98 (s, 3H), 3.83 (ddd, J=12.8, 7.2, 3.0 Hz, 2H), 3.71-3.56 (m, 4H), 3.51 (ddd, J=12.7, 7.2, 3.1 Hz, 2H), 3.32 (ddd, J=18.1, 11.4, 1.8 Hz, 1H), 2.87 (ddd, J=18.1, 10.2, 1.6 Hz, 1H), 2.67 (s, 3H), 2.13 (d, J=0.6 Hz, 3H). Mass (m/z): 469.3[M+H]$^{+}$.

Compound 271: (S)-(5-(3,5-difluorophenyl)-4,5-dihydro-1H-pyrazol-1-yl)(4-(2-(3,5-dimethyl-1H-1,2,4-triazol-1-yl)-5-fluoropyridin-4-yl)piperazin-1-yl)methanone

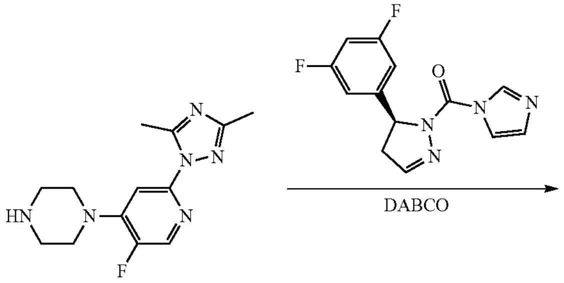

-continued

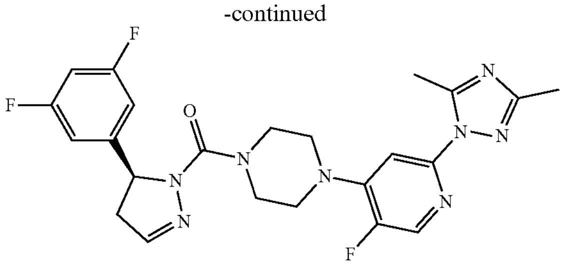

The titled compound 271 was prepared in 46.5% yield as a white solid according to the procedure outlined for compound 143. $^1$H NMR (400 MHz, Chloroform-d) δ 8.06 (d, J=4.8 Hz, 1H), 7.24 (s, 1H), 6.89-6.77 (m, 3H), 6.70 (tt, J=8.9, 2.3 Hz, 1H), 5.38-5.31 (m, 1H), 3.87 (ddd, J=13.8, 7.3, 3.2 Hz, 2H), 3.72 (ddd, J=13.5, 6.6, 3.1 Hz, 2H), 3.45 (ddd, J=10.3, 6.6, 3.2 Hz, 2H), 3.40-3.26 (m, 3H), 2.82-2.64 (m, 4H), 2.39 (s, 3H). Mass (m/z): 485.3[M+H]$^+$.

Compound 272: (S)-3-(1-(4-(2-(3,5-dimethyl-1H-1,2,4-triazol-1-yl)-5-fluoropyridin-4-yl)piperazine-1-carbonyl)-4,5-dihydro-1H-pyrazol-5-yl)-5-fluorobenzonitrile

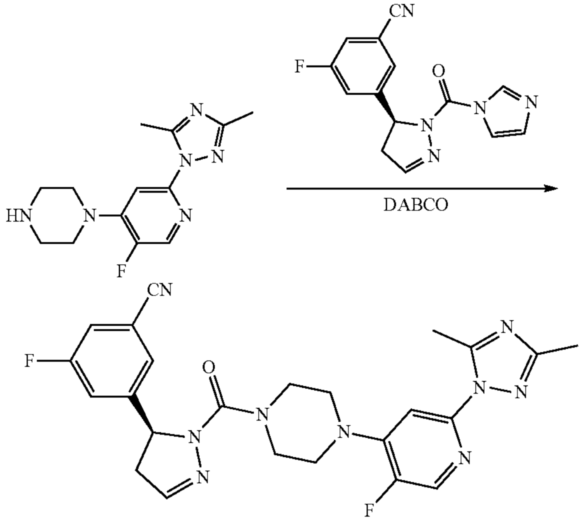

The titled compound 272 was prepared in 42% yield as a white solid according to the procedure outlined for compound 143. $^1$H NMR (400 MHz, Chloroform-d) δ 8.08 (d, J=4.8 Hz, 1H), 7.41 (t, J=1.4 Hz, 1H), 7.30-7.26 (m, 3H), 6.89 (t, J=1.6 Hz, 1H), 5.36 (dd, J=11.7, 9.9 Hz, 1H), 3.92-3.69 (m, 4H), 3.50-3.32 (m, 5H), 2.78 (s, 3H), 2.70 (ddd, J=18.3, 9.9, 1.6 Hz, 1H), 2.41 (s, 3H). Mass (m/z): 492.4[M+H]$^+$.

Compound 273: Preparation of (S)-3-(1-(4-(4-(4-bromo-3,5-dimethyl-1H-pyrazol-1-yl)pyrimidin yl)piperazine-1-carbonyl)-4,5-dihydro-1H-pyrazol-5-yl)-5-fluorobenzonitrile

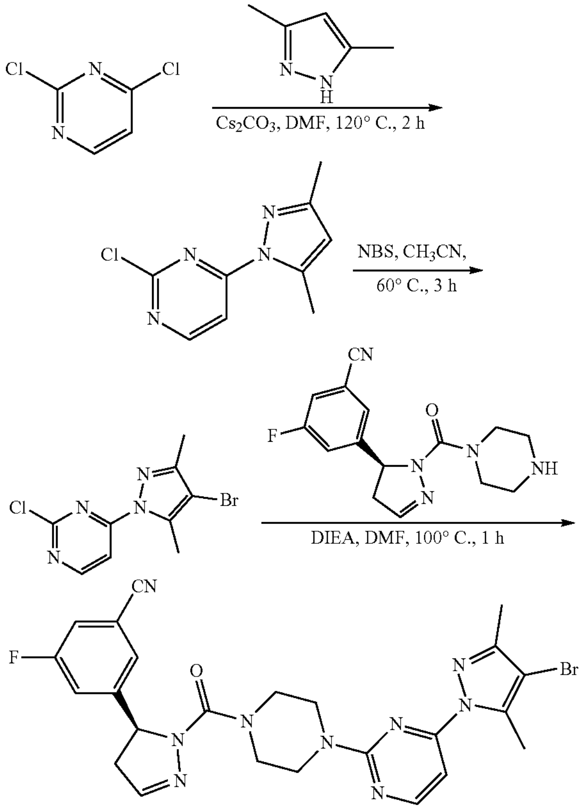

The titled compound 273 was prepared in a yield of 60% as a white solid from according to the procedure for 144. Mass (m/z): 554.3 [M+2H]$^+$. $^1$H NMR (400 MHz, Chloroform-d) δ 8.34 (d, J=5.6 Hz, 1H), 7.42 (t, J=1.5 Hz, 1H), 7.31-7.23 (m, 2H), 7.16 (d, J=5.6 Hz, 1H), 6.94-6.86 (m, 1H), 5.37 (dd, J=11.7, 10.0 Hz, 1H), 4.02-3.89 (m, 2H), 3.88-3.75 (m, 4H), 3.72-3.60 (m, 2H), 3.36 (ddd, J=18.2, 11.7, 1.8 Hz, 1H), 2.76-2.64 (m, 4H), 2.29 (s, 3H).

Compound 274: (S)-1-(2-(4-(5-(3-cyano-5-fluorophenyl)-4,5-dihydro-1H-pyrazole-1-carbonyl)piperazin-1-yl)pyrimidin-4-yl)-3,5-dimethyl-1H-pyrazole-4-carbonitrile

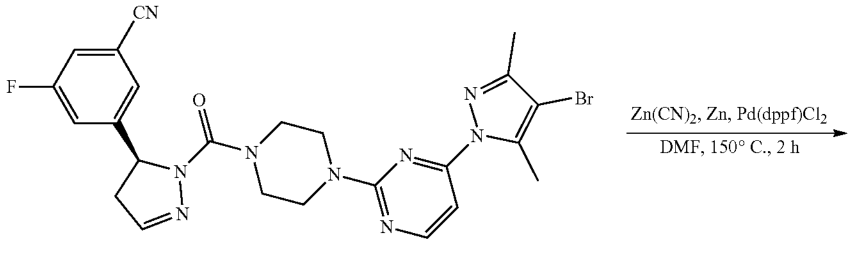

-continued
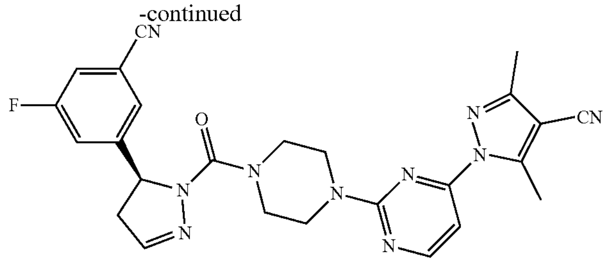
The titled compound 274 was prepared in a yield of 78% as a beige solid from according to the procedure for 238. Mass (m/z): 499.3[M+H]+. $^1$H NMR (301 MHz, Chloroform-d) δ 8.42 (d, J=5.6 Hz, 1H), 7.42 (t, J=1.5 Hz, 1H), 7.34-7.27 (m, 2H), 7.19 (d, J=5.5 Hz, 1H), 6.93-6.87 (m, 1H), 5.37 (t, J=10.8 Hz, 1H), 4.04-3.75 (m, 6H), 3.74-3.61 (m, 2H), 3.44-3.28 (m, 1H), 2.86 (s, 3H), 2.78-2.62 (m, 1H), 2.41 (s, 3H).
Compound 275: Preparation of (S)-1-(2-(4-(5-(3-cyano-5-fluorophenyl)-4,5-dihydro-1H-pyrazole-1-carbonyl)piperazin-1-yl)-5-fluoropyrimidin-4-yl)-3,5-dimethyl-1H-pyrazole-4-carbonitrile
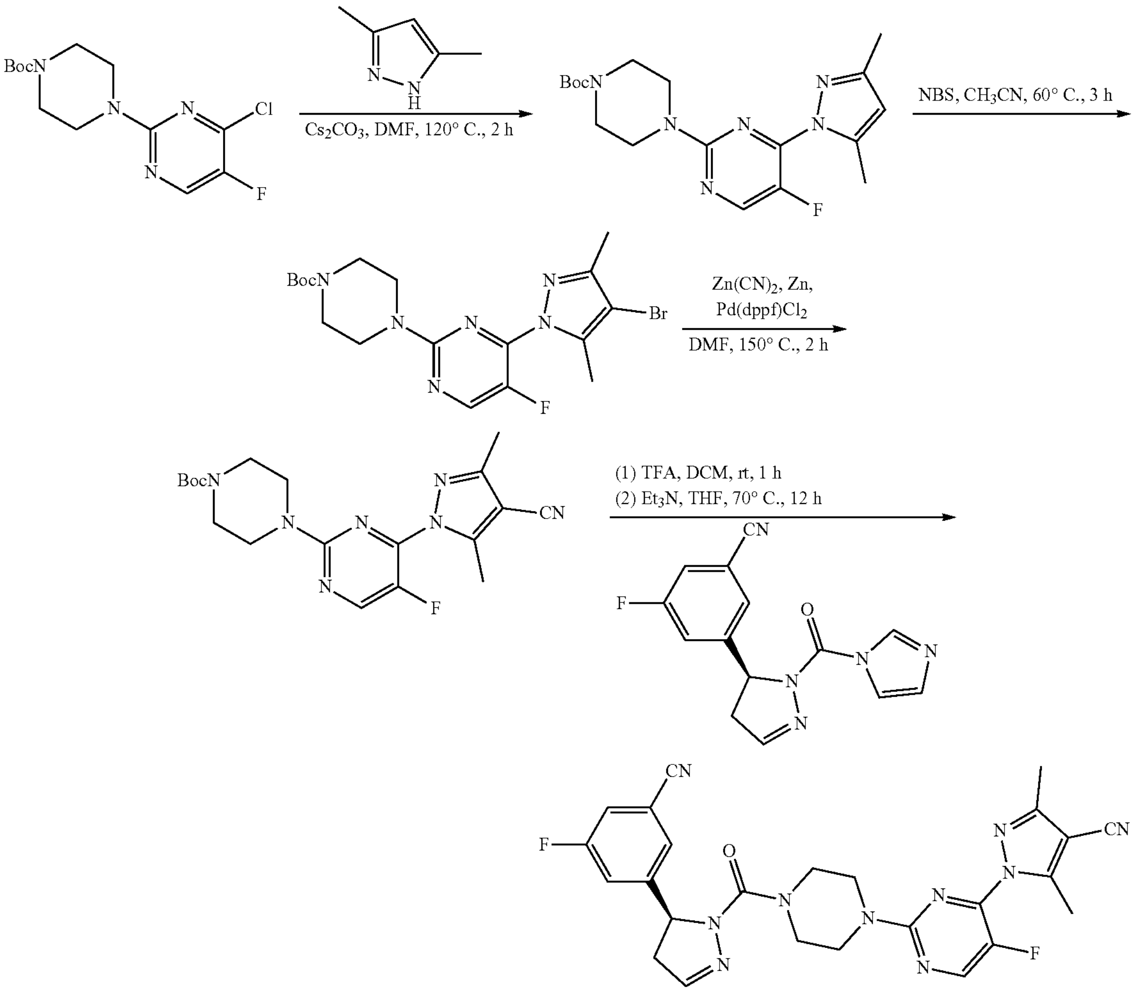

The titled compound 275 was prepared in a yield of 24% as a white solid according to the procedure for 143. Mass (m/z): 517.3 $[M+H]^+$. $^1H$ NMR (301 MHz, Chloroform-d) δ 8.41 (d, J=2.6 Hz, 1H), 7.41 (t, J=1.5 Hz, 1H), 7.34-7.27 (m, 2H), 6.90 (t, J=1.6 Hz, 1H), 542-5.31 (m, 1H), 3.92-3.71 (m, 6H), 3.70-3.59 (m, 2H), 3.37 (ddd, J=18.3, 11.7, 1.8 Hz, 1H), 2.84-2.67 (m, 1H), 2.64 (s, 3H), 2.43 (s, 3H).

Compound 276: Preparation of (S)-1-(2-(4-(5-(3-cyano-5-fluorophenyl)-4,5-dihydro-1H-pyrazole-1-carbonyl)piperazin-1-yl)pyrimidin-4-yl)-3,5-dimethyl-1H-pyrazole-4-carboxamide

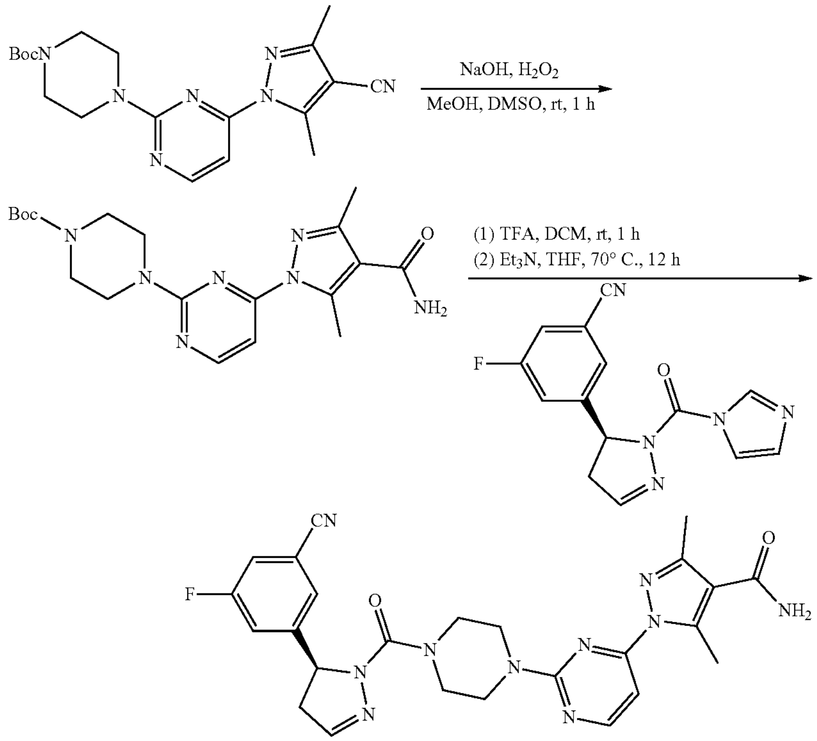

Step 1: tert-butyl 4-(4-(4-carbamoyl-3,5-dimethyl-1H-pyrazol-1-yl)pyrimidin-2-yl)piperazine-1-carboxylate (56.3 mg, 0.147 mmol) was dissolved in 2 mL MeOH and 1 mL DMSO. 0.3 mL 30% $H_2O_2$ and 0.15 mL 2N NaOH was added. Let it stir at r.t for 30 min. The solvent was evaporated to dryness and purified by Prep-TLC (DCM/MeOH=25/1) to give 32.3 mg white solid. Yield: 54.9%.

Step 2: The titled compound 276 was prepared in a yield of 10% as a white solid according to the procedure for 225. Mass (m/z): 517.3$[M+H]^+$. $^1H$ NMR (301 MHz, Chloroform-d) δ 8.38 (d, J=5.4 Hz, 1H), 7.42 (t, J=1.5 Hz, 1H), 7.34-7.27 (m, 2H), 7.11 (d, J=5.5 Hz, 1H), 6.93-6.89 (m, 1H), 5.64 (s, 2H), 5.37 (dd, J=11.6, 10.1 Hz, 1H), 4.02-3.72 (m, 6H), 3.71-3.57 (m, 2H), 3.36 (ddd, J=18.3, 11.7, 1.8 Hz, 1H), 2.94 (s, 3H), 2.69 (ddd, J=18.3, 10.1, 1.6 Hz, 1H), 2.47 (s, 3H).

Compound 277: Preparation of (S)-1-(2-(4-(5-(3-cyano-5-fluorophenyl)-4,5-dihydro-1H-pyrazole-1-carbonyl)piperazin-1-yl)-5-fluoropyrimidin-4-yl)-3,5-dimethyl-1H-pyrazole carboxamide

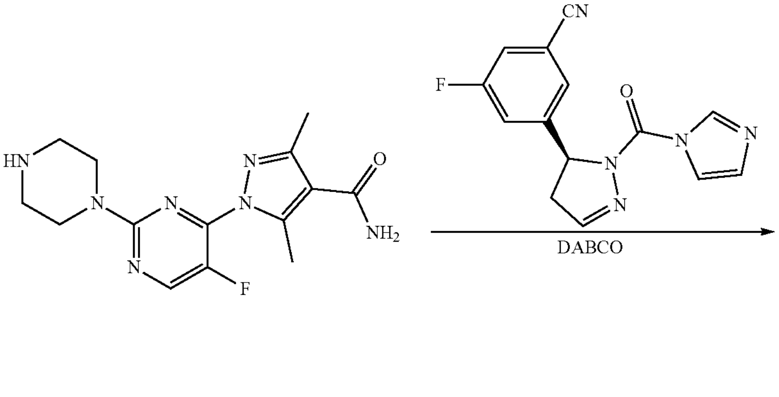

-continued

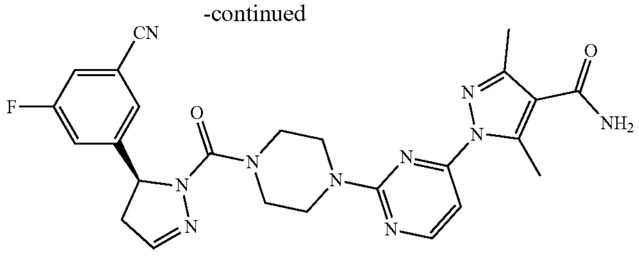

The titled compound 277 was prepared in a yield of 27% as a white solid according to the procedure for 143. Mass (m/z): 535.4[M+H]$^+$. $^1$H NMR (301 MHz, Chloroform-d) δ 8.38 (d, J=2.5 Hz, 1H), 7.43-7.38 (m, 1H), 7.31-7.21 (m, 2H), 6.91-6.86 (m, 1H), 6.04-5.57 (m, 2H), 5.35 (dd, J=11.6, 10.0 Hz, 1H), 3.94-3.70 (m, 6H), 3.68-3.54 (m, 2H), 3.35 (ddd, J=18.3, 11.6, 1.8 Hz, 1H), 2.77-2.61 (m, 4H), 2.50 (s, 3H).

Compound 278: Preparation of (S)-3-(1-(4-(6-(4-bromo-3,5-dimethyl-1H-pyrazol-1-yl)pyrimidin-4-yl)piperazine-1-carbonyl)-4,5-dihydro-1H-pyrazol-5-yl)-5-fluorobenzonitrile

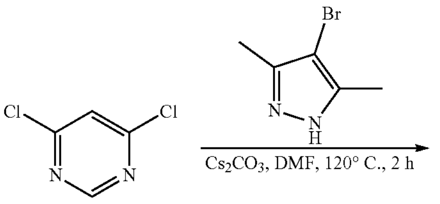

-continued

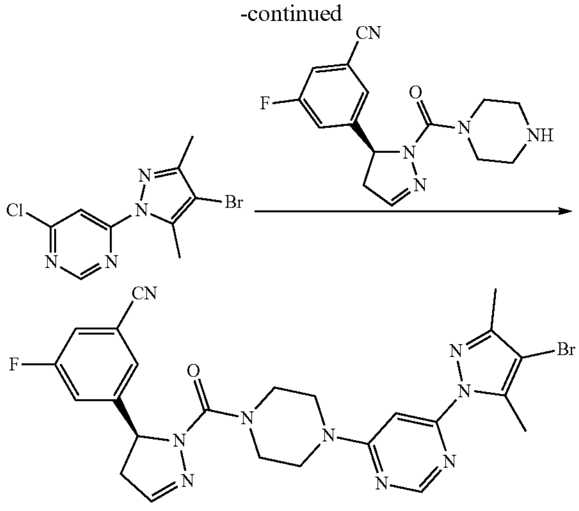

The titled compound 278 was prepared in a yield of 62% as a white solid according to the procedure for 144. Mass (m/z): 552.2, 554.3[M+H]$^+$. $^1$H NMR (400 MHz, Chloroform-d) δ 8.48 (s, 1H), 7.97 (d, J=1.0 Hz, 1H), 7.41 (t, J=1.4 Hz, 1H), 7.30-7.27 (m, 1H), 7.05 (s, 1H), 6.91-6.88 (m, 1H), 5.42-5.25 (m, 1H), 3.91-3.61 (m, 8H), 3.43-3.26 (m, 1H), 2.72-2.66 (m, 4H), 2.29 (s, 3H).

Compound 279: Preparation of (S)-1-(6-(4-(5-(3-cyano-5-fluorophenyl)-4,5-dihydro-1H-pyrazole-1-carbonyl)piperazin-1-yl)pyrimidin-4-yl)-3,5-dimethyl-1H-pyrazole-4-carbonitrile

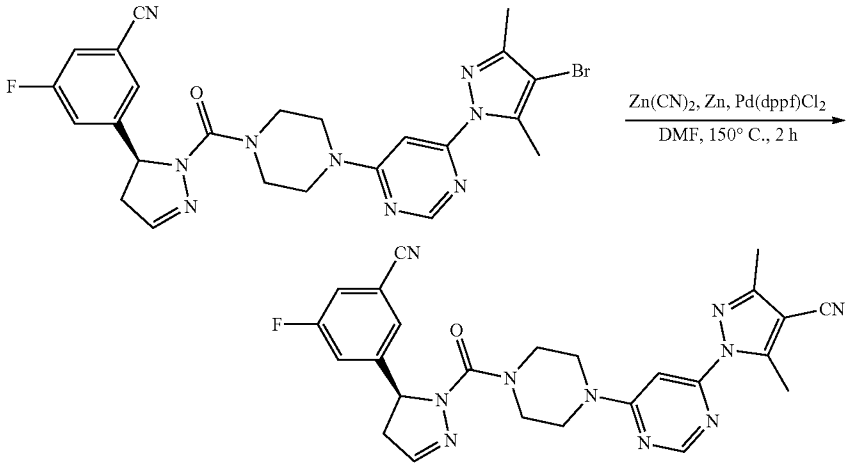

The titled compound 279 was prepared in a yield of 92% as a light yellow solid according to the procedure for 238. Mass (m/z): 499.4[M+H]+. $^1$H NMR (400 MHz, Chloroform-d) δ 8.49 (d, J=0.8 Hz, 1H), 7.41 (t, J=1.5 Hz, 1H), 7.29-7.27 (m, 1H), 7.27-7.24 (m, 1H), 7.07 (d, J=1.0 Hz, 1H), 6.91-6.89 (m, 1H), 5.47-5.28 (m, 1H), 3.94-3.61 (m, 8H), 3.43-3.30 (m, 1H), 2.85 (s, 3H), 2.75-2.65 (m, 1H), 2.40 (s, 3H).

Compound 280: Preparation of (S)-1-(6-(4-(5-(3,5-difluorophenyl)-4,5-dihydro-1H-pyrazole-1-carbonyl)piperazin-1-yl)pyrimidin-4-yl)-3,5-dimethyl-1H-pyrazole-4-carbonitrile

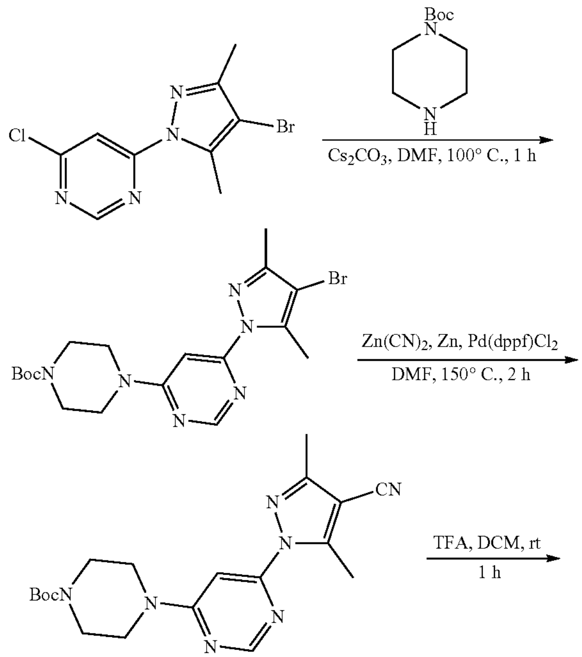

-continued

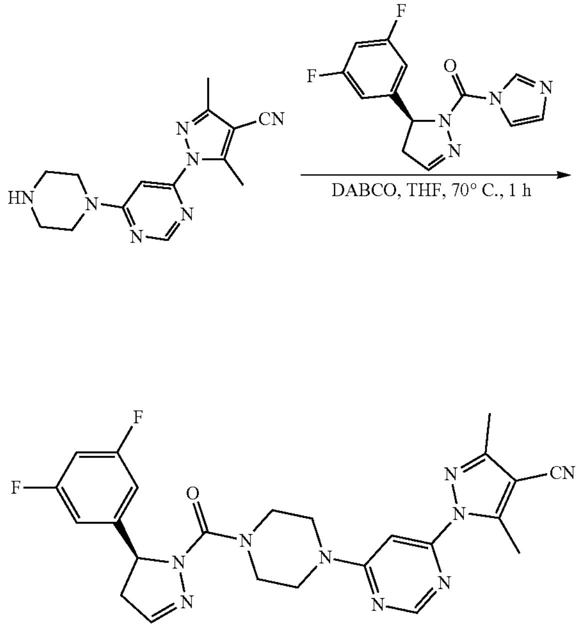

The titled compound 280 was prepared in a yield of 37.5% as a white solid according to the procedure for 152. Mass (m/z): 492.3[M+H]+. $^1$H NMR (400 MHz, Chloroform-d) δ 8.48 (d, J=0.9 Hz, 1H), 7.05 (d, J=1.0 Hz, 1H), 6.86 (t, J=1.7 Hz, 1H), 6.85-6.79 (m, 2H), 6.70 (tt, J=8.8, 2.3 Hz, 1H), 5.33 (dd, J=11.8, 9.8 Hz, 1H), 3.91-3.77 (m, 4H), 3.77-3.64 (m, 4H), 3.33 (ddd, J=18.3, 11.7, 1.8 Hz, 1H), 2.84 (s, 3H), 2.70 (ddd, J=18.3, 9.8, 1.6 Hz, 1H), 2.40 (s, 3H).

Compound 281: Preparation of (S)-1-(6-(4-(5-(3,5-difluorophenyl)-4,5-dihydro-1H-pyrazole-1-carbonyl)piperazin-1-yl)pyrimidin-4-yl)-3,5-dimethyl-1H-pyrazole-4-carboxamide

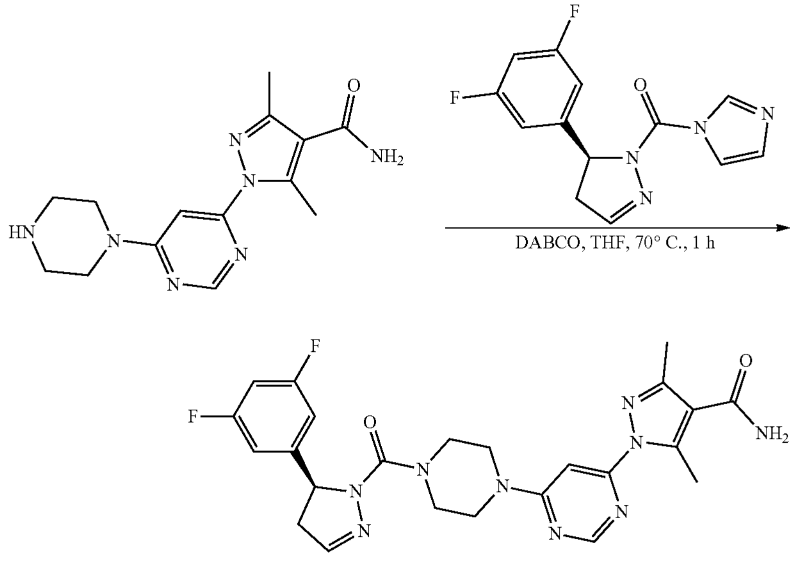

The titled compound 281 was prepared in a yield of 27% as a white solid according to the procedure for 152. Mass (m/z): 510.3[M+H]$^+$. $^1$H NMR (400 MHz, Chloroform-d) δ 8.51 (d, J=1.0 Hz, 1H), 7.00 (d, J=1.0 Hz, 1H), 6.87 (t, J=1.7 Hz, 1H), 6.84-6.79 (m, 2H), 6.70 (tt, J=8.8, 2.3 Hz, 1H), 5.33 (dd, J=11.7, 9.6 Hz, 1H), 4.03-3.78 (m, 4H), 3.76-3.63 (m, 4H), 3.34 (ddd, J=18.4, 11.7, 1.8 Hz, 1H), 2.89 (s, 3H), 2.71 (ddd, J=18.4, 9.6, 1.6 Hz, 1H), 2.48 (s, 3H).

Compound 282: Preparation of (S)-1-(6-(4-(5-(3-cyano-5-fluorophenyl)-4,5-dihydro-1H-pyrazole-1-carbonyl)piperazin-1-yl)pyrimidin-4-yl)-3,5-dimethyl-1H-pyrazole-4-carboxamide

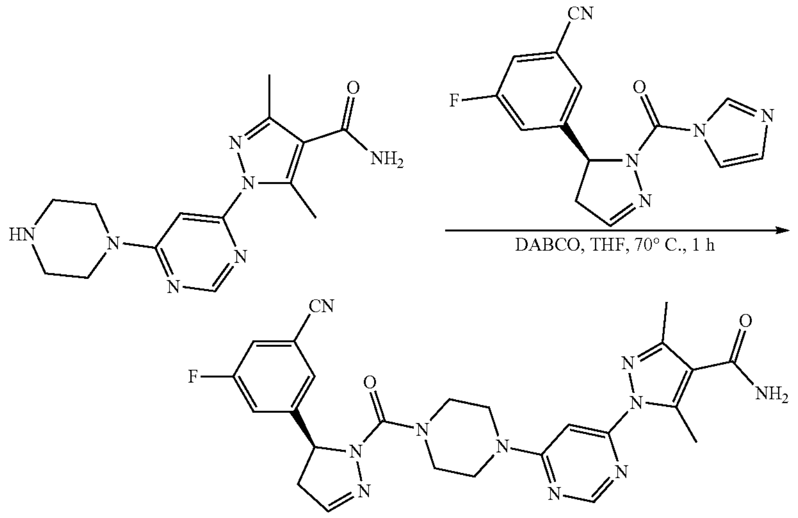

The titled compound 282 was prepared in a yield of 33% as a white solid according to the procedure for 152. Mass (m/z): 517.3[M+H]$^+$. $^1$H NMR (400 MHz, Chloroform-d) δ 8.51 (d, J=0.9 Hz, 1H), 7.41 (t, J=1.5 Hz, 1H), 7.30-7.27 (m, 1H), 7.27-7.24 (m, 1H), 7.01 (d, J=1.0 Hz, 1H), 6.90 (t, J=1.7 Hz, 1H), 5.36 (dd, J=11.7, 9.9 Hz, 1H), 3.92-3.77 (m, 4H), 3.76-3.64 (m, 4H), 3.37 (ddd, J=18.3, 11.7, 1.8 Hz, 1H), 2.90 (s, 3H), 2.71 (ddd, J=18.3, 9.9, 1.6 Hz, 1H), 2.48 (s, 3H).

Compound 283: Preparation of (S)-1-(2-(4-(5-(5-fluoropyridin-3-yl)-4,5-dihydro-1H-pyrazole-1-carbonyl)piperazin-1-yl)pyrimidin-4-yl)-3,5-dimethyl-1H-pyrazole-4-carbonitrile

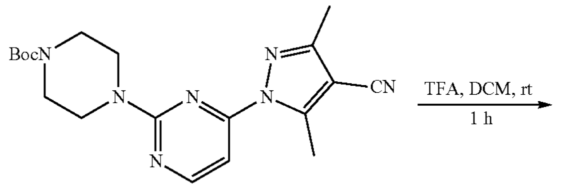

-continued

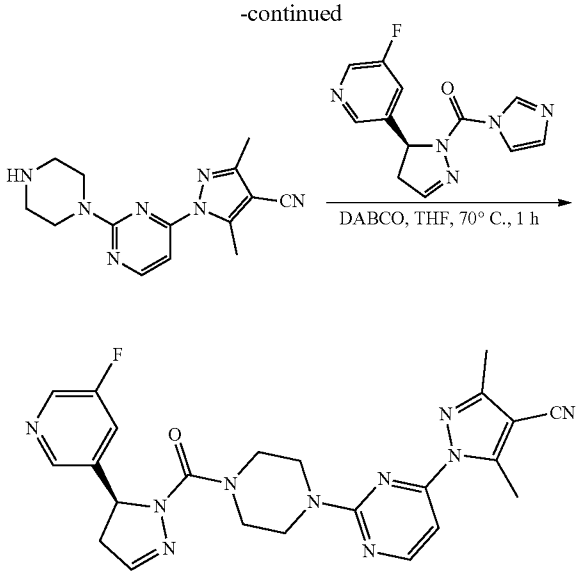

The titled compound 283 was prepared in a yield of 60% as a white solid according to the procedure for 152. Mass (m/z): 475.3[M+H]$^+$. $^1$H NMR (400 MHz, Chloroform-d) δ 8.43 (t, J=1.7 Hz, 1H), 8.42-8.38 (m, 2H), 7.37-7.32 (m, 1H), 7.12 (d, J=5.4 Hz, 1H), 6.93-6.90 (m, 1H), 5.42 (dd, J=11.7, 10.1 Hz, 1H), 3.96-3.86 (m, 2H), 3.84-3.74 (m, 4H), 3.71-3.61 (m, 2H), 3.38 (ddd, J=18.2, 11.7, 1.8 Hz, 1H), 2.85 (s, 3H), 2.76 (ddd, J=18.2, 10.1, 1.6 Hz, 1H), 2.40 (s, 3H).

Compound 284: Preparation of (S)-1-(6-(4-(5-(5-fluoropyridin-3-yl)-4,5-dihydro-1H-pyrazole-1-carbonyl)piperazin-1-yl)pyrimidin-4-yl)-3,5-dimethyl-1H-pyrazole-4-carboxamide

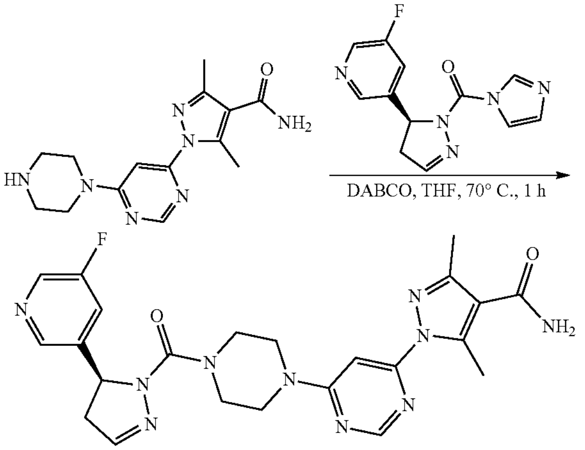

The titled compound 284 was prepared in a yield of 35% as a light green solid according to the procedure for 152. Mass (m/z): 493.3[M+H]$^+$. $^1$H NMR (400 MHz, Chloroform-d) δ 8.54-8.51 (m, 2H), 8.47-8.44 (m, 1H), 7.61-7.56 (m, 1H), 7.02-7.00 (m, 1H), 6.96-6.93 (m, 1H), 5.44 (dd, J=11.6, 10.0 Hz, 1H), 3.92-3.64 (m, 8H), 3.42 (ddd, J=18.3, 11.7, 1.9 Hz, 1H), 2.89 (s, 3H), 2.78 (ddd, J=18.3, 10.0, 1.6 Hz, 1H), 2.48 (s, 3H).

Compound 285: Preparation of (S)-1-(2-(4-(5-(5-fluoropyridin-3-yl)-4,5-dihydro-1H-pyrazole-1-carbonyl)piperazin-1-yl)pyrimidin-4-yl)-3,5-dimethyl-1H-pyrazole-4-carboxamide

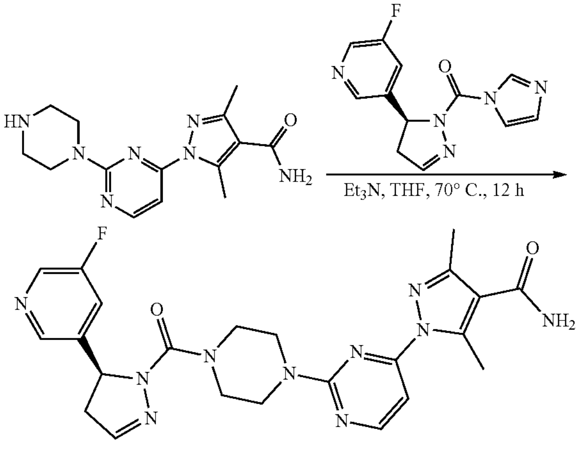

The titled compound 285 was prepared in a yield of 15% as a light yellow solid according to the procedure for 144. Mass (m/z): 493.3[M+H]$^+$. $^1$H NMR (400 MHz, Chloroform-d) δ 8.53 (s, 1H), 8.46 (s, 1H), 8.43 (d, J=5.8 Hz, 1H), 7.61 (d, J=8.3 Hz, 1H), 7.24 (d, J=5.8 Hz, 1H), 7.17 (s, 2H), 6.97-6.94 (m, 1H), 5.50-5.40 (m, 1H), 4.00-3.89 (m, 2H), 3.89-3.76 (m, 4H), 3.75-3.64 (m, 2H), 3.42 (ddd, J=18.3, 11.6, 1.8 Hz, 1H), 2.93 (s, 3H), 2.78 (ddd, J=18.3, 10.0, 1.6 Hz, 1H), 2.48 (s, 3H).

Compound 286: Preparation of (S)-1-(6-(4-(5-(5-fluoropyridin-3-yl)-4,5-dihydro-1H-pyrazole-1-carbonyl)piperazin-1-yl)pyrimidin-4-yl)-3,5-dimethyl-1H-pyrazole-4-carbonitrile

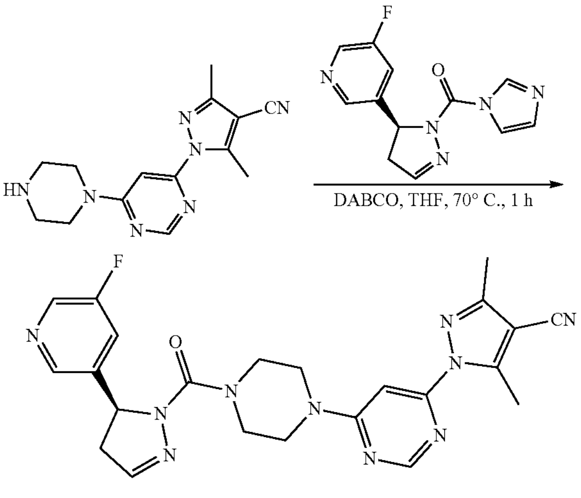

The titled compound 286 was prepared in a yield of 53% as a white solid according to the procedure for 152. Mass (m/z): 475.3[M+H]$^+$. $^1$H NMR (400 MHz, Chloroform-d) δ 8.48-8.46 (m, 1H), 8.43 (t, J=1.7 Hz, 1H), 8.39 (d, J=2.7 Hz, 1H), 7.36-7.31 (m, 1H), 7.06-7.03 (m, 1H), 6.91 (t, J=1.7 Hz, 1H), 5.40 (dd, J=11.7, 9.9 Hz, 1H), 3.89-3.76 (m, 4H), 3.75-3.63 (m, 4H), 3.38 (ddd, J=18.3, 11.7, 1.8 Hz, 1H), 2.84 (s, 3H), 2.76 (ddd, J=18.3, 10.0, 1.6 Hz, 1H), 2.40 (s, 3H).

Compound 287: Preparation of (S)-(4-(4-(4-chloro-3,5-dimethyl-1H-pyrazol-1-yl)pyrimidin-2-yl)piperazin-1-yl)(5-(5-fluoropyridin-3-yl)-4,5-dihydro-1H-pyrazol-1-yl)methanone

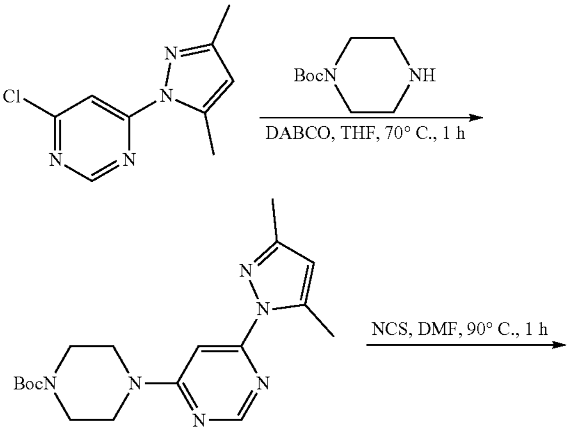

-continued

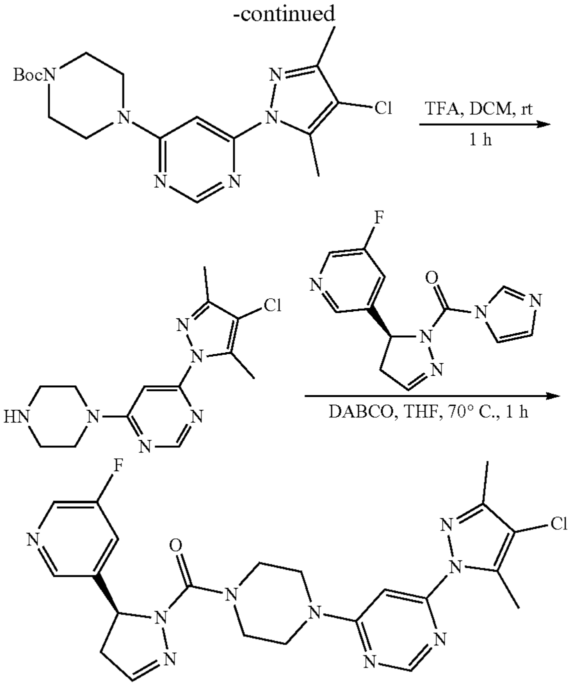

The titled compound 287 was prepared in a yield of 27% as a white solid according to the procedure for 152. Mass (m/z): 484.2[M+H]$^+$. $^1$H NMR (400 MHz, Chloroform-d) δ 8.44 (s, 1H), 8.40 (s, 2H), 7.41-7.36 (m, 1H), 6.92-6.87 (m, 1H), 6.02 (s, 1H), 5.41 (dd, J=11.6, 10.2 Hz, 1H), 3.94-3.83 (m, 2H), 3.82-3.70 (m, 4H), 3.67-3.56 (m, 2H), 3.38 (ddd, J=18.3, 11.7, 1.9 Hz, 1H), 2.75 (ddd, J=18.2, 10.1, 1.6 Hz, 1H), 2.37 (s, 3H), 2.30 (s, 3H).

Compound 288: Preparation of (S)-3-(1-(4-(4-(4-chloro-3,5-dimethyl-1H-pyrazol-1-yl)pyrimidin-2-yl)piperazine-1-carbonyl)-4,5-dihydro-1H-pyrazol-5-yl)-5-fluorobenzonitrile

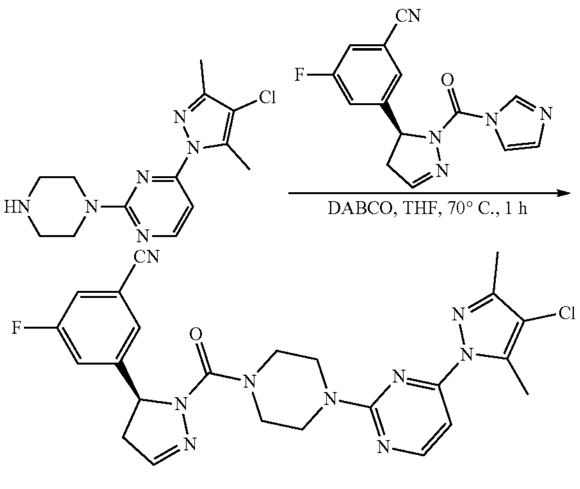

The titled compound 288 was prepared in a yield of 26% as a white solid according to the procedure for 152. Mass (m/z): 508.3[M+H]$^+$. $^1$H NMR (400 MHz, Chloroform-d) δ 8.40 (s, 1H), 7.43-7.39 (m, 1H), 7.30-7.23 (m, 2H), 6.91-6.86 (m, 1H), 6.02 (s, 1H), 5.36 (dd, J=11.7, 10.0 Hz, 1H), 3.95-3.84 (m, 2H), 3.83-3.68 (m, 4H), 3.67-3.57 (m, 2H), 3.35 (ddd, J=18.3, 11.7, 1.8 Hz, 1H), 2.69 (ddd, J=18.3, 10.0, 1.6 Hz, 1H), 2.37 (s, 3H), 2.31 (s, 3H).

Compound 289: Preparation of (S)-3-(1-(4-(6-(4-chloro-3,5-dimethyl-1H-pyrazol-1-yl)pyrimidin-4-yl)piperazine-1-carbonyl)-4,5-dihydro-1H-pyrazol-5-yl)-5-fluorobenzonitrile

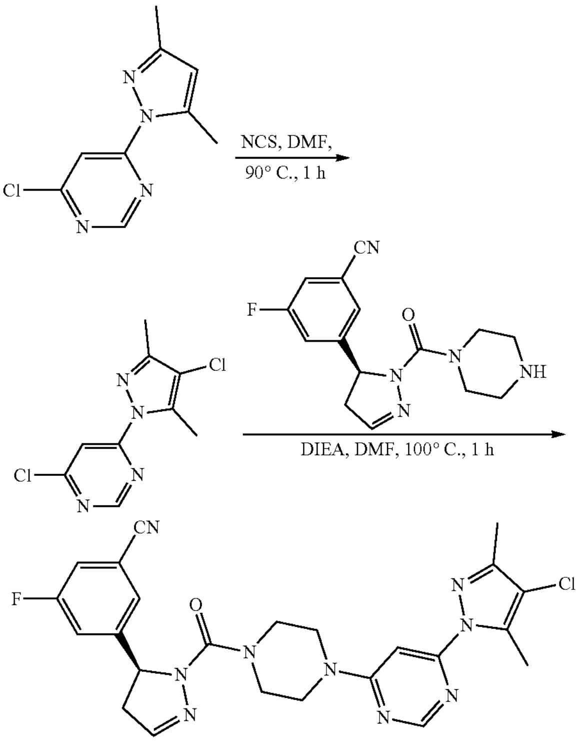

The titled compound 289 was prepared in a yield of 43% as a white solid according to the procedure for 144. Mass (m/z): 508.3[M+H]$^+$. $^1$H NMR (400 MHz, Chloroform-d) δ 8.45 (d, J=0.9 Hz, 1H), 7.41 (t, J=1.5 Hz, 1H), 7.31-7.21 (m, 2H), 7.02 (d, J=1.0 Hz, 1H), 6.89 (t, J=1.7 Hz, 1H), 5.36 (dd, J=11.7, 9.9 Hz, 1H), 3.89-3.75 (m, 4H), 3.75-3.61 (m, 4H), 3.36 (ddd, J=18.3, 11.7, 1.8 Hz, 1H), 2.76-2.66 (m, 1H), 2.67 (s, 3H), 2.28 (s, 3H).

Compound 290: Preparation of (S)-(4-(6-(4-chloro-3,5-dimethyl-1H-pyrazol-1-yl)pyrimidin-4-yl)piperazin-1-yl)(5-(5-fluoropyridin-3-yl)-4,5-dihydro-1H-pyrazol-1-yl)methanone

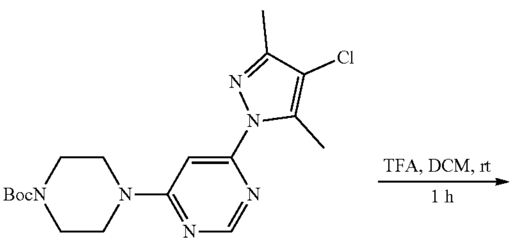

-continued

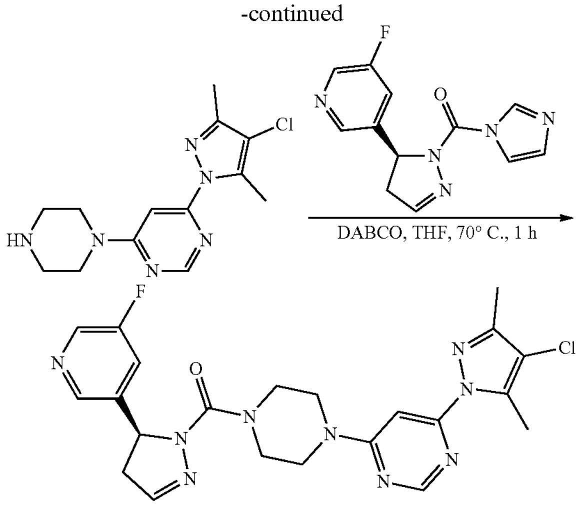

The titled compound 290 was prepared in a yield of 52% as a brown solid according to the procedure for 152. Mass (m/z): 484.3 $[M+H]^+$. $^1H$ NMR (400 MHz, Chloroform-d) δ 8.48-8.43 (m, 2H), 8.42-8.39 (m, 1H), 7.41 (d, J=8.8 Hz, 1H), 7.02 (s, 1H), 6.91 (s, 1H), 5.46-5.37 (m, 1H), 3.90-3.75 (m, 4H), 3.74-3.61 (m, 4H), 3.44-3.33 (m, 1H), 2.82-2.71 (m, 1H), 2.67 (s, 3H), 2.29 (s, 3H).

Compound 291: Preparation of (4-(4-(3,5-dimethyl-1H-1,2,4-triazol-1-yl)-5-fluoropyrimidin-2-yl)piperazin-1-yl)(5-(2-methylthiazol-5-yl)-4,5-dihydro-1H-pyrazol-1-yl)methanone

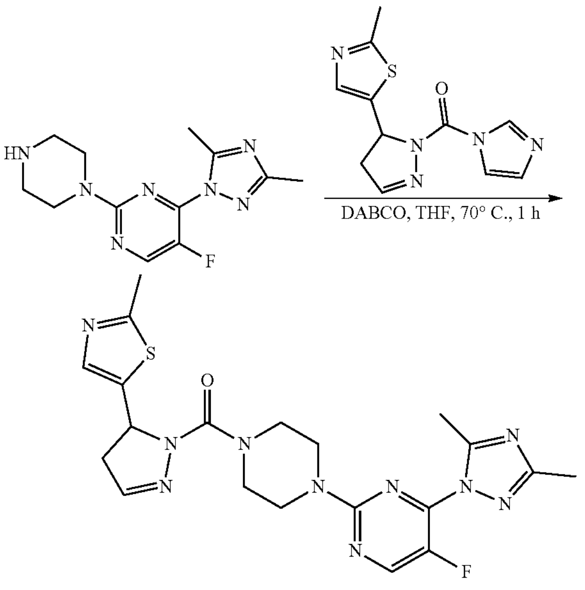

The titled compound 291 was prepared in a yield of 26% as a white solid according to the procedure for 152. Mass (m/z): 471.3 $[M+H]^+$. $^1H$ NMR (400 MHz, DMSO-$d_6$) δ 8.70 (d, J=3.1 Hz, 1H), 7.54-7.52 (m, 1H), 7.18-7.12 (m, 1H), 5.52-5.43 (m, 1H), 3.82-3.72 (m, 2H), 3.71-3.58 (m, 4H), 3.56-3.45 (m, 2H), 3.43-3.33 (m, 1H), 2.82 (ddd, J=18.3, 9.9, 1.7 Hz, 1H), 2.61 (s, 3H), 2.58 (s, 3H), 2.29 (s, 3H).

Compound 292: Preparation of (4-(2-(1,4-dimethyl-1H-pyrazol-5-yl)-5-fluoropyridin-4-yl)piperazin-1-yl)(5-(2-methylthiazol-5-yl)-4,5-dihydro-1H-pyrazol-1-yl)methanone

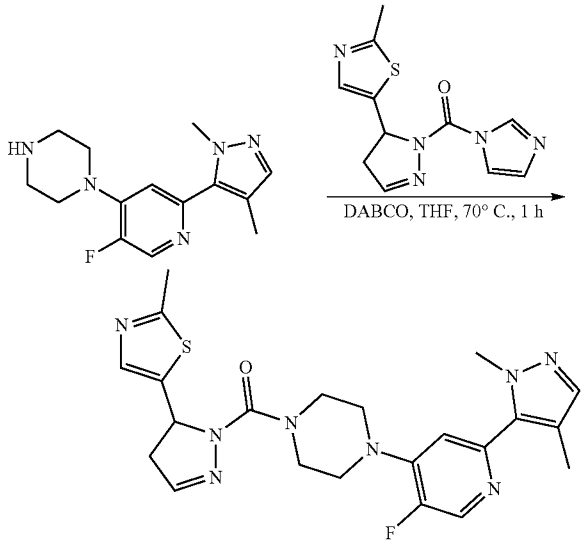

The titled compound 292 was prepared in a yield of 32% as an yellow solid according to the procedure for 152. Mass (m/z): 469.3 $[M+H]^+$. $^1H$ NMR (400 MHz, DMSO-$d_6$) δ 8.56 (d, J=6.6 Hz, 1H), 7.56-7.54 (m, 1H), 7.37 (s, 1H), 7.18 (d, J=7.8 Hz, 1H), 7.15-7.12 (m, 1H), 5.48 (dd, J=11.3, 9.7 Hz, 1H), 3.82 (s, 3H), 3.76-3.66 (m, 2H), 3.62-3.45 (m, 6H), 3.38 (ddd, J=18.4, 11.4, 1.9 Hz, 1H), 2.83 (ddd, J=18.3, 9.7, 1.6 Hz, 1H), 2.59 (s, 3H), 2.05 (s, 3H).

Compound 293: Preparation of (4-(2-(1,4-dimethyl-1H-pyrazol-5-yl)-5-fluoropyridin-4-yl)piperazin-1-yl)(5-(thiazol-5-yl)-4,5-dihydro-1H-pyrazol-1-yl) methanone

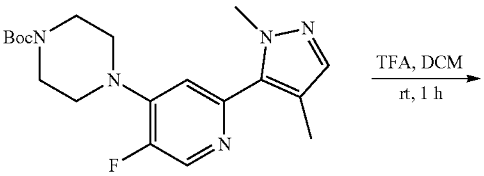

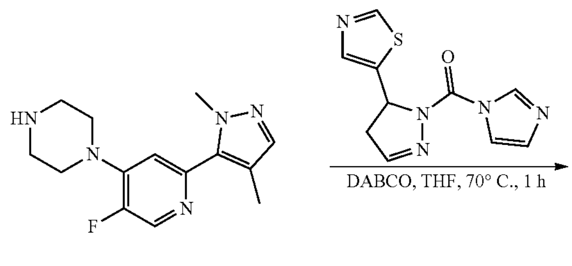

-continued

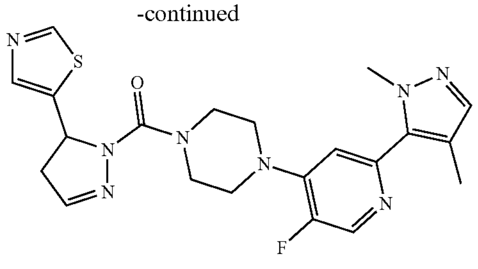

The titled compound 293 was prepared in a yield of 39% as a white solid according to the procedure for 152. Mass (m/z): 455.2 $[M+H]^+$. $^1H$ NMR (400 MHz, DMSO-$d_6$) δ 8.99-8.98 (m, 1H), 8.42 (d, J=5.5 Hz, 1H), 7.85-7.84 (m, 1H), 7.32-7.30 (m, 1H), 7.16 (t, J=1.6 Hz, 1H), 7.04 (d, J=7.6 Hz, 1H), 3.48-3.25 (m, 3H), 5.67-5.53 (m, 1H), 3.83 (s, 3H), 3.76-3.66 (m, 2H), 3.63-3.53 (m, 2H), 3.47-3.26 (m, 5H), 2.85 (ddd, J=18.3, 9.8, 1.6 Hz, 1H), 2.06 (s, 3H).

Compound 294: Preparation of (4-(2-(1,4-dimethyl-1H-pyrazol-5-yl)-5-fluoropyridin-4-yl)piperazin-1-yl)(5-(thiazol-2-yl)-4,5-dihydro-1H-pyrazol-1-yl) methanone

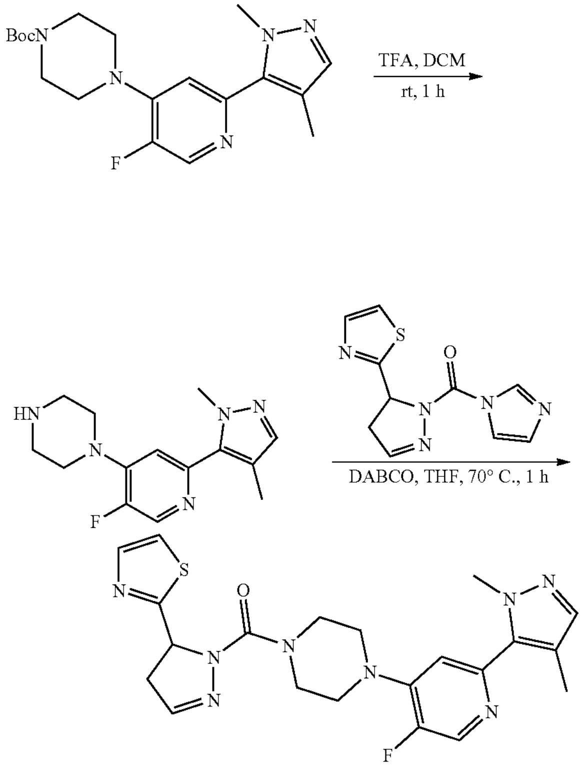

The titled compound 294 was prepared in a yield of 52% as a white solid according to the procedure for 152. Mass (m/z): 455.2 $[M+H]^+$. $^1H$ NMR (400 MHz, DMSO-$d_6$) δ 8.42 (d, J=5.5 Hz, 1H), 7.75 (d, J=3.3 Hz, 1H), 7.65 (d, J=3.2 Hz, 1H), 7.31 (s, 1H), 7.20-7.13 (m, 1H), 7.05 (d, J=7.6 Hz, 1H), 5.64 (dd, J=11.8, 8.9 Hz, 1H), 3.83 (s, 3H), 3.80-3.71 (m, 2H), 3.67-3.57 (m, 2H), 3.50-3.28 (m, 5H), 3.06 (ddd, J=18.5, 8.9, 1.6 Hz, 1H), 2.06 (s, 3H).

Compound 295: Preparation of (4-(6-(1,4-dimethyl-1H-pyrazol-5-yl)-3-fluoropyridin-2-yl)piperazin-1-yl)(5-(pyridin-3-yl)-4,5-dihydro-1H-pyrazol-1-yl) methanone

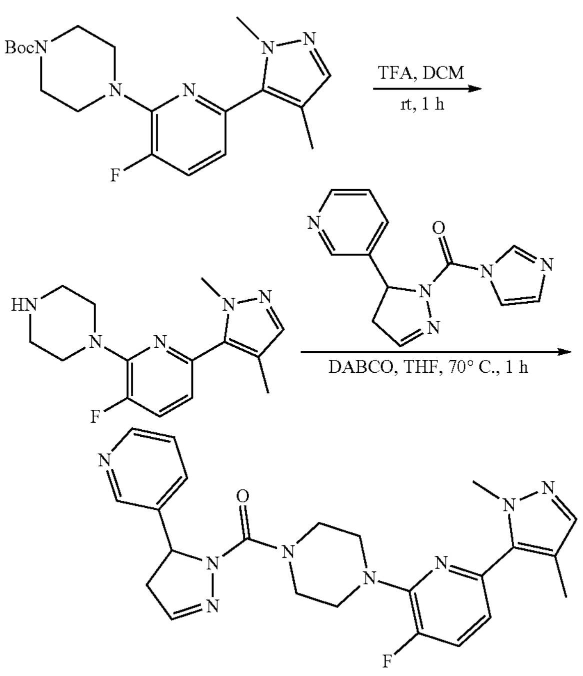

The titled compound 295 was prepared in a yield of 24% as a white solid according to the procedure for 152. Mass (m/z): 449.3 $[M+H]^+$. $^1H$ NMR (400 MHz, Chloroform-d) δ 8.62 (d, J=2.3 Hz, 1H), 8.53 (dd, J=4.9, 1.6 Hz, 1H), 7.68 (dt, J=7.9, 2.0 Hz, 1H), 7.34-7.28 (m, 3H), 6.91-6.85 (m, 2H), 5.39 (dd, J=11.7, 10.2 Hz, 1H), 3.97 (s, 3H), 3.88-3.79 (m, 2H), 3.71-3.64 (m, 2H), 3.62-3.47 (m, 4H), 3.36 (ddd, J=18.2, 11.8, 1.8 Hz, 1H), 2.75 (ddd, J=18.2, 10.1, 1.6 Hz, 1H), 2.13-2.11 (m, 3H).

Compound 296: Preparation of (4-(6-(1,4-dimethyl-1H-pyrazol-5-yl)-3-fluoropyridin-2-yl)piperazin yl) (5-(thiazol-5-yl)-4,5-dihydro-1H-pyrazol-1-yl) methanone

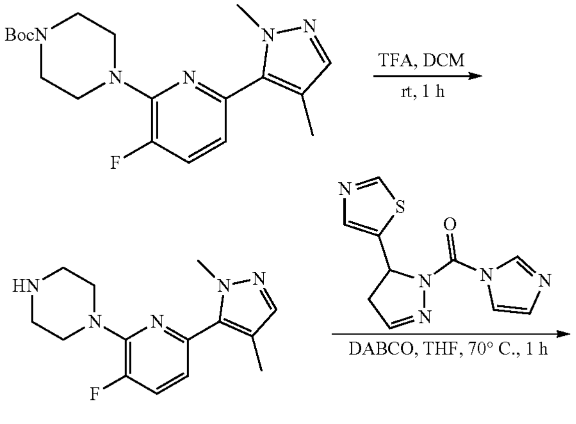

-continued

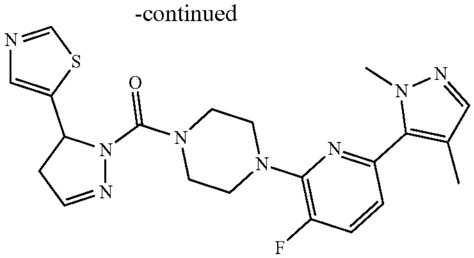

The titled compound 296 was prepared in a yield of 26% as a white solid according to the procedure for 152. Mass (m/z): 455.3 $[M+H]^+$. $^1$H NMR (400 MHz, Chloroform-d) δ 8.73 (s, 1H), 7.86-7.84 (m, 1H), 7.41-7.38 (m, 1H), 7.34 (dd, J=12.7, 8.0 Hz, 1H), 6.92-6.86 (m, 2H), 5.72 (dd, J=11.3, 10.3 Hz, 1H), 4.02 (s, 3H), 3.87-3.79 (m, 2H), 3.71-3.63 (m, 2H), 3.63-3.47 (m, 4H), 3.38 (ddd, J=18.2, 11.5, 1.8 Hz, 1H), 2.89 (ddd, J=18.1, 10.2, 1.6 Hz, 1H), 2.15-2.12 (m, 3H).

Compound 297: Preparation of (4-(6-(1,4-dimethyl-1H-pyrazol-5-yl)-3-fluoropyridin-2-yl)piperazin-1-yl)(5-(pyridin-2-yl)-4,5-dihydro-1H-pyrazol-1-yl) methanone

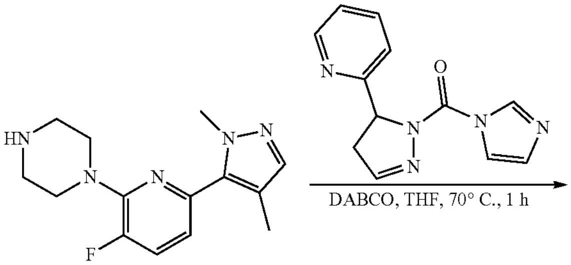

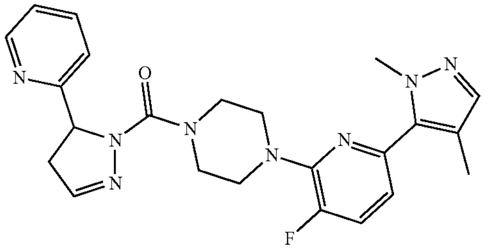

The titled compound 297 was prepared in a yield of 11% as a white solid according to the procedure for 152. Mass (m/z): 449.3 $[M+H]^+$. $^1$H NMR (400 MHz, Chloroform-d) δ 8.66 (d, J=5.2 Hz, 1H), 8.02-7.88 (m, 1H), 7.62-7.54 (m, 1H), 7.49-7.40 (m, 1H), 7.37-7.29 (m, 2H), 6.93 (t, J=1.6 Hz, 1H), 6.87 (dd, J=8.0, 2.7 Hz, 1H), 5.70-5.58 (m, 1H), 3.99 (s, 3H), 3.91-3.80 (m, 2H), 3.76-3.66 (m, 2H), 3.63-3.37 (m, 5H), 3.14 (ddd, J=18.1, 10.1, 1.6 Hz, 1H), 2.15-2.11 (m, 3H).

Compound 298: Preparation of (4-(6-(1,4-dimethyl-1H-pyrazol-5-yl)-3-fluoropyridin-2-yl)piperazin-1-yl)(5-(2-methylthiazol-4-yl)-4,5-dihydro-1H-pyrazol-1-yl)methanone

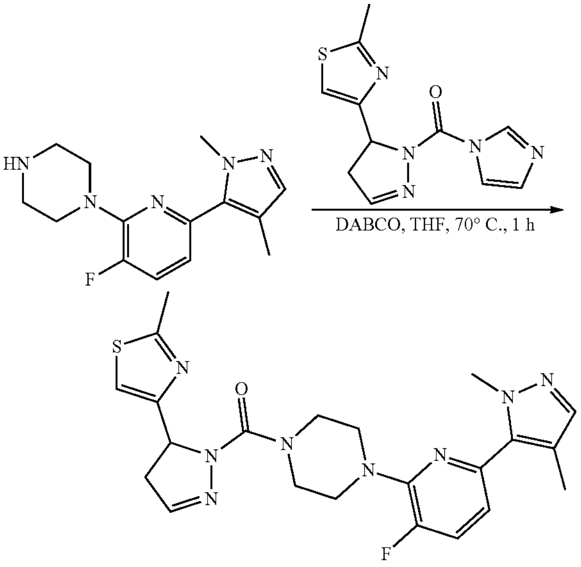

The titled compound 298 was prepared in a yield of 6% as a white solid according to the procedure for 152. Mass (m/z): 469.3 $[M+H]^+$. $^1$H NMR (400 MHz, Chloroform-d) δ 7.43 (s, 1H), 7.35 (dd, J=12.6, 8.0 Hz, 1H), 7.09 (s, 1H), 6.92-6.85 (m, 2H), 5.52 (dd, J=11.5, 10.1 Hz, 1H), 4.06 (s, 3H), 3.89-3.79 (m, 2H), 3.72-3.63 (m, 2H), 3.63-3.55 (m, 2H), 3.55-3.46 (m, 2H), 3.30-3.12 (m, 2H), 2.72 (s, 3H), 2.16-2.14 (m, 3H).

Compound 299: Preparation of (4-(6-(1,4-dimethyl-1H-pyrazol-5-yl)-3-fluoropyridin-2-yl)piperazin yl)(5-(4-methylthiazol-2-yl)-4,5-dihydro-1H-pyrazol-1-yl)methanone

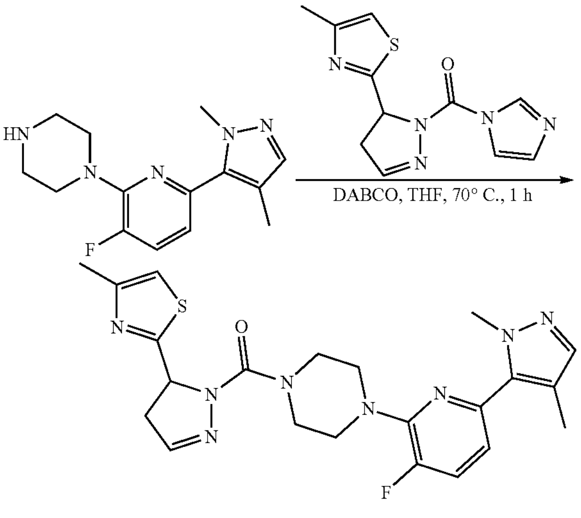

The titled compound 299 was prepared in a yield of 20% as a light yellow solid according to the procedure for 152. Mass (m/z): 469.3 $[M+H]^+$. $^1H$ NMR (400 MHz, Chloroform-d) δ 7.38-7.31 (m, 2H), 6.90-6.86 (m, 2H), 6.82-6.80 (m, 1H), 5.77 (dd, J=11.8, 9.4 Hz, 1H), 4.00 (s, 3H), 3.93-3.84 (m, 2H), 3.77-3.68 (m, 2H), 3.65-3.48 (m, 4H), 3.37 (ddd, J=18.3, 11.8, 1.8 Hz, 1H), 3.20 (ddd, J=18.4, 9.4, 1.7 Hz, 1H), 2.44-2.40 (m, 3H), 2.13 (s, 3H).

Compound 300: Preparation of (5-(3-chloropyridin-2-yl)-4,5-dihydro-1H-pyrazol-1-yl)(4-(6-(1,4-dimethyl-1H-pyrazol-5-yl)-3-fluoropyridin-2-yl)piperazin-1-yl)methanone

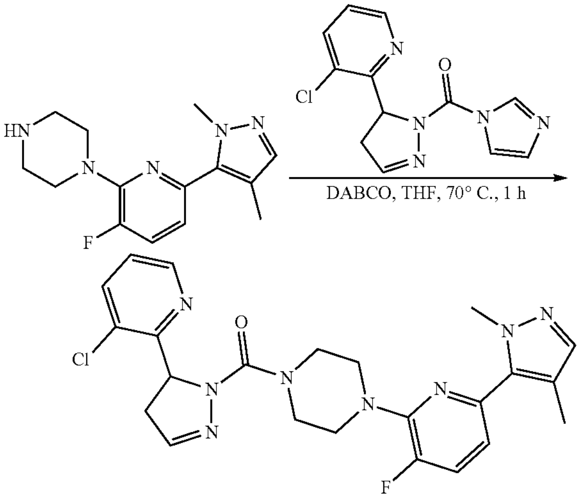

The titled compound 300 was prepared in a yield of 22% as a white solid according to the procedure for 152. Mass (m/z): 483.3 $[M+H]^+$. $^1H$ NMR (400 MHz, Chloroform-d) δ 8.47 (dd, J=4.6, 1.5 Hz, 1H), 7.68 (dd, J=8.1, 1.5 Hz, 1H), 7.36 (s, 1H), 7.32 (dd, J=12.7, 8.0 Hz, 1H), 7.16 (dd, J=8.1, 4.7 Hz, 1H), 6.89-6.83 (m, 2H), 5.92 (dd, J=11.8, 9.0 Hz, 1H), 4.00 (s, 3H), 3.89-3.78 (m, 2H), 3.77-3.66 (m, 2H), 3.61-3.47 (m, 4H), 3.32 (ddd, J=18.0, 11.9, 1.8 Hz, 1H), 2.87 (ddd, J=18.0, 9.0, 1.7 Hz, 1H), 2.13 (s, 3H).

Compound 301: (S)-(5-(3,5-difluorophenyl)-4,5-dihydro-1H-pyrazol-1-yl)(4-(2-(1,4-dimethyl-1H-pyrazol-5-yl)-5-fluoropyrimidin-4-yl)piperazin-1-yl)methanone

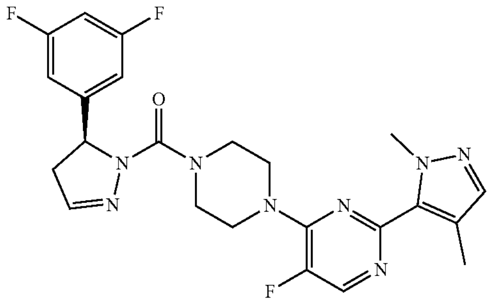 [SMILES: Cc1cnn(C)c1-c1ncc(F)c(N2CCN(C(=O)N3N=CC[C@H]3c3cc(F)cc(F)c3)CC2)n1]

The titled compound 301 was prepared in a yield of 11.2% as a white solid according to the procedure for 152. LC-MS (m/z) 485.1 $(M+H^+)$. $^1H$ NMR (400 MHz, Chloroform-d) δ 8.20 (d, J=6.3 Hz, 1H), 7.33 (d, J=0.7 Hz, 1H), 6.89-6.86 (m, 1H), 6.82 (dt, J=6.6, 2.2 Hz, 2H), 6.75-6.66 (m, 1H), 5.34 (dd, J=11.7, 9.8 Hz, 1H), 4.15 (s, 3H), 3.95-3.78 (m, 6H), 3.73-3.64 (m, 2H), 3.34 (ddd, J=18.4, 11.7, 1.8 Hz, 1H), 2.70 (ddd, J=18.3, 9.8, 1.6 Hz, 1H), 2.29 (s, 3H).

Compound 302: (S)-(4-(5-fluoro-4-(5-(trifluoromethyl)-1H-pyrazol-1-yl)pyrimidin-2-yl)piperazin-1-yl)(5-(3-fluorophenyl)-4,5-dihydro-1H-pyrazol-1-yl)methanone

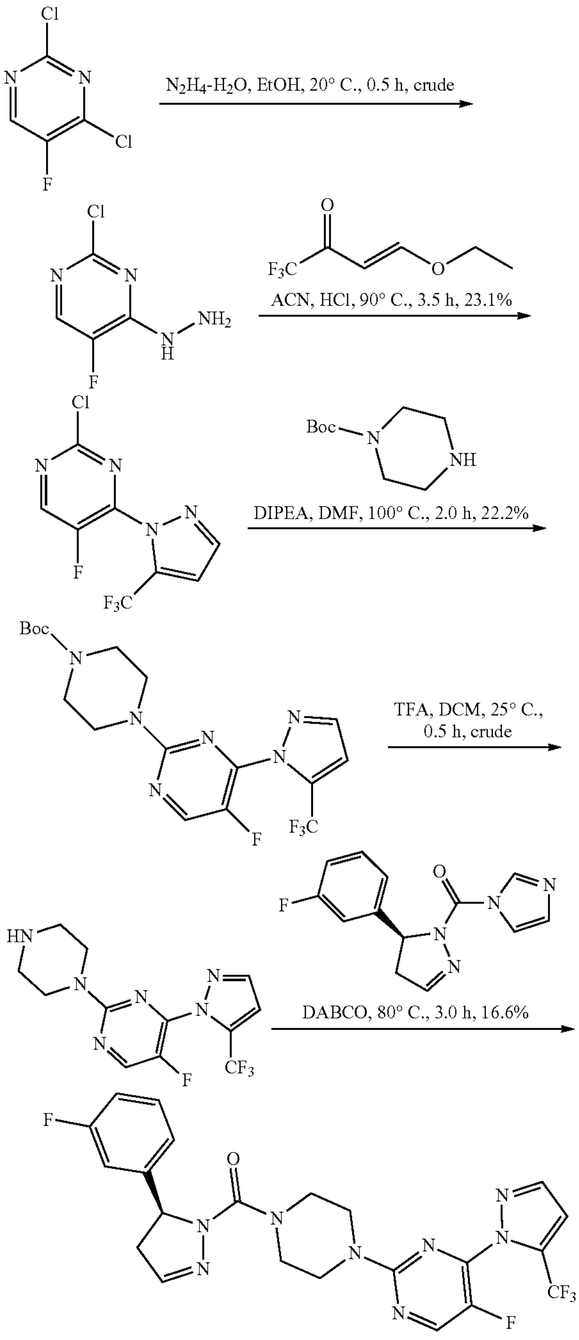

Step 1: 2,4-dichloro-5-fluoropyrimidine (10.0 g, 59.88 mmol), and $N_2H_4$—$H_2O$ (2.63 g, 65.86 mmol, 80 w %) were in EtOH (200 mL) under $N_2$ and the whole reaction mixture was stirred at 20° C. for 1.0 hours. The mixture was concentrated in vacuo to give 2-chloro-5-fluoro-4-hydrazineylpyrimidine (12.0 g, crude) as a white solid and used into next step reaction without purification. MS (m/z): 163.1 $[M+H]^+$.

Step 2: 2-chloro-5-fluoro-4-hydrazineylpyrimidine (3.2 g, crude), and (E)-4-ethoxy-1,1,1-trifluorobut-3-en-2-one (3.4 g, 20.12 mmol) were in ACN (5 mL) under $N_2$ and the whole reaction mixture was stirred at 90° C. for 3.0 hours. To this was added concentrated hydrochloric acid (5 mL) dropwise and the whole reaction mixture was stirred at 90° C. for another 0.5 hours. The mixture was extracted with EA, washed with brine, dried ($Na_2SO_4$), and concentrated in vacuo. Purification by silica gel chromatography to give 2-chloro-5-fluoro-4-(5-(trifluoromethyl)-1H-pyrazol-1-yl) pyrimidine (1.2 g, 23.1%) as a yellow solid. MS (m/z): 267.1 $[M+H]^+$.

Step 3: 2-chloro-5-fluoro-4-(5-(trifluoromethyl)-1H-pyrazol-1-yl)pyrimidine (1.2 g, 4.49 mmol), tert-butyl piperazine-1-carboxylate (1.67 g, 8.98 mmol), and DIEPA (1.16 g, 9.00 mmol) were in DMF (10 mL) under $N_2$ and the whole reaction mixture was stirred at 100° C. for 2.0 hours. The mixture was extracted with EA, washed with brine, dried ($Na_2SO_4$), and concentrated in vacuo. Purification by silica gel chromatography to give tert-butyl 4-(5-fluoro-4-(5-(trifluoromethyl)-1H-pyrazol-1-yl)pyrimidin-2-yl)piperazine-1-carboxylate (400 mg, 22.2%) as a yellow solid. MS (m/z): 417.2 $[M+H]^+$.

Step 4: tert-butyl 4-(5-fluoro-4-(5-(trifluoromethyl)-1H-pyrazol-1-yl)pyrimidin-2-yl)piperazine-1-carboxylate (300 mg, 0.72 mmol), TFA (2 mL) were in DCM (5 mL) under $N_2$ and the whole reaction mixture was stirred at 25° C. for 0.5 hours. The mixture was concentrated in vacuo to give 5-fluoro-2-(piperazin-1-yl)-4-(5-(trifluoromethyl)-1H-pyrazol-1-yl)pyrimidine (500 mg, crude) as a brown oil and used into next step reaction without purification. MS (m/z): 317.2 $[M+H]^+$.

Step 3: 5-fluoro-2-(piperazin-1-yl)-4-(5-(trifluoromethyl)-1H-pyrazol-1-yl)pyrimidine (100 mg, crude), (S)-(5-(3-fluorophenyl)-4,5-dihydro-1H-pyrazol-1-yl)(1H-imidazol-1-yl)methanone (40 mg, 0.14 mmol), and DABCO (200 mg, 1.78 mmol) were in THF (10 mL) under $N_2$. The solvent was removed under vacuum and the reaction mixture was stand at 80° C. for 3.0 h. The mixture was extracted with EA, washed with brine, dried ($Na_2SO_4$), and concentrated in vacuo. Purification by silica gel chromatography to give compound 302 (13.0 mg, 16.6%) as a white solid. LC-MS (m/z): 507.5 $[M+H]^+$. $^1$H NMR (400 MHz, CHLOROFORM-D) δ 8.46 (dd, J=2.8, 1.0 Hz, 1H), 8.40 (d, J=3.5 Hz, 1H), 7.34-7.27 (m, 1H), 7.09 (dt, J=7.7, 1.4 Hz, 1H), 7.01-6.91 (m, 2H), 6.86 (t, J=1.7 Hz, 1H), 6.75 (d, J=2.7 Hz, 1H), 5.37 (dd, J=11.7, 9.7 Hz, 1H), 3.95-3.85 (m, 2H), 3.84-3.73 (m, 4H), 3.69-3.60 (m, 2H), 3.33 (ddd, J=18.3, 11.8, 1.8 Hz, 1H), 2.73 (ddd, J=18.3, 9.8, 1.6 Hz, 1H).

Compound 303: (S)-(5-(3,5-difluorophenyl)-4,5-dihydro-1H-pyrazol-1-yl)(4-(5-fluoro-4-(3-(trifluoromethyl)-1H-pyrazol-1-yl)pyrimidin-2-yl)piperazin-1-yl)methanone

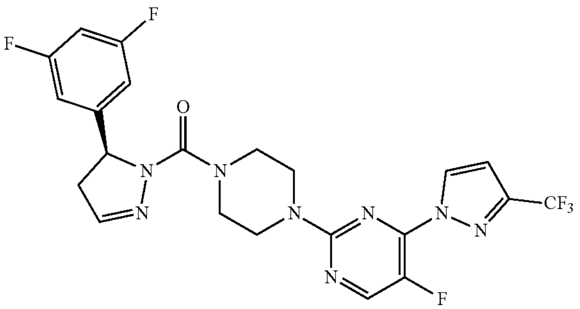 [SMILES: O=C(N1CCN(c2ncc(F)c(-n3ccc(C(F)(F)F)n3)n2)CC1)N1N=CC[C@H]1c1cc(F)cc(F)c1]

The titled compound 303 was prepared from (S)-(5-(3,5-difluorophenyl)-4,5-dihydro-1H-pyrazol-1-yl)(1H-imidazol-1-yl)methanone in a yield of 21.6% as a light yellow solid according to the procedure outlined for compound 147. Mass (m/z): 525.2$[M+H]^+$. $^1$H NMR (400 MHz, Chloroform-d) δ 8.46 (dt, J=2.4, 1.2 Hz, 1H), 8.40 (d, J=3.6 Hz, 1H), 6.87 (t, J=1.6 Hz, 1H), 6.85-6.80 (m, 2H), 6.75 (d, J=2.8 Hz, 1H), 6.70 (tt, J=8.8, 2.4 Hz, 1H), 5.34 (dd, J=11.6, 9.6 Hz, 1H), 3.97-3.86 (m, 2H), 3.85-3.74 (m, 4H), 3.70-3.60 (m, 2H), 3.33 (ddd, J=18.4, 11.6, 1.6 Hz, 1H), 2.70 (ddd, J=18.4, 9.6, 1.6 Hz, 1H).

Compound 304: (S)-3-fluoro-5-(1-(4-(5-fluoro-4-(5-(trifluoromethyl)-1H-pyrazol-1-yl)pyrimidin-2-yl) piperazine-1-carbonyl)-4,5-dihydro-1H-pyrazol-5-yl)benzonitrile

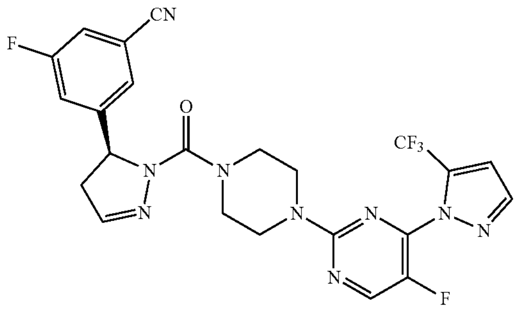 [SMILES: N#Cc1cc(F)cc([C@@H]2CC=NN2C(=O)N2CCN(c3ncc(F)c(-n4nccc4C(F)(F)F)n3)CC2)c1]

The titled compound 304 was prepared in a yield of 6.7% as a white solid according to the procedure outlined for compound 147. Mass (m/z): 532.3$[M+H]^+$. $^1$H NMR (400 MHz, Chloroform-d) δ 8.46 (dt, J=2.8, 1.2 Hz, 1H), 8.40 (d, J=3.6 Hz, 1H), 7.42 (t, J=1.6 Hz, 1H), 7.30-7.24 (m, 2H), 6.90 (t, J=1.6 Hz, 1H), 6.75 (d, J=2.8 Hz, 1H), 5.37 (dd, J=11.6, 10.0 Hz, 1H), 3.96-3.85 (m, 2H), 3.85-3.75 (m, 4H), 3.75-3.60 (m, 2H), 3.37 (ddd, J=18.4, 11.6, 1.6 Hz, 1H), 2.70 (ddd, J=18.4, 10.0, 1.6 Hz, 1H).

Compound 305: (S)-(5-(3,5-difluorophenyl)-4,5-dihydro-1H-pyrazol-1-yl)(4-(5-fluoro-4-(3-(trifluoromethyl)-1H-1,2,4-triazol-1-yl)pyrimidin-2-yl)piperazin-1-yl)methanone

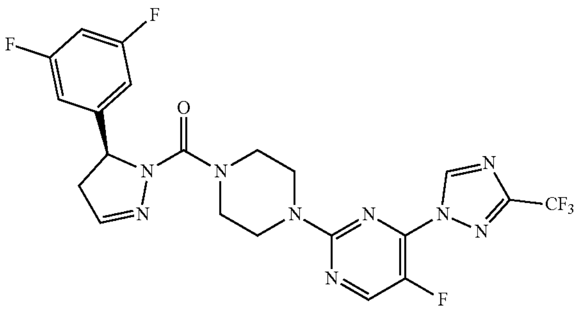

The titled compound 305 was prepared in a yield of 8% as a white solid according to the procedure outlined for compound 147. Mass (m/z): 536.3[M+H]$^+$. $^1$H NMR (400 MHz, Chloroform-d) δ 9.06 (d, J=0.8 Hz, 1H), 8.48 (d, J=2.8 Hz, 1H), 6.88-6.79 (m, 3H), 6.70 (tt, J=8.8, 2.4 Hz, 1H), 5.38-5.24 (m, 1H), 4.00-3.88 (m, 2H), 3.88-3.74 (m, 4H), 3.74-3.58 (m, 2H), 3.42-3.27 (m, 1H), 2.78-2.64 (m, 1H).

Compound 306: (S)-3-fluoro-5-(1-(4-(5-fluoro-4-(3-(trifluoromethyl)-1H-1,2,4-triazol-1-yl)pyrimidin-2-yl)piperazine-1-carbonyl)-4,5-dihydro-1H-pyrazol-5-yl)benzonitrile

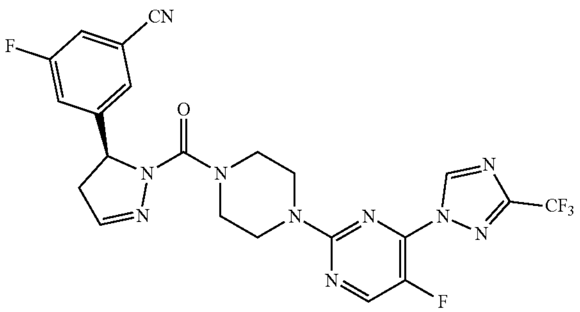 [SMILES: N#Cc1cc(F)cc([C@@H]2CC=NN2C(=O)N2CCN(c3ncc(F)c(-n4cnc(C(F)(F)F)n4)n3)CC2)c1]

The titled compound 306 was prepared in a yield of 6.0% as a white solid according to the procedure outlined for compound 147. $^1$H NMR (400 MHz, Chloroform-d) δ 9.06 (d, J=1.2 Hz, 1H), 8.48 (d, J=2.8 Hz, 1H), 7.41 (t, J=1.6 Hz, 1H), 7.30-7.24 (m, 2H), 6.93-6.87 (m, 1H), 5.37 (dd, J=11.6, 10.0 Hz, 1H), 3.98-3.87 (m, 2H), 3.86-3.75 (m, 4H), 3.71-3.62 (m, 2H), 3.37 (ddd, J=18.4, 11.6, 1.6 Hz, 1H), 2.70 (ddd, J=18.4, 10.0, 1.6 Hz, 1H).

Compound 307: (S)-(4-(5-fluoro-4-(5-(trifluoromethyl)-1H-pyrazol-1-yl)pyrimidin-2-yl)piperazin-1-yl)(5-phenyl-4,5-dihydro-1H-pyrazol-1-yl)methanone

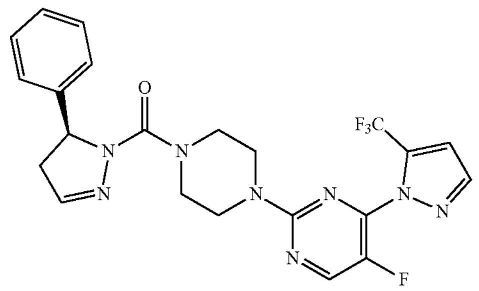 [SMILES: O=C(N1CCN(c2ncc(F)c(-n3nccc3C(F)(F)F)n2)CC1)N1N=CC[C@H]1c1ccccc1]

The titled compound 307 was prepared in a yield of 16% as a white solid according to the procedure outlined for compound 302. LC-MS (m/z): 489.5 [M+H]$^+$. $^1$H NMR (400 MHz, CHLOROFORM-D) δ 8.45 (dt, J=2.9, 1.0 Hz, 1H), 8.39 (d, J=3.5 Hz, 1H), 7.37-7.27 (m, 5H), 6.86 (t, J=1.7 Hz, 1H), 6.74 (d, J=2.7 Hz, 1H), 5.38 (dd, J=11.8, 9.7 Hz, 1H), 3.94-3.84 (m, 2H), 3.82-3.72 (m, 4H), 3.68-3.59 (m, 2H), 3.33 (ddd, J=18.3, 11.8, 1.8 Hz, 1H), 2.76 (ddd, J=18.3, 9.7, 1.6 Hz, 1H).

Compound 308: (S)-(4-(5-fluoro-4-(5-(trifluoromethyl)-1H-pyrazol-1-yl)pyrimidin-2-yl)piperazin-1-yl)(5-(5-fluoropyridin-3-yl)-4,5-dihydro-1H-pyrazol-1-yl)methanone

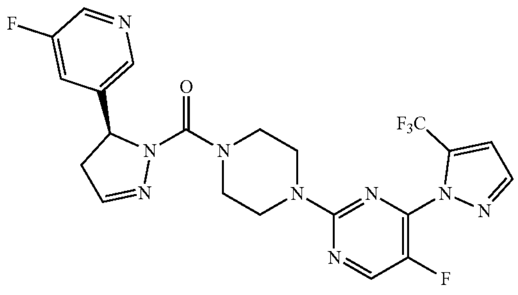 [SMILES: O=C(N1CCN(c2ncc(F)c(-n3nccc3C(F)(F)F)n2)CC1)N1N=CC[C@H]1c1cncc(F)c1]

The titled compound 308 was prepared in a yield of 20% as a white solid according to the procedure outlined for compound 302. LC-MS (m/z): 508.3 [M+H]$^+$. $^1$H NMR (400 MHz, CHLOROFORM-D) δ 8.47-8.44 (m, 2H), 8.41-8.36 (m, 2H), 7.39 (dt, J=8.8, 2.3 Hz, 1H), 6.91 (t, J=1.7 Hz, 1H), 6.75 (d, J=2.8 Hz, 1H), 5.46-5.38 (m, 1H), 3.97-3.87 (m, 2H), 3.85-3.74 (m, 4H), 3.69-3.62 (m, 2H), 3.39 (ddd, J=18.2, 11.7, 1.8 Hz, 1H), 2.76 (ddd, J=18.3, 10.1, 1.6 Hz, 1H).

Compound 309: (S)-(4-(5-fluoro-4-(3-methyl-1H-1,2,4-triazol-1-yl)pyrimidin-2-yl)piperazin-1-yl)(5-phenyl-4,5-dihydro-1H-pyrazol-1-yl)methanone

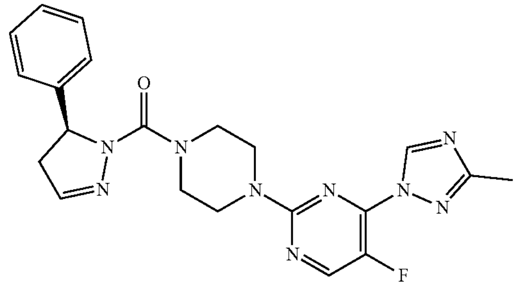 [SMILES: Cc1ncn(-c2nc(N3CCN(C(=O)N4N=CC[C@H]4c4ccccc4)CC3)ncc2F)n1]

The titled compound 309 was prepared in a yield of 12.6% as a light-yellow solid according to the procedure outlined for compound 147. LC-MS (m/z): 436.4 $[M+H]^+$. $^1H$ NMR (400 MHz, CHLOROFORM-D) δ 8.92 (s, 1H), 8.39 (d, J=3.3 Hz, 1H), 7.37-7.27 (m, 5H), 6.86 (t, J=1.7 Hz, 1H), 5.37 (dd, J=11.8, 9.7 Hz, 1H), 3.94-3.84 (m, 2H), 3.82-3.70 (m, 4H), 3.69-3.58 (m, 2H), 3.33 (ddd, J=18.3, 11.8, 1.8 Hz, 1H), 2.76 (ddd, J=18.3, 10.1, 1.6 Hz, 1H), 2.54 (s, 3H).

Compound 310: (S)-(4-(5-fluoro-4-(3-methyl-1H-1,2,4-triazol-1-yl)pyrimidin-2-yl)piperazin-1-yl)(5-(3-fluorophenyl)-4,5-dihydro-1H-pyrazol-1-yl)methanone

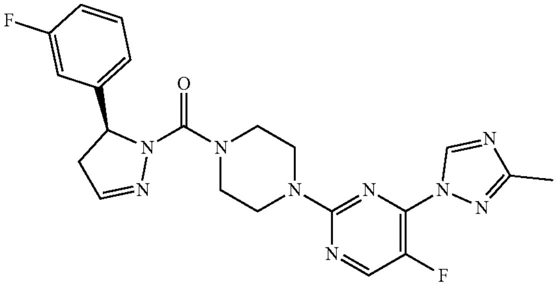 [SMILES: Cc1ncn(-c2nc(N3CCN(C(=O)N4N=CC[C@H]4c4cccc(F)c4)CC3)ncc2F)n1]

The titled compound 310 was prepared in a yield of 23.4% as a white solid according to the procedure outlined for compound 147. LC-MS (m/z): 454.5 $[M+H]^+$. $^1H$ NMR (400 MHz, CHLOROFORM-D) δ 8.92 (s, 1H), 8.40 (d, J=3.3 Hz, 1H), 7.35-7.28 (m, 1H), 7.09 (dt, J=7.8, 1.3 Hz, 1H), 7.02-6.91 (m, 2H), 6.87-6.83 (m, 1H), 5.36 (dd, J=11.7, 9.8 Hz, 1H), 3.96-3.85 (m, 2H), 3.84-3.71 (m, 4H), 3.69-3.58 (m, 2H), 3.33 (ddd, J=18.3, 11.8, 1.8 Hz, 1H), 2.77-2.69 (m, 1H), 2.54 (s, 3H).

Compound 311: (S)-(4-(5-fluoro-4-(3-methyl-1H-1,2,4-triazol-1-yl)pyrimidin-2-yl)piperazin-1-yl)(5-(5-fluoropyridin-3-yl)-4,5-dihydro-1H-pyrazol-1-yl)methanone

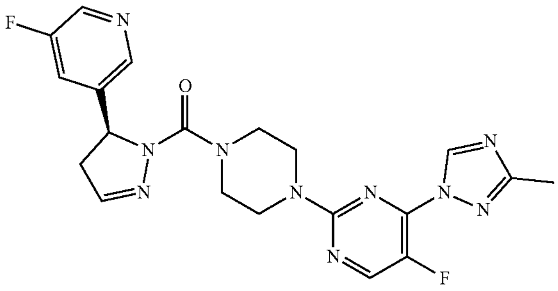 [SMILES: Cc1ncn(-c2nc(N3CCN(C(=O)N4N=CC[C@H]4c4cncc(F)c4)CC3)ncc2F)n1]

The titled compound 311 was prepared in a yield of 20% as a white solid according to the procedure outlined for compound 147. LC-MS (m/z): 455.5 $[M+H]^+$. $^1H$ NMR (400 MHz, CHLOROFORM-D) δ 8.91 (s, 1H), 8.46-8.41 (m, 1H), 8.39 (dd, J=4.2, 1.5 Hz, 2H), 7.36 (dt, J=9.4, 2.1 Hz, 1H), 6.94-6.86 (m, 1H), 5.41 (dd, J=11.7, 10.1 Hz, 1H), 3.95-3.83 (m, 2H), 3.84-3.72 (m, 4H), 3.70-3.58 (m, 2H), 3.37 (ddd, J=18.3, 11.8, 1.8 Hz, 1H), 2.82-2.70 (m, 1H), 2.53 (s, 3H).

Compound 312: (S)-(4-(5-fluoro-4-(3-(trifluoromethyl)-1H-1,2,4-triazol-1-yl)pyrimidin-2-yl)piperazin yl)(5-phenyl-4,5-dihydro-1H-pyrazol-1-yl)methanone

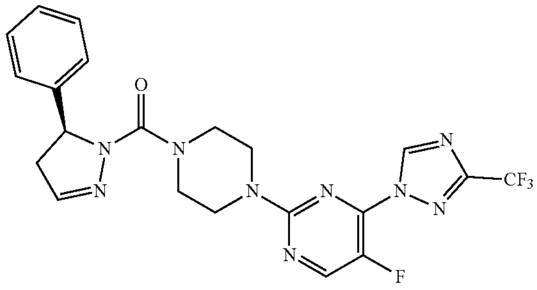 [SMILES: O=C(N1CCN(c2ncc(F)c(-n3cnc(C(F)(F)F)n3)n2)CC1)N1N=CC[C@H]1c1ccccc1]

The titled compound 312 was prepared in a yield of 4.2% as a light-yellow solid according to the procedure outlined for compound 147. LC-MS (m/z): 490.4 $[M+H]^+$. $^1H$ NMR (400 MHz, CHLOROFORM-D) δ 9.06 (d, J=0.9 Hz, 1H), 8.47 (d, J=2.9 Hz, 1H), 7.37-7.27 (m, 5H), 6.89-6.84 (m, 1H), 5.38 (dd, J=11.8, 9.7 Hz, 1H), 3.95-3.85 (m, 2H), 3.83-3.73 (m, 4H), 3.70-3.58 (m, 2H), 3.34 (ddd, J=18.4, 11.9, 1.8 Hz, 1H), 2.77 (ddd, J=18.3, 9.6, 1.6 Hz, 1H).

Compound 313: (S)-(4-(5-fluoro-4-(3-(trifluoromethyl)-1H-1,2,4-triazol-1-yl)pyrimidin-2-yl)piperazin-1-yl)(5-(3-fluorophenyl)-4,5-dihydro-1H-pyrazol-1-yl)methanone

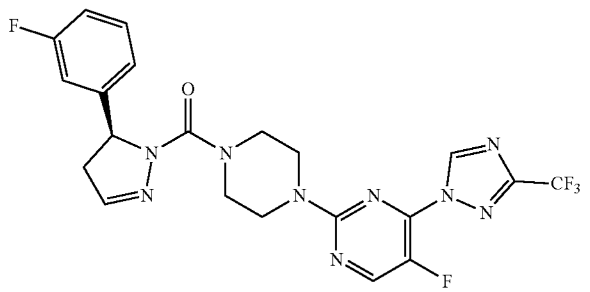 [SMILES: O=C(N1CCN(c2ncc(F)c(-n3cnc(C(F)(F)F)n3)n2)CC1)N1N=CC[C@H]1c1cccc(F)c1]

The titled compound 313 was prepared in a yield of 6.8% as a white solid according to the procedure outlined for compound 147. LC-MS (m/z): 508.5 $[M+H]^+$. $^1H$ NMR (400 MHz, CHLOROFORM-D) δ 9.06 (d, J=0.9 Hz, 1H), 8.48 (d, J=2.9 Hz, 1H), 7.30 (td, J=8.0, 5.9 Hz, 1H), 7.12-7.06 (m, 1H), 7.02-6.92 (m, 2H), 6.87 (t, J=1.7 Hz, 1H), 5.37 (dd, J=11.7, 9.7 Hz, 1H), 3.99-3.88 (m, 2H), 3.85-3.74 (m, 4H), 3.72-3.62 (m, 2H), 3.34 (ddd, J=18.3, 11.8, 1.8 Hz, 1H), 2.73 (ddd, J=18.3, 9.7, 1.6 Hz, 1H).

Compound 314: (S)-(4-(5-fluoro-4-(3-(trifluoromethyl)-1H-1,2,4-triazol-1-yl)pyrimidin-2-yl)piperazin-1-yl)(5-(5-fluoropyridin-3-yl)-4,5-dihydro-1H-pyrazol-1-yl)methanone

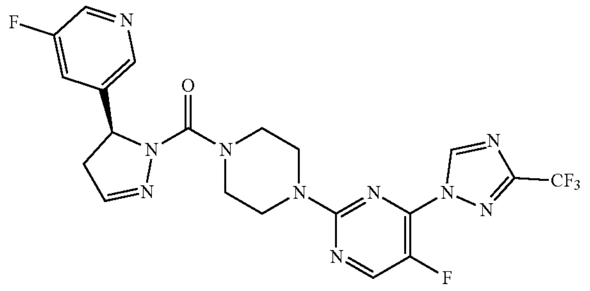 [SMILES: O=C(N1CCN(c2ncc(F)c(-n3cnc(C(F)(F)F)n3)n2)CC1)N1N=CC[C@H]1c1cncc(F)c1]

The titled compound 314 was prepared in a yield of 12.7% as a white solid according to the procedure outlined for compound 147. LC-MS (m/z): 508.4 $[M+H]^+$. $^1H$ NMR (400 MHz, CHLOROFORM-D) δ 9.06 (d, J=1.0 Hz, 1H), 8.53-8.31 (d, J=2.9 Hz, 3H), 7.36 (d, J=8.9 Hz, 1H), 6.91 (t, J=1.7 Hz, 1H), 5.42 (dd, J=11.7, 10.0 Hz, 1H), 3.99-3.87 (m, 2H), 3.87-3.73 (m, 4H), 3.73-3.60 (m, 2H), 3.39 (ddd, J=18.3, 11.7, 1.8 Hz, 1H), 2.76 (ddd, J=18.3, 10.0, 1.6 Hz, 1H).

Compound 315: (S)-(5-(3,5-difluorophenyl)-4,5-dihydro-1H-pyrazol-1-yl)(4-(5-fluoro-4-(5-(trifluoromethyl)-1H-pyrazol-1-yl)pyrimidin-2-yl)piperazin-1-yl)methanone

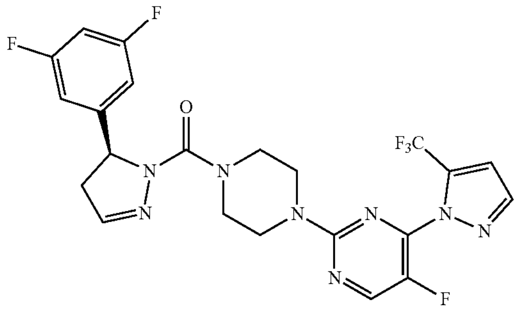 [SMILES: O=C(N1CCN(c2ncc(F)c(-n3nccc3C(F)(F)F)n2)CC1)N1N=CC[C@H]1c1cc(F)cc(F)c1]

The titled compound 315 was prepared from (S)-(5-(3,5-difluorophenyl)-4,5-dihydro-1H-pyrazol-1-yl)(1H-imidazol-1-yl)methanone in a yield of 59.6% as a white solid according to the procedure outlined for compound 302. Mass (m/z): 525.2$[M+H]^+$. $^1H$ NMR (400 MHz, Chloroform-d) δ 8.46 (dt, J=2.8, 1.2 Hz, 1H), 8.40 (d, J=3.6 Hz, 1H), 6.86 (t, J=1.6 Hz, 1H), 6.85-6.79 (m, 2H), 6.75 (d, J=2.8 Hz, 1H), 6.70 (tt, J=8.8, 2.4 Hz, 1H), 5.34 (dd, J=11.6, 9.6 Hz, 1H), 3.97-3.86 (m, 2H), 3.85-3.73 (m, 4H), 3.71-3.60 (m, 2H), 3.33 (ddd, J=18.4, 11.6, 1.6 Hz, 1H), 2.70 (ddd, J=18.4, 9.6, 1.6 Hz, 1H).

Compound 316: 4-(5-fluoro-4-(5-methyl-1,3,4-thiadiazol-2-yl)pyrimidin-2-yl)piperazin-1-yl)(5-(5-methylthiazol-2-yl)-4,5-dihydro-1H-pyrazol-1-yl)methanone

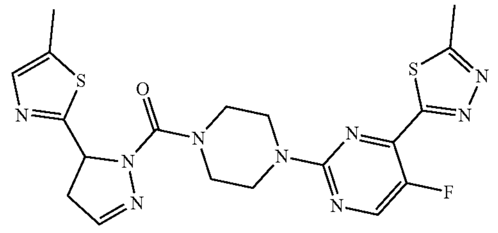 [SMILES: Cc1cnc(C2CC=NN2C(=O)N2CCN(c3ncc(F)c(-c4nnc(C)s4)n3)CC2)s1]

The titled compound 316 was prepared in a yield of 8.0% as a brown yellow solid according to the procedure outlined for compound 174. LC-MS (m/z): 474.5 $[M+H]^+$. $^1H$ NMR (400 MHz, Chloroform-d) δ 8.43 (d, J=2.4 Hz, 1H), 7.39 (s, 1H), 6.90 (d, J=1.7 Hz, 1H), 5.72 (t, J=10.5 Hz, 1H), 3.96-3.85 (m, 2H), 3.80 (d, J=9.4 Hz, 4H), 3.71-3.62 (m, 2H), 3.38-3.21 (m, 2H), 2.85 (s, 3H), 2.42 (d, J=1.0 Hz, 3H).

Compound 317: (4-(5-fluoro-4-(2-methyl-2H-1,2,3-triazol-4-yl)pyrimidin-2-yl)piperazin-1-yl)(5-(5-methylthiazol-2-yl)-4,5-dihydro-1H-pyrazol-1-yl)methanone

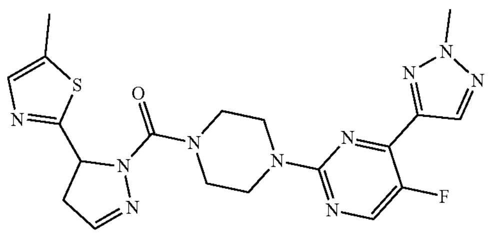 [SMILES: Cc1cnc(C2CC=NN2C(=O)N2CCN(c3ncc(F)c(-c4cnn(C)n4)n3)CC2)s1]

The titled compound 317 was prepared in a yield of 2.9% as a brown yellow solid according to the procedure outlined for compound 174. LC-MS (m/z): 457.5 $[M+H]^+$. $^1H$ NMR (400 MHz, Chloroform-d) δ 8.31 (d, J=2.6 Hz, 1H), 8.15 (d, J=2.0 Hz, 1H), 7.41 (s, 1H), 6.90 (s, 1H), 5.29 (s, 1H), 4.31 (s, 3H), 3.93-3.61 (m, 8H), 3.30 (d, J=45.3 Hz, 2H), 2.43 (s, 3H).

Compound 318: (S)-(4-(5-fluoro-4-(1-methyl-1H-1,2,4-triazol-5-yl)pyrimidin-2-yl)piperazin-1-yl)(5-(5-methylthiazol-2-yl)-4,5-dihydro-1H-pyrazol-1-yl)methanone

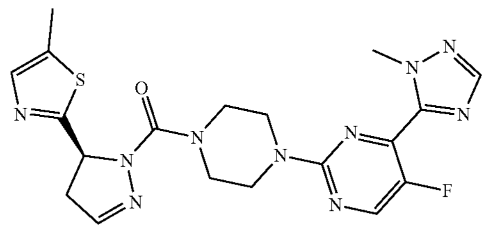 [SMILES: Cc1cnc([C@@H]2CC=NN2C(=O)N2CCN(c3ncc(F)c(-c4ncnn4C)n3)CC2)s1]

The titled compound 318 was prepared in a yield of 44.6% as a yellow solid according to the procedure outlined for compound 143. LC-MS (m/z): 457.5 $[M+H]^+$. $^1H$ NMR (400 MHz, Chloroform-d) δ 8.42 (d, J=2.3 Hz, 1H), 8.06 (s, 1H), 7.40 (s, 1H), 6.90 (d, J=1.7 Hz, 1H), 5.71 (t, J=10.5 Hz, 1H), 4.23 (s, 3H), 3.96-3.61 (m, 8H), 3.41-3.18 (m, 2H), 2.42 (s, 3H).

Compound 319: (S)-1-(5-fluoro-2-(4-(5-(5-methylthiazol-2-yl)-4,5-dihydro-1H-pyrazole-1-carbonyl)piperazin-1-yl)pyrimidin-4-yl)-5-methyl-1H-1,2,4-triazole-3-carbonitrile

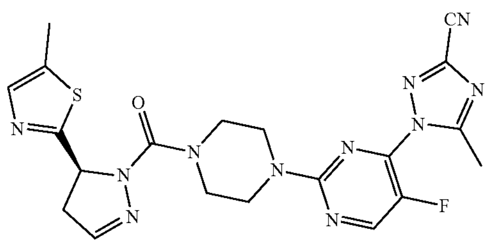 [SMILES: Cc1cnc([C@@H]2CC=NN2C(=O)N2CCN(c3ncc(F)c(-n4nc(C#N)nc4C)n3)CC2)s1]

The titled compound 319 was prepared in a yield of 6.0% as a white solid according to the procedure outlined for compound 144. Mass (m/z): 482.2$[M+H]^+$. $^1H$ NMR (400 MHz, Chloroform-d) δ 8.48 (d, J=2.4 Hz, 1H), 7.41 (s, 1H), 6.91 (s, 1H), 5.79-5.66 (m, 1H), 3.95-3.62 (m, 8H), 3.38-3.31 (m, 2H), 2.74 (s, 3H), 2.44 (s, 3H).

Biological Assays

Compounds 1-319 (denoted as Compound Nos. 1 through 319 in Table 3 and 4) of the disclosure were tested for binding and cellular RIP1 inhibitory activity following the experimental procedures described below.

Materials

Cell line: HT-29 (ATCC® HTB-38™)

Culture medium: McCOY's 5A, Gibco, Cat No. 16600-082

FBS, Gibco, Cat No. 10099-141C

Trypsin: Gibco, Cat No. 25200-056

DMSO: Sigma, Cat No. 67-68-5, 1L

Assay plate: Corning #3903

Compound dilution plate: Corning #3357

Inducers: TNFα, GenScript, Cat No. Z01001-50, SmacM, Cat. No., HY-15989, MedChemExpress (MCE) Z_VAD FMK, TargetMol, T6013

Cell Titer-Glo® Luminescent Cell Viability Assay Kit: Promega, Cat No. G7573

EnVision: PerkinElmer, 2105-0010

Methods

Cell Seeding

1. HT-29 cells were checked every day to make sure that they were healthy and growing as expected. They were subjected to sub-culturing when they were approximately 80% confluent.

2. The culture medium, McCOY's 5A medium (Gibco, Cat No. 16600-082) with 10% fetal bovine serum or FBS (Gibco, Cat No. 10099-141C), was pre-warmed in a 37° C. water bath for at least 30 min.

3. When the cells had reached a desired level of confluency of 80% in a T75 flask, the medium was aspirated, and the cells were washed with warm phosphate buffered saline or PBS two times.

4. 2-3 ml fresh warm trypsin (Gibco, Cat No. 25200-056) solution was added to the washed cells. The flask with the cells was transferred to a 37° C. incubator.

5. After 5 minutes, the side of the flask was tapped, and the flask was examined under a microscope for detachment of the cells to the flask. If necessary, the cells were kept in the incubator for an additional 5-10 minutes, with occasional tapping, until lifting was complete.

6. The trypsin reaction was neutralized by transferring 6-9 ml cell culture medium to sterile 15 ml conical tubes, and by centrifuging the cell culture at 300×g for 7 minutes to pellet the cells (supernatant decanted).

7. The cells were resuspended in fresh cell culture medium and the cell counting was performed using a hemocytometer.

8. 100 μl of the resuspended cell culture medium containing ~5,000 cells were transferred into each well of the sterile 96-well cell culture plate (Corning 3903) and cultured overnight at 37° C. with 5% CO2.

Compound Titration and Treatment

1. All test compounds were dissolved in DMSO (Dimethyl sulfoxide) to create a 20 mM stock.

2. 3 μl of each compound 20 mM stock was mixed with 27 μl DMSO, and the compound solution was further diluted at a titration ratio of 1:3 (20 μl compound solution+40 μl DMSO) till the 10 points end.

3. All culture medium was removed from assay plates filled with HT-29 cell cultures. The cells were then washed with 1 PBS, and resuspended in fresh, FBS-free McCOY's 5A medium containing a cocktail of TNF-α (10 ng/ml), a SMAC mimetic compound (6 μM) and Z-VAD-fluoromethylketone or zVAD-FMK (10 μM) to stimulate the HT-29 cells to increase RIP1 kinase levels and necroptosis.

4. 0.5 μL of the diluted compound solution was added to the corresponding 96-well assay plates.

5. The assay plates were incubated for 20 hours at 37° C. with 5% CO2.

Cell Viability Detection

1. The CellTiter-Glo® Luminescent Cell Viability Assay was employed to detect the ATP levels of viable HT-29 cells.

2. The CellTiter-Glo® buffer and the lyophilized substrate were equilibrated to room temperature prior to use.

3. The CellTiter-Glo® substrate was resuspended with CellTiter-Glo® buffer, then mixed by gently vortexing to obtain a homogeneous solution.

4. 20 μl the enzyme/substrate mixture was transferred by multi-channel pipetting into 96-well assay plates.

5. The assay plates were placed on an orbital shaker and the contents were shaken for 3 minutes to induce cell lysis.

6. The assay plates were incubated at room temperature for 10 minutes to stabilize the luminescent signal.

7. The luminescence signals were read and recorded with EnVision.

8. The geometric mean EC50 values were calculated from 10 points response dose with duplicates. RIP1 inhibitory activity of compounds 1-319 is summarized in Tables 3 and 4. In Tables 3 and 4, activity is provided as follows: +++=0.1 nM≤EC50<100 nM; ++=100 nM≤EC50<1000 nM; +=1000 nM≤EC50<10000 nM.

The invention claimed is:

1. A compound of formula Ia:

Ia

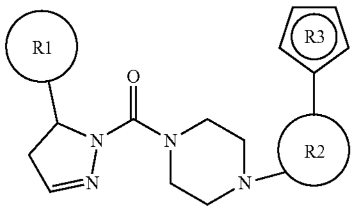

R1 is C6 aryl comprising 0 or 1 N heteroatoms or C5 aryl comprising 1 or 2 N heteroatoms and an O or S heteroatom, wherein the C5 aryl and C6 aryl are optionally substituted with halogen, CN, or C1 to C3 alkyl;

R2 is C6 aryl comprising 0, 1 or 2 N or 3N heteroatoms or C5 aryl comprising 1 or 2 N heteroatoms and an O or S heteroatom, wherein the C5 aryl and C6 aryl are optionally substituted with halogen, CN, C1 to C3 alkoxy, or C1 to C3 alkyl optionally substituted with OH;

R3 is C5 to C8 aryl comprising 1, 2, 3 or 4 N heteroatoms, or 1 or 2 N heteroatoms and an O or S heteroatom, substituted with 0-3 substituents selected from halide, optionally-substituted N, S or O, and optionally-substituted hydrocarbyl;

or a salt, hydrate or stereoisomer thereof.

2. The compound of claim 1 wherein:

the R3 substituents are independently C0-C6: aldehyde, aldimine, alkanoyloxy, alkoxy, alkoxycarbonyl, alkyloxy, alkyl, alkenyl, alkynyl, amine, azo, halogens, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3);

R2 comprises N2, N4 or N2/N4;

R3 comprises N1, N1/N2, N2/N3, N3/N4, N2/N5; N2/N4, S2/N4, N2/S4, S3/N4, N2/S3, N3/O4, N2/N3/S5, N2/N3/O5, N2/N3/N5, N2/N3/N4 or N2/N3/N4/N5; or any combination of the foregoing substituents.

3. The compound, salt, hydrate, or stereoisomer of claim 1, wherein the compound has following structural formula II(1):

II(1)

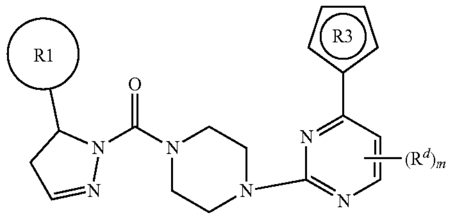

wherein $R^d$ is selected from halogen, CN, C1 to C3 alkoxy, and C1 to C3 alkyl optionally substituted with OH, and wherein m is 0, 1, or 2.

4. The compound, salt, hydrate, or stereoisomer of claim 1, wherein the compound has following structural formula II(2):

II(2)

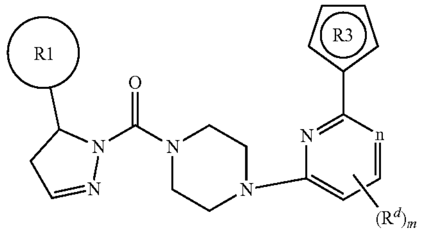

wherein $R^d$ is selected from halogen, CN, C1 to C3 alkoxy, and C1 to C3 alkyl optionally substituted with OH, and wherein m is 0, 1, or 2.

5. The compound, salt, hydrate, or stereoisomer of claim 1, wherein the compound has following structural formula II(3):

II(3)

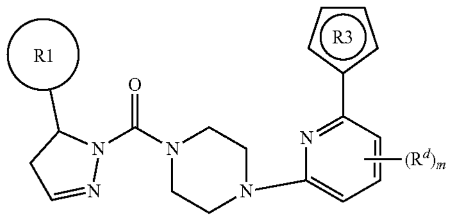

wherein $R^d$ is selected from halogen, CN, C1 to C3 alkoxy, and C1 to C3 alkyl optionally substituted with OH, and wherein m is 0, 1, or 2.

6. The compound, salt, hydrate, or stereoisomer of claim 1, wherein the compound has following structural formula II(4):

II(4)

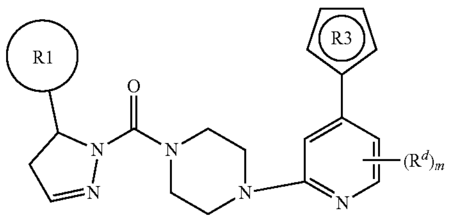

wherein $R^d$ is selected from halogen, CN, C1 to C3 alkoxy, and C1 to C3 alkyl optionally substituted with OH, and wherein m is 0, 1, or 2.

7. The compound, salt, hydrate, or stereoisomer of claim 1, wherein the compound has following structural formula II(5):

II(5)

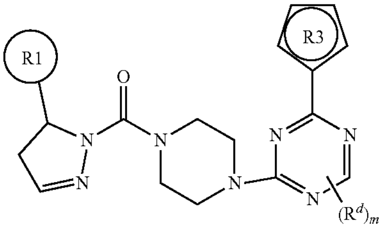

wherein $R^d$ is selected from halogen, CN, C1 to C3 alkoxy, and C1 to C3 alkyl optionally substituted with OH, and wherein m is 0 or 1.

8. The compound, salt, hydrate, or stereoisomer of claim 1, wherein the compound has following structural formula II(6):

II(6)

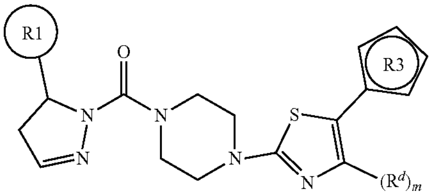

wherein $R^d$ is selected from halogen, CN, C1 to C3 alkoxy, and C1 to C3 alkyl optionally substituted with OH, and wherein m is 0 or 1.

9. The compound, salt, hydrate, or stereoisomer of claim 1, wherein the compound has following structural formula II(7):

II(7)

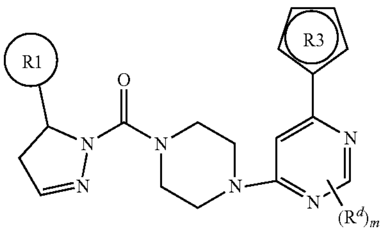

wherein $R^d$ is selected from halogen, CN, C1 to C3 alkoxy, and C1 to C3 alkyl optionally substituted with OH, and wherein m is 0, 1, or 2.

10. The compound, salt, hydrate, or stereoisomer of claim 1, wherein the compound has following structural formula II(8):

II(8)

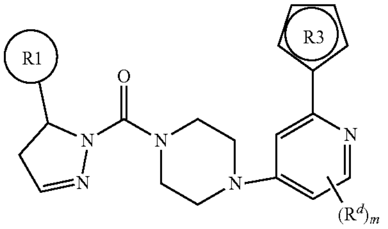

wherein $R^d$ is selected from halogen, CN, C1 to C3 alkoxy, and C1 to C3 alkyl optionally substituted with OH, and wherein m is 0, 1, or 2.

11. The compound, salt, hydrate, or stereoisomer of claim 1, wherein the compound has following structural formula III(1):

III(1)

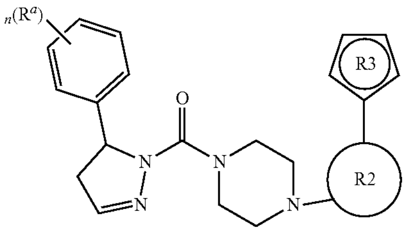

wherein $R^a$ is selected from halogen, CN, and C1 to C3 alkyl, and wherein n is 0, 1, 2, or 3.

12. The compound, salt, hydrate, or stereoisomer of claim 1, wherein the compound has following structural formula III(2):

III(2)

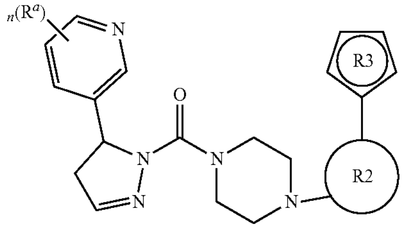

wherein $R^a$ is selected from halogen, CN, and C1 to C3 alkyl, and wherein n is 0, 1, 2, or 3.

13. The compound, salt, hydrate, or stereoisomer of claim 1, wherein the compound has following structural formula III(3):

III(3)

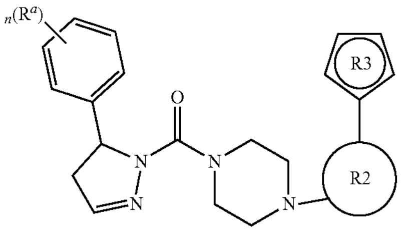

wherein $R^a$ is selected from halogen, CN, and C1 to C3 alkyl, and wherein n is 0, 1, 2, or 3.

14. The compound, salt, hydrate, or stereoisomer of claim 1, wherein the compound has following structural formula III(4):

III(4)

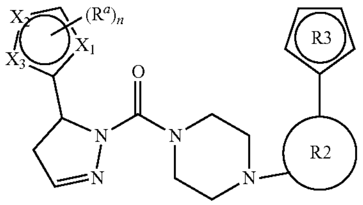

wherein $X_1$ is S, $X_2$ is C, and $X_3$ is N, or $X_1$ is S, $X_2$ is N, and $X_3$ is C, or $X_1$ is N, $X_2$ is O, and $X_3$ is C, or $X_1$ is N, $X_2$ is S, and $X_3$ is C; wherein $R^a$ is selected from halogen, CN, and C1 to C3 alkyl; and wherein n is 0, 1, or 2.

15. The compound, salt, hydrate, or stereoisomer of claim 1, wherein the compound has following structural formula IV(1):

IV(1)

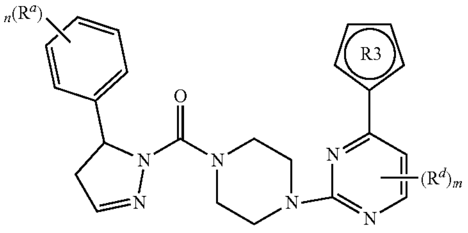

wherein $R^a$ is selected from halogen, CN, and C1 to C3 alkyl, n is 0, 1, 2, or 3; and wherein $R^d$ is selected from halogen, CN, C1 to C3 alkoxy, and C1 to C3 alkyl optionally substituted with OH, m is 0, 1, or 2.

16. The compound, salt, hydrate, or stereoisomer of claim 1, wherein the compound has following structural formula IV(2):

IV(2)

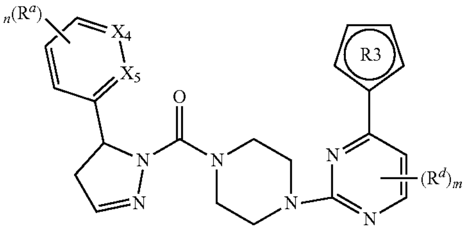

wherein $X_4$ is N and $X_5$ is C, or $X_4$ is C and $X_5$ is N; wherein $R^a$ is selected from halogen, CN, and C1 to C3 alkyl, n is 0, 1, 2, or 3; and wherein $R^d$ is selected from halogen, CN, C1 to C3 alkoxy, and C1 to C3 alkyl optionally substituted with OH, m is 0, 1, or 2.

17. The compound, salt, hydrate, or stereoisomer of claim 1, wherein the compound has following structural formula IV(3):

IV(3)

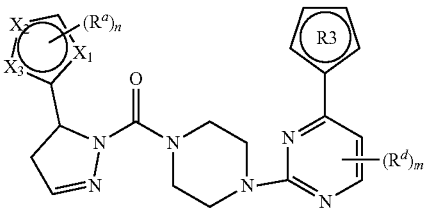

wherein $X_1$ is S, $X_2$ is C, and $X_3$ is N, or $X_1$ is S, $X_2$ is N, and $X_3$ is C, or $X_1$ is N, $X_2$ is O, and $X_3$ is C, or $X_1$ is N, $X_2$ is S, and $X_3$ is C; wherein $R^a$ is selected from halogen, CN, and C1 to C3 alkyl, n is 0, 1, 2, or 3; and wherein $R^d$ is selected from halogen, CN, C1 to C3 alkoxy, and C1 to C3 alkyl optionally substituted with OH, m is 0, 1, or 2.

18. The compound, salt, hydrate, or stereoisomer of claim 1, wherein R3 is

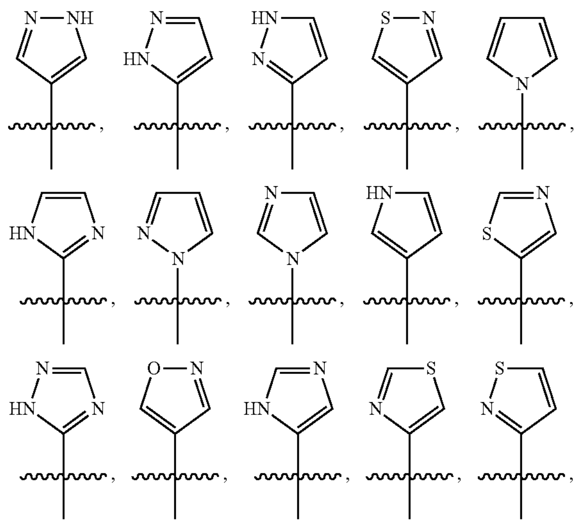

-continued

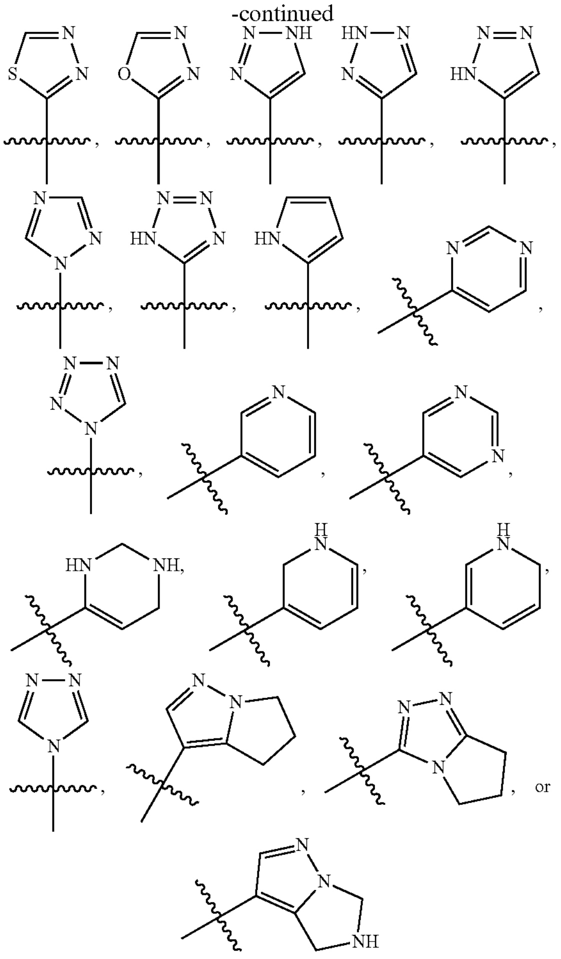

substituted with 0-3 substituents selected from halide, optionally-substituted N, S or O, and optionally-substituted hydrocarbyl.

19. The compound, salt, hydrate, or stereoisomer of claim 1, wherein R3 is

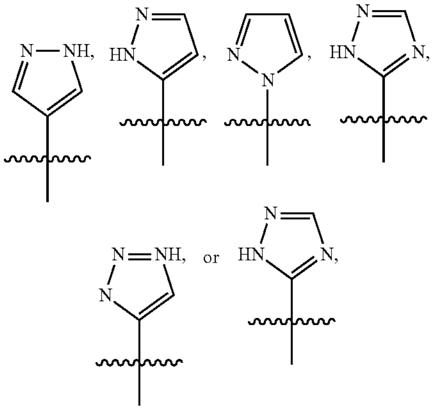

20. The compound, salt, hydrate, or stereoisomer of claim 1, wherein R3 is substituted with 0-3 $R^e$, wherein $R^e$, for each occurrence, is independently selected from:

halogen, cyano, $C_1$-$C_6$ alkyl, $C_3$-$C_6$ cycloalkyl, 3- to 6-membered heterocyclyl, $C_2$-$C_6$ alkenyl, $C_1$-$C_6$ alkoxy, —C(=O)($C_1$-$C_6$ alkyl), —C(=O)($C_3$-$C_6$ cycloalkyl), —C(=O)(3- to 6-membered heterocyclyl), =O, —$NO_2$, —C(=O)$OR^s$, —C(=O)$NR^pR^q$, —$NR^pR^q$, —$NR^p$C(=O)$R^s$, —$NR^p$C(=O)$OR^s$, —$NR^p$C(=O)$NR^qR^r$, —$NR^p$S(=O)$_w$$R^s$, —$OR^s$, —OC(=O)$R^s$, —OC(=O)$OR^s$, —OC(=O)$NR^pR^q$, —S(=O)$_w$$R^s$, and —S(=O)$_w$$NR^pR^q$; wherein the $C_1$-$C_6$ alkyl, $C_3$-$C_6$ cycloalkyl, 3- to 6-membered heterocyclyl, the $C_2$-$C_6$ alkenyl, and the $C_1$-$C_6$ alkoxy of $R^e$, the $C_1$-$C_6$ alkyl of —C(=O)($C_1$-$C_6$ alkyl), the $C_3$-$C_6$ cycloalkyl of —C(=O)($C_3$-$C_6$ cycloalkyl), and the 3- to 6-membered heterocyclyl of —C(=O)(3- to 6-membered heterocyclyl) are each optionally substituted with 1 to 3 groups selected from halogen, cyano, =O, —C(=O)$R^s$, —C(=O)$OR^s$, —C(=O)$NR^pR^q$, —$NR^pR^q$, —$NR^p$C(=O)$R^s$, —$NR^p$C(=O)$OR^s$, —$NR^p$C(=O)$NR^qR^r$, —$NR^p$S(=O)$_w$$R^s$, —$OR^s$, —OC(=O)$R^s$, —OC(=O)$OR^s$, —OC(=O)$NR^pR^q$, —S(=O)$_w$$R^s$, —S(=O)$_w$$NR^pR^q$, $C_3$-$C_6$ cycloalkyl, and 3- to 6-membered heterocyclyl; wherein $R^p$, $R^q$, $R^r$, and $R^s$, for each occurrence, are each independently selected from hydrogen, OH, $NH_2$, $C_1$-$C_4$ alkyl, $C_3$-$C_6$ cycloalkyl, and 3- to 6-membered heterocyclyl; wherein the $C_1$-$C_4$ alkyl, $C_3$-$C_6$ cycloalkyl, and 3- to 6-membered heterocyclyl of any one of $R^p$, $R^q$, $R^r$, and $R^s$ are optionally substituted with 1 to 3 groups selected from halogen, cyano, —OH, $C_1$-$C_6$ alkyl, —O($C_1$-$C_6$ alkyl), —C(=O)N($C_1$-$C_6$ alkyl)($C_1$-$C_6$ alkyl), —C(=O)NH ($C_1$-$C_6$ alkyl), —C(=O)(3- to 6-membered heterocyclyl), —C(=O)($C_3$-$C_6$ cycloalkyl), $C_3$-$C_6$ cycloalkyl, phenyl, and 3- to 6-membered heterocyclyl; and wherein w is an integer selected from 0, 1, and 2.

21. The compound, salt, hydrate or stereoisomer of claim 1, wherein R3 is substituted with 0-3 $R^e$, wherein $R^e$, for each occurrence, is independently selected from: halogen; cyano; =O; —$NO_2$; 4- to 6-membered heterocyclyl optionally substituted with oxo; —C(=O)($C_1$-$C_3$ alkyl); —C(=O)(4- to 6-membered heterocyclyl);

—C(=O)$OR^s$, wherein $R^s$ are H or $C_1$-$C_3$ alkyl;

—$OR^s$, wherein $R^s$ is H or $C_1$-$C_3$ alkyl; $C_1$-$C_3$ alkyl, optionally substituted with OH, $NH_2$, cyano, halogen, $C_1$-$C_3$ alkoxyl, 3- to 4-membered cycloalkyl, 4- to 6-membered heterocyclyl, —C(=O)OH, —C(=O)(4- to 6-membered heterocyclyl), —C(=O)NH$(CH_2)_2$OH, or —C(=O)$NH_2$;

—C(=O) $NR^pR^q$, wherein $R^p$ and $R^q$ each are independently selected from Hand $C_1$-$C_3$ alkyl;

—$NR^pR^q$, wherein $R^p$ and $R^q$ each is independently selected from H and $C_1$-$C_3$ alkyl;

—$NR^p$C(=O)$R^s$, wherein $R^p$ is selected from H and $C_1$-$C_3$ alkyl, and $R^s$ is selected from 3- to 4-membered cycloalkyl and $C_1$-$C_3$ alkyl optionally substituted 3- to 4-membered cycloalkyl;

—$NR^p$S(=O)$_w$$R^s$, wherein $R^p$ is selected from H and $C_1$-$C_3$ alkyl, and $R^s$ is selected from $C_1$-$C_3$ alkyl, and wherein w is 2;

—S(=O)$_w$$R^s$, wherein $R^s$ is selected from $C_1$-$C_3$ alkyl and wherein w is 0 or 2.

22. The compound, salt, hydrate, or stereoisomer of claim 1, wherein R3 is substituted with 1-3 $R^e$, wherein $R^e$, for each occurrence, is independently selected from:

Cl, Br, I, CN, methyl, ethyl, —$CF_3$, —$CH_2F$, —$CHF_2$, —$CH_2CF_3$, —$CH_2OH$, —$CH_2CN$, —$CH_2CH_2OH$, —$CH_2CH_2OCH_3$, —$CH_2C$(=O)$NH_2$,

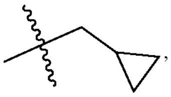
,
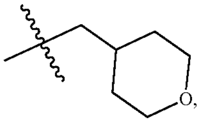
,

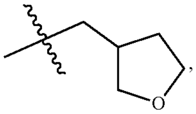
,
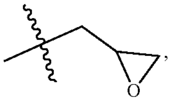
,

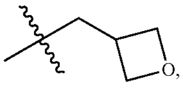
,
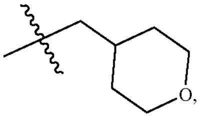
,

-OH, $-OCH_3$, $=O$, $-C(=O)CH_3$,

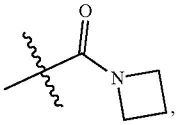 [SMILES: *C(=O)N1CCC1]
, $-C(=O)OCH_3$, $-C(=O)OCH_2CH_3$, $-C(=O)NH_2$, $-C(=O)OH$, $NH_2$, $-NHC(=O)CH_3$,

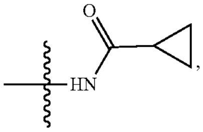
,
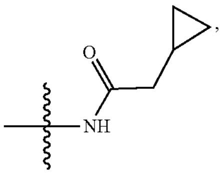
, $-NO_2$, $-NHS(=O)_2CH_2CH_3$, $-S(=O)_2CH_2CH_3$, and $-S(=O)_2CH_3$.

23. The compound, salt, hydrate, or stereoisomer of claim 1, wherein R3 is substituted with 1-3 $R^e$, wherein $R^e$, for each occurrence, is independently selected from: Cl, CN, methyl, $-CF_3$, $-CH_2OH$, $-CH_2C(=O)NH_2$, $-C(=O)OCH_3$, $-C(=O)NH_2$, and $-C(=O)OH$.

24. The compound, salt, hydrate, or stereoisomer of claim 1, wherein R3 is substituted with 1-3 $R^e$, wherein $R^e$, for each occurrence, is independently selected from: CN, methyl, Cl, and $-C(=O)NH_2$.

25. The compound, salt, hydrate, or stereoisomer of claim 1, wherein wherein the C5 aryl and C6 aryl of R1 are optionally substituted with F, Cl, Br, CN, or methyl; wherein the C5 aryl and C6 aryl of R2 are optionally substituted with F, Cl, CN, —OCH3, or —CH2OH.

26. The compound, salt, hydrate, or stereoisomer of claim 1, wherein the compound has a structure selected from the group consisting of:

1

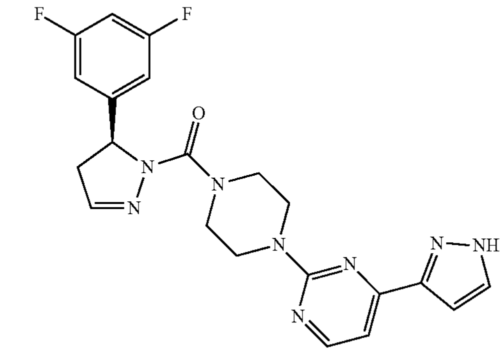

2

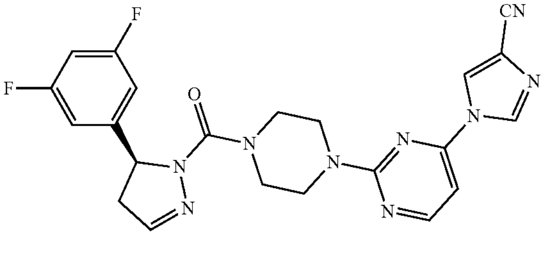

3

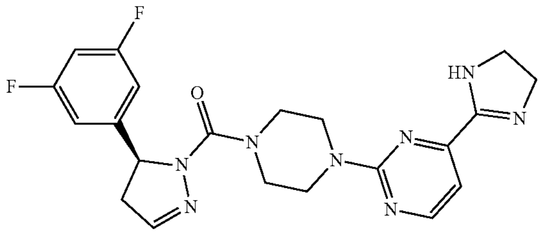

4

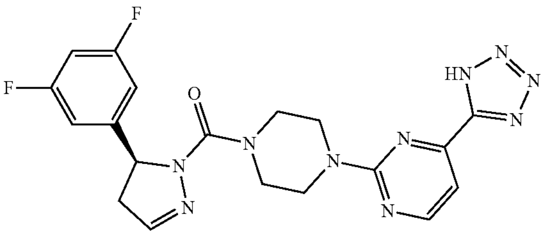

5

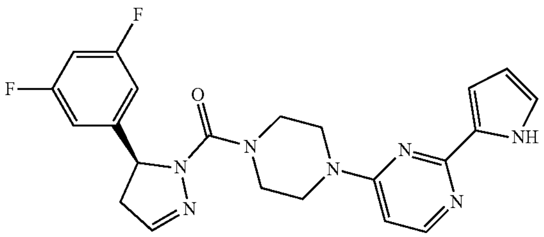

-continued
6
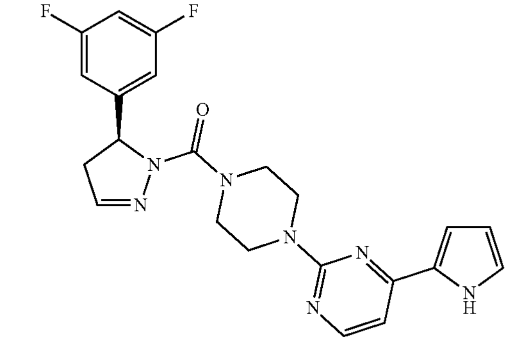
7
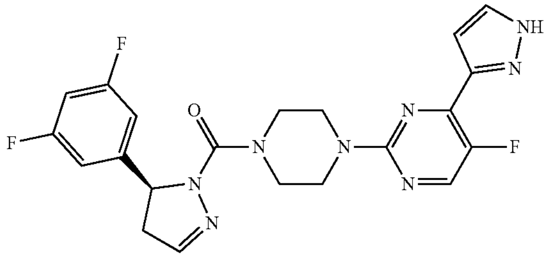
8
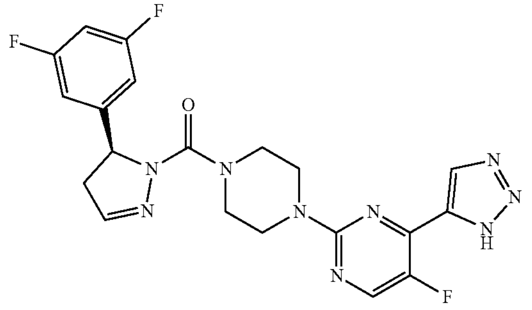
9
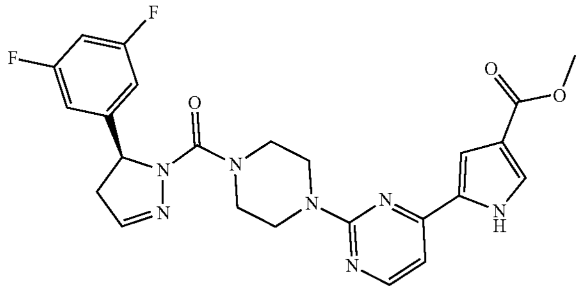
10
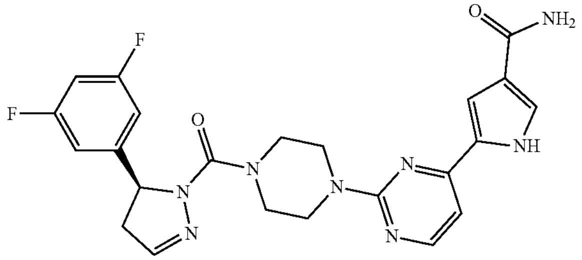
-continued
11
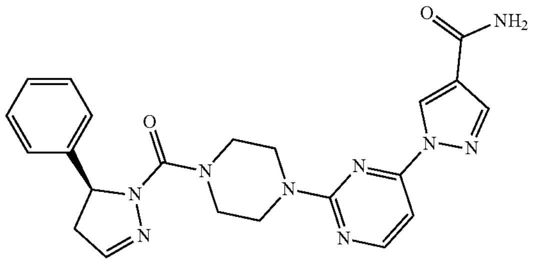
12
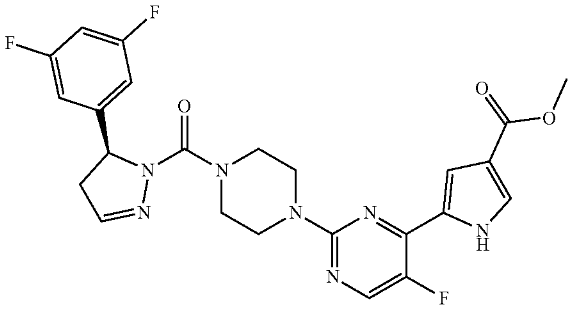
13
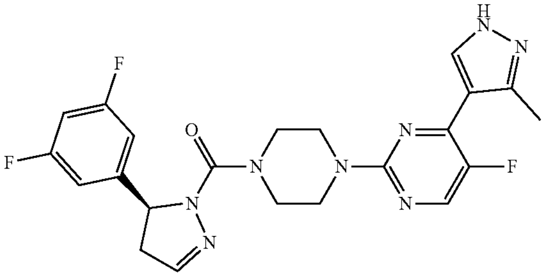
14
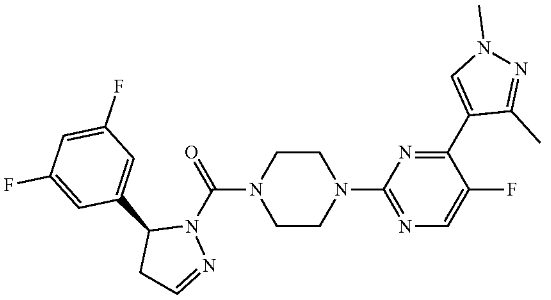
15
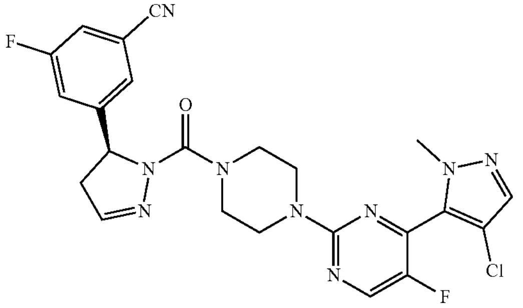

-continued
16
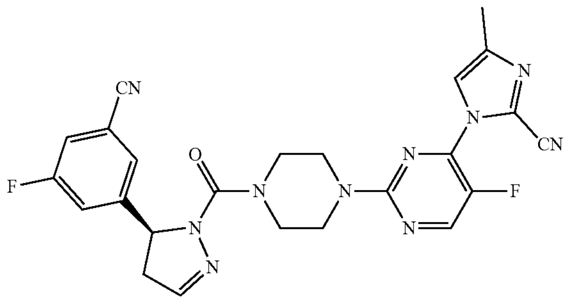
17
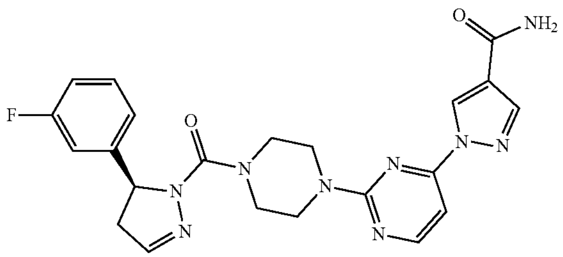
18
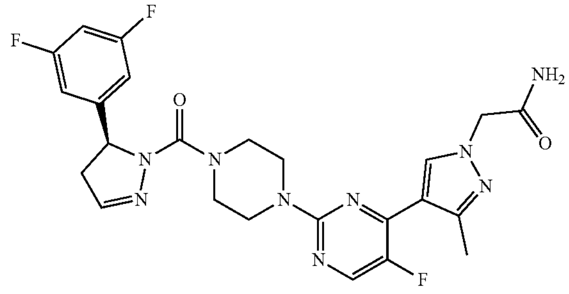
19
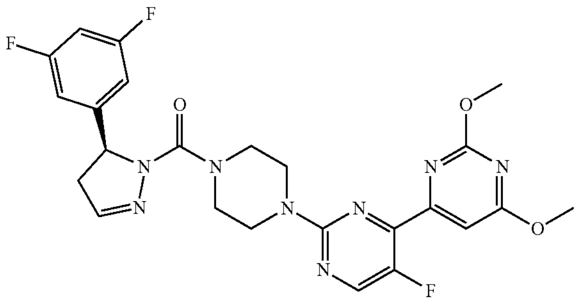
20
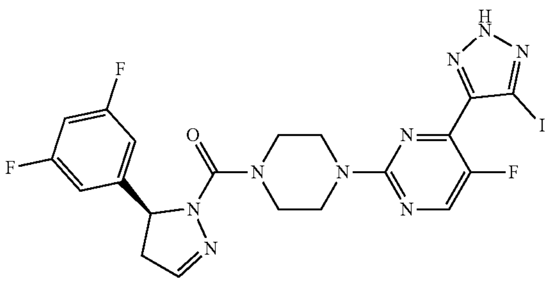
-continued
21
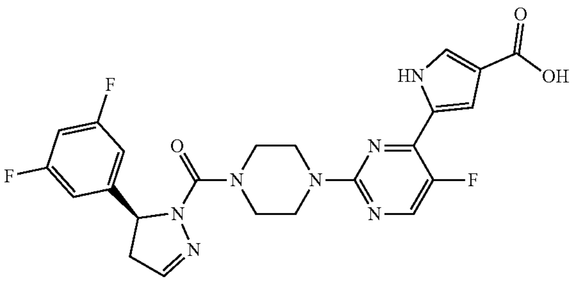
22
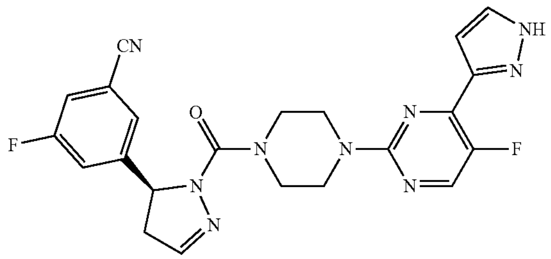
23
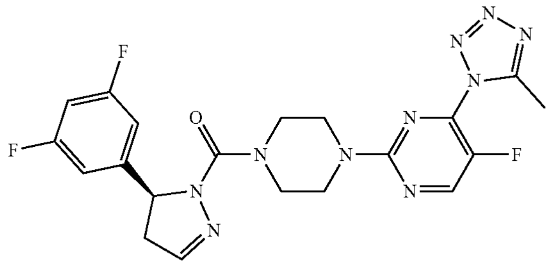
24
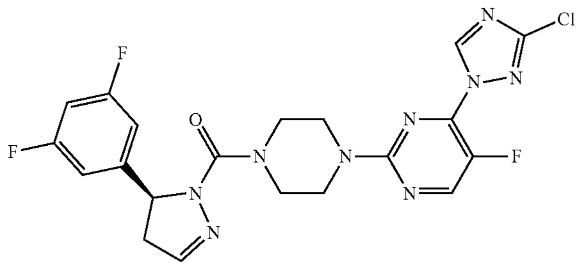
25
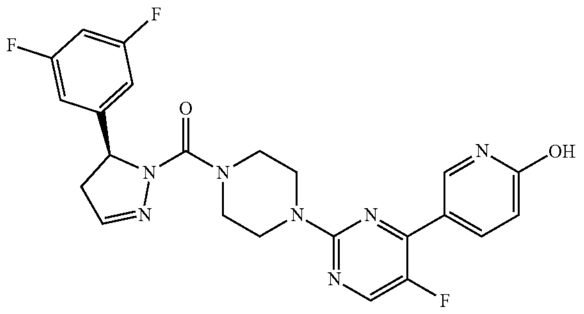

-continued
26
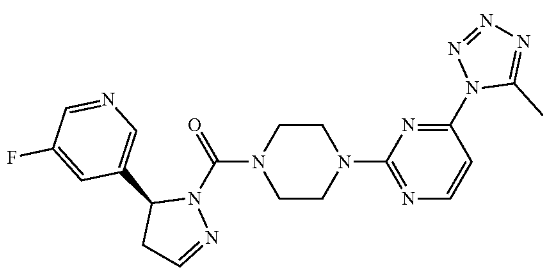
27
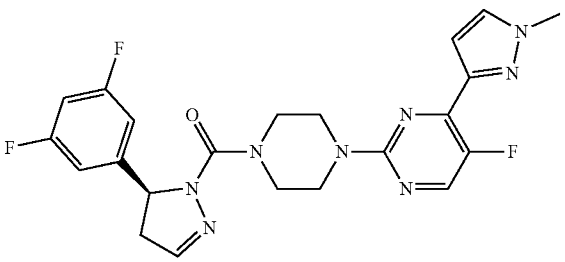
28
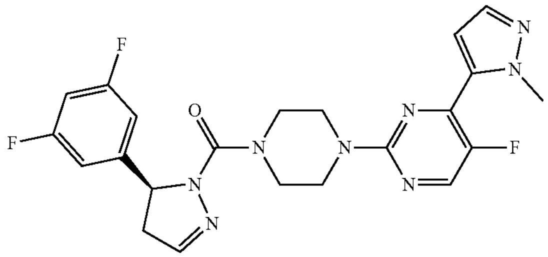
29
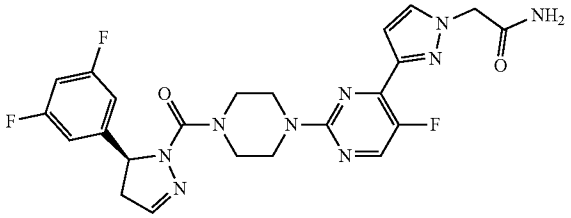
30
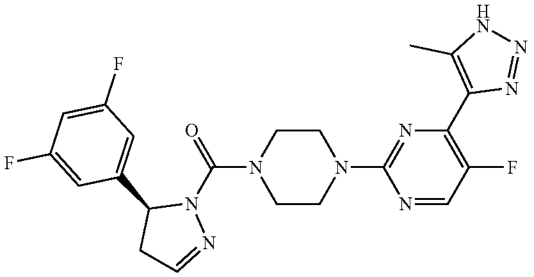
-continued
31
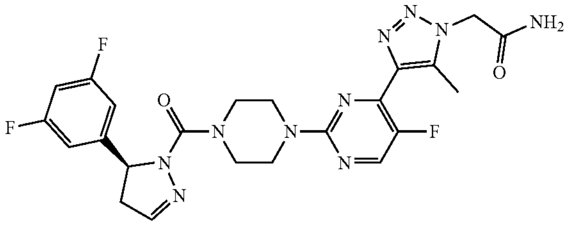
32
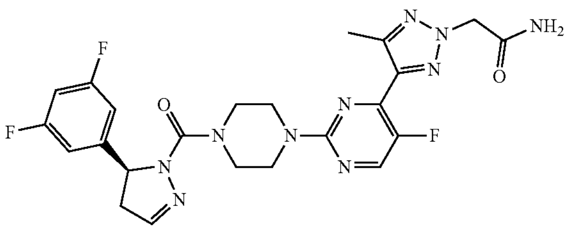
33
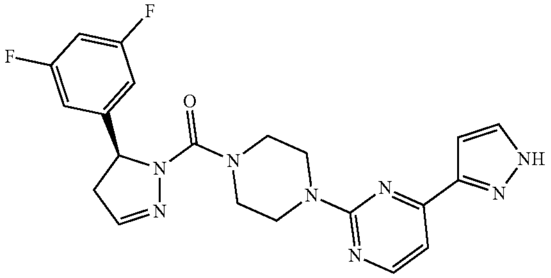
34
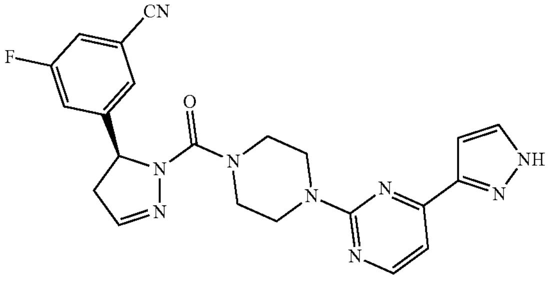
35
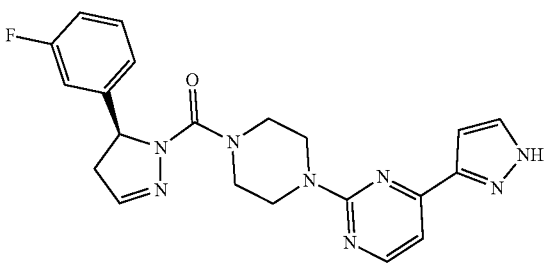

-continued
36
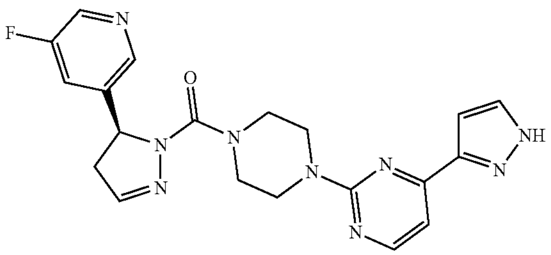
37
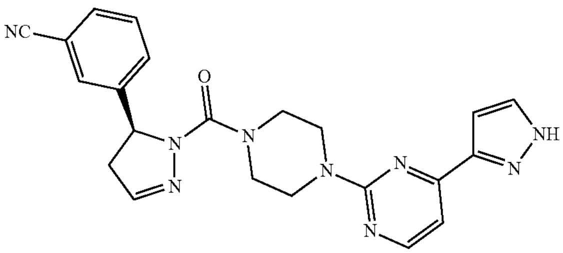
38
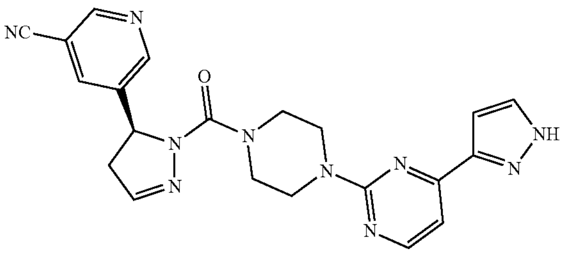
39
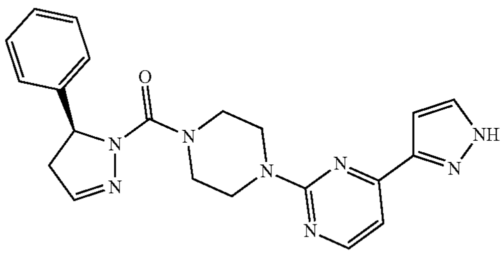
40
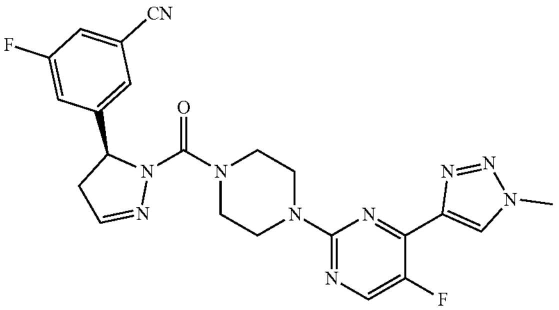
-continued
41
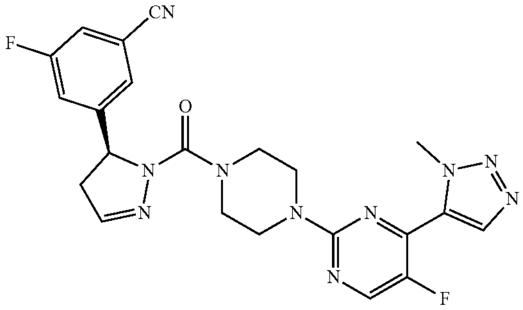
42
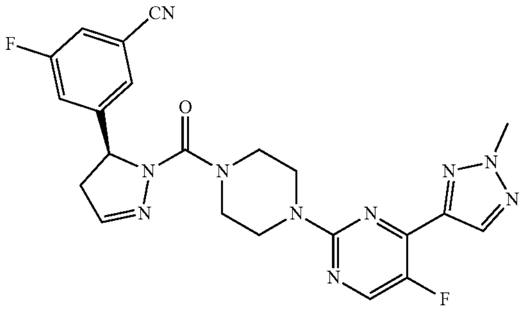
43
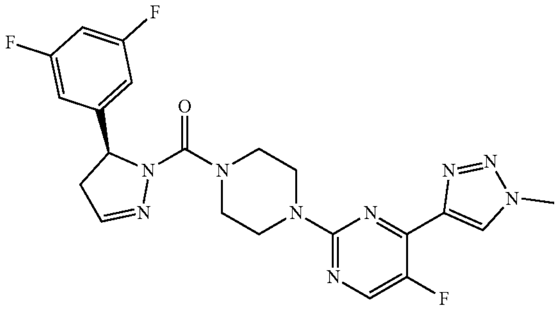
44
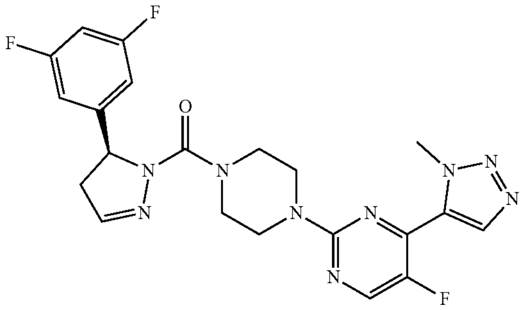
45
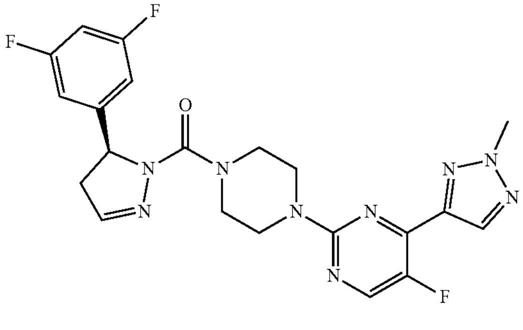

-continued
46
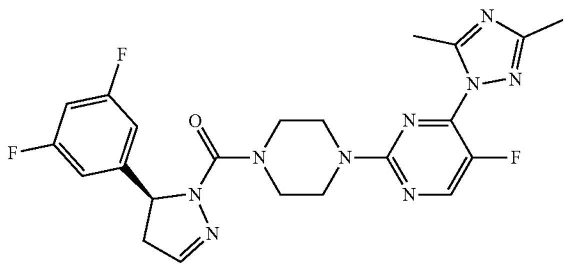
47
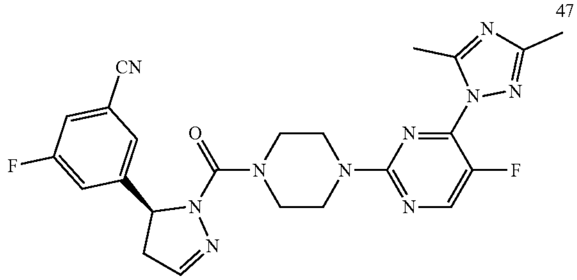
48
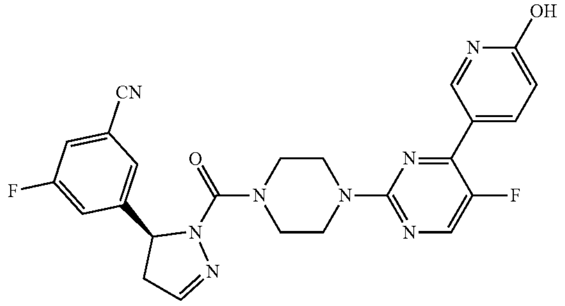
49
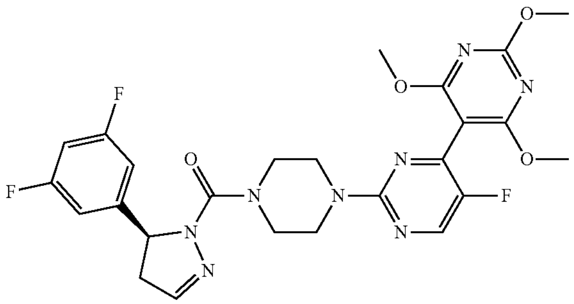
50
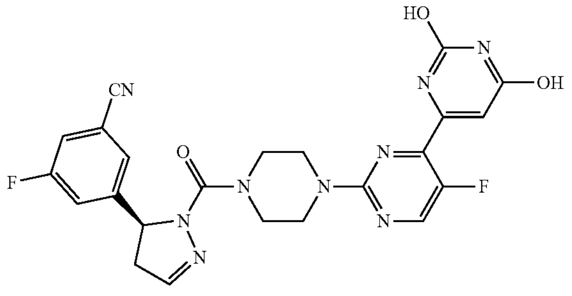
-continued
51
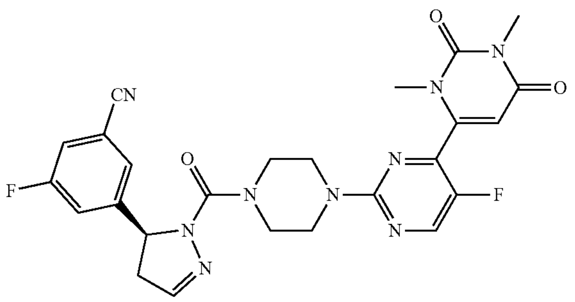
52
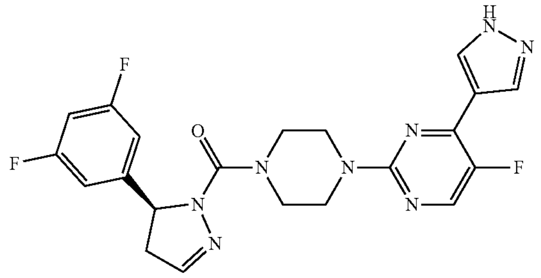
53
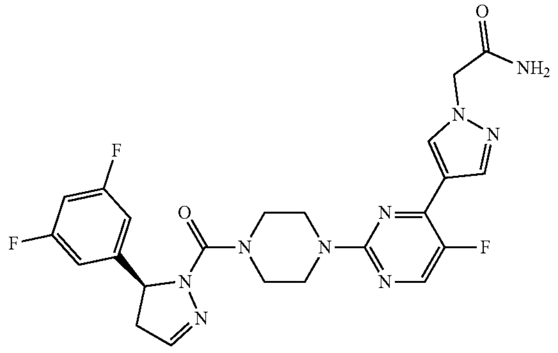
54
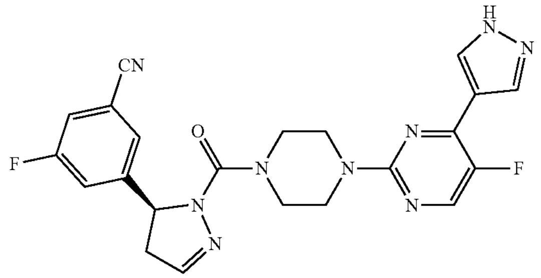
55
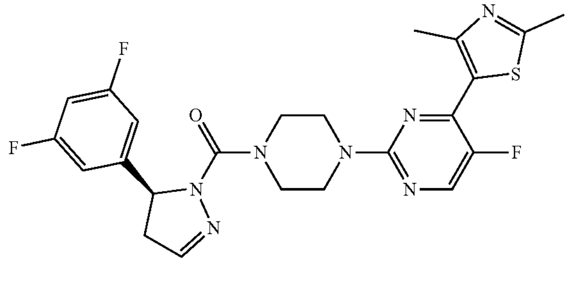

-continued
56
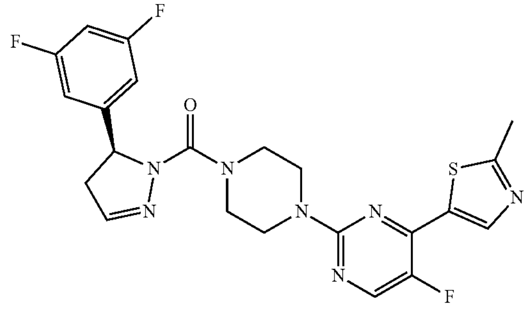
57
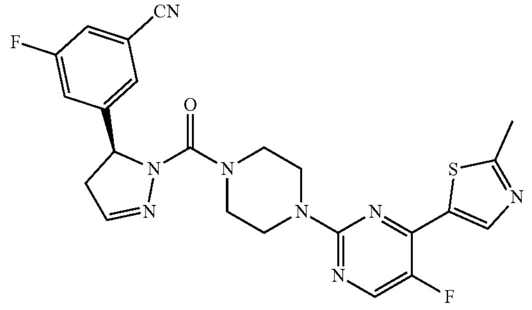
58
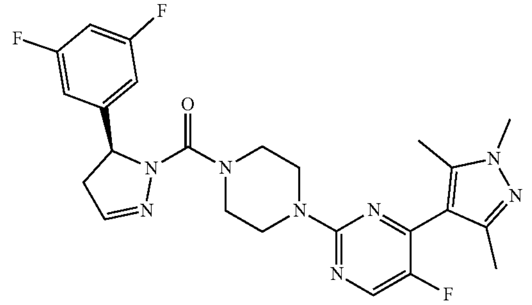
59
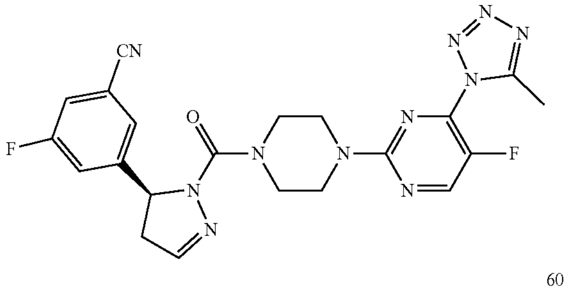
60
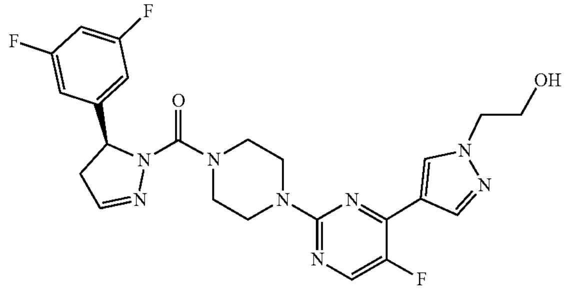
-continued
61
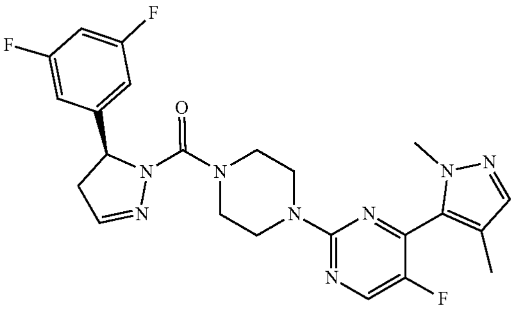
62
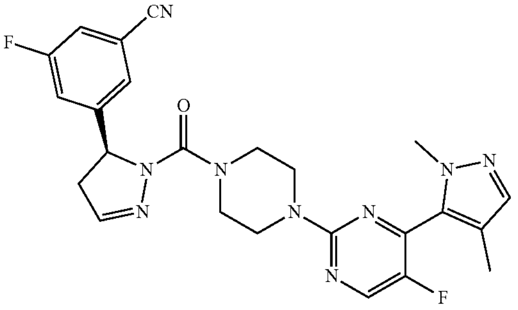
63
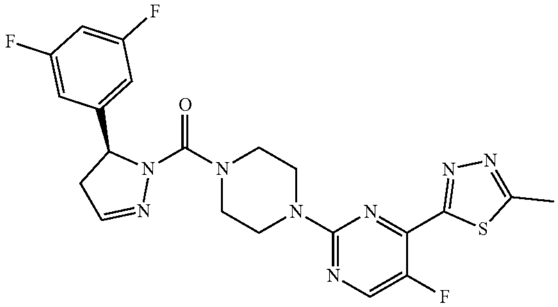
64
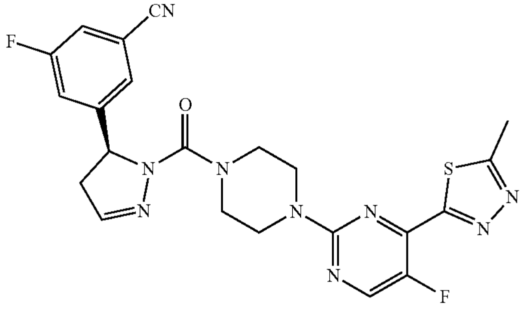
65
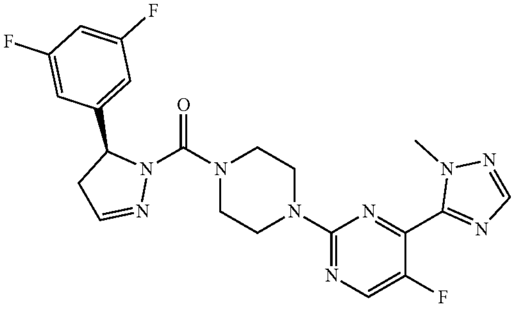

-continued
66
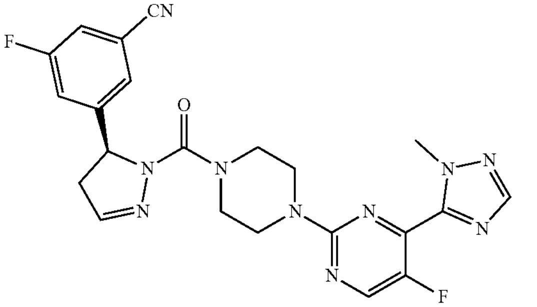
67
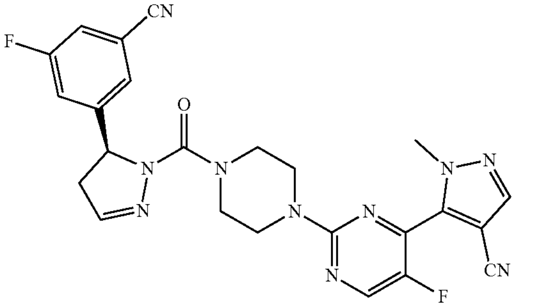
68
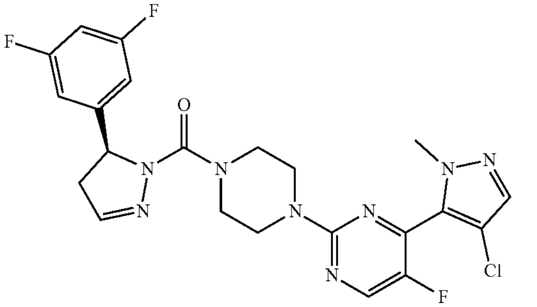
69
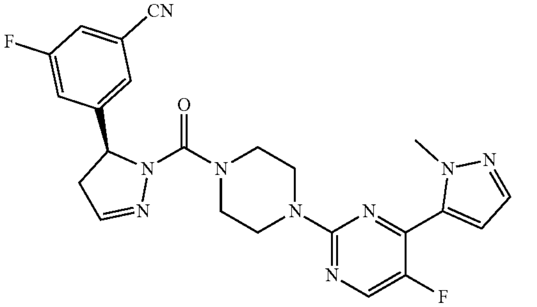
70
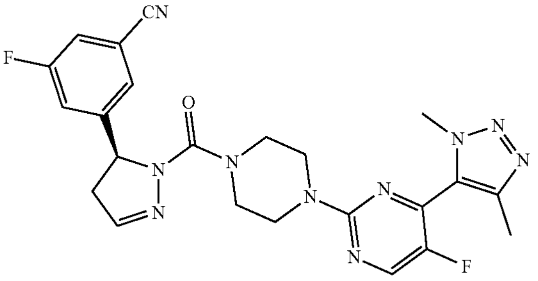
-continued
71
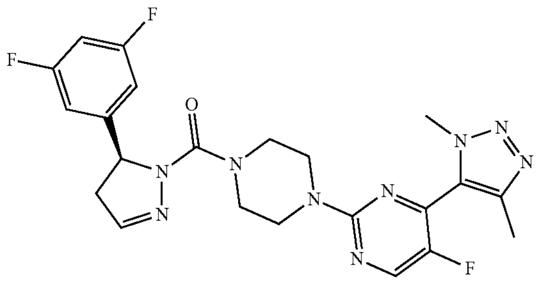
72
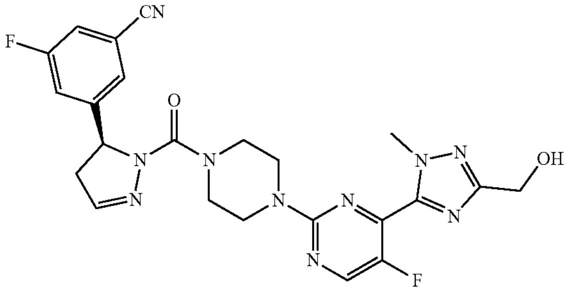
73
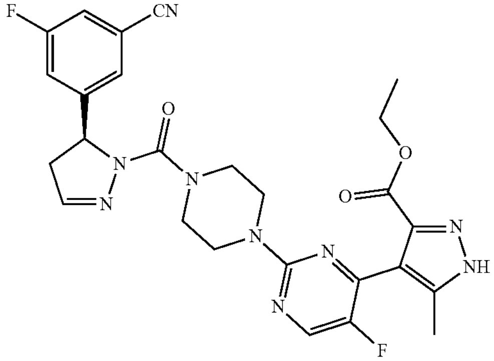
74
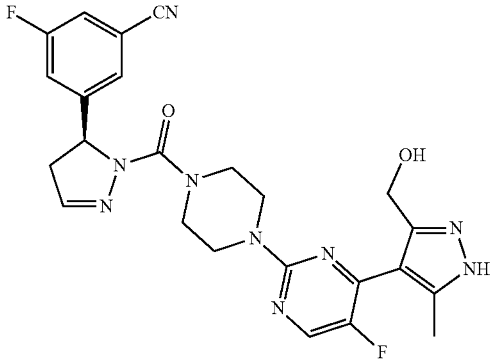
75
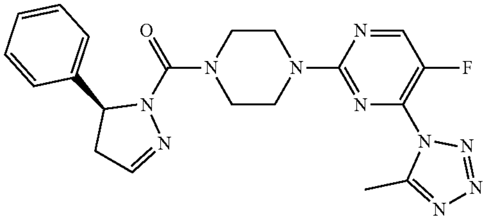

-continued
76
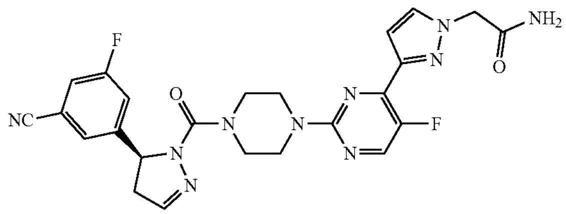
77
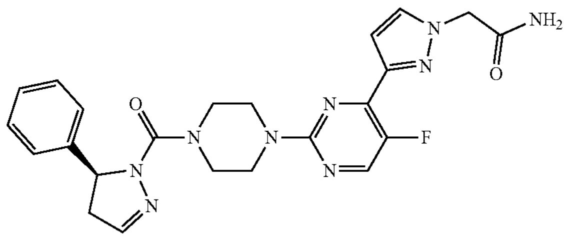
lp;3p
78
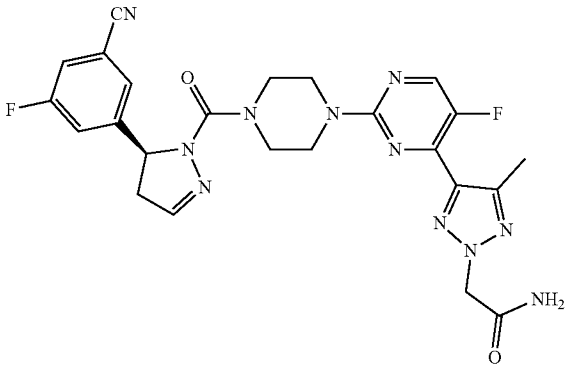
79
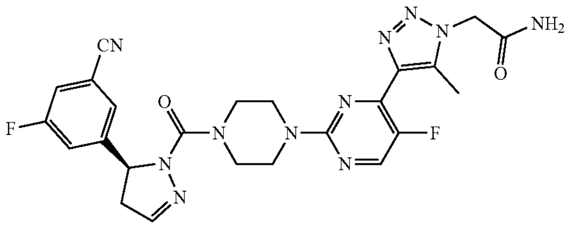
80
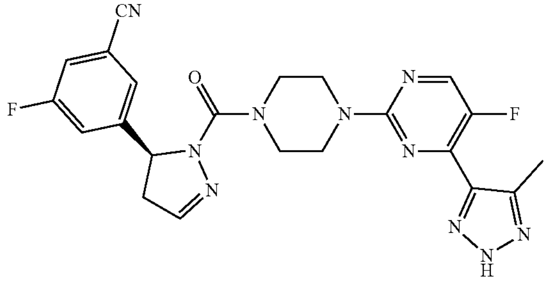
-continued
81
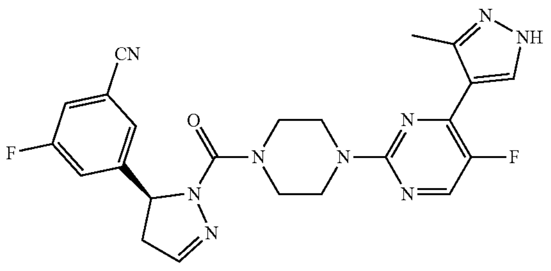
82
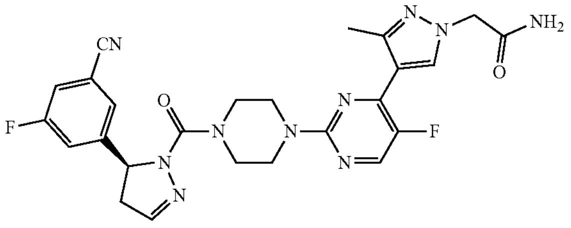
83
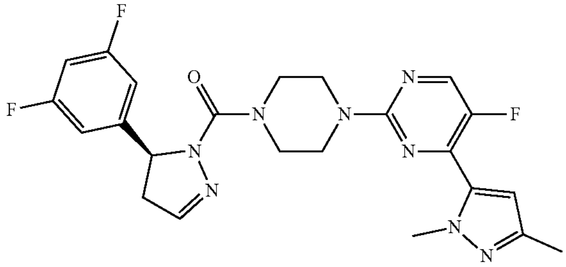
84
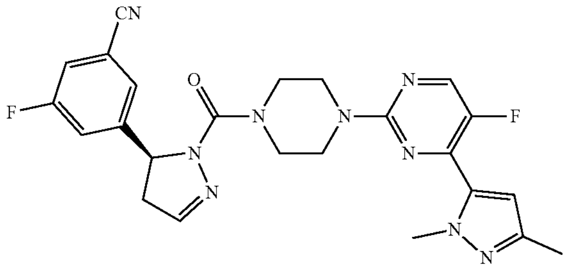
85
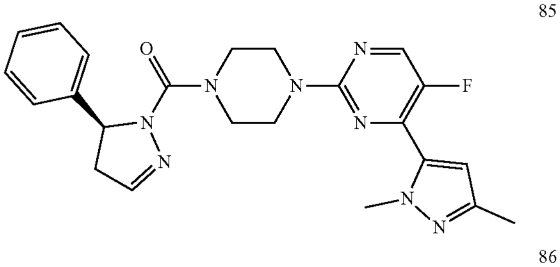
86
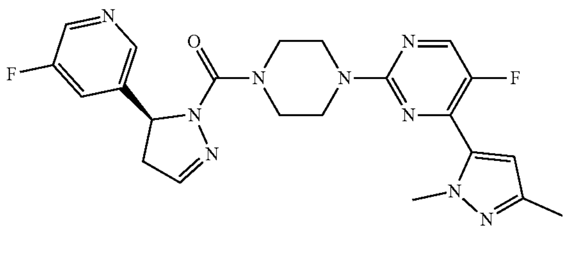

-continued
87
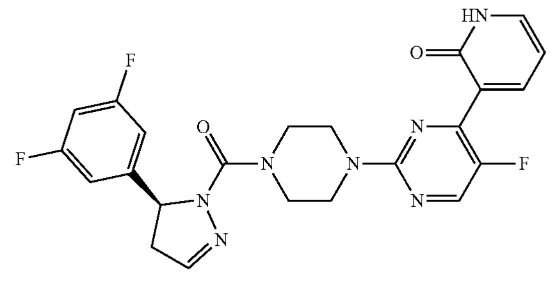
88
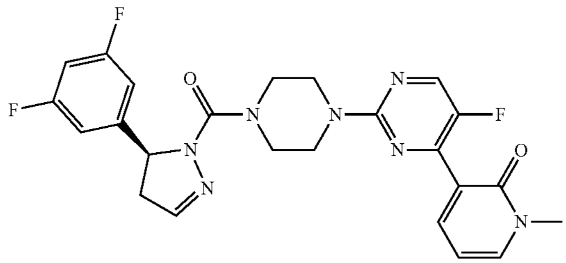
89
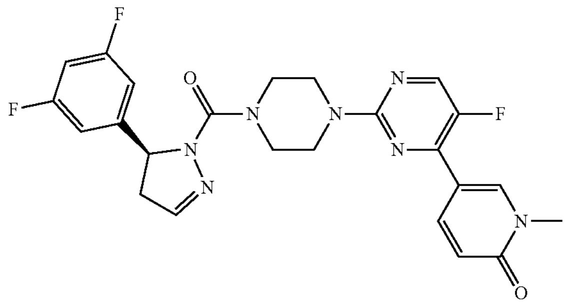
90
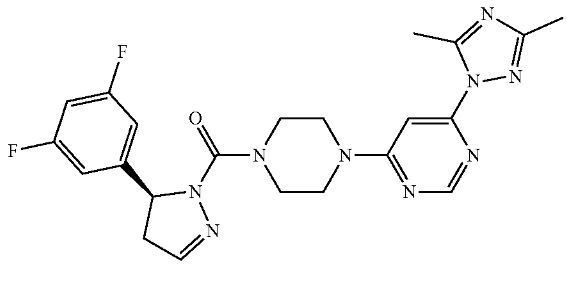
91
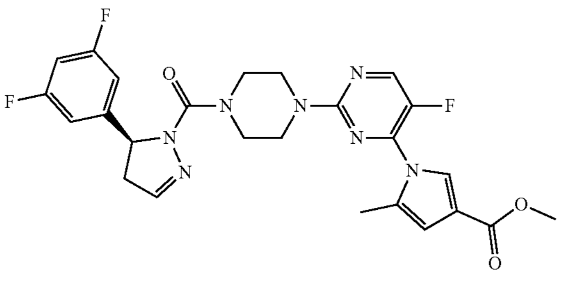
-continued
92
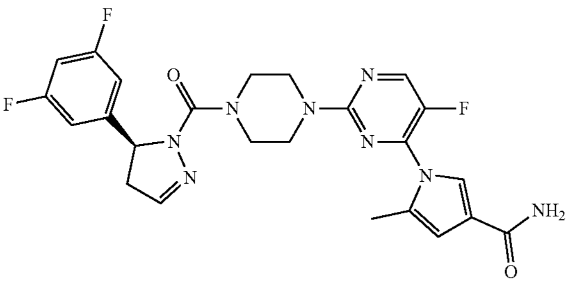
93
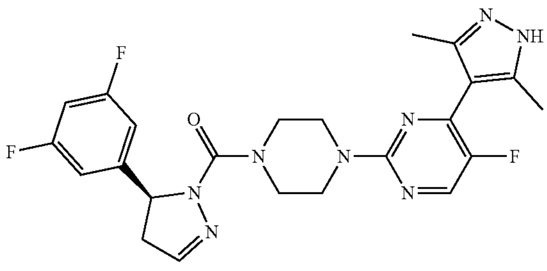
94
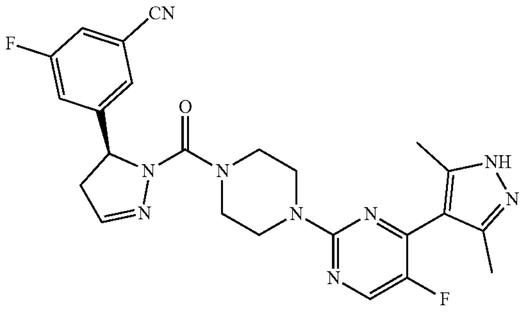
95
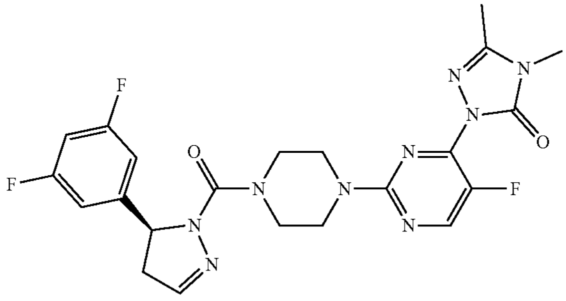
96
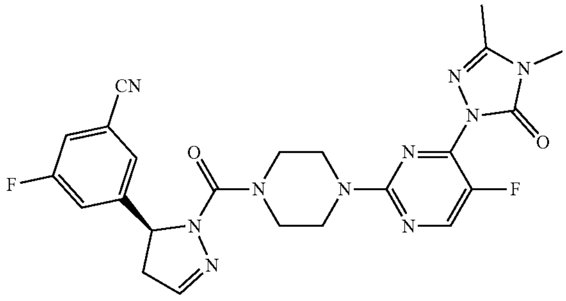

-continued
97
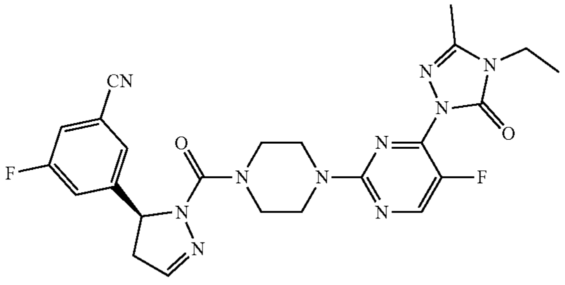
98
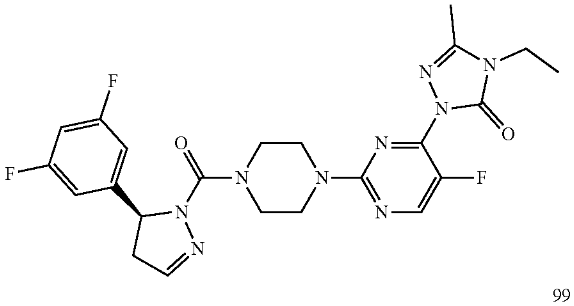
99
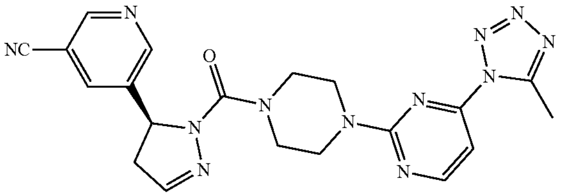
100
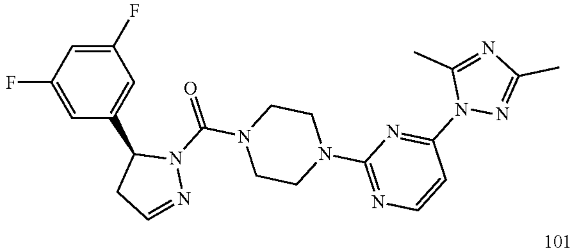
101
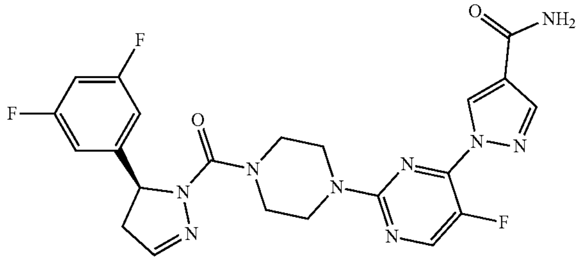
-continued
102
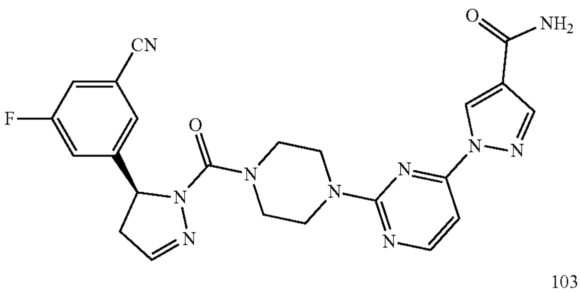
103
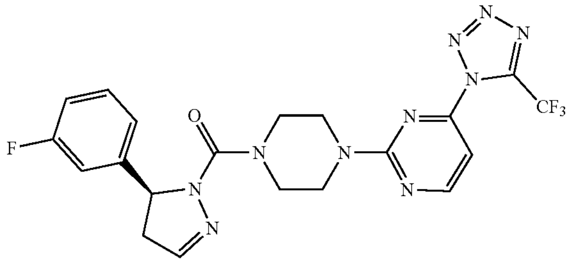
104
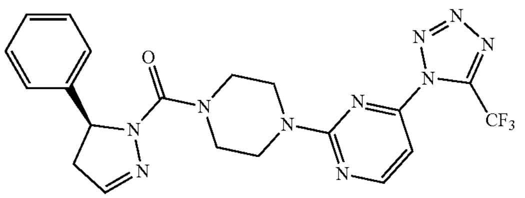
105
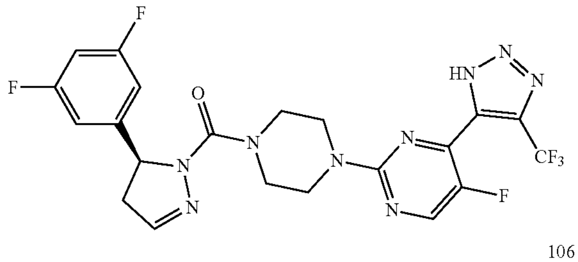
106
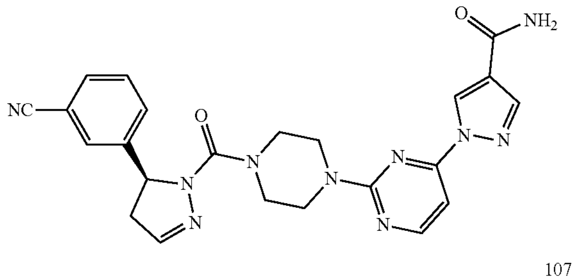
107
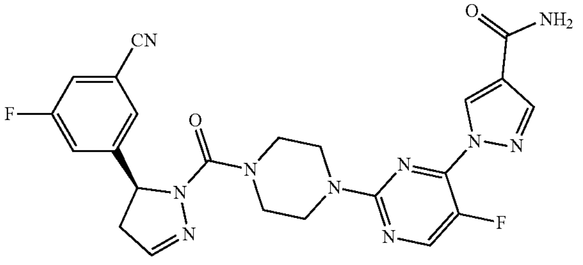

-continued
108
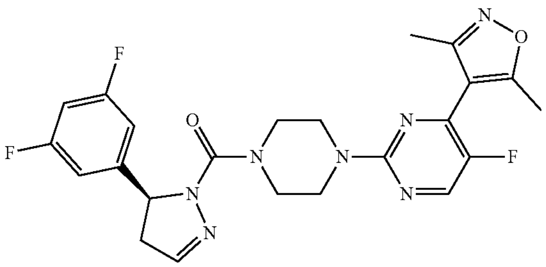
109
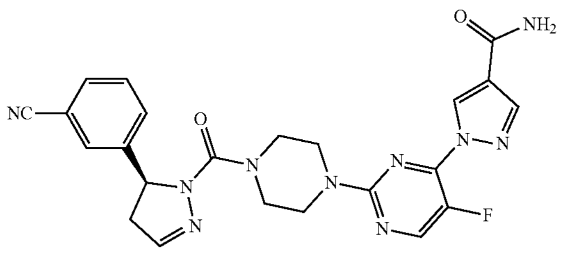
110
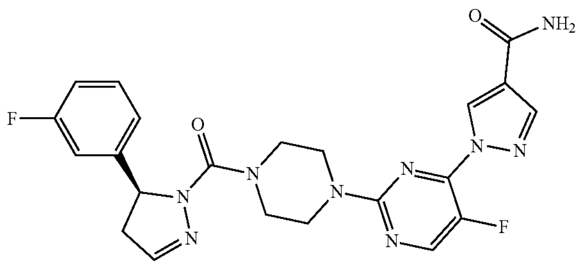
111
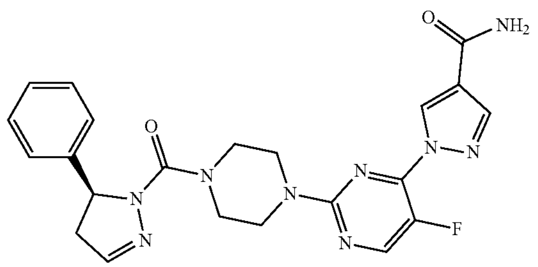
112
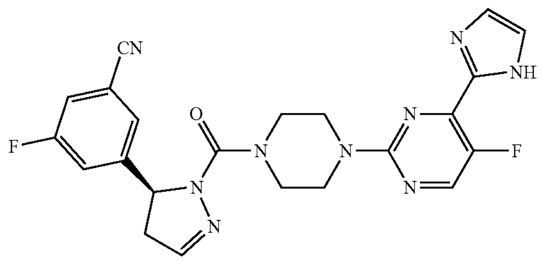
-continued
113
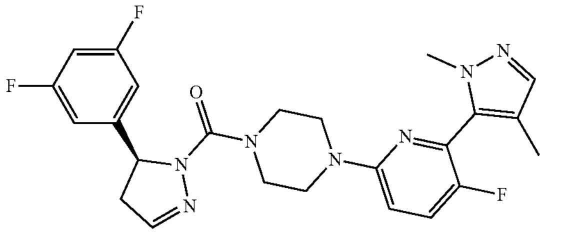
114
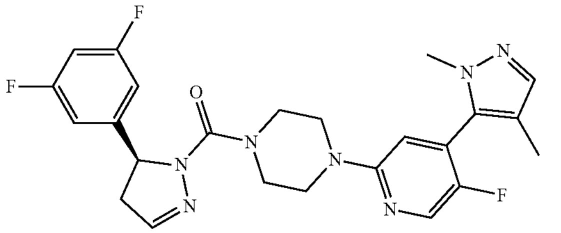
115
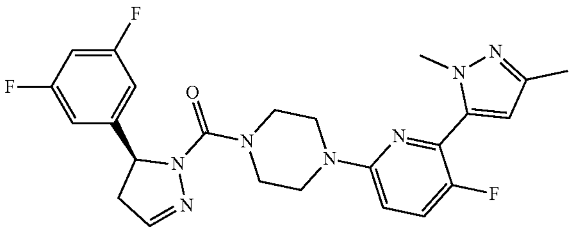
116
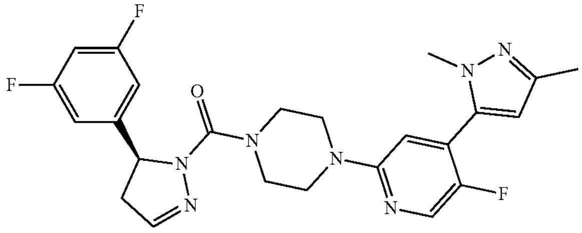
117
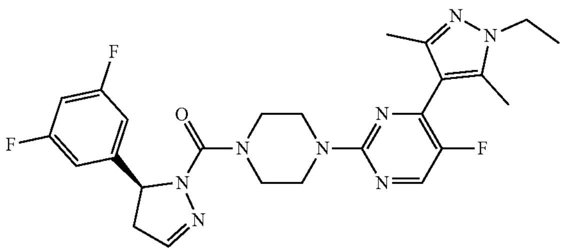
118
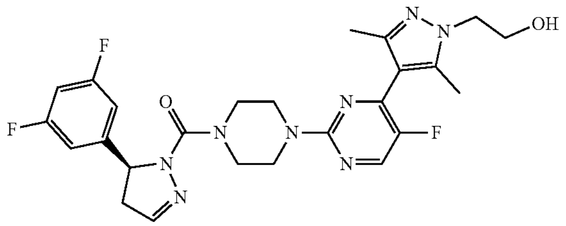

-continued
119
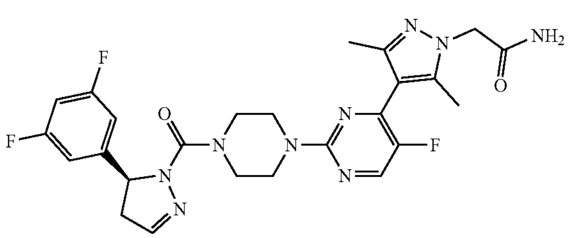
120
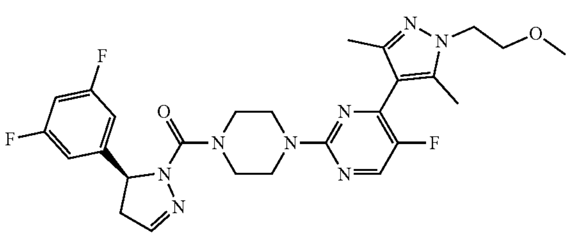
121
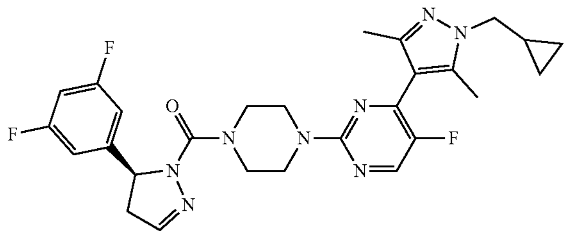
122
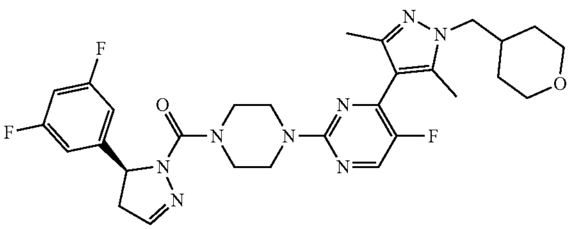
123
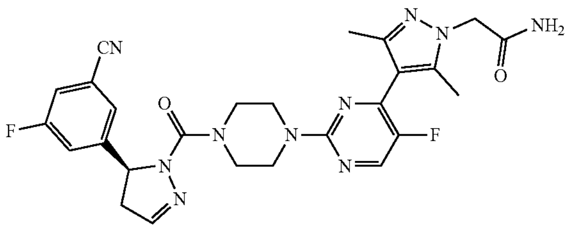
124
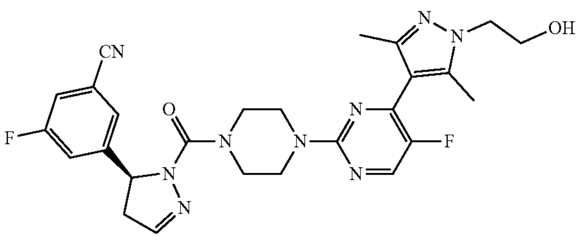
-continued
125
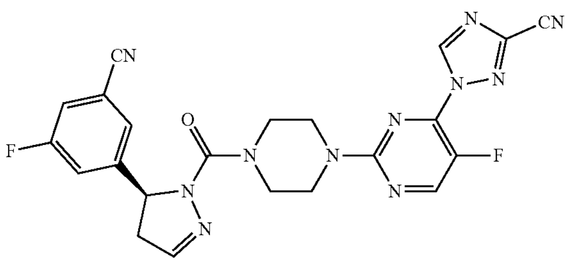
126
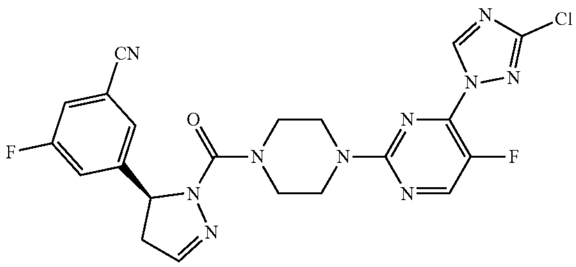
127
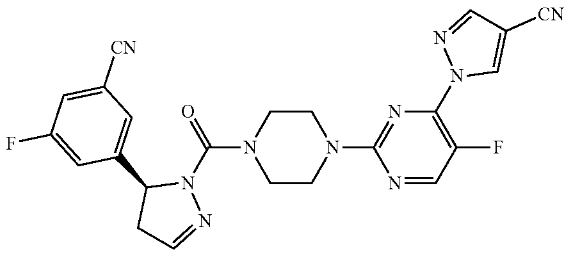
128
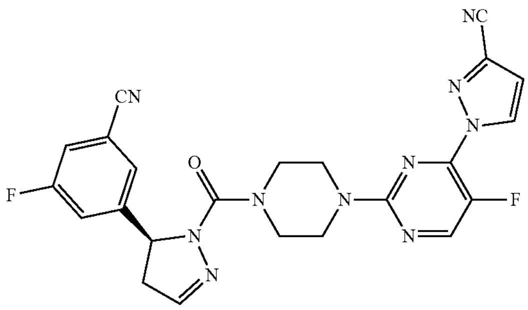
129
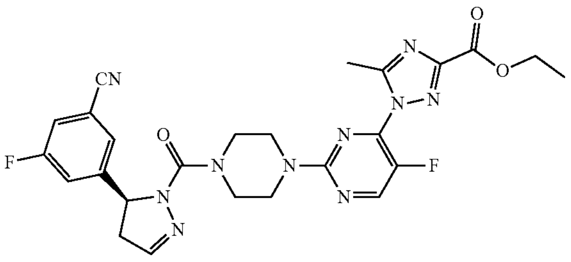

-continued
130
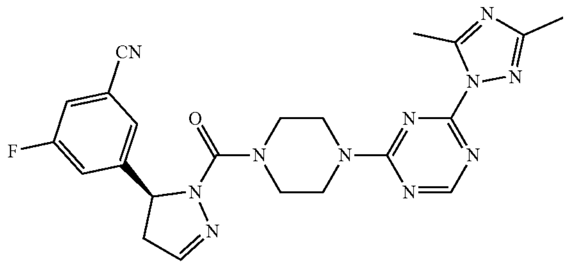
131
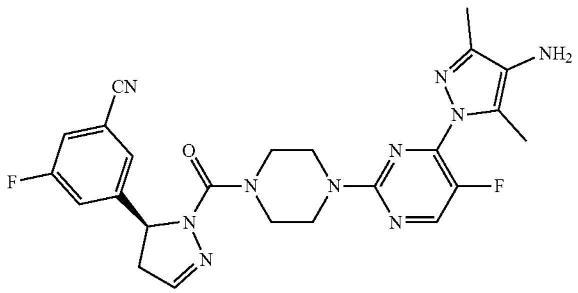
132
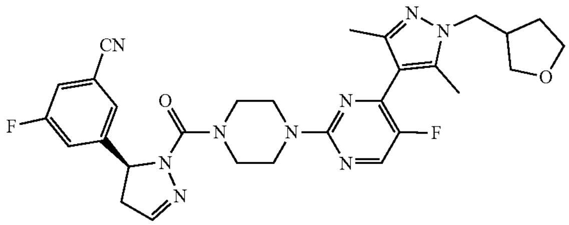
133
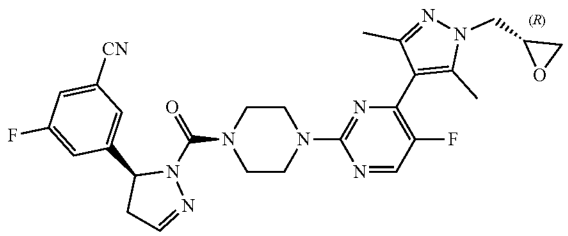
134
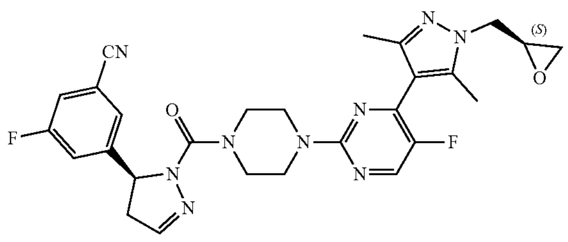
135
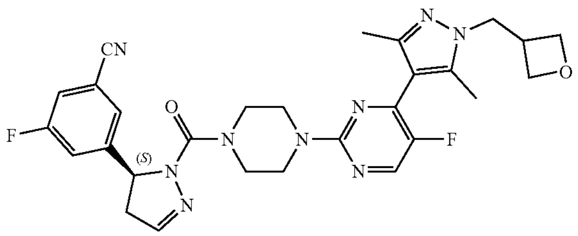
-continued
136
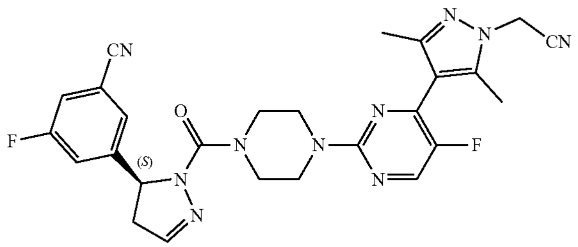
137
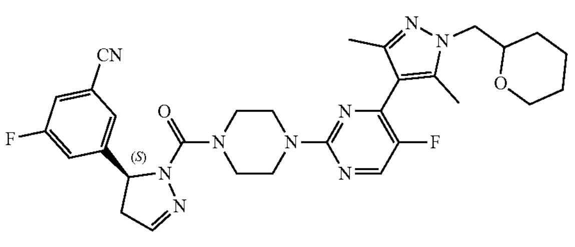
138
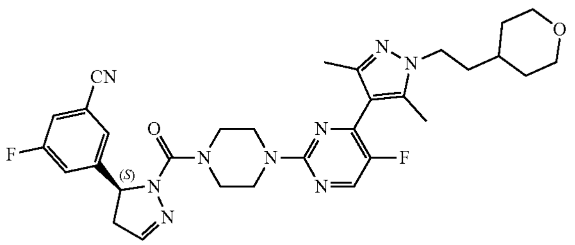
139
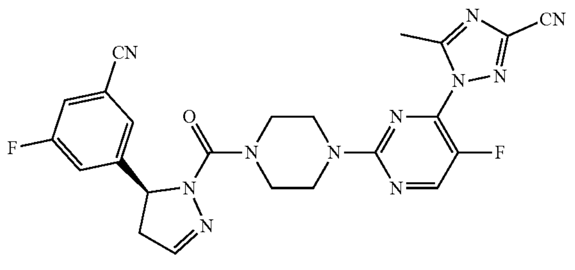
140
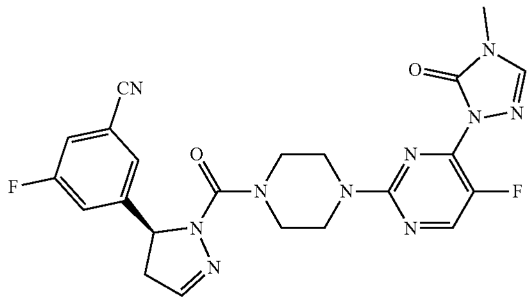

141
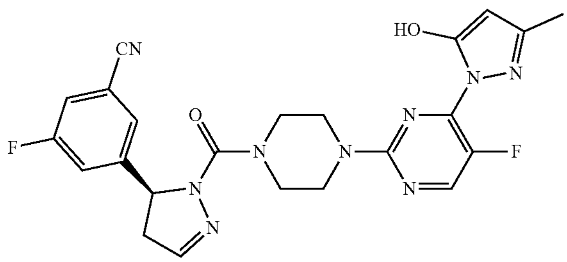
142
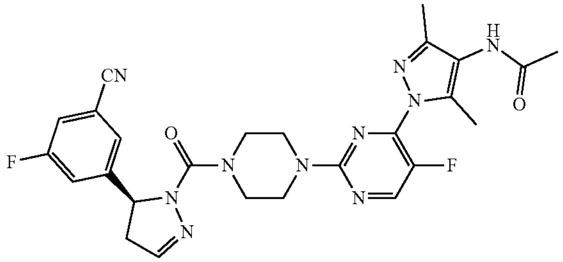
143
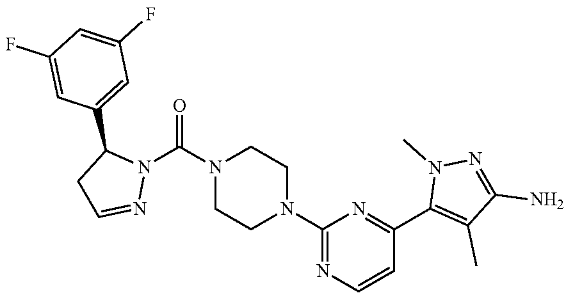
144
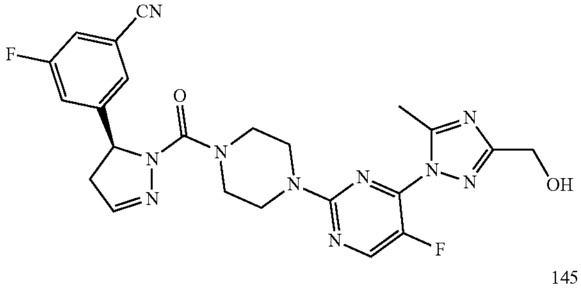
145
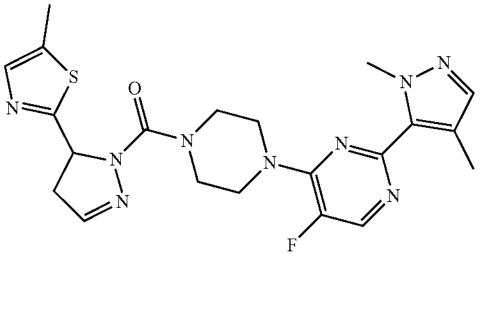
146
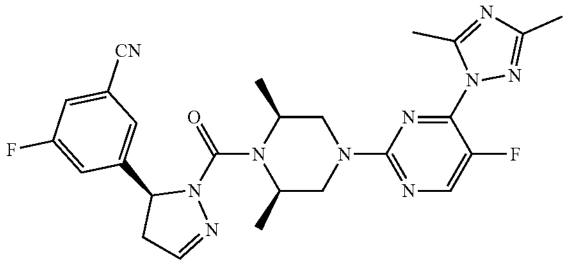
147
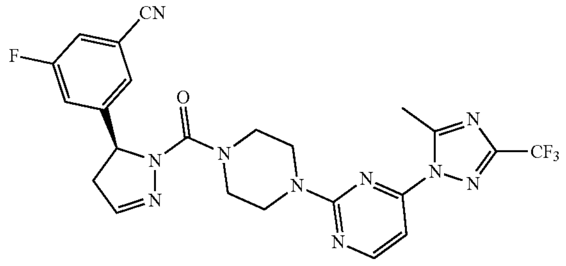
148
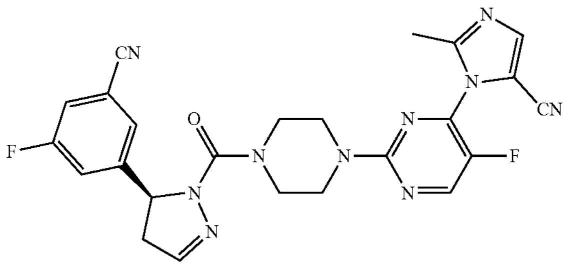
149
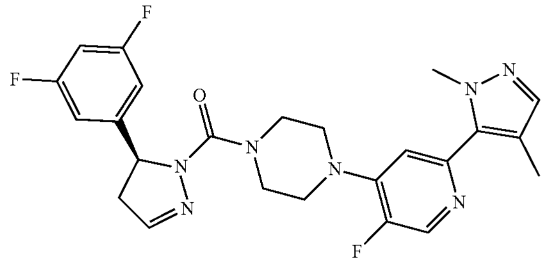
150
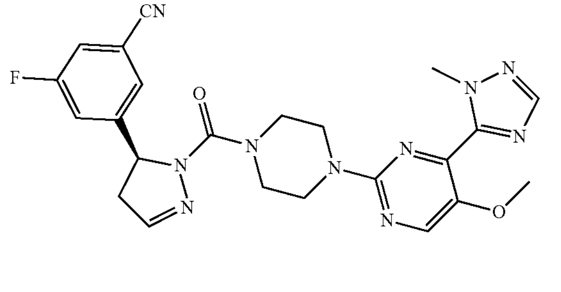

-continued
151
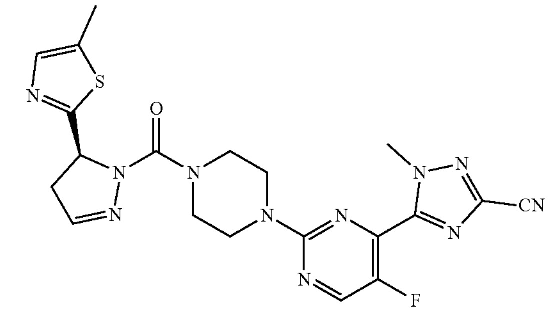
152
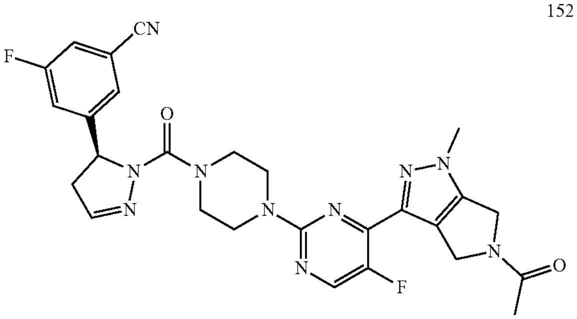
153
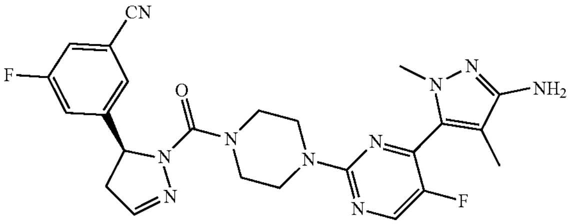
154
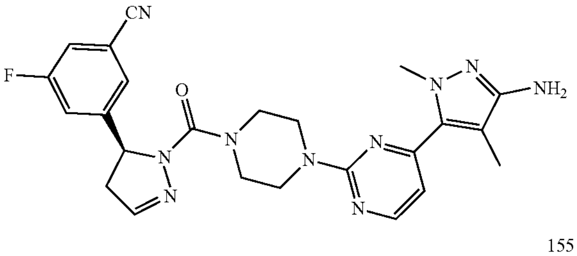
155
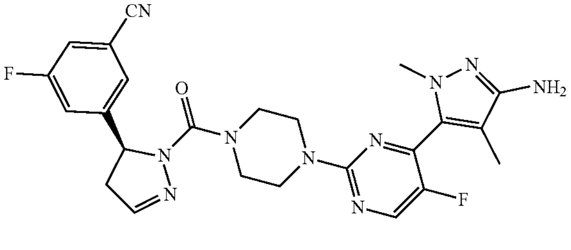
-continued
156
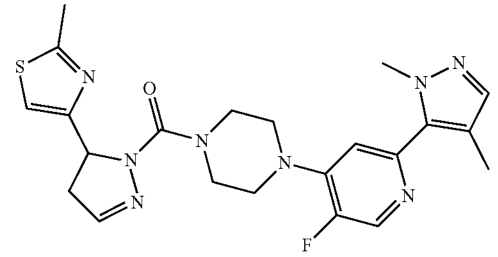
157
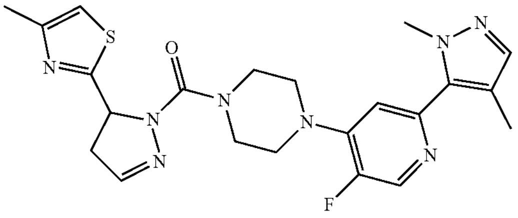
158
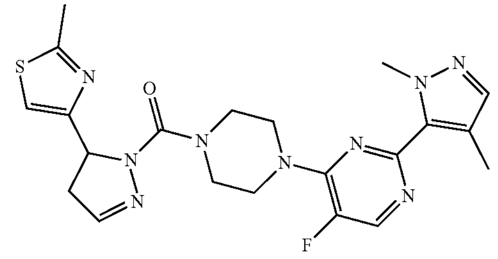
159
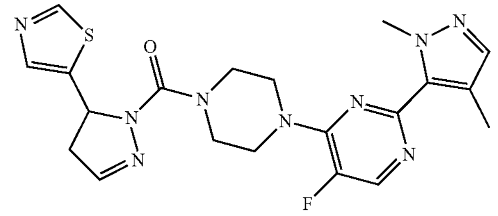
160
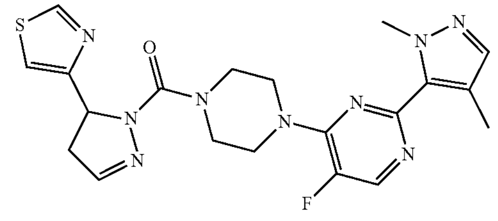
161
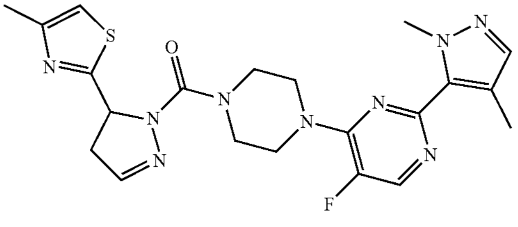

-continued
162
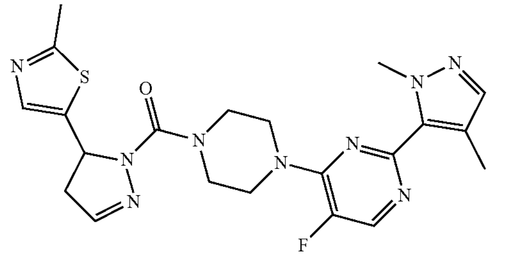
163
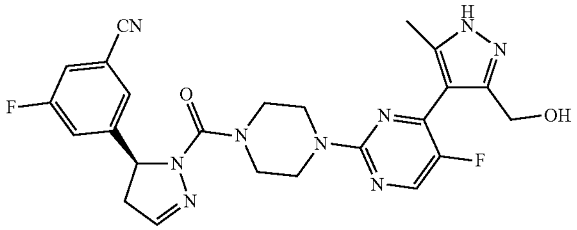
164
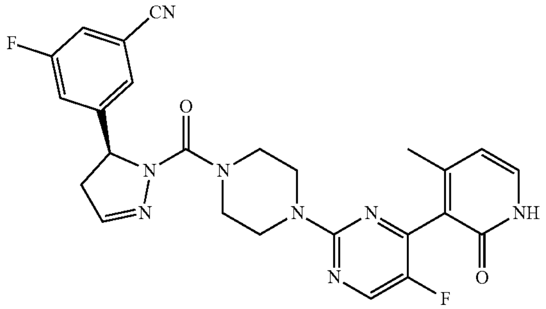
165
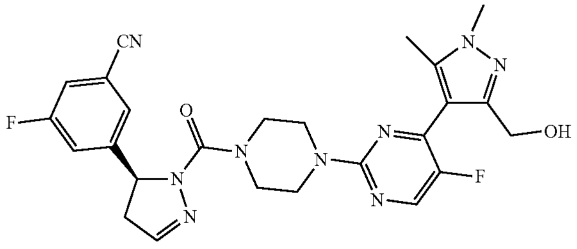
166
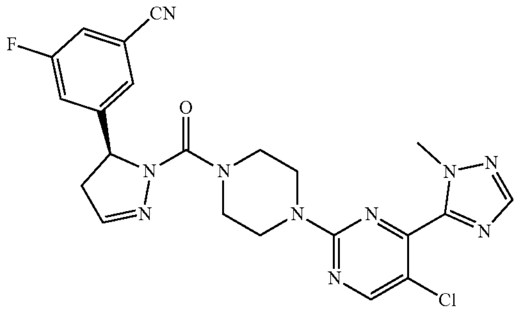
-continued
167
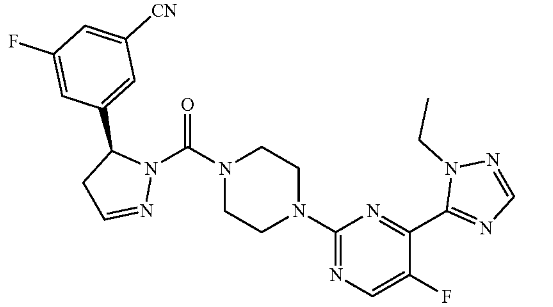
168
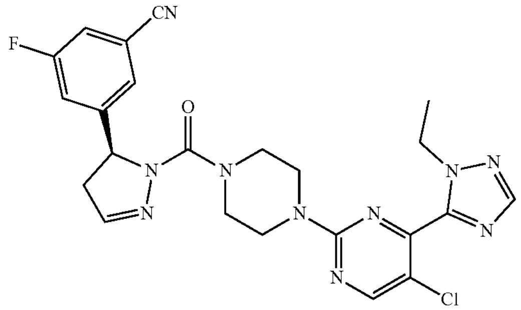
169
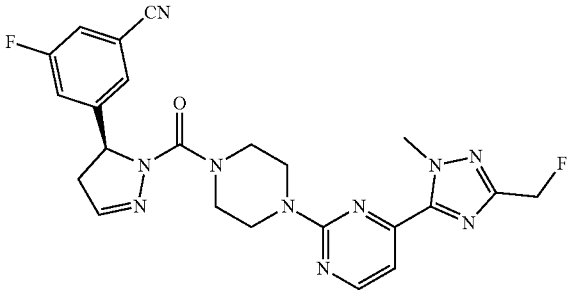
170
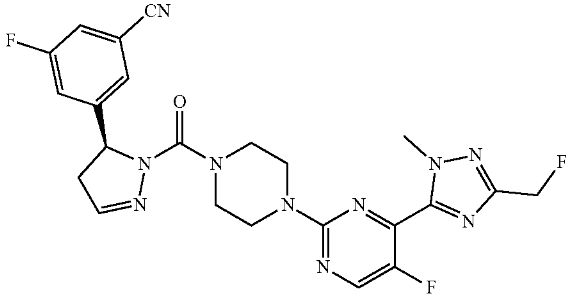
171
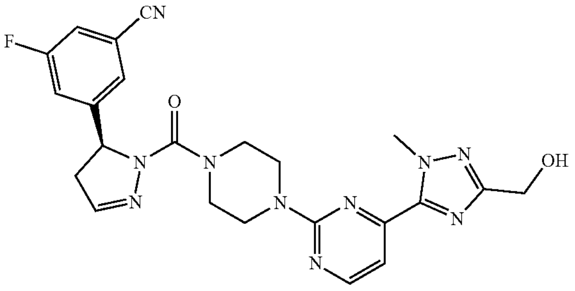

172
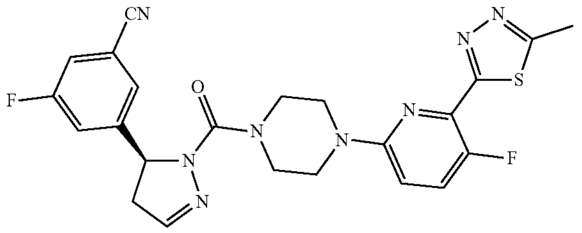
173
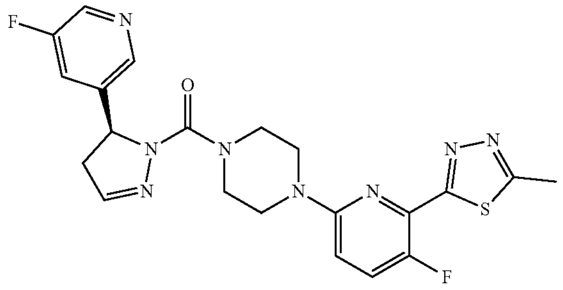
174
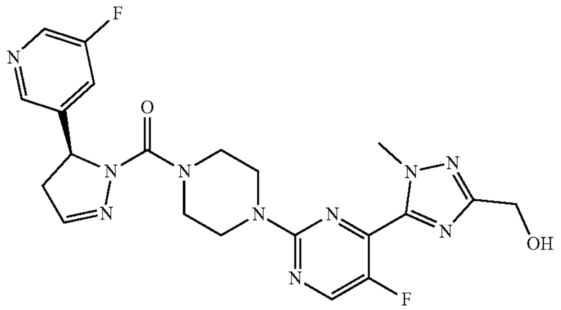
175
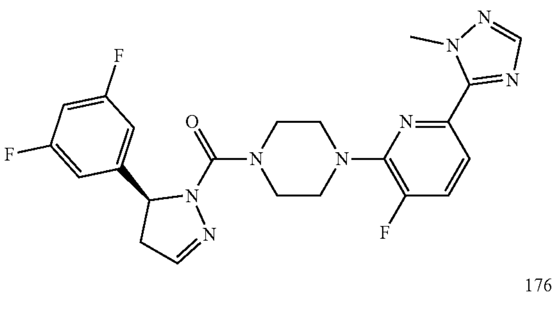
176
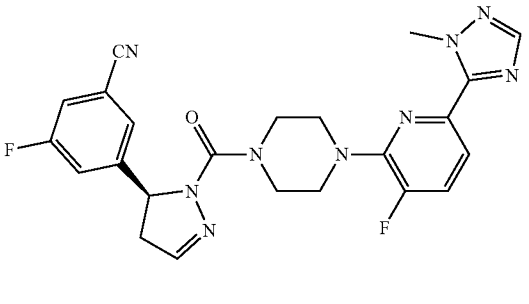
177
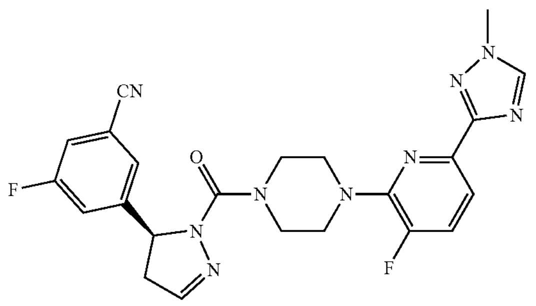
178
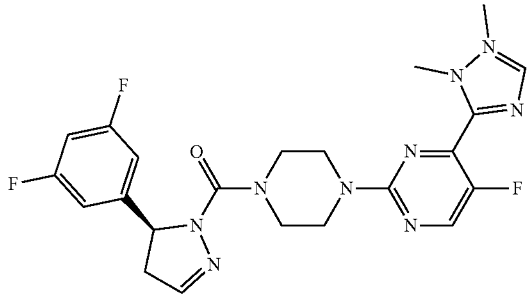
179
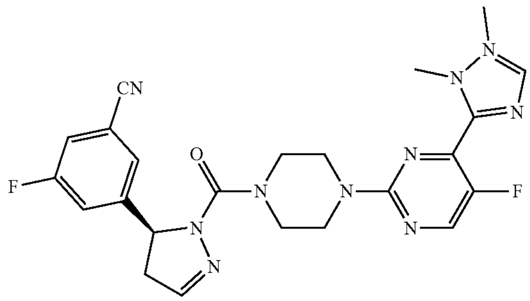
180
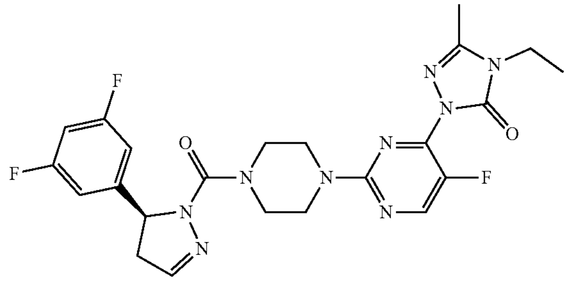
181
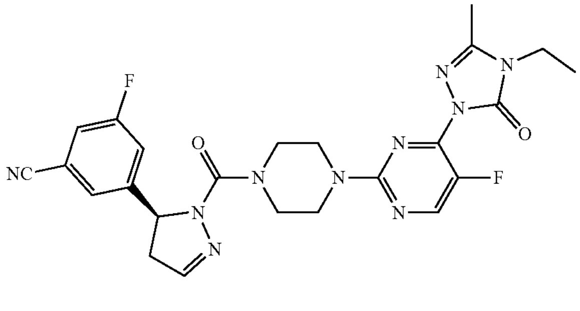

-continued
182
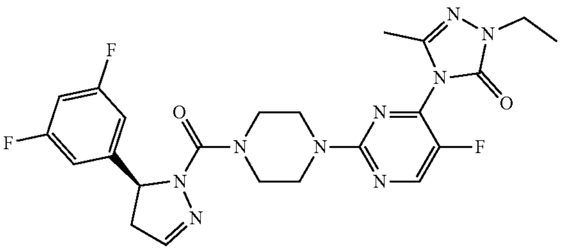
183
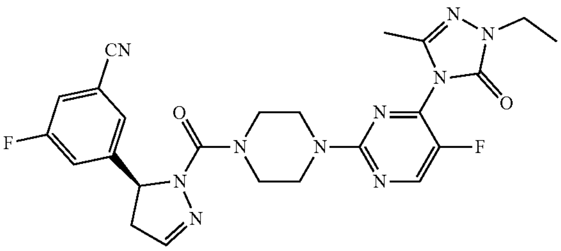
184
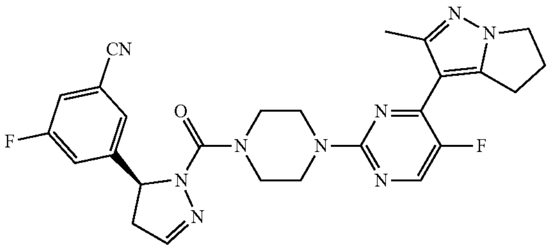
185
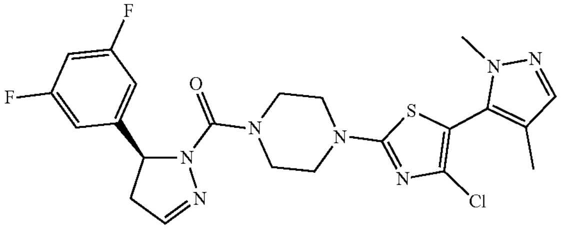
186
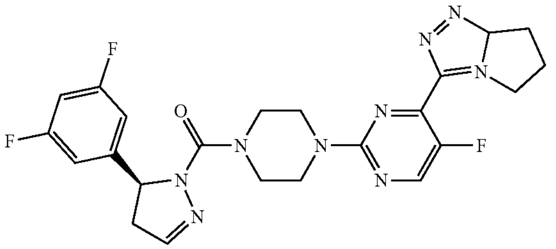
187
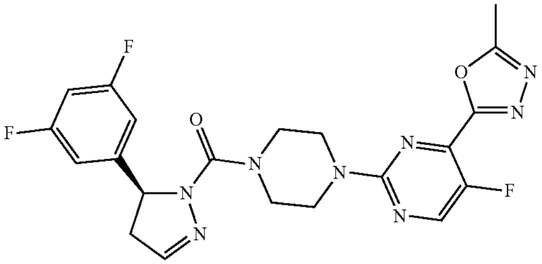
-continued
188
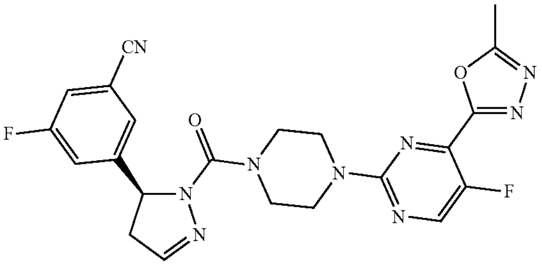
189
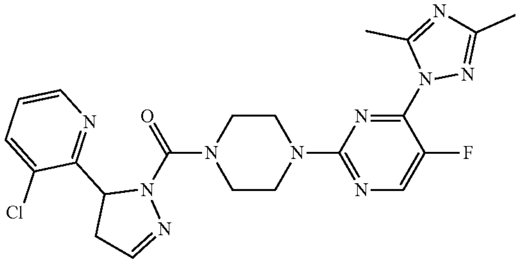
190
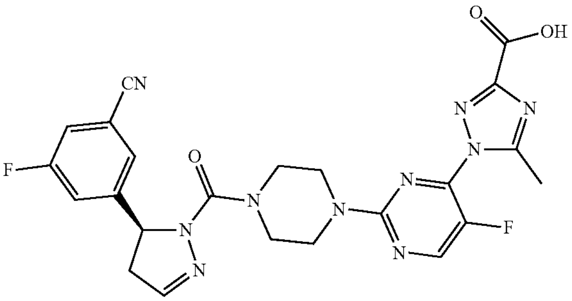
191
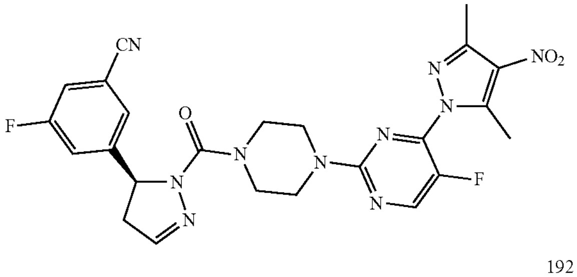
192
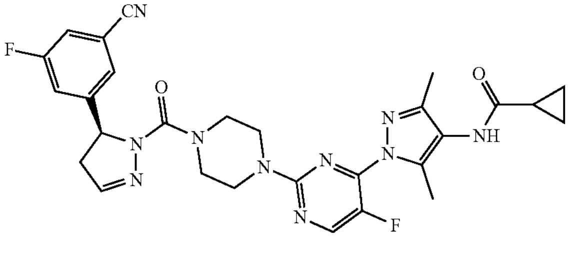

193
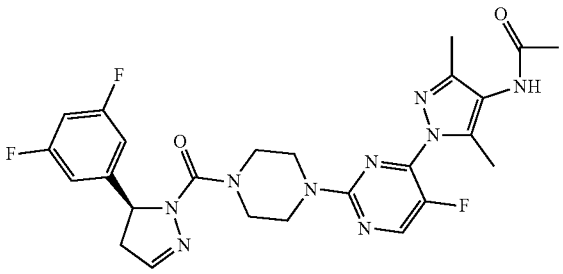
194
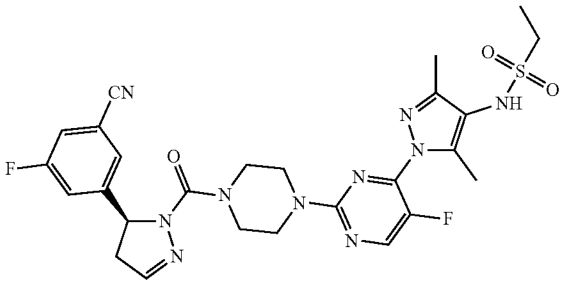
195
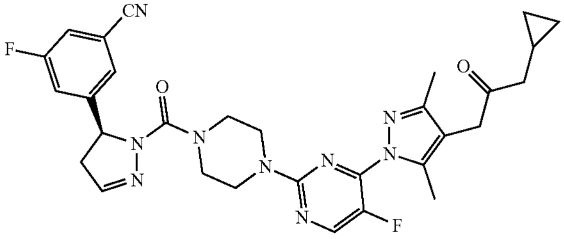
196
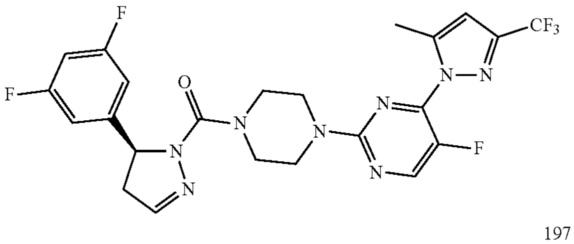
197
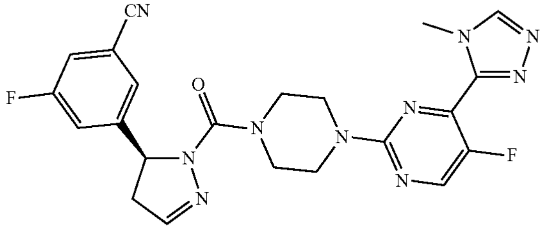
198
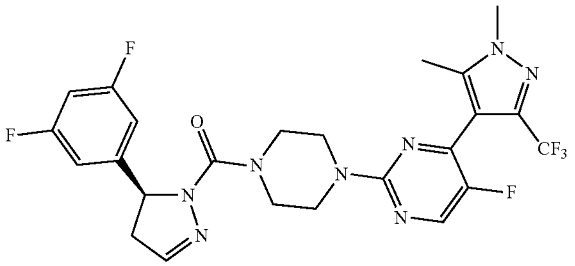
199
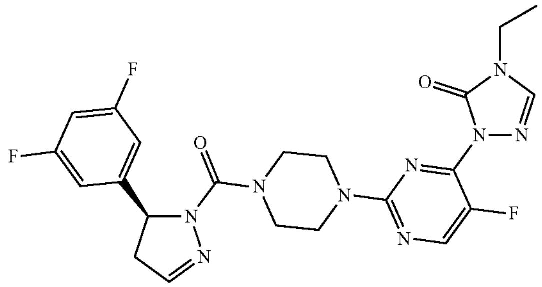
200
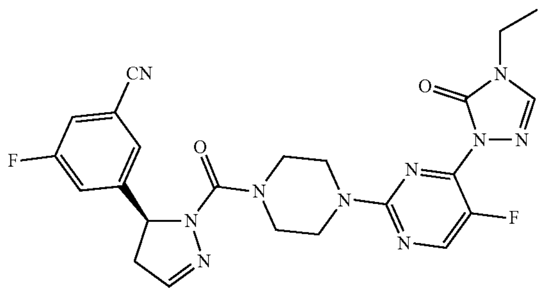
201
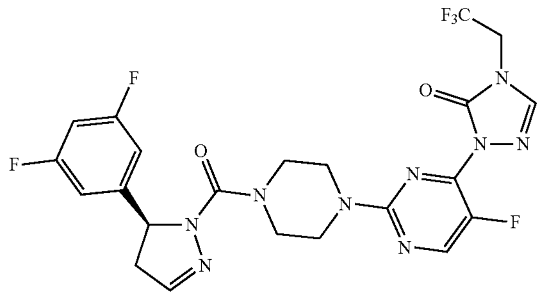
202
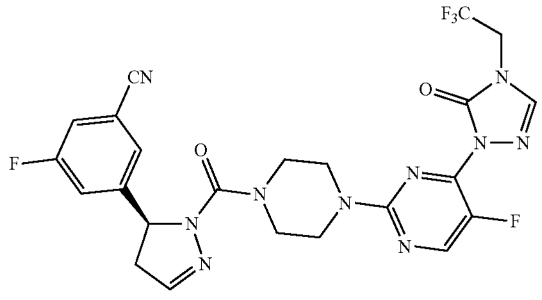

-continued
203
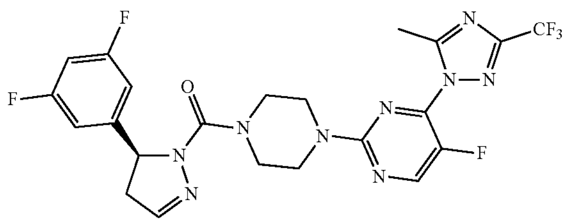
204
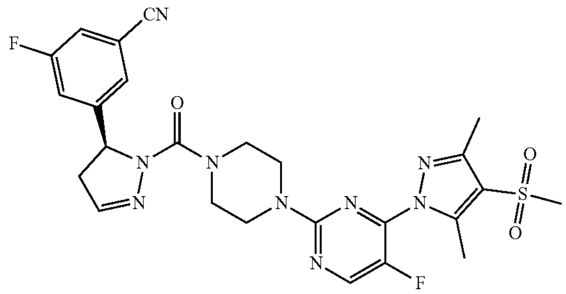
205
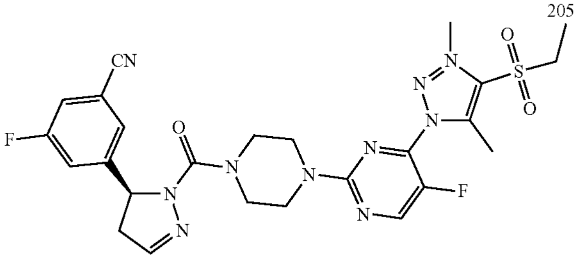
206
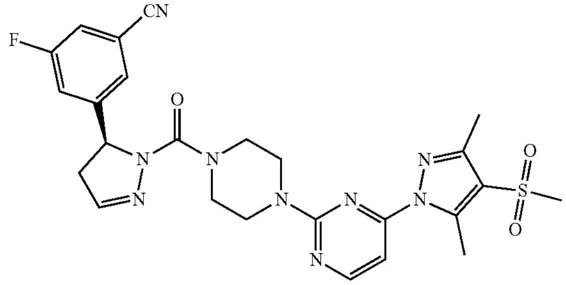
207
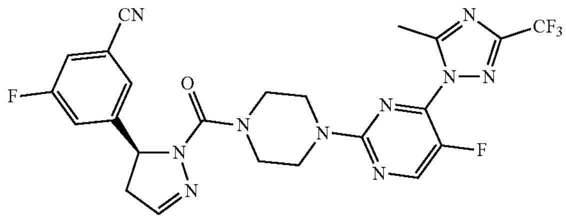
-continued
208
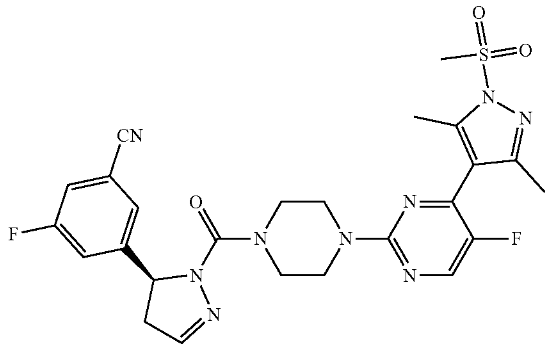
209
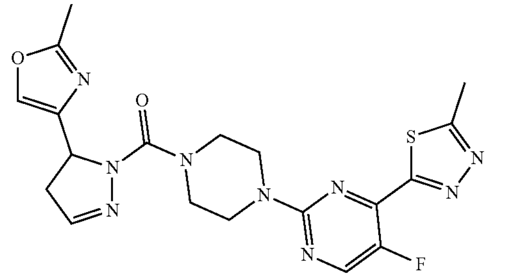
210
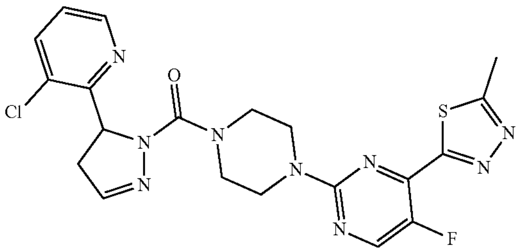
211
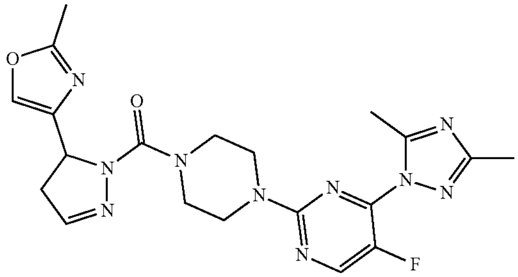
212
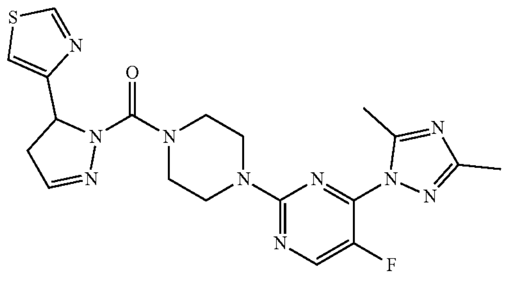

-continued
213
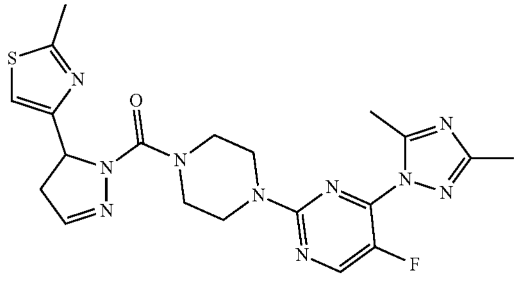
214
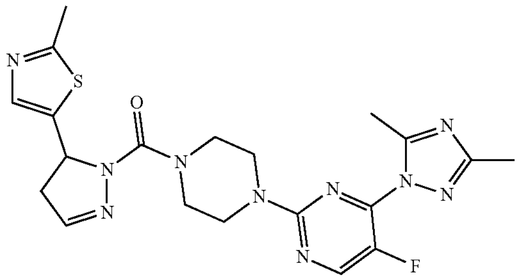
215
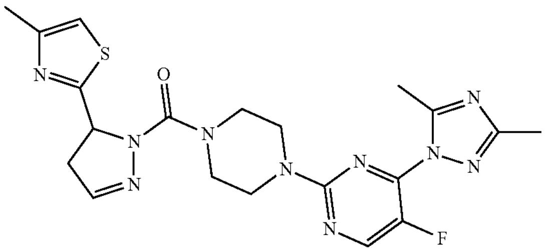
216
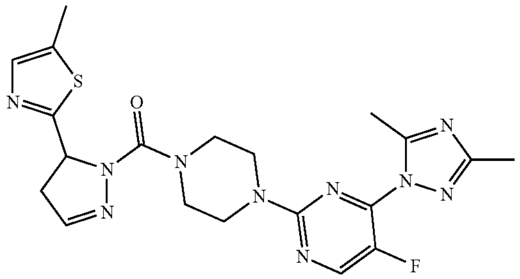
217
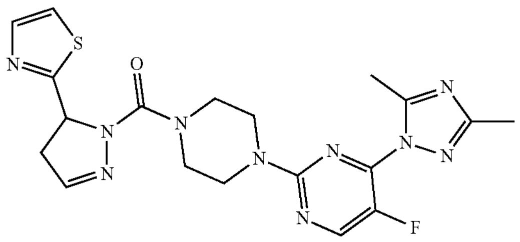
-continued
218
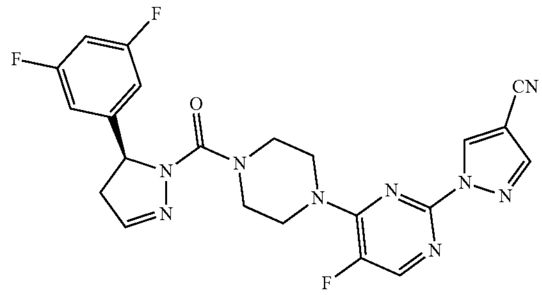
219
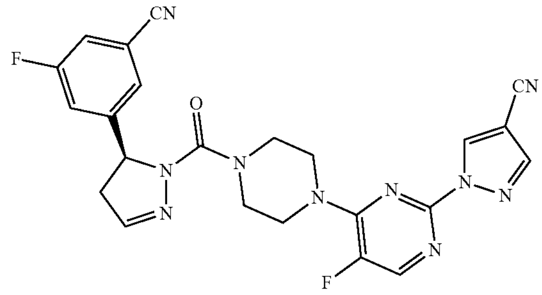
220
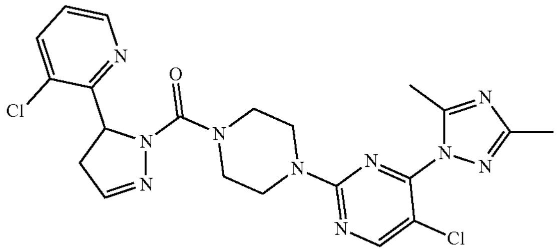
221
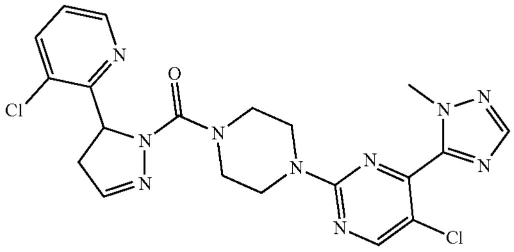
222
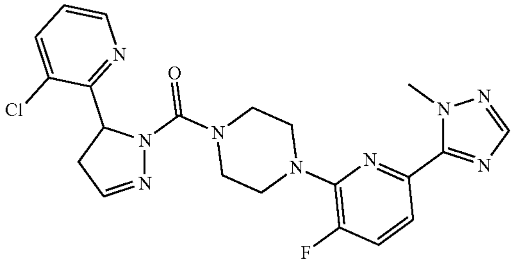

-continued
223
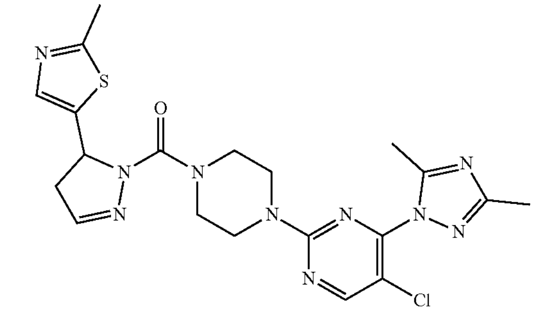
224
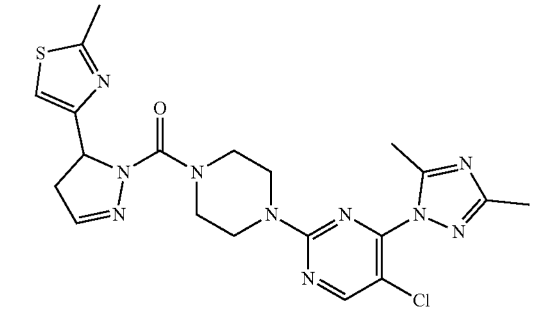
225
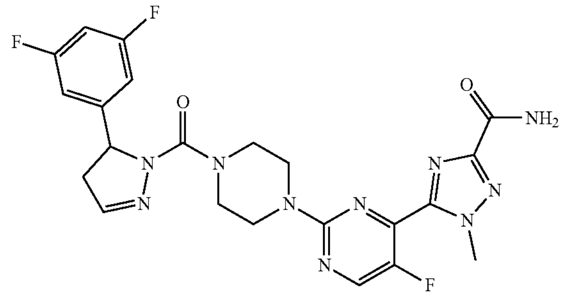
226
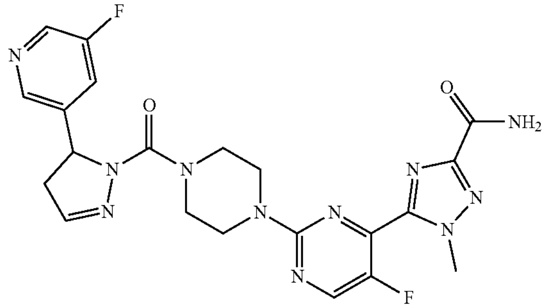
227
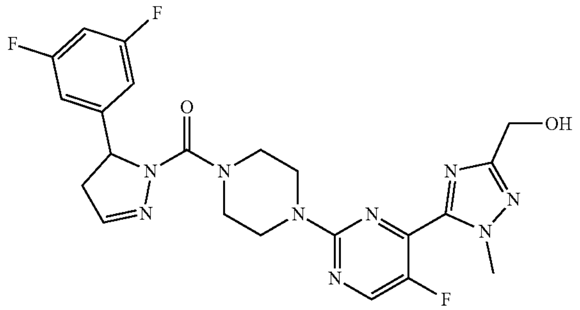
-continued
228
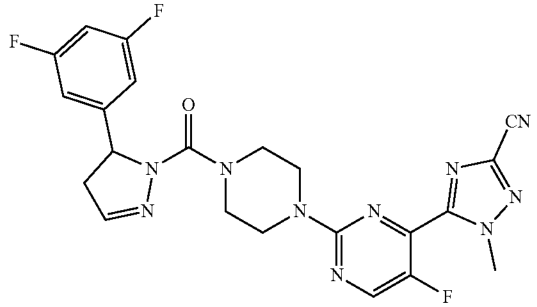
229
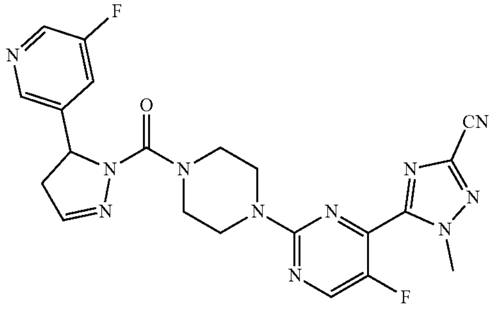
230
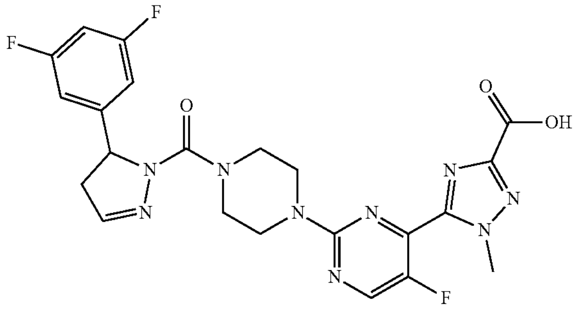
231
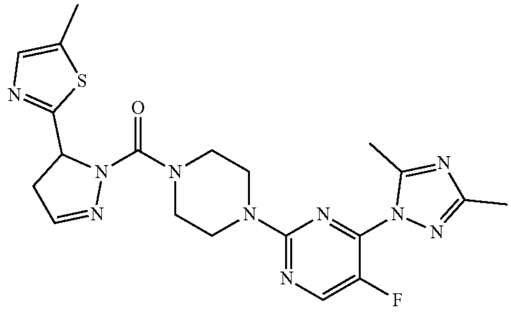
232
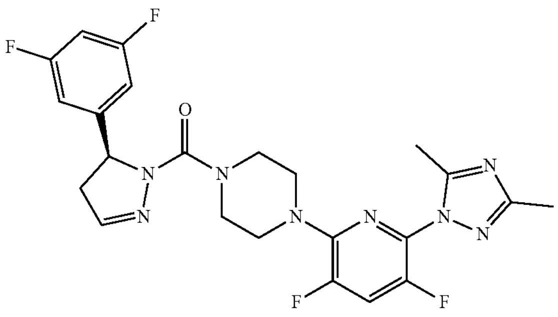

-continued
233
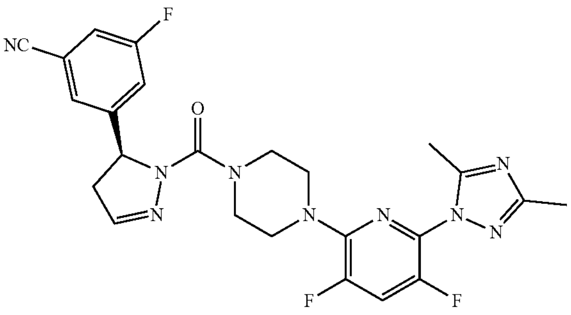
234
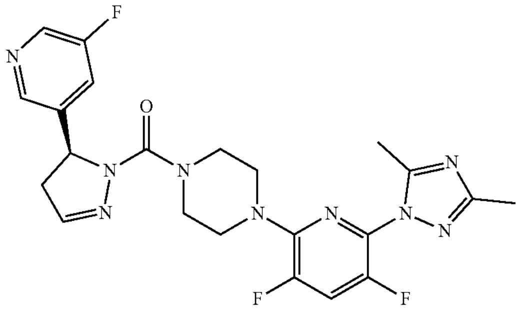
235
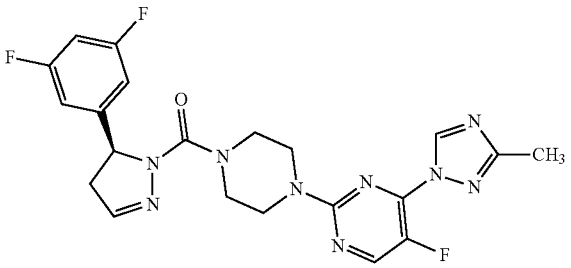
236
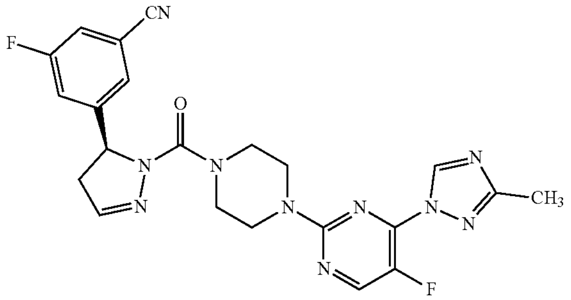
237
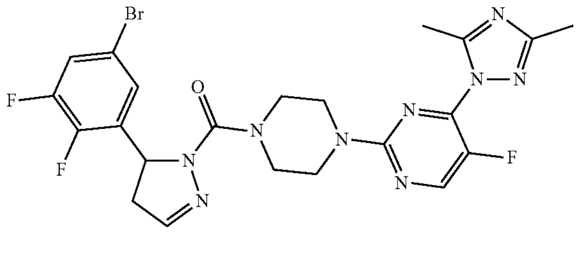
-continued
238
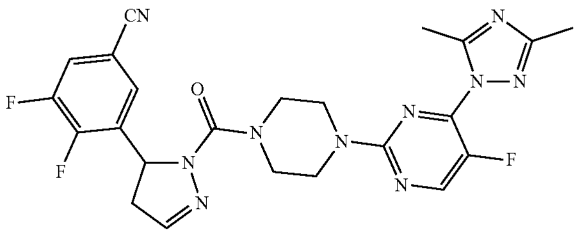
239
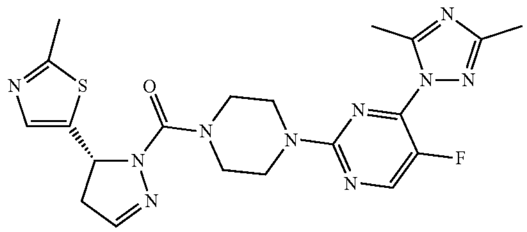
240
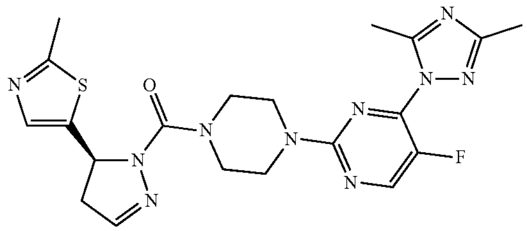
241
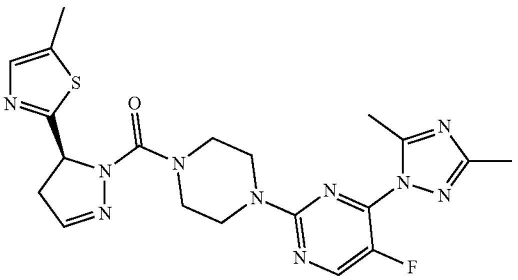
242
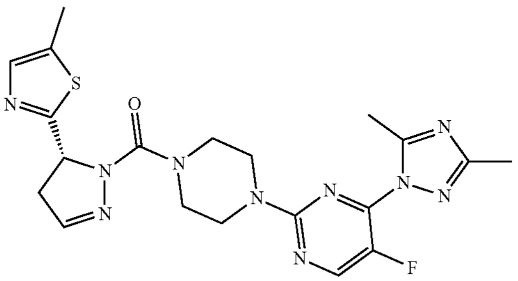

-continued
243
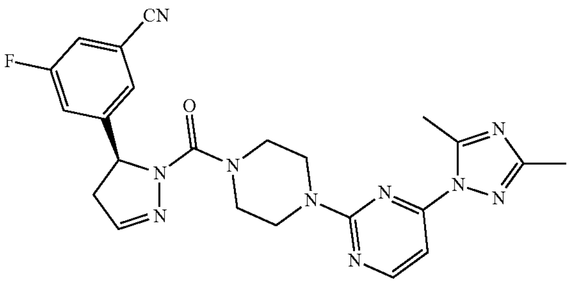
244
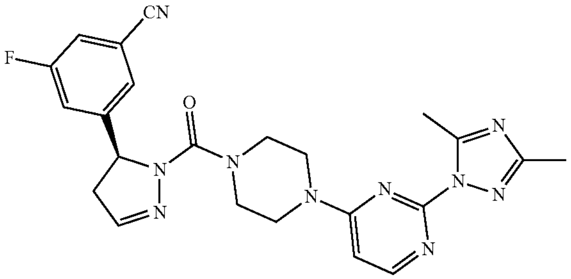
245
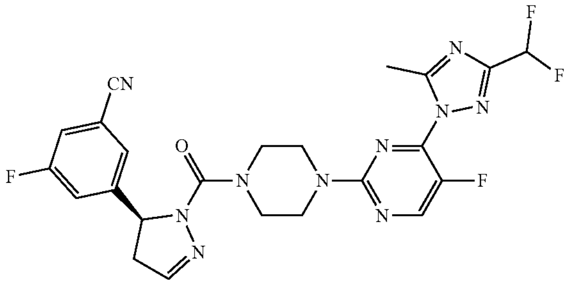
246
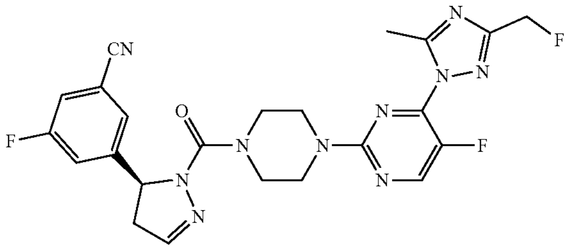
247
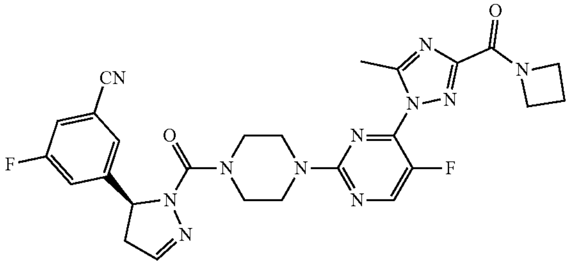
-continued
248
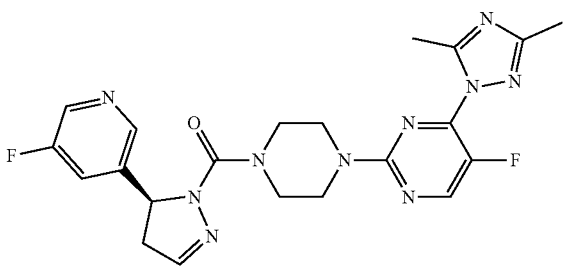
249
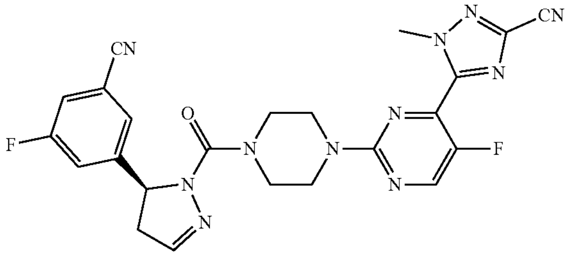
250
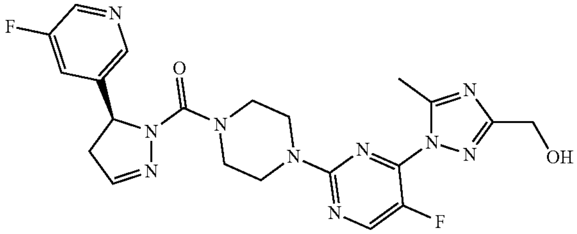
251
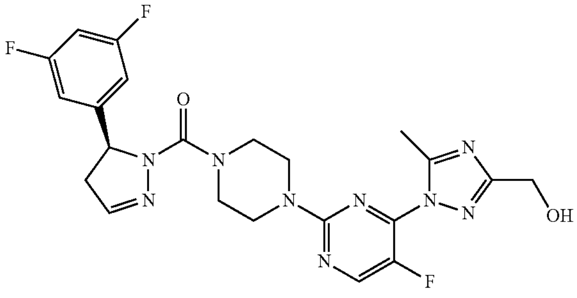
252
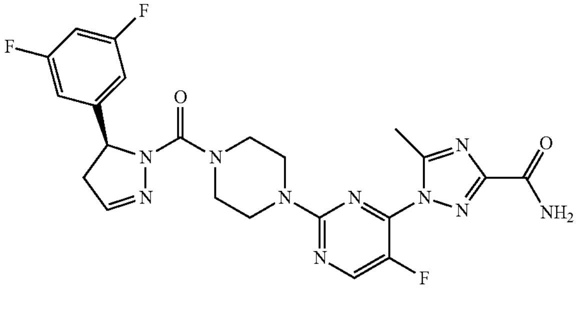

-continued
253
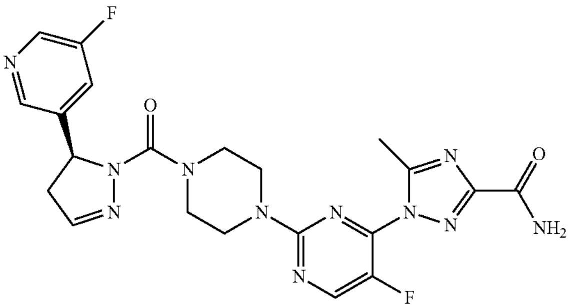
254
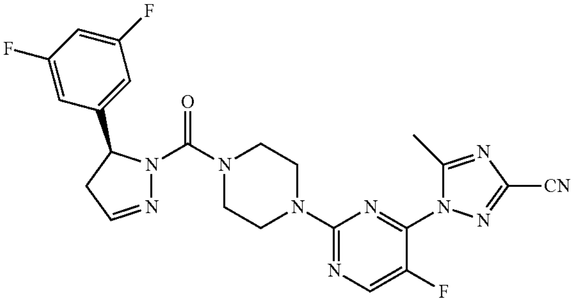
255
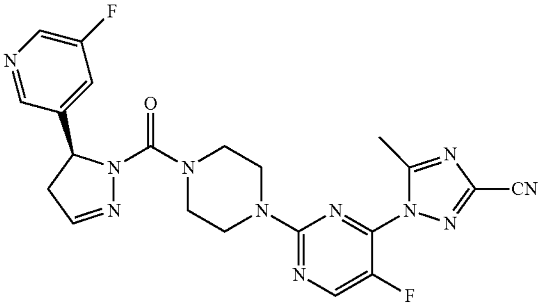
256
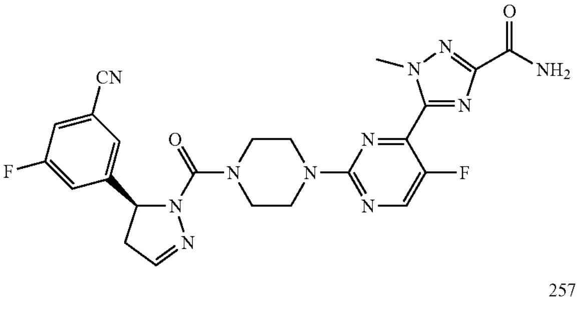
257
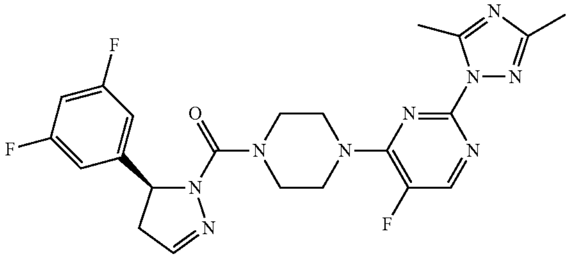
-continued
258
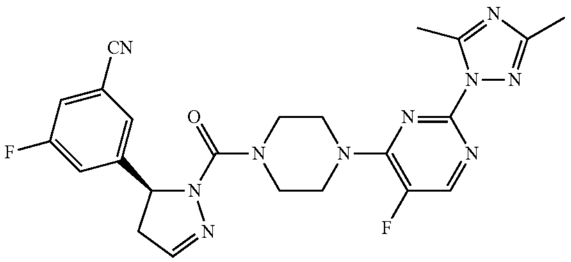
259
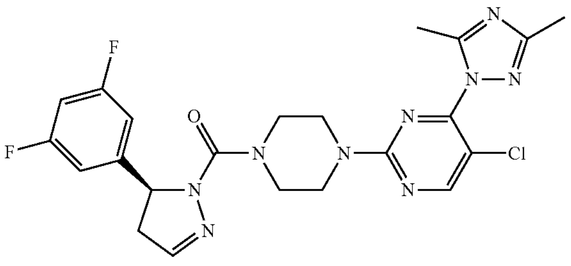
260
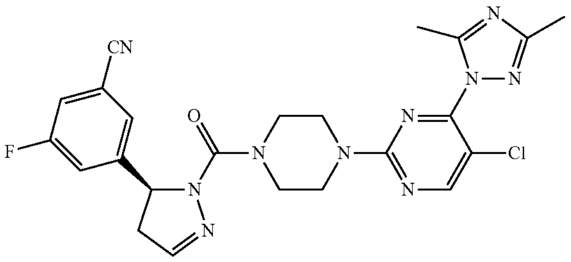
261
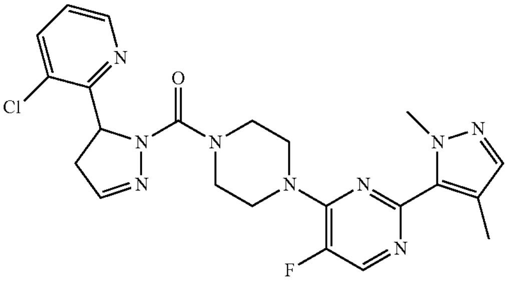
262
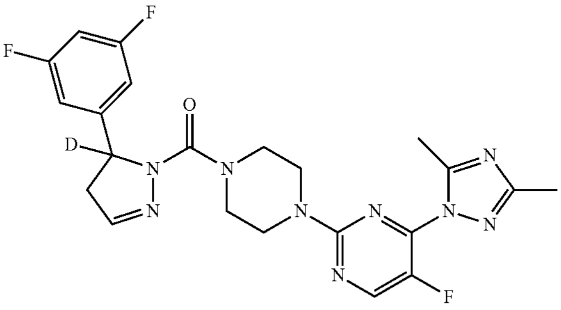

-continued
263
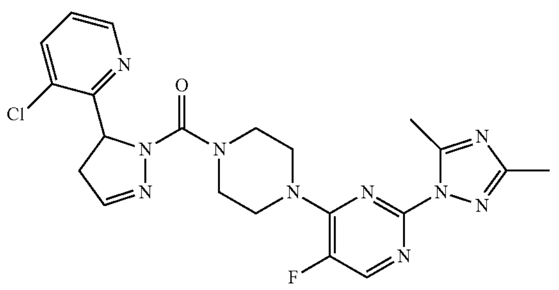
264
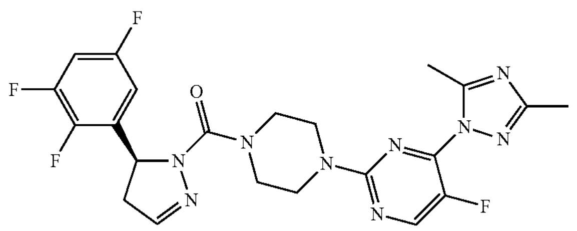
265
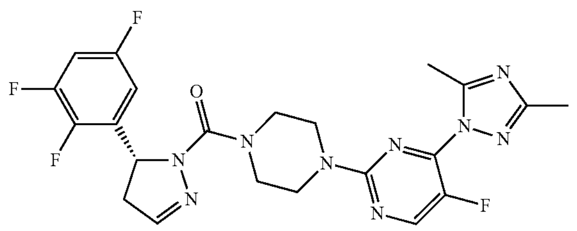
266
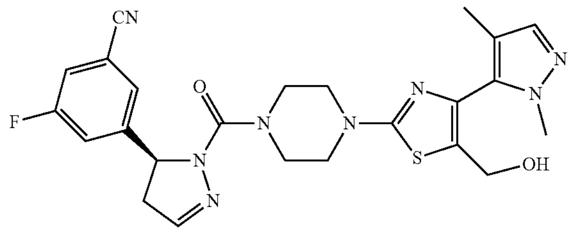
267
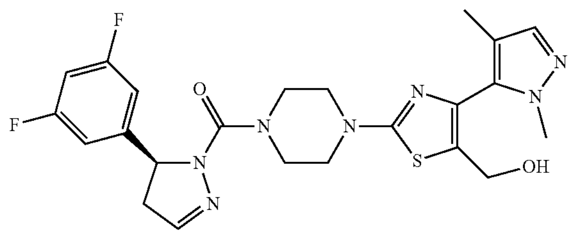
268
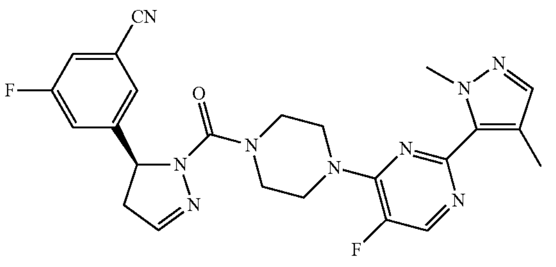
-continued
269
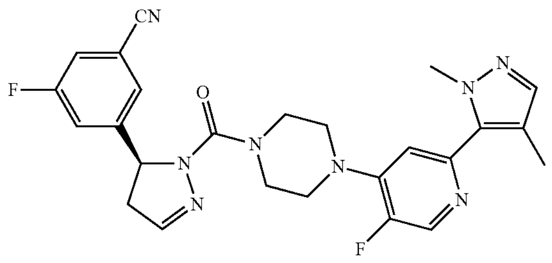
270
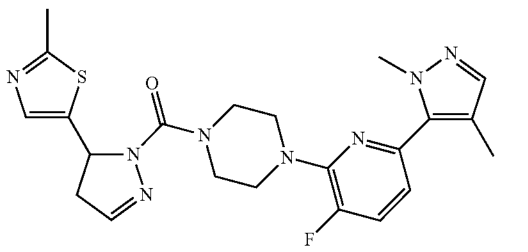
271
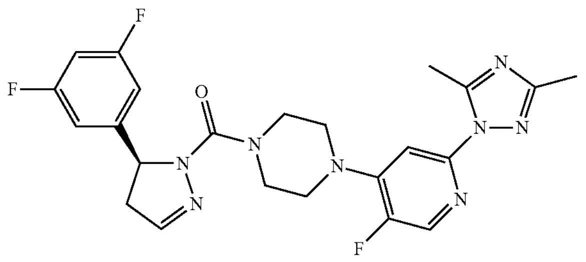
272
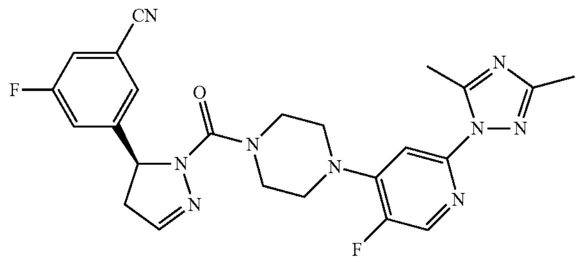
273
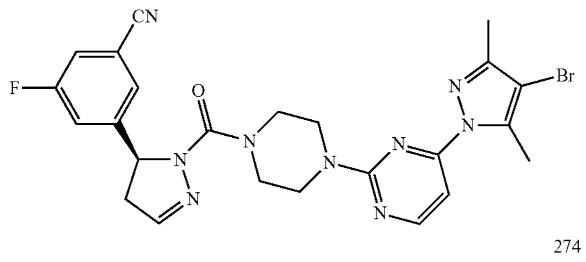
274
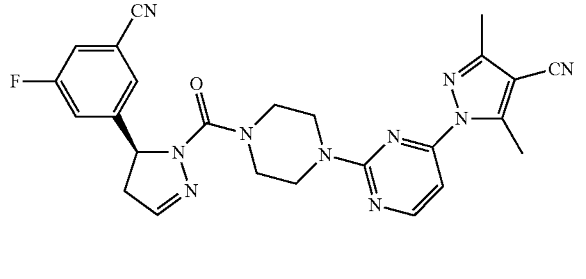

-continued
275
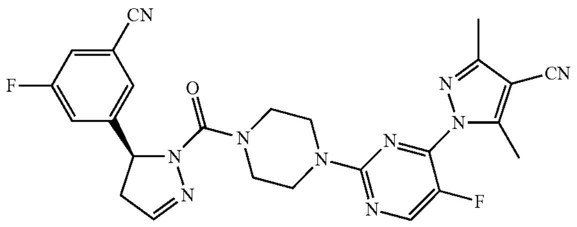
276
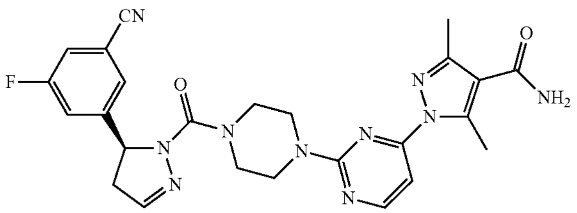
277
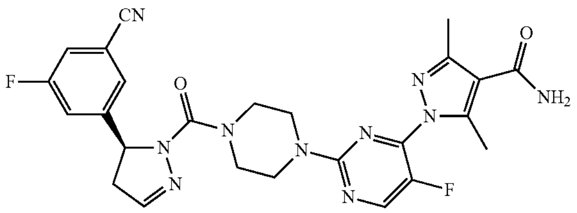
278
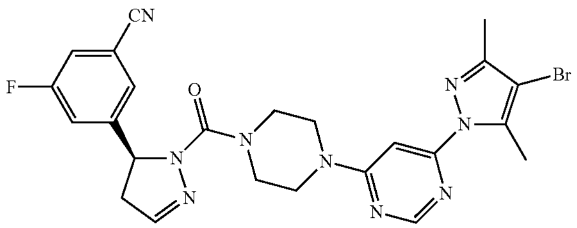
279
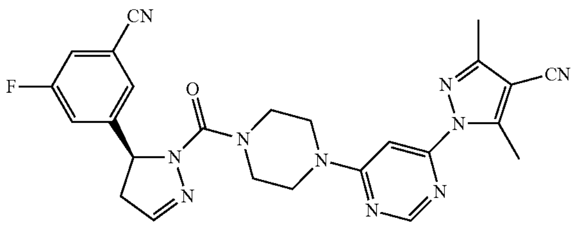
280
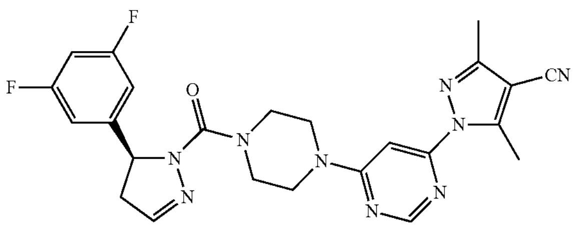
-continued
281
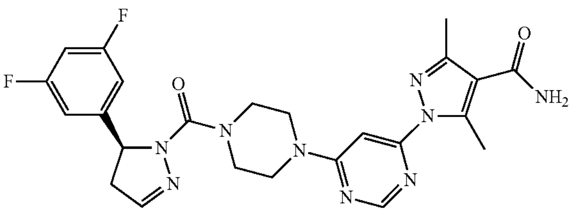
282
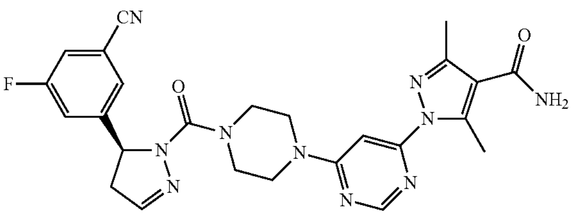
283
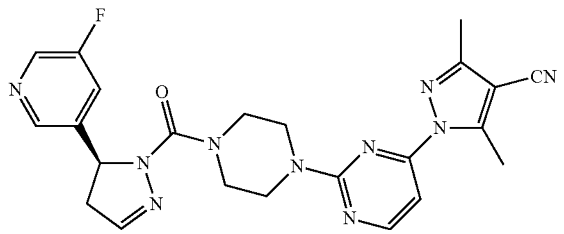
284
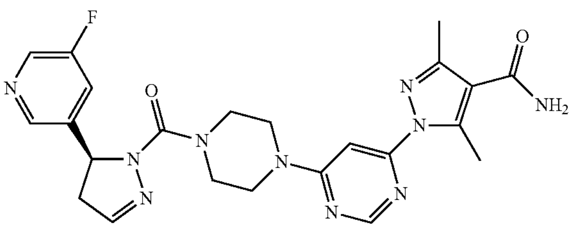
285
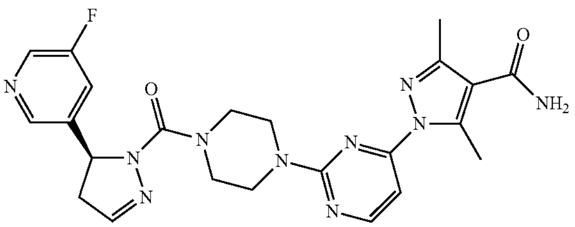
286
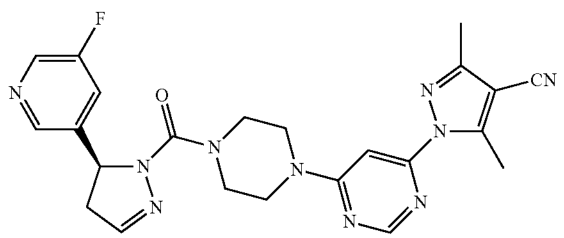

-continued
287
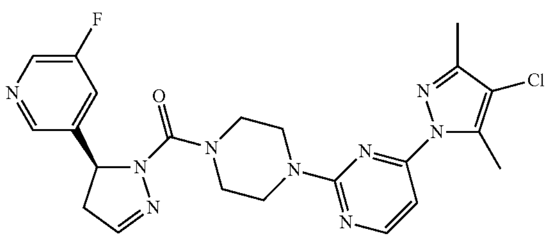
288
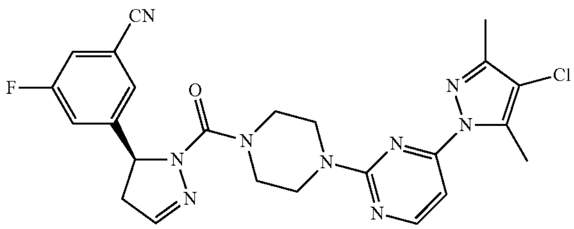
289
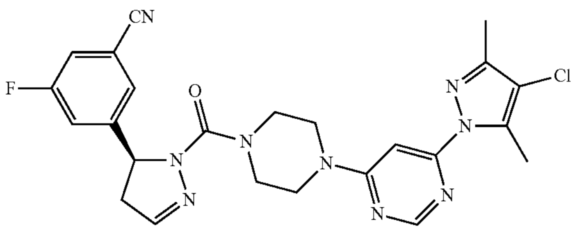
290
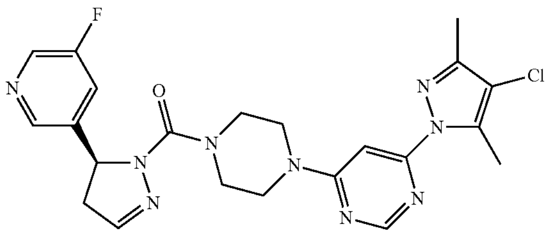
291
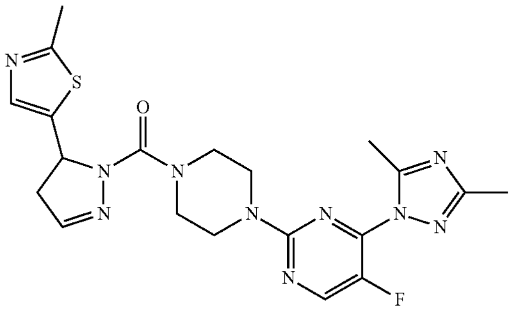
292
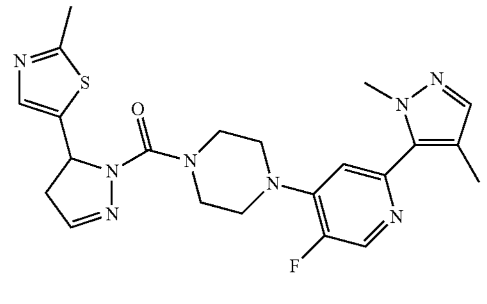
-continued
293
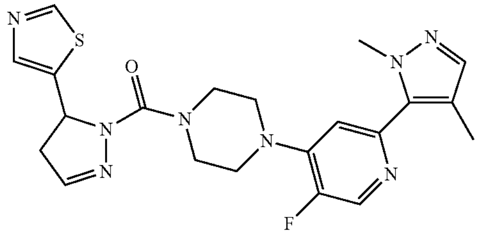
294
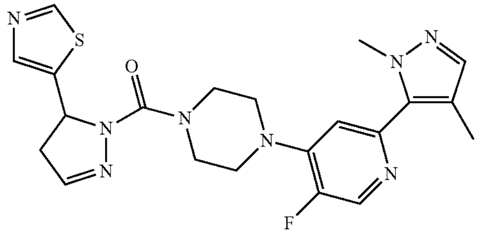
295
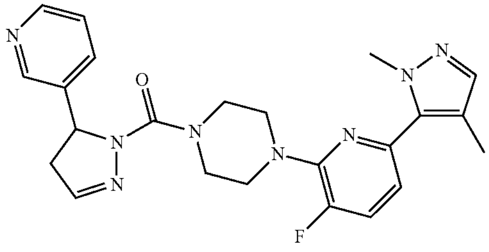
296
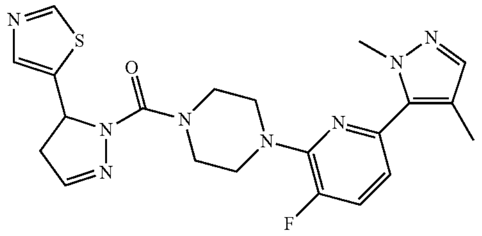
297
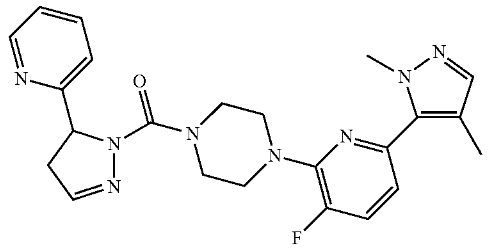
298
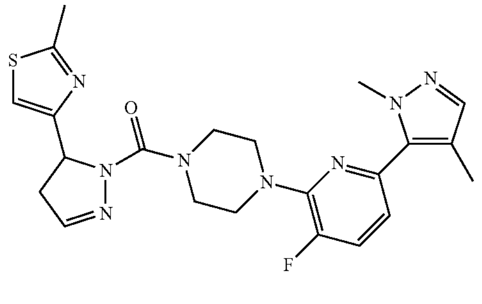

-continued
299
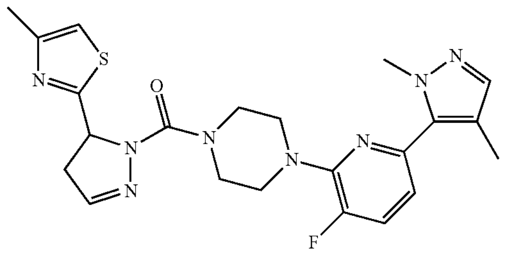
300
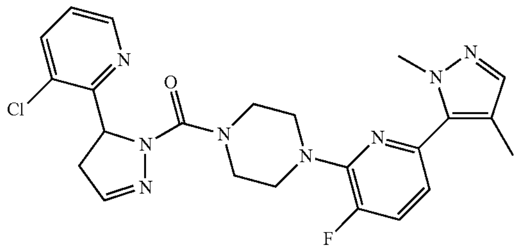
301
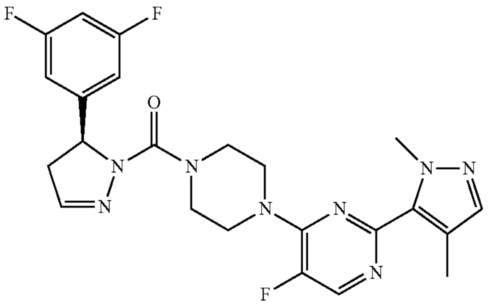
302
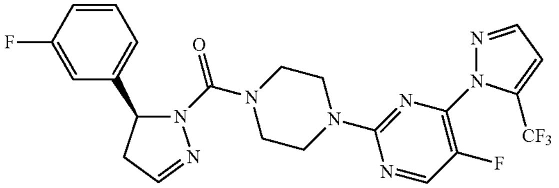
303
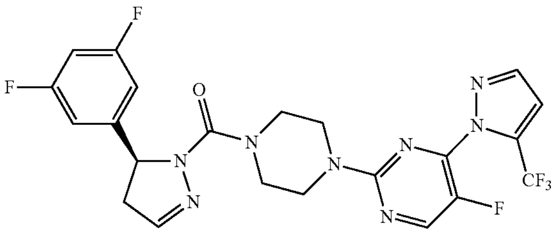
304
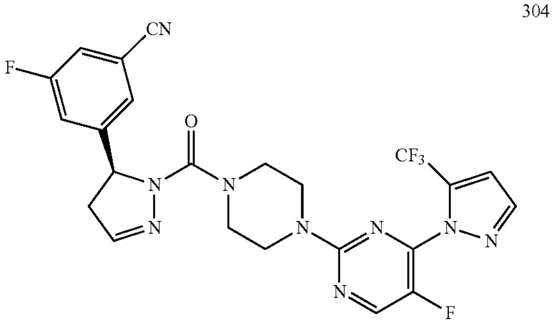
-continued
305
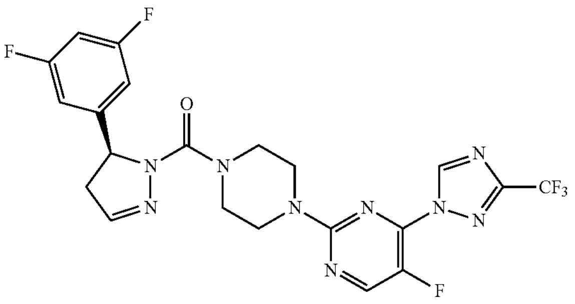
306
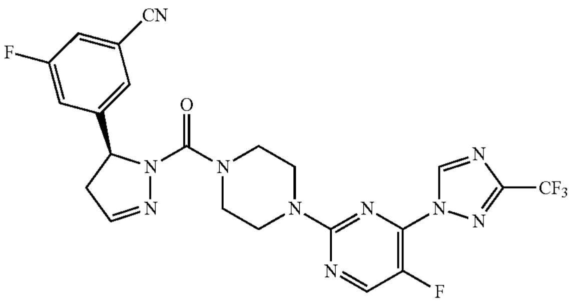
307
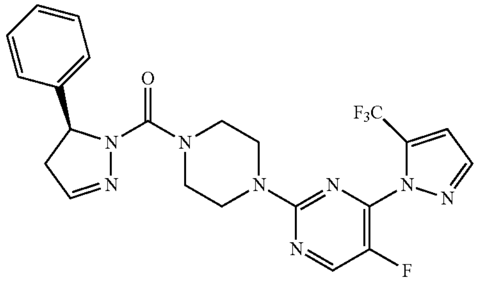
308
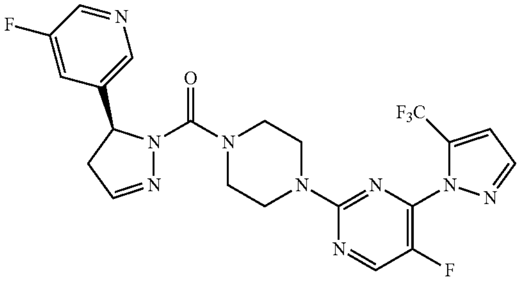
309
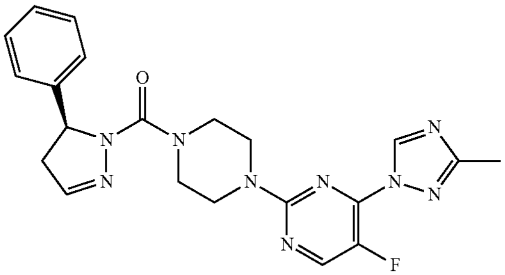

-continued

310

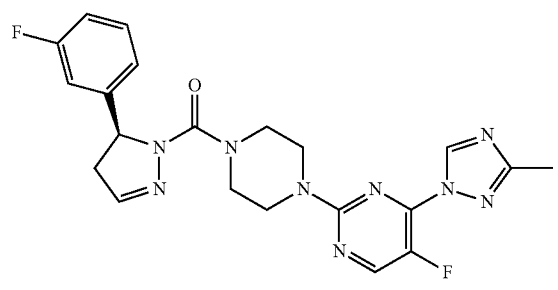

311

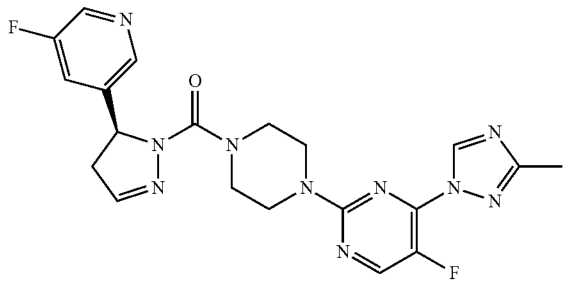

312

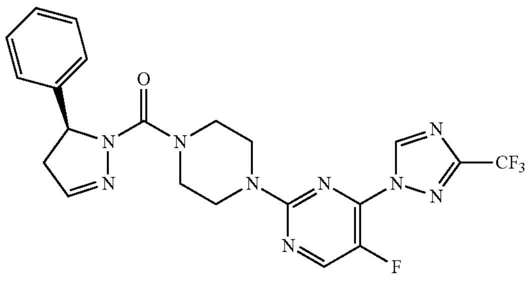

313

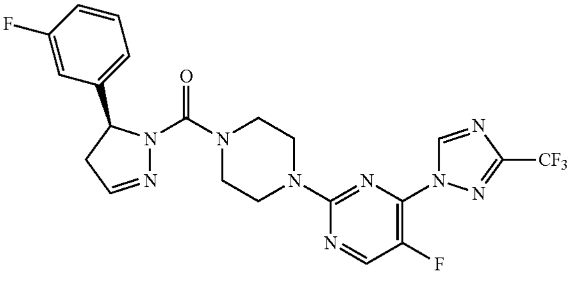

314

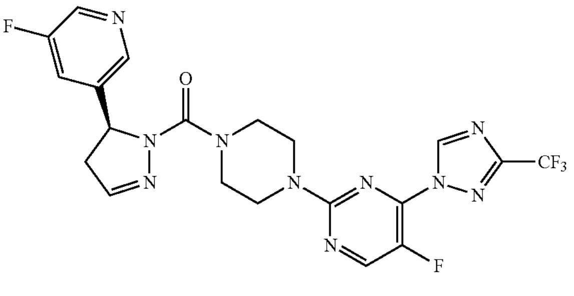

-continued

315

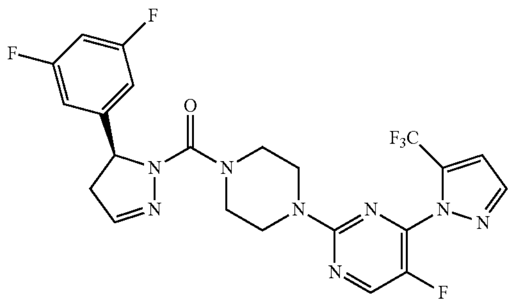

316

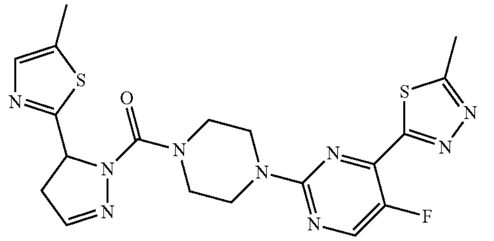

317

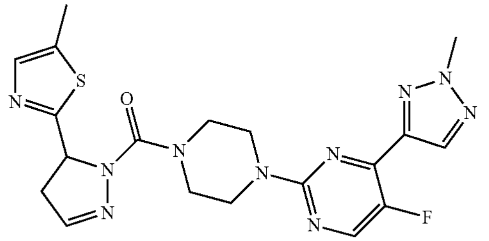

318

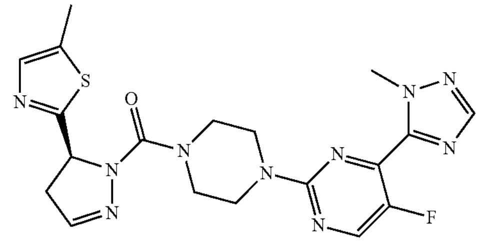

and

319

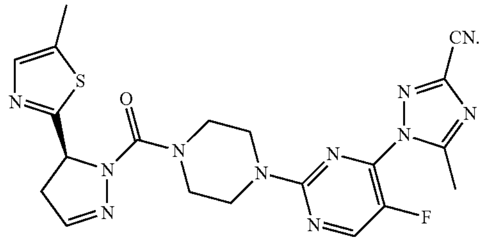

27. A pharmaceutical composition comprising a therapeutically effective amount of the compound, salt, hydrate or stereoisomer of claim 1 and one or more pharmaceutically acceptable excipients, in predetermined, unit dosage form.

28. A method of inhibiting necrosis, necroptosis, ferroptosis, or human RIP1 in a person in need thereof, comprising administering to the person a therapeutically effective amount of the compound, salt, hydrate, or stereoisomer of claim 1 or a pharmaceutical composition comprising the compound, salt, hydrate or stereoisomer of claim 1.

* * * * *